US008067436B2

(12) United States Patent
Bannen et al.

(10) Patent No.: US 8,067,436 B2
(45) Date of Patent: Nov. 29, 2011

(54) C-MET MODULATORS AND METHODS OF USE

(75) Inventors: Lynne Canne Bannen, Pacifica, CA (US); Diva Sze-Ming Chan, San Francisco, CA (US); Jeff Chen, San Francisco, CA (US); Lisa Esther Dalrymple, San Leandro, CA (US); Timothy Patrick Forsyth, Hayward, CA (US); Tai Phat Huynh, Oakland, CA (US); Vasu Jammalamadaka, Pleasanton, CA (US); Richard George Khoury, Redwood City, CA (US); James William Leahy, San Leandro, CA (US); Morrisson B. Mac, San Francisco, CA (US); Grace Mann, Brisbane, CA (US); Larry W. Mann, Richland, MI (US); John M. Nuss, Danville, CA (US); Jason Jevious Parks, Sacramento, CA (US); Craig Stacy Takeuchi, Burlingame, CA (US); Yong Wang, Forster City, CA (US); Wie Xu, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 949 days.

(21) Appl. No.: 11/753,514

(22) Filed: May 24, 2007

(65) Prior Publication Data
US 2009/0105299 A1    Apr. 23, 2009

Related U.S. Application Data

(63) Continuation of application No. 11/586,751, filed on Oct. 26, 2006, which is a continuation of application No. 10/573,336, filed as application No. PCT/US2004/031523 on Sep. 24, 2004, now abandoned.

(60) Provisional application No. 60/506,181, filed on Sep. 26, 2003, provisional application No. 60/535,377, filed on Jan. 9, 2004, provisional application No. 60/577,384, filed on Jun. 4, 2004.

(51) Int. Cl.
*A61K 31/47* (2006.01)
*A61K 31/4709* (2006.01)
*A61K 31/517* (2006.01)
*A61K 31/5377* (2006.01)

(52) U.S. Cl. ........ 514/312; 546/153; 544/119; 544/287; 544/363; 544/128; 514/234.5; 514/235.2; 514/252.17; 514/253.07; 514/266.2; 514/266.22; 514/266.3

(58) Field of Classification Search ............... 514/266.2, 514/266.3, 312, 314; 544/284, 287; 546/153, 546/159, 155

See application file for complete search history.

(56) References Cited

U.S. PATENT DOCUMENTS

| 5,238,951 | A | 8/1993 | Sher |
| 5,480,883 | A | 1/1996 | Spada et al. |
| 5,650,415 | A | 7/1997 | Tang et al. |
| 5,747,498 | A | 5/1998 | Schnur et al. |
| 5,770,599 | A | 6/1998 | Gibson |
| 5,962,458 | A | 10/1999 | Lohmann et al. |
| 6,071,921 | A | 6/2000 | Lohmann et al. |
| 6,103,728 | A | 8/2000 | Tang et al. |
| 6,126,917 | A | 10/2000 | Mishani et al. |
| 6,143,764 | A | 11/2000 | Kubo et al. |
| 6,184,225 | B1 | 2/2001 | Thomas et al. |
| 6,204,267 | B1 | 3/2001 | Tang et al. |
| 6,235,746 | B1 | 5/2001 | Davis et al. |
| 6,288,082 | B1 | 9/2001 | Wissner et al. |
| 6,294,532 | B1 | 9/2001 | Thomas et al. |
| 6,337,335 | B1 | 1/2002 | Hutchings et al. |
| 6,344,455 | B1 | 2/2002 | Bridges et al. |
| 6,344,459 | B1 | 2/2002 | Bridges et al. |
| 6,358,962 | B2 | 3/2002 | Uckun et al. |
| 6,362,336 | B1 | 3/2002 | Lohmann et al. |
| 6,391,874 | B1 | 5/2002 | Cockerill et al. |
| 6,403,580 | B1 | 6/2002 | Himmelsbach et al. |
| 6,414,148 | B1 | 7/2002 | Thomas et al. |
| 6,432,406 | B1 | 8/2002 | Goldberg et al. |
| 6,448,261 | B1 | 9/2002 | Bakthavatchalam et al. |
| 6,469,013 | B2 | 10/2002 | Uckun et al. |

(Continued)

FOREIGN PATENT DOCUMENTS

EP    1044969 A2    10/2000

(Continued)

OTHER PUBLICATIONS

Abounader et al., "In vivo targeting of SF/HGF and c-met expression via UlsnRNA/ribozymes inhibits glioma growth and angiogenesis and promotes apoptosis," *FASEB J.*, 16 (1): 108-110 (Jan. 2002).

(Continued)

*Primary Examiner* — Emily Bernhardt
(74) *Attorney, Agent, or Firm* — Honigman, Miller, Schwartz & Cohn; Heidi M. Berven; Jonathan P. O'Brien

(57) ABSTRACT

The present invention provides compounds for modulating protein kinase enzymatic activity for modulating cellular activities such as proliferation, differentiation, programmed cell death, migration and chemoinvasion. More specifically, the invention provides quinazolines and quinolines which inhibit, regulate, and/or modulate kinase receptor, particularly c-Met, KDF, c-Kit, flt-3 and flt-4, signal transduction pathways related to the changes in cellular activities as mentioned above, compositions which contain these compounds, and methods of using them to treat kinase-dependent diseases and conditions. The present invention also provides methods for making compounds as mentioned above, and compositions which contain these compounds.

4 Claims, No Drawings

U.S. PATENT DOCUMENTS

| | | | |
|---|---|---|---|
| 6,472,391 B2 | 10/2002 | Matsumo et al. |
| 6,476,031 B1 | 11/2002 | Chakravarty et al. |
| 6,476,040 B1 | 11/2002 | Norris et al. |
| 6,495,556 B2 | 12/2002 | Uckun et al. |
| 6,514,971 B1 | 2/2003 | Thomas et al. |
| 6,521,618 B2 | 2/2003 | Boschelli et al. |
| 6,521,629 B2 | 2/2003 | Fox |
| 6,525,046 B1 | 2/2003 | Cirillo et al. |
| 6,552,027 B2 | 4/2003 | Uckun et al. |
| 6,562,818 B1 | 5/2003 | Bridges |
| 6,593,333 B1 | 7/2003 | Cumming |
| 6,602,863 B1 | 8/2003 | Bridges et al. |
| 6,608,048 B2 | 8/2003 | Tsou et al. |
| 6,608,071 B2 | 8/2003 | Altmann et al. |
| 6,627,634 B2 | 9/2003 | Himmelsbach et al. |
| 6,630,489 B1 | 10/2003 | Crawley |
| 6,642,242 B2 | 11/2003 | Collis et al. |
| 6,649,620 B2 | 11/2003 | Collis et al. |
| 6,653,305 B2 | 11/2003 | Himmelsbach et al. |
| 6,656,946 B2 | 12/2003 | Himmelsbach et al. |
| 6,664,390 B2 | 12/2003 | Barth et al. |
| 6,673,803 B2 | 1/2004 | Thomas et al. |
| 6,723,726 B1 | 4/2004 | Cockerill et al. |
| 6,727,256 B1 | 4/2004 | Carter et al. |
| 6,734,303 B2 | 5/2004 | Ahman et al. |
| 6,740,651 B2 | 5/2004 | Himmelsbach et al. |
| 6,759,410 B1 | 7/2004 | Adams et al. |
| 6,809,097 B1 | 10/2004 | Thomas et al. |
| 7,579,473 B2 * | 8/2009 | Bannen et al. ............... 546/153 |
| 2002/0032208 A1 | 3/2002 | Lohmann et al. |
| 2002/0049197 A1 | 4/2002 | Himmelsbach et al. |
| 2002/0137757 A1 | 9/2002 | Uckun et al. |
| 2002/0161010 A1 | 10/2002 | Chakravarty et al. |
| 2002/0161226 A1 | 10/2002 | Uckun et al. |
| 2002/0165243 A1 | 11/2002 | Uckun et al. |
| 2002/0169165 A1 | 11/2002 | Kath et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177600 A1 | 11/2002 | Griffin et al. |
| 2002/0177601 A1 | 11/2002 | Himmelsbach et al. |
| 2003/0013728 A1 | 1/2003 | Uckun et al. |
| 2003/0018029 A1 | 1/2003 | Barker et al. |
| 2003/0045525 A1 | 3/2003 | Collis et al. |
| 2003/0045537 A1 | 3/2003 | Lee et al. |
| 2003/0065180 A1 | 4/2003 | Tsou et al. |
| 2003/0069230 A1 | 4/2003 | Becker et al. |
| 2003/0069248 A1 | 4/2003 | Chakravarty et al. |
| 2003/0087907 A1 | 5/2003 | Kubo et al. |
| 2003/0100753 A1 | 5/2003 | Boulton et al. |
| 2003/0149056 A1 | 8/2003 | Wissner et al. |
| 2003/0149062 A1 | 8/2003 | Jung et al. |
| 2003/0153568 A1 | 8/2003 | Kusack et al. |
| 2003/0171386 A1 | 9/2003 | Connell et al. |
| 2003/0176451 A1 | 9/2003 | Carter et al. |
| 2004/0242603 A1 | 12/2004 | Fujiwara et al. |

FOREIGN PATENT DOCUMENTS

| | | | |
|---|---|---|---|
| EP | 1117653 A1 | 7/2001 |
| EP | 1153920 A | 11/2001 |
| EP | 1243582 A1 | 9/2002 |
| EP | 0875506 B1 | 2/2003 |
| EP | 0880508 B1 | 4/2003 |
| EP | 1304110 A | 4/2003 |
| EP | 0912570 B1 | 9/2003 |
| EP | 0973746 B1 | 9/2003 |
| EP | 0977737 B1 | 9/2003 |
| EP | 1340748 A1 | 9/2003 |
| EP | 1411046 A1 | 4/2004 |
| EP | 1143950 B1 | 3/2005 |
| EP | 1301440 B1 | 3/2005 |
| JP | 11-158149 A | 6/1999 |
| JP | 2002-030083 A | 1/2002 |
| WO | WO 95/15758 A | 6/1995 |
| WO | WO 95/19774 A | 7/1995 |
| WO | WO 96/09294 A | 3/1996 |
| WO | WO 96/15118 A | 5/1996 |
| WO | WO 96/40142 A | 12/1996 |
| WO | WO 97/03069 A | 1/1997 |
| WO | WO 97/17329 A | 5/1997 |
| WO | WO 97/22596 A | 6/1997 |
| WO | WO 97/30035 A | 8/1997 |
| WO | WO 97/32856 A | 9/1997 |
| WO | WO 98/13350 A | 4/1998 |
| WO | WO 98/13354 A | 4/1998 |
| WO | WO 99/10349 A | 3/1999 |
| WO | WO 00/18761 A | 4/2000 |
| WO | WO 00/20402 A | 4/2000 |
| WO | WO 00/21955 A | 4/2000 |
| WO | WO 00/43366 A | 7/2000 |
| WO | WO 00/47212 A | 8/2000 |
| WO | WO 00/55141 A | 9/2000 |
| WO | WO 00/56338 A | 9/2000 |
| WO | WO 00/56720 A | 9/2000 |
| WO | WO 00/68201 A | 11/2000 |
| WO | WO 01/21596 A | 3/2001 |
| WO | WO 01/21597 A | 3/2001 |
| WO | WO 01/47890 A | 7/2001 |
| WO | WO 01/68186 A | 9/2001 |
| WO | WO 01/94341 A | 12/2001 |
| WO | WO 02/00188 A | 1/2002 |
| WO | WO 02/00649 A | 1/2002 |
| WO | WO 02/16352 A | 2/2002 |
| WO | WO 02/18351 A | 3/2002 |
| WO | WO 02/30924 A | 4/2002 |
| WO | WO 02/30926 A | 4/2002 |
| WO | WO 02/32872 A | 4/2002 |
| WO | WO 02/34744 A | 5/2002 |
| WO | WO 02/36570 A | 5/2002 |
| WO | WO 02/44166 A | 6/2002 |
| WO | WO 02/085895 A | 10/2002 |
| WO | WO 03/033472 A | 4/2003 |
| WO | WO 03/045395 A | 6/2003 |
| WO | WO 03/047584 A | 6/2003 |
| WO | WO 03/048159 A | 6/2003 |
| WO | WO 03/050108 A | 6/2003 |
| WO | WO 03/053960 A | 7/2003 |
| WO | WO 03/055491 A | 7/2003 |
| WO | WO 03/055492 A | 7/2003 |
| WO | WO 03/055866 A | 7/2003 |
| WO | WO 03/064413 A | 8/2003 |
| WO | WO 03/064421 A | 8/2003 |
| WO | WO 03/064431 A | 8/2003 |
| WO | WO 03/066060 A | 8/2003 |
| WO | WO 03/082831 A | 10/2003 |
| WO | WO 03/089439 A | 10/2003 |
| WO | WO 03/093238 A | 11/2003 |
| WO | WO 2004/006846 A | 1/2004 |
| WO | WO 2004/018473 A | 4/2004 |
| WO | WO 2004/035572 A | 4/2004 |
| WO | WO 2004/039782 A | 5/2004 |
| WO | WO 2004/041829 A | 5/2004 |
| WO | WO 2004/054585 A | 7/2004 |
| WO | WO 2004/055003 A | 7/2004 |
| WO | WO 2004/058267 A | 7/2004 |
| WO | WO 2004/060373 A | 7/2004 |
| WO | WO 2005/003140 A | 1/2005 |
| WO | WO 2005/005389 A | 1/2005 |
| WO | WO 2005/030140 A | 4/2005 |

OTHER PUBLICATIONS

Abrams et al., "SU11248 inhibits KIT and platelet-derived growth factor receptor β in preclinical models of human small cell lung cancer," *Mol. Cancer Ther.*, 2: 471-478 (2003).

Altomare et al., "*SIR92*—a program for automatic solution of crystal structures by direct methods," *J. Appl. Cryst.*, 27(3): 435 (Jun. 1994).

Apperley et al., "Response to imatinib mesylate in patients with chronic myeloproliferative diseases with rearrangements of the platelet-derived growth factor receptor beta," *N. Engl. J. Med.*, 347 (7): 481-487 (Aug. 15, 2002).

Beebe et al., "Pharmacological characterization of CP-547,632, a novel vascular endothelial growth factor receptor-2 tyrosine kinase inhibitor for cancer therapy," *Cancer Res.*, 63: 7301-7309 (Nov. 1, 2003).

Beghini et al., "c-kit activating mutations and mast cell proliferation in human leukemia," *Blood*, 92 (2): 701-702 (1998).

Beghini et al., "C-kit mutations in core binding factor leukemias," *Blood*, 95 (2): 726-727 (Jan. 15, 2000).

Bello et al., "Combinatorial administration of molecules that simultaneously inhibit angiogenesis and invasion leads to increased therapeutic efficacy in mouse models of malignant glioma," *Clin. Cancer Res.*, 10 (13): 4527-4537 (Jul. 1, 2004).

Berge et al., "Pharmaceutical salts," *J. Pharm. Sci.*, 66 (1): 1-19 (Jan. 1977).

Bergsland et al., "Bevacizumab (BV) + chemotherapy (CT) may improve survival in metastatic colorectal cancer (MCRC) subjects with unfavorable prognostic indicators," *Proc. Am. Soc. Clin. Oncol.*, 20: Abstract 2247 (2001).

Bergstrom et al., "Epidermal Growth Factor Receptor Signaling Activates Met in Human Anaplastic Thyroid Carcinoma Cells," *Exp. Cell Res.*, 259 (1): 293-299 (Aug. 25, 2000).

Besmer et al., "A new acute transforming feline retrovirus and relationship of its oncogene v-*kit* with the protein kinase gene family," *Nature*, 320 (6061): 415-421 (Apr. 3-9, 1986).

Birchmeier et al., "Met, metastasis, motility and more," *Nat. Rev. Mol. Cell Biol.*, 4 (12): 915-925 (Dec. 2003).

Blackledge et al., "Gefitinib ('Iressa', ZD1839) and new epidermal growth factor receptor inhibitors," *Br. J. Cancer*, 90 (3): 566-572 (Feb. 9, 2004).

Blagosklonny, "STI-571 must select for drug-resistant cells but 'no cell breathes fire out of its nostrils like a dragon'," *Leukemia*, 16: 570-572 (2002).

Blume-Jensen et al., "The kit receptor promotes cell survival via activation of PI 3-kinase and subsequent Akt-mediated phosphorylation of Bad on Ser136," *Curr. Biol.*, 8 (13): 779-782 (Jun. 18, 1998).

Bolen, "Nonreceptor tyrosine protein kinases," *Oncogene*, 8 (8): 2025-2031 (Aug. 1993).

Bonasera et al., "Potential $^{18}$F-labeled biomarkers for epidermal growth factor receptor tyrosine kinase," *Nucl. Med. Biol.*, 28 (4): 357-374 (2001).

Boschelli et al., "Synthesis and Src kinase inhibitory activity of a series of 4-phenylamino-3-quinolinecarbonitriles," *J. Med. Chem.*, 44 (5): 822-833 (Mar. 1, 2001).

Bottaro et al., "Out of air is not out of action," *Nature*, 423: 593-595 (Jun. 5, 2003).

Broudy et al., "Signaling via Src family kinases is required for normal internalization of the receptor c-Kit," *Blood*, 94 (6): 1979-1986 (Sep. 15, 1999).

Butterfield, "Response of severe systemic mastocytosis to interferon alpha," *Br. J. Dermatol.*, 138 (3): 489-495 (Mar. 1998).

Cao et al., "Neutralizing monoclonal antibodies to hepatocyte growth factor/scatter factor (HGF/SF) display antitumor activity in animal models," *Proc. Natl. Acad. Sci. USA*, 98 (13); 7443-7448 (Jun. 19, 2001).

Cherrington et al., "New Paradigms for the Treatment of Cancer: The Role of Anti-Angiogenesis Agents," in: *Advances in Cancer Research* (Klein et al., eds.), 1-38 (Academic Press, San Diego, CA, USA, 2000).

Chian et al., "Phosphatidylinositol 3 kinase contributes to the transformation of hematopoietic cells by the D816V c-Kit mutant," *Blood*, 98 (5): 1365-1373 (Sep. 1, 2001).

Christensen et al., "A selective small molecule inhibitor of c-Met kinase inhibits c-Met-dependent phenotypes in vitro and exhibits cytoreductive antitumor activity in vivo," *Cancer Res.*, 63: 7345-7355 (Nov. 1, 2003).

Christensen et al., "Characterization of selective c-Met inhibitors with cytocidal activity against human tumor," *Proc. Am. Assoc. Cancer Res.*, 44 (*2nd ed.*): 932-933, Abstract 4963 (Jul. 11-14, 2003).

Cohen et al., "Approval summary for imatinib mesylate capsules in the treatment of chronic myelogenous leukemia," *Clin. Cancer Res.*, 8: 935-942 (May 2002).

Cools et al., "The FIP1L1-PDGFRα kinase in hypereosinophilic syndrome and chronic eosinophilic leukemia," *Curr. Opin. Hematol.*, 11 (1): 51-57 (Jan. 2004).

Dagher et al., "Approval summary: Imatinib mesylate in the treatment of metastatic and/or unresectable malignant gastrointestinal stromal tumors," *Clin. Cancer Res.*, 8: 2034-2038 (Oct. 2002).

Dai et al., "Distribution of STI-571 to the brain is limited by P-glycoprotein-mediated efflux," *J. Pharmacol. Exp. Ther.*, 304 (3): 1085-1092 (Mar. 2003).

Demetri et al., "Clinical activity and tolerability of the multi-targeted tyrosine kinase inhibitor SU11248 in patients (pts) with metastatic gastrointestinal stromal tumor (GIST) refractory to imatinib mesylate," *Proc. Am. Soc. Clin. Oncol.*, 22: 814, Abstract 3273 (2003).

Drevs et al., "Surrogate markers for the assessment of biological activity of the VEGF-receptor inhibitor PTK787/ZK 222584 (PTK/ZK) in two clinical phase I trials," *Proc. Am. Soc. Clin. Oncol.*, 21: 85a, Abstract 337 (2002).

Eisenberg et al., "Pharmacotherapy of gastrointestinal stromal tumors," *Expert Opin. Pharmacother.*, 4 (6): 869-874 (Jun. 2003).

Ferrara et al., "The biology of VEGF and its receptors," *Nat. Med.*, 9 (6): 669-676 (Jun. 2003).

Follenzi et al., "Cross-talk between the proto-oncogenes Met and Ron," *Oncogene*, 19 (27): 3041-3049 (2000).

Funakoshi et al., "Hepatocyte growth factor: from diagnosis to clinical applications," *Clin. Chem. Acta*, 327 (1-2): 1-23 (Jan. 2003).

Fyfe et al., "Bevacizumab plus irinotecan/5-FU/leucovorin for treatment of metastatic colorectal cancer results in survival benefit in all pre-specified patient subgroups," *Proc. Am. Soc. Clin. Oncol.*, 22: Abstract 3617 (2004).

Gerritsen et al., "Using gene expression profiling to identify the molecular basis of the synergistic actions of hepatocyte growth factor and vascular endothelial growth factor in human endothelial cells," *Br. J. Pharmacol.*, 140 (4), 595-610 (Oct. 2003).

Gilliland et al., "Role of FLT3 in leukemia," *Curr. Opin. Hematol.*, 9 (4): 274-281 (Jul. 2002).

Hedrick et al., "Post-progression therapy (PPT) effect on survival in AVF2107, a phase III trial of bevacizumab in first-line treatment of metastatic colorectal cancer (mCRC)," *Proc. Am. Soc. Clin. Oncol.*, 22: Abstract 3517 (2004).

Heinrich et al., "Kinase mutations and imatinib response in patients with metastatic gastrointestinal stromal tumor," *J. Clin. Oncol.*, 21 (23): 4342-4349 (Dec. 1, 2003).

Herbst et al., "A phase I study of the VEGF/PDGF receptor tyrosine kinase inhibitor AG-013736 in patients with advanced solid tumors: Safety, pharmacokinetics, and dceMRT," *AARC-NCI-EORTC International Conference on Molecular Targets and Cancer Therapeutics*, Abstract C253 (2003).

Hirota et al., "Gain-of-function mutations of c-*kit* in human gastrointestinal stromal tumors," *Science*, 279 (5350): 577-580 (Jan. 23, 1998).

Holash et al., "VEGF-Trap: A VEGF blocker with potent antitumor effects," *Proc. Natl. Acad. Sci. USA*, 99 (17): 11393-11398 (Aug. 20, 2002).

Hongyo et al., "Specific c-*kit* mutations in sinonasal natural killer/t-cell lymphoma in China and Japan," *Cancer Res.*, 60: 2345-2347 (May 1, 2000).

Hu-Lowe et al., "Pharmacological activities of AG013736, a small molecule inhibitor of VEGF/PDGR receptor tyrosine kinases," *Proc. Am. Assoc. Cancer Res.*, 43: Abstract 5357 (Mar. 2002).

Ingram et al., "Genetic and biochemical evidence that haploinsufficiency of the *Nf1* tumor suppressor gene modulates melanocyte and mast cell fates in vivo," *J. Exp. Med.*, 191 (1): 181-187 (Jan. 3, 2000).

Jo et al., "Cross-talk between epidermal growth factor receptor and c-Met signal pathways in transformed cells," *J. Biol. Chem.*, 275 (12): 8806-8811 (Mar. 24, 2000).

Johnson et al., "Phase II study of STI571 (Gleevec™) for patients with small cell lung cancer," *Proc. Am. Soc. Clin. Oncol.*, 21: Abstract 1171 (2002).

Kabbinavar et al., "Bevacizumab (a monoclonal antibody to vascular endothelial growth factor) to prolong progression-free survival in first-line colorectal cancer (CRC) in subjects who are not suitable candidates for first-line CPT-11," *Proc. Am. Soc. Clin. Oncol.*, 22: Abstract 3516 (2004).

Kelly et al., "CT53518, a novel selective FLT3 antagonist for the treatment of acute myelogenous leukemia (AML)," *Cancer Cell*, 1 (5): 421-432 (Jun. 2002).

Kim, "Reduced c-Met expression by an adenovirus expressing a c-Met ribozyme inhibits tumorigenic growth and lymph node metastases of PC3-LN4 prostate tumor cells in an orthotopic nude mouse model," *Clin. Cancer Res.*, 9: 5161-70 (Nov. 1, 2003).
Kindler et al., "Bevacizumab (B) plus gemcitabine (G) in patient (pts) with advanced pancreatic cancer (PC): Updated results of a multi-center phase II trial," *Proc. Am. Soc. Clin. Oncol.*, 22: Abstract 4009 (2004).
Kissel, "Point mutation in kit receptor tyrosine kinase reveals essential roles for kit signaling in spermatogenesis and oogenesis without affecting other kit responses," *EMBO J.*, 19 (6): 1312-1326 (Mar. 15, 2000).
Kiyokawa et al., "Overexpression of ERK, an EPH family receptor protein tyrosine kinase, in various human tumors," *Cancer Res.*, 54 (14): 3645-3650 (Jul. 15, 1994).
Kong-Beltran et al., "The Sema domain of Met is necessary for receptor dimerization and activation," *Cancer Cell*, 6 (1): 75-84 (Jul. 2004).
Krishnaswamy et al., "The Human Mast Cell: Functions in Physiology and Disease," *Front. Biosci.*, 6: D1109-D1127 (2001).
Kubo et al., "Synthesis and structure-activity relationship for new series of 4-phenoxyquinoline derivatives as specific inhibitors of platelet-derived growth factor receptor tyrosine kinase," *Bioorg. Med. Chem.*, 11 (23), 5117-5133 (Nov. 17, 2003).
Laird et al., "Small molecule tyrosine kinase inhibitors: clinical development of anticancer agents," *Expert Opin. Investig. Drugs*, 12 (1): 51-64 (Jan. 2003).
Lehmann et al., "IFNα treatment in systemic mastocytosis," *Ann. Hematol.*, 78 (10): 483-494 (Oct. 1999).
Lennartsson et al., "Phosphorylation of Shc by Src family kinases is necessary for stem cell factor receptor/c-*kit* mediated activation of the Ras/MAP kinase pathway and c-*fos* induction," *Oncogene*, 18 (4): 5546-5553 (Sep. 30, 1999).
Lev et al., "A specific combination of substrates is involved in signal transduction by the kit-encoded receptor," *EMBO J.*, 10 (3): 647-654 (Mar. 1991).
Lindahl et al., "Pericyte loss and microaneurysm formation in PDGF-B-deficient mice," *Science*, 277 (5323): 242-245 (Jul. 11, 1997).
Liotta et al., "The microenvironment of the tumour-host interface," *Nature*, 411: 375-379 (May 17, 2001).
Longati et al., "Receptor tyrosine kinases as therapeutic targets: the model of the MET oncogene," *Curr Drug Targets*, 2 (1): 41-55 (Mar. 2001).
Longley et al., "Activating and dominant inactivating c-*KIT* catalytic domain mutations in distinct clinical forms of human mastocytosis," *Proc. Natl. Acad. Sci. USA*, 96 (4): 1609-1614 (Feb. 16, 1999).
Lynch et al., "Neurofibromatosis I," *Neurol. Clin. N. Am.*, 20 (3): 841-865 (Aug. 2002).
Ma et al., "c-*MET* mutational analysis in small cell lung cancer," *Cancer Res.*, 63: 6272-6281 (Oct. 1, 2003).
Ma et al., "c-Met: Structure, functions and potential for therapeutic inhibition," *Cancer Metastasis Rev.*, 22 (4): 309-325 (2003).
Maher, "Malignant glioma: genetics and biology of a grave matter," *Genes Dev.*, 15: 1311-1333 (2001).
Maki et al., "Differential sensitivity to imatinib of 2 patients with metastatic sarcoma arising from dermatofibrosarcoma protuberans," *Int. J. Cancer*, 100: 623-626 (2002).
Manley et al., "Therapies directed at vascular endothelial growth factor," *Expert Opin. Investig. Drugs*, 11 (12): 1715-1736 (Dec. 2002).
Marone et al., "Treatment of mastocytosis: pharmacologic basis and current concepts," *Leuk. Res.*, 25 (7): 583-894 (Jul. 2001).
Mass et al., "Bevacizumab in combination with 5-FU/leucovorin improves survival in patients with metastatic colorectal cancer: A combined analysis," *Proc. Am. Soc. Clin. Oncol.*, 22: Abstract 3616 (2004).
Matter, "Tumor angiogenesis as a therapeutic target," *Drug Discov. Today*, 6 (19): 1005-1024 (Oct. 1, 2001).
Maulik et al., "c-Met/HGF pathway inhibition through a novel tyrosine kinase inhibitor in small cell lung cancer," *Proc. Am. Assoc. Cancer Res.*, 44 (*2nd ed.*): 1238, Abstract 6200 (Jul. 11-14, 2003).
Maulik et al., "Role of the hepatocyte growth factor receptor, c-Met, in oncogenesis and potential for therapeutic inhibition.," *Cytokine Growth Factor Rev.*, 13 (1): 41-59 (Feb. 2002).

Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," *Clin. Cancer Res.*, 9: 327-337 (Jan. 2003).
Michieli et al., "Targeting the tumor and its microenvironment by a dual-function decoy Met receptor," *Cancer Cell*, 6 (1): 61-73 (Jul. 2004).
Miknyoczki et al., "The TRK tyrosine kinase inhibitor CEP-701 (KT-5555) exhibits significant antitumor efficacy in preclinical xenograft models of human pancreatic ductal adenocarcinoma," *Clin. Cancer Res.*, 5: 2205-2212 (Aug. 1999).
Morgan et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," *J. Clin. Oncol.*, 21 (21): 3955-3964 (Nov. 2003).
Moss et al., "Hair depigmentation is a biological readout for pharmacological inhibition of KIT in mice and humans," *J. Pharmacol Exp. Ther.*, 307 (2): 476-480 (2003).
Mufti et al., "Myelodysplastic syndrome," *American Society of Hematology Education Program Book*, 1: 176-199 (2003).
Murray et al., "SU11248 inhibits tumor growth and CSF-1R-dependent osteolysis in an experimental breast cancer bone metastasis model," *Clin. Exp. Metastasis*, 20 (8): 757-766 (Dec. 2003).
Nath et al., "Shedding of c-Met is regulated by crosstalk between a G-protein coupled receptor and the EGF receptor and is mediated by a TIMP-3 sensitive metalloproteinase," *J. Cell Sci.*, 114 (6): 1213-1220 (2001).
O'Farrell et al., "An innovative phase I clinical study demonstrates inhibition of FLT3 phosphorylation by SU11248 in acute myeloid leukemia patients," *Clin. Cancer Res.*, 9: 5465-5476 (Nov. 15, 2003).
O'Farrell et al., "Analysis of biomarkers of SU11248 action in an exploratory study in patients with advanced malignancies," *Proc. Am. Soc. Clin. Oncol.*, 22: 234, Abstract 939 (2003).
Ogita et al., "Synthesis and structure-activity relationship of diarylamide urea derivatives as selective inhibitors of the proliferation of human coronary artery smooth muscle cells," *Bioorg. Med. Chem.*, 10 (6): 1865-1871 (Jun. 2002).
Pai, "Prostaglandins promote colon cancer cell invasion; signaling by cross-talk between two distinct growth factor receptors," *FASEB J.*, 17: 1640-1647 (2003).
Pennacchietti et al., "Hypoxia promotes invasive growth by transcriptional activation of the met protooncogene," *Cancer Cell*, 3 (4): 347-361 (Apr. 2003).
Plowman et al., "Receptor tyrosine kinases as targets for drug intervention," *Drug News Perspect.*, 7 (6): 334-339 (1994).
Potapova et al., *Proc. Am. Assoc. Cancer Res.*, Abstract 4875 (2003).
Propper et al., "Phase I and pharamacokinetic study of PKC412, an inhibitor of protein kinase C,"*J. Clin. Oncol.*, 19 (5): 1485-1492 (Mar. 1, 2001).
Ratain et al., *AACR-NCI-EORTC International Conference on Molecular Targets and Cancer Therapeutics*, Abstract C254 (2003).
Reilly, "Class III Receptor Tyrosine Kinases: Role in Leukaemogenesis," *Br. J. Haematol.*, 116 (4): 744-757 (Mar. 2002).
Reilly, "FLT3 and its role in the pathogenesis of acute myeloid leukaemia," *Leuk. Lymphoma*, 44 (1): 1-7 (Jan. 2003).
Riegel et al., "The synthesis of some 4-quinolinols and 4-chloroquinolines by the ethoxymethyenemalonic ester method," *J. Am. Chem. Soc.*, 68: 1264-1266 (1946).
Rubin et al., "Molecular targeting of platelet-derived growth factor B by imatinib mesylate in a patient with metastatic dermatofibrosarcoma protuberans," *J. Clin. Oncol.*, 20 (17): 3586-3591 (Sep. 1, 2002).
Ruggeri et al., "CEP-7055: a novel, orally active pan inhibitor of vascular endothelial growth factor receptor tyrosine kinases with potent antiangiogenic activity and antitumor efficacy in preclinical models," *Cancer Res.*, 63: 5978-5991 (Sep. 15, 2003).
Ryan et al., "Role for the stem cell factor/KIT complex in Schwann cell neoplasia and mast cell proliferation associated with neurofibromatosis," *J. Neurosci. Res.*, 37 (3): 415-432 (Feb. 15, 1994).

Sattler et al., "The novel small molecule drug SU-MI-2 induces apoptosis in cells transformed by the oncogenic TPR-MET tyrosine kinase," *Proc. Am. Assoc. Cancer Res.*, 44 (*2nd ed.*): 202, Abstract 1005 (Jul. 11-14, 2003).

Saucier et al., "The Shc adaptor protein is critical for VEGF induction by Met/HGF and ErbB2 receptors and for early onset of tumor angiogenesis," *Proc. Natl. Acad. Sci.* USA, 101 (8): 2345-2350 (Feb. 24, 2004).

Sawyers, "Finding the next Gleevec: FLT3 targeted kinase inhibitor therapy for acute myeloid leukemia," *Cancer Cell*, 1 (5): 413-415 (Jun. 2002).

Scheving et al., "Integral Role of the EGF Receptor in HGF-Mediated Hepatocyte Proliferation," *Biochem. Biophys. Res. Commun.*, 290 (1): 197-203 (Jan. 11, 2002).

Shealy et al., "υ-Triazolo[4,5-*d*]pyrimidines. II. *O*-Substituted Derivatives of 8-Azaguanine and 8-Azahypoxanthine," *J. Org. Chem.*, 27 (12): 4518-4523 (Dec. 1962).

Shimizu et al., "The dermatofibrosarcoma protuberans-associated collagen type Iα1/platelet-derived growth factor (PDGF) B-chain fusion gene generates a transforming protein that is processed to functional PDGF-BB," *Cancer Res.*, 59: 3719-3723 (Aug. 1, 1999).

Singer et al., "Prognostic value of *KIT* mutation type, mitotic activity, and histologic subtype in gastrointestinal stromal tumors," *J. Clin. Oncol.*, 20 (18): 3898-3905 (Sep. 2002).

Smith et al., "Single agent CEP-701, a novel FLT3 inhibitor, shows biologic and clinical activity in patients with relapsed or refractory acute myeloid leukemia." *Blood*, 103 (10); 3669-3676 (May 15, 2004).

Soria et al., "Imatinib in small cell lung cancer," *Lung Cancer*, 41 (Suppl. 1): S49-S53 (2003).

Stabile et al., "Inhibition of human non-small cell lung tumors by a c-Met antisense/U6 expression plasmid strategy," *Gene Ther.*, 11 (3): 325-335 (Feb. 2004).

Steward et al., *Proc. Am. Soc. Clin. Oncol.*, 22, Abstract 1098 (2003).

Sui et al., "Synergistic activation of MAP kinase (ERK1/2) by erythropoietin and stem cell factor is essential for expanded erythropoiesis," *Blood*, 92 (4): 1149-1242 (Aug. 15, 1998).

Takai et al., "Expression of receptor tyrosine kinase EphB4 and its ligand ephrin-B2 is associated with malignant potential in endometrial cancer," *Oncol. Rep.*, 8 (3): 567-573 (May-Jun. 2001).

Thomas et al., "Pharmacodynamic results using dynamic contrast enhanced magnetic resonance imaging, of 2 phase 1 studies of the VEGF inhibitor PTK787/ZK 222584 in patients with liver metastases from colorectal cancer," *Proc. Am. Soc. Clin. Oncol.*, 20: Abstract 279 (2001).

Tian et al., "Activating c-kit gene mutations in human germ cell tumors," *Am. J. Pathol.*, 154 (6): 1643-1647 (Jun. 1999).

Timokhina et al., "Kit signaling through PI 3-kinase and Src kinase pathways: an essential role for Rac1 and JNK activation in mast cell proliferation," *EMBO J.*, 17 (21); 6250-6262 (Nov. 2, 1998).

Tomioka et al., "Inhibition of growth, invasion, and metastasis of human pancreatic carcinoma cells by NK4 in an orthotopic mouse model," *Cancer Res.*, 61 (20): 7518-7524 (Oct. 15, 2001).

Toner et al., "PET imaging study of SU11248 in patients with advanced malignancies," *Proc. Am. Soc. Clin. Oncol.*, 22: Abstract 767 (2003).

Washington et al., "The effect of ketoconazole (KETO), a potent CYP3A4 inhibitor, on SU011248 pharmacokinetics (PK) in caucasian and Asian healthy subjects," *Proc. Am. Soc. Clin. Oncol.*, 22: Abstract 553 (2003).

Wedge et al., "ZD6474 inhibits vascular endothelial growth factor signaling, angiogenesis, and tumor growth following oral administration," *Cancer Res.*, 62: 4646-4655 (Aug. 15, 2002).

Weisberg et al., "Inhibition of mutant FLT3 receptors in leukemia cells by small molecule tyrosine kinase inhibitor PKC412," *Cancer Cell*, 1: 433-443 (Jun. 2002).

Wilhelm et al., AACR-NCI-EORTC International Conference on Molecular Targets and Caner Therapeutics, Abstract A78 (2003).

Wood et al., "PTK787/ZK 222584, a novel and potent inhibitor of vascular endothelial growth factor receptor tyrosine kinases, impairs vascular endothelial growth factor-induced responses and tumor growth after oral administration," *Cancer Res.*, 60: 2178-2789 (Apr. 15, 2000).

Wright et al., "Synthesis and hypotensive properties of new 4-aminoquinolines," *J. Med. Chem.*, 14 (11): 1060-1066 (Nov. 1971).

Xin et al., "Hepatocyte growth factor enhances vascular endothelial growth factor-induced angiogenesis in vitro and in vivo," *Am. J. Pathol.*, 158 (3): 1111-1120 (Mar. 2001).

Yang et al., "A randomized double-blind placebo-controlled trial of bevacizumab (anti-VEGF antibody) demonstrating a prolongation in time to progression in patients with metastatic renal cancer," *Proc. Am. Soc. Clin. Oncol.*, 21: Abstract 15 (2002).

Yarden et al., "Untangling the ErbB signalling network," *Nat. Rev. Mol. Cell Biol.*, 2 (2): 127-137 (Feb. 2001).

Yucel et al., "c-Met overexpression in supraglottic laryngeal squamous cell carcinoma and its relation to lymph node metastases," *Otolaryngol. Head Neck Surg.*, 130 (6): 698-703 (2004).

Yung et al., "A phase I trial of PTK787/ZK 222584 (PTK/ZK), a novel oral VEGFR TK inhibitor in recurrent glioblastoma," *Proc. Am. Soc. Clin. Oncol.*, 21: Abstract 315 (2002).

Zhang et al., "Modulation of tumor angiogenesis by stem cell factor," *Cancer Res.*, 60: 6757-6762 (Dec. 1, 2000).

Zheng et al., "A chimeric Fab antibody serves as an antagonist to the HGF/SGF receptor cMet," *Proc. Am. Assoc. Cancer Res.*, 44 (*2nd ed*): 1139, Abstract 5717 (Jul. 11-14, 2003).

Zhou, "The Eph family receptors and ligands," *Pharmacol Ther.*, 77 (3): 151-181 (Mar. 1998).

\* cited by examiner

C-MET MODULATORS AND METHODS OF USE

CROSS-REFERENCE TO RELATED APPLICATIONS

This application is a continuation of U.S. patent application Ser. No. 11/586,751, filed on Oct. 26, 2006, which is a continuation of U.S. patent application Ser. No. 10/573,336, filed on Sep. 16, 2006, now abandoned, which is a national phase application under 35 U.S.C. §371 of International Patent Application No. PCT/US2004/031523, filed on Sep. 24, 2004, which claims the benefit of U.S. Provisional Patent Application 60/506,181 filed on Sep. 26, 2003, and which also claims the benefit of U.S. Provisional Patent Application No. 60/535,377 filed on Jan. 9, 2004, and which also claims the benefit of U.S. Provisional Patent Application No. 60/577,384 filed on Jun. 4, 2004, each of which is hereby incorporated by reference in its entirety for all purposes.

FIELD OF THE INVENTION

This invention relates to compounds for modulating protein kinase enzymatic activity for modulating cellular activities such as proliferation, differentiation, programmed cell death, migration and chemoinvasion. Even more specifically, the invention relates to quinazolines and quinolines which inhibit, regulate and/or modulate kinase receptor signal transduction pathways related to the changes in cellular activities as mentioned above, compositions which contain these compounds, methods of using them to treat kinase-dependent diseases and conditions, synthesis of the compounds as well as processes for formulating the compounds for pharmaceutical purposes.

BACKGROUND OF THE INVENTION

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-Kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Falc, Jal, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers (GIST). Gleevec is a c-Kit and Abl kinase inhibitor.

Modulation (particularly inhibition) of cell proliferation and angiogenesis, two key cellular processes needed for tumor growth and survival (Matter A. Drug Disc Technol 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation, with respect to antiangiogenic and antiproliferative activity is c-Met. The kinase, c-Met, is the prototypic member of a subfamily of heterodimeric receptor tyrosine kinases (RTKs) which include Met, Ron and Sea. Expression of c-Met occurs in a wide variety of cell types including epithelial, endothelial and mesenchymal cells where activation of the receptor induces cell migration, invasion, proliferation and other biological activities associated with "invasive cell growth." As such, signal transduction through c-Met receptor activation is responsible for many of the characteristics of tumor cells.

The endogenous ligand for c-Met is the hepatocyte growth factor (HGF), a potent inducer of angiogenesis, also known as "scatter factor" (SF). Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See: Maulik et al Cytokine & Growth Factor Reviews 2002 13, 41-59).

Tumor growth progression requires the recruitment of new blood vessels into the tumor from preexisting vessels as well as invasion, adhesion and proliferation of malignant cells. Accordingly, c-Met overexpression has been demonstrated on a wide variety of tumor types including breast, colon, renal, lung, squamous cell myeloid leukemia, hemangiomas, melanomas, astrocytomas, and glioblastomas. Additionally activating mutations in the kinase domain of c-Met have been identified in hereditary and sporadic renal papilloma and squamous cell carcinoma. (See: Maulik et al Cytoline & growth Factor reviews 2002 13, 41-59; Longati et al Curr Drug Targets 2001, 2, 41-55; Funakoshi et al Clinica Chimica Acta 2003 1-23). Thus modulation of c-Met is desirable as a means to treat cancer and cancer-related disease.

The Eph receptors comprise the largest family of receptor tyrosine kinases and are divided into two groups, EphA and EphB, based on their sequence homology. The ligands for the Eph receptors are ephrin, which are membrane anchored. Ephrin A ligands bind preferentially to EphA receptors whilst ephrin B ligands bind to EphB receptors. Binding of ephrin to Eph receptors causes receptor autophosphorylation and typically requires a cell-cell interaction since both receptor and ligand are membrane bound.

Overexpression of Eph receptors has been linked to increased cell proliferation in a variety of tumors (Zhou R 1998 Pharmacol Ther. 77, 151-181; Kiyokawa E, Takai S, Tanaka M et al 1994 Cancer Res 54, 3645-3650; Takai N Miyazaki T, Fujisawa K, Nasu K and Miyakawa. 2001 Oncology reports 8, 567-573). The family of Eph receptor tyrosine kinases and their ephrin ligands play important roles in a variety of processes during embryonic development and also in pathological angiogenesis and potentially metastasis. Therefore modulation of Eph receptor kinase activity should provide means to treat or prevent disease states associated with abnormal cell proliferation such as those described above.

Inhibition of EGF, VEGF and ephrin signal transduction will prevent cell proliferation and angiogenesis, two key cellular processes needed for tumor growth and survival (Matter A. Drug Disc. Technol. 2001 6, 1005-1024). EGF and VEGF receptors are previously described targets for small molecule inhibition. KDR and flt-4 are both VEGF receptors.

One particularly attractive target for small-molecule modulation is c-Kit. The proto-oncogene c-Kit was first identified as the oncogenic component of the acutely transforming Hardy-Zuckerman 4-feline sarcoma virus (Besmer et al Nature 1986 320:415-421). c-Kit (also called stem cell factor receptor or steel factor receptor) is a type 3 receptor tyrosine kinase (RTK) belonging to the platelet-derived growth factor receptor subfamily. c-Kit binds the ligand stem cell factor (SCF), and triggers its multiple signal transduction pathways including Src family kinases, phosphatidyl-inositol 3 kinase, the Ras-Raf-Map kinase cascade, and phospholipase C (Broudy et al Blood 1999 94: 1979-1986; Lennartsson et al Oncogene 1999 18: 5546-5553; Timokhina et al EMBO J. 1998 17; 6250-6262; Chian et al Blood 2001 98(5)1365-1373; Blume-Jensen et al. Curr Biol 1998 8:779-782; Kissel et al EMBO J. 2000 19:1312-1326; Lennartsson et al. Oncogene 1999 18: 5546-5553; Sue et al Blood, 199892:1242-1149; Lev etal EMBO J. 1991 10:647-654). c-Kit is required for normal hematopoiesis, melanonogenesis, and gametogenesis. c-Kit is expressed in mast cells, immature myeloid cells, melanocytes, epithelial breast cells and the interstitial cells of Cajal (ICC). In mast cells, it is required not only for the differentiation, maturation, chemotaxis, and haptotaxis but also for the promotion of survival and proliferation.

Mutations in c-Kit have been implicated in human disease. Mutations in the juxtamembrane domain are found in many human gastrointestinal stromal tumors, and mutations in the kinase domain are found in mastocytosis, germ cell tumors, acute myeloid leukemia (AML), NK lymphoma, and other hematologic disorders (Hirota et al Science 1998 279:577-580; Singer et al J Clin Oncol 2002 203898-3905; Longley et al Proc Natl Aca Sci USA 1999: 1609-1614; Tian et al Am J Pathol 1999 154: 1643-1647; Beghini et al Blood 2000 95:726-727; Hongyo et al Cancer Res 2000 60:2345-2347). These mutations result in ligand-independent tyrosine kinase activity, autophosphorylation of c-Kit, uncontrolled cell proliferation, and stimulation of downstream signaling pathways. Overexpression of c-Kit and c-Kit ligand have also been described in other tumors including small-cell lung cancer, neuroblastomas, gynecological tumors, and colon carcinoma, which might result in autocrine or paracrine c-Kit activation.

The overexpression of c-Kit has also been implicated in the development of neoplasia associated with neurofibromatosis type 1 (NF1). Mutations in the tumor suppressor gene NF1 lead to a deficiency in neurofibromin, a GTPase-activating protein for Ras. This deficiency results in abnormal proliferation of Schwann cells in the peripheral nervous system, and predisposes affected individuals to peripheral nerve sheath tumors (neurofibromas), astrocytomas (optic pathway gliomas), learning disabilities, seizures, strokes, macrocephaly, vascular abnormalities, and juvenile myelomonocytic leukemia (Lynch & Gutmann Neurol Clin 2002 20:841-865). Genetic experiments in mice demonstrate that haploinsufficiency at NF1 partially rescues some of the phenotypes associated with mutations in the gene for c-Kit, indicating that these genes function along a common developmental pathway (Ingram, et al. J. Exp Med 2000 191:181-187). Also, c-Kit is expressed in schwannoma cells from NF1 patients, but not in normal schwann cells (Ryan et al. J Neurosci Res 1994 37:415-432). These data indicate that elevated c-Kit expression and sensitivity to stem cell factor may play important roles in the development of proliferative disorders associated with NF-1. Therefore, c-Kit inhibitors may be effective chemotherapeutic agents for treating patients with NF-1.

GISTs are the most common mesenchymal tumors of the gastrointestinal tract, and they are generally resistant to chemotherapy and radiation therapy. However, recent results with the c-Kit/BCR-Abl inhibitor ST1571 indicate that targeting c-Kit may be an effective therapeutic strategy for this disease (Eisenberg & Mehren Expert Opin Pharmacother 2003 4:869-874). Malignant mast cell disease often suggests an extremely poor prognosis, and no reliable effective chemotherapeutic agents have been identified (Marone et al Leulc Res 2001 25:583-594). Systemic mast cell disorders have been treated with interferon-alpha, although the effectiveness of this therapy has been variable (Lehmann & Lammle Ann Hematol 1999 78:483-484; Butterfield Br J Dennatol 1998 138: 489-495). Therefore, activated c-Kit might serve as a therapeutic target in GISTs and mast cell disease, as well as other disorders associated with activated c-Kit.

Flt-3 is normally expressed on hematopoietic progenitor cells and a subset of mature myeloid and lymphoid cells, where it modulates cell survival and proliferation. Flt-3 is constitutively activated via mutation, either in the juxtamembrane region or in the activation loop of the kinase domain, in a large proportion of patients with AML (Reilly Leuk Lymphoma 2003 44: 1-7). Also, mutations in flt-3 are significantly correlated with poor prognosis in AML patients (Sawyers Cancer Cell 2002 1: 413-415).

Accordingly, the identification of small-molecule compounds that specifically inhibit, regulate and/or modulate the signal transduction of kinases, particularly including c-Met, KDR, c-Kit, flt-3, and flt-4, is desirable as a means to treat or prevent disease states associated with abnormal cell proliferation and angiogenesis, and is an object of this invention.

Quinolines and quinazolines bearing substitution, for example at the two, four, six and seven positions of their fused ring system have been shown to be particularly attractive targets for kinase inhibition by a number of groups. Conventional quinoline and quinazoline kinase inhibitors typically have fairly simple substitution about the quinoline or quinazoline fused ten-membered ring system, but recently more complex molecules are being disclosed. For example, we have previously disclosed, in U.S. provisional patent applications 60/506,181 and 60/535,377 which are both incorporated by reference herein in their entirety for all purposes, that certain quinolines and quinazolines are particularly well suited as kinase modulators, more particularly inhibitors of for example c-Met, KDR, c-Kit, flt-3, and flt-4. These molecules in some cases are particularly complex and although they can be made via conventional methods, more efficient routes are desirable, especially in a pharmaceutical setting.

International patent application publication no. WO 01/21597 discloses substituted quinazolines linked, via a heteroatom, to an optionally substituted aromatic ring containing at least one nitrogen atom. WO 01/21597 states that the disclosed compounds inhibit aurora 2 kinase and are useful in the treatment of proliferative disease such as cancer.

U.S. patent application publication no. US 2004/0242603 discloses substituted quinolines and quinazolines linked, via a heteroatom, to a substituted phenylene. US 2004/0242603 states that the disclosed compounds have autophosphorylation inhibitory activity and antitumor activity.

International patent application publication no. WO 2005/005389 discloses bivalent malonamide derivatives, including derivatives in which substituted aryl substituents are bonded directly to the nitrogen atoms on either side of the malonamide moiety. WO 2005/005389 states that the disclosed compounds are inhibitors of raf kinase.

Conventional methods of making quinolines and quinazolines with the aforementioned substitution patterns usually involve linear construction of a quinoline or quinazoline template upon which relatively simple substitutions are appended. With the advent of more complex substitution about such quinolines and quinazolines (vide supra), for example side chains containing cyclic and bicyclic systems with multiple functional groups, conventional methods of synthesis become problematic due to the linear or serial reactions used. Indeed, as such molecules become more complex and the utility of such complex groups is realized, the quinoline and quinazoline ring system becomes more of a substructure than a main structure of such inhibitors. Thus it is desirable to find more efficient methods of synthesis, particularly convergent syntheses which are an object of this invention.

SUMMARY OF THE INVENTION

In one aspect, the present invention provides compounds for modulating kinase activity and methods of treating diseases mediated by kinase activity utilizing the compounds and pharmaceutical compositions thereof. Diseases mediated by kinase activity include, but are not limited to, diseases characterized in part by migration, invasion, proliferation and other biological activities associated with invasive cell growth. In particular to this invention is modulation, even more particularly inhibition, of c-Met, KDR, c-Kit, flt-3, and flt-4.

In another aspect, the invention provides methods of screening for modulators of c-Met, KDR, c-Kit, flt-3, and flt-4 activity. The methods comprise combining a composition of the invention, a kinase, e.g. c-Met, KDR, c-Kit, flt-3, or flt-4, and at least one candidate agent and determining the effect of the candidate agent on the c-Met, KDR, c-Kit, flt-3, or flt-4, activity.

In yet another aspect, the invention also provides pharmaceutical kits comprising one or more containers filled with one or more of the ingredients of pharmaceutical compounds and/or compositions of the present invention, including, one or more kinase, e.g. c-Met, KDR, c-Kit, flt-3, or flt-4, enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In another aspect, the invention also provides a diagnostic agent comprising a compound of the invention and, optionally, pharmaceutically acceptable adjuvants and excipients.

In still yet another aspect, the present invention provides processes for making compounds, and pharmaceutical compositions thereof, for modulating kinase activity and treating diseases mediated by kinase activity. In particular to this invention are methods for making quinolines and quinazolines used for modulation of kinase activity, even more particularly inhibition of kinase activity, and yet even more particularly inhibition of c-Met, KDR, c-Kit, flt-3, and flt-4.

These and other features and advantages of the present invention will be described in more detail below with reference to the associated drawings.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as atherosclerosis, myocardioinfarction, ischemia, stroke and restenosis; other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

Thus, in one aspect the present invention comprises a compound for modulating kinase activity according to Formula I,

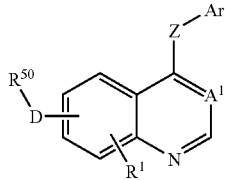

or a pharmaceutically acceptable salt, hydrate, or prodrug thereof, wherein,
$R^1$ is selected from —H, halogen, —$OR^3$, —$NO_2$, —$NH_2$, —$NR^3R^4$, and optionally substituted lower alkyl;
$A^1$ is selected from =N—, =C(H)—, and =C(CN)—;
Z is selected from —$S(O)_{0-2}$—, —O—, and —$NR^5$—;
Ar is either a group of formula II, or of formula III,

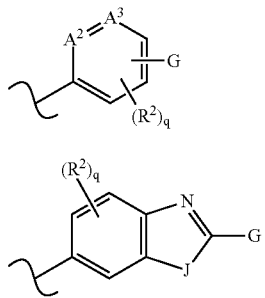

wherein,
$R^1$ is selected from —H, halogen, trihalomethyl, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, and optionally substituted lower alkyl;
q is 0 to 4;
G is a group -B-L-T, wherein
B is selected from absent, —$N(R^{13})$—, —$N(SO_2R^{13})$—, —O—, —$S(O)_{0-2}$—, and —C(=O)—;
L is selected from absent, —C(=S)$N(R^{13})$—, —C(=$NR^{14}$)$N(R^{13})$—, —$SO_2N(R^{13})$—, —$SO_2$—, —C(=O)$N(R^{13})$—, —$N(R^{13})$—, —C(=O)$C_{1-2}$alkylN$(R^{13})$—, —$N(R^{13})C_{1-2}$alkylC(=O)—, —C(=O)$C_{0-1}$alkylC(=O)$N(R^{13})$—, —$C_{0-4}$alkylene-, —C(=O)$C_{0-1}$alkylC(=O)$OR^3$—, —C(=$NR^{14}$)$C_{0-1}$alkylC(=O)—, —C(=O)—, —C(=O)$C_{0-1}$alkylC(=O)—, and an optionally substituted four to six-membered heterocyclyl containing between one and three annular heteroatoms including at least one nitrogen; and
T is selected from —H, —$R^{13}$, —$C_{0-4}$alkylQ, —$C_{0-4}$alkylQ, —$OC_{0-4}$alkylQ, —$C_{0-4}$alkylOQ, —$N(R^{13})C_{0-4}$alkylQ, —$SO_2C_{0-4}$alkylQ, —C(=O)$C_{0-4}$alkylQ, —$C_{0-4}$alkylN$(R^{13})$Q, and —C(=O)$N(R^{13})C_{0-4}$alkylQ, wherein each of the aforementioned $C_{0-4}$alkyl is optionally substituted;
J is selected from —$S(O)_{0-2}$—, —O—, and —$NR^{15}$—;
$R^3$ is —H or $R^4$;
$R^4$ is selected from optionally substituted lower alkyl, optionally substituted aryl, optionally substituted lower arylalkyl, optionally substituted heterocyclyl, and optionally substituted lower heterocyclylalkyl; or
$R^3$ and $R^4$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P;
$A^2$ and $A^3$ are each independently selected from =N—, =C($R^2$)—;
$R^5$ is —H or optionally substituted lower alkyl;
D is selected from —O—, —$S(O)_{0-2}$—, and —$NR^{15}$—;
$R^{50}$ is either $R^3$, or according to formula IV;

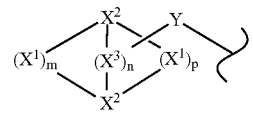

wherein $X^1$, $X^2$, and optionally $X^3$, represent the atoms of a saturated bridged ring system, said saturated bridged ring system comprising up to four annular heteroatoms represented by any of $X^1$, $X^2$, and $X^3$; wherein,
each $X^1$ is independently selected from —C($R^6$)$R^7$—, —O—, —$S(O)_{0-2}$—, and —$NR^8$—;
each $X^2$ is independently an optionally substituted bridgehead methine or a bridgehead nitrogen;
each $X^3$ is independently selected from —C($R^6$)$R^7$—, —O—, —$S(O)_{0-2}$—, and —$NR^8$—;
Y is either:
an optionally substituted lower alkylene linker, between D and either 1) any annular atom of the saturated bridged ring system, except $X^2$ when $X^2$ is a bridgehead nitrogen, or 2) any heteroatom, represented by any of $R^6$ or $R^7$; provided there are at least two carbon atoms between D and any annular heteroatom of the saturated bridged ring system or any heteroatom represented by any of $R^6$ or $R^7$;
or Y is absent, when Y is absent, said saturated bridged ring system, is directly attached to D via an annular carbon of said saturated bridged ring system, unless D is —$SO_2$—, in which case said saturated bridged ring system, is directly attached to D via an any annular atom of said saturated bridged ring system;
m and p are each independently 1-4;
n is 0-2, when n=0, then there is a single bond between the two bridgehead $X^2$'s;
$R^6$ and $R^7$ are each independently selected from —H, halogen, trihalomethyl, —CN, —$NH_2$, —$NO_2$, —$OR^3$, —$NR^3R^4$, —$S(O)_{0-2}R^4$, —$SO_2NR^3R^4$, —$CO_2R^3$, —$C(O)NR^3R^4$, —$N(R^3)SO_2R^4$, —$N(R^3)C(O)R^3$, —$NCO_2R^3$, —$C(O)R^3$, optionally substituted lower alkyl, optionally substituted aryl, optionally substituted lower arylalkyl, optionally substituted heterocyclyl, optionally substituted lower heterocyclylalkyl, and a bond to either Y or D; or
$R^6$ and $R^7$, when taken together are oxo; or
$R^6$ and $R^7$, when taken together with a common carbon to which they are attached, form a optionally substituted three- to seven-membered spirocyclyl, said optionally substituted three- to seven-membered spirocyclyl optionally containing at least one additional annular heteroatom selected from N, O, S, and P;
$R^8$ is selected from —$R^3$, Y, —$SO_2NR^3R^4$, —$CO_2R^4$, —C(O)NR^3R^3$, —$SO_2R^4$, and —C(O)$R^3$;

$R^{13}$ is selected from —H, —C(=O)$R^3$, —C(=O)O$R^3$, —C(=O)S$R^3$, —SO$_2$$R^4$, —C(=O)N($R^3$)$R^3$, and optionally substituted lower alkyl, two $R^{13}$, together with the atom or atoms to which they are attached, can combine to form a heteroalicyclic optionally substituted with between one and four of $R^{60}$, said heteroalicyclic can have up to four annular heteroatoms, and said heteroalicyclic can have an aryl or heteroaryl fused thereto, in which case said aryl or heteroaryl is optionally substituted with an additional one to four of $R^{60}$;

$R^{14}$ is selected from —H, —NO$_2$, —NH$_2$, —N($R^3$)$R^4$, —CN, —O$R^3$, optionally substituted lower alkyl, optionally substituted heteroalicyclylalkyl, optionally substituted aryl, optionally substituted arylalkyl and optionally substituted heteroalicyclic;

$R^{15}$ is a group -$M^1$-$M^2$, wherein $M^1$ is selected from absent, —C(=S)N($R^{13}$)—, —C(=N$R^{14}$)N($R^{13}$)—, —SO$_2$N($R^{13}$)—, —SO$_2$—, —C(=O)N($R^{13}$)—, —C(=O)C(=O)N($R^{13}$)—, —C$_{0-4}$alkylene-, —C(=O)—, and an optionally substituted four to six-membered heterocyclyl annular containing between one and three heteroatoms including at least one nitrogen; and $M^2$ is selected from —H, —C$_{0-6}$alkyl, alkoxy, —C(=O)C$_{0-4}$alkylQ, —C$_{0-4}$alkylQ, —OC$_{0-4}$alkylQ-, —N($R^{13}$)C$_{0-4}$alkylQ-, and —C(=O)N($R^{13}$)C$_{0-4}$alkylQ; and Q is a five- to ten-membered ring system, optionally substituted with between zero and four of $R^{20}$;

$R^{20}$ is selected from —H, halogen, trihalomethyl, —CN, —NO$_2$, —NH$_2$, —O$R^3$, —N$R^3$$R^4$, —S(O)$_{0-2}$$R^3$, —SO$_2$N$R^3$$R^3$, —CO$_2$$R^3$, —C(O)N$R^3$$R^3$, —N($R^3$)SO$_2$$R^3$, —N($R^3$)C(O)$R^3$, —N($R^3$)CO$_2$$R^3$, —C(O)$R^3$, and optionally substituted lower alkyl;

$R^{60}$ is selected from —H, halogen, trihalomethyl, —CN, —NO$_2$, —NH$_2$, —O$R^3$, —N$R^3$$R^4$, —S(O)$_{0-2}$$R^3$, —SO$_2$N$R^3$$R^3$, —CO$_2$$R^3$, —C(O)N$R^3$$R^3$, —N($R^3$)SO$_2$$R^3$, —N($R^3$)C(O)$R^3$, —N($R^3$)CO$_2$$R^3$, —C(O)$R^3$, optionally substituted lower alkyl, optionally substituted aryl, optionally substituted heteroarylalkyl, and optionally substituted arylalkyl;

two of $R^{60}$, when attached to a non-aromatic carbon, can be oxo;

with the proviso, only when Ar is according to formula II, if Y is a C$_{1-6}$ alkylene; Z is —NH— or —N(CH$_3$)—; $R^1$ is a C$_{1-6}$alkyl optionally substituted in the 2-position by —OH or a C$_{1-4}$alkoxy group; $R^2$ is —H or halogen; n=Q; and the atoms, $X^1$, of one bridge of the saturated bridged ring system, when combined with both bridgehead atoms, $X^2$, of the saturated bridged ring system, represent:

1) either a pyrrolidine or a piperidine, and any atom, $X^1$ or $X^2$, of either of said pyrrolidine or said piperidine is attached to Y, then the other bridge of said saturated bridged ring system cannot be any one of —OC(O)CH$_2$—, —CH$_2$OC(O)—, —OC(O)CH$_2$CH$_2$—, —CH$_2$OC(O)CH$_2$—, —CH$_2$CH$_2$OC(O)—, —OC(O)CH$_2$NH—, —OC(O)CH$_2$N(C$_{1-4}$alkyl)-, and —OC(O)CH$_2$O—; or 2) either a piperazine or a 4-(C$_{1-4}$alkyl)-piperazine, and any atom, $X^1$ or $X^2$, of either of said piperazine or said 4-(C$_{1-4}$alkyl)-piperazine is attached to Y, then the other bridge of said saturated bridged ring system, only when attached via the 2- and the 3-position of either of said piperazine or said 4-(C$_{1-4}$alkyl)-piperazine, cannot be one of —CH$_2$OC(O)CH$_2$—, —CH$_2$CH$_2$OC(O)—, and either of the two aforementioned bridges optionally substituted by one or two C$_{1-2}$alkyl groups; or 3) a piperazine, and any atom, $X^1$ or $X^2$, of said piperazine is attached to Y, then the other bridge of said saturated bridged ring system, only when attached via the 3- and the 4-position of said piperazine, cannot be one of —C(O)OCH$_2$CH$_2$—, —CH$_2$OC(O)CH$_2$—, and either of the two aforementioned bridges optionally substituted by one or two C$_{1-2}$alkyl groups, and only when either of the two aforementioned bridges are attached to the 3-position of said piperazine via their left-hand end as depicted above; or 4) a 2-oxomorpholine, said 2-oxomorpholine attached to Y via its 4-position, then the other bridge of said saturated bridged ring system, only when attached via the 5- and the 6-position of said 2-oxomorpholine, cannot be one of —(CH$_2$)$_g$—, —CH$_2$WCH$_2$—, —CH$_2$WCH$_2$CH$_2$—, and —CH$_2$CH$_2$WCH$_2$—, wherein W is —O—, —S(O)$_{0-2}$—, —NH—, or —N(C$_{1-4}$alkyl)- wherein g is 2, 3, or 4;

and with the proviso that when Z is —O—, Ar is according to formula II, and the portion of G directly attached to Ar is selected from:

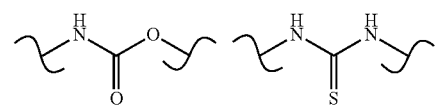

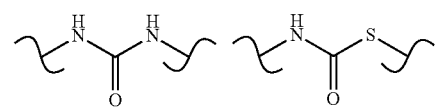

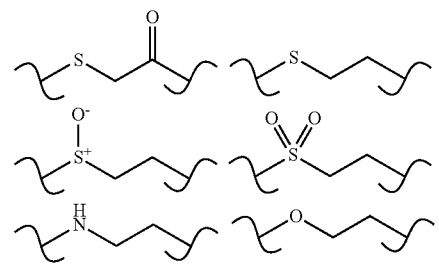

then $R^{50}$ must be of formula IV;

and with the proviso that when Ar is phenylene or substituted phenylene, Z is —S(O)$_{0-2}$— or —O—, then the portion of G directly attached to Ar cannot contain

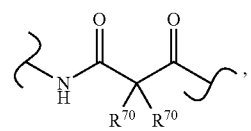, when $R^{70}$ is selected from —H, C$_{1-4}$alkyl, and C$_{1-4}$alkoxyl.

In one example, the compound is according to Formula I, wherein Z is either —O— or —NR$^5$—.
In another example, the compound is according to Formula I, wherein Z is either —O— or —NR$^5$— and G is selected from the following:
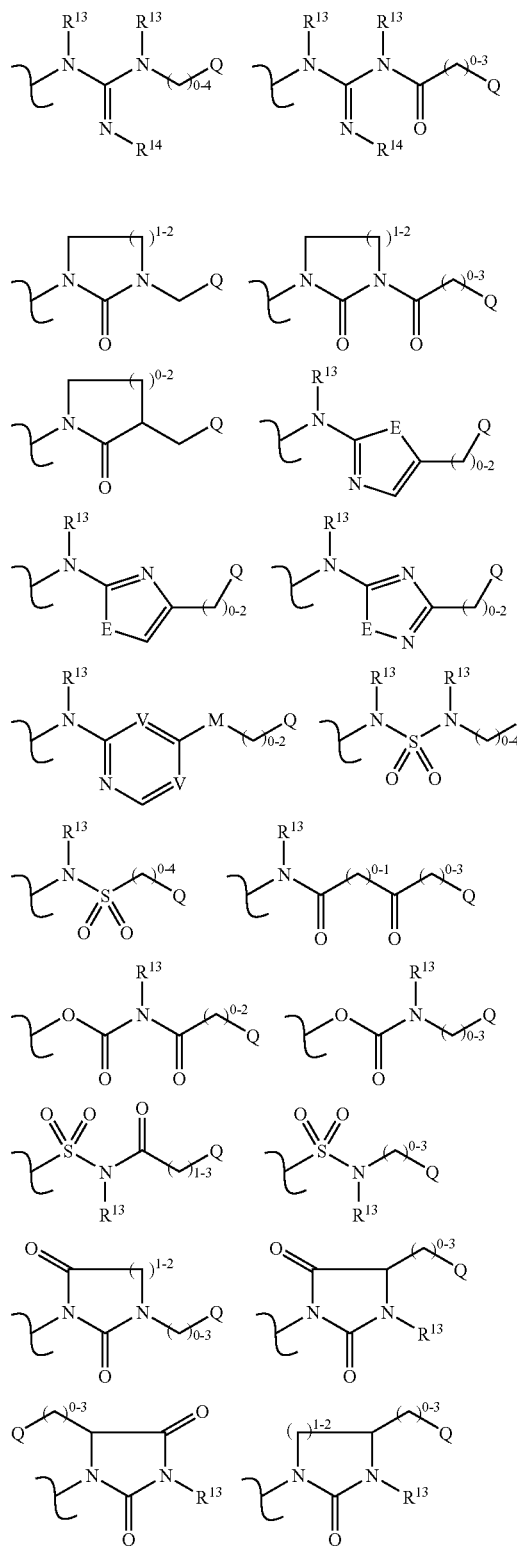
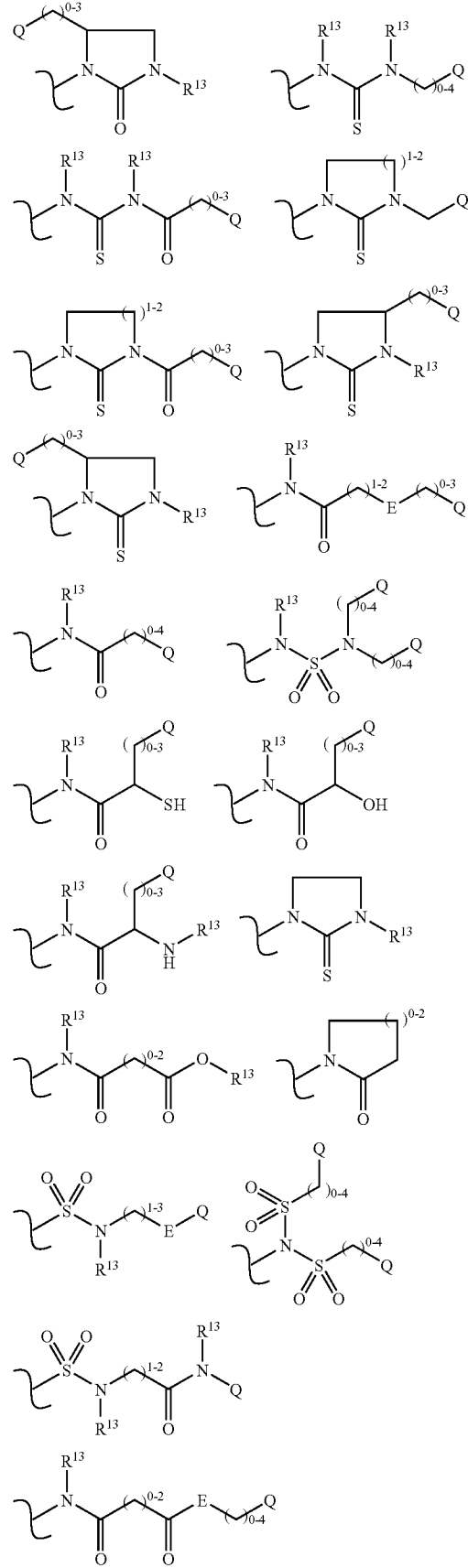

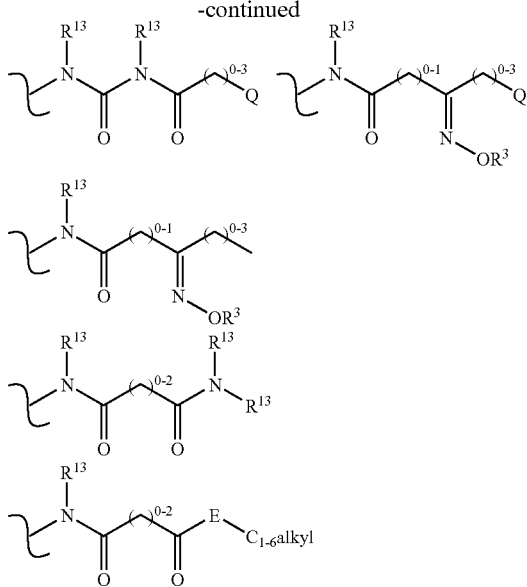

wherein Q, $R^{20}$, and $R^{13}$ are as defined above; each E is selected from —O—, —N($R^{13}$)—, —CH$_2$—, and —S(O)$_{0-2}$—; M is selected from —O—, —N($R^{13}$)—, —CH$_2$—, and —C(=O)N($R^{13}$)—; each V is independently either =N— or =C(H)—; each methylene in any of the above formulae is independently optionally substituted with $R^{25}$; and $R^{25}$ is selected from halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, optionally substituted aryl, optionally substituted arylalkyl, heteroarylalkyl, and optionally substituted lower alkyl; two of $R^{25}$, together with the carbon or carbons to which they are attached, can combine to form a three- to seven-membered alicyclic or heteroalicyclic, two of $R^{25}$ on a single carbon can be oxo.

In another example, the compound is according to the preceding paragraph, wherein Ar is according to one of formula Ia, IIb, and IIIa.

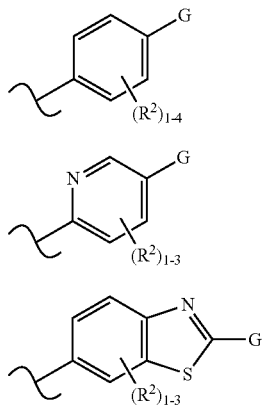

In another example, the compound is according to the preceding paragraph, wherein D is —O— and $R^1$ is —OR$^3$.

In another example, the compound is according to the preceding paragraph, wherein —O—R$^{50}$ and $R^1$ are interchangeably located at the 6-position and 7-position of the quinazoline or quinoline according to formula I.

In another example, the compound is according to the preceding paragraph, wherein $R^1$ is —OH or —OC$_{1-6}$ alkyl.

In another example, the compound is according to the preceding paragraph, wherein $A^1$ is =N— or =C(H)—.

In another example, the compound is according to the preceding paragraph, wherein G is selected from:

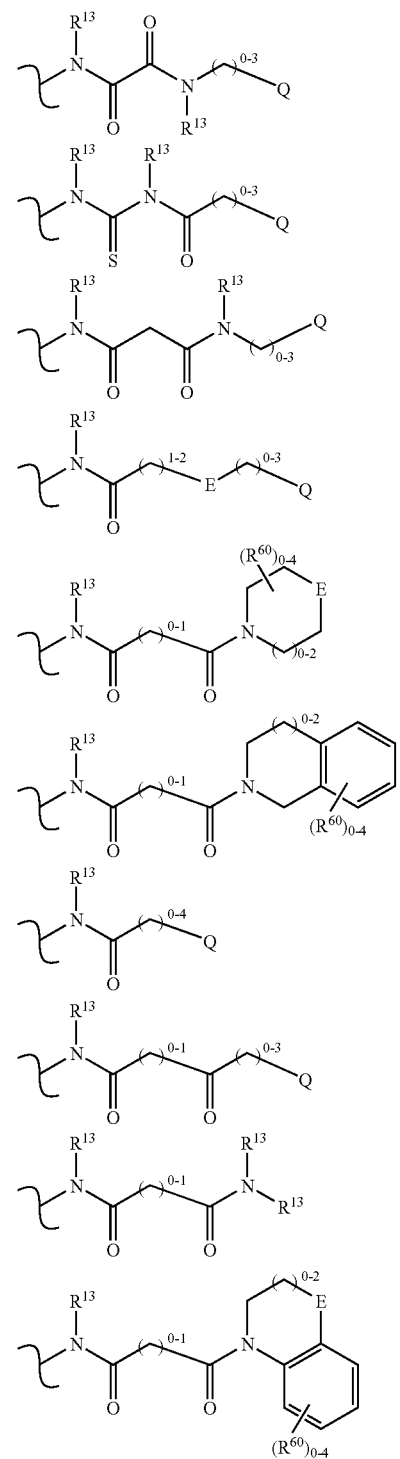

-continued

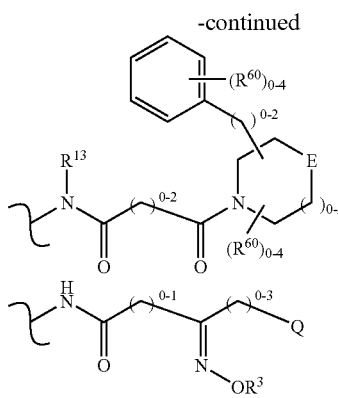

wherein Q, $R^{20}$, $R^{13}$, E, and $R^{60}$ are as defined above; each methylene in any of the above formulae, other than those in a depicted ring, is independently optionally substituted with $R^{25}$; and $R^{25}$ is selected from halogen, trihalomethyl, oxo, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, optionally substituted aryl, optionally substituted arylalkyl, heteroarylalkyl, and optionally substituted lower alkyl; two of $R^{25}$, together with the carbon or carbons to which they are attached, can combine to form a three- to seven-membered alicyclic or heteroalicyclic.

In another example, the compound is according to the preceding paragraph, wherein Q is selected from:

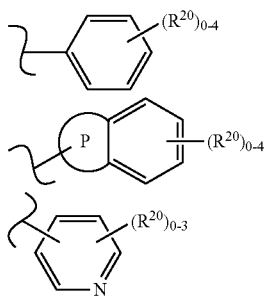

wherein $R^{20}$ is defined as above, and P is a five- to seven-membered ring, including the two shared carbons of the aromatic ring to which P is fused, P optionally containing between one and three heteroatoms.

In another example, the compound is according to the preceding paragraph, wherein Ar is according to formula Ia, and G is selected from:

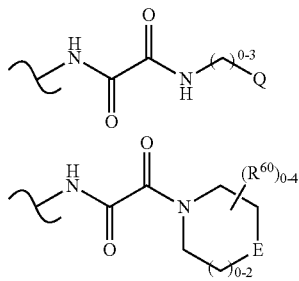

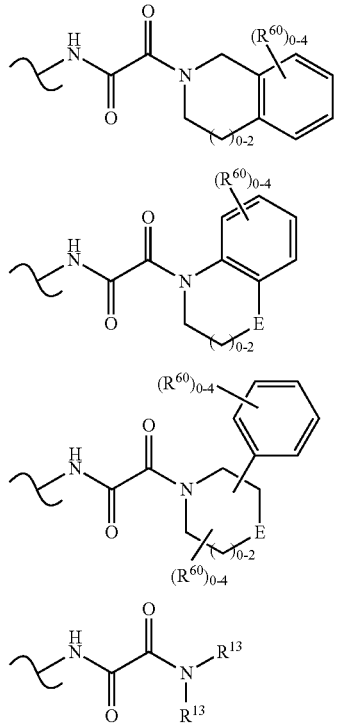

wherein Q, $R^{20}$, $R^{13}$, E, and $R^{60}$ are as defined above, and each methylene in any of the above formulae, other than those in a depicted ring, is independently optionally substituted with $R^{25}$; and $R^{25}$ is selected from halogen, trihalomethyl, oxo, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, optionally substituted aryl, optionally substituted arylalkyl, heteroarylalkyl, and optionally substituted lower alkyl; two of $R^{25}$, together with the carbon or carbons to which they are attached, can combine to form a three- to seven-membered alicyclic or heteroalicyclic.

In another example, the compound is as defined two paragraphs above, and G is selected from:

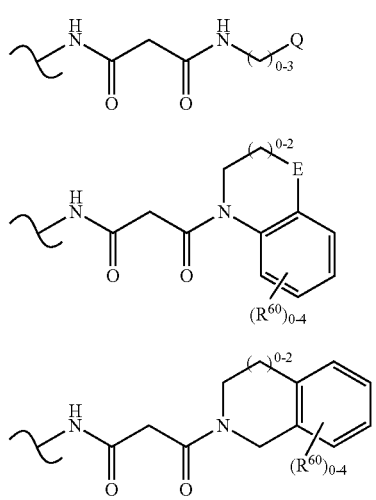

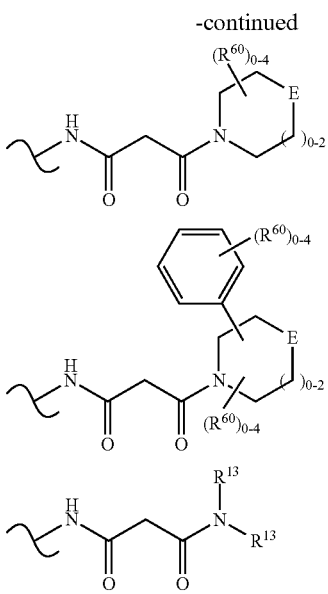

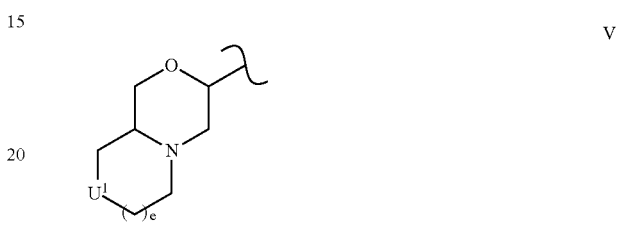

wherein Q, $R^{20}$, $R^{13}$, E, and $R^{60}$ are as defined above, and each methylene in any of the above formulae, other than those depicted in a ring, is independently optionally substituted with $R^{25}$; and $R^{25}$ is selected from halogen, trihalomethyl, oxo, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, optionally substituted aryl, optionally substituted arylalkyl, heteroarylalkyl, and optionally substituted lower alkyl; two of $R^{25}$, together with the carbon or carbons to which they are attached, can combine to form a three- to seven-membered alicyclic or heteroalicyclic.

In another example, the compound is according to either of the two preceding paragraphs, wherein the methylene between the two carbonyls of the depicted formulae is di-substituted with either optionally substituted lower alkyl, or an optionally substituted spirocycle.

In another example, the compound is as defined three paragraphs above or as defined two paragraphs above, wherein $R^{50}$ is a heteroalicylic or a $C_{1-6}$alkyl-heteroalicylic.

In another example, the compound is according to the preceding paragraph, wherein at least one of $R^2$ is halogen.

In another example, the compound is as defined two paragraphs above, wherein $R^{50}$ is according to formula IV.

In another example, the compound is according to the preceding paragraph, wherein the saturated bridged ring system according to formula IV has a geometry selected from the group consisting of [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2], and [2.2.1].

In another example, the compound is according to the preceding paragraph, wherein Y is selected from —$CH_2CH_2CH_2CH_2$—, —$CH_2CH_2CH_2$—, —$CH_2CH_2$—, —$CH_2$—, and absent.

In another example, the compound is according to the preceding paragraph, wherein n is 0 and the saturated bridged ring system according to formula IV has a geometry selected from the group consisting of [4.4.0], [4.3.0], [4.2.0], [4.1.0], [3.3.0], [3.2.0], and [3.1.0].

In another example, the compound is according to the preceding paragraph, wherein said saturated bridged ring system contains at least one annular nitrogen or at least one annular oxygen.

In another example, the compound is according to the preceding paragraph, wherein said saturated bridged ring system contains —$NR^8$—, wherein $R^8$ is selected from —H, optionally substituted lower alkyl, —$CO_2R^3$, —$C(O)NR^3R^3$, —$SO_2R^3$, and —$C(O)R^3$.

In another example, the compound is as defined two paragraphs above, wherein said saturated bridged ring system is of formula V,

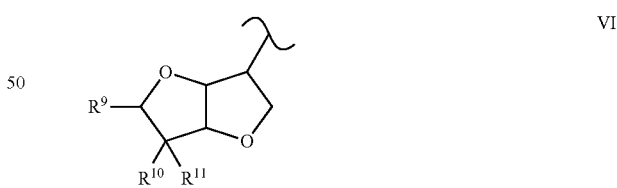

wherein $U^1$ is selected from —O—, —$S(O)_{0-2}$—, —$NR^8$—, —$CR^6R^7$—, and absent; and e is 0 or 1.

In another example, the compound is according to the preceding paragraph, wherein Y is —$CH_2$—.

In another example, the compound is according to the preceding paragraph, wherein $U^1$ is —$NR^8$—, wherein $R^8$ is selected from —H, optionally substituted lower alkyl, —$CO_2R^3$, —$C(O)NR^3R^3$, —$SO_2R^3$, and —$C(O)R^3$.

In another example, the compound is as defined two paragraphs above, wherein $U^1$ is —O—.

In another example, the compound is as defined three paragraphs above, wherein $U^1$ is absent.

In another example, the saturated bridged ring system is according to formula IV with a geometry selected from the group consisting of [4.4.0], [4.3.0], [4.2.0], [4.1.0], [3.3.0], [3.2.0], and [3.1.0] and contains at least one annular nitrogen or at least one annular oxygen, wherein n is 0 and Y is selected from —$CH_2CH_2$—, —$CH_2$—, and absent.

In another example, the compound is according to the preceding paragraph, wherein said saturated bridged ring system is of formula VI,

VI $R^9$, $R^{10}$, $R^{11}$ wherein $R^9$, $R^{10}$, and $R^{11}$ are each independently selected from —H, and —$OR^{12}$; or
$R^9$ is selected from —H, and —$OR^{12}$, and $R^{10}$ and $R^{11}$, when taken together, are either an optionally substituted alkylidene or an oxo;
$R^{12}$ is selected from —H, —$C(O)R^3$, optionally substituted lower alkylidene, optionally substituted lower arylalkylidyne, optionally substituted lower heterocyclylalkylidyne, optionally substituted lower alkylidene, optionally substituted lower alkylidenearyl, optionally substituted lower alkylideneheterocyclyl, optionally substituted lower alkyl, optionally substituted lower alkylaryl, optionally substituted aryl, optionally substituted lower heterocyclylalkyl, and optionally substituted heterocyclyl;

or two $R^{12}$'s, when taken together, form 1) a corresponding spirocyclic ketal when said two $R^{12}$'s stem from $R^{10}$ and $R^{11}$, or 2) a corresponding cyclic ketal when said two $R^{12}$'s stem from $R^9$ and one of $R^{10}$ and $R^{11}$.

In another example, the compound is according to the preceding paragraph, wherein one of $R^{10}$ and $R^{11}$ is —$OR^2$, wherein $R^{12}$ is selected from —H, —C(O)$R^3$, and optionally substituted lower alkyl; and $R^9$ and the other of $R^{10}$ and $R^{11}$ are both —H.

In another example, the compound is according to the preceding paragraph, wherein Y is either —$CH_2$— or absent.

In another example, the compound is according to the preceding paragraph, wherein $R^9$ is an alkyl group containing at least one fluorine substitution thereon.

In another example, the saturated bridged ring system is of formula VII, wherein $R^8$ is selected from —H, optionally substituted lower alkyl, —$CO_2R^3$, C(O)$NR^3R^3$, —$SO_2R^3$, and —C(O)$R^3$.

VII

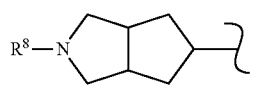

In another example, the compound is according to the preceding paragraph, wherein Y is either —$CH_2$— or absent.

In another example, the compound is according to the preceding paragraph, wherein $R^8$ is methyl or ethyl.

In another example, the saturated bridged ring system is of formula VIII.

VIII

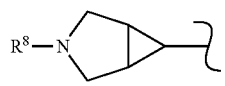

wherein $R^8$ is selected from —H, optionally substituted lower alkyl, —$CO_2R^3$, —C(O)$NR^3R^3$, —$SO_2R^3$, and —C(O)$R^3$.

In another example, the compound is according to the preceding paragraph, wherein Y is —$CH_2$—.

In another example, the compound is according to the preceding paragraph, wherein $R^8$ is methyl or ethyl.

In another example, the said saturated bridged ring system is of formula IX

IX wherein $U^2$ is selected from —O—, —$S(O)_{0-2}$—, —$NR^8$—, —$CR^6R^7$—, and absent.

In another example, the compound is according to the preceding paragraph, wherein $R^3$ of formula IX is selected from —H and optionally substituted alkyl.

In another example, the compound is according to the preceding paragraph, wherein $U^2$ is either —$CR^6R^7$— or absent.

In another example, the compound is according to the preceding paragraph, wherein $U^2$ is either —$CH_2$— or absent.

In another example, the compound is according to the preceding paragraph, wherein Y is —$CH_2$—.

In another example, the saturated bridged ring system is according to formula X, wherein $R^8$ is selected from —H, optionally substituted lower alkyl, —$CO_2R^3$, C(O)$NR^3R^3$, —$SO_2R^3$, and —C(O)$R^3$.

X

In another example, the compound is according to the preceding paragraph, wherein $R^8$ is methyl or ethyl.

In another example, the compound is selected from Table 1.

TABLE 1

| Entry | Name | Structure |
|---|---|---|
| 1 | N-[({3-fluoro-4-[(6-(methyloxy)-7-{[(3aR,6aS)-octahydrocyclopenta[c]pyrrol-5-ylmethyl]oxy}quinazolin-4-yl)oxy]phenyl}amino)carbonothioyl]-2-phenylacetamide | 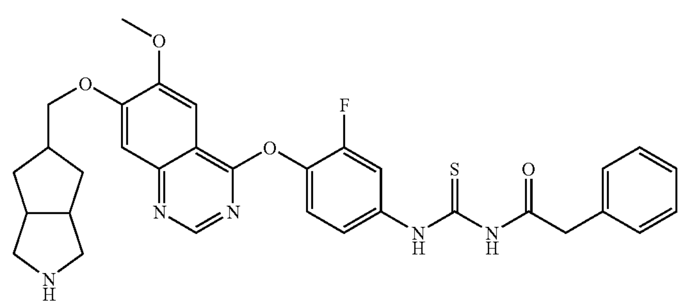 |

TABLE 1-continued

| Entry | Name | Structure |
|---|---|---|
| 2 | N-{[(3-fluoro-4-{[7-({[(3aR,6aS)-2-methyloctahydrocyclopenta[c]pyrrol-5-yl]methyl}oxy)-6-(methyloxy)quinazolin-4-yl]oxy}phenyl)amino]carbonothioyl}-2-phenylacetamide | 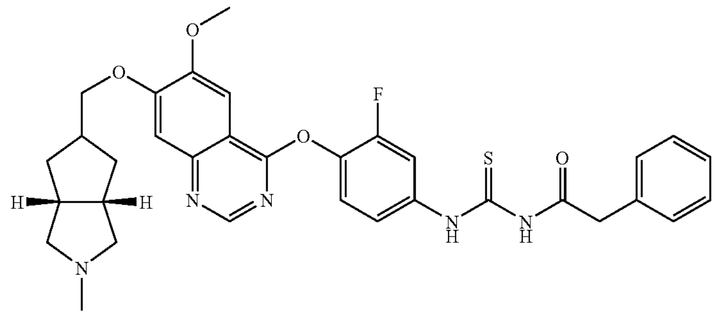 |
| 3 | N-{[(4-{[6,7-bis(methyloxy)quinolin-4-yl]oxy}-3-fluorophenyl)(methyl)amino]carbonothioyl}-2-phenylacetamide | 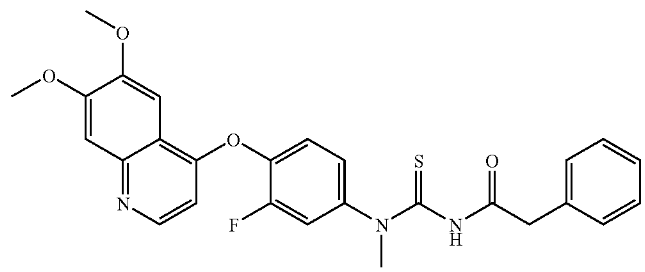 |
| 4 | 1-(4-{[6,7-bis(methyloxy)quinolin-4-yl]oxy}-3-fluorophenyl)imidazolidin-2-one | 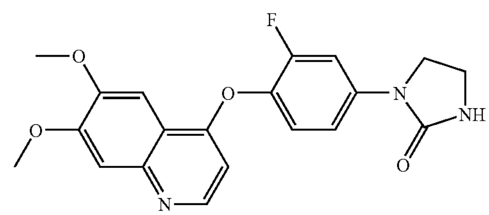 |
| 5 | 1-(4-{[6,7-bis(methyloxy)quinolin-4-yl]oxy}-3-fluorophenyl)-3-(phenylmethyl)imidazolidin-2-one | 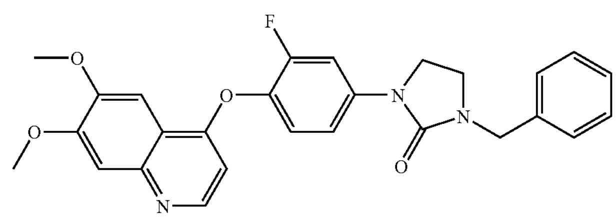 |
| 6 | 1-(4-{[6,7-bis(methyloxy)quinolin-4-yl]oxy}-3-fluorophenyl)-3-(phenylacetyl)imidazolidin-2-one | 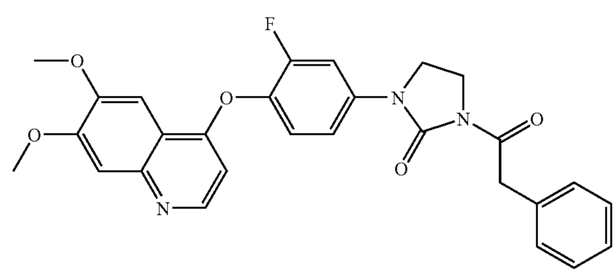 |
| 7 | ethyl [(4-{[6,7-bis(methyloxy)quinolin-4-yl]oxy}-3-fluorophenyl)amino](oxo)acetate | 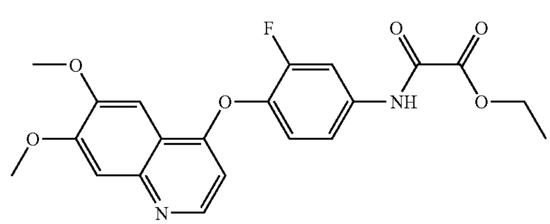 |

TABLE 1-continued

| Entry | Name | Structure |
|---|---|---|
| 8 | N-{[(4-{[6,7-bis(methyloxy)quinazolin-4-yl]amino}-3-fluorophenyl)amino]carbonothioyl}-2-phenylacetamide | 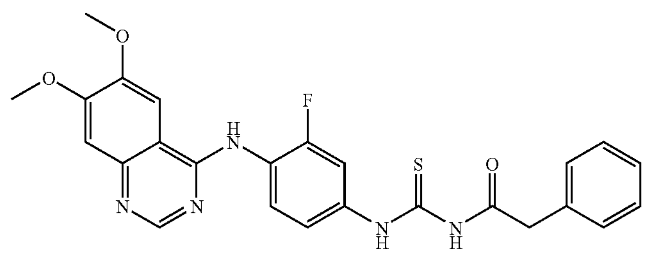 |
| 9 | N'-(4-{[6,7-bis(methyloxy)quinolin-4-yl]oxy}-3-fluorophenyl)-N-methyl-N-(2-phenylethyl)sulfamide | 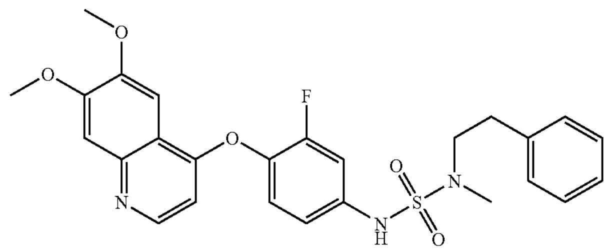 |
| 10 | N-(4-{[6,7-bis(methyloxy)quinolin-4-yl]oxy}-3-fluorophenyl)-3-(phenylmethyl)-1,2,4-oxadiazol-5-amine | 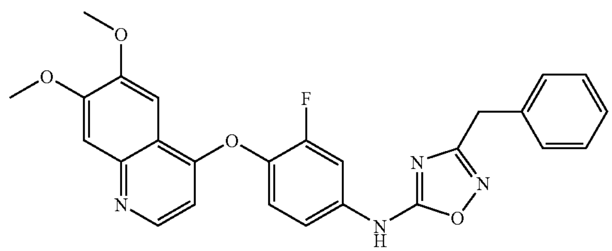 |
| 11 | 1-(4-{[6,7-bis(methyloxy)quinolin-4-yl]oxy}-3-fluorophenyl)piperidin-2-one | 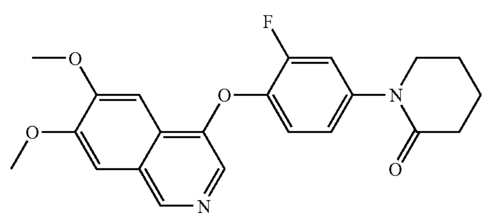 |
| 12 | N-(4-{[6,7-bis(methyloxy)quinolin-4-yl]oxy}-3-fluorophenyl)-N'-(phenylmethyl)ethanediamide | 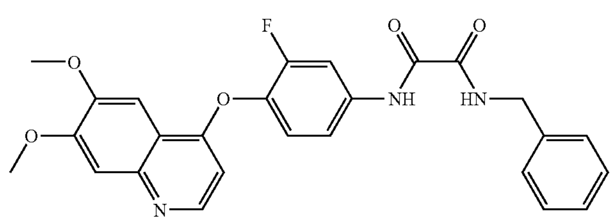 |
| 13 | N-(4-{[6,7-bis(methyloxy)quinolin-4-yl]oxy}-3-fluorophenyl)-4-phenyl-1,3-thiazol-2-amine | 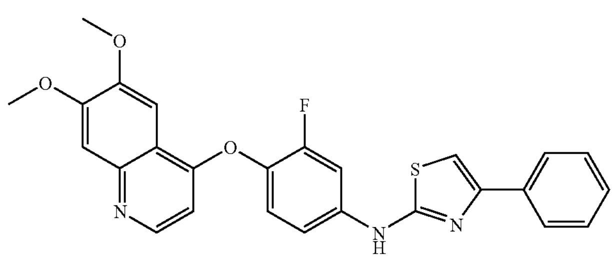 |

TABLE 1-continued

| Entry | Name | Structure |
|---|---|---|
| 14 | N-(4-{[6,7-bis(methyloxy)quinolin-4-yl]oxy}-3-fluorophenyl)-N'-(2-phenylethyl)ethanediamide | 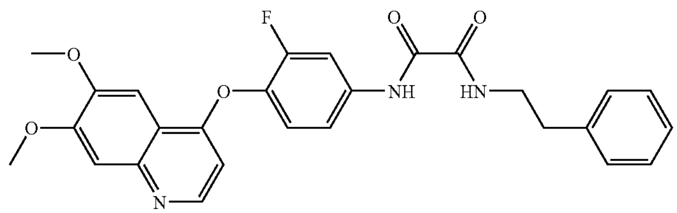 |
| 15 | N-(4-{[6,7-bis(methyloxy)quinolin-4-yl]oxy}-3-fluorophenyl)-1-phenylmethanesulfonamide | 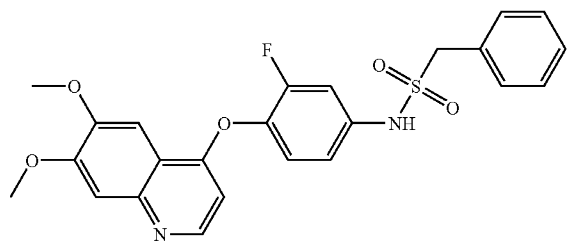 |
| 16 | N-(4-{[6,7-bis(methyloxy)quinolin-4-yl]oxy}-3-fluorophenyl)-2-phenylethanesulfonamide | 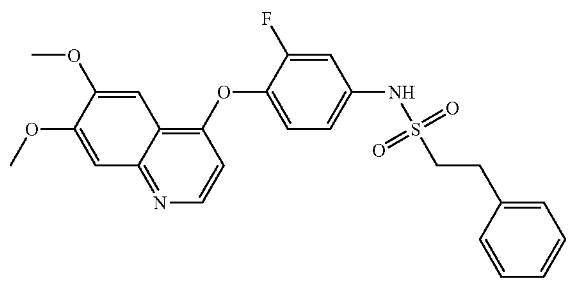 |
| 17 | 4-{[6,7-bis(methyloxy)quinolin-4-yl]oxy}-3-fluoro-N-(phenylmethyl)benzenesulfonamide | 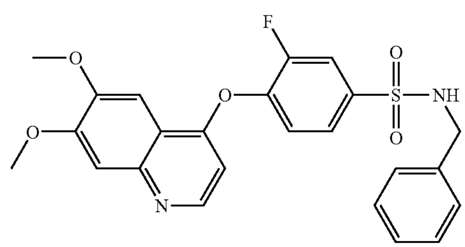 |
| 18 | 4-{[6,7-bis(methyloxy)quinolin-4-yl]oxy}-3-fluoro-N-methyl-N-(phenylmethyl)benzenesulfonamide | 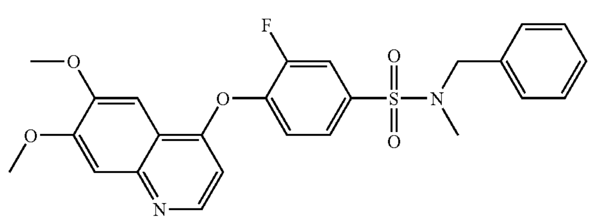 |
| 19 | 4-{[6,7-bis(methyloxy)quinolin-4-yl]oxy}-3-fluoro-N-(2-phenylethyl)benzenesulfonamide | 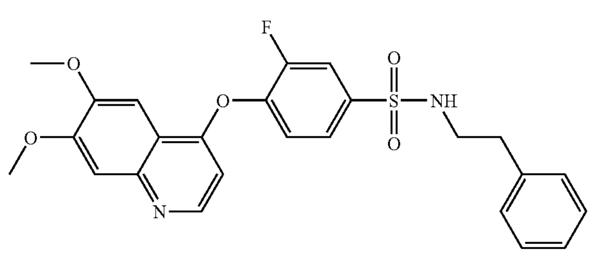 |

TABLE 1-continued

| Entry | Name | Structure |
|---|---|---|
| 20 | 4-{[6,7-bis(methyloxy)quinolin-4-yl]oxy}-3-fluoro-N-methyl-N-(2-phenylethyl)benzenesulfonamide | 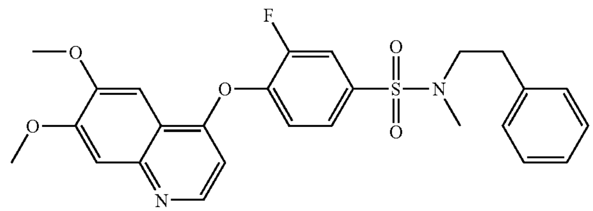 |
| 21 | 4-{[6,7-bis(methyloxy)quinolin-4-yl]oxy}-3-fluoro-N-(3-phenylpropyl)benzenesulfonamide | 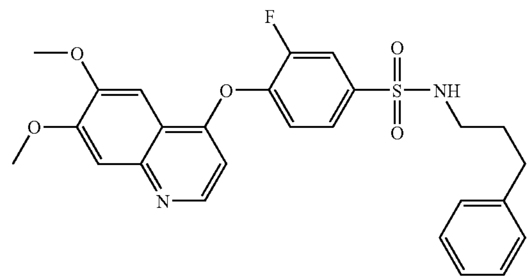 |
| 22 | 1-(4-{[6,7-bis(methyloxy)quinolin-4-yl]oxy}-3-fluorophenyl)pyrrolidin-2-one | 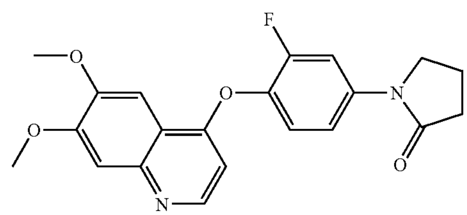 |
| 23 | 4-{[6,7-bis(methyloxy)quinolin-4-yl]oxy}phenyl (phenylmethyl)carbamate | 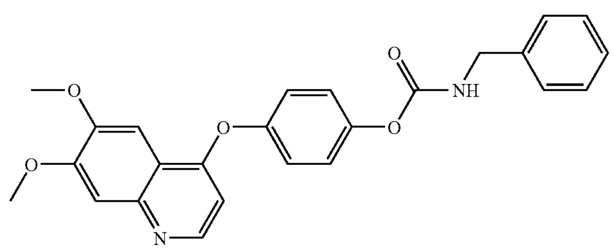 |
| 24 | 4-{[6,7-bis(methyloxy)quinolin-4-yl]oxy}phenyl (2-phenylethyl)carbamate | 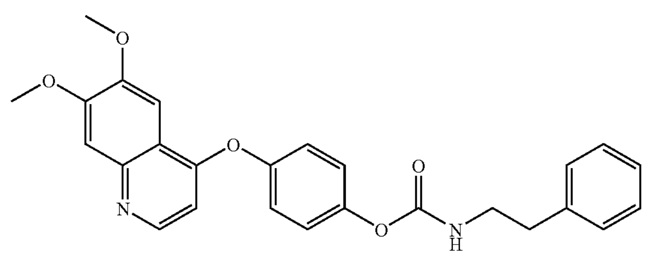 |
| 25 | 4-{[6,7-bis(methyloxy)quinolin-4-yl]oxy}-3-fluoro-N-methyl-N-(3-phenylpropyl)benzenesulfonamide | 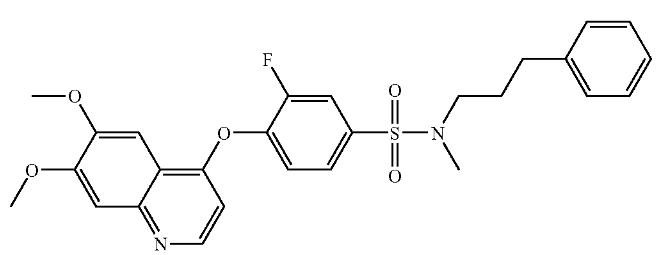 |

TABLE 1-continued

| Entry | Name | Structure |
|---|---|---|
| 26 | N-(4-{[6,7-bis(methyloxy)quinolin-4-yl]oxy}-3-fluorophenyl)-N'-phenylethanediamide | 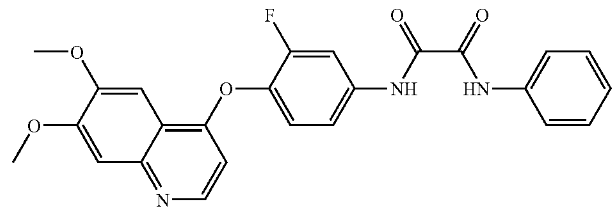 |
| 27 | N-{[(3-fluoro-4-{[7-{[(2-methyloctahydrocyclopenta[c]pyrrol-5-yl)methyl]oxy}-6-(methyloxy)quinolin-4-yl]oxy}phenyl)amino]carbonothioyl}-2-phenylacetamide | 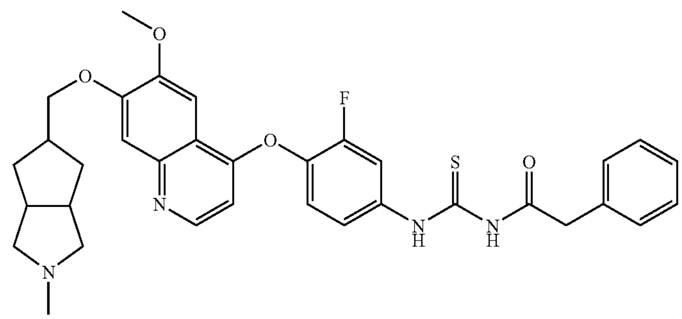 |
| 28 | N-[(Z)-[(4-{[6,7-bis(methyloxy)quinolin-4-yl]oxy}-3-fluorophenyl)amino](imino)methyl]-2-phenylacetamide | 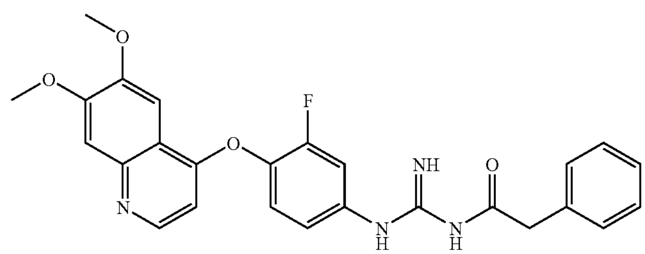 |
| 29 | 4-{[6,7-bis(methyloxy)quinolin-4-yl]oxy}-3-fluoro-N-[2-(phenyloxy)ethyl]benzenesulfonamide | 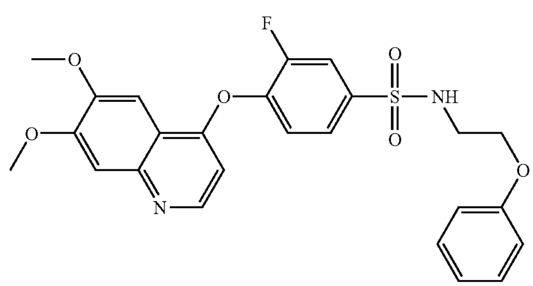 |
| 30 | N,N-(4-{[6,7-bis(methyloxy)quinolin-4-yl]oxy}-3-fluorophenyl)-bis-(3-phenylpropane-1-sulfonamide) | 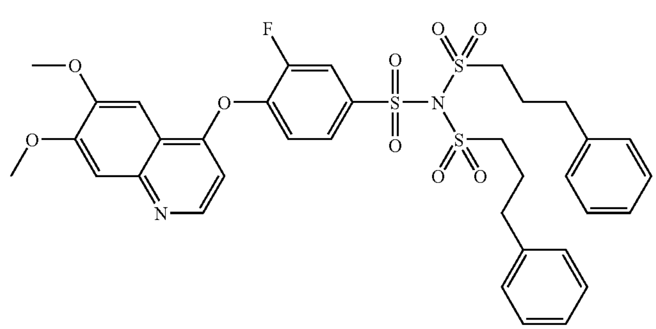 |

TABLE 1-continued

| Entry | Name |
|---|---|
| 31 | N-(4-{[6,7-bis(methyloxy)quinolin-4-yl]oxy}-3-fluorophenyl)-3-phenylpropane-1-sulfonamide |
| 32 | N2-[(4-{[6,7-bis(methyloxy)quinolin-4-yl]oxy}-3-fluorophenyl)sulfonyl]-N1-phenylglycinamide |
| 33 | N-(6-{[6,7-bis(methyloxy)quinolin-4-yl]oxy}pyridin-3-yl)-2-phenylacetamide |
| 34 | N-{[(6-{[6,7-bis(methyloxy)quinolin-4-yl]oxy}pyridin-3-yl)amino]carbonothioyl}-2-phenylacetamide |
| 35 | 6-{[6,7-bis(methyloxy)quinolin-4-yl]oxy}-1,3-benzothiazol-2-amine |
| 36 | 6-{[6,7-bis(methyloxy)quinolin-4-yl]oxy}-5-fluoro-1,3-benzothiazol-2-amine |

TABLE 1-continued

| Entry | Name | Structure |
|---|---|---|
| 37 | N-(6-{[6,7-bis(methyloxy)quinolin-4-yl]oxy}-5-fluoro-1,3-benzothiazol-2-yl)-2-phenylacetamide | 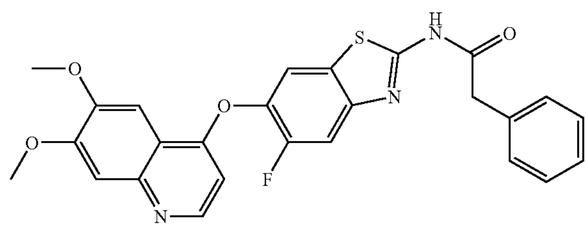 |
| 38 | N-(4-{[6,7-bis(methyloxy)quinolin-4-yl]oxy}-3-fluorophenyl)-N'-(2-morpholin-4-ylethyl)ethanediamide | 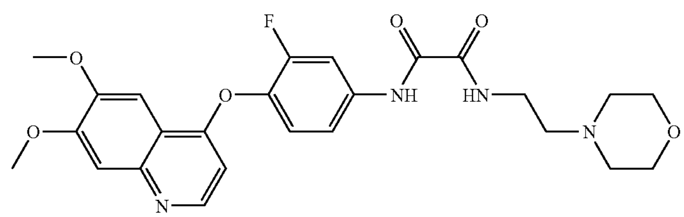 |
| 39 | benzyl-{[4-(6,7-dimethoxy-quinolin-4-yloxy)-3-fluoro-phenylcarbamoyl]-methyl}-carbamic acid tert-butyl ester | 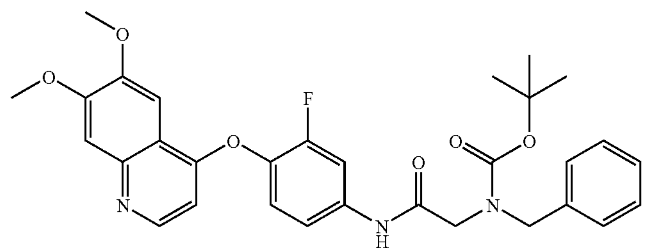 |
| 40 | N1-(4-{[6,7-bis(methyloxy)quinolin-4-yl]oxy}-3-fluorophenyl)-N2-(phenylmethyl)glycinamide | 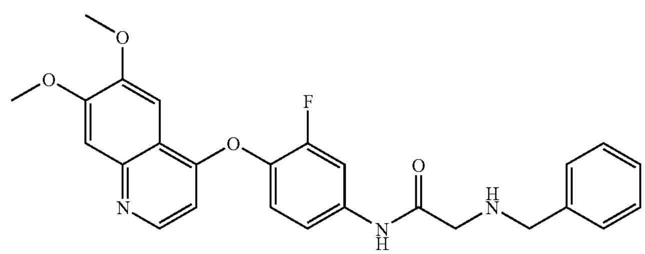 |
| 41 | N2-acetyl-N1-(4-{[6,7-bis(methyloxy)quinolin-4-yl]oxy}-3-fluorophenyl)-N2-(phenylmethyl)glycinamide | 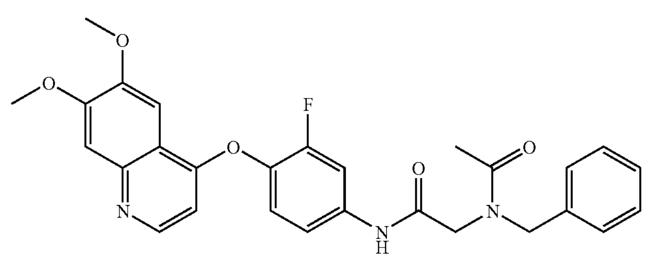 |
| 42 | N-(6-{[6,7-bis(methyloxy)quinolin-4-yl]oxy}-1,3-benzothiazol-2-yl)-2-phenylacetamide | 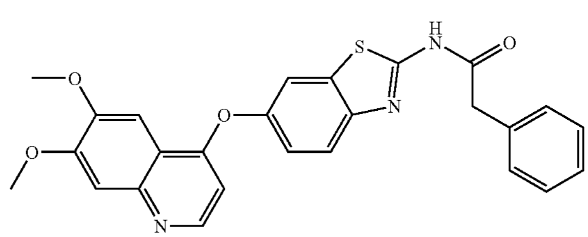 |

TABLE 1-continued

| Entry | Name | Structure |
|---|---|---|
| 43 | benzyl-{[6-(6,7-dimethoxy-quinolin-4-yloxy)-pyridin-3-ylcarbamoyl]-methyl}-carbamic acid tert-butyl ester | 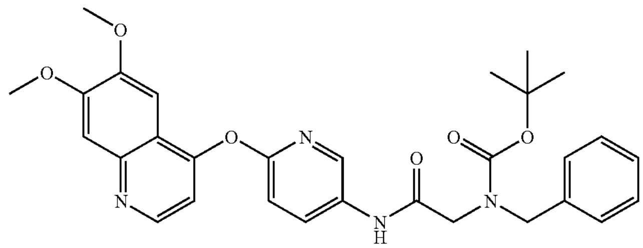 |
| 44 | N1-(6-{[6,7-bis(methyloxy)quinolin-4-yl]oxy}pyridin-3-yl)-N2-(phenylmethyl)glycinamide | 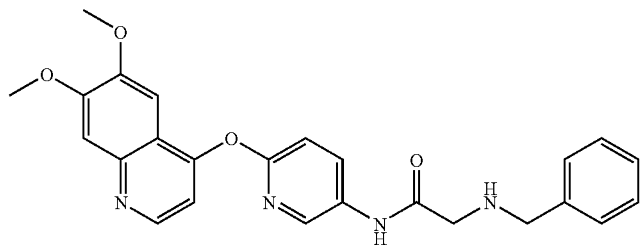 |
| 45 | N2-acetyl-N1-(6-{[6,7-bis(methyloxy)quinolin-4-yl]oxy}pyridin-3-yl)-N2-(phenylmethyl)glycinamide | 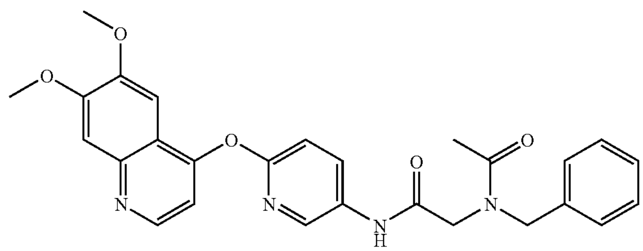 |
| 46 | N-(6-{[6,7-bis(methyloxy)quinolin-4-yl]oxy}pyridin-3-yl)-3-phenylpropanamide | 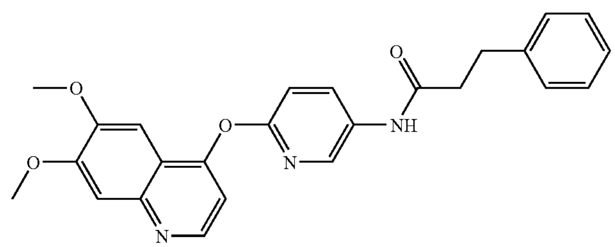 |
| 47 | N-(6-{[6,7-bis(methyloxy)quinolin-4-yl]oxy}pyridin-3-yl)-4-phenylbutanamide | 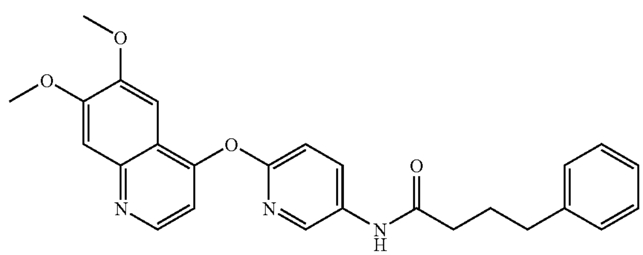 |
| 48 | N1-(6-{[6,7-bis(methyloxy)quinolin-4-yl]oxy}pyridin-3-yl)-N2-methyl-N2-(phenylmethyl)glycinamide | 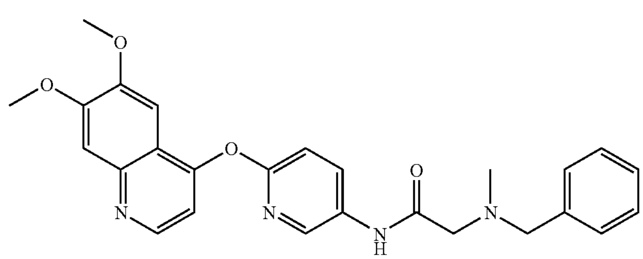 |

TABLE 1-continued

| Entry | Name | Structure |
|---|---|---|
| 49 | N-(4-{[6,7-bis(methyloxy)quinolin-4-yl]oxy}-3-fluorophenyl)-N'-{2-[4-(methyloxy)phenyl]ethyl}ethanediamide | 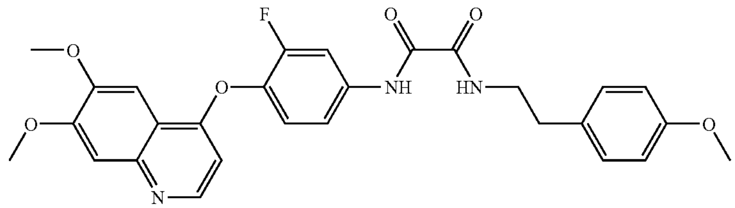 |
| 50 | N1-(4-{[6,7-bis(methyloxy)quinolin-4-yl]oxy}-3-fluorophenyl)-N2-methyl-N2-(phenylmethyl)glycinamide | 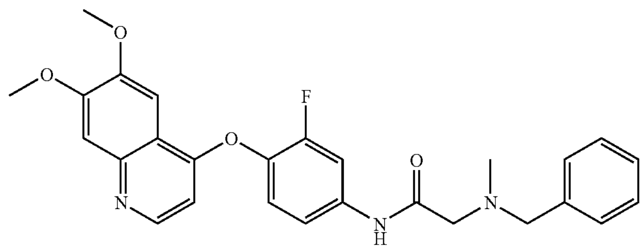 |
| 51 | 4-[(2-amino-1,3-benzothiazol-6-yl)oxy]-6,7-bis(methyloxy)-1-(2-oxo-2-phenylethyl)quinolinium | 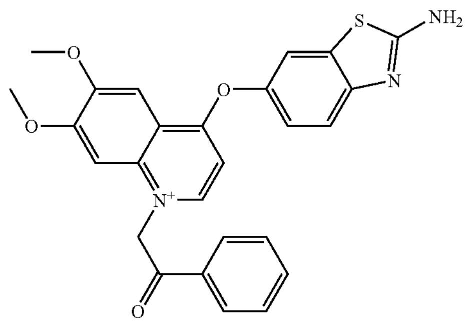 |
| 52 | N-{[(4-{[6,7-bis(methyloxy)quinolin-4-yl]amino}phenyl)amino]carbonothioyl}-2-phenylacetamide | 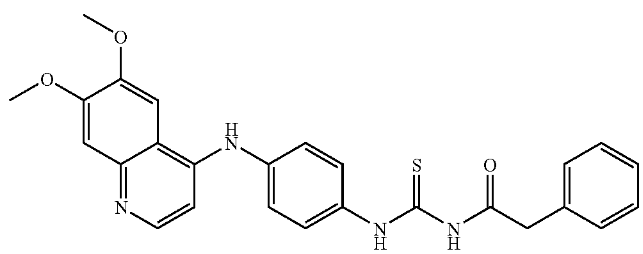 |
| 53 | N-(6-{[6,7 bis(methyloxy)quinolin-4-yl]oxy}-5-fluoro-1,3-benzothiazol-2-yl)-3-phenylpropanamide | 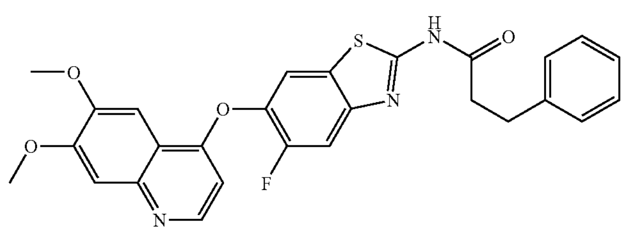 |
| 54 | N-{[(6-{[6,7-bis(methyloxy)quinolin-4-yl]oxy}-5-chloropyridin-3-yl)amino]carbonothioyl}-2-phenylacetamide | 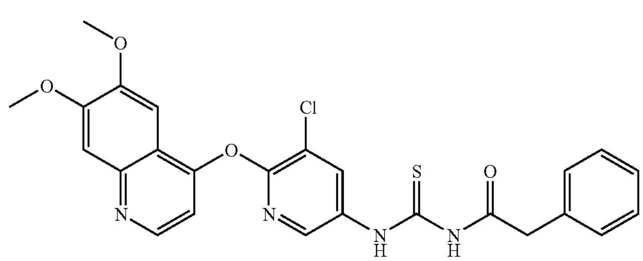 |

TABLE 1-continued

| Entry | Name | Structure |
|---|---|---|
| 55 | N-(4-{[6,7-bis(methyloxy)quinolin-4-yl]oxy}-3-fluorophenyl)-N'-(2,3-dihydro-1H-inden-1-yl)ethanediamide | 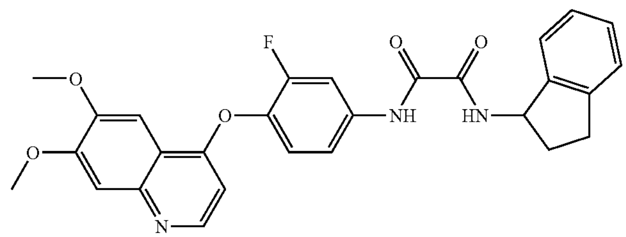 |
| 56 | N-(4-{[6,7-bis(methyloxy)quinolin-4-yl]oxy}-3-fluorophenyl)-N'-(2,3-dihydro-1H-inden-2-yl)ethanediamide | 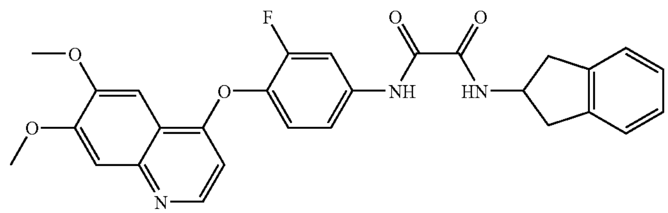 |
| 57 | N-(4-{[6,7-bis(methyloxy)quinolin-4-yl]oxy}-3-fluorophenyl)-N'-(1,2,3,4-tetrahydronaphthalen-1-yl)ethanediamide | 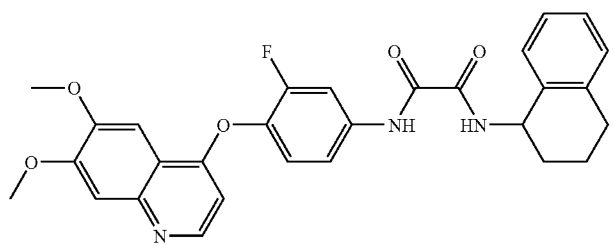 |
| 58 | N'-(4-{[6,7-bis(methyloxy)quinolin-4-yl]oxy}-3-fluorophenyl)-N-(2-phenylethyl)-N-(phenylmethyl)sulfamide | 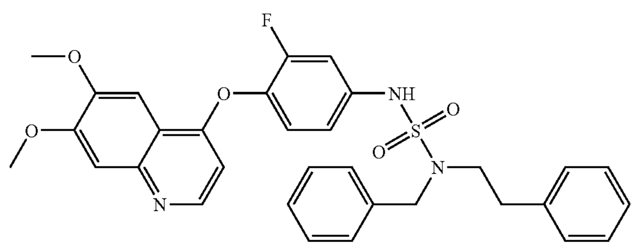 |
| 59 | N1-(4-{[6,7-bis(methyloxy)quinolin-4-yl]oxy}-3-fluorophenyl)-N2-(trifluoroacetyl)glycinamide | 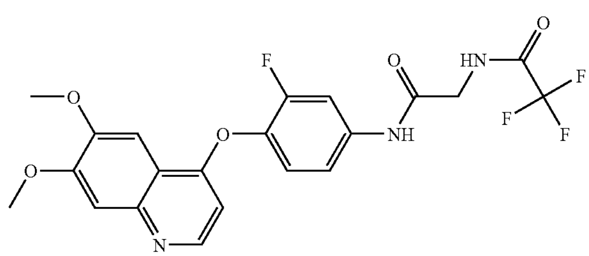 |
| 60 | N-{[4-(6,7-dimethoxy-quinolin-4-yloxy)-3-fluorophenylcarbamoyl]-methyl}benzamide | 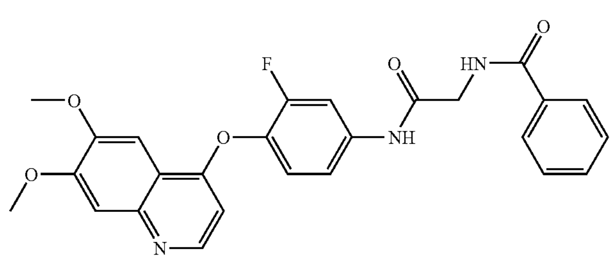 |

TABLE 1-continued

| Entry | Name | Structure |
|---|---|---|
| 61 | N-(6-{[6,7-bis(methyloxy)quinolin-4-yl]oxy}pyridin-3-yl)-N'-(4-fluorophenyl)propanediamide | 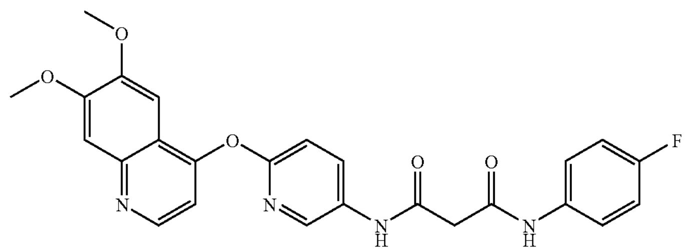 |
| 62 | N-(4-{[6,7-bis(methyloxy)quinolin-4-yl]oxy}-3-fluorophenyl)-N'-[(2S)-1,2,3,4-tetrahydronaphthalen-2-yl]ethanediamide | 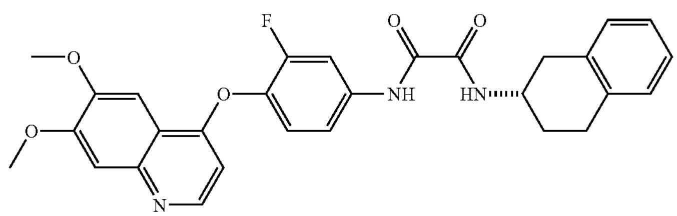 |
| 63 | N-(4-{[6,7-bis(methyloxy)quinolin-4-yl]oxy}-3-fluorophenyl)-N'-[2-(4-methylphenyl)ethyl]ethanediamide | 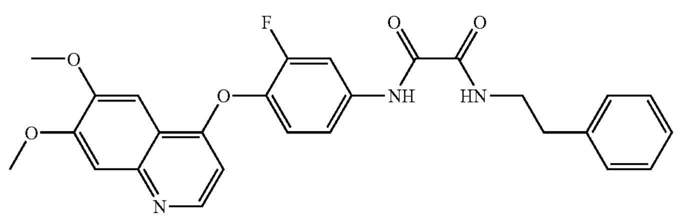 |
| 64 | N-(4-{[6,7-bis(methyloxy)quinolin-4-yl]oxy}-3-fluorophenyl)-N'-(2-phenylpropyl)ethanediamide | 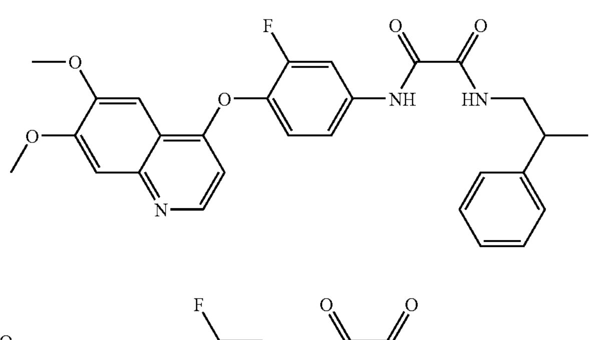 |
| 65 | N-(4-{[6,7-bis(methyloxy)quinolin-4-yl]oxy}-3-fluorophenyl)-N'-[2-(4-chlorophenyl)ethyl]ethanediamide | 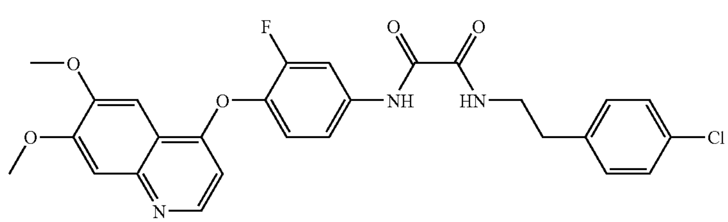 |

TABLE 1-continued

| Entry | Name | Structure |
|---|---|---|
| 66 | N-(4-{[6,7-bis(methyloxy)quinolin-4-yl]oxy}-3-fluorophenyl)-N,N'-bis(phenylmethyl)sulfamide | 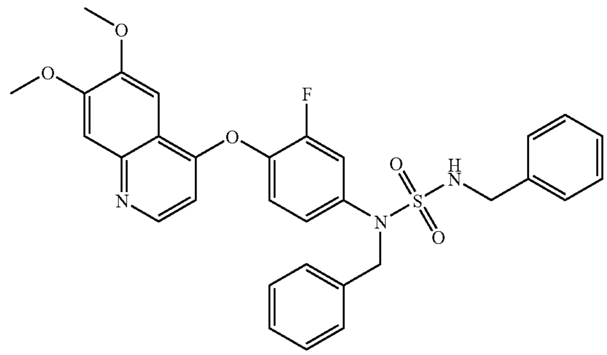 |
| 67 | N-(4-{[6,7-bis(methyloxy)quinolin-4-yl]oxy}-3-fluorophenyl)-N,N'-bis(2-phenylethyl)sulfamide | 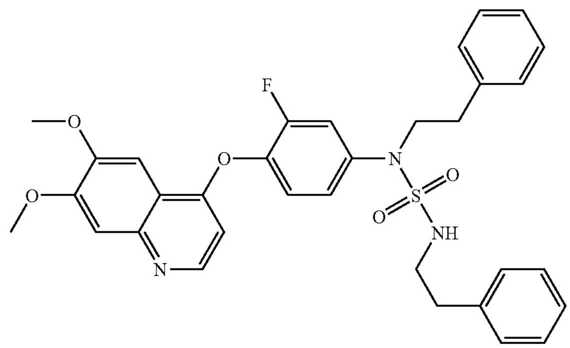 |
| 68 | ethyl [(6-{[6,7-bis(methyloxy)quinolin-4-yl]oxy}-5-chloropyridin-3-yl)amino](oxo)acetate | 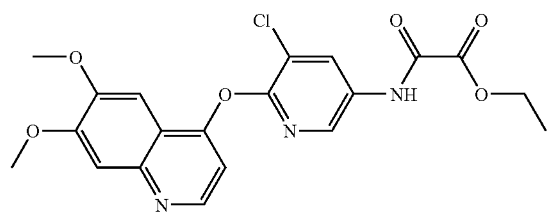 |
| 69 | N-(6-{[6,7-bis(methyloxy)quinolin-4-yl]oxy}-5-chloropyridin-3-yl)-N'-(2-phenylethyl)ethanediamide | 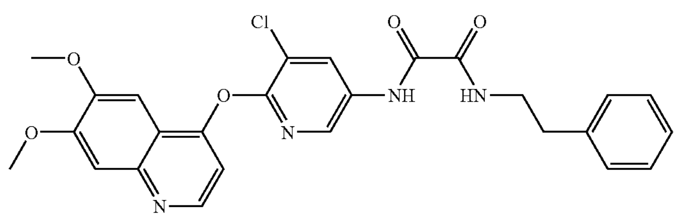 |
| 70 | N-(6-{[6,7-bis(methyloxy)quinolin-4-yl]oxy}-5-chloropyridin-3-yl)-N'-(4-fluorophenyl)propanediamide | 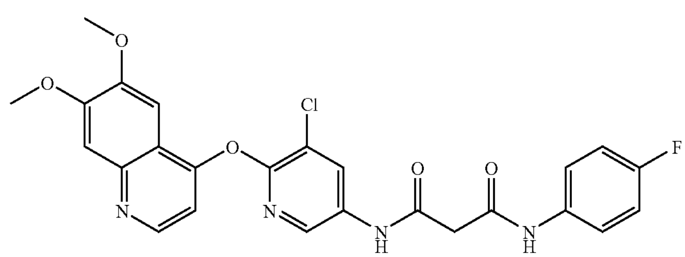 |
| 71 | N-(4-{[6,7-bis(methyloxy)quinolin-4-yl]oxy}-3-fluorophenyl)-N'-(1,2,3,4-tetrahydronaphthalen-2-yl)ethanediamide | 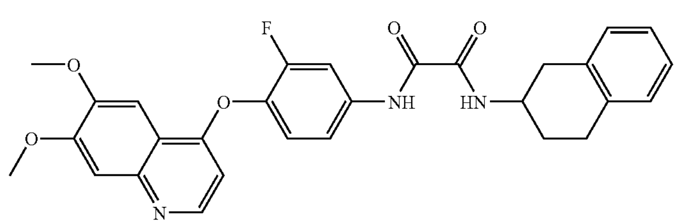 |

TABLE 1-continued

| Entry | Name | Structure |
|---|---|---|
| 72 | N-(4-{[6,7-bis(methyloxy)quinolin-4-yl]oxy}-3-fluorophenyl)-N'-[2-(1-methylpyrrolidin-2-yl)ethyl]ethanediamide | 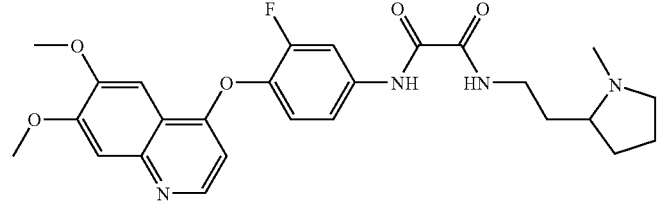 |
| 73 | N-(4-{[6,7-bis(methyloxy)quinolin-4-yl]oxy}-3-fluorophenyl)-N'-[2-(phenyloxy)ethyl]ethanediamide | 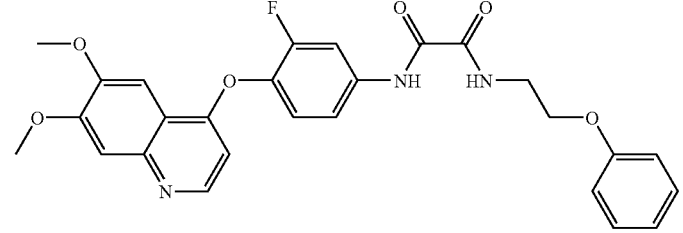 |
| 74 | N-(4-{[6,7-bis(methyloxy)quinolin-4-yl]oxy}-3-fluorophenyl)-N'-[2-hydroxy-1-(phenylmethyl)ethyl]urea | 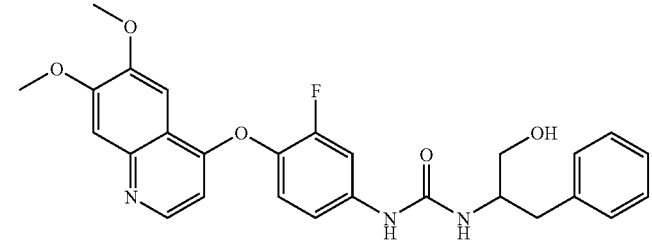 |
| 75 | 1-(4-{[6,7-bis(methyloxy)quinolin-4-yl]oxy}-3-fluorophenyl)-3-[(4-methylphenyl)sulfonyl]-4-(phenylmethyl)imidazolidin-2-one | 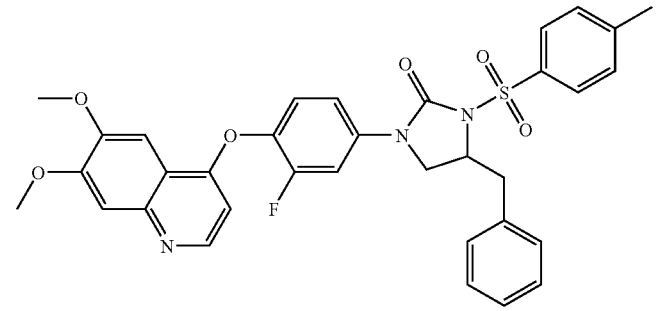 |
| 76 | N'-(4-{[6,7-bis(methyloxy)quinolin-4-yl]oxy}-3-fluorophenyl)-N-methyl-N-(2-phenylethyl)ethanediamide | 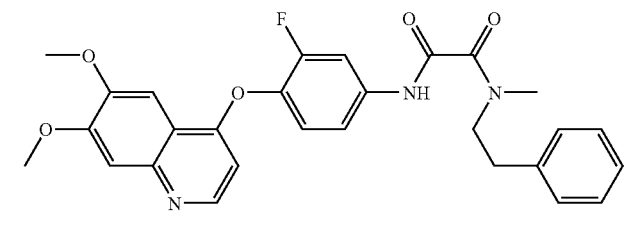 |
| 77 | N-(4-{[6,7-bis(methyloxy)quinolin-4-yl]oxy}-3-fluorophenyl)-N'-{[3-(trifluoromethyl)phenyl]methyl}ethanediamide | 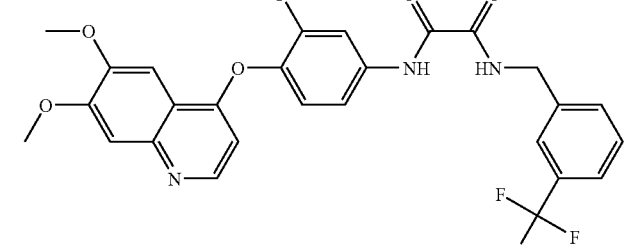 |

TABLE 1-continued

| Entry | Name | Structure |
|---|---|---|
| 78 | N-(4-{[6,7-bis(methyloxy)quinolin-4-yl]oxy}-3-fluorophenyl)-N'-{2-[3-(trifluoromethyl)phenyl]ethyl}ethanediamide | 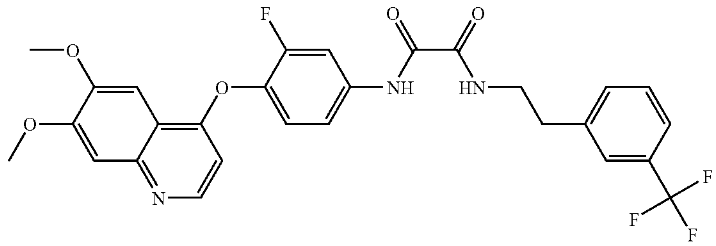 |
| 79 | N-(6-{[6,7-bis(methyloxy)quinolin-4-yl]oxy}-5-chloropyridin-3-yl)3-oxo-4-phenylbutanamide | 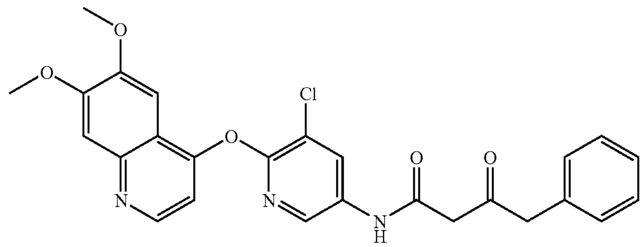 |
| 80 | N-(6-{[6,7-bis(methyloxy)quinolin-4-yl]oxy}-5-chloropyridin-3-yl)-2-[3-(trifluoromethyl)phenyl]acetamide | 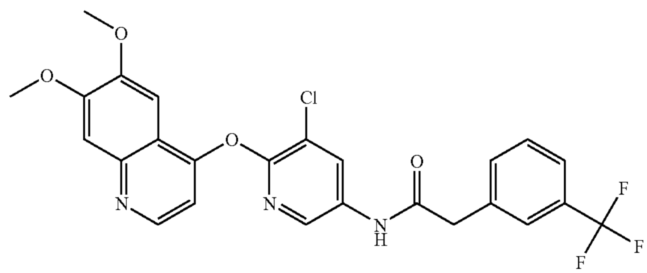 |
| 81 | 6-{[6,7-bis(methyloxy)quinolin-4-yl]oxy}-5-fluoro-N-[2-(phenyloxy)ethyl]-1,3-benzothiazol-2-amine | 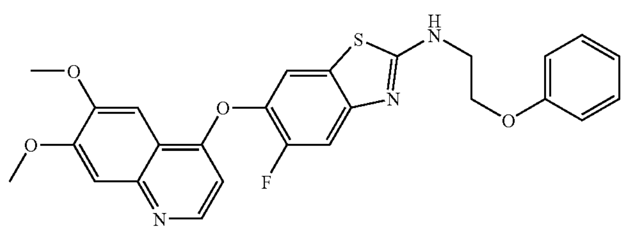 |
| 82 | 6-{[6,7-bis(methyloxy)quinolin-4-yl]oxy}-5-fluoro-N-(2-piperidin-1-ylethyl)-1,3-benzothiazol-2-amine | 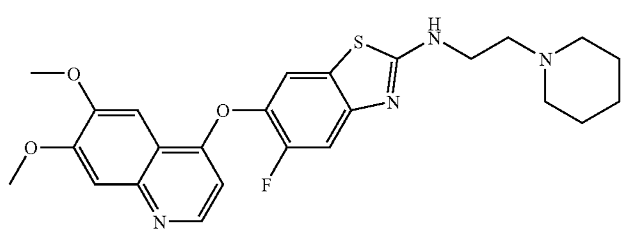 |
| 83 | 6-{[6,7-bis(methyloxy)quinolin-4-yl]oxy}-5-fluoro-N-methyl-N-(2-phenylethyl)-1,3-benzothiazol-2-amine | 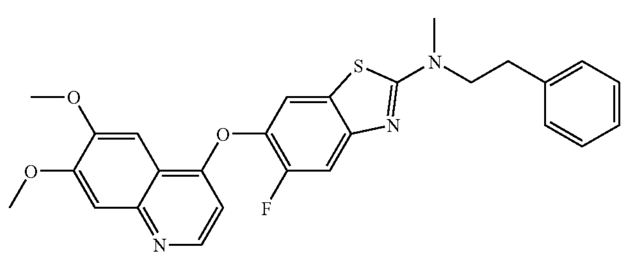 |

TABLE 1-continued

| Entry | Name | Structure |
|---|---|---|
| 84 | 6-{[6,7-bis(methyloxy)quinolin-4-yl]oxy}-5-fluoro-N-(2-pyrrolidin-1-ylethyl)-1,3-benzothiazol-2-amine | 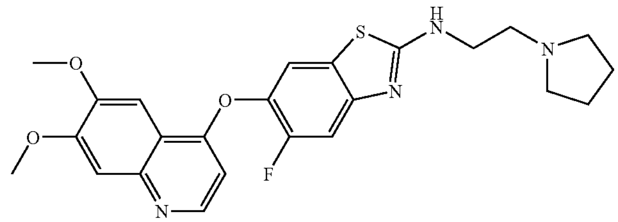 |
| 85 | 6-{[6,7-bis(methyloxy)quinolin-4-yl]oxy}-5-fluoro-N-{[3-(trifluoromethyl)phenyl]methyl}-1,3-benzothiazol-2-amine | 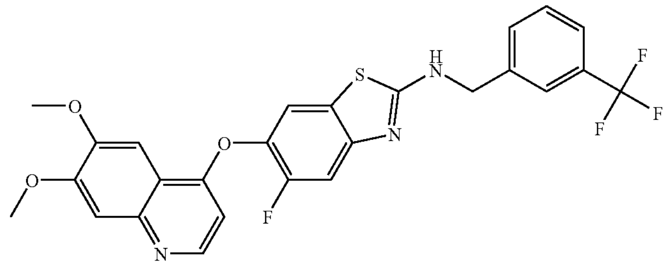 |
| 86 | 6-{[6,7-bis(methyloxy)quinolin-4-yl]oxy}-5-fluoro-N-{2-[3-(trifluoromethyl)phenyl]ethyl}-1,3-benzothiazol-2-amine | 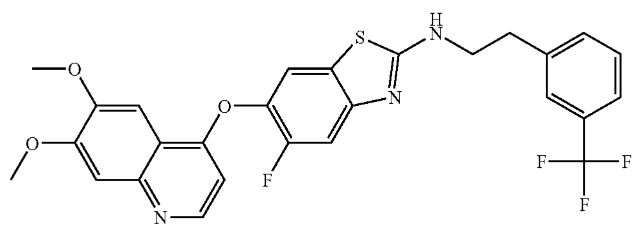 |
| 87 | N-(6-{[6,7-bis(methyloxy)quinolin-4-yl]oxy}-5-chloropyridin-3-yl)-N'-[3-(trifluoromethyl)phenyl]propanediamide | 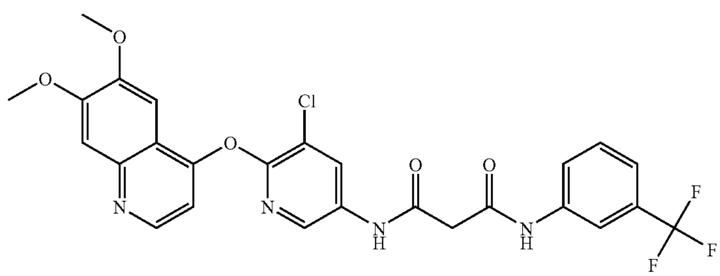 |
| 88 | N-(6-{[6,7-bis(methyloxy)quinolin-4-yl]oxy}-5-fluoro-1,3-benzothiazol-2-yl)-2-[3-(trifluoromethyl)phenyl]acetamide | 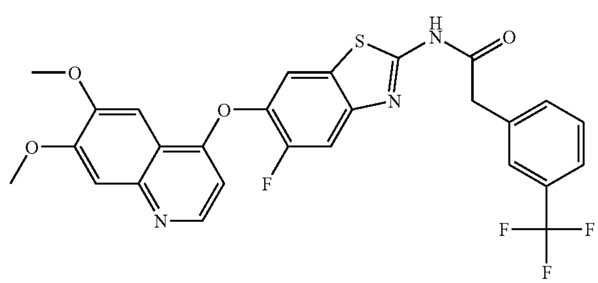 |
| 89 | N1-(4-{[6,7-bis(methyloxy)quinolin-4-yl]oxy}-3-fluorophenyl)-N2-{[3-(trifluoromethyl)phenyl]methyl}glycinamide | 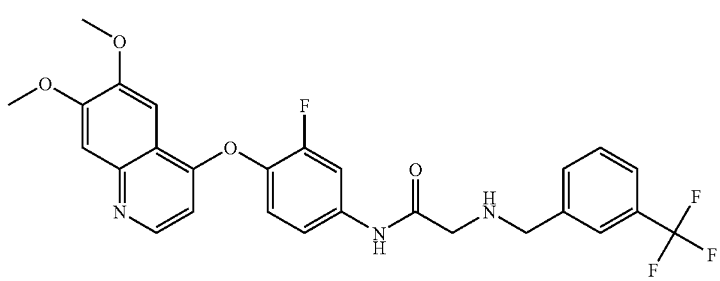 |

TABLE 1-continued

| Entry | Name | Structure |
|---|---|---|
| 90 | N1-(4-{[6,7-bis(methyloxy)quinolin-4-yl]oxy}-3-fluorophenyl)-N2-(2-phenylethyl)glycinamide | 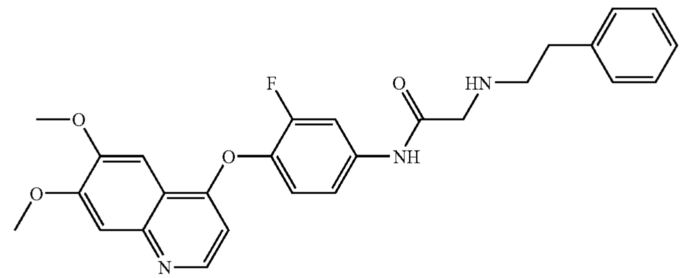 |
| 91 | N1-(4-{[6,7-bis(methyloxy)quinolin-4-yl]oxy}-3-fluorophenyl)-N2-{2-[3-(trifluoromethyl)phenyl]ethyl}glycinamide | 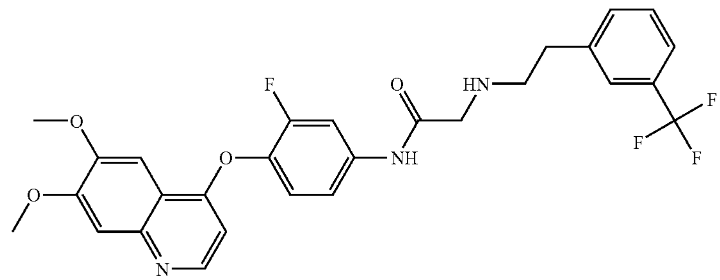 |
| 92 | benzyl-{[5-chloro-6-(6,7-dimethoxy-quinolin-4-yloxy)-pyridin-3-ylcarbamoyl]-methyl}-carbamic acid tert-butyl ester | 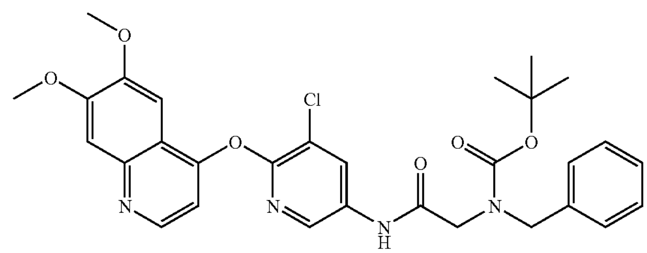 |
| 93 | N1-(6-{[6,7-bis(methyloxy)quinolin-4-yl]oxy}-5-chloropyridin-3-yl)-N2-(phenylmethyl)glycinamide | 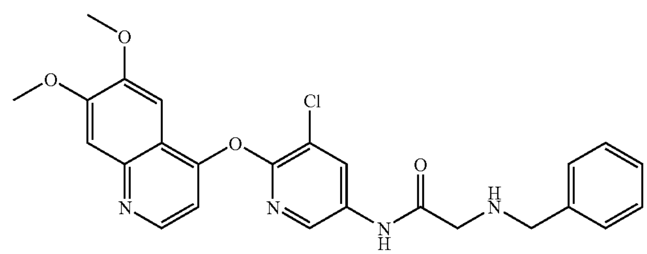 |
| 94 | N-(6-{[6,7-bis(methyloxy)quinolin-4-yl]oxy}-5-fluoro-1,3-benzothiazol-2-yl)-2-[3,5-bis(trifluoromethyl)phenyl]acetamide | 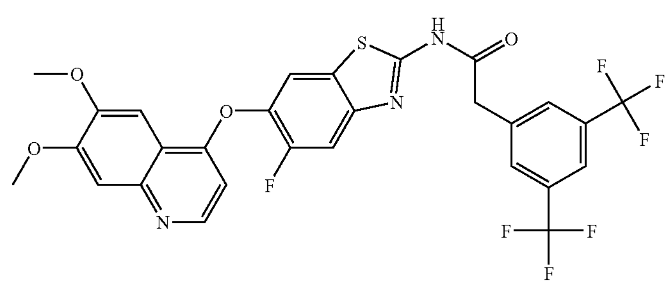 |
| 95 | N-(6-{[6,7-bis(methyloxy)quinolin-4-yl]oxy}-5-fluoro-1,3-benzothiazol-2-yl)-2-[2-chloro-5-(trifluoromethyl)phenyl]acetamide | 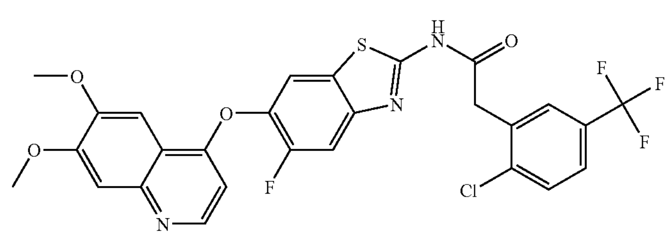 |

TABLE 1-continued

| Entry | Name | Structure |
|---|---|---|
| 96 | N-{3-fluoro-4-[(6-(methyloxy)-7-{[(1-methylpiperidin-4-yl)methyl]oxy}quinolin-4-yl)oxy]phenyl}-N'-(2-phenylethyl)ethanediamide | 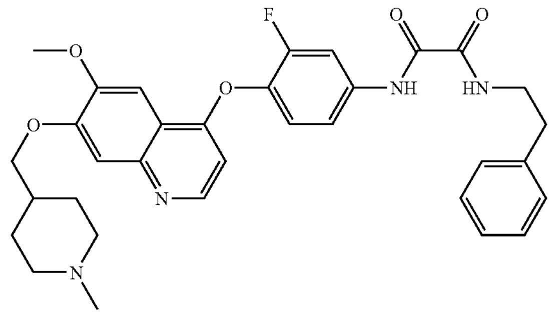 |
| 97 | N-(4-{[6,7-bis(methyloxy)quinolin-4-yl]oxy}-3-fluorophenyl)-N'-(1,2,3,4-tetrahydroisoquinolin-1-ylmethyl)ethanediamide | 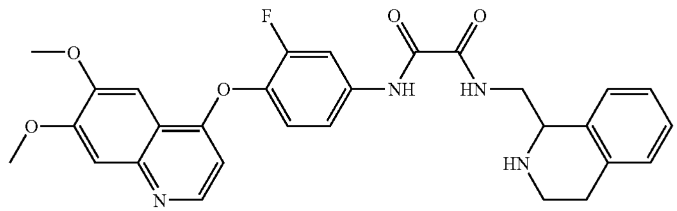 |
| 98 | N-(4-{[6,7-bis(methyloxy)quinolin-4-yl]oxy}-3-fluorophenyl)-N'-[(2-methyl-1,2,3,4-tetrahydroisoquinolin-1-yl)methyl]ethanediamide | 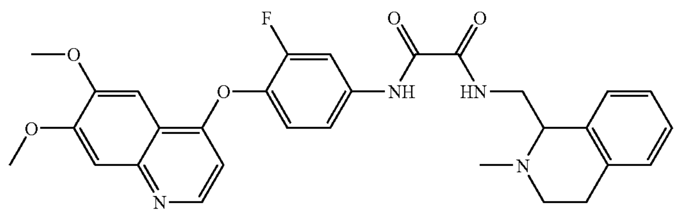 |
| 99 | N1-(4-{[6,7-bis(methyloxy)quinolin-4-yl]oxy}-3-fluorophenyl)-N2-methyl-N2-{[3-(trifluoromethyl)phenyl]methyl}glycinamide | 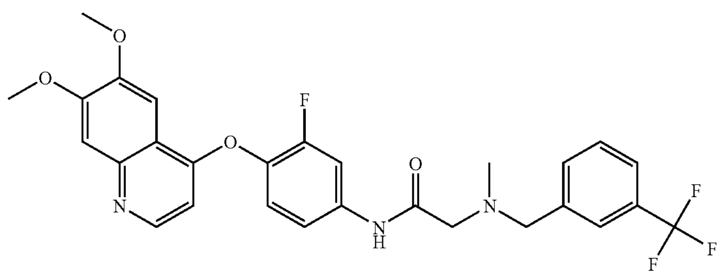 |
| 100 | N1-(4-{[6,7-bis(methyloxy)quinolin-4-yl]oxy}-3-fluorophenyl)-N2-methyl-N2-{2-[3-(trifluoromethyl)phenyl]ethyl}glycinamide | 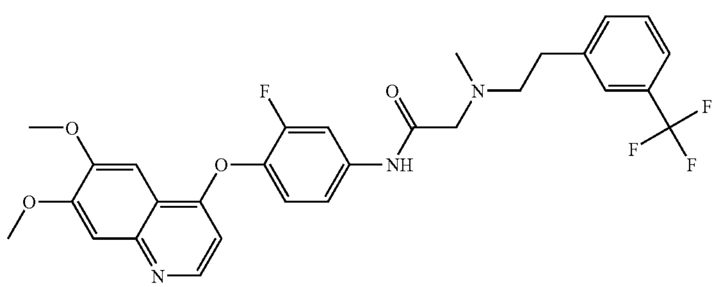 |
| 101 | N1-(4-{[6,7-bis(methyloxy)quinolin-4-yl]oxy}-3-fluorophenyl)-N2-methyl-N2-(2-phenylethyl)glycinamide | 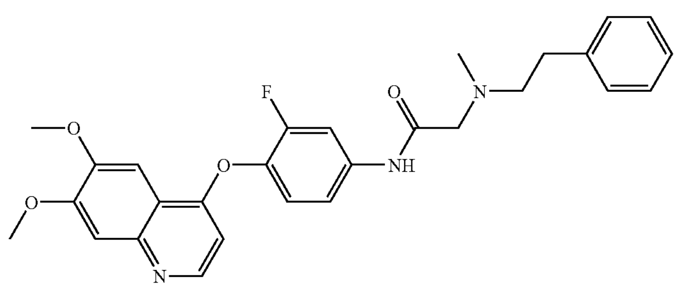 |

TABLE 1-continued

| Entry | Name | Structure |
|---|---|---|
| 102 | 1-(4-{[6,7-bis(methyloxy)quinolin-4-yl]oxy}-3-fluorophenyl)-4-(phenylmethyl)imidazolidin-2-one | 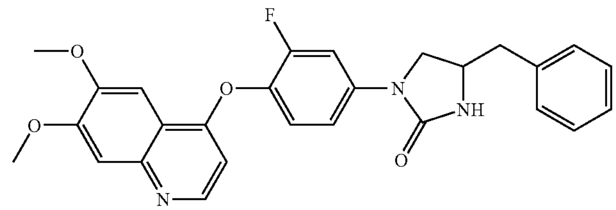 |
| 103 | N-(6-{[6,7-bis(methyloxy)quinolin-4-yl]oxy}pyridazin-3-yl)-N'-(4-fluorophenyl)propanediamide | 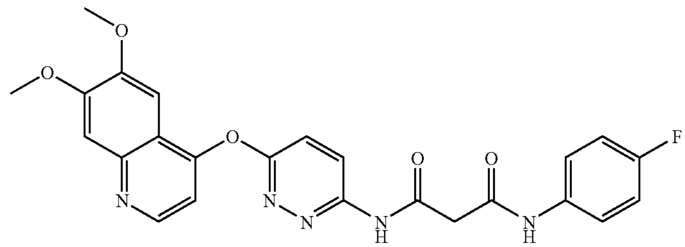 |
| 104 | N-(6-{[6,7-bis(methyloxy)quinolin-4-yl]oxy}-5-chloropyridin-3-yl)-N'-(2-chlorophenyl)propanediamide | 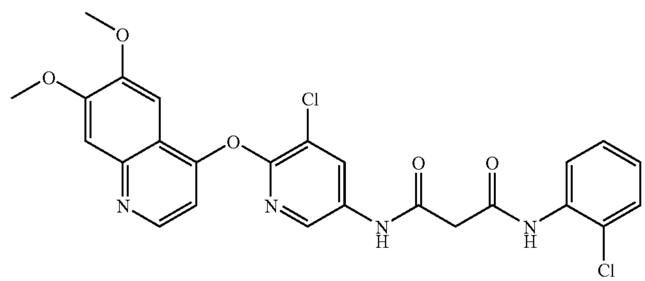 |
| 105 | N-(6-{[6,7-bis(methyloxy)quinolin-4-yl]oxy}-5-chloropyridin-3-yl)-N'-(3-chlorophenyl)propanediamide | 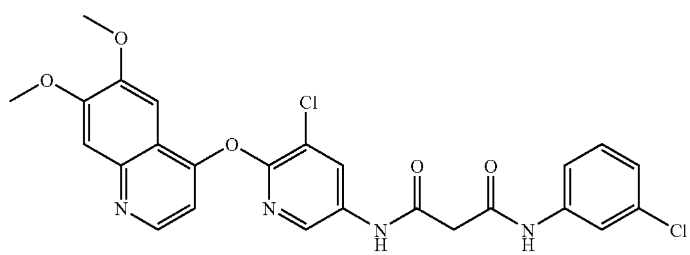 |
| 106 | N1-(6-{[6,7-bis(methyloxy)quinolin-4-yl]oxy}-5-chloropyridin-3-yl)-N2-methyl-N2-(phenylmethyl)glycinamide | 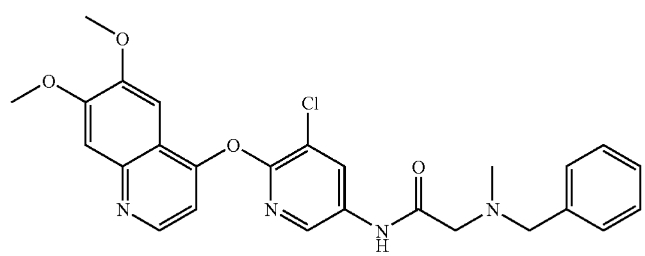 |
| 107 | N-(6-{[6,7-bis(methyloxy)quinolin-4-yl]oxy}-5-chloropyridin-3-yl)-N'-(4-chlorophenyl)propanediamide | 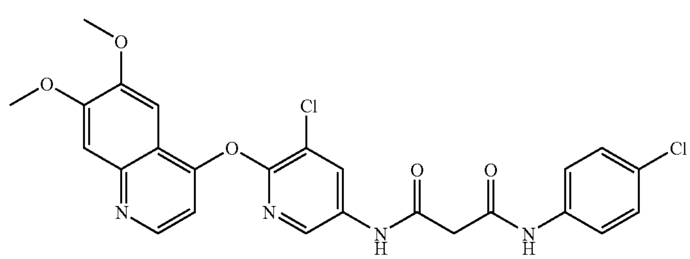 |

TABLE 1-continued

| Entry | Name | Structure |
|---|---|---|
| 108 | (2E)-N-(4-{[6,7-bis(methyloxy)quinolin-4-yl]oxy}phenyl)-2-[(methyloxy)imino]propanamide | 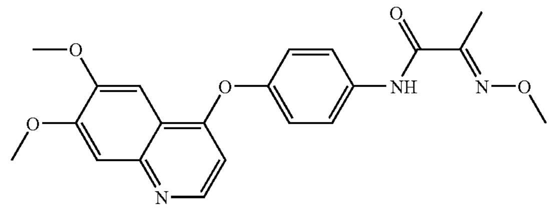 |
| 109 | (2E)-N-(4-{[6,7-bis(methyloxy)quinolin-4-yl]oxy}phenyl)-2-[(ethyloxy)imino]propanamide | 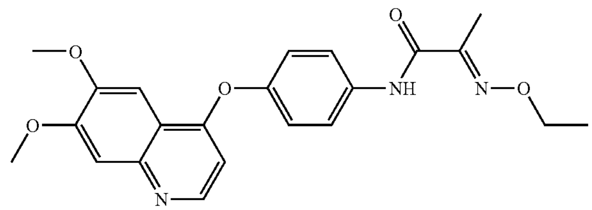 |
| 110 | (2E)-N-(4-{[6,7-bis(methyloxy)quinolin-4-yl]oxy}phenyl)-2-{[(phenylmethyl)oxy]imino}propanamide | 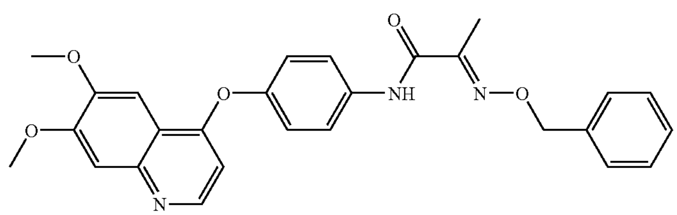 |
| 111 | N-(4-{[6,7-bis(methyloxy)quinolin-4-yl]oxy}phenyl)-1-(phenylmethyl)prolinamide | 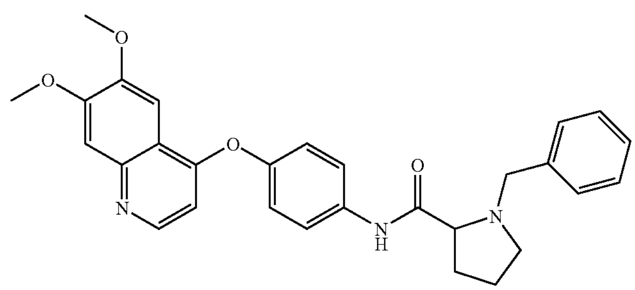 |
| 112 | 1-(4-{[6,7-bis(methyloxy)quinolin-4-yl]oxy}phenyl)-3-[(4-methylphenyl)sulfonyl]-4-(phenylmethyl)imidazolidin-2-one | 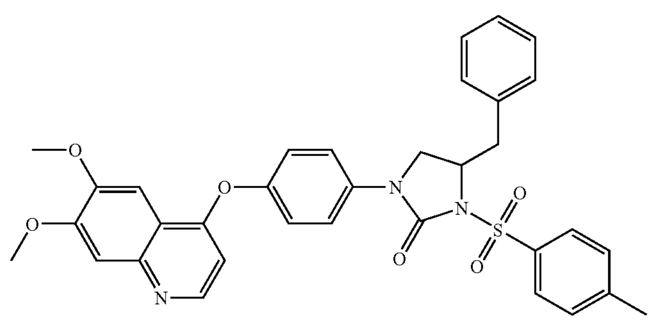 |
| 113 | 1-(4-{[6,7-bis(methyloxy)quinolin-4-yl]oxy}phenyl)-4-(phenylmethyl)imidazolidin-2-one | 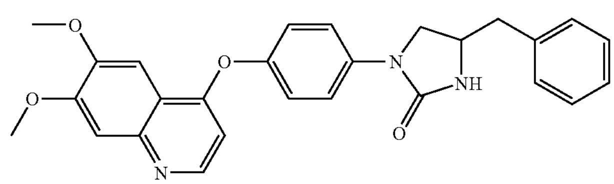 |

TABLE 1-continued

| Entry | Name | Structure |
|---|---|---|
| 114 | N-(4-{[6,7-bis(methyloxy)quinolin-4-yl]oxy}phenyl)-4-(phenylmethyl)-4,5-dihydro-1,3-oxazol-2-amine | 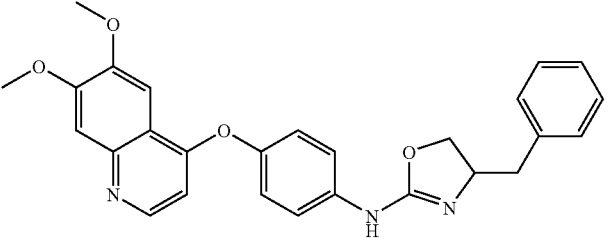 |
| 115 | 6,7-bis(methyloxy)-4-({4-[4-(phenylmethyl)piperazin-1-yl]phenyl}oxy)quinoline | 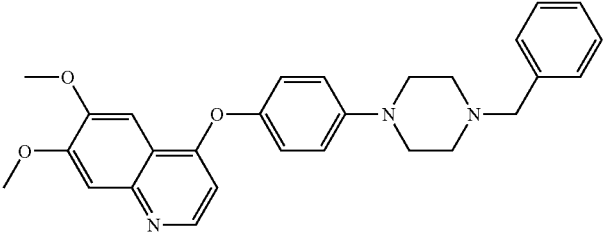 |
| 116 | 1-(4-{[6,7-bis(methyloxy)quinolin-4-yl]oxy}phenyl)-4-(phenylmethyl)piperazin-2-one | 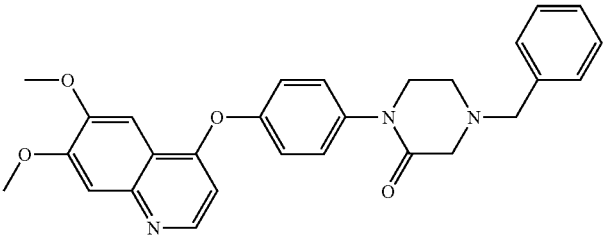 |
| 117 | N1-(4-{[6,7-bis(methyloxy)quinolin-4-yl]oxy}phenyl)-N2-(phenylmethyl)alaninamide | 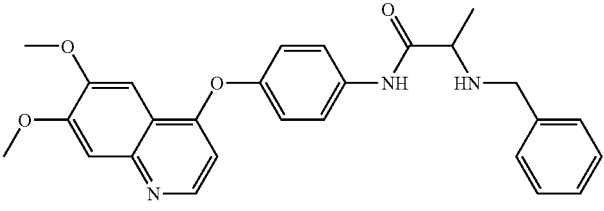 |
| 118 | N1-(4-{[6,7-bis(methyloxy)quinolin-4-yl]oxy}phenyl)-N2-methyl-N2-(phenylmethyl)alaninamide | 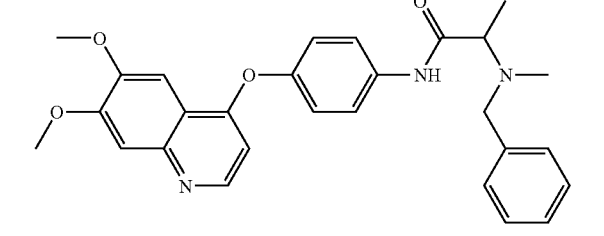 |
| 119 | N1-(4-{[6,7-bis(methyloxy)quinolin-4-yl]oxy}phenyl)-N2-(phenylmethyl)leucinamide | 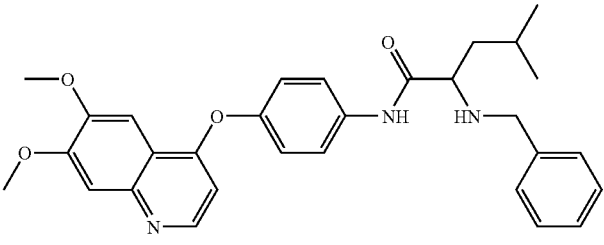 |

TABLE 1-continued

| Entry | Name | Structure |
|---|---|---|
| 120 | N1-(4-{[6,7-bis(methyloxy)quinolin-4-yl]oxy}phenyl)-N2-methyl-N2-(phenylmethyl)leucinamide | 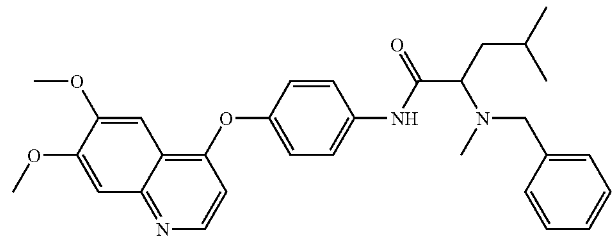 |
| 121 | N1-(4-{[6,7-bis(methyloxy)quinolin-4-yl]oxy}phenyl)-N2-(phenylmethyl)valinamide | 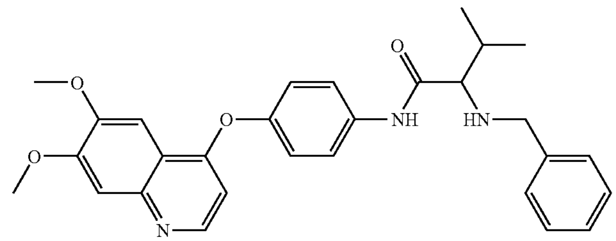 |
| 122 | 4-(6,7-dimethoxy-quinolin-4-ylamino)-N-(3-phenyl-propyl)-benzamide | 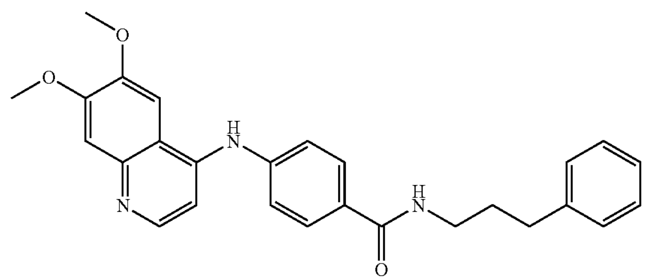 |
| 123 | 4-benzyl-1-[4-(6,7-dimethoxy-quinolin-4-yloxy)-phenyl]-tetrahydro-pyrimidin-2-one | 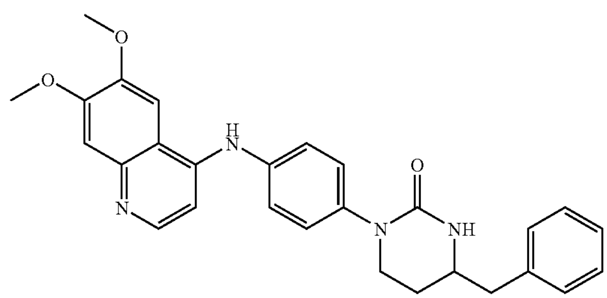 |
| 124 | N-{3-Fluoro-4-[6-methoxy-7-(piperidin-4-ylmethoxy)-quinolin-4-yloxy]-phenyl}-N'-phenethyl-oxalamide | 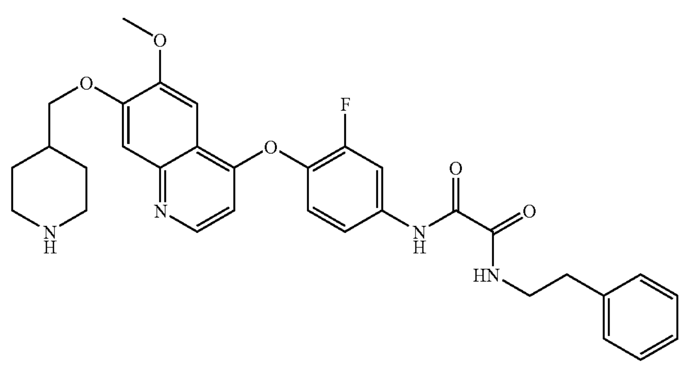 |

TABLE 1-continued

| Entry | Name | Structure |
|---|---|---|
| 125 | 2-(Benzyl-methyl-amino)-N-[4-(6,7-dimethoxy-quinolin-4-yloxy)-phenyl]-3-methyl-butyramide (note: Alphabetic order of prefixes ignored while selecting parent chain) | 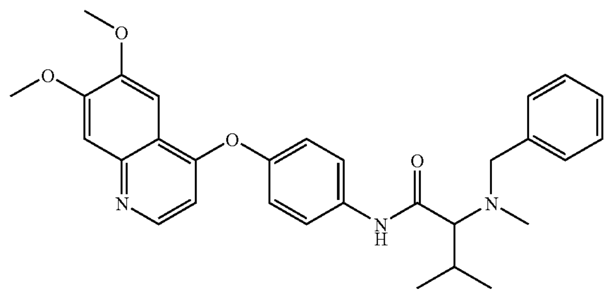 |
| 126 | N-[4-(6,7-Dimethoxy-quinolin-4-yloxy)-phenyl]-2-phenoxyimino-propionamide | 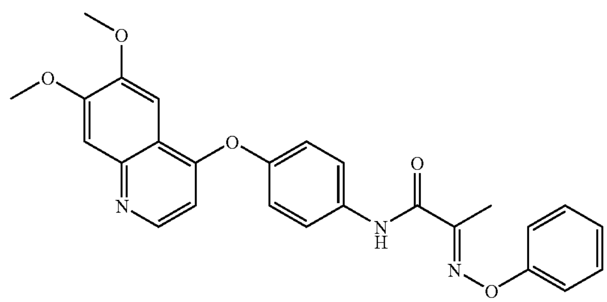 |
| 127 | 2-Benzyloxyimino-N-[4-(6,7-dimethoxy-quinolin-4-yloxy)-phenyl]-2-phenyl-acetamide | 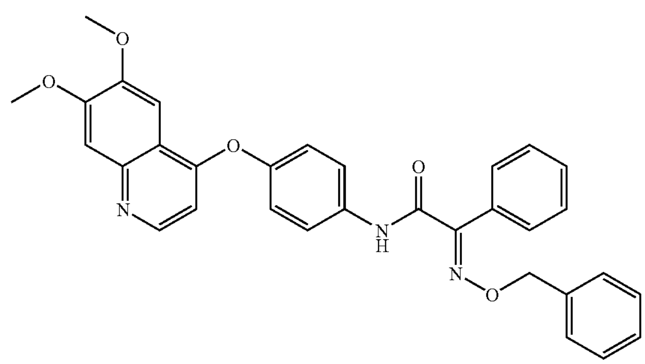 |
| 128 | 4-[4-(4-Benzyl-piperidin-1-yl)-phenoxy]-6,7-dimethoxy-quinoline | 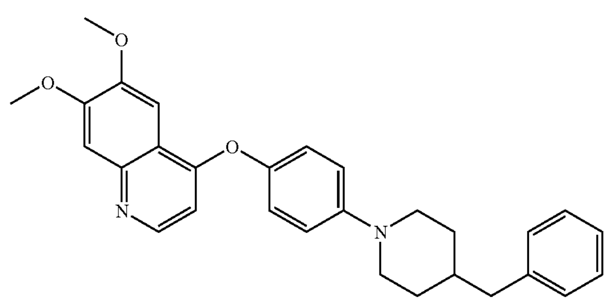 |

TABLE 1-continued

| Entry | Name | Structure |
|---|---|---|
| 129 | N-[4-(6,7-Dimethoxy-quinolin-4-yloxy)-3-fluoro-phenyl]-N'-(2-isopropyl-1,2,3,4-tetrahydro-isoquinolin-1-ylmethyl)-oxalamide | 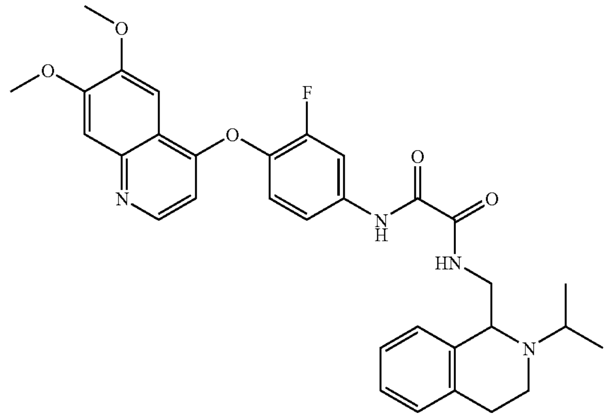 |
| 130 | N-[4-(6,7-Dimethoxy-quinolin-4-yloxy)-3-fluoro-phenyl]-N'-(2-ethyl-1,2,3,4-tetrahydro-isoquinolin-1-ylmethyl)-oxalamide | 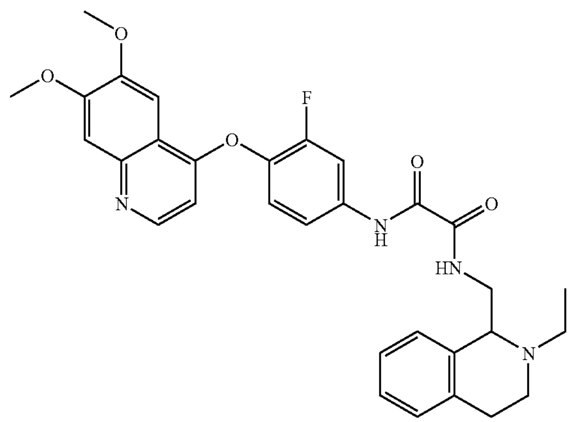 |
| 131 | 4-(4-{3-Chloro-5-[2-(4-fluoro-phenylcarbamoyl)-acetylamino]-pyridin-2-yloxy}-6-methoxy-quinolin-7-yloxymethyl)-piperidine-1-carboxylic acid tert-butyl ester | 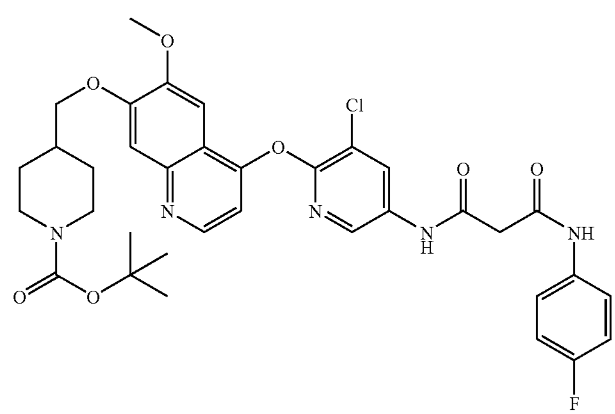 |

TABLE 1-continued
| Entry | Name | Structure |
|---|---|---|
| 132 | N-{5-Chloro-6-[6-methoxy-7-(piperidin-4-ylmethoxy)-quinolin-4-yloxy]-pyridin-3-yl}-N'-(4-fluoro-phenyl)-malonamide | 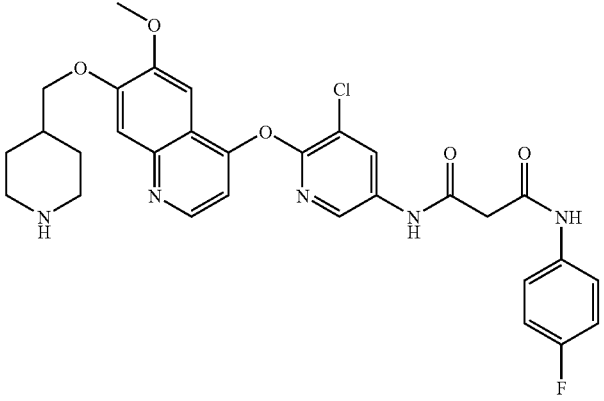 |
| 133 | N-{5-Chloro-6-[6-methoxy-7-(1-methyl-piperidin-4-ylmethoxy)-quinolin-4-yloxy]-pyridin-3-yl}-N'-(4-fluoro-phenyl)-malonamide | 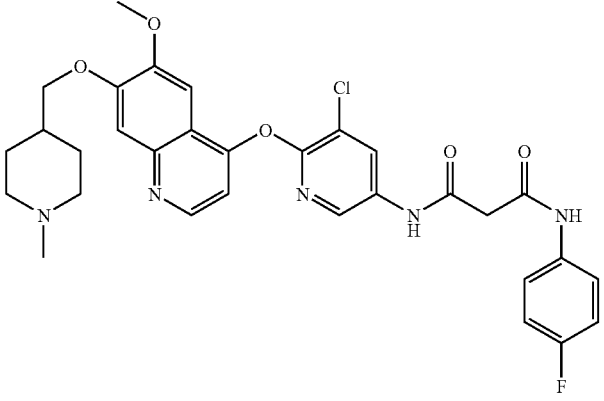 |
| 134 | N-{4-[7-(3-Diethylamino-propoxy)-6-methoxy-quinolin-4-yloxy]-3-fluoro-phenyl}-N'-phenethyl-oxalamide | 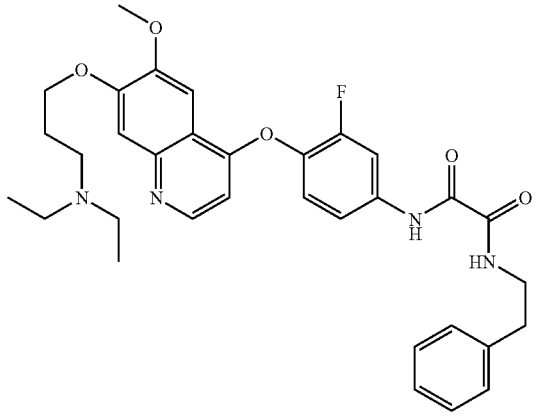 |

TABLE 1-continued

| Entry | Name | Structure |
|---|---|---|
| 135 | N-{3-Fluoro-4-[6-methoxy-7-(3-morpholin-4-yl-propoxy)-quinolin-4-yloxy]-phenyl}-N'-phenethyl-oxalamide | 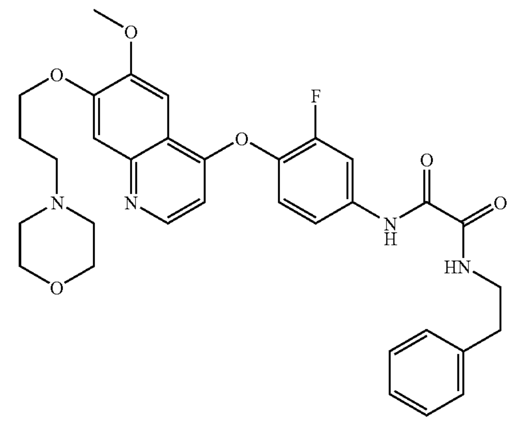 |
| 136 | N-{3-Fluoro-4-[6-methoxy-7-(3-piperidin-1-yl-propoxy)-quinolin-4-yloxy]-phenyl}-N'-phenethyl-oxalamide | 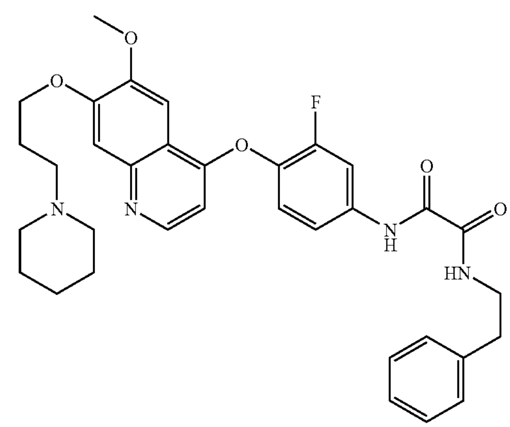 |
| 137 | N-{4-[7-(2-Diethylamino-ethoxy)-6-methoxy-quinolin-4-yloxy]-3-fluoro-phenyl}-N'-phenethyl-oxalamide | 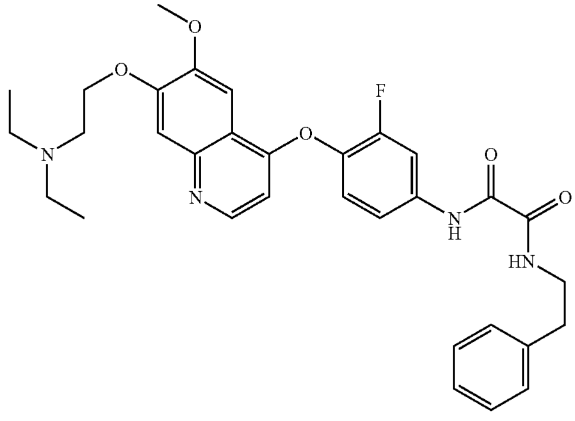 |

TABLE 1-continued

| Entry | Name | Structure |
|---|---|---|
| 138 | N-{3-Fluoro-4-[6-methoxy-7-(1-methyl-piperidin-4-ylmethoxy)-quinolin-4-yloxy]-phenyl}-N'-methyl-N'-phenethyl-oxalamide | 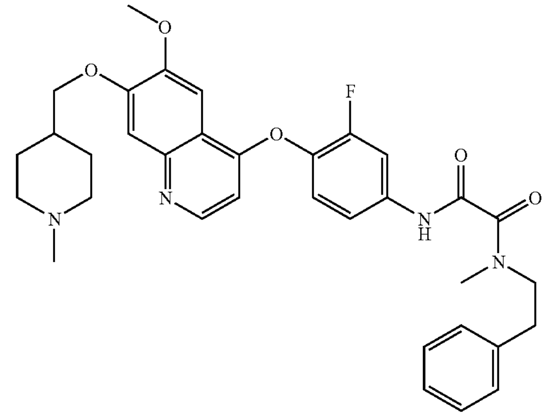 |
| 139 | N-{3-Fluoro-4-[6-methoxy-7-(2-methyl-octahydro-cyclopenta[c]pyrrol-5-ylmethoxy)-quinolin-4-yloxy]-phenyl}-N'-phenethyl-oxalamide | 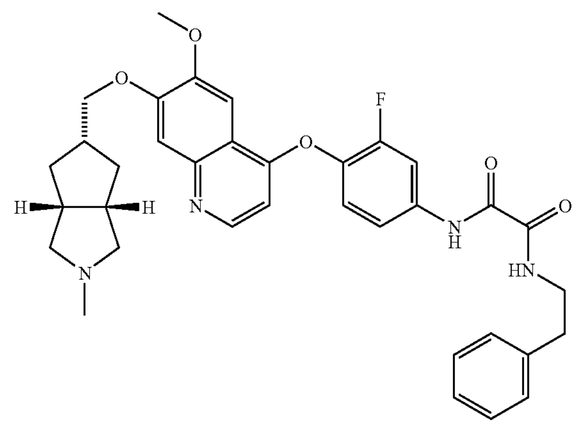 |
| 140 | N-{3-Fluoro-4-[6-methoxy-7-(2-methyl-octahydro-cyclopenta[c]pyrrol-5-ylmethoxy)-quinazolin-4-yloxy]-phenyl}-N'-phenethyl-oxalamide | 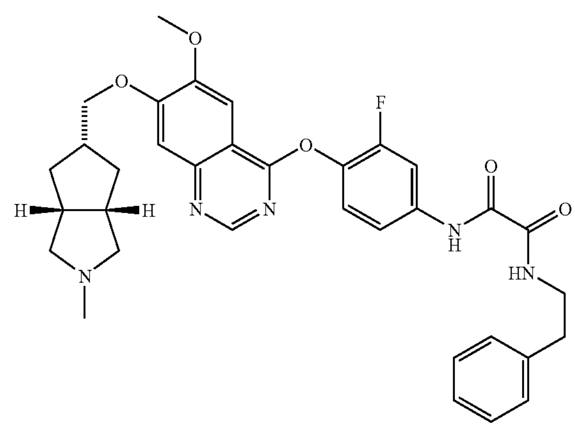 |

TABLE 1-continued

| Entry | Name | Structure |
|---|---|---|
| 141 | 2-(3,4-Dihydro-1H-isoquinolin-2-yl)-N-{3-fluoro-4-[6-methoxy-7-(1-methyl-piperidin-4-ylmethoxy)-quinolin-4-yloxy]-phenyl}-2-oxo-acetamide | 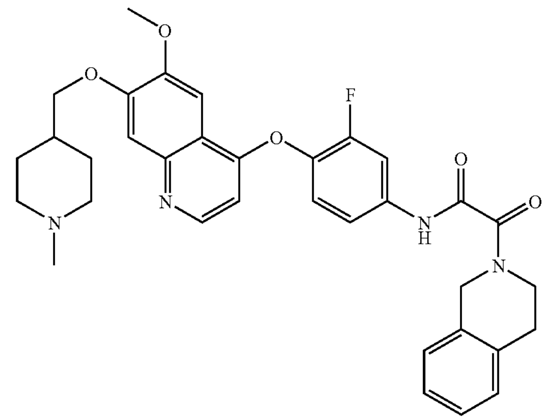 |
| 142 | N-{3-Fluoro-4-[6-methoxy-7-piperidin-4-ylmethoxy)-quinolin-4-yloxy]-phenyl}-2-oxo-2-(3-phenyl-pyrrolidin-1-yl)-acetamide | 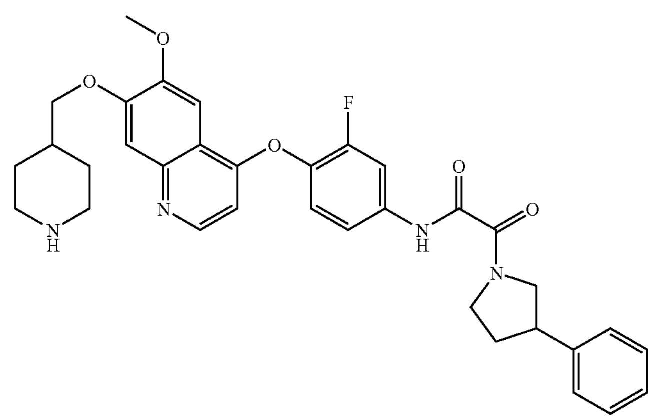 |
| 143 | N-{3-Fluoro-4-[6-methoxy-7-(piperidin-4-ylmethoxy)-quinolin-4-yloxy]-phenyl}-2-oxo-2-(2-phenyl-morpholin-4-yl)-acetamide | 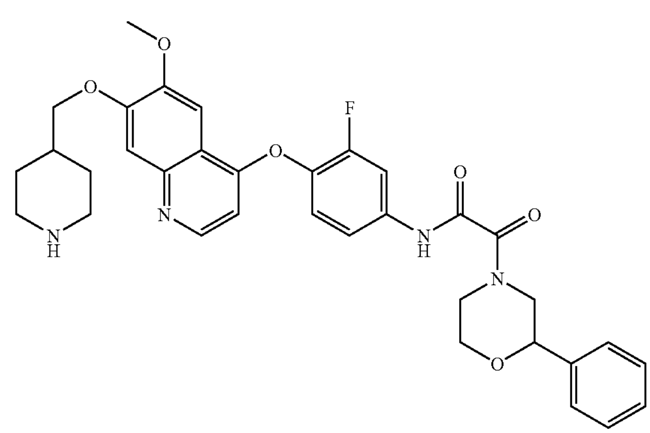 |

TABLE 1-continued

| Entry | Name | Structure |
|---|---|---|
| 144 | N-(2-Dimethylamino-2-phenyl-ethyl)-N'-{3-fluoro-4-[6-methoxy-7-(piperidin-4-ylmethoxy)-quinolin-4-yloxy]-phenyl}-oxalamide | 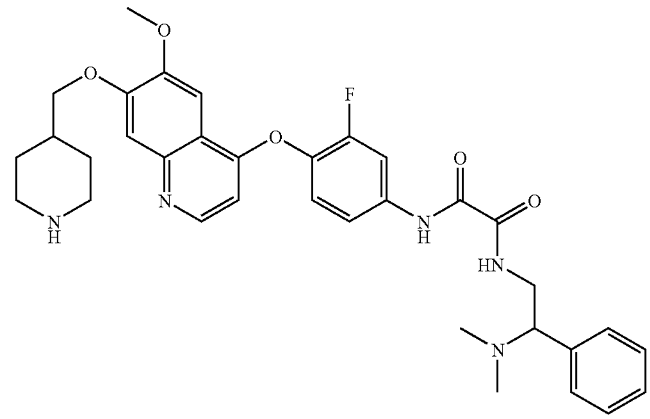 |
| 145 | N-{3-Fluoro-4-[6-methoxy-7-(piperidin-4-ylmethoxy)-quinolin-4-yloxy]-phenyl}-N'-(2-oxo-2-phenyl-ethyl)-oxalamide | 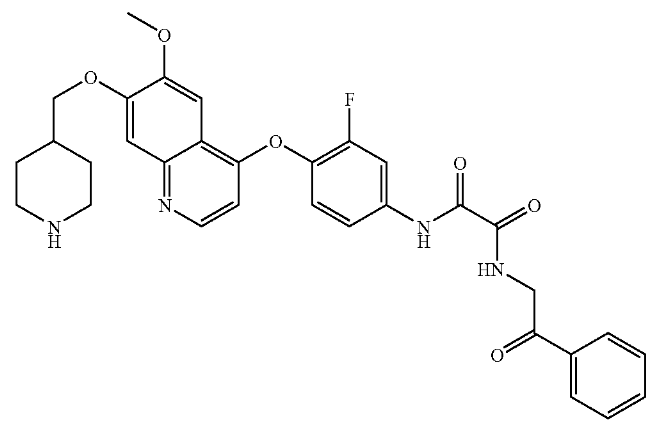 |
| 146 | N-[5-Chloro-6-(6,7-dimethoxy-quinolin-4-yloxy)-pyridin-3-yl]-2,2-difluoro-N'-(4-fluoro-phenyl)-malonamide | 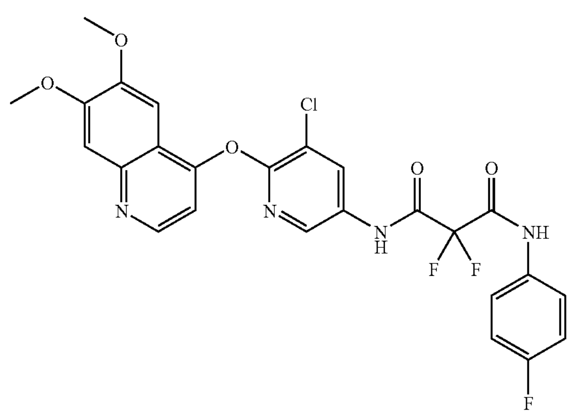 |

TABLE 1-continued

| Entry | Name | Structure |
|---|---|---|
| 147 | N-Benzyl-N'-{3-fluoro-4-[6-methoxy-7-(1-methyl-piperidin-4-ylmethoxy)-quinolin-4-yloxy]-phenyl}-oxalamide | 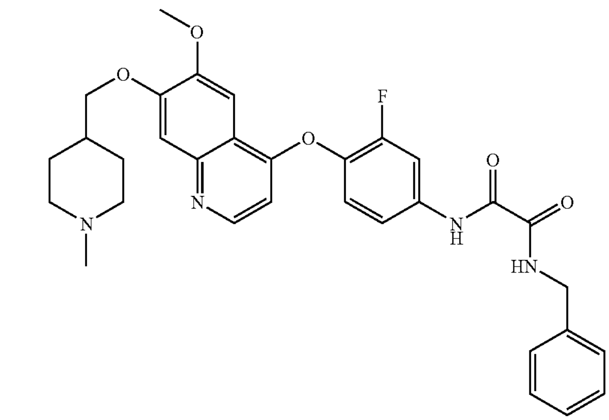 |
| 148 | N-{3-Fluoro-4-[6-methoxy-7-(piperidin-4-ylmethoxy)-quinolin-4-yloxy]-phenyl}-N'-[2-(2-fluoro-phenyl)-ethyl]-oxalamide | 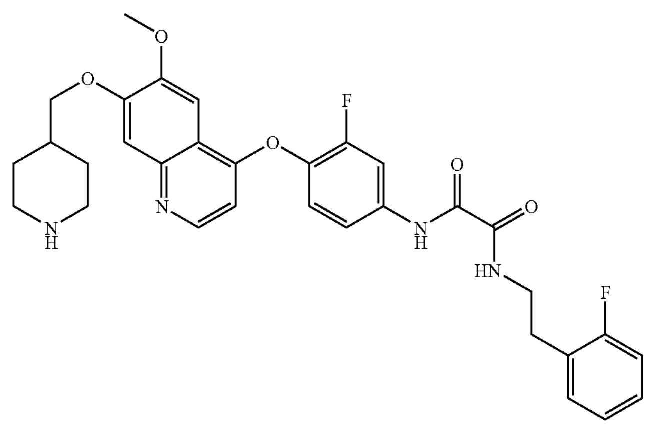 |
| 149 | N-[2-(3-Chloro-phenyl)-ethyl]-N'-{3-fluoro-4-[6-methoxy-7-(piperidin-4-ylmethoxy)-quinolin-4-yloxy]-phenyl}-oxalamide | 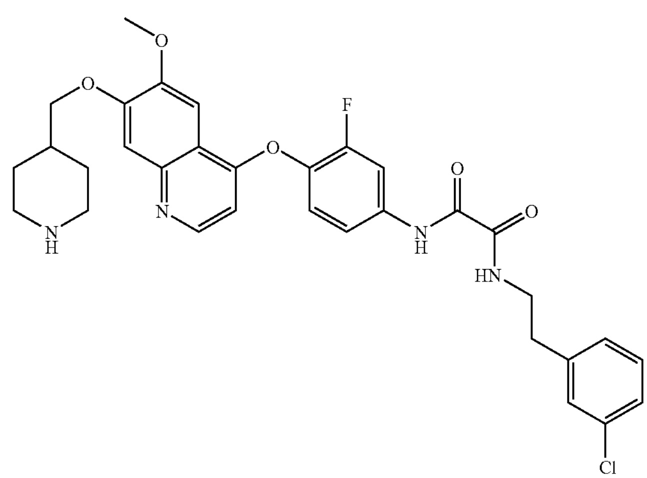 |

TABLE 1-continued
| Entry | Name | Structure |
|---|---|---|
| 150 | N-{3-Fluoro-4-[6-methoxy-7-(piperidin-4-ylmethoxy)-quinolin-4-yloxy]-phenyl}-N'-[2-(2-methoxy-phenyl)-ethyl]-oxalamide | 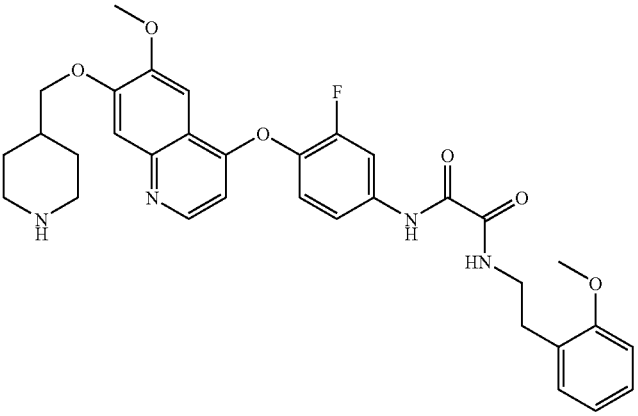 |
| 151 | N-{3-Fluoro-4-[6-methoxy-7-(piperidin-4-ylmethoxy)-quinolin-4-yloxy]-phenyl}-N'-(2-pyridin-3-yl-ethyl)-oxalamide | 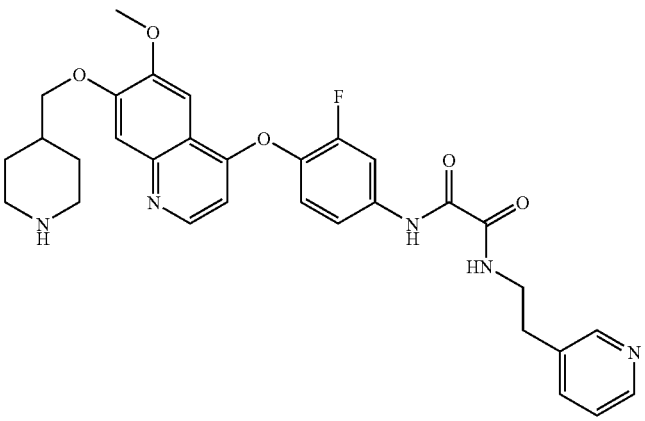 |
| 152 | N-Benzyl-N'-{3-fluoro-4-[6-methoxy-7-(piperidin-4-ylmethoxy)-quinolin-4-yloxy]-phenyl}-oxalamide | 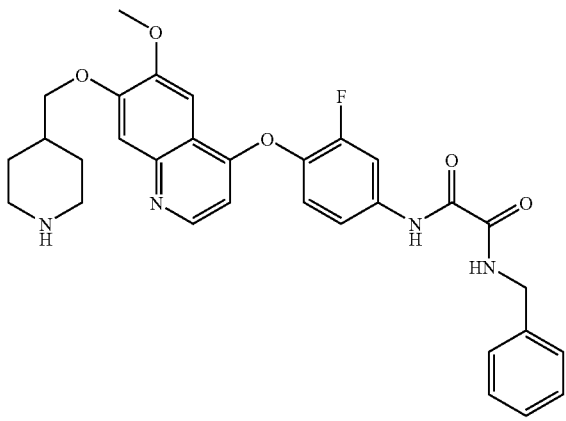 |

TABLE 1-continued

| Entry | Name | Structure |
|---|---|---|
| 153 | N-[2-(2,5-Dimethoxy-phenyl)-ethyl]-N'-{3-fluoro-4-[6-methoxy-7-(piperidin-4-ylmethoxy)-quinolin-4-yloxy]-phenyl}-oxalamide | 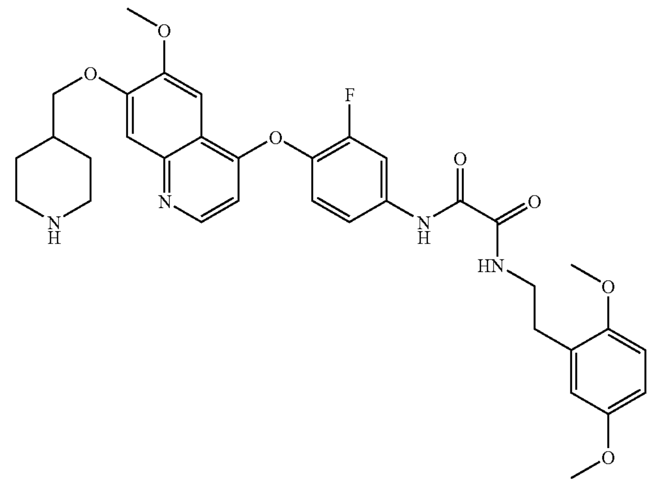 |
| 154 | N-{3-Fluoro-4-[6-methoxy-7-(piperidin-4-ylmethoxy)-quinolin-4-yloxy]-phenyl}-N'-[2-(2-trifluoromethyl-phenyl)-ethyl]-oxalamide | 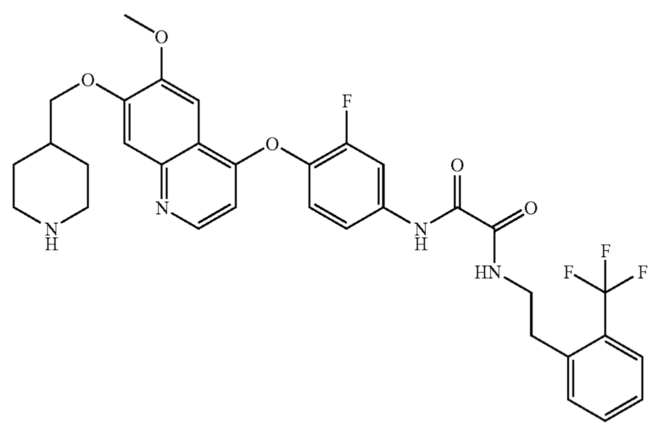 |
| 155 | N-[2-(2-Ethoxy-phenyl)-ethyl]-N'-{3-fluoro-4-[6-methoxy-7-(piperidin-4-ylmethoxy)-quinolin-4-yloxy]-phenyl}-oxalamide | 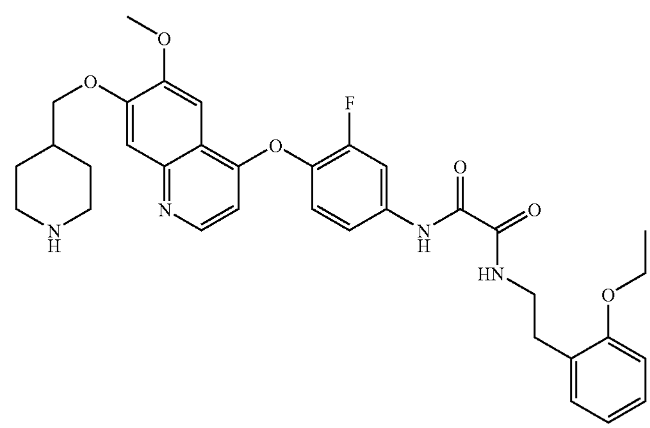 |

TABLE 1-continued

| Entry | Name | Structure |
|---|---|---|
| 156 | N-[2-(2,4-Dimethyl-phenyl)-ethyl]-N'-{3-fluoro-4-[6-methoxy-7-(piperidin-4-ylmethoxy)-quinolin-4-yloxy]-phenyl}-oxalamide | 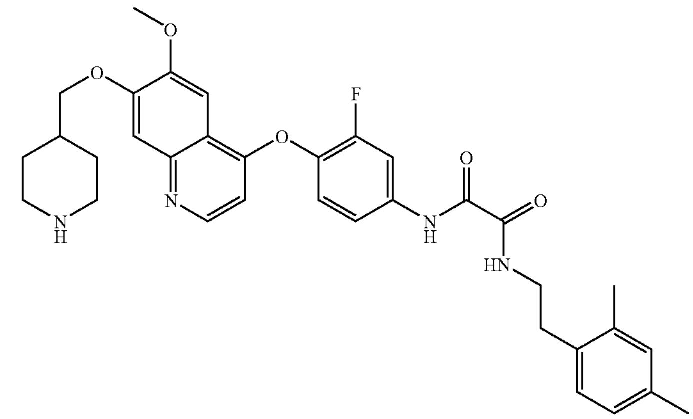 |
| 157 | N-{3-Fluoro-4-[6-methoxy-7-(piperidin-4-ylmethoxy)-quinolin-4-yloxy]-phenyl}-N'-(1S-phenyl-2-p-tolyl-ethyl)-oxalamide | 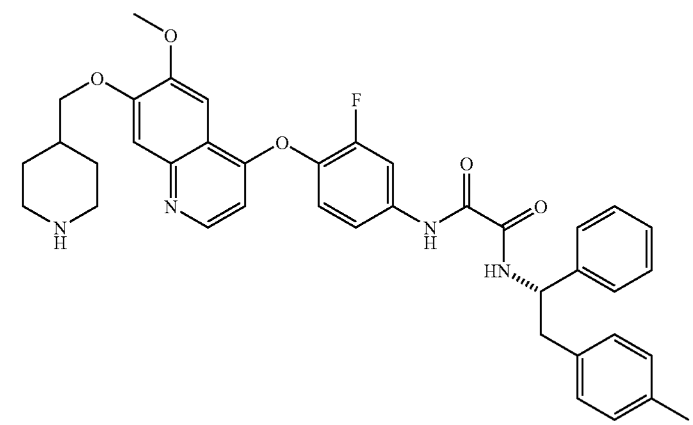 |
| 158 | N-[2-(4-Chloro-phenyl)-ethyl]-N'-{3-fluoro-4-[6-methoxy-7-(piperidin-4-ylmethoxy)-quinolin-4-yloxy]-phenyl}-oxalamide | 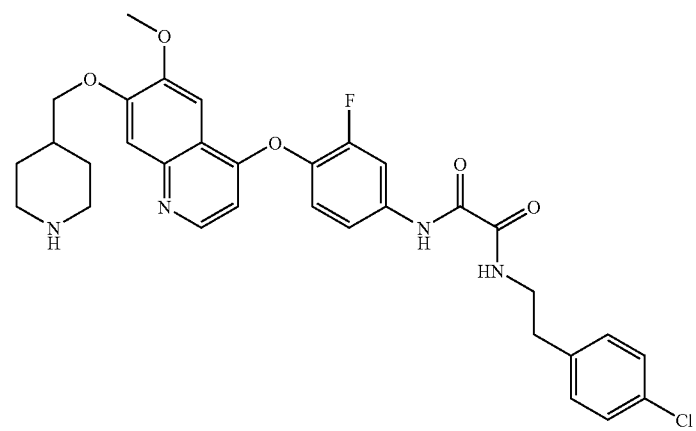 |
| 159 | N-{3-Fluoro-4-[6-methoxy-7-(1-methyl-piperidin-4-ylmethoxy)-quinolin-4-yloxy]-phenyl}-oxalamic acid | 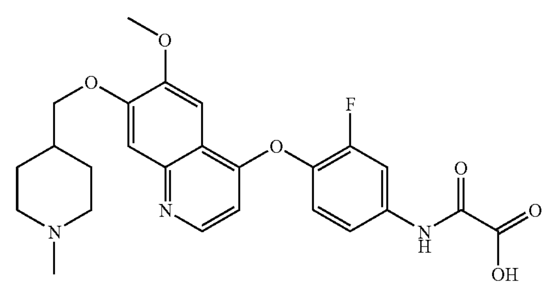 |

TABLE 1-continued

| Entry | Name | Structure |
|---|---|---|
| 160 | N-{3-Fluoro-4-[6-methoxy-7-(piperidin-4-ylmethoxy)-quinolin-4-yloxy]-phenyl}-N'-[2-(3-fluoro-phenyl)-ethyl]-oxalamide | 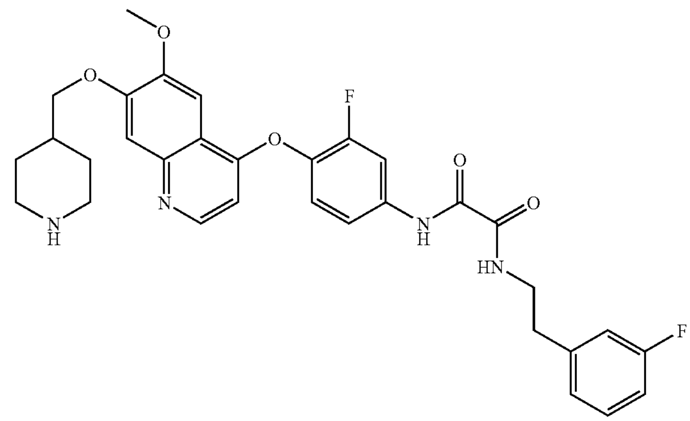 |
| 161 | N-[2-(2-Chloro-phenyl)-ethyl]-N'-{3-fluoro-4-[6-methoxy-7-(piperidin-4-ylmethoxy)-quinolin-4-yloxy]-phenyl}-oxalamide | 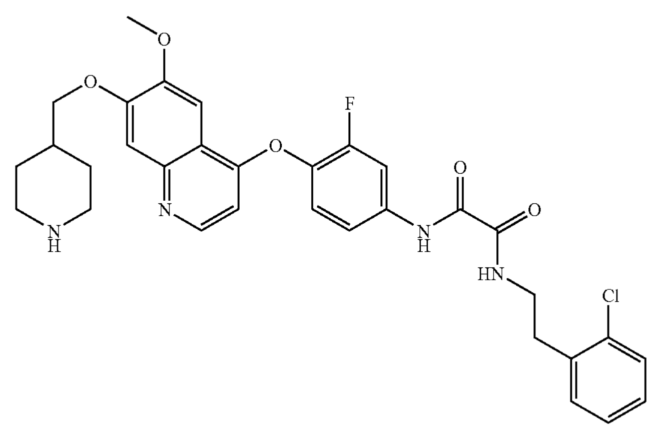 |
| 162 | N-{3-Fluoro-4-[6-methoxy-7-(piperidin-4-ylmethoxy)-quinolin-4-yloxy]-phenyl}-N'-[2-(3-methoxy-phenyl)-ethyl]-oxalamide | 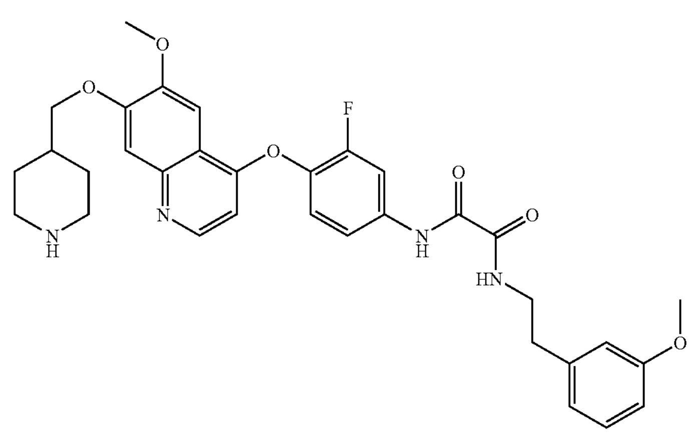 |

TABLE 1-continued

| Entry | Name | Structure |
|---|---|---|
| 163 | N-(1,2-Diphenyl-ethyl)-N'-{3-fluoro-4-[6-methoxy-7-(piperidin-4-ylmethoxy)-quinolin-4-yloxy]-phenyl}-oxalamide | 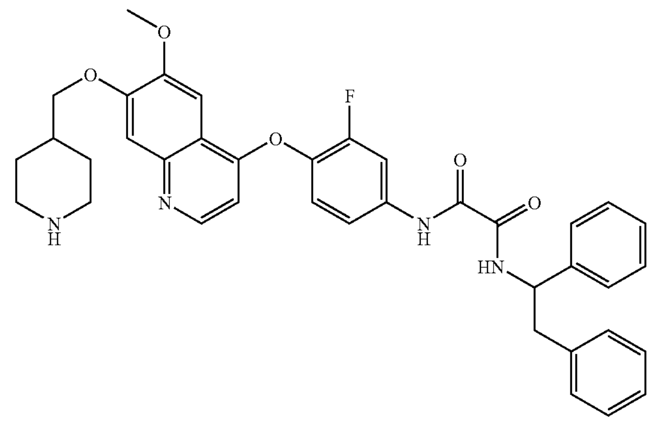 |
| 164 | N-[2-(2,4-Dichloro-phenyl)-ethyl]-N'-{3-fluoro-4-[6-methoxy-7-(piperidin-4-ylmethoxy)-quinolin-4-yloxy]-phenyl}-oxalamide | 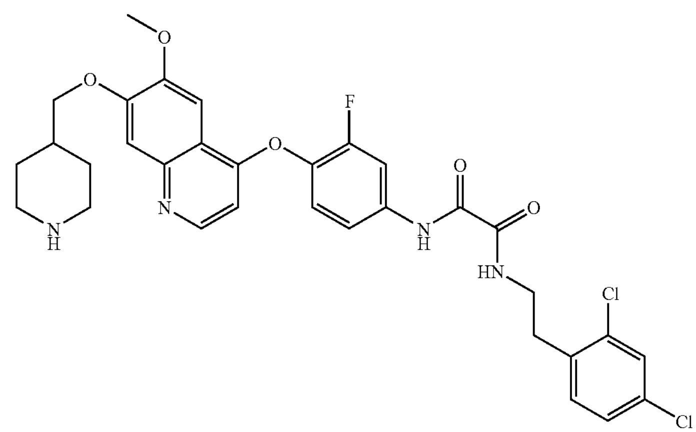 |
| 165 | N-[2-(3,4-Dimethoxy-phenyl)-ethyl]-N'-{3-fluoro-4-[6-methoxy-7-(piperidin-4-ylmethoxy)-quinolin-4-yloxy]-phenyl}-oxalamide | 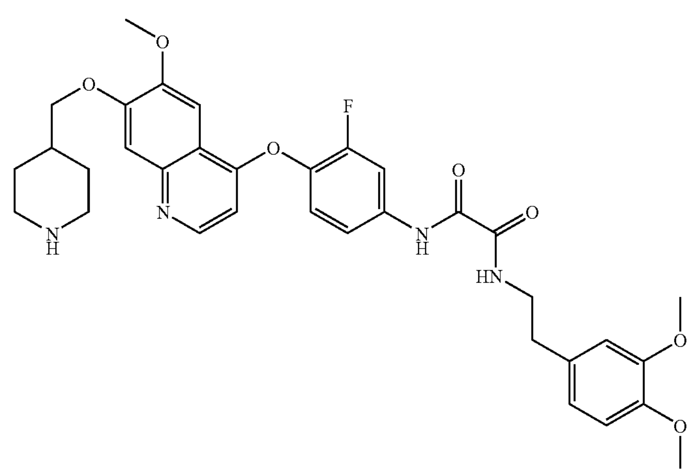 |

| Entry | Name | Structure |
|---|---|---|
| 166 | N-[2-(4-Ethyl-phenyl)-ethyl]-N'-{3-fluoro-4-[6-methoxy-7-(piperidin-4-ylmethoxy)-quinolin-4-yloxy]-phenyl}-oxalamide | 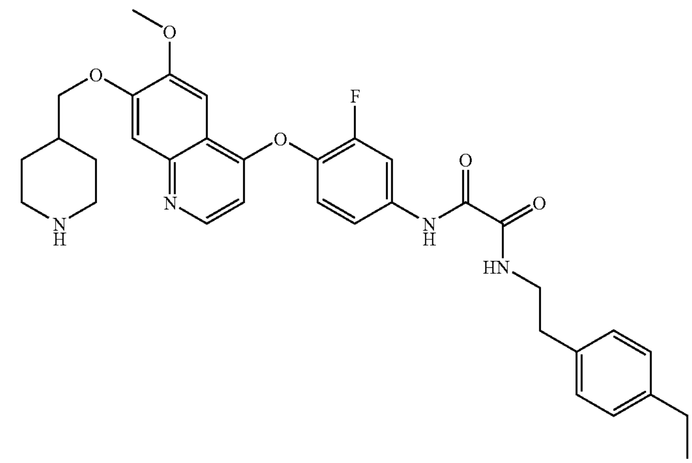 |
| 167 | N-[2-(4-Ethoxy-phenyl)-ethyl]-N'-{3-fluoro-4-[6-methoxy-7-(piperidin-4-ylmethoxy)-quinolin-4-yloxy]-phenyl}-oxalamide | 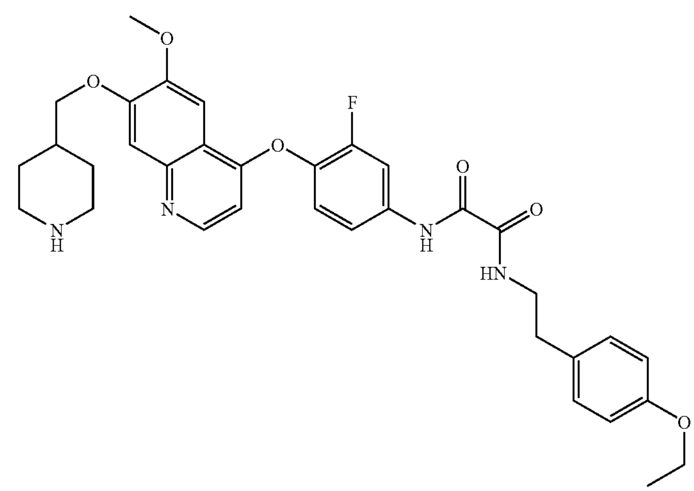 |
| 168 | N-[2-(4-Ethoxy-3-methoxy-phenyl)-ethyl]-N'-{3-fluoro-4-[6-methoxy-7-(piperidin-4-ylmethoxy)-quinolin-4-yloxy]-phenyl}-oxalamide | 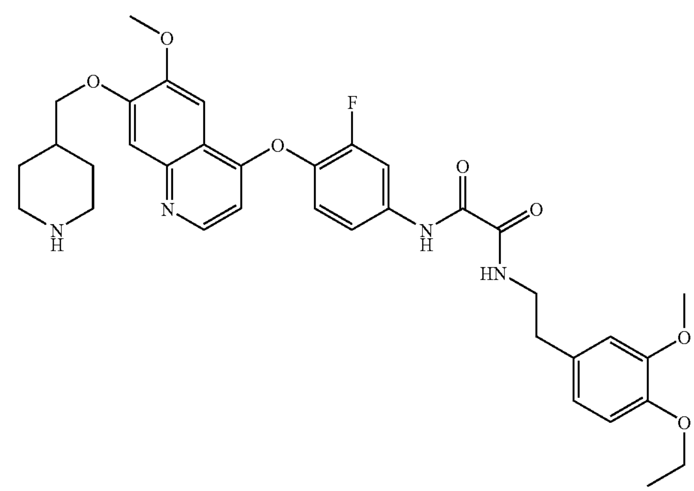 |

TABLE 1-continued

| Entry | Name | Structure |
|---|---|---|
| 169 | N-{3-Fluoro-4-[6-methoxy-7-(piperidin-4-ylmethoxy)-quinolin-4-yloxy]-phenyl}-N'-[2-(4-phenoxy-phenyl)-ethyl]-oxalamide | 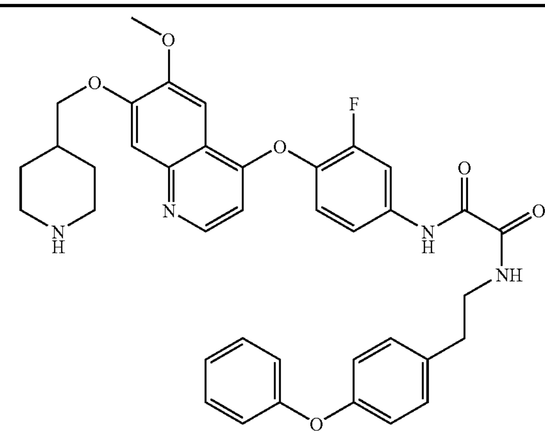 |
| 170 | N-[2-(3-Ethoxy-4-methoxy-phenyl)-ethyl]-N'-{3-fluoro-4-[6-methoxy-7-(piperidin-4-ylmethoxy)-quinolin-4-yloxy]-phenyl}-oxalamide | 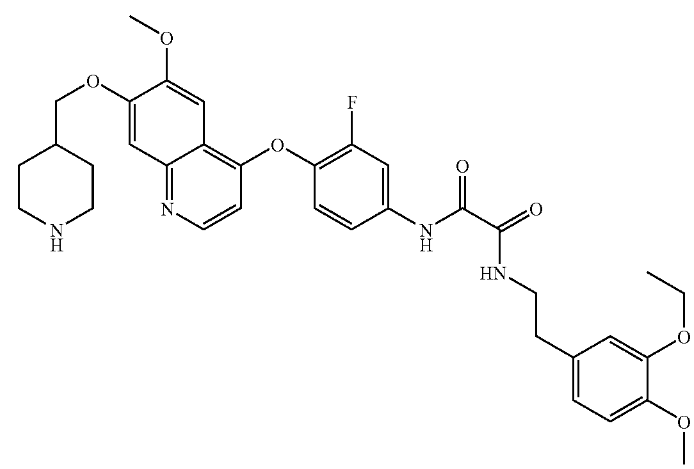 |
| 171 | N-{3-Fluoro-4-[6-methoxy-7-(piperidin-4-ylmethoxy)-quinolin-4-yloxy]-phenyl}-N'-(2-pyridin-2-yl-ethyl)-oxalamide | 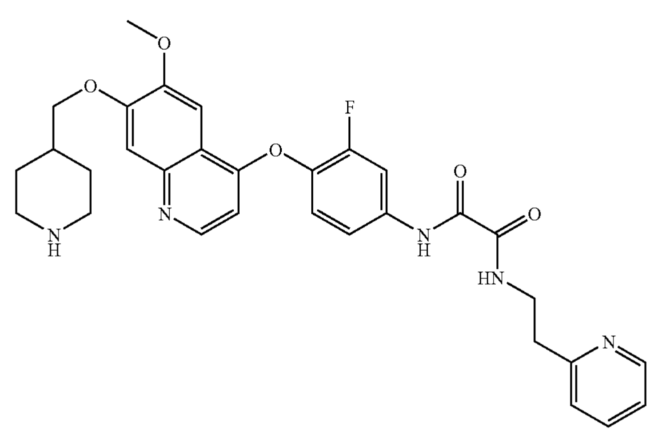 |

TABLE 1-continued

| Entry | Name | Structure |
|---|---|---|
| 172 | N-{3-Fluoro-4-[6-methoxy-7-(piperidin-4-ylmethoxy)-quinolin-4-yloxy]-phenyl}-N'-(2-pyridin-4-yl-ethyl)-oxalamide | 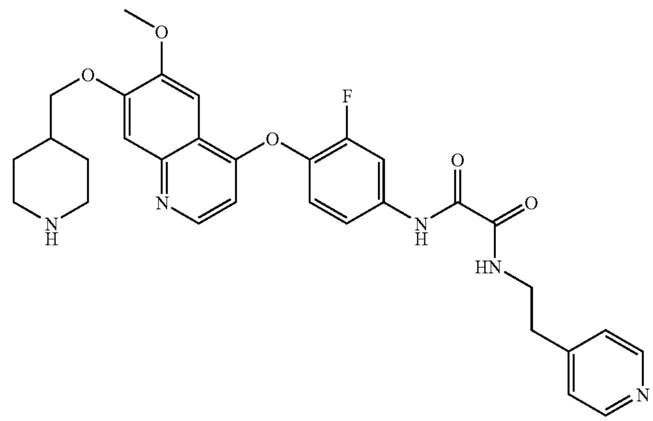 |
| 173 | N-{3-Fluoro-4-[6-methoxy-7-(piperidin-4-ylmethoxy)-quinolin-4-yloxy]-phenyl}-N'-[2-(4-fluoro-phenyl)-ethyl]-oxalamide | 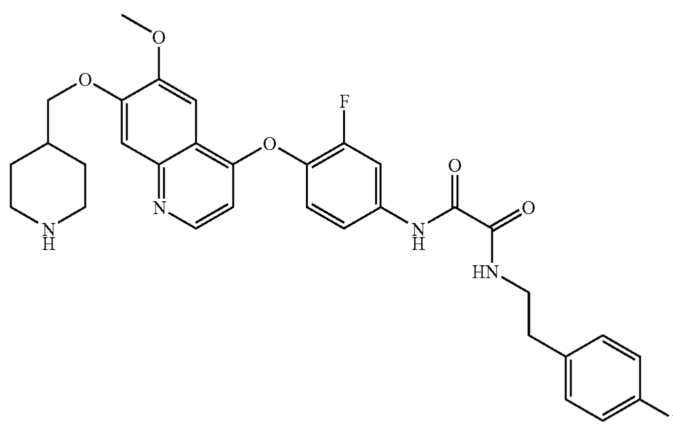 |
| 174 | N-[2-(2-Bromo-phenyl)-ethyl]-N'-{3-fluoro-4-[6-methoxy-7-(piperidin-4-ylmethoxy)-quinolin-4-yloxy]-phenyl}-oxalamide | 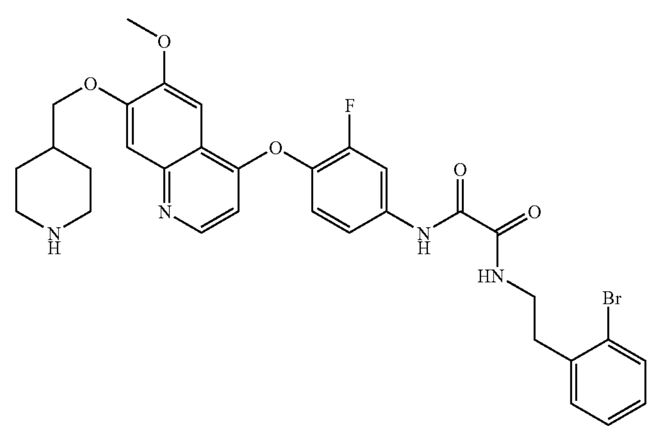 |

TABLE 1-continued

| Entry | Name | Structure |
|---|---|---|
| 175 | N-[2-(2-Chloro-6-fluoro-phenyl)-ethyl]-N'-{3-fluoro-4-[6-methoxy-7-(piperidin-4-ylmethoxy)-quinolin-4-yloxy]-phenyl}-oxalamide | 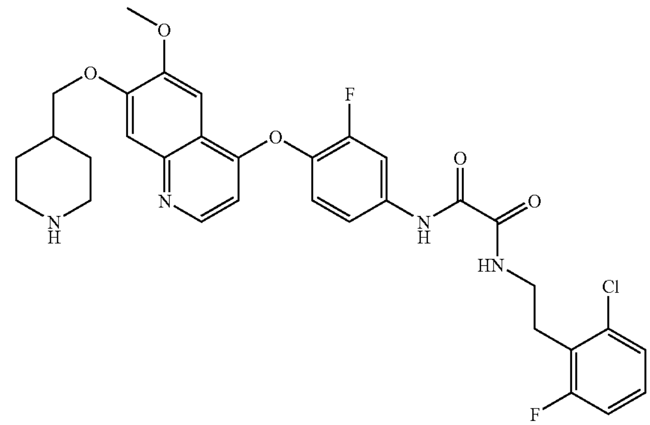 |
| 176 | N-{3-Fluoro-4-[6-methoxy-7-(piperidin-4-ylmethoxy)-quinolin-4-yloxy]-phenyl}-N'-(2R-phenyl-propyl)-oxalamide | 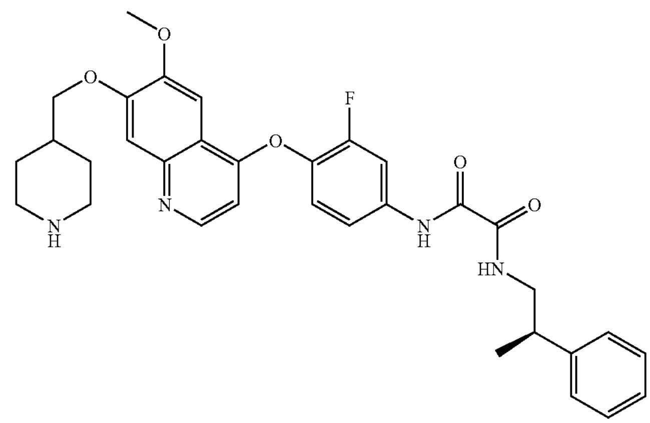 |
| 177 | N-{3-Fluoro-4-[6-methoxy-7-(piperidin-4-ylmethoxy)-quinolin-4-yloxy]-phenyl}-N'-indan-1-yl-oxalamide | 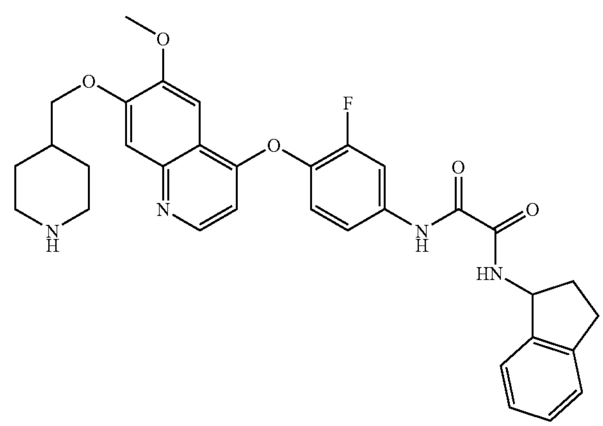 |
| 178 | N-{3-Fluoro-4-[6-methoxy-7-(1-methyl-piperidin-4-ylmethoxy)-quinolin-4-yloxy]-phenyl}-N'-isobutyl-oxalamide | 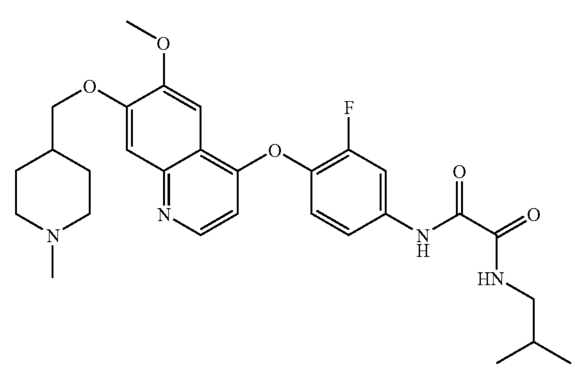 |

| Entry | Name | Structure |
|---|---|---|
| 179 | N-{3-Fluoro-4-[6-methoxy-7-(1-methyl-piperidin-4-ylmethoxy)-quinolin-4-yloxy]-phenyl}-N'-(3-methyl-butyl)-oxalamide | 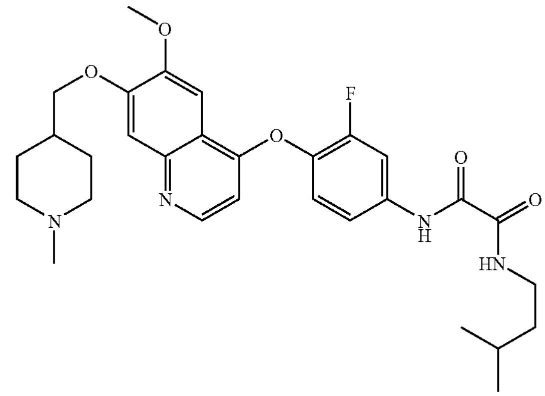 |
| 180 | N-{3-Fluoro-4-[6-methoxy-7-(1-methyl-piperidin-4-ylmethoxy)-quinolin-4-yloxy]-phenyl}-N'-(2R-phenyl-propyl)-oxalamide | 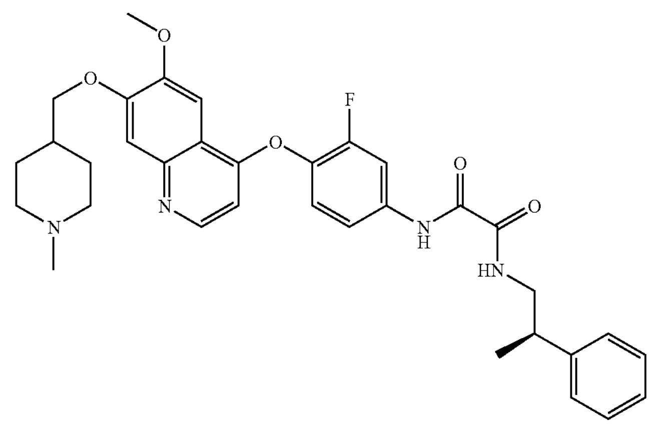 |
| 181 | N-{3-Fluoro-4-[6-methoxy-7-(1-methyl-piperidin-4-ylmethoxy)-quinolin-4-yloxy]-phenyl}-N'-(2-phenyl-propyl)-oxalamide | 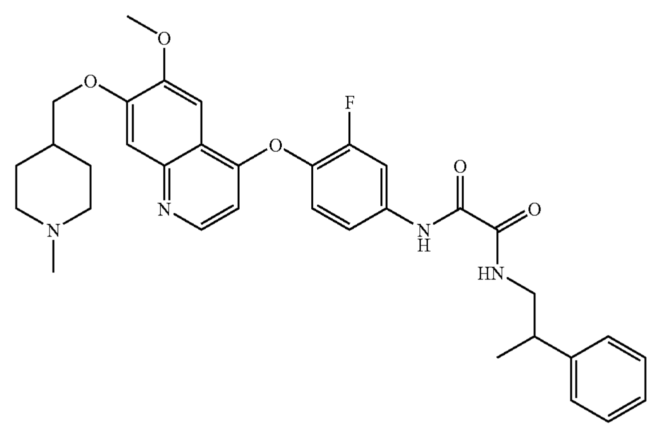 |

TABLE 1-continued

| Entry | Name | Structure |
|---|---|---|
| 182 | N-{3-Fluoro-4-[6-methoxy-7-(1-methyl-piperidin-4-ylmethoxy)-quinolin-4-yloxy]-phenyl}-N'-indan-2-yl-oxalamide | 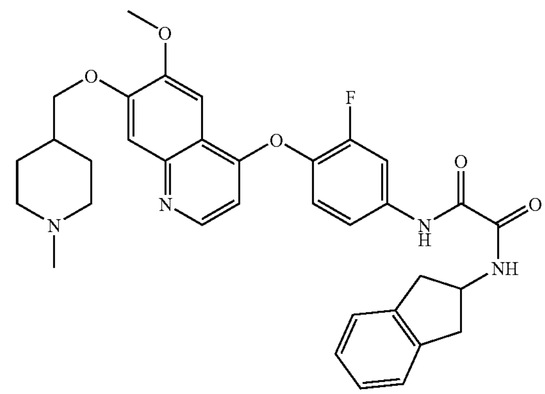 |
| 183 | N-{3-Fluoro-4-[6-methoxy-7-(piperidin-4-ylmethoxy)-quinolin-4-yloxy]-phenyl}-N'-(1R-phenyl-ethyl)-oxalamide | 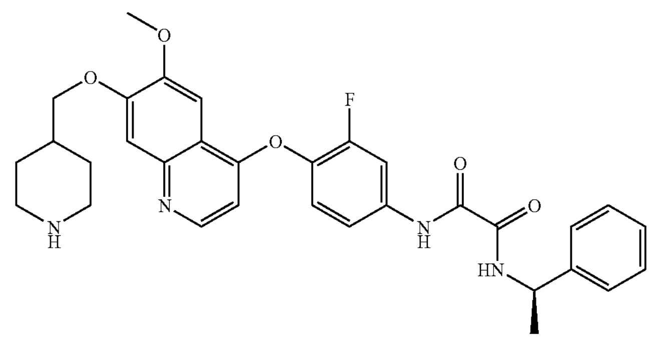 |
| 184 | N-{3-Fluoro-4-[6-methoxy-7-(piperidin-4-ylmethoxy)-quinolin-4-yloxy]-phenyl}-N'-(1S-phenyl-ethyl)-oxalamide | 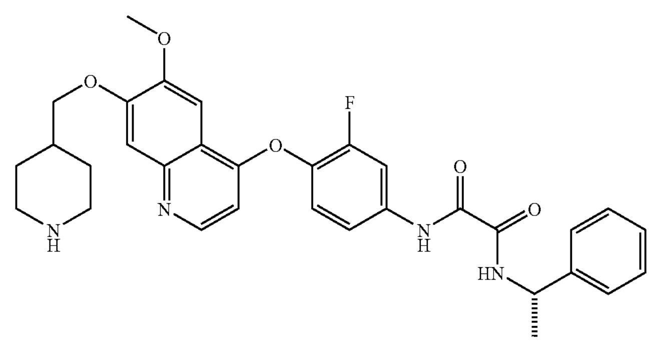 |
| 185 | N-[2-(3-Bromo-phenyl)-ethyl]-N'-{3-fluoro-4-[6-methoxy-7-(piperidin-4-ylmethoxy)-quinolin-4-yloxy]-phenyl}-oxalamide | 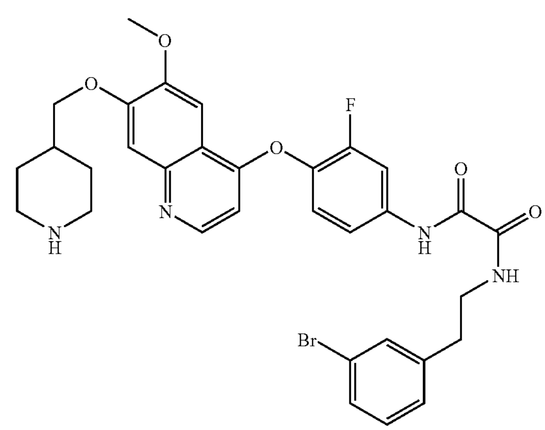 |

TABLE 1-continued

| Entry | Name | Structure |
|-------|------|-----------|
| 186 | N-[2-(2,6-Dichloro-phenyl)-ethyl]-N'-{3-fluoro-4-[6-methoxy-7-(piperidin-4-ylmethoxy)-quinolin-4-yloxy]-phenyl}-oxalamide | 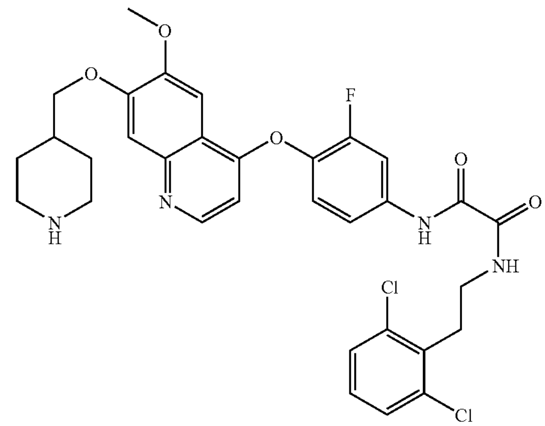 |
| 187 | N-[2-(2,4-Dichloro-phenyl)-ethyl]-N'-{3-fluoro-4-[6-methoxy-7-(piperidin-4-ylmethoxy)-quinolin-4-yloxy]-phenyl}-oxalamide | 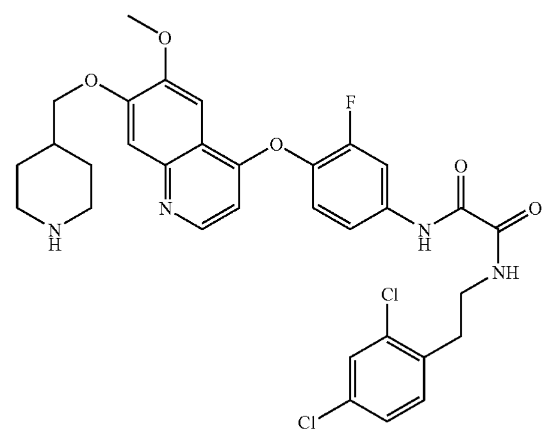 |
| 188 | N-(2-Benzo[1,3]dioxol-5-yl-ethyl)-N'-{3-fluoro-4-[6-methoxy-7-(piperidin-4-ylmethoxy)-quinolin-4-yloxy]-phenyl}-oxalamide | 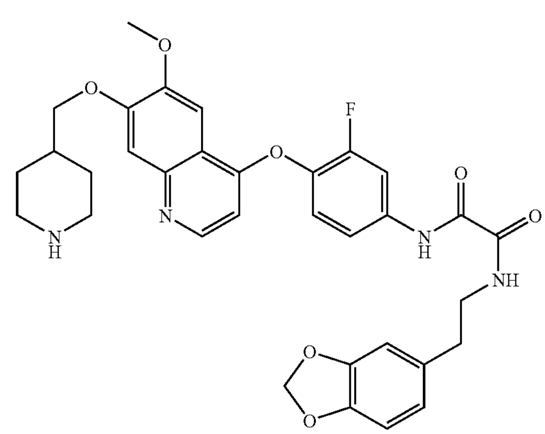 |

TABLE 1-continued
| Entry | Name | Structure |
|---|---|---|
| 189 | N-[2-(3-Bromo-4-methoxy-phenyl)-ethyl]-N'-{3-fluoro-4-[6-methoxy-7-(piperidin-4-ylmethoxy)quinolin-4-yloxy]-phenyl}-oxalamide | 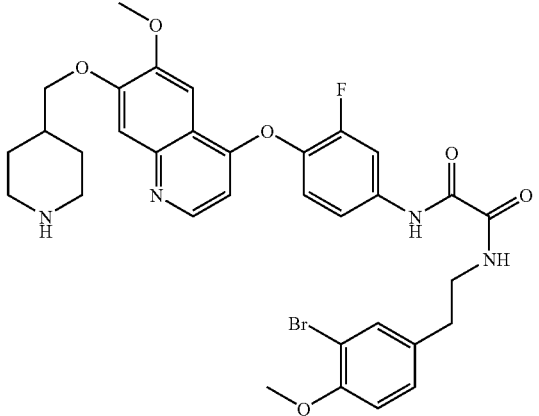 |
| 190 | N-[2-(3,5-Dimethoxy-phenyl)-ethyl]-N'-{3-fluoro-4-[6-methoxy-7-(piperidin-4-ylmethoxy)-quinolin-4-yloxy]-phenyl}-oxalamide | 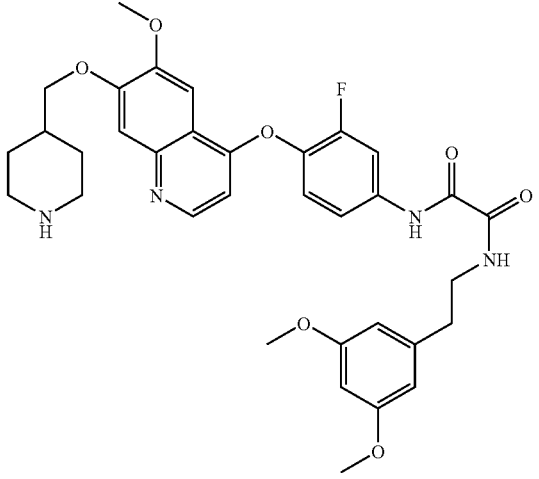 |
| 191 | N-{3-Fluoro-4-[6-methoxy-7-(piperidin-4-ylmethoxy)-quinolin-4-yloxy]-phenyl}-N'-(2-o-tolyl-ethyl)-oxalamide | 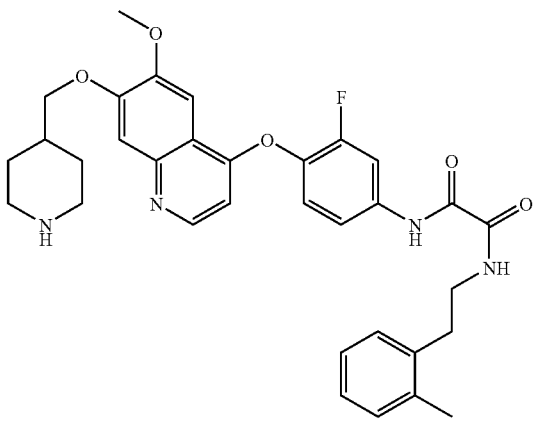 |

TABLE 1-continued

| Entry | Name | Structure |
|---|---|---|
| 192 | N-{3-Fluoro-4-[6-methoxy-7-(piperidin-4-ylmethoxy)-quinolin-4-yloxy]-phenyl}-N'-(2-m-tolyl-ethyl)-oxalamide | 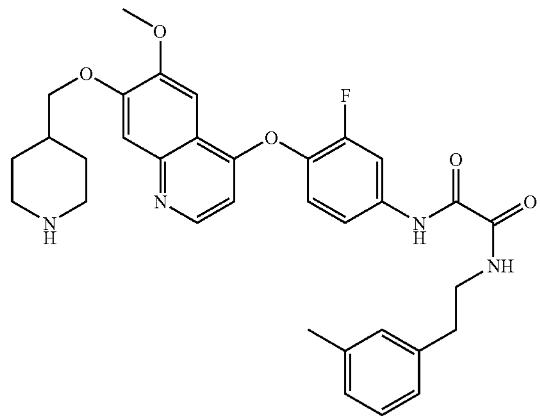 |
| 193 | N-[2-(3-Ethoxy-phenyl)-ethyl]-N'-{3-fluoro-4-[6-methoxy-7-(piperidin-4-ylmethoxy)-quinolin-4-yloxy]-phenyl}-oxalamide | 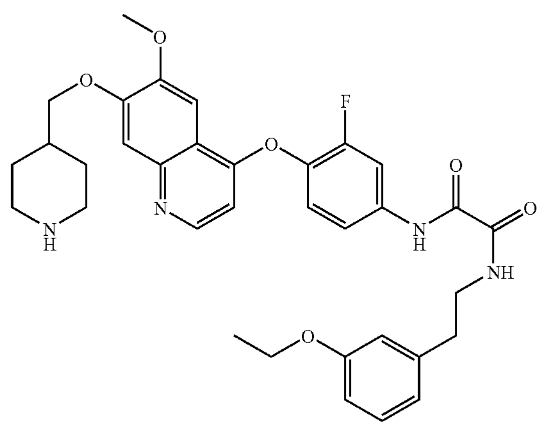 |
| 194 | N-[2-(3,4-Dimethyl-phenyl)-ethyl]-N'-{3-fluoro-4-[6-methoxy-7-(piperidin-4-ylmethoxy)-quinolin-4-yloxy]-phenyl}-oxalamide | 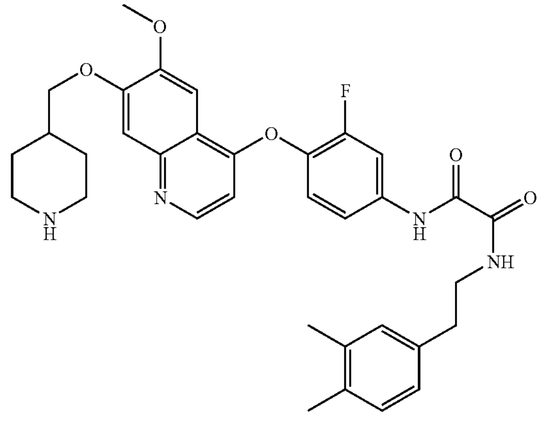 |

TABLE 1-continued

| Entry | Name | Structure |
|---|---|---|
| 195 | N-[2-(2,5-Dimethyl-phenyl)-ethyl]-N'-{3-fluoro-4-[6-methoxy-7-(piperidin-4-ylmethoxy)-quinolin-4-yloxy]-phenyl}-oxalamide | 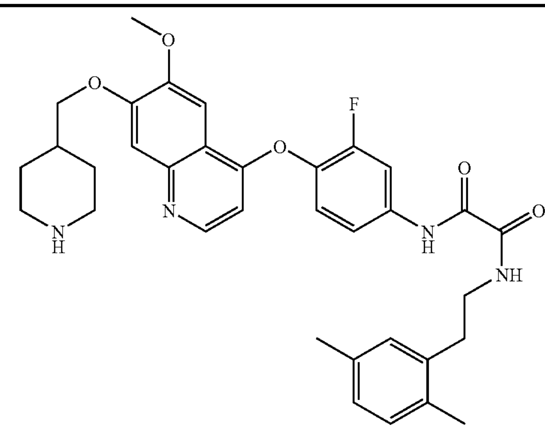 |
| 196 | N-[2-(3-Chloro-4-propoxy-phenyl)-ethyl]-N'-{3-fluoro-4-[6-methoxy-7-(piperidin-4-ylmethoxy)-quinolin-4-yloxy]-phenyl}-oxalamide | 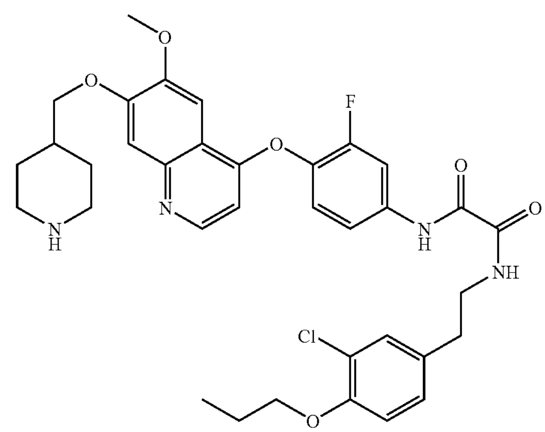 |
| 197 | N-[2-(4-Butoxy-3-chloro-phenyl)-ethyl]-N'-{3-fluoro-4-[6-methoxy-7-(piperidin-4-ylmethoxy)-quinolin-4-yloxy]-phenyl}-oxalamide | 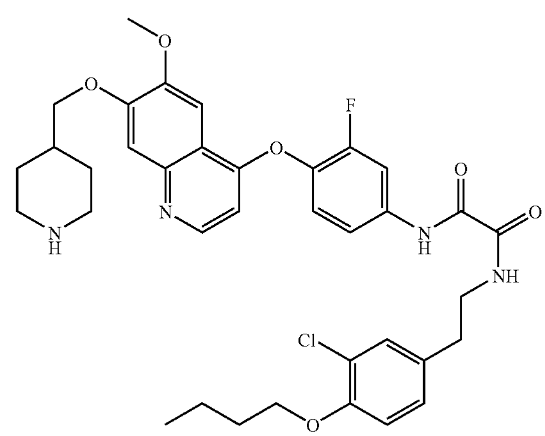 |

TABLE 1-continued

| Entry | Name | Structure |
|---|---|---|
| 198 | N-[2-(4-tert-Butyl-phenyl)-ethyl]-N'-{3-fluoro-4-[6-methoxy-7-(piperidin-4-ylmethoxy)-quinolin-4-yloxy]-phenyl}-oxalamide | 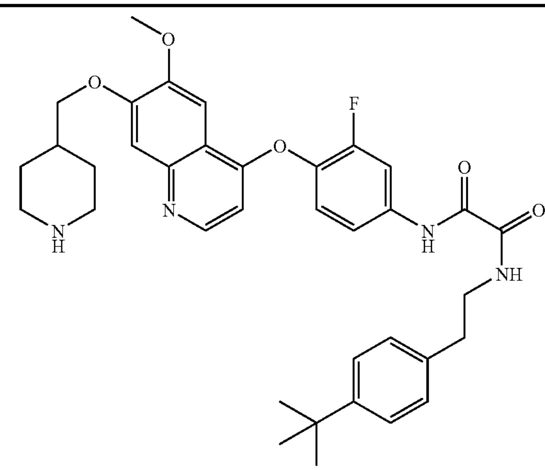 |
| 199 | N-{3-Fluoro-4-[6-methoxy-7-(piperidin-4-ylmethoxy)-quinolin-4-yloxy]-phenyl}-N'-[2-(4-sulfamoyl-phenyl)-ethyl]-oxalamide | 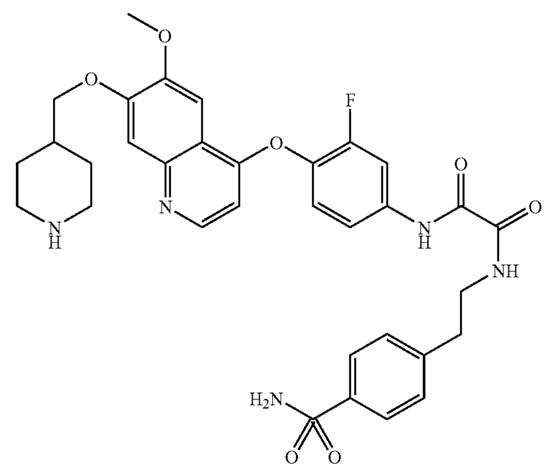 |
| 200 | N-{3-Fluoro-4-[6-methoxy-7-(piperidin-4-ylmethoxy)-quinolin-4-yloxy]-phenyl}-N'-[2-(4-hydroxy-3-methoxy-phenyl)-ethyl]-oxalamide | 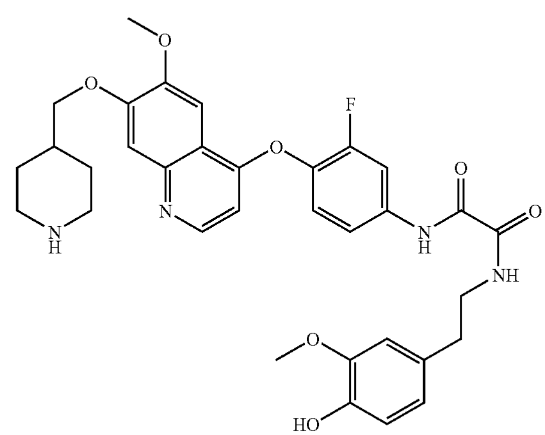 |

US 8,067,436 B2

TABLE 1-continued

| Entry | Name | Structure |
|---|---|---|
| 201 | N-{3-Fluoro-4-[6-methoxy-7-(piperidin-4-ylmethoxy)-quinolin-4-yloxy]-phenyl}-N'-[2-(3-hydroxy-4-methoxy-phenyl)-ethyl]-oxalamide | 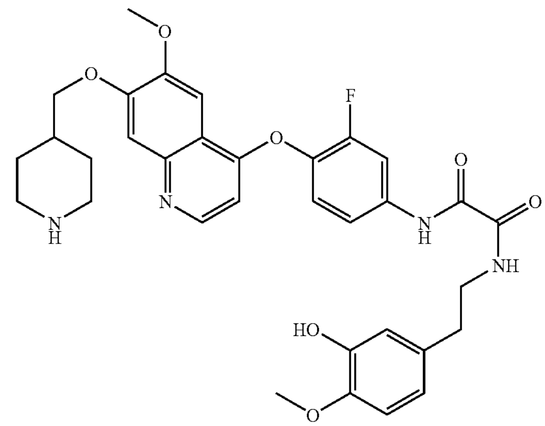 |
| 202 | N-(2,4-Dichloro-benzyl)-N'-{3-fluoro-4-[6-methoxy-7-(piperidin-4-ylmethoxy)-quinolin-4-yloxy]-phenyl}-oxalamide | 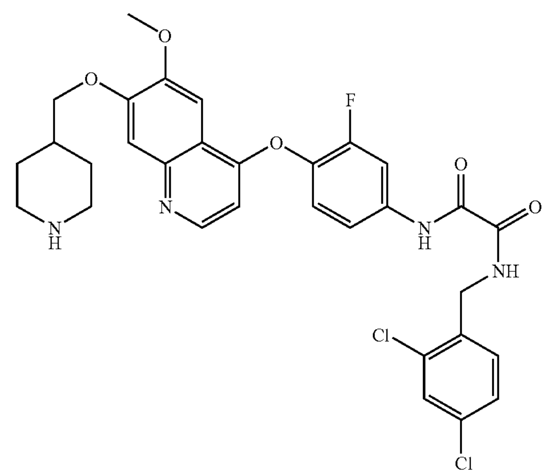 |
| 203 | N-{3-Fluoro-4-[6-methoxy-7-(piperidin-4-ylmethoxy)-quinolin-4-yloxy]-phenyl}-N'-(4-fluoro-2-trifluoromethyl-benzyl)-oxalamide | 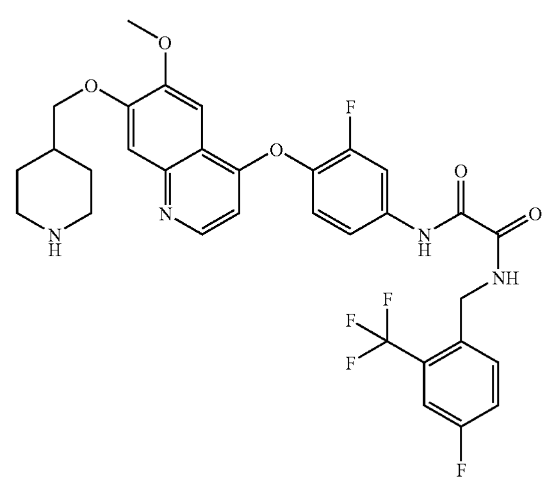 |

TABLE 1-continued

| Entry | Name | Structure |
|---|---|---|
| 204 | N-{3-Fluoro-4-[6-methoxy-7-(piperidin-4-ylmethoxy)-quinolin-4-yloxy]-phenyl}-N'-(1-p-tolyl-ethyl)-oxalamide | 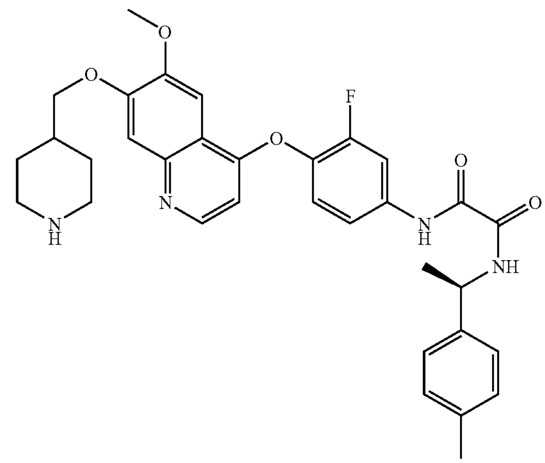 |
| 205 | N-{3-Fluoro-4-[6-methoxy-7-(piperidin-4-ylmethoxy)-quinolin-4-yloxy]-phenyl}-N'-(3-fluoro-4-trifluoromethyl-benzyl)-oxalamide | 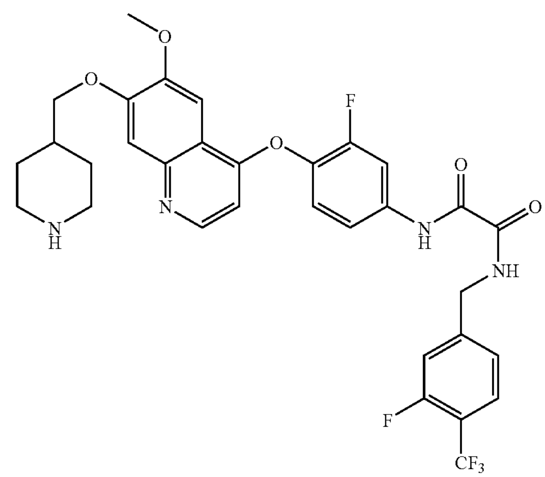 |
| 206 | N-(3-Chloro-4-fluoro-benzyl)-N'-{3-fluoro-4-[6-methoxy-7-(piperidin-4-ylmethoxy)-quinolin-4-yloxy]-phenyl}-oxalamide | 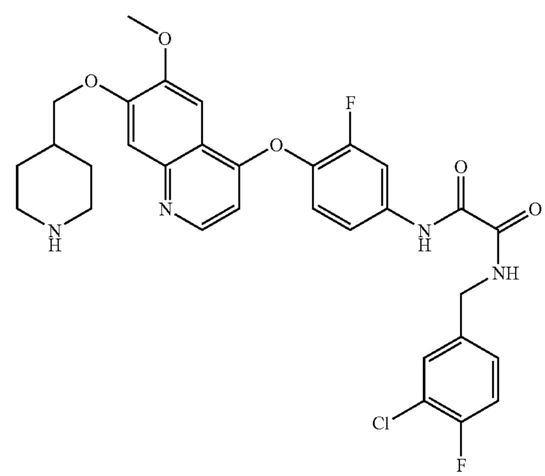 |

TABLE 1-continued

| Entry | Name | Structure |
|---|---|---|
| 207 | N-{3-Fluoro-4-[6-methoxy-7-(piperidin-4-ylmethoxy)-quinolin-4-yloxy]-phenyl}-N'-[1-(3-methoxy-phenyl)-ethyl]-oxalamide | 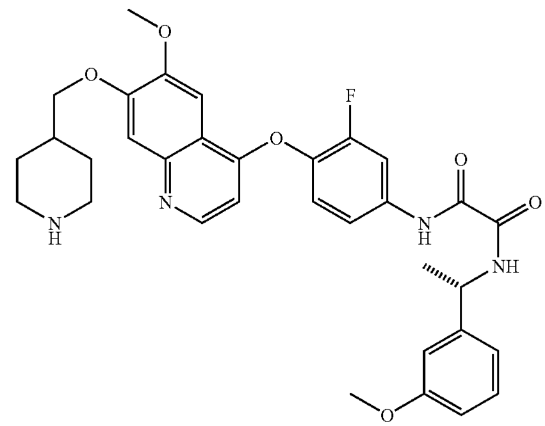 |
| 208 | N-{3-Fluoro-4-[6-methoxy-7-(piperidin-4-ylmethoxy)-quinolin-4-yloxy]-phenyl}-N'-(1-naphthalen-2-yl-ethyl)-oxalamide | 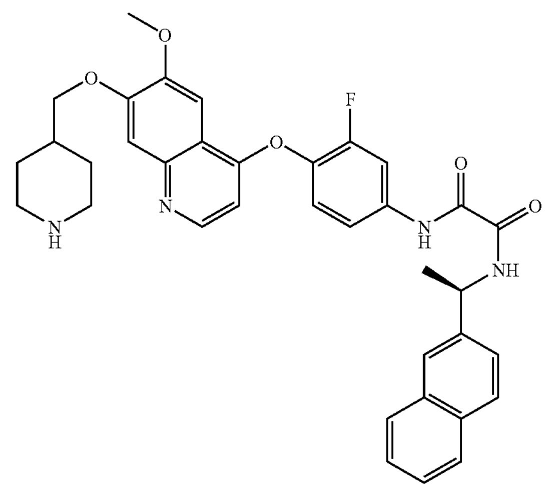 |
| 209 | N-(4-Chloro-3-trifluoromethyl-benzyl)-N'-{3-fluoro-4-[6-methoxy-7-(piperidin-4-ylmethoxy)-quinolin-4-yloxy]-phenyl}-oxalamide | 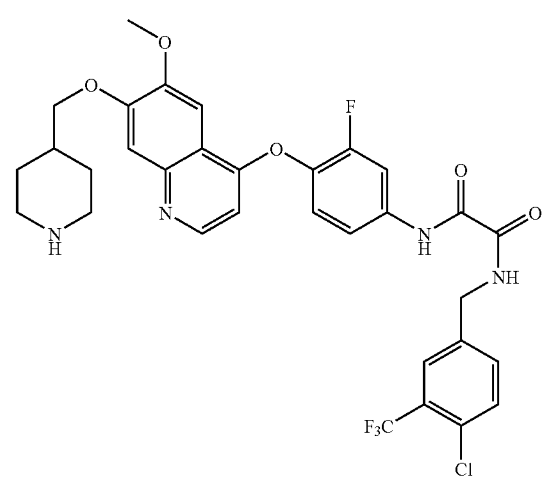 |

TABLE 1-continued

| Entry | Name | Structure |
|---|---|---|
| 210 | N-{3-Fluoro-4-[6-methoxy-7-(piperidin-4-ylmethoxy)-quinolin-4-yloxy]-phenyl}-N'-(1-p-tolyl-ethyl)-oxalamide | 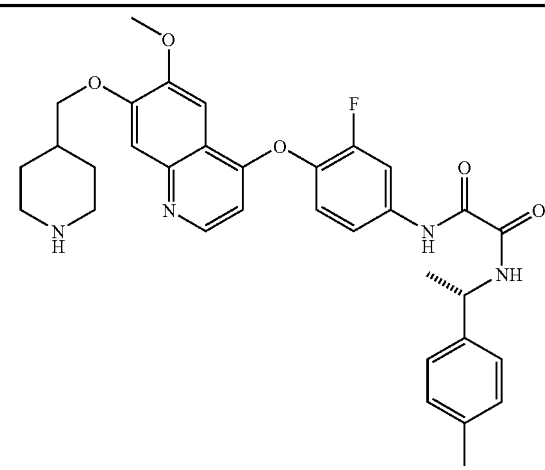 |
| 211 | N-{3-Fluoro-4-[6-methoxy-7-(piperidin-4-ylmethoxy)-quinolin-4-yloxy]-phenyl}-N'-(6-trifluoromethyl-pyridin-3-ylmethyl)-oxalamide | 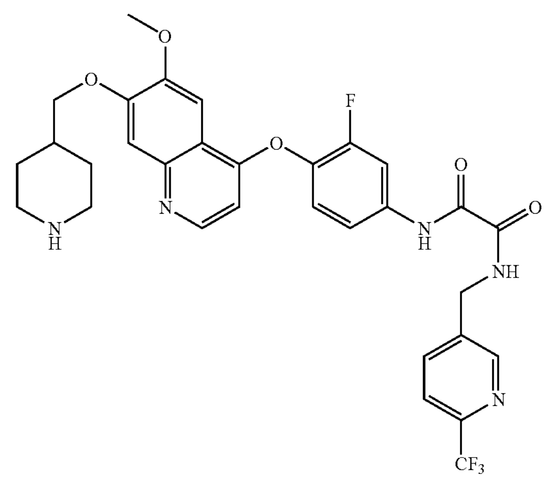 |
| 212 | N-{3-Fluoro-4-[6-methoxy-7-(piperidin-4-ylmethoxy)-quinolin-4-yloxy]-phenyl}-N'-(2-methyl-benzyl)-oxalamide | 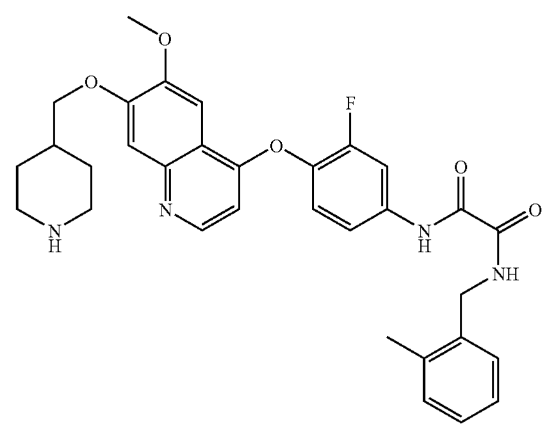 |

TABLE 1-continued

| Entry | Name | Structure |
|---|---|---|
| 213 | N-{3-Fluoro-4-[6-methoxy-7-(piperidin-4-ylmethoxy)-quinolin-4-yloxy]-phenyl}-N'-(3-methyl-benzyl)-oxalamide | 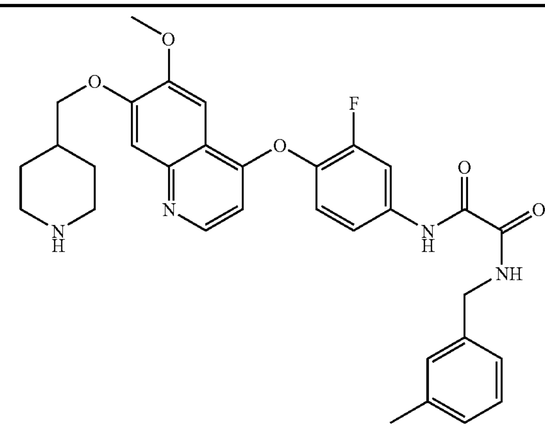 |
| 214 | N-{3-Fluoro-4-[6-methoxy-7-(piperidin-4-ylmethoxy)-quinolin-4-yloxy]-phenyl}-N'-(4-fluoro-3-trifluoromethyl-benzyl)-oxalamide | 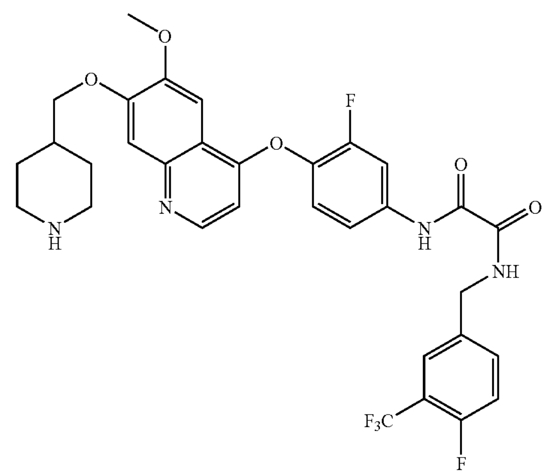 |
| 215 | N-(3,5-Dichloro-benzyl)-N'-{3-fluoro-4-[6-methoxy-7-(piperidin-4-ylmethoxy)-quinolin-4-yloxy]-phenyl}-oxalamide | 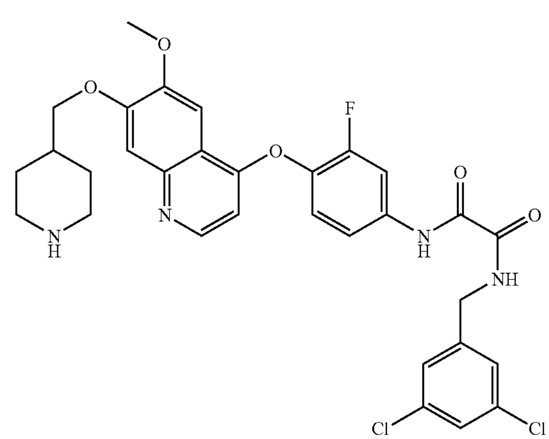 |

TABLE 1-continued

| Entry | Name | Structure |
|---|---|---|
| 216 | N-{3-Fluoro-4-[6-methoxy-7-(piperidin-4-ylmethoxy)-quinolin-4-yloxy]-phenyl}-N'-(1R,2,3,4-tetrahydro-naphthalen-1-yl)-oxalamide | 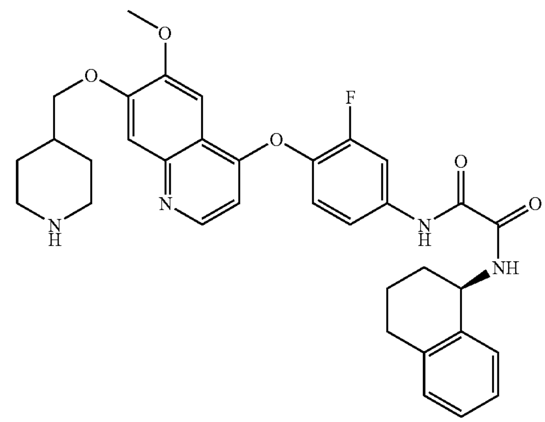 |
| 217 | N-{3-Fluoro-4-[6-methoxy-7-(piperidin-4-ylmethoxy)-quinolin-4-yloxy]-phenyl}-N'-(1S,2,3,4-tetrahydro-naphthalen-1-yl)-oxalamide | 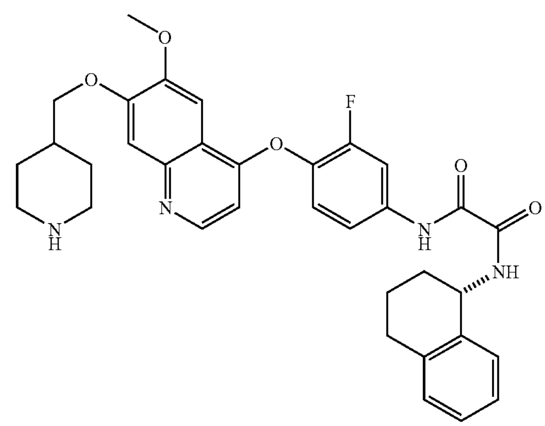 |
| 218 | N-Cyclopentyl-N'-{3-fluoro-4-[6-methoxy-7-(piperidin-4-ylmethoxy)-quinolin-4-yloxy]-phenyl}-oxalamide | 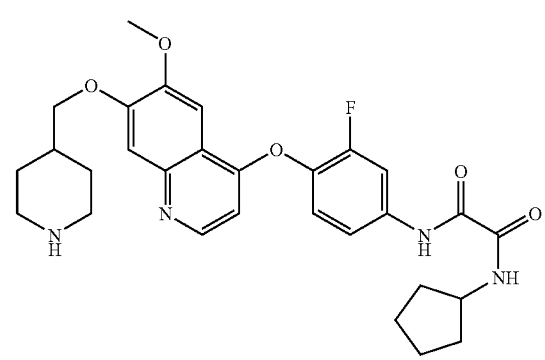 |

TABLE 1-continued

| Entry | Name | Structure |
|---|---|---|
| 219 | N-[1-(4-Bromo-phenyl)-ethyl]-N'-{3-fluoro-4-[6-methoxy-7-(piperidin-4-ylmethoxy)-quinolin-4-yloxy]-phenyl}-oxalamide | 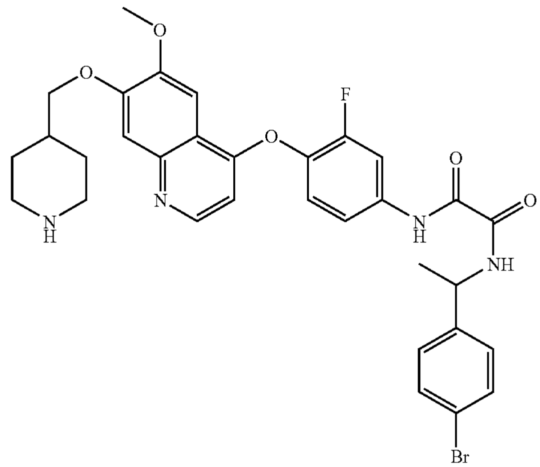 |
| 220 | N-(2-Fluoro-benzyl)-N'-{3-fluoro-4-[6-methoxy-7-(piperidin-4-ylmethoxy)-quinolin-4-yloxy]-phenyl}-oxalamide | 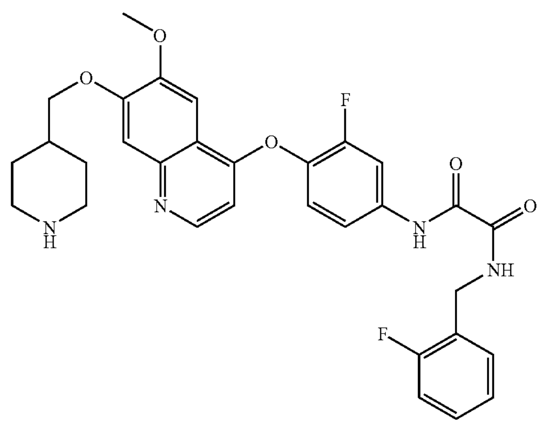 |
| 221 | N-[2-(3,4-Dichloro-phenyl)-ethyl]-N'-{3-fluoro-4-[6-methoxy-7-(piperidin-4-ylmethoxy)-quinolin-4-yloxy]-phenyl}-oxalamide | 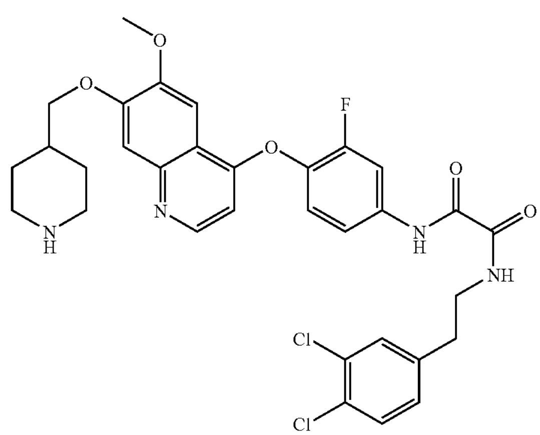 |

| Entry | Name | Structure |
|---|---|---|
| 222 | N-(4-Fluoro-benzyl)-N'-{3-fluoro-4-[6-methoxy-7-(piperidin-4-ylmethoxy)-quinolin-4-yloxy]-phenyl}-oxalamide | 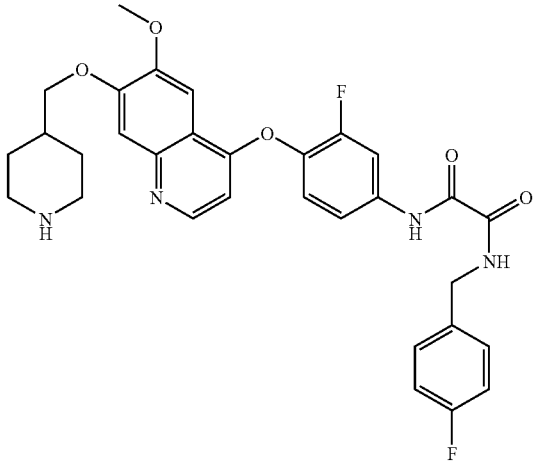 |
| 223 | N-(2,3-Difluoro-benzyl)-N'-{3-fluoro-4-[6-methoxy-7-(piperidin-4-ylmethoxy)-quinolin-4-yloxy]-phenyl}-oxalamide | 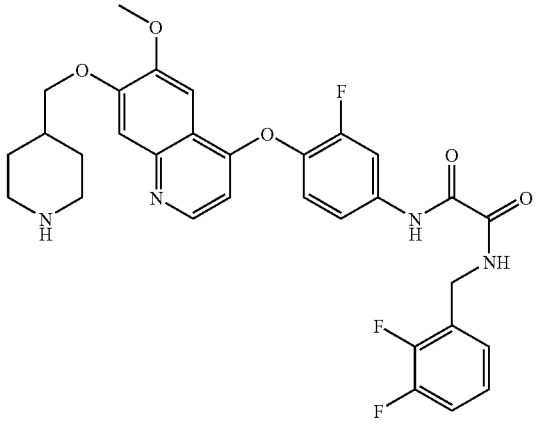 |
| 224 | N-{3-Fluoro-4-[6-methoxy-7-(piperidin-4-ylmethoxy)-quinolin-4-yloxy]-phenyl}-N'-(2-phenoxy-ethyl)-oxalamide | 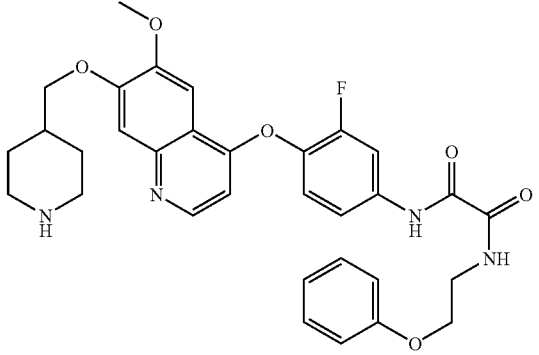 |

TABLE 1-continued

| Entry | Name | Structure |
|---|---|---|
| 225 | N-(2,2-Diphenyl-ethyl)-N'-{3-fluoro-4-[6-methoxy-7-(piperidin-4-ylmethoxy)-quinolin-4-yloxy]-phenyl}-oxalamide | 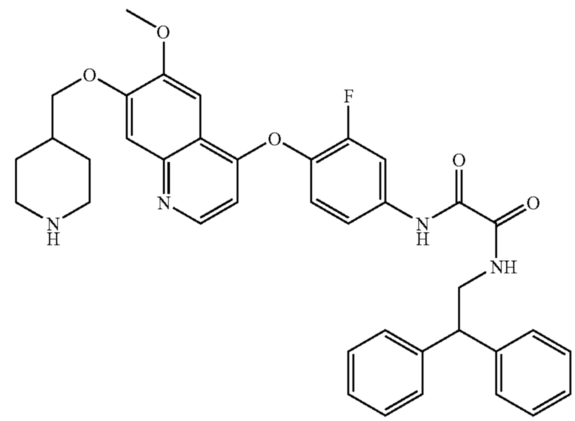 |
| 226 | N-{3-Fluoro-4-[6-methoxy-7-(piperidin-4-ylmethoxy)-quinolin-4-yloxy]-phenyl}-N'-[2-(4-methoxy-phenyl)-ethyl]-oxalamide | 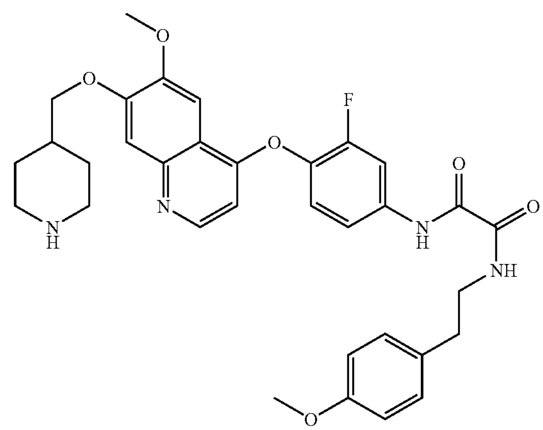 |
| 227 | N-{3-Fluoro-4-[6-methoxy-7-(piperidin-4-ylmethoxy)-quinolin-4-yloxy]-phenyl}-N'-(2-phenyl-propyl)-oxalamide | 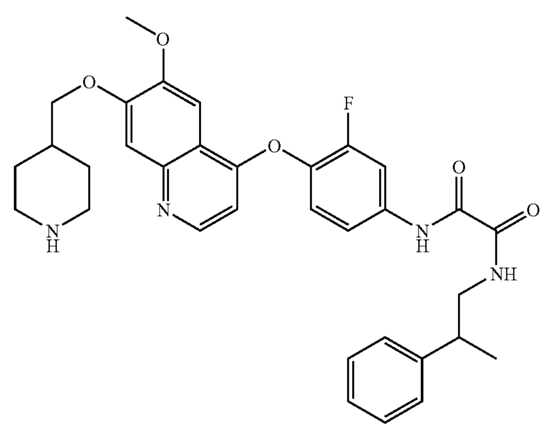 |

TABLE 1-continued

| Entry | Name | Structure |
|---|---|---|
| 228 | N-[2-(4-Bromo-phenyl)-ethyl]-N'-{3-fluoro-4-[6-methoxy-7-(piperidin-4-ylmethoxy)-quinolin-4-yloxy]-phenyl}-oxalamide | 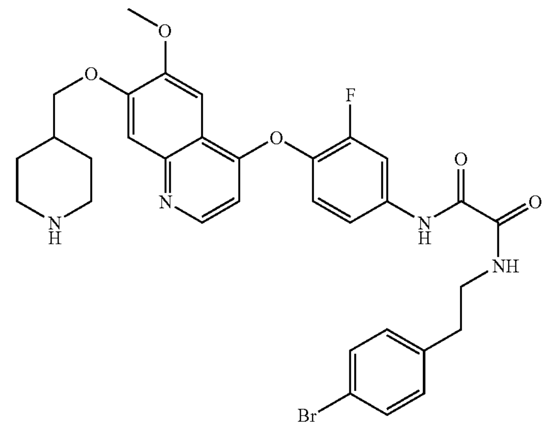 |
| 229 | N-{4-[7-(1-Ethyl-piperidin-4-ylmethoxy)-6-methoxy-quinolin-4-yloxy]-3-fluoro-phenyl}-2-oxo-2-(2-phenyl-morpholin-4-yl)-acetamide | 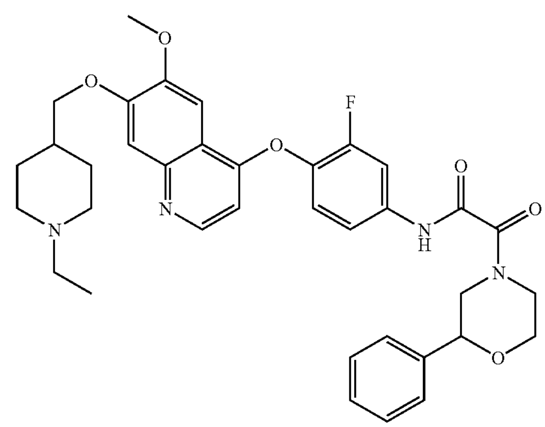 |
| 230 | N-{3-Fluoro-4-[6-methoxy-7-(piperidin-4-ylmethoxy)-quinolin-4-yloxy]-phenyl}-N'-(3-fluoro-5-trifluoromethyl-benzyl)-oxalamide | 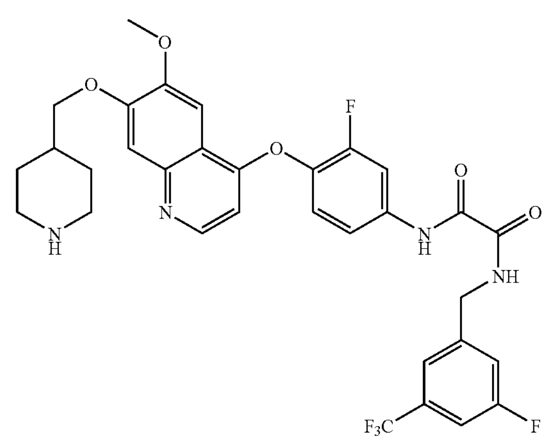 |

TABLE 1-continued

| Entry | Name | Structure |
|---|---|---|
| 231 | N-(3,5-Difluoro-benzyl)-N'-{3-fluoro-4-[6-methoxy-7-(piperidin-4-ylmethoxy)-quinolin-4-yloxy]-phenyl}-oxalamide | 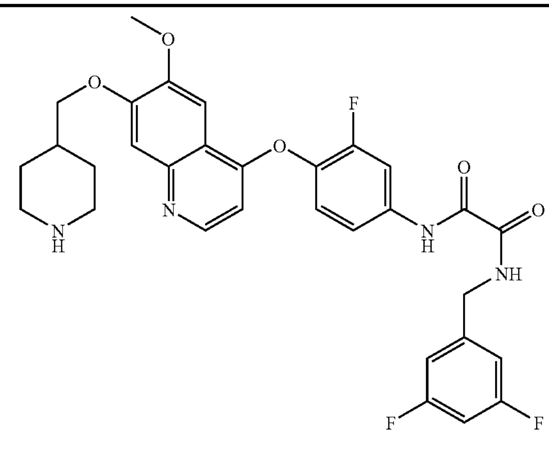 |
| 232 | N-(2-Chloro-5-trifluoromethyl-benzyl)-N'-{3-fluoro-4-[6-methoxy-7-(piperidin-4-ylmethoxy)-quinolin-4-yloxy]-phenyl}-oxalamide | 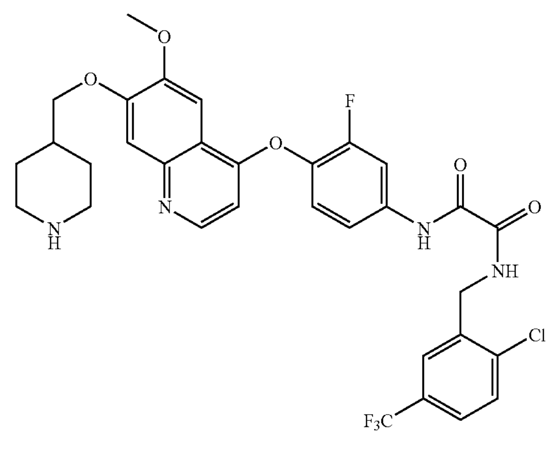 |
| 233 | N-[4-(6,7-Dimethoxy-quinolin-4-yloxy)-3-fluoro-phenyl]-N'-(2-dimethylamino-2-phenyl-ethyl)-oxalamide | 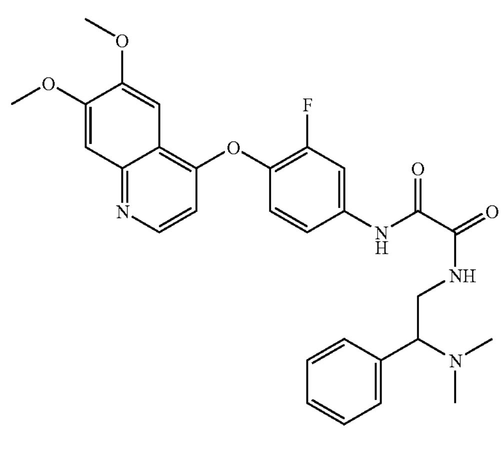 |

TABLE 1-continued

| Entry | Name | Structure |
|---|---|---|
| 234 | N-{3-Fluoro-4-[6-methoxy-7-(piperidin-4-ylmethoxy)-quinolin-4-yloxy]-phenyl}-N'-(4-methoxy-benzyl)-oxalamide | 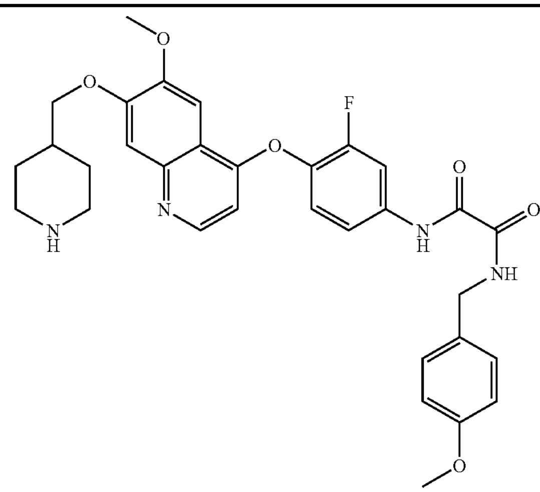 |
| 235 | N-{3-Fluoro-4-[6-methoxy-7-(piperidin-4-ylmethoxy)-quinolin-4-yloxy]-phenyl}-N'-(4-trifluoromethyl-benzyl)-oxalamide | 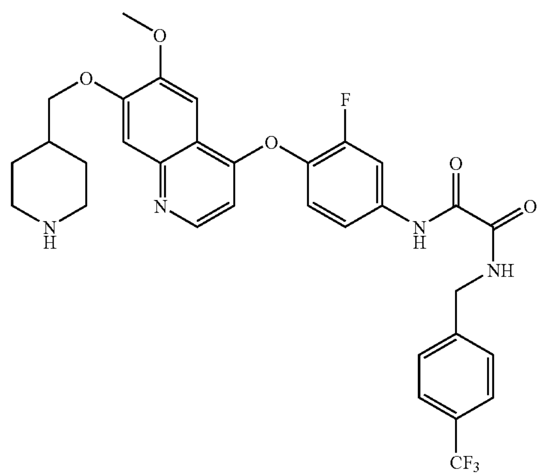 |
| 236 | N-{3-Fluoro-4-[6-methoxy-7-(piperidin-4-ylmethoxy)-quinolin-4-yloxy]-phenyl}-N'-(3-methoxy-benzyl)-oxalamide | 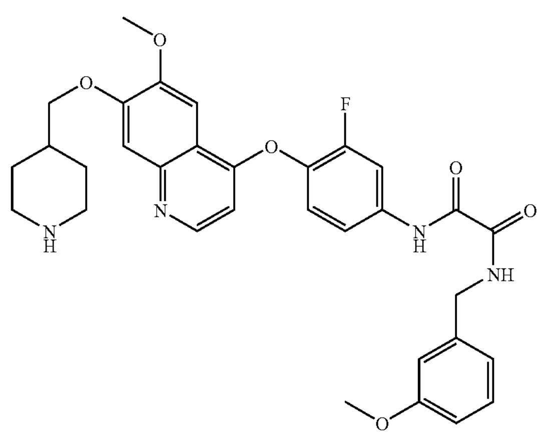 |

TABLE 1-continued
| Entry | Name | Structure |
|---|---|---|
| 237 | N-{3-Fluoro-4-[6-methoxy-7-(piperidin-4-ylmethoxy)-quinolin-4-yloxy]-phenyl}-N'-(3-trifluoromethyl-benzyl)-oxalamide | 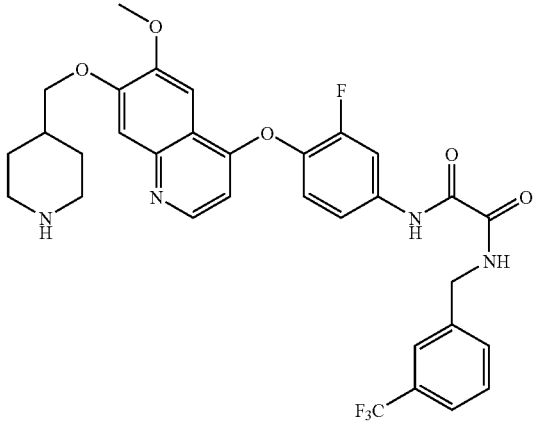 |
| 238 | N-{3-Fluoro-4-[6-methoxy-7-(piperidin-4-ylmethoxy)-quinolin-4-yloxy]-phenyl}-N'-(3-trifluoromethoxy-benzyl)-oxalamide | 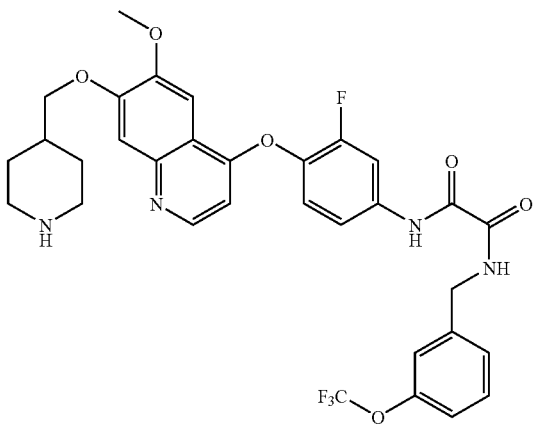 |
| 239 | N-{3-Fluoro-4-[6-methoxy-7-(piperidin-4-ylmethoxy)-quinolin-4-yloxy]-phenyl}-N'-(2-methoxy-benzyl)-oxalamide | 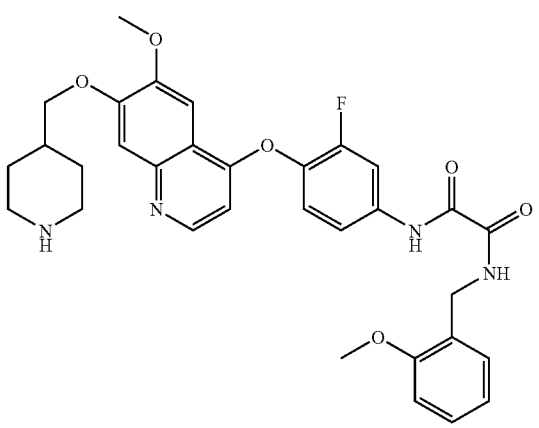 |

TABLE 1-continued

| Entry | Name | Structure |
|---|---|---|
| 240 | N-{3-Fluoro-4-[6-methoxy-7-(piperidin-4-ylmethoxy)-quinolin-4-yloxy]-phenyl}-N'-(2-trifluoromethyl-benzyl)-oxalamide | 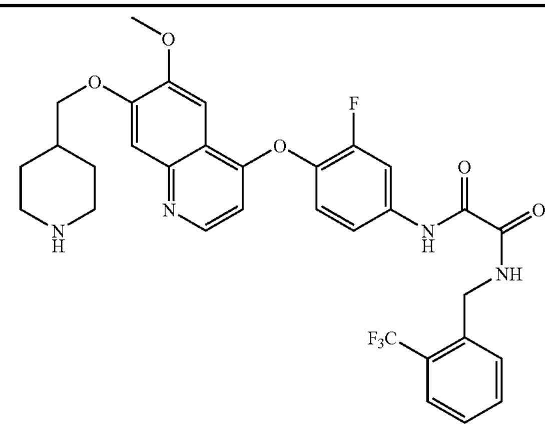 |
| 241 | N-(3-Chloro-benzyl)-N'-{3-fluoro-4-[6-methoxy-7-(piperidin-4-ylmethoxy)-quinolin-4-yloxy]-phenyl}-oxalamide | 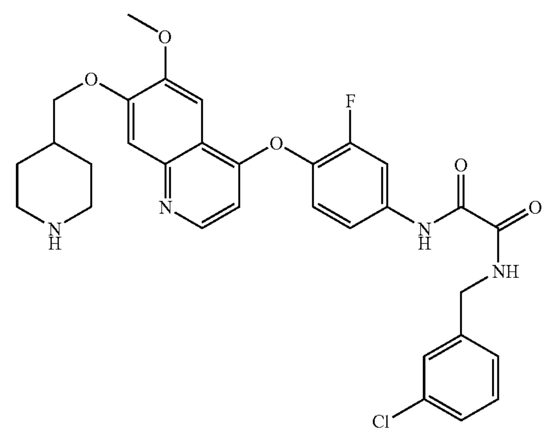 |
| 242 | N-{3-Fluoro-4-[6-methoxy-7-(piperidin-4-ylmethoxy)-quinolin-4-yloxy]-phenyl}-N'-(2-trifluoromethoxy-benzyl)-oxalamide | 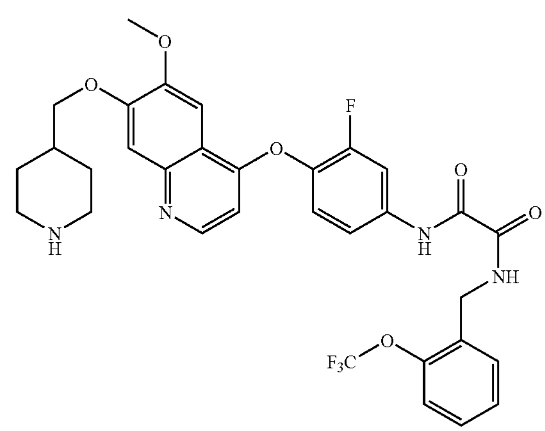 |

TABLE 1-continued

| Entry | Name | Structure |
|---|---|---|
| 243 | N-(2-Chloro-benzyl)-N'-{3-fluoro-4-[6-methoxy-7-(piperidin-4-ylmethoxy)-quinolin-4-yloxy]-phenyl}-oxalamide | 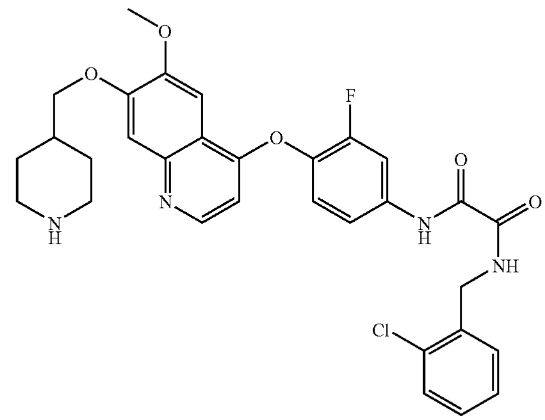 |
| 244 | N-{3-Fluoro-4-[6-methoxy-7-(piperidin-4-ylmethoxy)-quinolin-4-yloxy]-phenyl}-N'-(4-trifluoromethoxy-benzyl)-oxalamide | 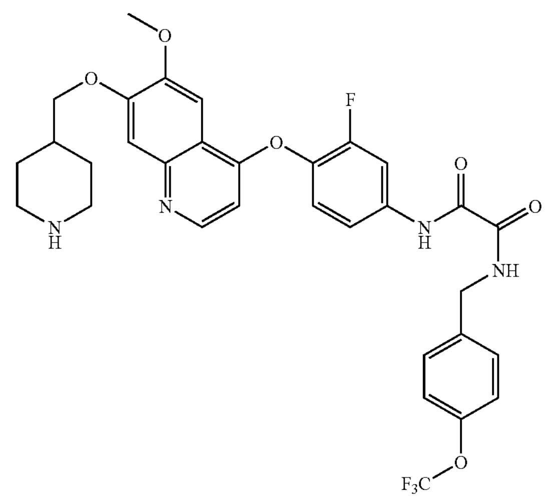 |
| 245 | N-{3-Fluoro-4-[6-methoxy-7-(1-methyl-piperidin-4-ylmethoxy)-quinolin-4-yloxy]-phenyl}-N'-(4-methoxy-benzyl)-oxalamide | 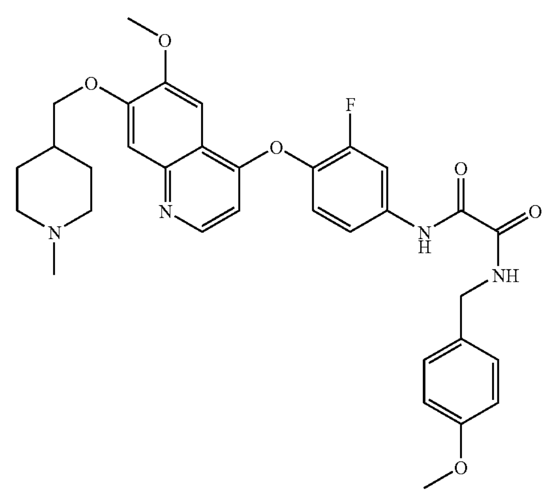 |

TABLE 1-continued

| Entry | Name | Structure |
|---|---|---|
| 246 | N-{3-Fluoro-4-[6-methoxy-7-(1-methyl-piperidin-4-ylmethoxy)-quinolin-4-yloxy]-phenyl}-N'-(4-trifluoromethyl-benzyl)-oxalamide | 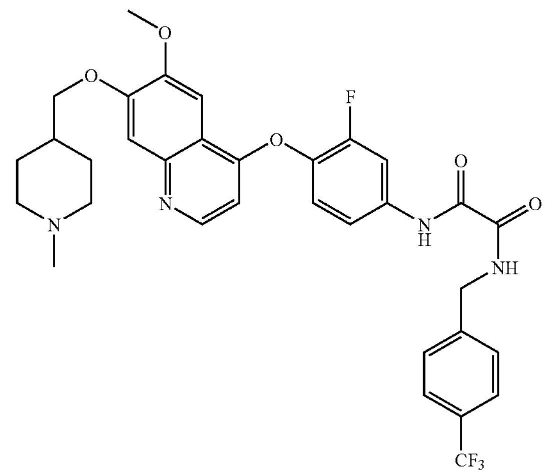 |
| 247 | N-{4-[7-(Azetidin-3-ylmethoxy)6-methoxy-quinolin-4-yloxy]-3-fluoro-phenyl}-N'-phenethyl-oxalamide | 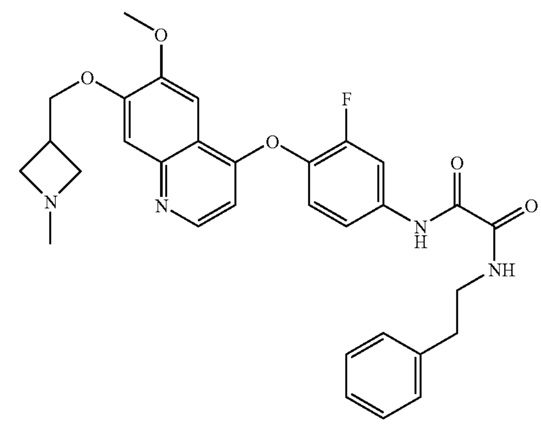 |
| 248 | N-{3-Fluoro-4-[6-methoxy-7-(1-methyl-azetidin-3-ylmethoxy)-quinolin-4-yloxy]-phenyl}-N'-phenethyl-oxalamide | 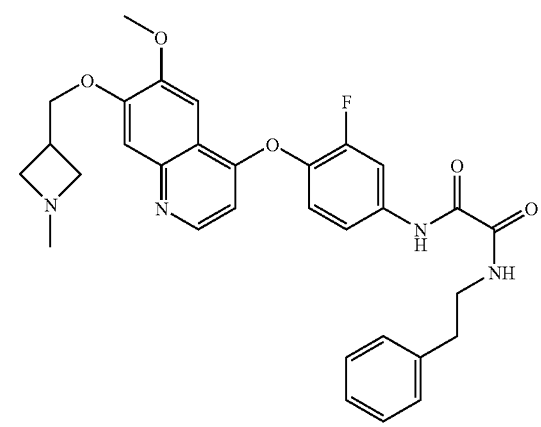 |

TABLE 1-continued

| Entry | Name | Structure |
|---|---|---|
| 249 | N-{3-Fluoro-4-[6-methoxy-7-(piperidin-4-ylmethoxy)-quinolin-4-yloxy]-phenyl}-N'-(2-hydroxy-2-phenyl-ethyl)-oxalamide | 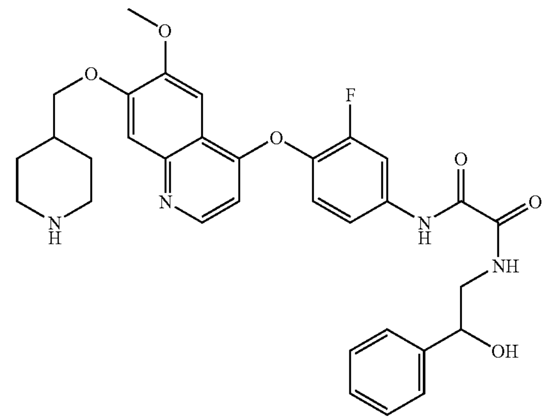 |
| 250 | N-[5-Chloro-6-(6,7-dimethoxy-quinolin-4-yloxy)-pyridin-3-yl]-N'-(2,4-difluoro-phenyl)-malonamide | 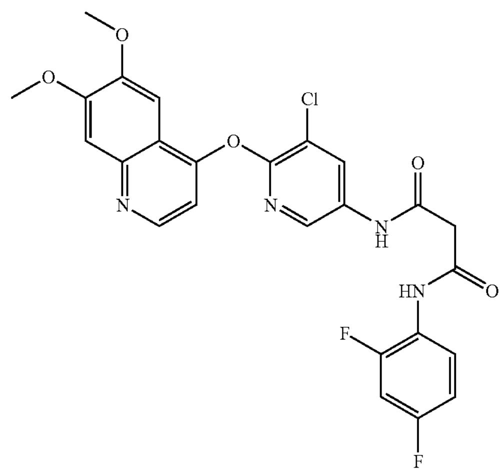 |
| 251 | N-[5-Chloro-6-(6,7-dimethoxy-quinolin-4-yloxy)-pyridin-3-yl]-N'-(4-fluoro-phenyl)-N'-methyl-malonamide | 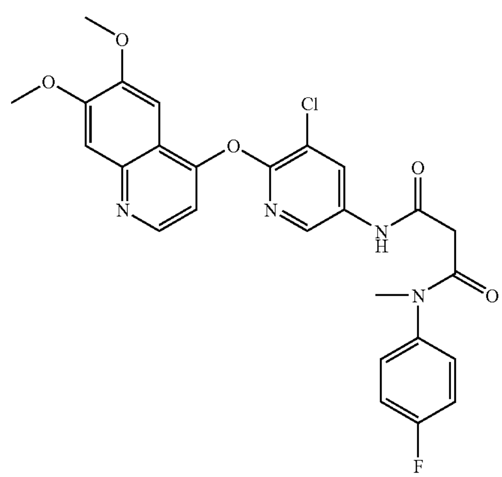 |

TABLE 1-continued

| Entry | Name | Structure |
|-------|------|-----------|
| 252 | N-{3-Fluoro-4-[6-methoxy-7-(piperidin-4-ylmethoxy)-quinolin-4-yloxy]-phenyl}-N'-(1R-phenyl-propyl)-oxalamide | 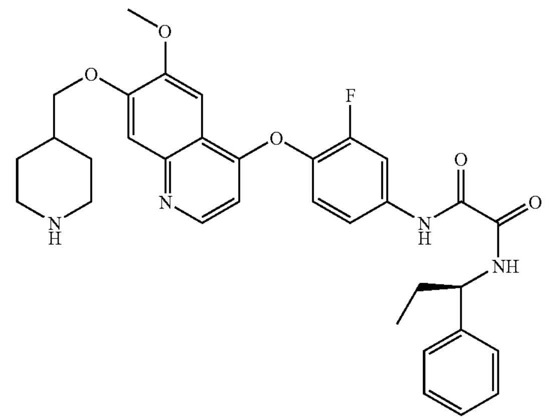 |
| 253 | N-{3-Fluoro-4-[6-methoxy-7-(piperidin-4-ylmethoxy)-quinolin-4-yloxy]-phenyl}-N'-(1R-phenyl-propyl)-oxalamide | 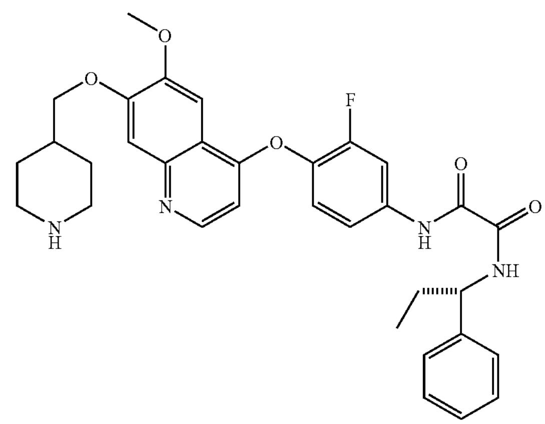 |
| 254 | N-(3,4-Difluoro-benzyl)-N'-{3-fluoro-4-[6-methoxy-7-(piperidin-4-ylmethoxy)-quinolin-4-yloxy]-phenyl}-oxalamide | 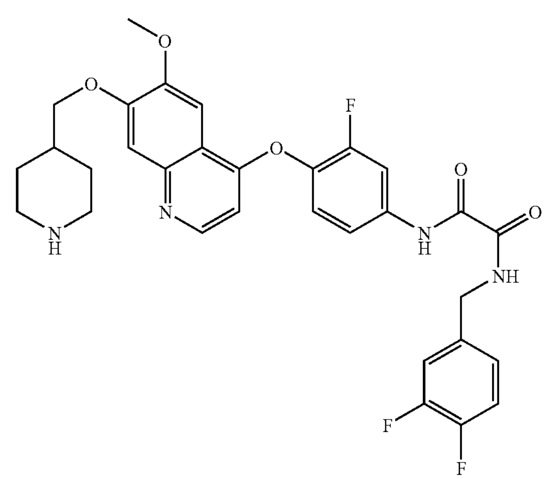 |

TABLE 1-continued

| Entry | Name | Structure |
|---|---|---|
| 255 | N-(2,6-Difluoro-benzyl)-N'-{3-fluoro-4-[6-methoxy-7-(piperidin-4-ylmethoxy)-quinolin-4-yloxy]-phenyl}-oxalamide | 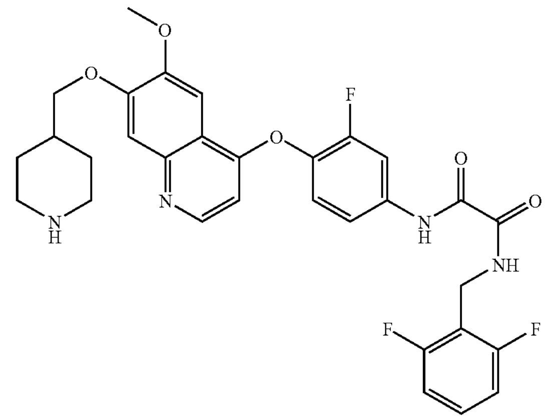 |
| 256 | N-{3-Fluoro-4-[6-methoxy-7-(1-methyl-piperidin-4-ylmethoxy)-quinolin-4-yloxy]-phenyl}-N'-[2-(4-fluoro-phenyl)-ethyl]-oxalamide | 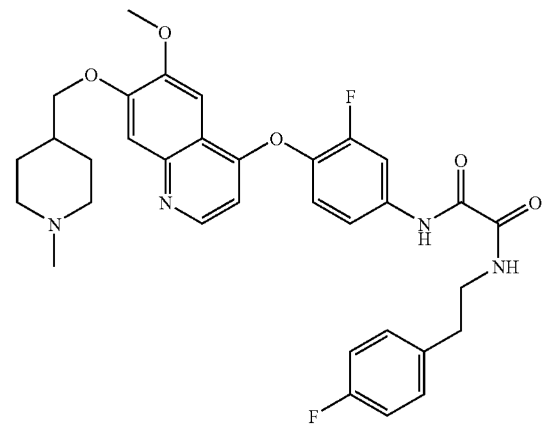 |
| 257 | N-{3-Fluoro-4-[6-methoxy-7-(1-methyl-piperidin-4-ylmethoxy)-quinolin-4-yloxy]-phenyl}-N'-phenyl-oxalamide | 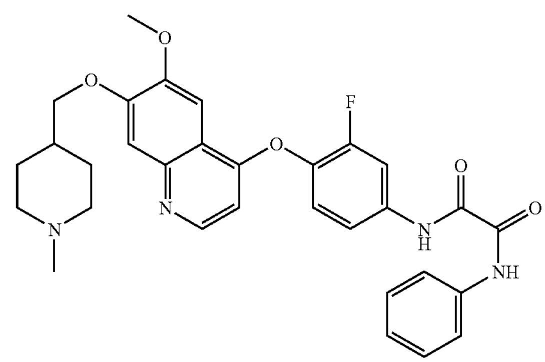 |
| 258 | N-{3-Fluoro-4-[6-methoxy-7-(piperidin-4-ylmethoxy)-quinolin-4-yloxy]-phenyl}-N'-(3-fluoro-phenyl)-oxalamide | 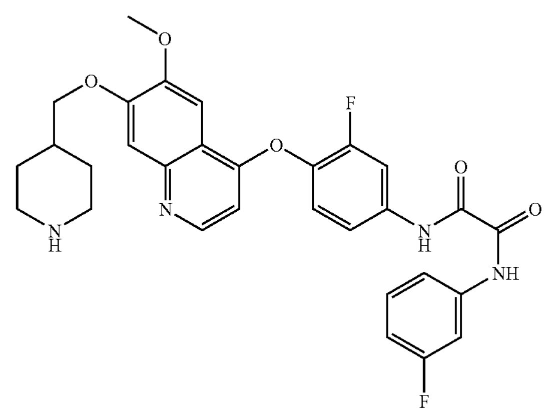 |

TABLE 1-continued

| Entry | Name | Structure |
|---|---|---|
| 259 | N(4-Chloro-3-fluoro-phenyl)-N'-{3-fluoro-4-[6-methoxy-7-(piperidin-4-ylmethoxy)-quinolin-4-yloxy]-phenyl}-oxalamide | 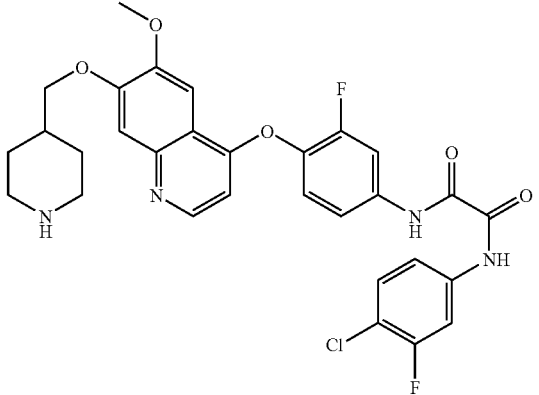 |
| 260 | N-(3,4-Dimethoxy-phenyl)-N'-{3-fluoro-4-[6-methoxy-7-(piperidin-4-ylmethoxy)-quinolin-4-yloxy]-phenyl}-oxalamide | 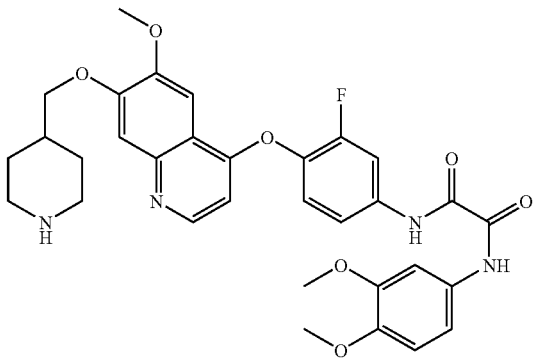 |
| 261 | N-{3-Fluoro-4-[6-methoxy-7-(piperidin-4-ylmethoxy)-quinolin-4-yloxy]-phenyl}-N'-(3-methyl-butyl)-oxalamide | 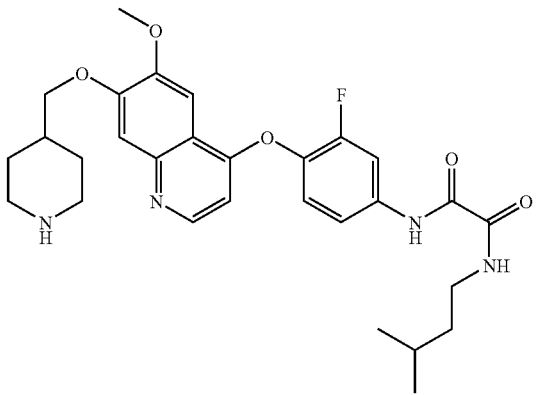 |
| 262 | N-(3,3-Dimethyl-butyl)-N'-{3-fluoro-4-[6-methoxy-7-piperidin-4-ylmethoxy)-quinolin-4-yloxy]-phenyl}-oxalamide | 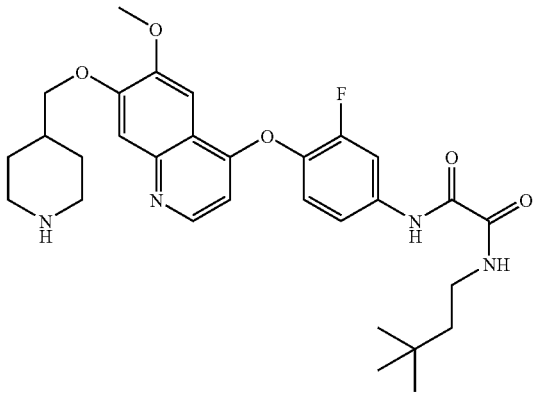 |

US 8,067,436 B2

151    152

TABLE 1-continued

| Entry | Name | Structure |
|---|---|---|
| 263 | N-{5-Chloro-6-[6-methoxy-7-(3-piperidin-1-yl-propoxy)-quinolin-4-yloxy]-pyridin-3-yl}-N'-(4-fluoro-phenyl)-malonamide | 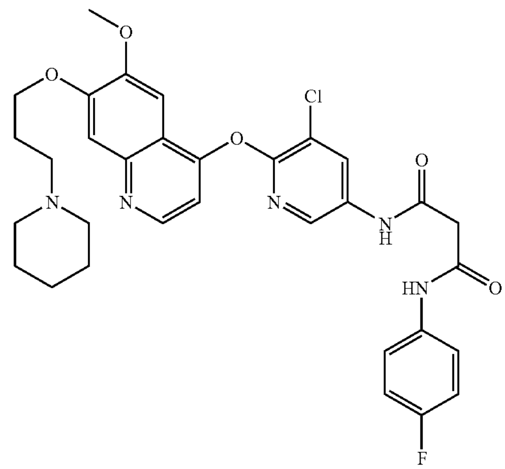 |
| 264 | N-{5-Chloro-6-[6-methoxy-7-(3-morpholin-4-yl-propoxy)-quinolin-4-yloxy]-pyridin-3-yl}-N'-(4-fluoro-phenyl)-malonamide | 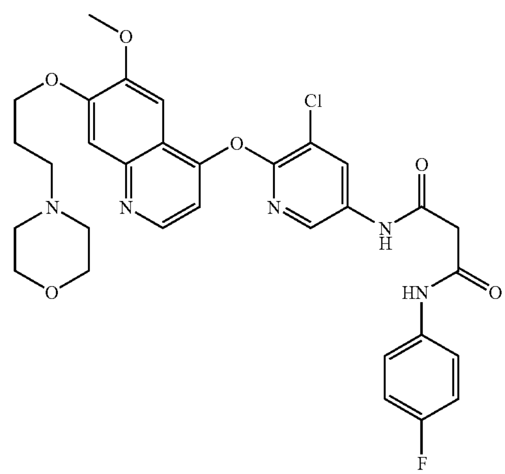 |
| 265 | N-{5-Chloro-6-[7-(3-diethylamino-propoxy)-6-methoxy-quinolin-4-yloxy]-pyridin-3-yl}-N'-(4-fluoro-phenyl)-malonamide | 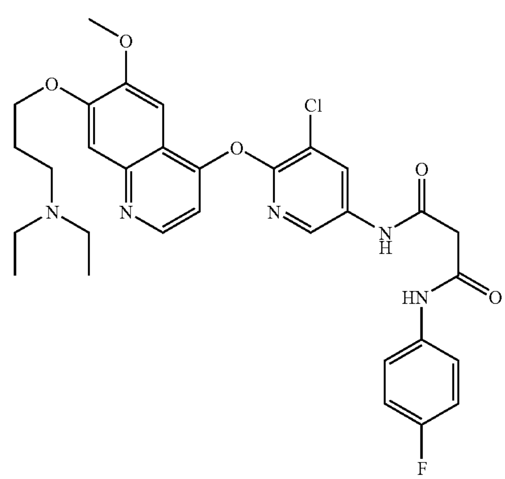 |

TABLE 1-continued

| Entry | Name | Structure |
|---|---|---|
| 266 | N-(4-Chloro-benzyl)-N'-{3-fluoro-4-[6-methoxy-7-(piperidin-4-ylmethoxy)-quinolin-4-yloxy]-phenyl}-oxalamide | 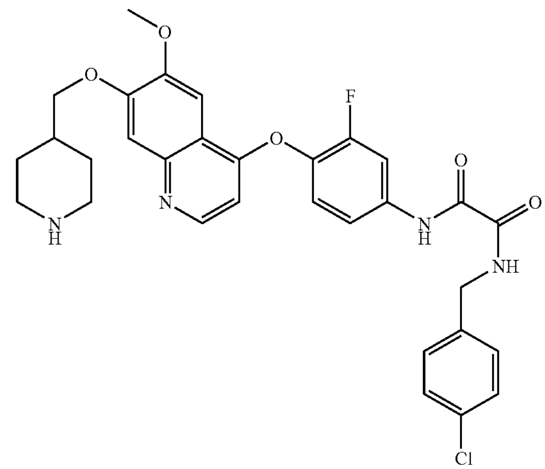 |
| 267 | N-(3,5-Dimethoxy-benzyl)-N'-{3-fluoro-4-[6-methoxy-7-(piperidin-4-ylmethoxy)-quinolin-4-yloxy]-phenyl}-oxalamide | 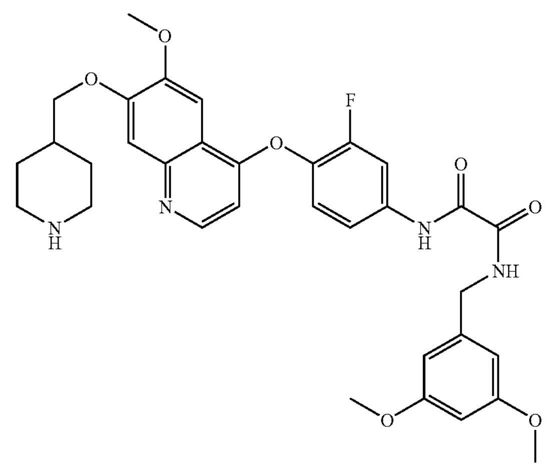 |
| 268 | N-(4-Butyl-benzyl)-N'-{3-fluoro-4-[6-methoxy-7-(piperidin-4-ylmethoxy)-quinolin-4-yloxy]-phenyl}-oxalamide | 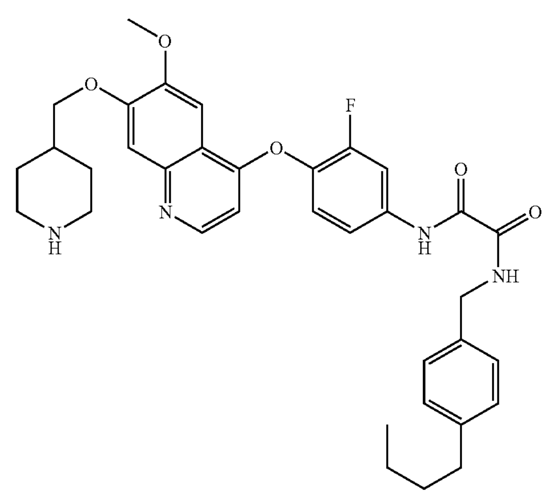 |

TABLE 1-continued

| Entry | Name | Structure |
|-------|------|-----------|
| 269 | N-{3-Fluoro-4-[6-methoxy-7-(piperidin-4-ylmethoxy)-quinolin-4-yloxy]-phenyl}-N'-(2-p-tolyl-ethyl)-oxalamide | 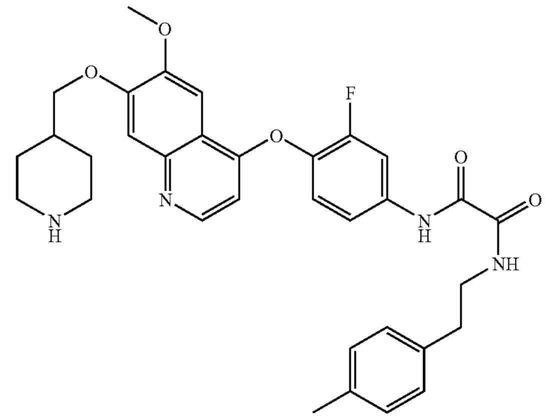 |
| 270 | N-(3,5-Bis-trifluoromethyl-benzyl)-N'-{3-fluoro-4-[6-methoxy-7-(piperidin-4-ylmethoxy)-quinolin-4-yloxy]-phenyl}-oxalamide | 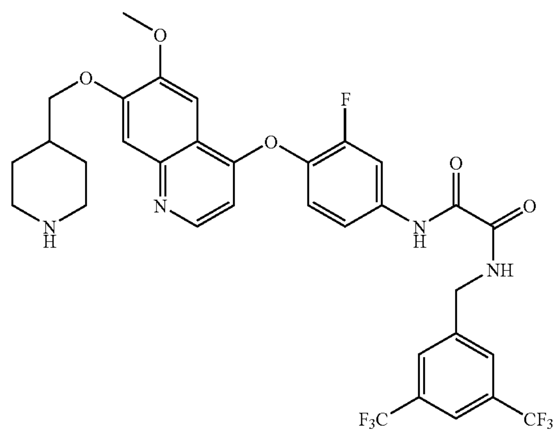 |
| 271 | N-{3-Fluoro-4-[6-methoxy-7-(piperidin-4-ylmethoxy)-quinolin-4-yloxy]-phenyl}-N'-pyrazin-2-ylmethyl-oxalamide | 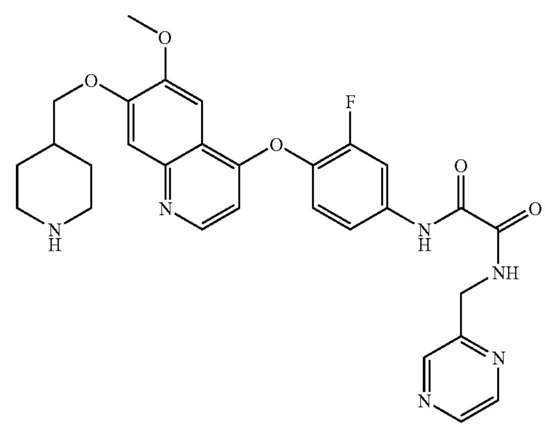 |

TABLE 1-continued
| Entry | Name | Structure |
|---|---|---|
| 272 | N-{3-Fluoro-4-[6-methoxy-7-(piperidin-4-ylmethoxy)-quinolin-4-yloxy]-phenyl}-N'-pyridin-2-ylmethyl-oxalamide | 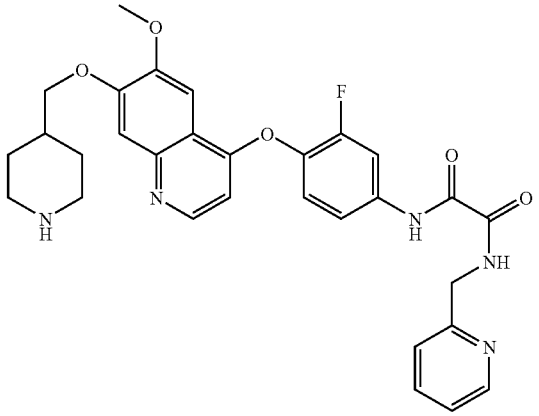 |
| 273 | N-{3-Fluoro-4-[6-methoxy-7-(piperidin-4-ylmethoxy)-quinazolin-4-yloxy]-phenyl}-N'-phenethyl-oxalamide | 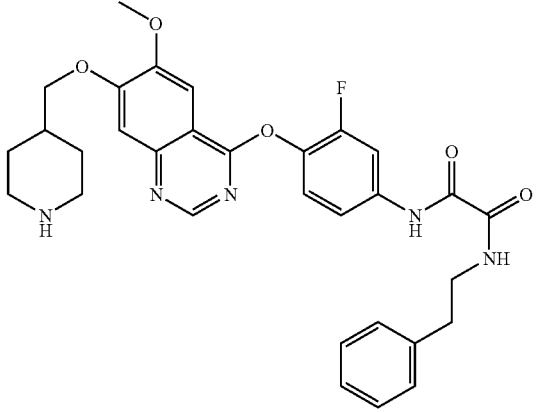 |
| 274 | N-{3-Fluoro-4-[6-methoxy-7-(1-methyl-piperidin-4-ylmethoxy)-quinazolin-4-yloxy]-phenyl}-N'-phenethyl-oxalamide | 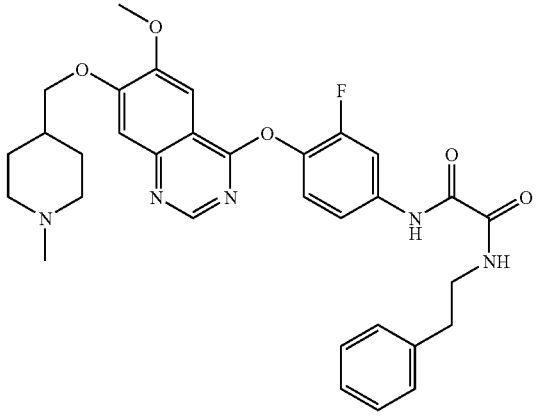 |

TABLE 1-continued

| Entry | Name | Structure |
|---|---|---|
| 275 | N-{3-Fluoro-4-[6-methoxy-7-(piperidin-4-ylmethoxy)-quinolin-4-yloxy]-phenyl}-N'-(2-fluoro-3-trifluoromethyl-benzyl)-oxalamide | 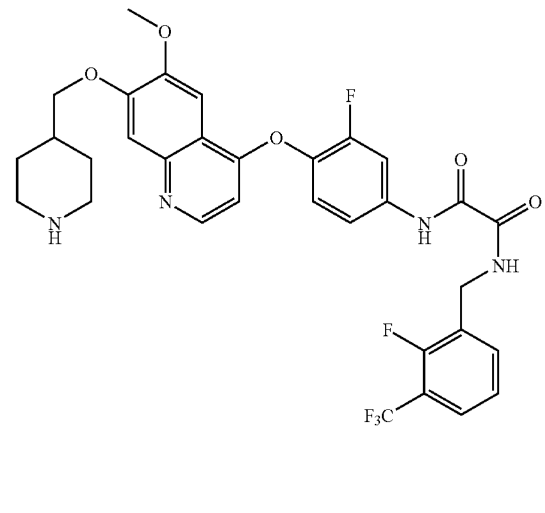 |
| 276 | N-[2-(2-Bromo-6-methoxy-phenyl)-ethyl]-N'-{3-fluoro-4-[6-methoxy-7-(piperidin-4-ylmethoxy)-quinolin-4-yloxy]-phenyl}-oxalamide | 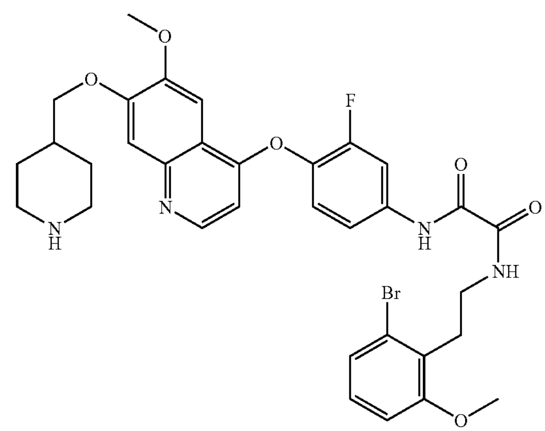 |
| 277 | N-[2-(3,4-Dimethoxy-phenyl)-ethyl]-N'-{3-fluoro-4-[6-methoxy-7-(piperidin-4-ylmethoxy)-quinolin-4-yloxy]-phenyl}-N-methyl-oxalamide | 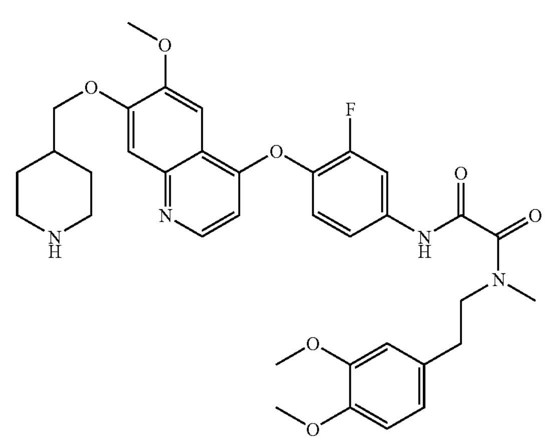 |

TABLE 1-continued

| Entry | Name | Structure |
|---|---|---|
| 278 | N-[2-(5-Bromo-2-methoxy-phenyl)-ethyl]-N'-{3-fluoro-4-[6-methoxy-7-(piperidin-4-ylmethoxy)-quinolin-4-yloxy]-phenyl}-oxalamide | 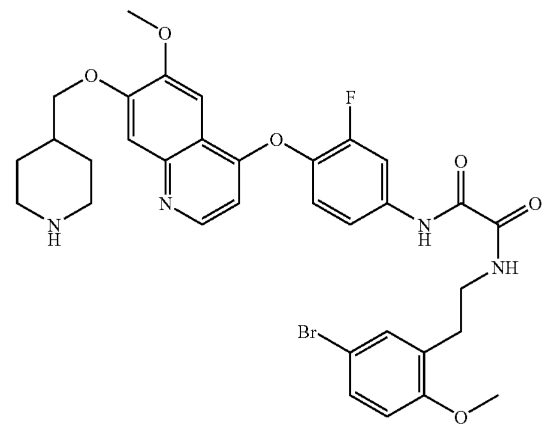 |
| 279 | N-{3-Fluoro-4-[6-methoxy-7-(piperidin-4-ylmethoxy)-quinolin-4-yloxy]-phenyl}-N'-(2-fluoro-5-trifluoromethyl-benzyl)-oxalamide | 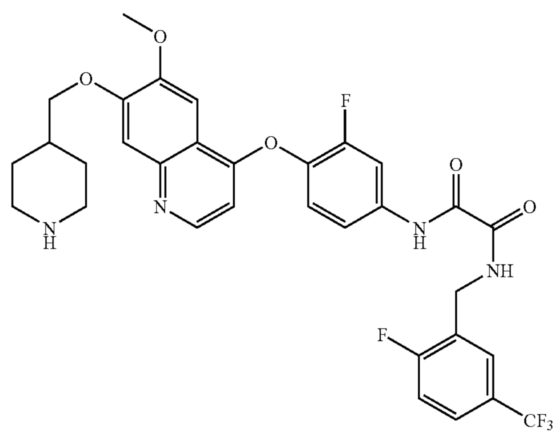 |
| 280 | N-{3-Fluoro-4-[6-methoxy-7-(piperidin-4-ylmethoxy)-quinolin-4-yloxy]-phenyl}-N'-[1-(4-fluoro-phenyl)-ethyl]-oxalamide | 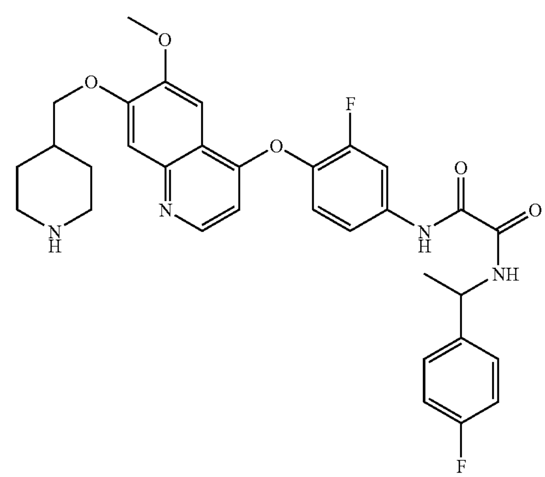 |

TABLE 1-continued

| Entry | Name | Structure |
|---|---|---|
| 281 | N-(1S-Benzyl-2-oxo-2-pyrrolidin-1-yl-ethyl)-N'-{3-fluoro-4-[6-methoxy-7-(piperidin-4-ylmethoxy)-quinolin-4-yloxy]-phenyl}-oxalamide | 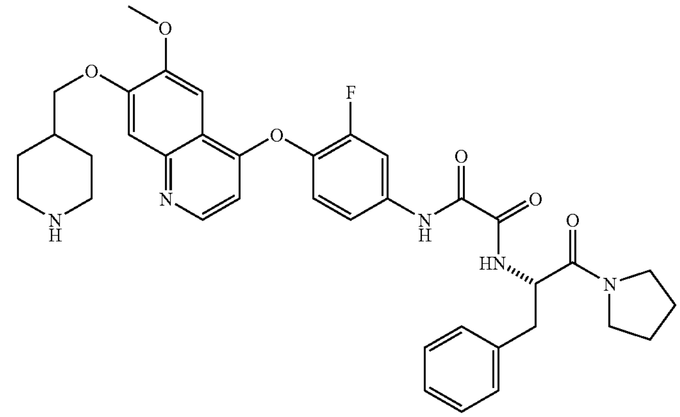 |
| 282 | N-{3-Fluoro-4-[6-methoxy-7-(octahydro-cyclopenta[c]pyrrol-5-ylmethoxy)-quinazolin-4-yloxy]-phenyl}-N'-phenethyl-oxalamide | 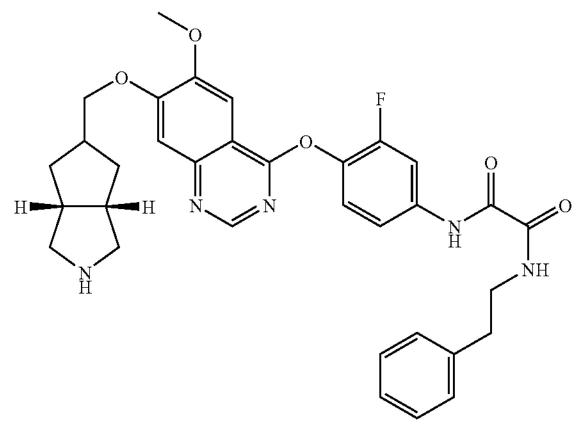 |
| 283 | N-[2-(4-Amino-phenyl)-ethyl]-N'-{3-fluoro-4-[6-methoxy-7-(piperidin-4-ylmethoxy)-quinolin-4-yloxy]-phenyl}-oxalamide | 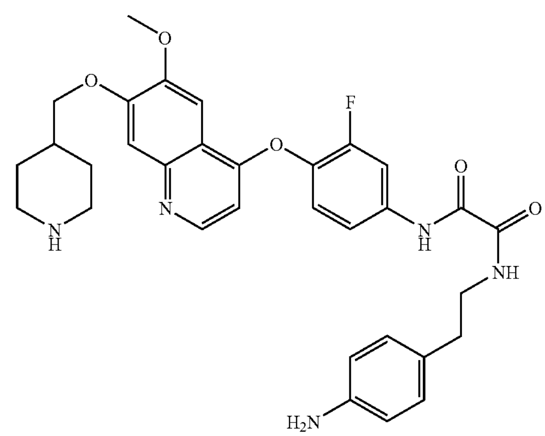 |

TABLE 1-continued

| Entry | Name | Structure |
|---|---|---|
| 284 | 2-(4-Benzyl-piperidin-1-yl)-N-{3-fluoro-4-[6-methoxy-7-(piperidin-4-ylmethoxy)-quinolin-4-yloxy]-phenyl}-2-oxo-acetamide | 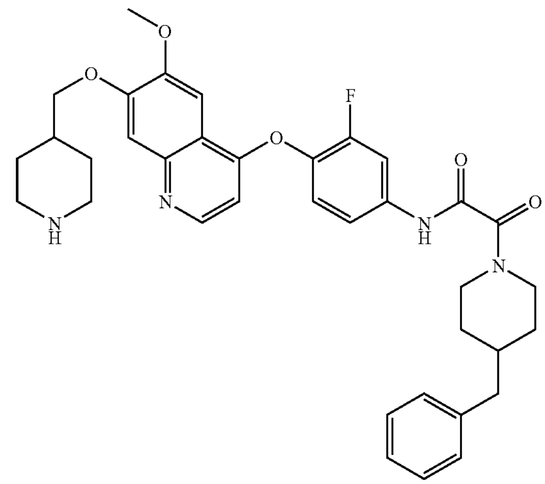 |
| 285 | N-[4-(6,7-Dimethoxy-quinolin-4-yloxy)-phenyl]-N'-(4-fluoro-phenyl)-malonamide | 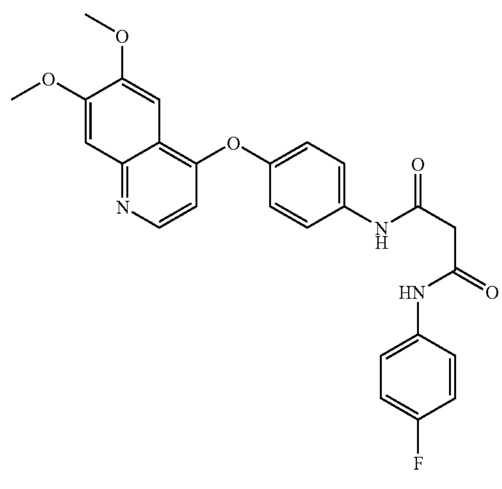 |
| 286 | N-[5-Chloro-6-(6,7-dimethoxy-quinolin-4-yloxy)-pyridin-3-yl]-N'-(3-fluoro-phenyl)-malonamide | 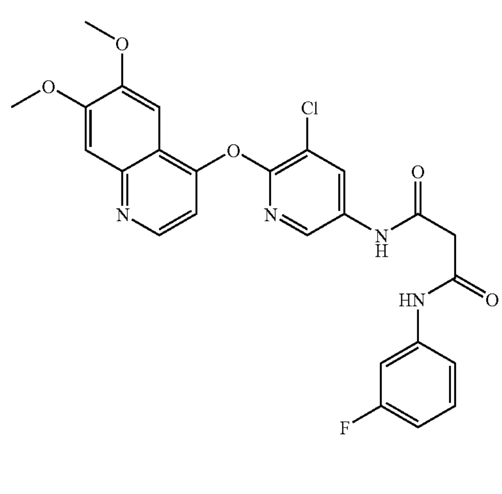 |

TABLE 1-continued

| Entry | Name | Structure |
|---|---|---|
| 287 | N-[5-Chloro-6-(6,7-dimethoxy-quinolin-4-yloxy)-pyridin-3-yl]-N'-phenyl-malonamide | 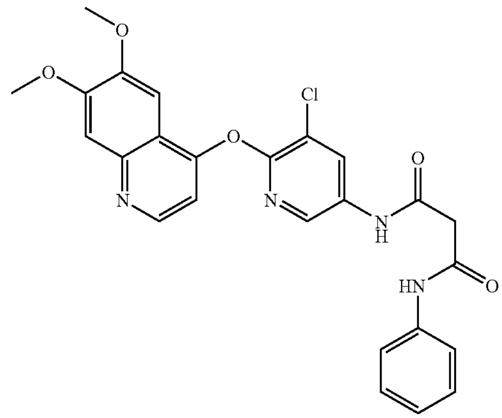 |
| 288 | N-[5-Chloro-6-(6,7-dimethoxy-quinolin-4-yloxy)-pyridin-3-yl]-N'-(4-fluoro-phenyl)-2,2-dimethyl-malonamide | 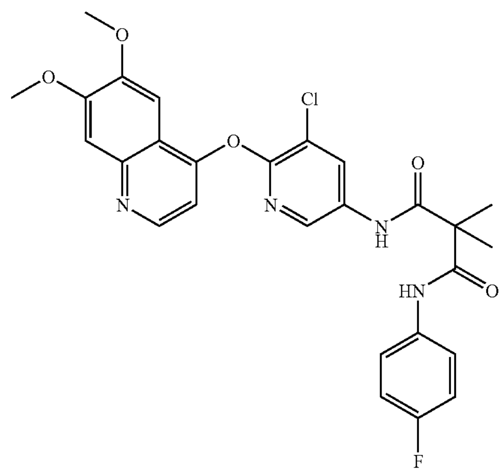 |
| 289 | N-Ethyl-N'-{3-fluoro-4-[6-methoxy-7-(piperidin-4-ylmethoxy)-quinolin-4-yloxy]-phenyl}-oxalamide | 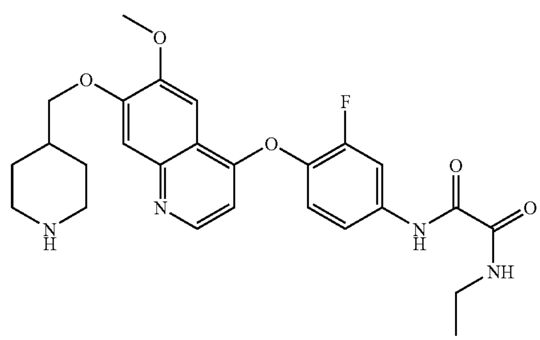 |
| 290 | N-{3-Fluoro-4-[6-methoxy-7-(piperidin-4-ylmethoxy)-quinolin-4-yloxy]-phenyl}-N'-isopropyl-oxalamide | 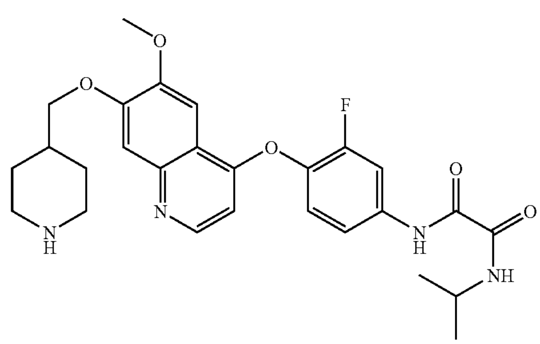 |

TABLE 1-continued

| Entry | Name | Structure |
|---|---|---|
| 291 | N-Butyl-N'-{3-fluoro-4-[6-methoxy-7-(piperidin-4-ylmethoxy)-quinolin-4-yloxy]-phenyl}-oxalamide | 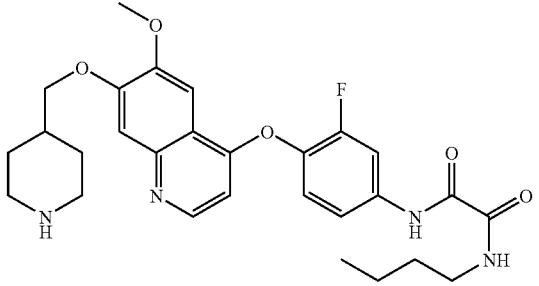 |
| 292 | N-{3-Fluoro-4-[6-methoxy-7-(piperidin-4-ylmethoxy)-quinolin-4-yloxy]-phenyl}-N'-(2-methoxy-ethyl)-oxalamide | 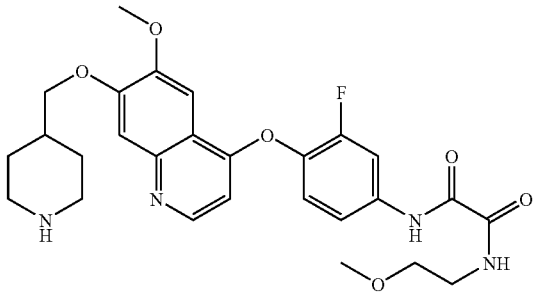 |
| 293 | N-Cyclopropylmethyl-N'-{3-fluoro-4-[6-methoxy-7-(piperidin-4-ylmethoxy)-quinolin-4-yloxy]-phenyl}-oxalamide | 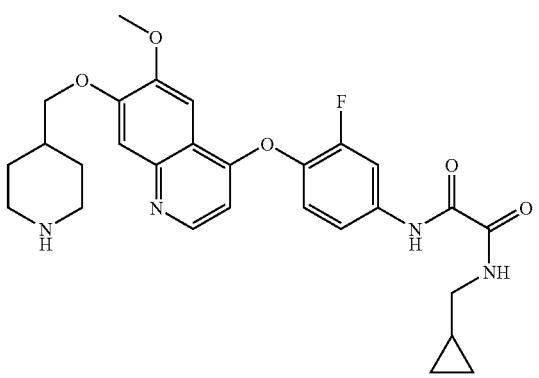 |
| 294 | N-{3-Fluoro-4-[6-methoxy-7-(piperidin-4-ylmethoxy)-quinolin-4-yloxy]-phenyl}-N'-(2-morpholin-4-yl-ethyl)-oxalamide | 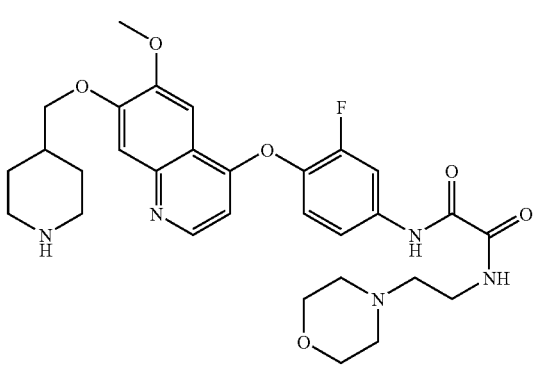 |

TABLE 1-continued

| Entry | Name | Structure |
|---|---|---|
| 295 | N-{3-Fluoro-4-[6-methoxy-7-(piperidin-4-ylmethoxy)-quinolin-4-yloxy]-phenyl}-2-oxo-2-pyrrolidin-1-yl-acetamide | 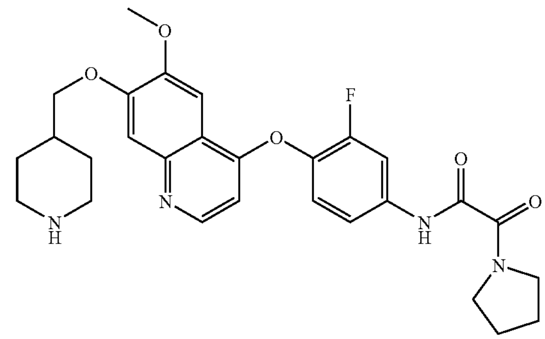 |
| 296 | N-Ethyl-N'-{3-fluoro-4-[6-methoxy-7-(piperidin-4-ylmethoxy)-quinolin-4-yloxy]-phenyl}-N-methyl-oxalamide | 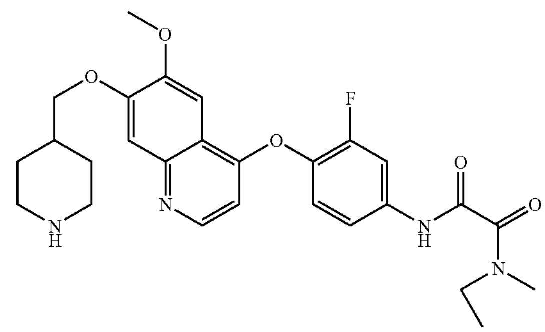 |

In another aspect, the invention comprises a compound for modulating kinase activity of formula A-B-C, or a pharmaceutically acceptable salt, hydrate, or prodrug thereof, wherein, A is selected from:

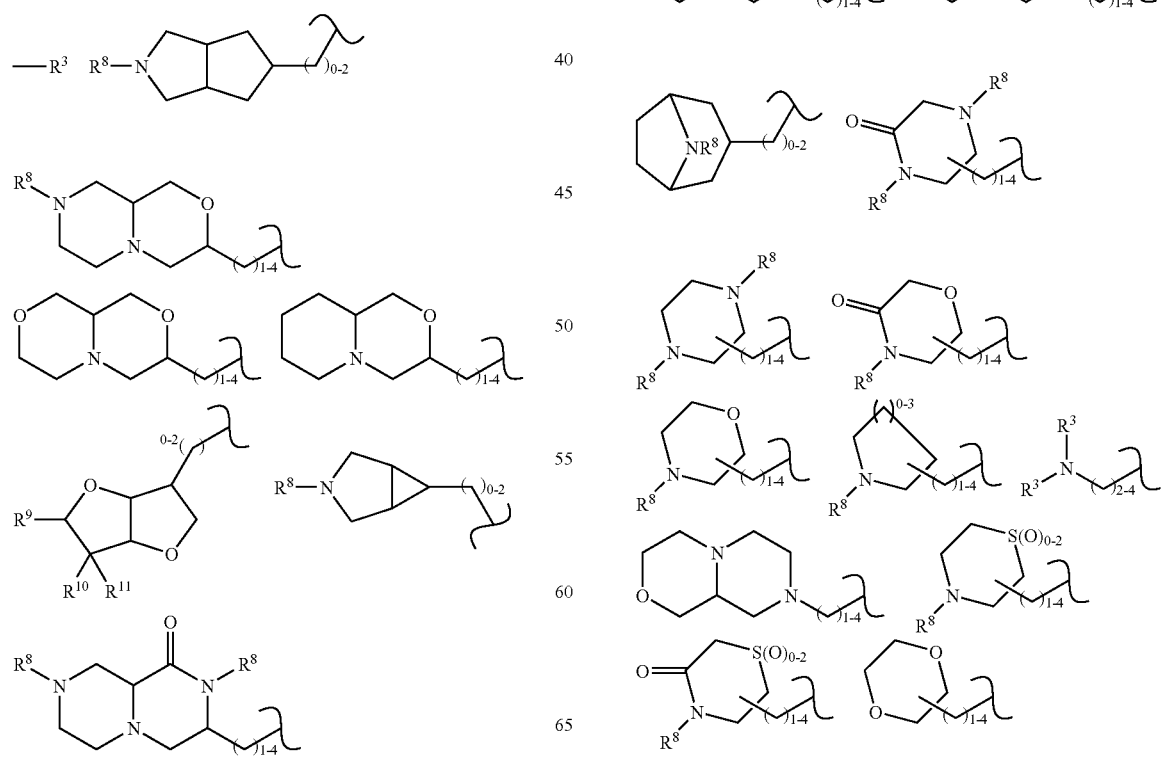

B is selected from:

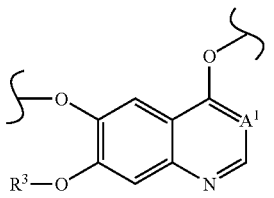

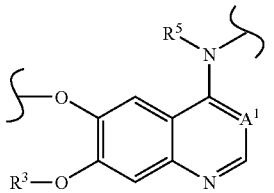

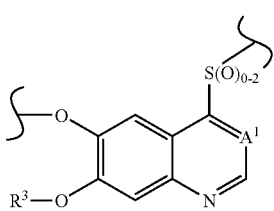

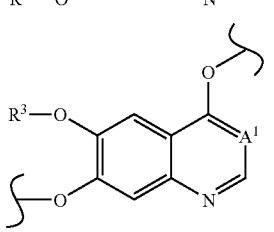

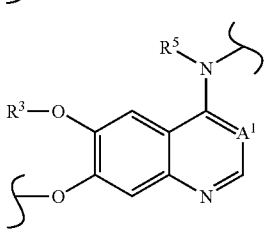

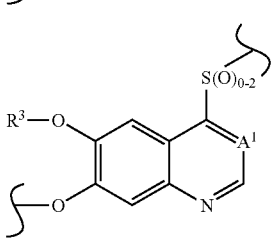

and, C is selected from:

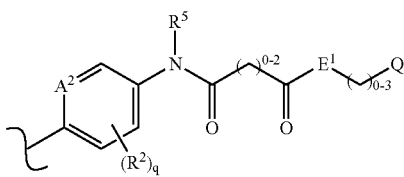

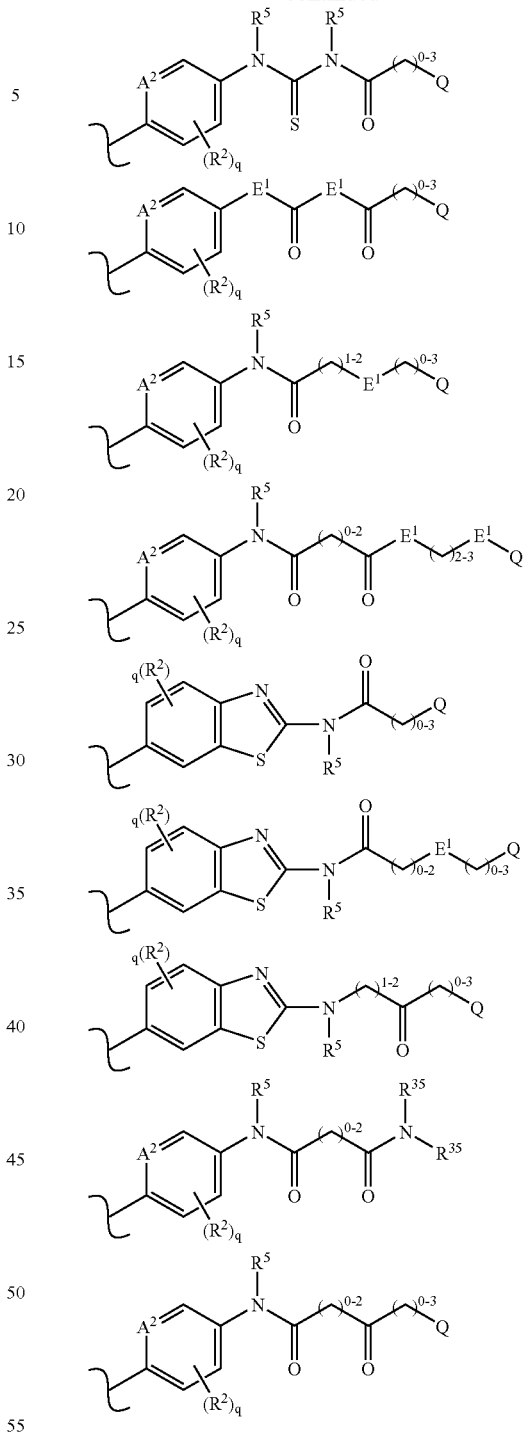

wherein $R^2$ is selected from —H, halogen, trihalomethyl, —CN, —NH$_2$, —NO$_2$, —OR$^3$, —NR$^3$R$^3$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, and optionally substituted lower alkyl;

q is 0 to 2;

each $R^3$ is independently selected from —H, optionally substituted lower alkyl, optionally substituted aryl, optionally substituted arylalkyl, and optionally substituted heteroarylalkyl;

two R³, together with the nitrogen to which they are attached, form a four- to seven-membered heteroalicyclic, said four- to seven-membered heteroalicyclic optionally containing one additional heteroatom; when one said additional heteroatom is a nitrogen, then said nitrogen is optionally substituted with a group selected from —H, trihalomethyl, —SO₂R⁵, —SO₂NR⁵R⁵, —CO₂R⁵, —C(O)NR⁵R⁵, —C(O)R⁵, and optionally substituted lower alkyl;

each R³⁵ is independently selected from —H, —C(═O)R³, —C(═O)OR³, —C(═O)SR³, —SO₂R³, —C(═O)N(R³)R³, and optionally substituted lower alkyl;

two R³⁵, together with the nitrogen to which they are attached, can combine to form a heteroalicyclic optionally substituted with between one and four of R⁶⁰, said heteroalicyclic may have an additional annular heteroatom, and said heteroalicyclic may have an aryl fused thereto, said aryl optionally substituted with an additional one to four of R⁶⁰;

A¹ is selected from ═N—, ═C(H)—, and ═C(CN)—;
A² is either ═N— or ═C(H)—;
R⁵ is —H or optionally substituted lower alkyl;
R⁸ is selected from R³, —SO₂NR³R³, —CO₂R³, —C(O)NR³R³, —SO₂R³, and —C(O)R³;
R⁹, R¹⁰, and R¹¹ are each independently selected from —H, and —OR¹²; or
R⁹ is selected from —H, and —OR¹², and R¹⁰ and R¹¹, when taken together, are either an optionally substituted alkylidene or an oxo; and
R¹² is selected from —H, —C(O)R³, optionally substituted lower alkylidene, optionally substituted lower arylalkylidyne, optionally substituted lower heterocyclylalkylidyne, optionally substituted lower alkylidene, optionally substituted lower alkylidenearyl, optionally substituted lower alkylideneheterocyclyl, optionally substituted lower alkyl, optionally substituted lower alkylaryl, optionally substituted aryl, optionally substituted lower heterocyclylalkyl, and optionally substituted heterocyclyl;
or two R¹²'s, when taken together, form 1) a corresponding spirocyclic ketal when said two R¹²'s stem from R¹⁰ and R¹¹, or 2) a corresponding cyclic ketal when said two R¹²'s stem from R⁹ and one of R¹⁰ and R¹¹;
E¹ is selected from —O—, —CH₂—, —N(R⁵)—, and —S(O)₀₋₂—;
Q is a five- to ten-membered ring system, optionally substituted with between zero and four of R²⁰;
R²⁰ is selected from —H, halogen, trihalomethyl, —CN, —NO₂, —NH₂, —OR³, —NR³R³, —S(O)₀₋₂R³, —SO₂NR³R³, —CO₂R³, —C(O)NR³R³, —N(R³)SO₂R³, —N(R³)C(O)R³, —N(R³)CO₂R³, —C(O)R³, and optionally substituted lower alkyl;
R⁶⁰ is selected from —H, halogen, trihalomethyl, —CN, —NO₂, —NH₂, —OR³, —NR³R³, —S(O)₀₋₂R³, —SO₂NR³R³, —CO₂R³, —C(O)NR³R³, —N(R³)SO₂R³, —N(R³)C(O)R³, —N(R³)CO₂R³, —C(O)R³, optionally substituted lower alkyl, optionally substituted aryl, optionally substituted heteroarylalkyl, and optionally substituted arylalkyl;
two of R⁶⁰, when attached to a non-aromatic carbon, can be oxo;
each methylene in any of the above formulae is independently optionally substituted with R²⁵;
each R²⁵ is independently selected from halogen, trihalomethyl, —CN, —NO₂, —NH₂, —OR³, —NR¹R³, —S(O)₀₋₂ R³, —SO₂NR³R³, —CO₂R³, —C(O)NR³R³, —N(R³)SO₂R³, —N(R³)C(O)R³, —N(R¹³)CO₂R³, —C(O)R³, optionally substituted aryl, optionally substituted arylalkyl, heteroarylalkyl, and optionally substituted lower alkyl; two of R²⁵, together with the carbon or carbons to which they are attached, can combine to form a three- to seven-membered alicyclic or heteroalicyclic, two of R²⁵ on a single carbon can be oxo;

with the proviso that when B is selected from:

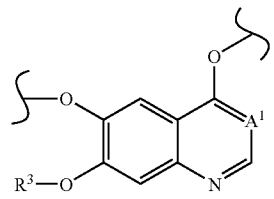

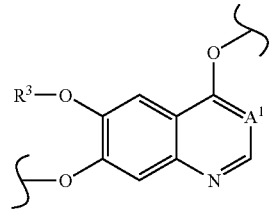

and C contains

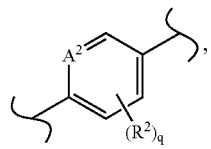

and the remaining portion of C contains one of:

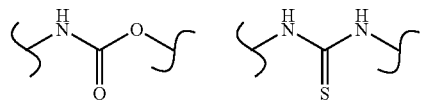

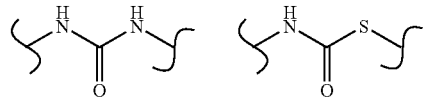

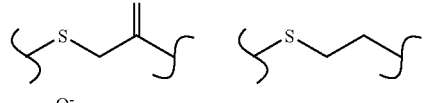

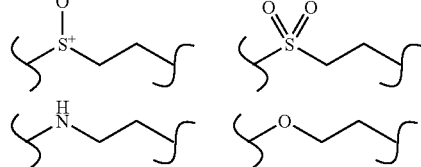

directly attached to

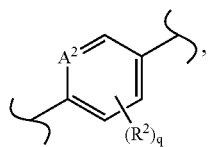

then A must be one of:

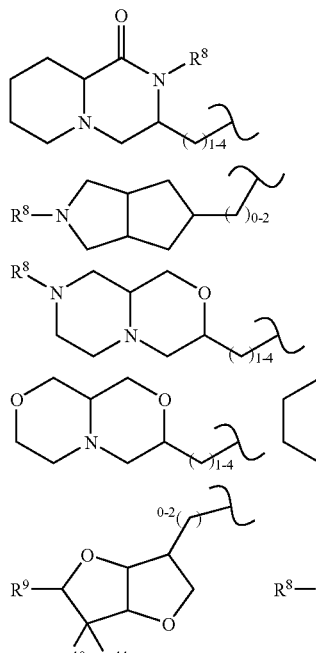

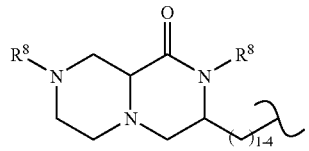

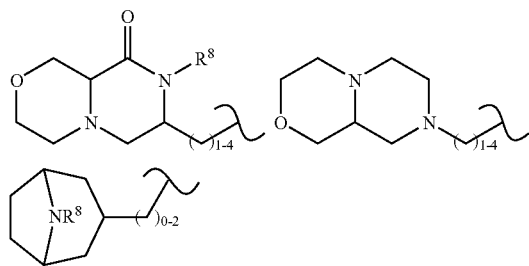

and with the proviso that when C contains

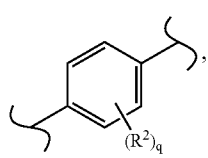

and B is selected from:

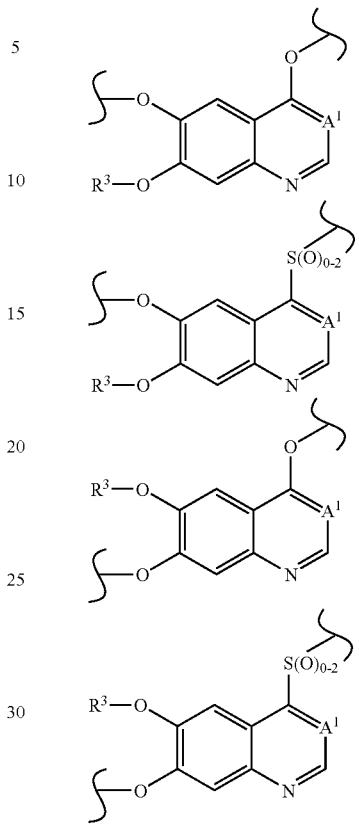

then the portion of C directly attached to

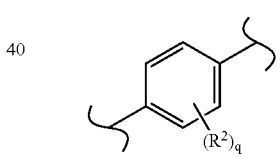

cannot contain

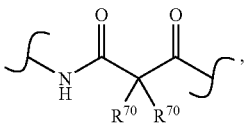

when $R^{70}$ is selected from —H, $C_{1-4}$alkyl, and $C_{1-4}$alkoxyl.

In another example the compound is according to the preceding paragraph, wherein Q is selected from phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl;

each optionally substituted with between one and four of $R^{20}$; wherein each $R^{20}$ is independently selected from —H, halogen, trihalomethyl, —CN, —NO$_2$, —NH$_2$, —OR$^3$, —NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, and optionally substituted lower alkyl.

In another example the compound is according to the preceding paragraph, wherein B is either of the following:

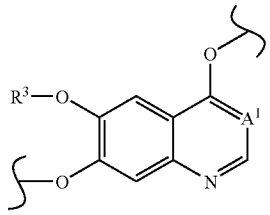

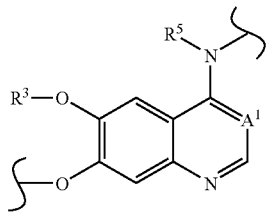

wherein $A^1$ is either =N— or =C(H)—.

In another example the compound is according to the preceding paragraph, wherein B is

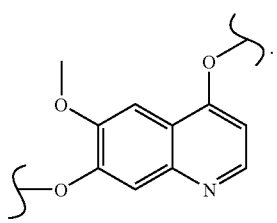

In another example the compound is according to the preceding paragraph, wherein C is selected from:

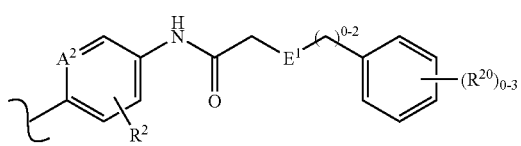

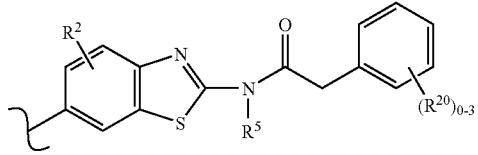

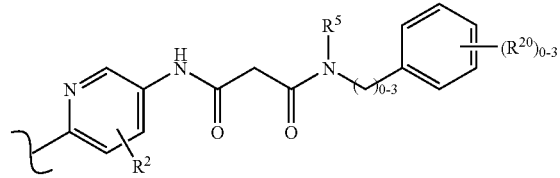

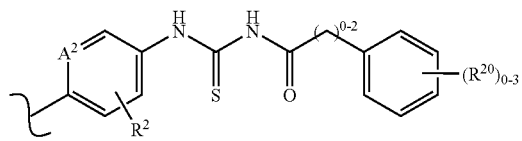

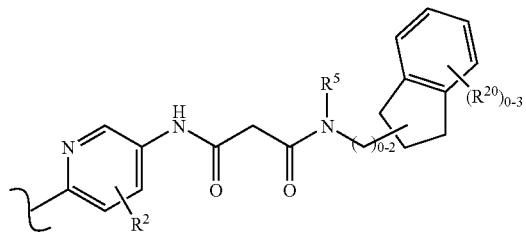

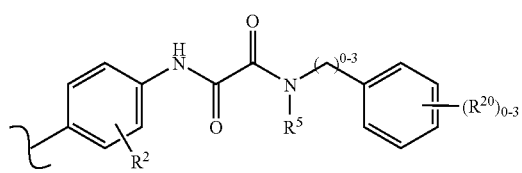

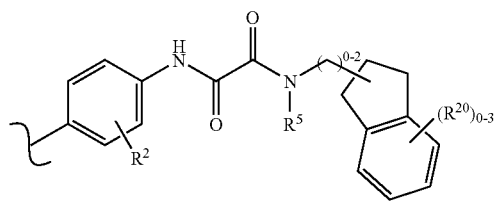

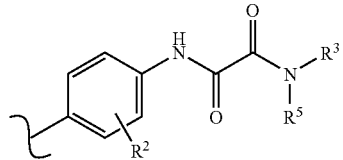

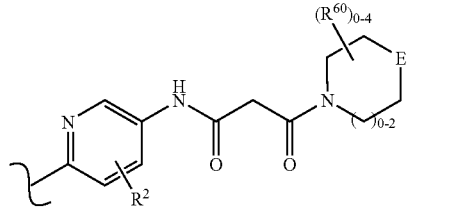

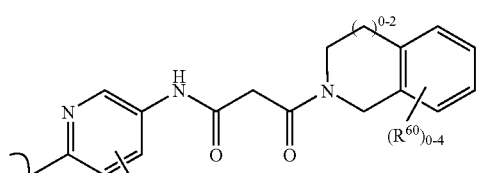

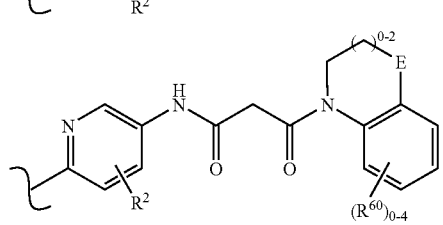

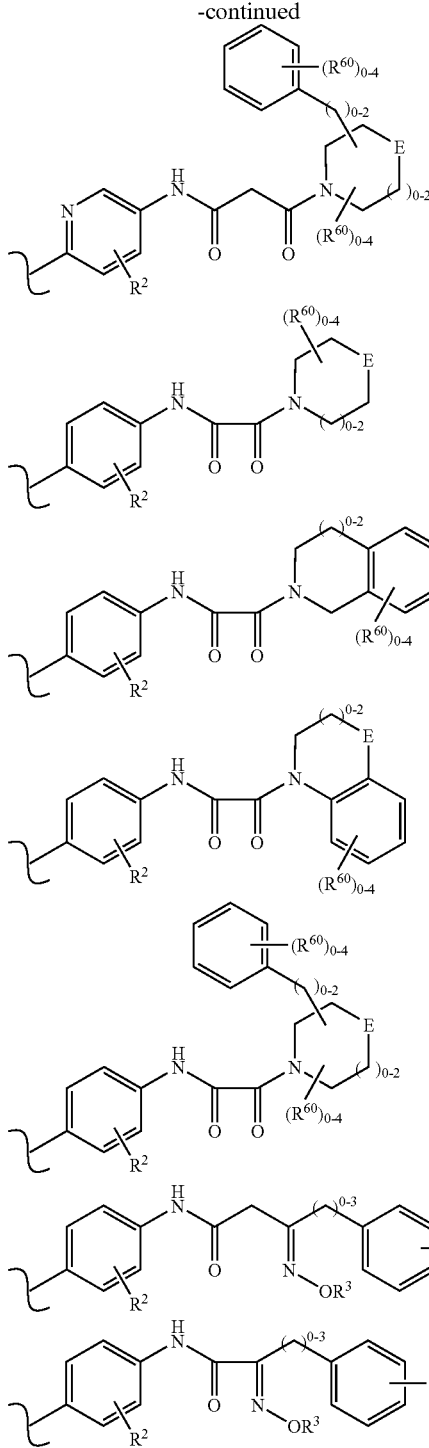

wherein $R^2$, $R^3$, $R^5$, $R^{20}$, $R^{25}$ and $R^{60}$ are as defined above.

In another example the compound is according to the preceding paragraph, $R^2$ is selected from halogen, trihalomethyl, —CN, —NO$_2$, —OR$^3$, —NR$^3$R$^3$, —CO$_2$R$^3$, —C(O)NR$^3$R$^3$, —N(R$^3$)C(O)R$^3$, —N(R$^3$)CO$_2$R$^3$, —C(O)R$^3$, and optionally substituted lower alkyl In another example the compound is according to the preceding paragraph, wherein $R^1$ is halogen.

In another example the compound is according to the preceding paragraph, wherein $R^2$ is either fluorine or chlorine.

In another aspect, the invention comprises a compound for modulating kinase activity according to Formula XI,

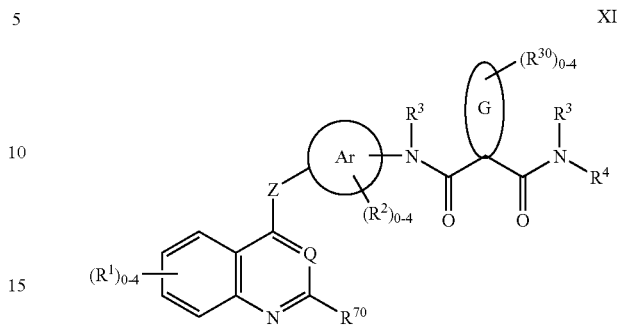

or a pharmaceutically acceptable salt, hydrate, or prodrug thereof, wherein, each $R^1$ is independently selected from halogen, —OR$^3$, —NO$_2$, —NH$_2$, —NR$^3$R$^4$, -D-R$^{50}$ and optionally substituted C$_{1-6}$alkyl;

$R^{70}$ is selected from —H, halogen, —OR$^3$, —S(O)$_{0-2}$R$^3$, —NO$_2$, —NH$_2$, —NR$^3$R$^4$, and optionally substituted C$_{1-6}$alkyl;

Q is selected from =N—, =C(H)—, and =C(CN)—;

Z is selected from —S(O)$_{0-2}$—, —O—, and —NR$^5$—;

Ar is either a five- or six-membered arylene or a five- or six-membered heteroarylene containing between one and three heteroatoms;

G is either an optionally substituted cycloalkyl or an optionally substituted heteroalicyclic;

each $R^2$ is independently selected from halogen, trihalomethyl, —CN, —NO$_2$, —NH$_2$, —OR$^3$, —NR$^3$R$^4$, —S(O)$_{0-2}$ R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, and optionally substituted C$_{1-6}$alkyl;

each $R^3$ is independently —H or $R^4$;

each $R^4$ is independently selected from optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl; or $R^3$ and $R^4$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P;

$R^5$ is —H or optionally substituted C$_{1-6}$alkyl;

each D is independently selected from —O—, —S(O)$_{0-2}$—, and —NR$^5$—;

each $R^{50}$ is independently either $R^3$, or according to formula XII;

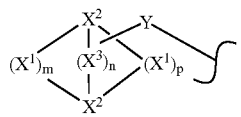

wherein $X^1$, $X^2$, and optionally $X^3$, represent the atoms of a saturated bridged ring system, said saturated bridged ring system comprising up to four annular heteroatoms represented by any of $X^1$, $X^2$, and $X^3$; wherein, each $X^1$ is independently selected from —C($R^6$)$R^7$—, —O—, —S(O)$_{0-2}$—, and —N$R^8$—;

each $X^2$ is independently an optionally substituted bridgehead methine or a bridgehead nitrogen;

each $X^3$ is independently selected from —C($R^6$)$R^7$—, —O—, —S(O)$_{0-2}$—, and —N$R^8$—;

Y is either:

an optionally substituted lower alkylene linker, between D and either 1) any annular atom of the saturated bridged ring system, except $X^2$ when $X^2$ is a bridgehead nitrogen, or 2) any heteroatom, represented by any of $R^6$ or $R^7$; provided there are at least two carbon atoms between D and any annular heteroatom of the saturated bridged ring system or any heteroatom represented by any of $R^6$ or $R^7$;

or Y is absent, when Y is absent, said saturated bridged ring system, is directly attached to D via an annular carbon of said saturated bridged ring system, unless D is —SO$_2$—, in which case said saturated bridged ring system, is directly attached to D via an any annular atom of said saturated bridged ring system;

m and p are each independently one to four;

n is zero to two, when n equals zero, then there is a single bond between the two bridgehead $X^2$ s;

$R^6$ and $R^7$ are each independently selected from —H, halogen, trihalomethyl, —CN, —NH$_2$, —NO$_2$, —O$R^3$, —N$R^3R^4$, —S(O)$_{0-2}R^4$, —SO$_2$N$R^3R^4$, —CO$_2R^3$, —C(O)N$R^3R^4$, —N($R^3$)SO$_2R^4$, —N($R^3$)C(O)$R^3$, —NCO$_2R^3$, —C(O)$R^3$, optionally substituted C$_{1-6}$alkyl, optionally substituted aryl, optionally substituted aryl C$_{1-6}$alkyl, optionally substituted heterocyclyl, optionally substituted heterocyclyl C$_{1-6}$alkyl, and a bond to either Y or D; or $R^6$ and $R^7$, when taken together are oxo; or $R^6$ and $R^7$, when taken together with a common carbon to which they are attached, form a optionally substituted three- to seven-membered spirocyclyl, said optionally substituted three- to seven-membered spirocyclyl optionally containing at least one additional annular heteroatom selected from N, O, S, and P;

$R^8$ is selected from —$R^3$, Y, —SO$_2$N$R^3R^4$, —CO$_2R^4$, —C(O)N$R^3R^3$, —SO$_2R^4$, and —C(O)$R^3$; and each $R^{30}$ is independently selected from halogen, trihalomethyl, —CN, —NO$_2$, —NH$_2$, —O$R^3$, —N$R^3R^4$, —S(O)$_{0-2}$ $R^3$, —SO$_2$N$R^3R^3$, —CO$_2R^3$, —C(O)N$R^3R^3$, —N($R^3$)SO$_2R^3$, —N($R^3$)C(O)$R^3$, —N($R^3$)CO$_2R^3$, —C(O)$R^3$, and optionally substituted C$_{1-6}$alkyl.

In one example, the compound is according to Formula XI, wherein Z is either —O— or —N$R^5$—.

In another example, the compound is according to the preceding paragraph, wherein at least one of $R^1$ is -D-$R^{50}$.

In another example, the compound is according to the preceding paragraph, wherein D is —O— and at least one other $R^1$ is —O$R^3$.

In another example, the compound is according to the preceding paragraph, of formula XIIIa or XIIb:

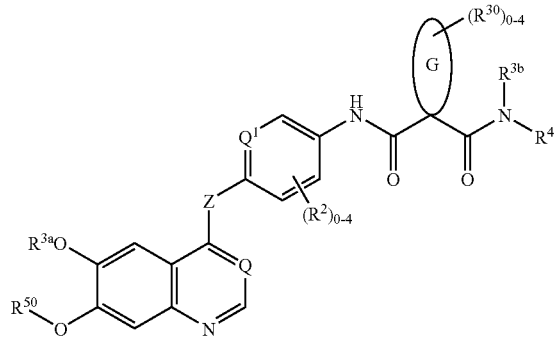

XIIIa

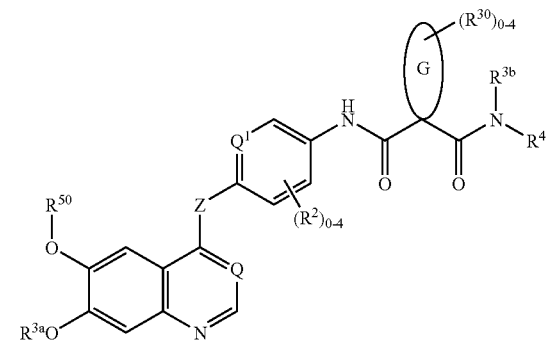

XIIIb wherein $Q^1$ is either =N— or =C(H)—.

In another example, the compound is according to formula XIIa or formula XIIIb, wherein $R^{50}$ is selected from C$_{1-6}$alkyl optionally substituted with at least one of optionally substituted amino, optionally substituted C$_{1-6}$alkyl amino, optionally substituted C$_{1-6}$dialkyl amino, optionally substituted heteroalicylic, and a group of formula XII.

In another example, the compound is according to the preceding paragraph, wherein $R^{3a}$ is C$_{1-6}$alkyl.

In another example, the compound is according to the preceding paragraph, wherein Z is —O—.

In another example, the compound is according to the preceding paragraph, wherein G is selected from cyclopropyl, aziridine, cyclobutyl, and azetidine, each optionally substituted with between zero and four of $R^{30}$.

In another example, the compound is according to the preceding paragraph, wherein Q is either =N— or =C(H)—.

In another example, the compound is according to the preceding paragraph, wherein $R^2$ is selected from —H, halogen, C$_{1-6}$ alkyl and perfluoro C$_{1-6}$ alkyl.

In another example, the compound is according to the preceding paragraph, wherein —N($R^{3b}$)$R^4$ is selected from the following:

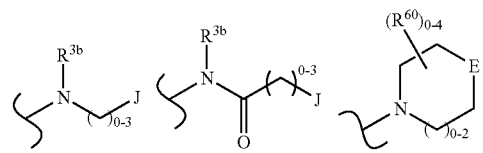

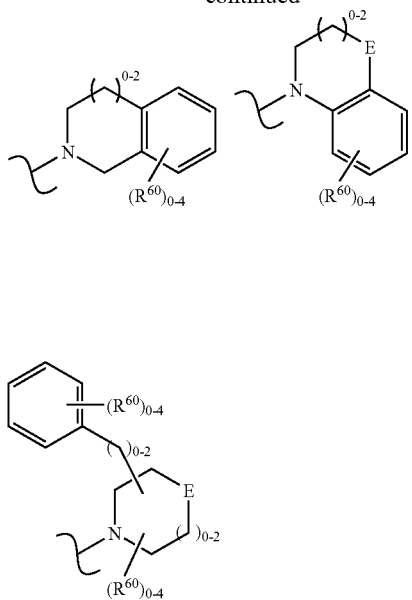

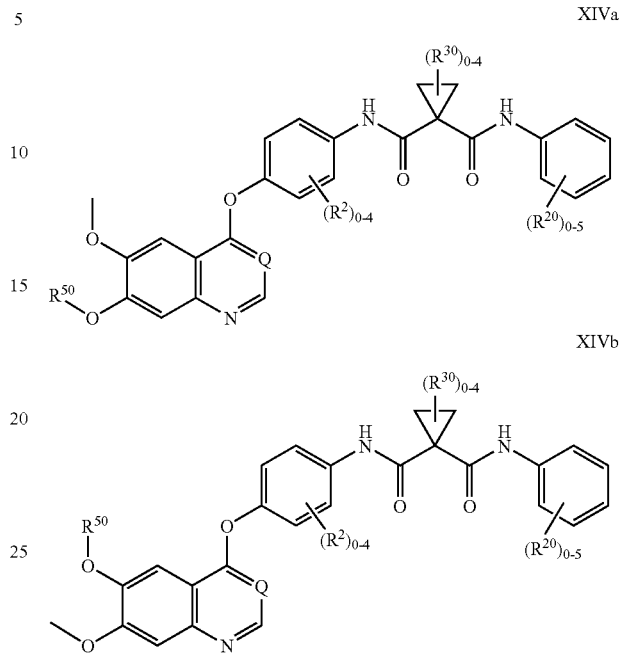

In another example, the compound is according to the preceding paragraph, of formula XIVa or XIVb:

wherein J, is a five- to ten-membered ring, optionally substituted with between zero and five of $R^{20}$;

each $R^{20}$ is independently selected from —H, halogen, trihalomethyl, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

two of $R^{20}$, together with the atom or atoms to which they are attached, combine to form an optionally substituted three- to seven-membered heteroalicyclic, said optionally substituted three- to seven-membered heteroalicyclic either spiro- to J or fused to J;

E is selected from —O—, —$N(R^5)$—, —$CH_2$—, and —$S(O)_{0-2}$—;

each $R^{60}$ is independently selected from halogen, trihalomethyl, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, optionally substituted $C_{1-6}$alkyl, optionally substituted aryl, optionally substituted heteroaryl $C_{1-6}$alkyl, and optionally substituted aryl $C_{1-6}$alkyl;

each methylene in any of the above formulae, other than those in a depicted ring, is independently optionally substituted with $R^{25}$; and $R^{25}$ is selected from halogen, trihalomethyl, oxo, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, optionally substituted aryl, optionally substituted aryl $C_{1-6}$alkyl, heteroaryl $C_{1-6}$alkyl, and optionally substituted $C_{1-6}$alkyl; or two of $R^{25}$, together with the carbon or carbons to which they are attached, can combine to form a three- to seven-membered alicyclic or heteroalicyclic;

$R^{3b}$ is equivalent to $R^3$ as defined above; and $R^4$ and $R^5$ are as defined above.

In another example, the compound is according to the preceding paragraph, wherein $R^{50}$ is $C_{1-6}$alkyl optionally substituted with a group selected from optionally substituted amino, an optionally substituted alkylamino, optionally substituted dialkylamino, and optionally substituted heteroalicyclic.

In another example, the compound is according to the preceding paragraph, wherein the heteroalicyclic portion of $R^{50}$ is selected from the group consisting of piperidine, piperazine, morpholine, thiomorpholine, thiomorpholine 1-oxide, thiomorpholine 1,1-dioxide, 2-oxo-morpholine, pyrrolidine, and azepine.

In another example, the compound is as defined two paragraphs above, wherein $R^{50}$ is according to formula XII.

In another example, the compound is according to the preceding paragraph, wherein the saturated bridged ring system according to formula XII has a geometry selected from the group consisting of [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2], and [2.2.1].

In another example, the compound is according to the preceding paragraph, wherein Y is selected from —$CH_2CH_2CH_2CH_2$—, —$CH_2CH_2CH_2$—, —$CH_2CH_2$—, —$CH_2$—, and absent.

In another example, the compound is according to the preceding paragraph, wherein n is 0 and the saturated bridged ring system according to formula XII has a geometry selected from the group consisting of [4.4.0], [4.3.0], [4.2.0], [4.1.0], [3.3.0], [3.2.0], and [3.1.0].

In another example, the compound is according to the preceding paragraph, wherein said saturated bridged ring system contains at least one annular nitrogen or at least one annular oxygen.

In another example, the compound is according to the preceding paragraph, wherein said saturated bridged ring system contains —$NR^8$—, wherein $R^8$ is selected from —H, optionally substituted $C_{1-6}$alkyl, —$CO_2R^3$, —$C(O)NR^3R^3$, —$SO_2R^3$, and —$C(O)R^3$.

In another example, the compound is as defined two paragraphs above, wherein said saturated bridged ring system is of formula XV,

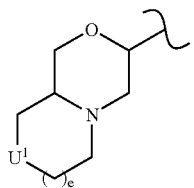

XV wherein $U^1$ is selected from —O—, —S(O)$_{0-2}$—, —NR$^8$—, —CR$^6$R$^7$—, and absent; and e is 0 or 1.

In another example, the compound is according to the preceding paragraph, wherein Y is —CH$_2$—.

In another example, the compound is according to the preceding paragraph, wherein $U^1$ is —NR$^8$, wherein R$^8$ is selected from —H, optionally substituted lower alkyl, —CO$_2$R$^3$, —C(O)NR$^3$R$^3$, —SO$_2$R$^3$, and —C(O)R$^3$.

In another example, the compound is as defined two paragraphs above, wherein $U^1$ is —O—.

In another example, the compound is as defined three paragraphs above, wherein $U^1$ is absent.

In another example, the saturated bridged ring system is according to formula XII and has a geometry selected from the group consisting of [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2], and [2.2.1], and Y is selected from —CH$_2$CH$_2$—, —CH$_2$—, and absent.

In another example, the compound is according to the preceding paragraph, wherein said saturated bridged ring system is of formula XVI,

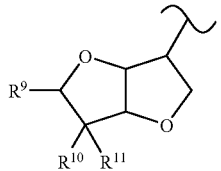

XVI wherein R$^9$, R$^{10}$, and R$^{11}$ are each independently selected from —H, and —OR$^{12}$; or R$^9$ is selected from —H, and —OR$^{12}$, and R$^{10}$ and R$^{11}$, when taken together, are either an optionally substituted alkylidene or an oxo;

R$^{12}$ is selected from —H, —C(O)R$^3$, optionally substituted lower alkylidene, optionally substituted lower arylalkylidyne, optionally substituted lower heterocyclylalkylidyne, optionally substituted lower alkylidene, optionally substituted lower alkylidenearyl, optionally substituted lower alkylideneheterocyclyl, optionally substituted lower alkyl, optionally substituted lower alkylaryl, optionally substituted aryl, optionally substituted lower heterocyclylalkyl, and optionally substituted heterocyclyl;

or two R$^{12}$'s, when taken together, form 1) a corresponding spirocyclic ketal when said two R$^{12}$'s stem from R$^{10}$ and R$^{11}$, or 2) a corresponding cyclic ketal when said two R$^{12}$'s stem from R$^9$ and one of R$^{10}$ and R$^{11}$.

In another example, the compound is according to the preceding paragraph, wherein one of R$^{10}$ and R$^{11}$ is —OR$^{12}$, wherein R$^{12}$ is selected from —H, —C(O)R$^3$, and optionally substituted lower alkyl; and R$^9$ and the other of R$^{10}$ and R$^{11}$ are both —H.

In another example, the compound is according to the preceding paragraph, wherein Y is either —CH$_2$— or absent.

In another example, the compound is as defined three paragraphs above, wherein R$^9$ is an alkyl group containing at least one fluorine substitution thereon.

In another example, the compound is as defined eleven paragraphs above, wherein said saturated bridged ring system is of formula XVII, wherein R$^8$ is selected from —H, optionally substituted C$_{1-6}$alkyl, —CO$_2$R$^3$, —C(O)NR$^3$R$^3$, —SO$_2$R$^3$, and —C(O)R$^3$.

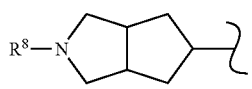

XVII

In another example, the compound is according to the preceding paragraph, wherein Y is either —CH$_2$— or absent.

In another example, the compound is according to the preceding paragraph, wherein R$^8$ is methyl or ethyl.

In another example, the compound is according to the preceding paragraph, wherein at least one of R$^2$ is halogen.

In another example, the compound is as defined fifteen paragraphs above, wherein said saturated bridged ring system is of formula XVIII, wherein R$^8$ is selected from —H, optionally substituted C$_{1-6}$alkyl, —CO$_2$R$^3$, —C(O)NR$^3$R$^3$, —SO$_2$R$^3$, and —C(O)R$^3$.

XVIII

In another example, the compound is according to the preceding paragraph, wherein Y is —CH$_2$—.

In another example, the compound is according to the preceding paragraph, wherein R$^8$ is methyl or ethyl.

In another example, the compound is as defined nineteen paragraphs above, wherein said saturated bridged ring system is of formula XIX

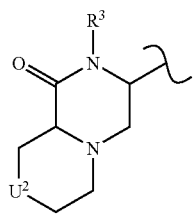

XIX wherein $U^2$ is selected from —O—, —S(O)$_{0-2}$—, —NR$^8$—, —CR$^6$R$^7$—, and absent.

In another example, the compound is according to the preceding paragraph, wherein R$^3$ of formula XIX is selected from —H and optionally substituted alkyl.

In another example, the compound is according to the preceding paragraph, wherein $U^2$ is either —CR$^6$R$^7$— or absent.

In another example, the compound is according to the preceding paragraph, wherein $U^2$ is either —$CH_2$— or absent.

In another example, the compound is according to the preceding paragraph, wherein Y is —$CH_2$—.

In another example, the compound is as defined above, wherein said saturated bridged ring system is according to formula XX, wherein $R^8$ is selected from —H, optionally substituted $C_{1-6}$alkyl, —$CO_2R^3$, —$C(O)NR^3R^3$, —$SO_2R^3$, and —$C(O)R^3$.

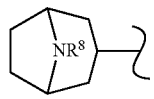

XX

In another example, the compound is according to the preceding paragraph, wherein $R^8$ is methyl or ethyl.

In another example, the compound is according to formula XIVa or XIVb, wherein $R^2$ is selected from $C_{1-6}$ alkyl, perfluoro $C_{1-6}$ alkyl, and halogen.

In another example, the compound is according to the preceding paragraph, wherein $R^2$ is selected from perfluoro $C_{1-3}$ alkyl and halogen.

In another example, the compound is according to formula XIVa or XIVb, wherein $R^{20}$ is selected from halogen, —CN, —$NO_2$, —$NH_2$, —$OR^3$, —$NR^3R^4$, —$N(R^3)SO_2R^3$, —$N(R^3)C(O)R^3$, —$N(R^3)CO_2R^3$, optionally substituted heterocyclyl, and optionally substituted heterocyclyl $C_{1-6}$alkyl, and (two of $R^{20}$) together with the atom or atoms to which they are attached, an optionally substituted three- to six-membered heteroalicyclic, said optionally substituted three- to six-membered heteroalicyclic fused to the phenyl as in XIVa or XIVb.

In another example, the compound is according to the preceding paragraph, wherein $R^{20}$ is selected from halogen, —$NR^3R^4$, optionally substituted heterocyclyl, and optionally substituted heterocyclyl $C_{1-6}$alkyl, and (two of $R^{20}$) together with the atom or atoms to which they are attached, an optionally substituted five- to six-membered heteroalicyclic, said optionally substituted five- to six-membered heteroalicyclic fused to the phenyl as in XIVa or XIVb.

In another example, the compound is according to the preceding paragraph, wherein $R^2$ is selected from $C_{1-6}$ alkyl, perfluoro $C_{1-6}$ alkyl, and halogen.

In another example, the compound is according to the preceding paragraph, wherein $R^2$ is selected from perfluoro $C_{1-3}$ alkyl and halogen.

In another example, the compound is selected from Table 2.

TABLE 2

| Entry | Name | Structure |
|---|---|---|
| 1 | N-(6-{[6,7-bis(methyloxy)quinolin-4-yl]oxy}-5-chloropyridin-3-yl)-N'-(4-fluorophenyl)cyclopropane-1,1-dicarboxamide | 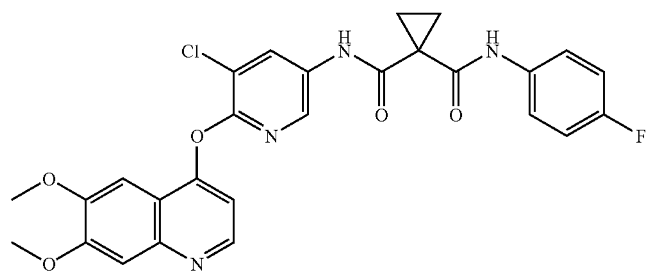 |
| 2 | N-(6-{[6,7-bis(methyloxy)quinolin-4-yl]oxy}-5-chloropyridin-3-yl)-N'-(4-fluorophenyl)cyclobutane-1,1-dicarboxamide | 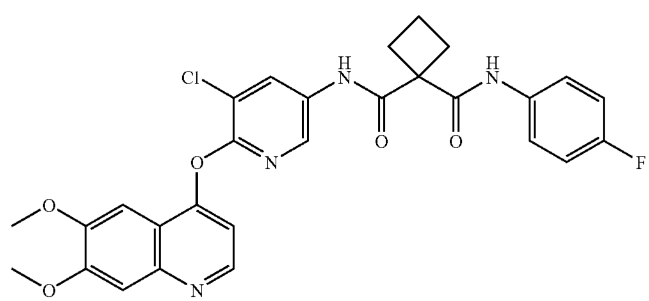 |
| 3 | N-(6-{[6,7-bis(methyloxy)quinolin-4-yl]oxy}-5-chloropyridin-3-yl)-N'-(phenylmethyl)cyclopropane-1,1-dicarboxamide | 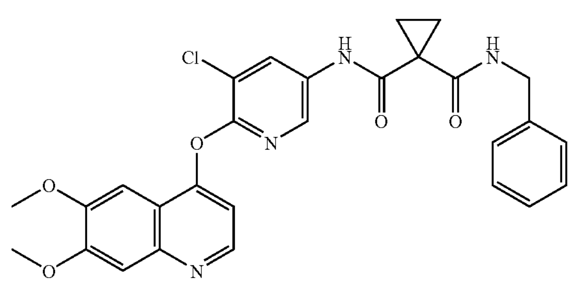 |

TABLE 2-continued

| Entry | Name | Structure |
|---|---|---|
| 4 | N-(6-{[6,7-bis(methyloxy)quinolin-4-yl]oxy}-5-chloropyridin-3-yl)-N'-phenylcyclopropane-1,1-dicarboxamide | 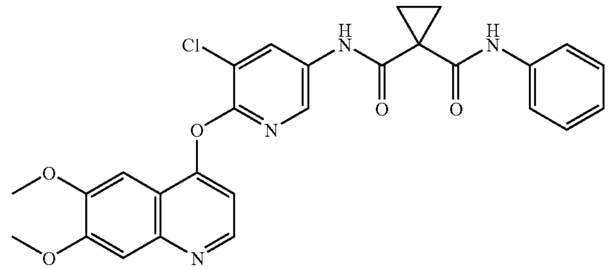 |
| 5 | N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide | 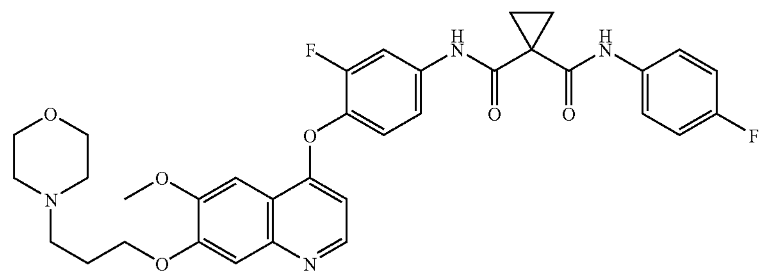 |
| 6 | N-[3-fluoro-4-({6-(methyloxy)-7-[(3-piperidin-1-ylpropyl)oxy]quinolin-4-yl}oxy)phenyl]-N'-{4-fluorophenyl)cyclopropane-1,1-dicarboxamide | 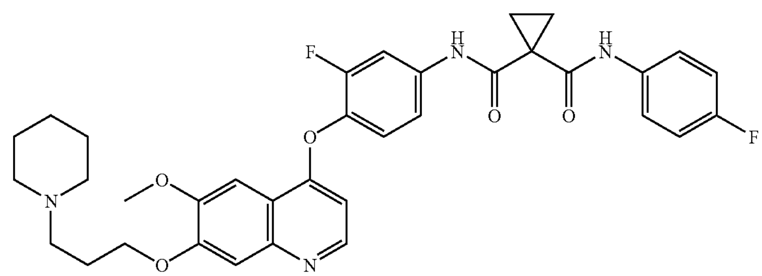 |
| 7 | N-[3-fluoro-4-({6-(methoxy)-7-[(3-piperidin-1-ylpropyl)oxy]quinolin-4-yl}oxy)phenyl]-N'-(4-fluorophenyl)cyclobutane-1,1-dicarboxamide | 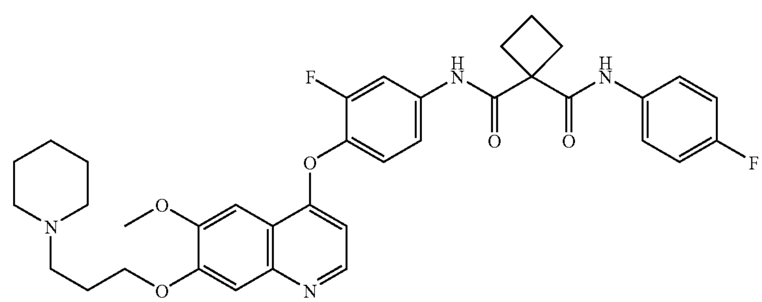 |
| 8 | N-(6-{[6,7-bis(methyloxy)quinolin-4-yl]oxy}-5-chloropyridin-3-yl)-N'-(2-phenylethyl)cyclopropane-1,1-dicarboxamide | 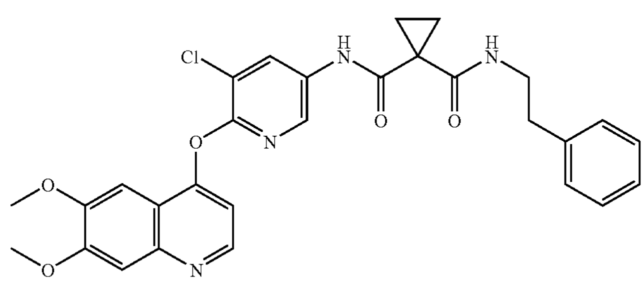 |

TABLE 2-continued

| Entry | Name | Structure |
|---|---|---|
| 9 | N-(6-{[6,7-bis(methyloxy)quinolin-4-yl]oxy}-2-methylpyridin-3-yl)-N'-(4-fluorophenyl)cyclopropane-1,1-dicarboxamide | 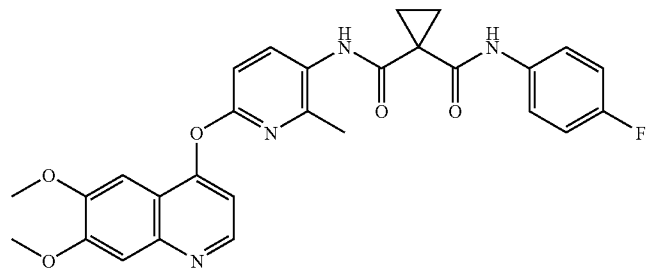 |
| 10 | N-{4-[(7-chloroquinolin-4-yl)oxy]-3-fluorophenyl}-N'-(4-fluorophenyl)cyclopropane-1,1-dicarboxamide | 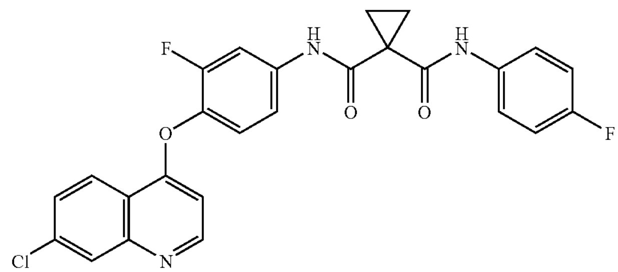 |
| 11 | N-{4-[(7-chloroquinolin-4-yl)oxy]phenyl}-N'-(4-fluorophenyl)cyclopropane-1,1-dicarboxamide | 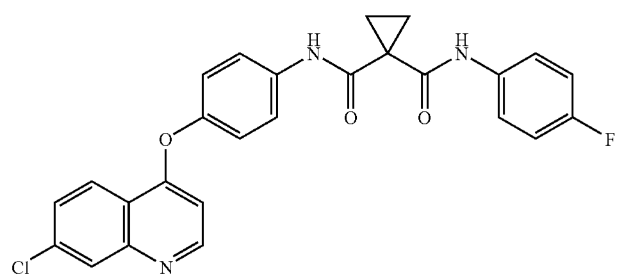 |
| 12 | N-(4-{[6,7-bis(methyloxy)quinolin-4-yl]oxy}phenyl)-N'-(4-fluorophenyl)cyclopropane-1,1-dicarboxamide | 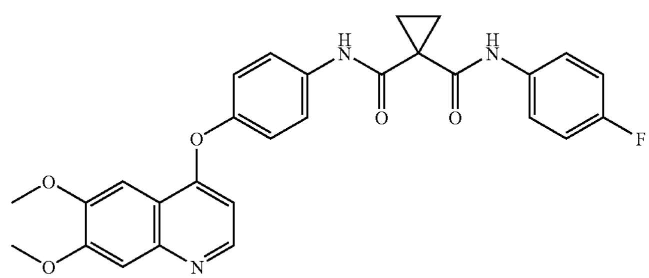 |
| 13 | N-(4-{[6,7-bis(methyloxy)quinazolin-3-4-yl]oxy}phenyl)-N'-(4-fluorophenyl)cyclopropane-1,1-dicarboxamide | 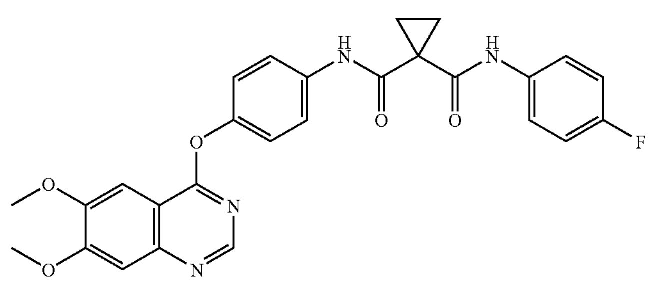 |

TABLE 2-continued

| Entry | Name | Structure |
|---|---|---|
| 14 | N-(4-{[6,7-bis(methyloxy)quinazolin-4-yl]oxy}-3-fluorophenyl)-N'-(4-fluorophenyl)cyclopropane-1,1-dicarboxamide | 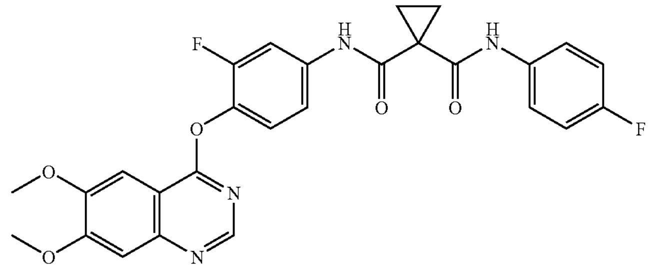 |
| 15 | N-[3-fluoro-4-({6-(methyloxy)-7-[(3-morpholin-4-ylpropyl)oxy]quinazolin-4-yl}oxy)phenyl]-N'-(4-fluorophenyl)cyclopropane-1,1-dicarboxamide | 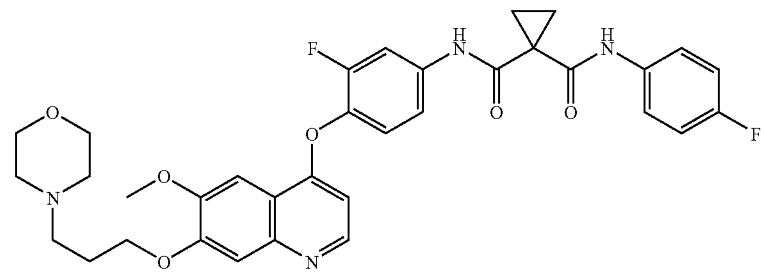 |
| 16 | N-{5-chloro-6-[(6-(methyloxy)-7-{[(1-methylpiperidin-4-yl)methyl]oxy}quinolin-4-yl)oxy]pyridin-3-yl}-N'-(4-fluorophenyl)cyclopropane-1,1-dicarboxamide | 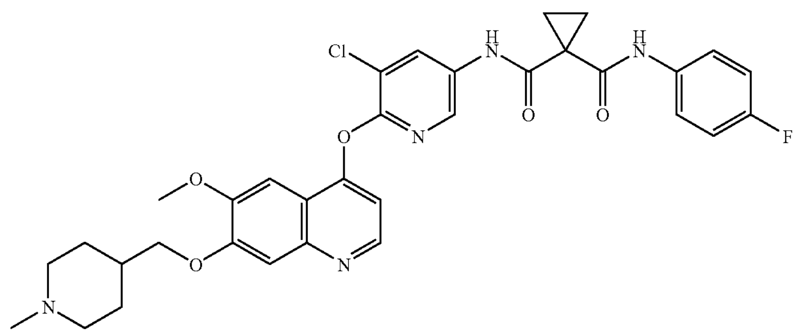 |
| 17 | N-[5-chloro-6-({6-(methyloxy)-7-[(piperidin-4-ylmethyl)oxy]quinolin-4-yl}oxy)pyridin-3-yl]-N'-(4-fluorophenyl)cyclopropane-1,1-dicarboxamide | 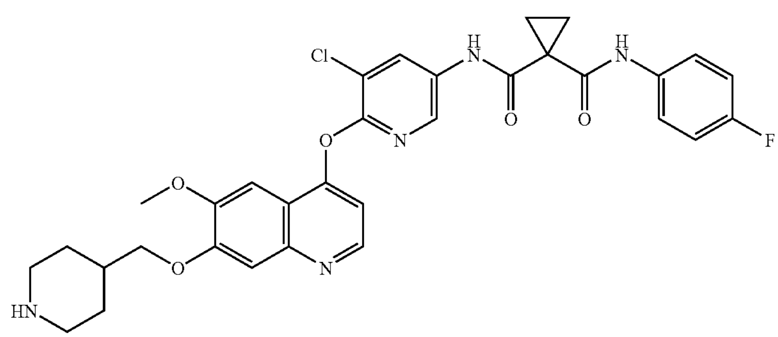 |
| 18 | N-[5-chloro-6-({6-(methyloxy)-7-[(phenylmethyl)oxy]quinolin-4-yl}oxy)pyridin-3-yl]-N'-(4-fluorophenyl)cyclopropane-1,1-dicarboxamide | 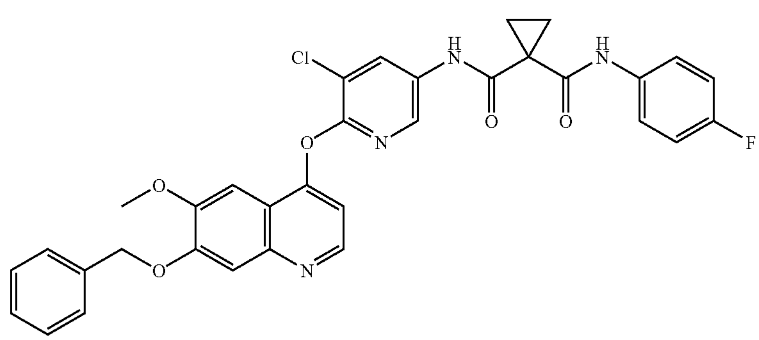 |

TABLE 2-continued

| Entry | Name |
|---|---|
| 19 | N-(4-{[7-{[2-(diethylamino)ethyl]oxy}-6-(methyloxy)quinolin-4-yl]oxy}-3-fluorophenyl)-N'-(4-fluorophenyl)cyclopropane-1,1-dicarboxamide |
| 20 | N-(4-{[7-{[2-(diethylamino)ethyl]oxy}-6-(methyloxy)quinolin-4-yl]oxy}-3-fluorophenyl)-N'-(4-fluorophenyl)cyclobutane-1,1-dicarboxamide |
| 21 | N-{3-fluoro-4-[(6-(methyloxy)-7-{[(1-methylpiperidin-4-yl)methyl]oxy}quinazolin-4-yl)oxy]phenyl}-N'-(4-fluorophenyl)cyclopropane-1,1-dicarboxamide |
| 22 | N-(4-{[6,7-bis(methyloxy)quinolin-4-yl]oxy}-2-methylphenyl)-N'-(4-fluorophenyl)cyclopropane-1,1-dicarboxamide |
| 23 | N-(4-fluorophenyl)-N'-[2-methyl-6-({6-(methyloxy)-7-[(3-ylpropyl)oxy]quinolin-4-yl}oxy)pyridin-3-yl]cyclopropane-1,1-dicarboxamide |

TABLE 2-continued

| Entry | Name | Structure |
|---|---|---|
| 24 | N-(4-{[6,7-bis(methyloxy)quinolin-4-yl]oxy}-3-fluorophenyl)-N'-(4-fluorophenyl)cyclopropane-1,1-dicarboxamide | 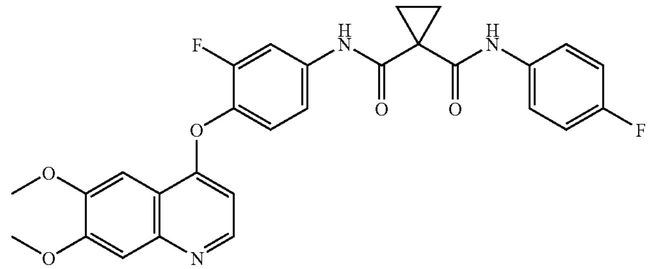 |
| 25 | N-(6-{[6,7-bis(methyloxy)quinolin-4-yl]oxy}-5-chloro-2-methylpyridin-3-yl)-N'-(4-fluorophenyl)cyclopropane-1,1-dicarboxamide | 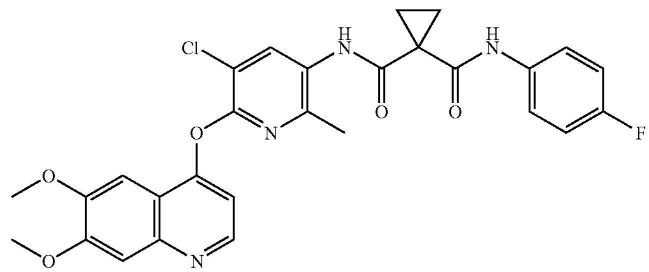 |
| 26 | N-[3-fluoro-4-({7-(methyloxy)-6-[(3-morpholin-4-ylpropyl)oxy]quinazolin-4-yl}oxy)phenyl]-N'-(4-fluorophenyl)cyclopropane-1,1-dicarboxamide | 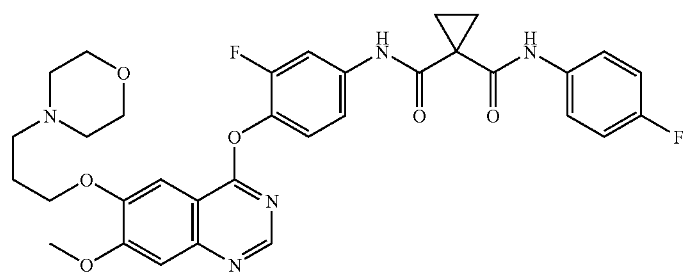 |
| 27 | N-(4-{[6,7-bis(methyloxy)quinolin-4-yl]oxy}-3,5-difluorophenyl)-N'-(4-fluorophenyl)cyclopropane-1,1-dicarboxamide | 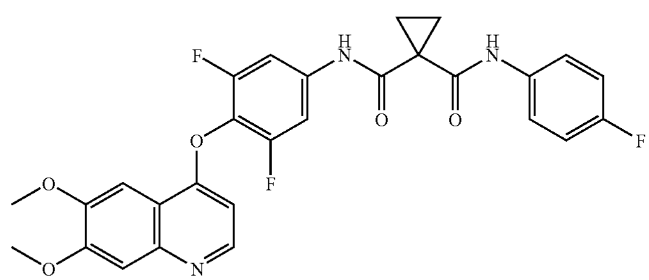 |
| 28 | N-(4-{[6,7-bis(methyloxy)quinolin-4-yl]oxy}-2,5-difluorophenyl)-N'-(4-fluorophenyl)cyclopropane-1,1-dicarboxamide | 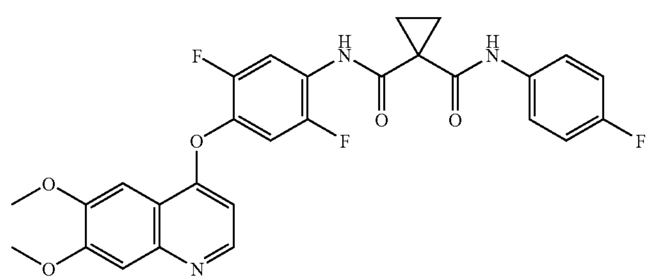 |

TABLE 2-continued

| Entry | Name | Structure |
|---|---|---|
| 29 | N-[3-fluoro-4-({7-(methyloxy)-6-[(3-morpholin-4-ylpropyl)oxy]quinolin-4-yl}oxy)phenyl]-N'-(4-fluorophenyl)cyclopropane-1,1-dicarboxamide | 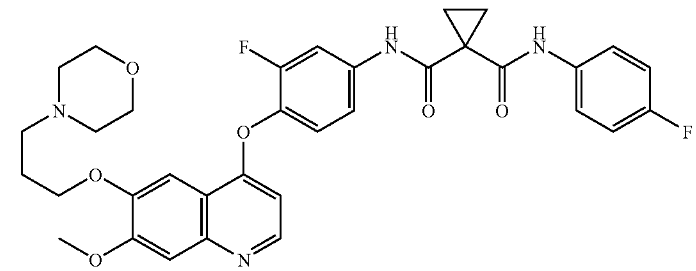 |
| 30 | N-{3-fluoro-4-[(6-(methyloxy)-7-(2-methyl octahydrocyclopenta[c]pyrrol-5-ylmethoxy)quinazolin-4-yl)oxy]phenyl}-N'-(4-fluorophenyl)cyclopropane-1,1-dicarboxamide | 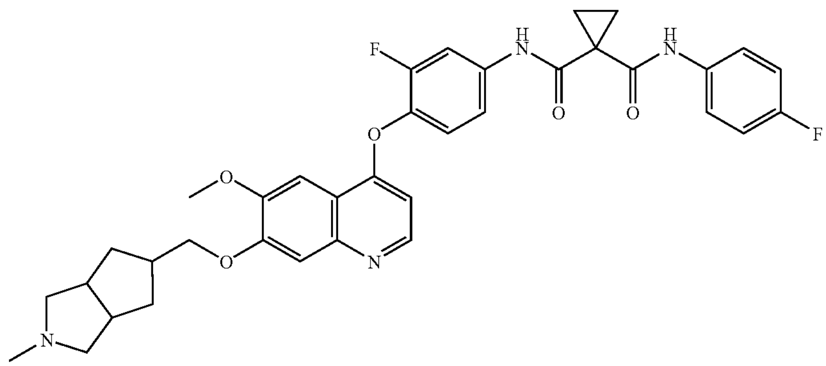 |
| 31 | N-{3-fluoro-4-[(7-(methyloxy)-6-{[(1-methylpiperidin-4-yl)methyl]oxy}quinazolin-4-yl)oxy]phenyl}-N'-(4-fluorophenyl)cyclopropane-1,1-dicarboxamide | 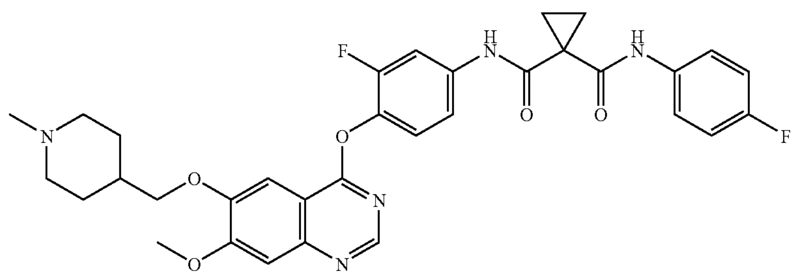 |
| 32 | N-[5-fluoro-2-methyl-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide | 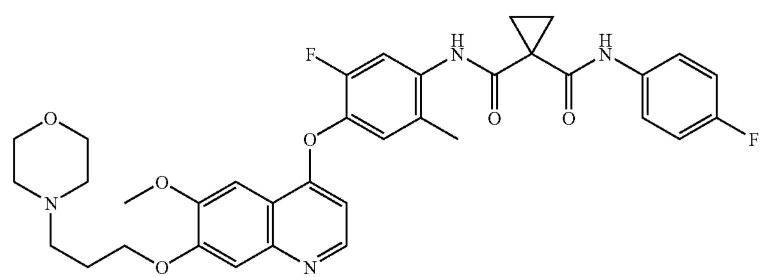 |
| 33 | N-(4-{[6,7-bis(methyloxy)quinolin-4-yl]oxy}-2,3,5-trifluorophenyl)-N'-(4-fluorophenyl)cyclopropane-1,1-dicarboxamide | 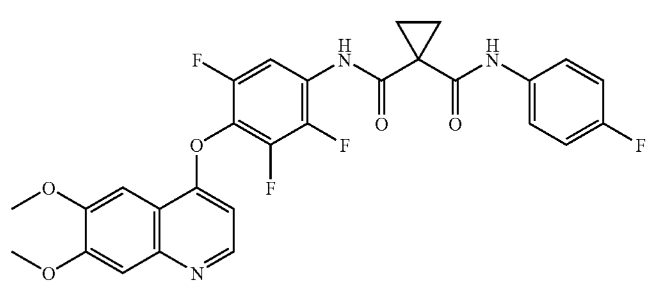 |

TABLE 2-continued

| Entry | Name | Structure |
|---|---|---|
| 34 | N-(4-{[6,7-bis(methyloxy)quinolin-4-yl]oxy}-5-fluoro-2-methylphenyl)-N'-(4-fluorophenyl)cyclopropane-1,1-dicarboxamide | 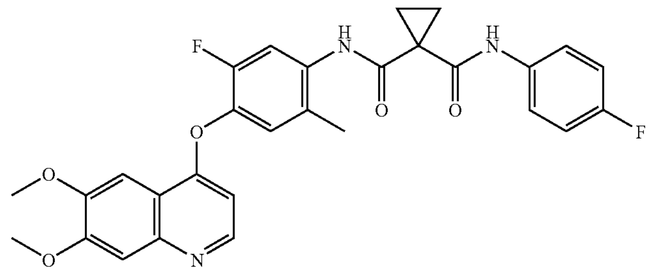 |
| 35 | N-(4-{[6,7-bis(methyloxy)quinolin-4-yl]oxy}-2-chloro-5-methylphenyl)-N'-(4-fluorophenyl)cyclopropane-1,1-dicarboxamide | 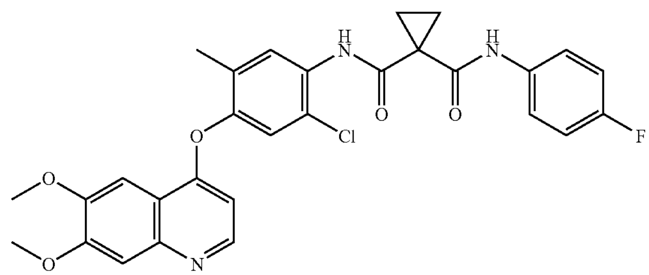 |
| 36 | N-(3-fluoro-4-{[6-hydroxy-7-(methyloxy)quinolin-4-yl]oxy}phenyl)-N'-(4-fluorophenyl)cyclopropane-1,1-dicarboxamide | 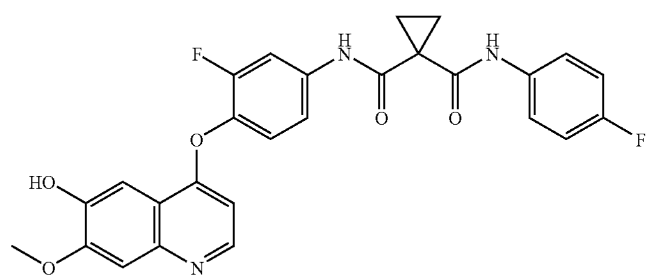 |
| 37 | N-(4-fluorophenyl)-N'-[2-methyl-4-({6-(methyloxy)-7-[(3-morpholin-4-ylpropyl)oxy]quinolin-4-yl}oxy)phenyl]cyclopropane-1,1-dicarboxamide | 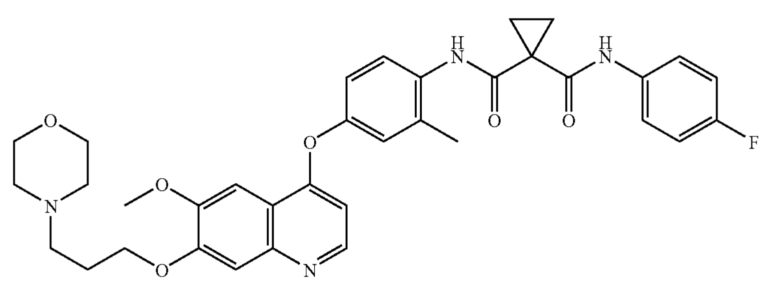 |

TABLE 2-continued

| Entry | Name | Structure |
|---|---|---|
| 38 | N-[3-fluoro-4-({6-(methyloxy)-7-[(3-piperazin-1-ylpropyl)oxy]quinolin-4-yl}oxy)phenyl]-N'-(4-fluorophenyl)cyclopropane-1,1-dicarboxamide | 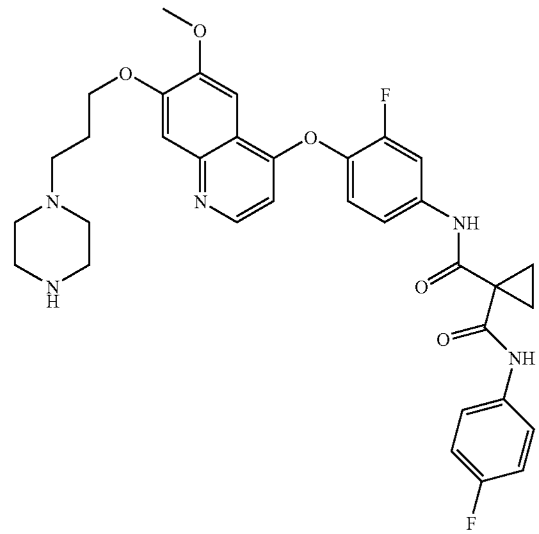 |
| 39 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclopropane-1,1-dicarboxamide | 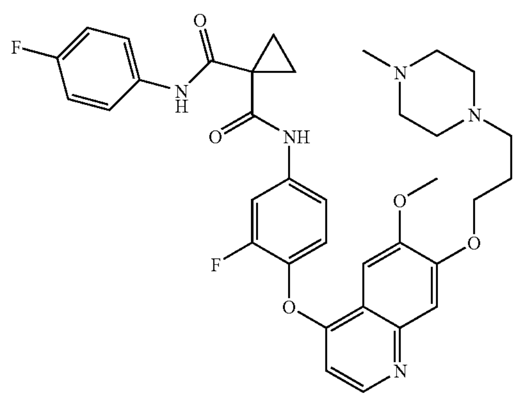 |
| 40 | N-{3-fluoro-4-[(6-(methyloxy)-7-{[(1-methylpiperidin-4-yl)methyl]oxy}quinolin-4-yl)oxy]phenyl}-N'-(4-fluorophenyl)cyclopropane-1,1-dicarboxamide | 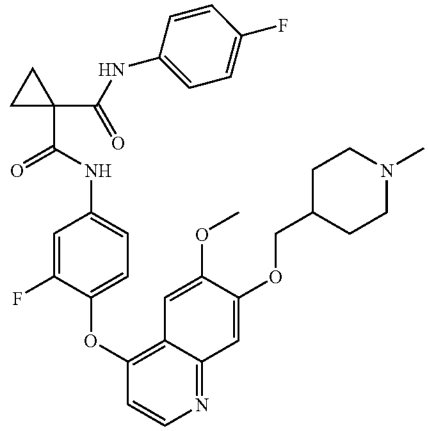 |

TABLE 2-continued

| Entry | Name | Structure |
|---|---|---|
| 41 | N-(4-fluorophenyl)-N'-[4-({6-(methyloxy)-7-[(3-morpholin-4-ylpropyl)oxy]quinolin-4-yl}oxy)phenyl]cyclopropane-1,1-dicarboxamide | 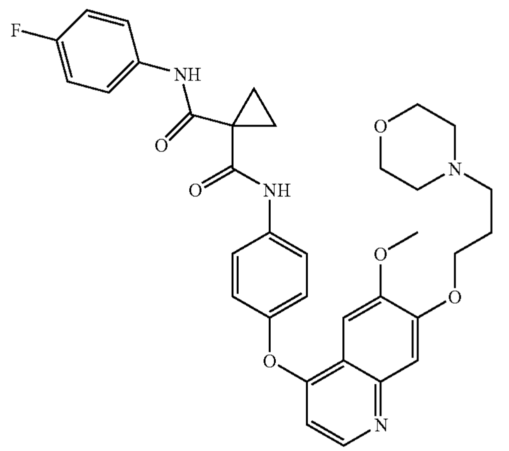 |
| 42 | N-(4-{[7-{[3-(diethylamino)propyl]oxy}-6-(methyloxy)quinolin-4-yl]oxy}-3-fluorophenyl)-N'-(4-fluorophenyl)cyclopropane-1,1-dicarboxamide | 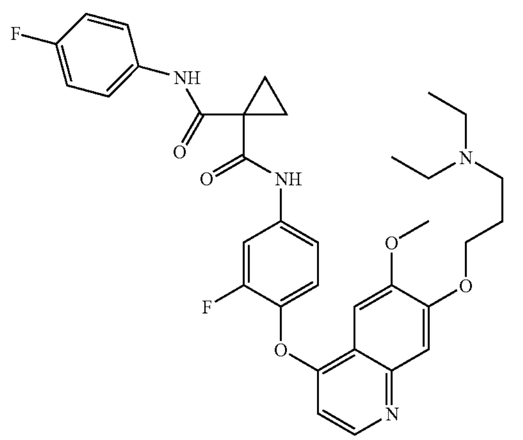 |
| 43 | N-(4-{[6,7-bis(methyloxy)quinolin-4-yl]oxy}-2-chloro-5-fluorophenyl)-N'-(4-fluorophenyl)cyclopropane-1,1-dicarboxamide | 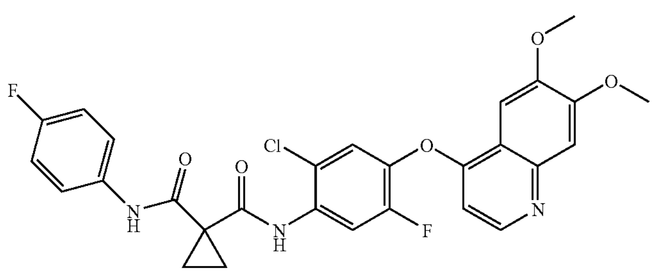 |
| 44 | N-(4-{[6,7-bis(methyloxy)-2-(methylthio)quinolin-4-yl]oxy}-3-fluorophenyl)-N'-(4-fluorophenyl)cyclopropane-1,1-dicarboxamide | 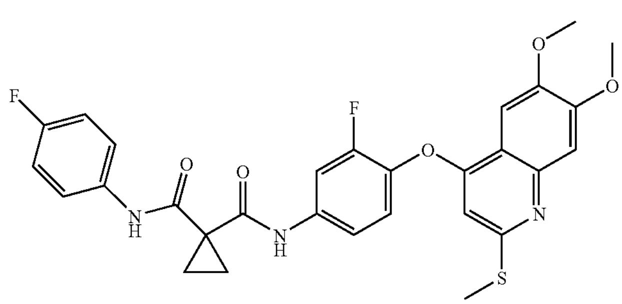 |

TABLE 2-continued

| Entry | Name | Structure |
|---|---|---|
| 45 | N-(4-fluorophenyl)-N'-(4-{[2-methyl-6,7-bis(methyloxy)quinazolin-4-yl]oxy}phenyl)cyclopropane-1,1-dicarboxamide | 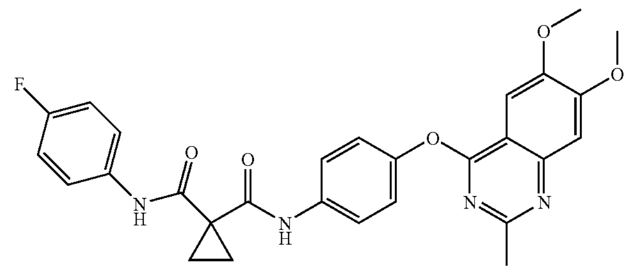 |
| 46 | N-(4-{[2-amino-6,7-bis(methyloxy)quinolin-4-yl]oxy}-3-fluorophenyl)-N'-(4-fluorophenyl)cyclopropane-1,1-dicarboxamide | 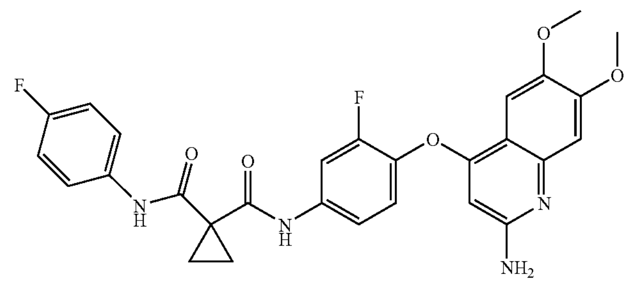 |
| 47 | N-(3-fluoro-4-{[2-(methylamino)-6,7-bis(methyloxy)quinolin-4-yl]oxy}phenyl)-N'-(4-fluorophenyl)cyclopropane-1,1-dicarboxamide | 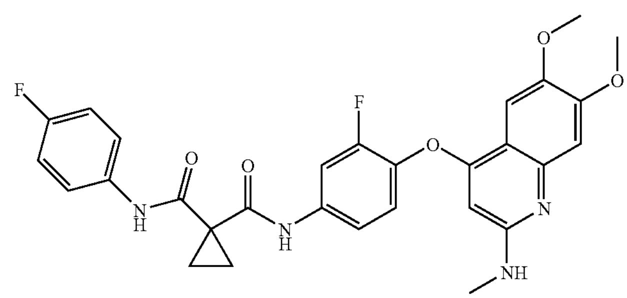 |
| 48 | (1S,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide | 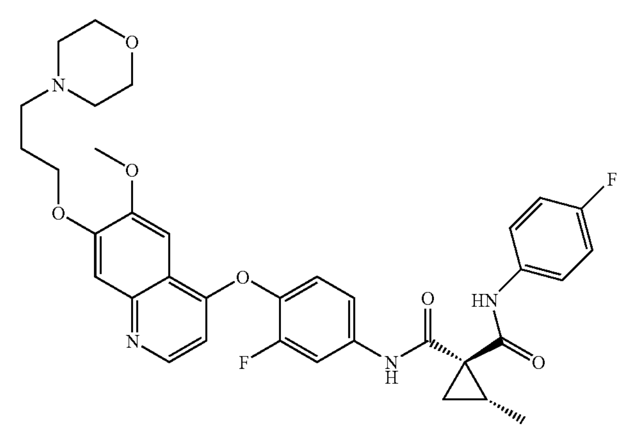 |

TABLE 2-continued

| Entry | Name | Structure |
|-------|------|-----------|
| 49 | (1R,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide | 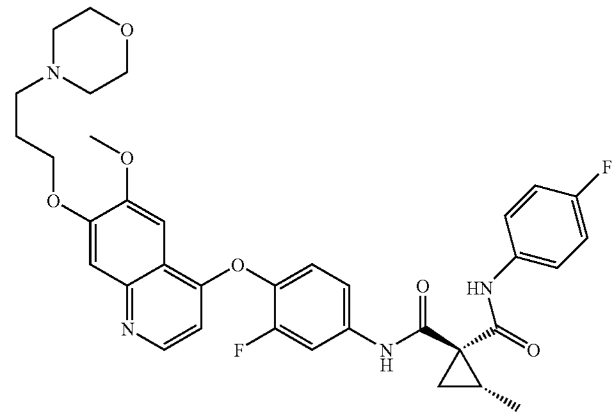 |
| 50 | N-(4-{[6-{[3-(diethylamino)propyl]oxy}-7-{methyloxy}quinolin-4-yl]oxy}-3-fluorophenyl)-N'-(4-fluorophenyl)cyclopropane-1,1-dicarboxamide | 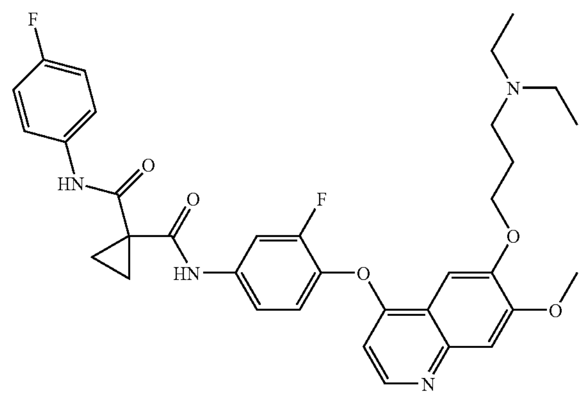 |
| 51 | N-(4-{[6-{[2-(diethylamino)ethyl]oxy}-7-(methyloxy)quinolin-4-yl]oxy}-3-fluorophenyl)-N'-(4-fluorophenyl)cyclopropane-1,1-dicarboxamide | 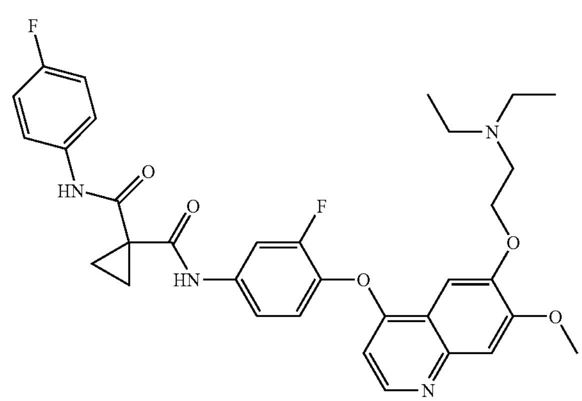 |

TABLE 2-continued

| Entry | Name | Structure |
|---|---|---|
| 52 | 1,1-dimethylethyl 4-(3-{[4-[(2-fluoro-4-{[(1-{[(4-fluorophenyl)amino]carbonyl}cyclopropyl)carbonyl]amino}phenyl)oxy]-6-(methyloxy)quinolin-7-yl]oxy}propyl)piperazine-1-carboxylate | 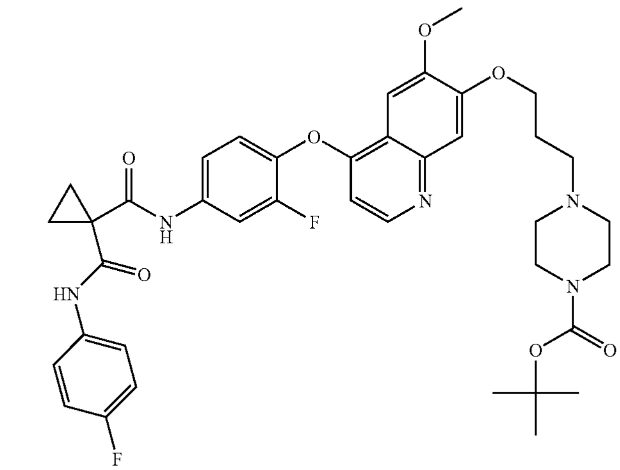 |
| 53 | (1R,2R)-N-[3-fluoro-4-({6-(methyloxy)-7-[(3-morpholin-4-ylpropyl)oxy]quinazolin-4-yl}oxy)phenyl]-N'-(4-fluorophenyl)-2-methylcyclopropane-1,1-dicarboxamide | 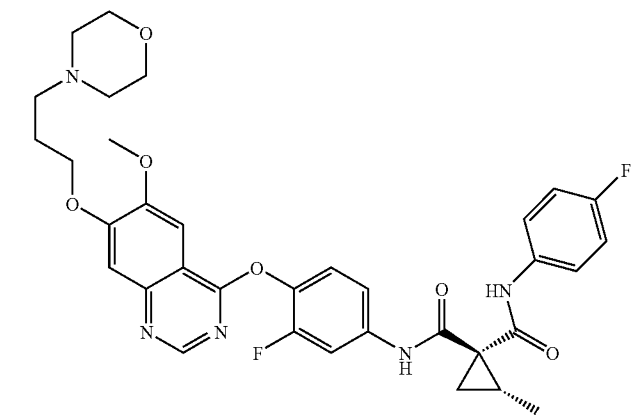 |
| 54 | (1R,2R)-N-(4-{[7-{[2-(diethylamino)ethyl]oxy}-6-(methyloxy)quinazolin-4-yl]oxy}-3-fluorophenyl)-N'-{4-fluorophenyl}-2-methylcyclopropane-1,1-dicarboxamide | 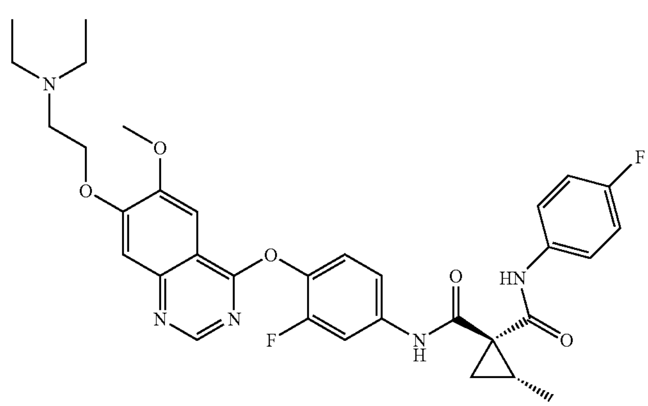 |

TABLE 2-continued

| Entry | Name | Structure |
|---|---|---|
| 55 | N-(4-{[7-{[3-(diethylamino)propyl]oxy}-6-(methyloxy)quinazolin-4-yl]oxy}-3-fluorophenyl)-N'-(4-fluorophenyl)cyclopropane-1,1-dicarboxamide | 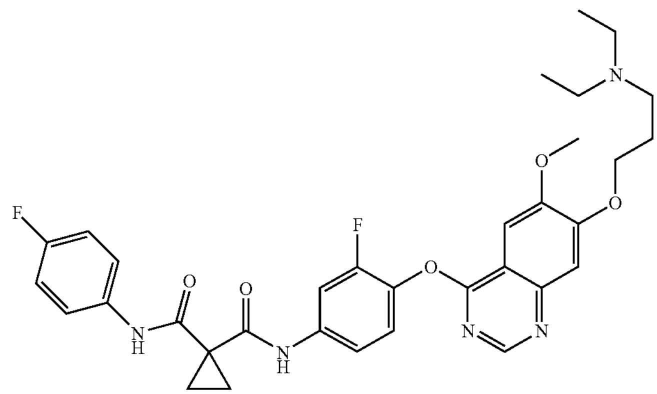 |
| 56 | N-(4-{[7-{[3-(4-acetylpiperazin-1-yl)propyl]oxy}-6-(methyloxy)quinolin-4-yl]oxy}-3-fluorophenyl)-N'-(4-fluorophenyl)cyclopropane-1,1-dicarboxamide | 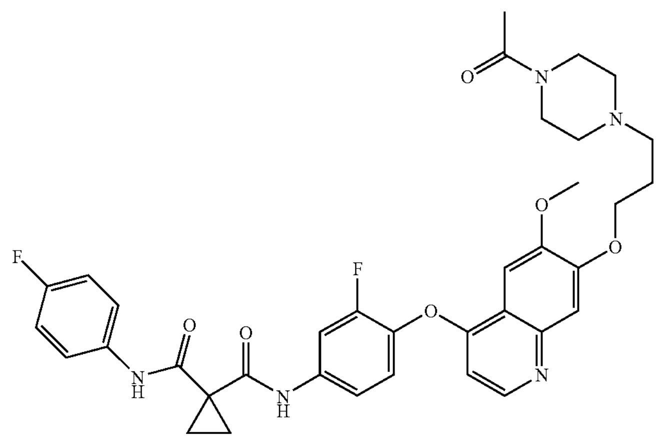 |
| 57 | 1,1-dimethylethyl 4-(3-{[4-[(2-fluoro-4-{[(((1R,2R)-1-{[(4-fluorophenyl)amino]carbonyl}-2-methylcyclopropyl)carbonyl]amino}phenyl)oxy]-6-(methyloxy)quinolin-7-yl]oxy}propyl)piperazine-1-carboxylate | 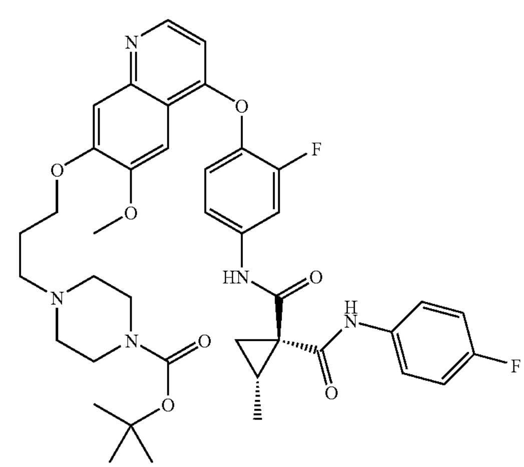 |

TABLE 2-continued

| Entry | Name | Structure |
|---|---|---|
| 58 | N-(4-{[6,7-bis(methyloxy)quinolin-4-yl]oxy}phenyl)-N'-(4-fluorophenyl)-1-(phenylmethyl)azetidine-3,3-dicarboxamide | 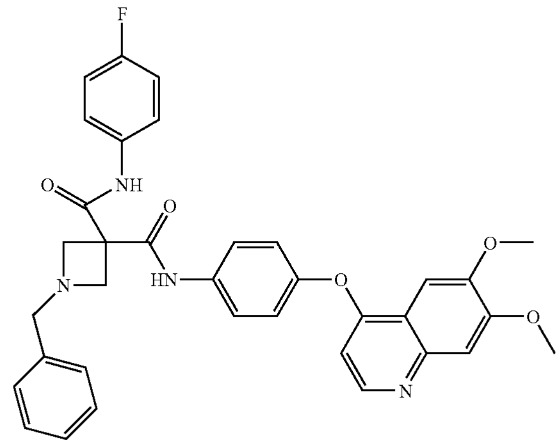 |
| 59 | N-(4-{[6,7-bis(methyloxy)quinolin-4-yl]oxy}phenyl)-N'-(4-fluorophenyl)azetidine-3,3-dicarboxamide | 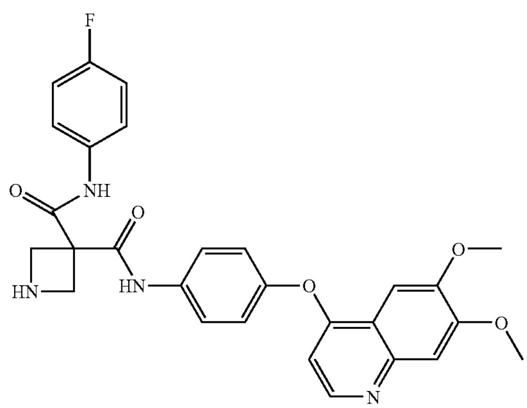 |
| 60 | (1R,2S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide | 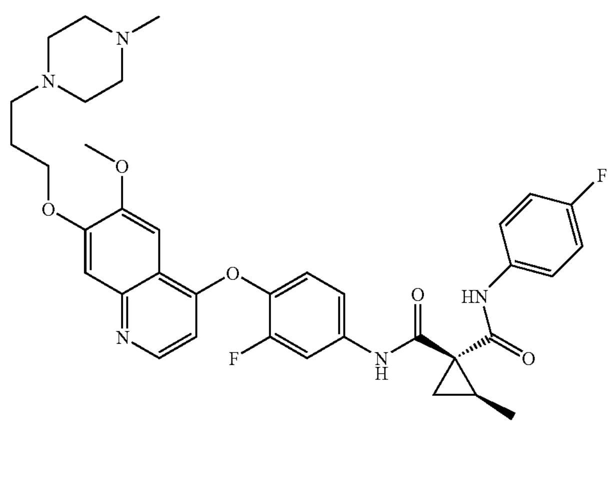 |

TABLE 2-continued

| Entry | Name | Structure |
|---|---|---|
| 61 | (1R,2R)-N-{3-fluoro-4-[(6-{methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide | 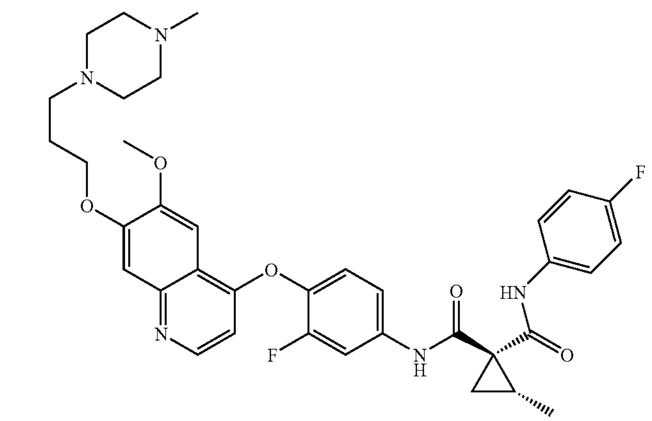 |
| 62 | (1R,2R)-N-[3-fluoro-4-({6-(methyloxy)-7-[(3-piperazin-1-ylpropyl)oxy]quinolin-4-yl}oxy)phenyl]-N'-(4-fluorophenyl)-2-methylcyclopropane-1,1-dicarboxamide | 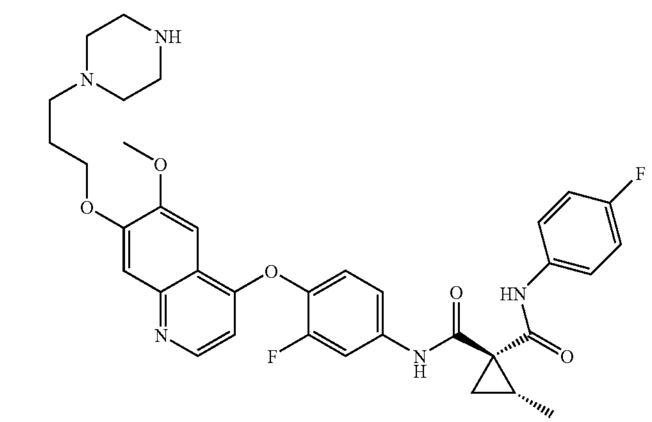 |
| 63 | N-(3-fluoro-4-{[7-({3-[4-(1-methylethyl)piperazin-1-yl]propyl}oxy)-6-(methyloxy)quinolin-4-yl]oxy}phenyl)-N'-(4-fluorophenyl)cyclopropane-1,1-dicarboxamide | 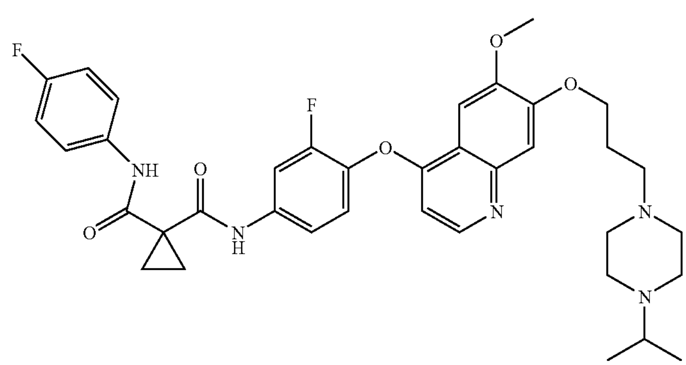 |
| 64 | N-(4-{(7-{[3-(diethylamino)propyl]oxy}-6-(methyloxy)quinazolin-4-yl]oxy}-3-fluorophenyl)-N'-(4-fluorophenyl)cyclopropane-1,1-dicarboxamide | 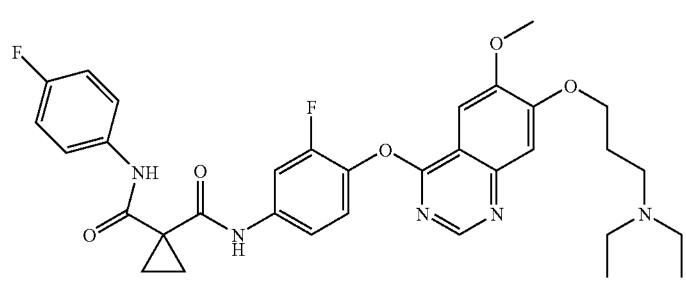 |

TABLE 2-continued

| Entry | Name | Structure |
|---|---|---|
| 65 | (1R,2R)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide | 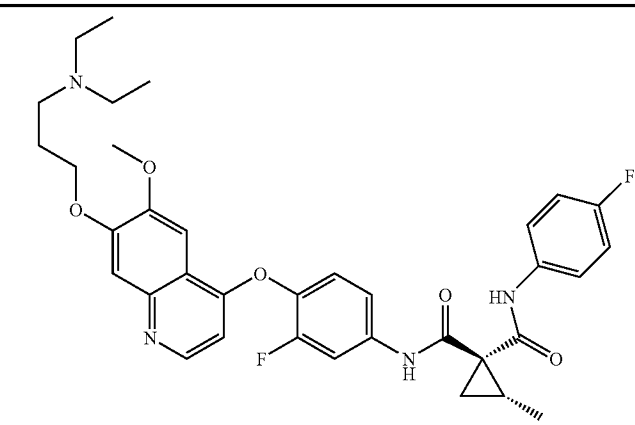 |
| 66 | (1R,2R)-N-(4-{[7-{[2-(diethylamino)ethyl]oxy}-6-(methyloxy)quinolin-4-yl]oxy}-3-fluorophenyl)-N'-(4-fluorophenyl)-2-methylcyclopropane-1,1-dicarboxamide | 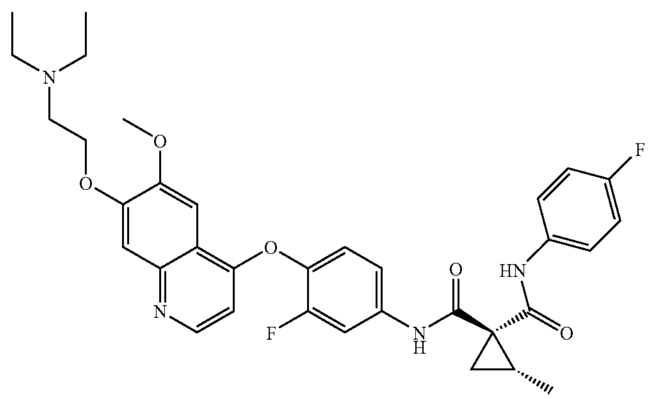 |
| 67 | (1R,2S)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide | 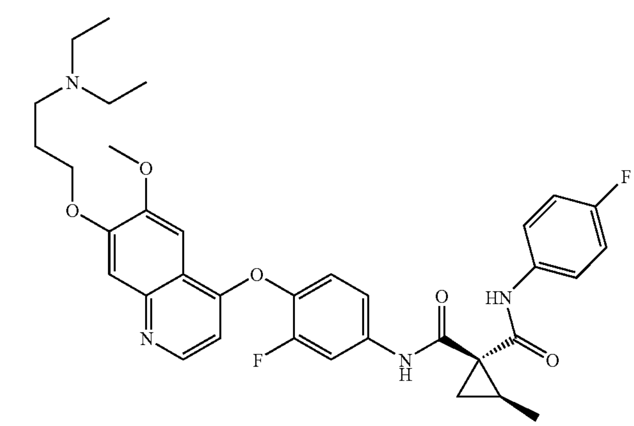 |
| 68 | (1R,2S)-N-(4-{[7-{[2-(diethylamino)ethyl]oxy}-6-(methyloxy)quinolin-4-yl]oxy}-3-fluorophenyl)-N'-(4-fluorophenyl)-2-methylcyclopropane-1,1-dicarboxamide | 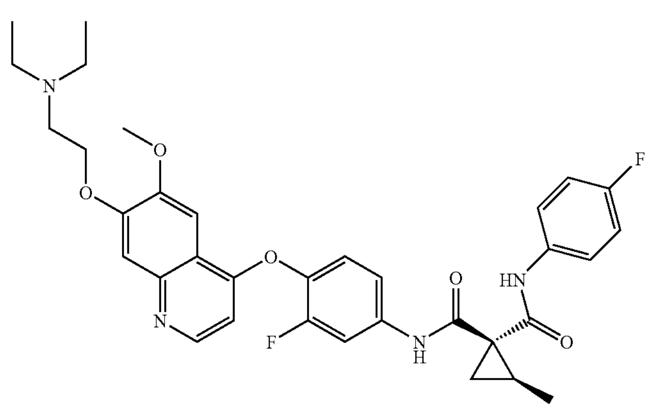 |

TABLE 2-continued

| Entry | Name | Structure |
|---|---|---|
| 69 | N-(4-{[7-{[2-(diethylamino)ethyl]oxy}-6-(methyloxy)quinazolin-4-yl]oxy}-3-fluorophenyl)-N'-(4-fluorophenyl)cyclobutane-1,1-dicarboxamide | 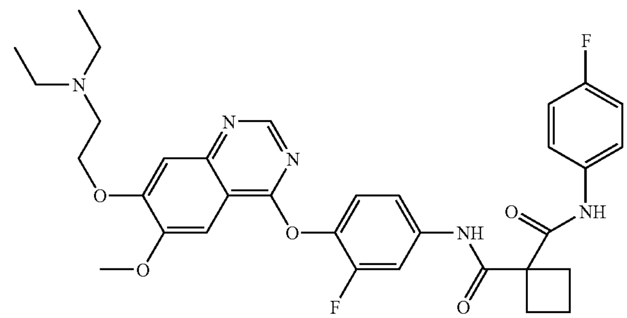 |
| 70 | (1R,2S)-N-[3-fluoro-4-({6-(methyloxy)-7-[(3-piperazin-1-ylpropyl)oxy]quinolin-4-yl}oxy)phenyl]-N'-(4-fluorophenyl)-2-methylcyclopropane-1,1-dicarboxamide | 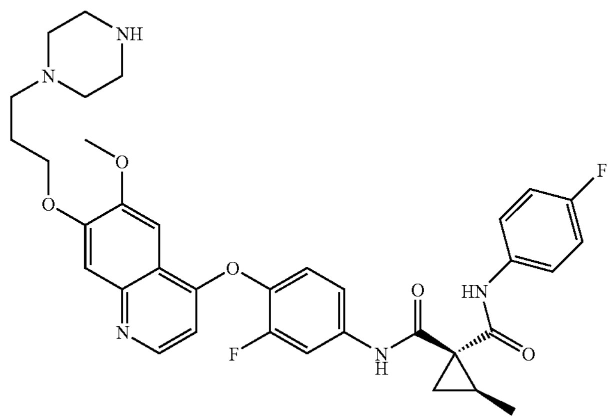 |
| 71 | (1R,2R,3S)-N-[3-fluoro-4-({6-(methyloxy)-7-[(3-morpholin-4-ylpropyl)oxy]quinolin-4-yl}oxy)phenyl]-N'-(4-fluorophenyl)-2,3-dimethylcyclopropane-1,1-dicarboxamide | 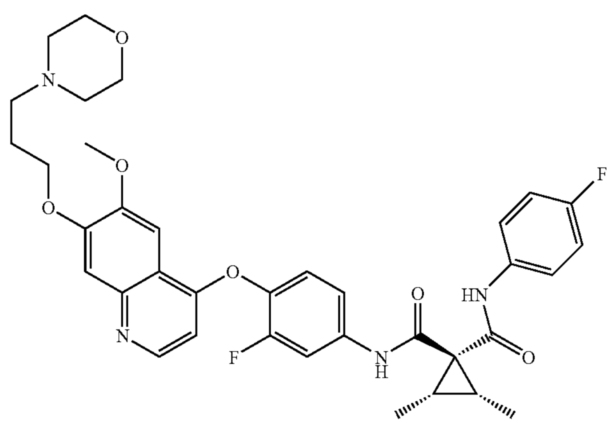 |
| 72 | (1R,2R,3S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2,3-dimethylcyclopropane-1,1-dicarboxamide | 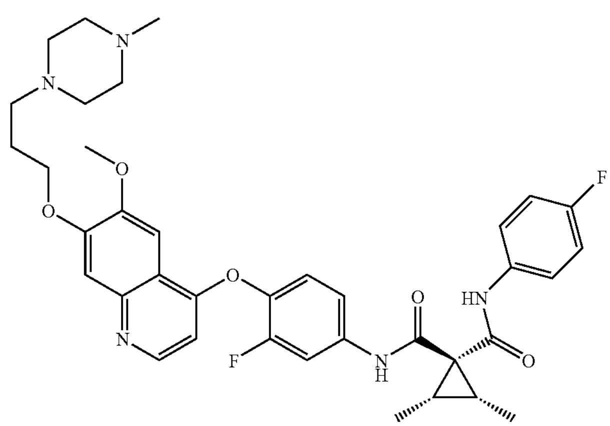 |

TABLE 2-continued

| Entry | Name | Structure |
|---|---|---|
| 73 | (1R,2R,3S)-N-[3-fluoro-4-({6-(methyloxy)-7-[(3-morpholin-4-ylpropyl)oxy]quinazolin-4-yl}oxy)phenyl]-N'-(4-fluorophenyl)-2,3-dimethylcyclopropane-1,1-dicarboxamide | 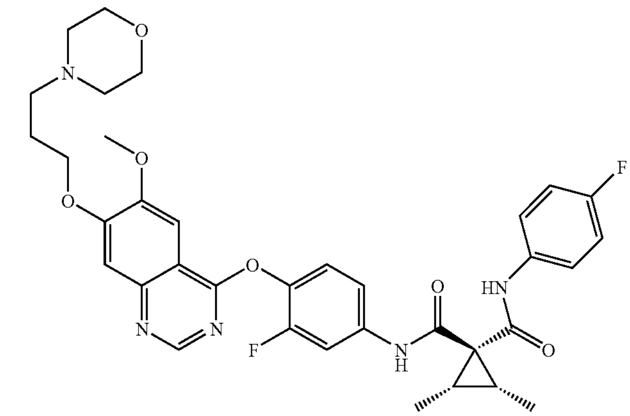 |
| 74 | (1R,2R,3S)-N-{3-fluoro-4-(6-(methyloxy)-7-{[3-(4-methylpiperazin-1-yl)propyl]oxy}quinazolin-4-yl)oxy]phenyl}-N'-(4-fluorophenyl)-2,3-dimethylcyclopropane-1,1-dicarboxamide | 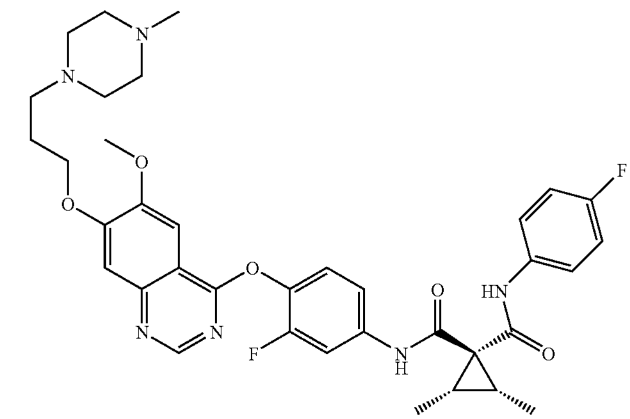 |
| 75 | N-[3-fluoro-4-({6-(methyloxy)-7-[(3-morpholin-4-ylpropyl)oxy]quinazolin-4-yl}oxy)phenyl]-N'-(4-fluorophenyl)cyclobutane-1,1-dicarboxamide | 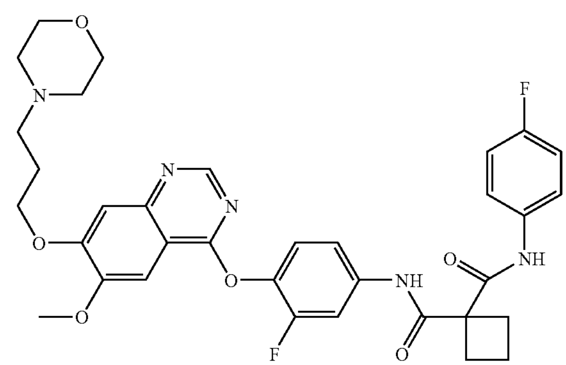 |
| 76 | (2R,3R)-N-[3-fluoro-4-({6-(methyloxy)-7-[(3-morpholin-4-ylpropyl)oxy]quinolin-4-yl}oxy)phenyl]-N'-(4-fluorophenyl)-2,3-dimethylcyclopropane-1,1-dicarboxamide | 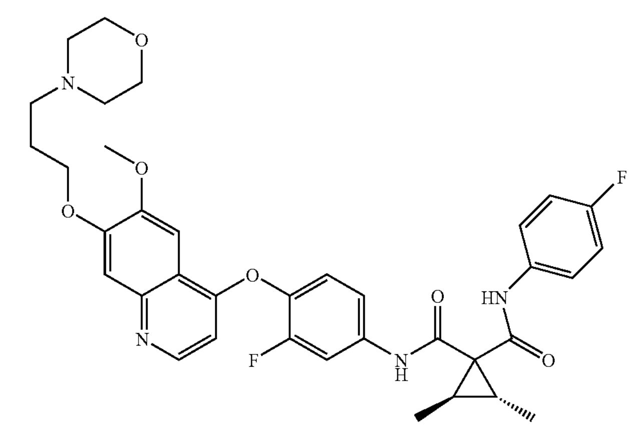 |

TABLE 2-continued

| Entry | Name | Structure |
|---|---|---|
| 77 | (2R,3R)-N-(4-{[7-{[3-(diethylamino)propyl]oxy}-6-(methyloxy)quinolin-4-yl]oxy}-3-fluorophenyl)-N'-{4-fluorophenyl)-2,3-dimethylcyclopropane-1,1-dicarboxamide | 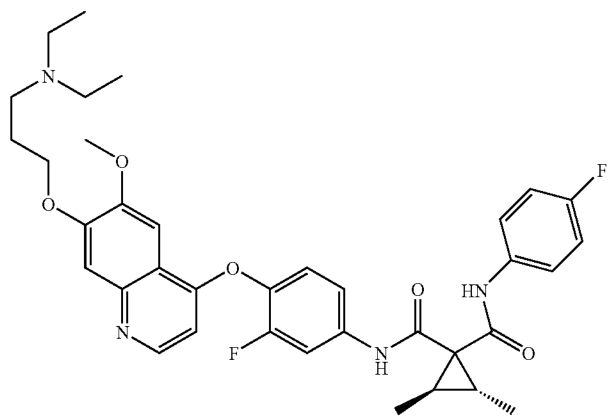 |
| 78 | N-(4-{[7-{[3-(diethylamino)propyl]oxy}-6-(methyloxy)quinolin-4-yl]oxy}-3-fluorophenyl)-N'-(4-fluorophenyl)-2,2-dimethylcyclopropane-1,1-dicarboxamide | 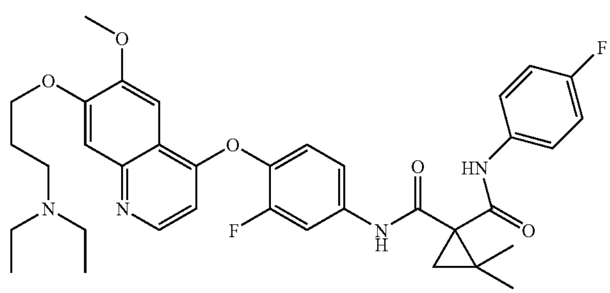 |
| 79 | N-[3-fluoro-4-({6-(methyloxy)-7-[(3-morpholin-4-ylpropyl)oxy]quinazolin-4-yl}oxy)phenyl]-N'-(4-fluorophenyl)-2,2-dimethylcyclopropane-1,1-dicarboxamide | 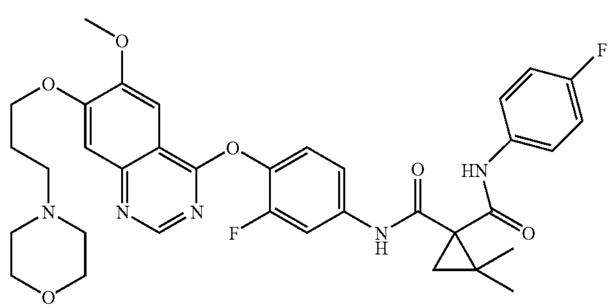 |
| 80 | (1R,2R,3S)-N-(4-{[7-{[3-(diethylamino)propyl]oxy}-6-(methyloxy)quinolin-4-yl]oxy}-3-fluorophenyl)-N'-(4-fluorophenyl)-2,3-dimethylcyclopropane-1,1-dicarboxamide | 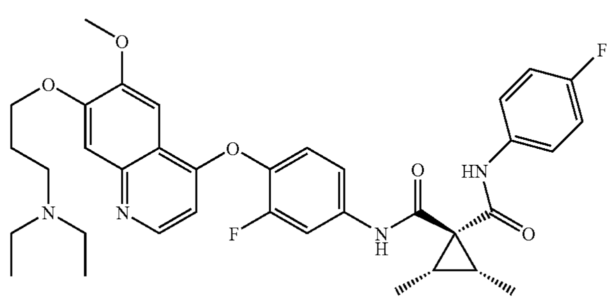 |

TABLE 2-continued

| Entry | Name | Structure |
|---|---|---|
| 81 | N-(4-{[7-{[2-(diethylamino)ethyl]oxy}-6-(methyloxy)quinolin-4-yl]oxy}-3-fluorophenyl)-N'-(4-fluorophenyl)-2,2-dimethylcyclopropane-1,1-dicarboxamide | 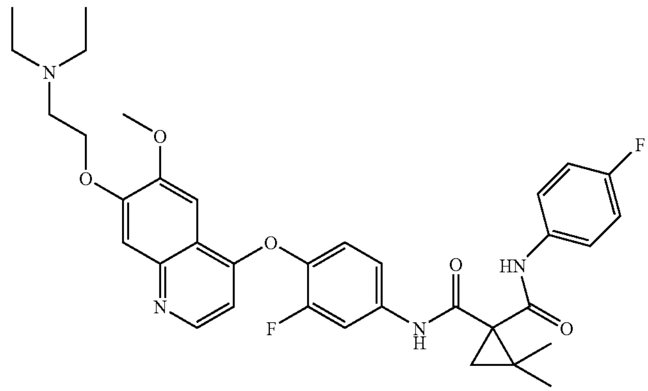 |
| 82 | (1R,2R,3S)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide | 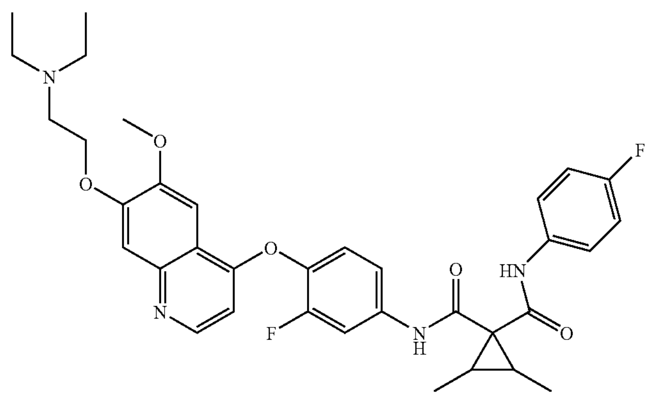 |
| 83 | N-[3-fluoro-4-({6-(methyloxy)-7-[(3-morpholin-4-ylpropyl)oxy]quinolin-4-yl}oxy)phenyl]-N'-(4-fluorophenyl)-2,2-dimethylcyclopropane-1,1-dicarboxamide | 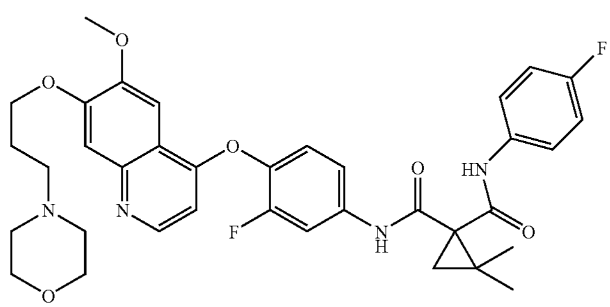 |
| 84 | N-(4-{[7-{[2-(diethylamino)ethyl]oxy}-6-(methyloxy)quinazolin-4-yl]oxy}-3-fluorophenyl)-N'-(4-fluorophenyl)-2,2-dimethylcyclopropane-1,1-dicarboxamide | 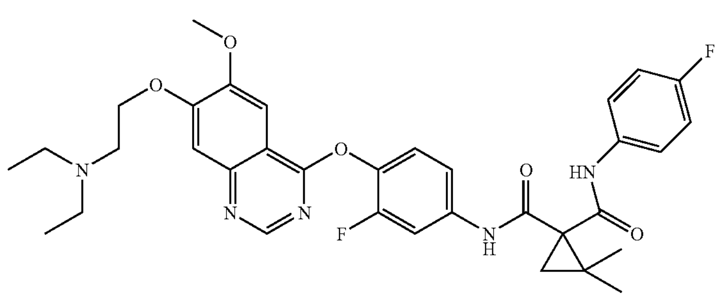 |

TABLE 2-continued

| Entry | Name | Structure |
|---|---|---|
| 85 | N-(4-{[7-{[3-(diethylamino)propyl]oxy}-6-(methyloxy)quinazolin-4-yl]oxy}-3-fluorophenyl)-N'-(4-fluorophenyl)-2,2-dimethylcyclopropane-1,1-dicarboxamide | 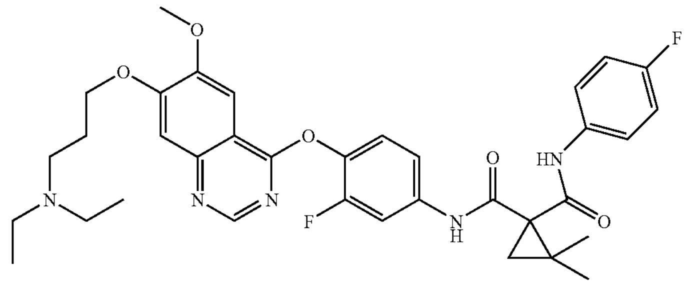 |
| 86 | N-(4-{[7-{[3-(diethylamino)propyl]oxy}-6-(methyloxy)quinazolin-4-yl]oxy}-3-fluorophenyl)-N'-(4-fluorophenyl)cyclobutane-1,1-dicarboxamide | 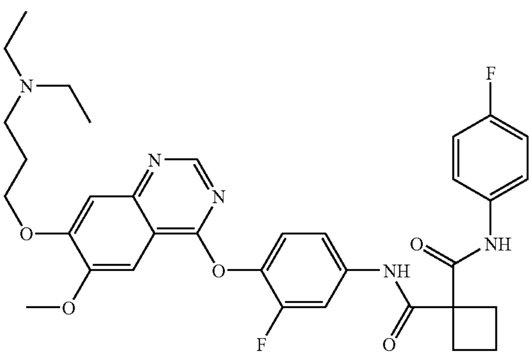 |
| 87 | N-{3-fluoro-4-[(6-(methyloxy)-7-{[3-(4-methylpiperazin-1-yl)propyl]oxy}quinazolin-4-yl)oxy]phenyl}-N'-(4-fluorophenyl)cyclobutane-1,1-dicarboxamide | 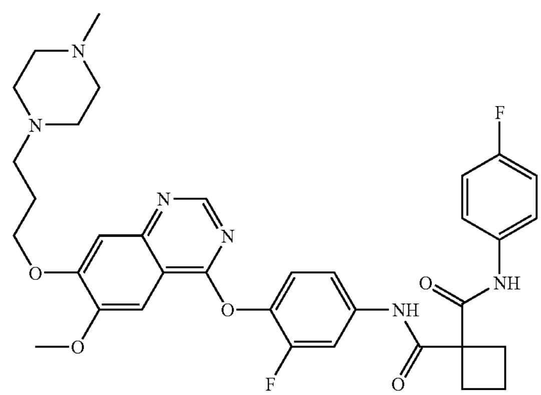 |
| 88 | N-[3-fluoro-4-({6-(methyloxy)-7-[(3-piperazin-1-ylpropyl)oxy]quinazolin-4-yl}oxy)phenyl]-N'-(4-fluorophenyl)cyclobutane-1,1-dicarboxamide | 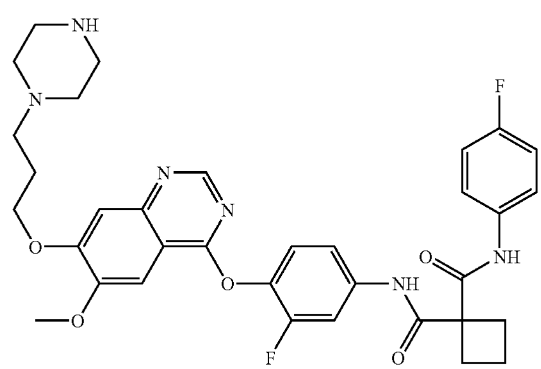 |

TABLE 2-continued

| Entry | Name | Structure |
|---|---|---|
| 89 | (2R,3R)-N-[3-fluoro-4-({6-(methyloxy)-7-[(3-morpholin-4-ylpropyl)oxy]quinazolin-4-yl}oxy)phenyl]-N'-(4-fluorophenyl)-2,3-dimethylcyclopropane-1,1-dicarboxamide | 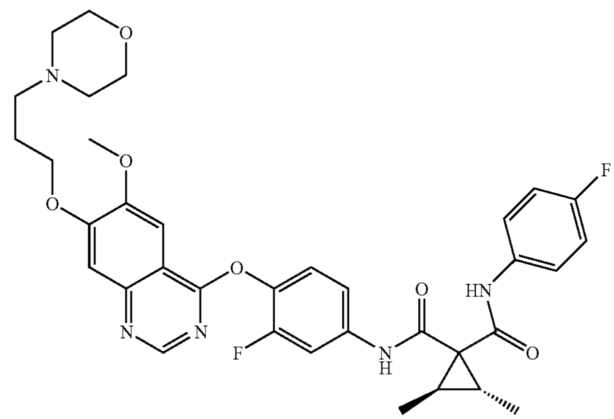 |
| 90 | N-(4-{[7-{[3-(diethylamino)propyl]oxy}-6-(methyloxy)quinolin-4-yl]oxy}-3-fluorophenyl)-N'-(4-fluorophenyl)cyclobutane-1,1-dicarboxamide | 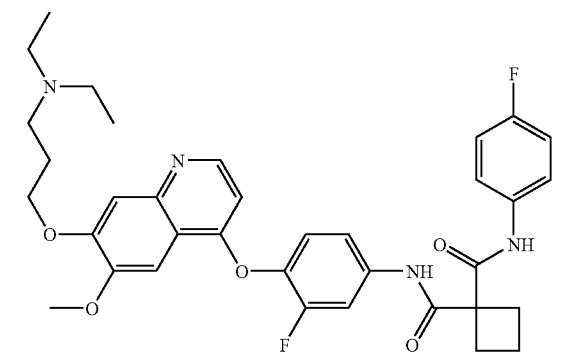 |
| 91 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclobutane-1,1-dicarboxamide | 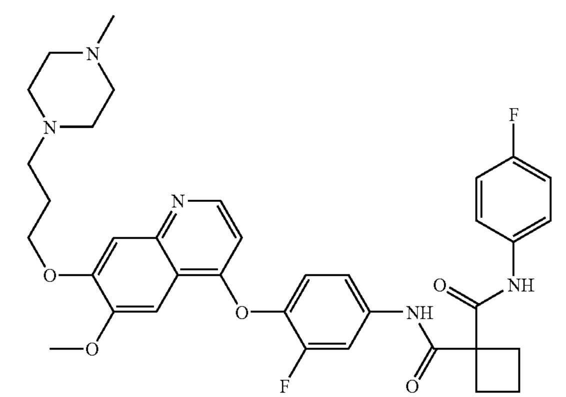 |
| 92 | (1R,2R)-N-(4-{[7{[3-(diethylamino)propyl]oxy}-6-(methyloxy)quinazolin-4-yl]oxy}-3-fluorophenyl)-N'-(4-fluorophenyl)-2-methylcyclopropane-1,1-dicarboxamide | 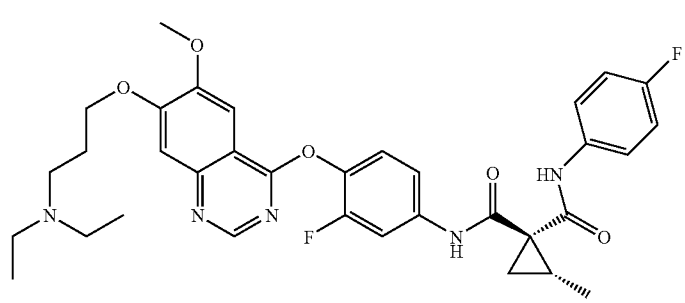 |

TABLE 2-continued

| Entry | Name | Structure |
|---|---|---|
| 93 | (1R,2R)-N-{3-fluoro-4-[(6-(methyloxy)-7-{[3-(4-methylpiperazin-1-yl)propyl]oxy}quinazolin-4-yl)oxy]phenyl}-N'-(4-fluorophenyl)-2-methylcyclopropane-1,1-dicarboxamide | 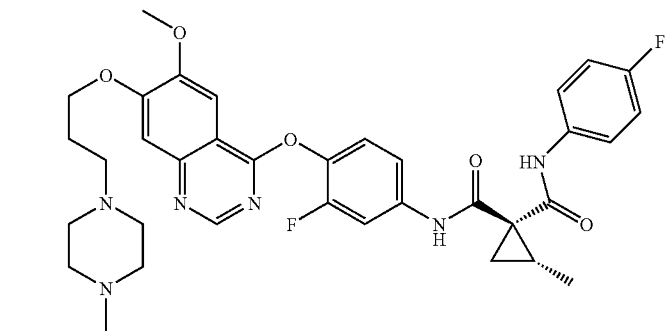 |
| 94 | (2R,3R)-N-(4-{[7-{[2-(diethylamino)ethyl]oxy}-6-(methyloxy)quinazolin-4-yl]oxy}-fluorophenyl)-N'-(4-fluorophenyl)-2,3-dimethylcyclopropane-1,1-dicarboxamide | 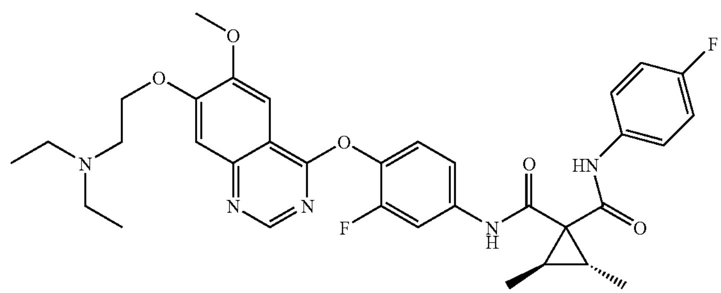 |
| 95 | (2R,3R)-N-(4-{[7-{[3-(diethylamino)propyl]oxy}-6-(methyloxy)quinazolin-4-yl]oxy}-3-fluorophenyl)-N'-(4-fluorophenyl)-2,3-dimethylcyclopropane-1,1-dicarboxamide | 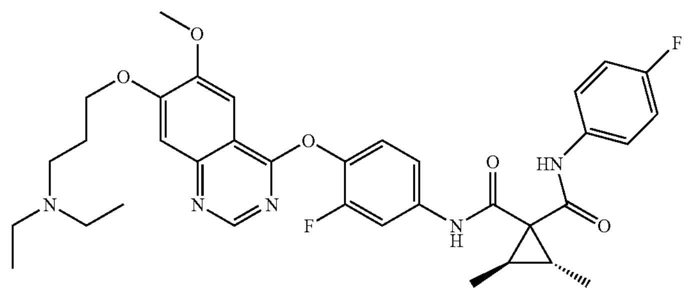 |
| 96 | (1R,2R)-N-[3-fluoro-4-({6-(methyloxy)-7-[(3-ylpropyl)oxy]quinazolin-4-yl}oxy)phenyl]-N'-(4-fluorophenyl)-2-methylcyclopropane-1,1-dicarboxamide | 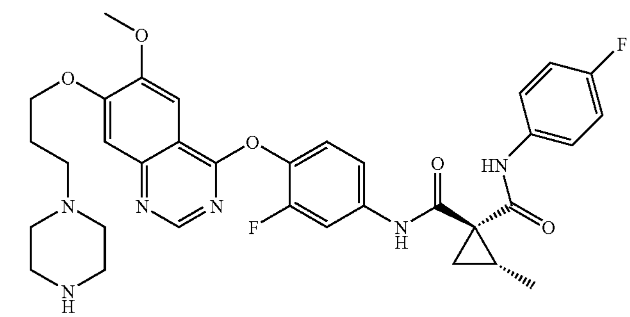 |
| 97 | (2R,3R)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide | 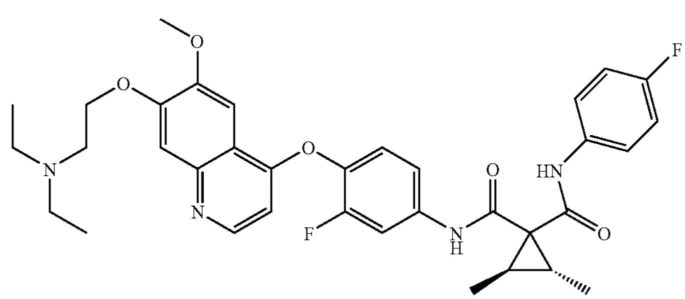 |

TABLE 2-continued

| Entry | Name | Structure |
|---|---|---|
| 98 | N-(4-{[6,7-bis(methyloxy)quinolin-4-yl]oxy}phenyl)-N'-[(4-fluorophenyl)methyl]cyclopropane-1,1-dicarboxamide | 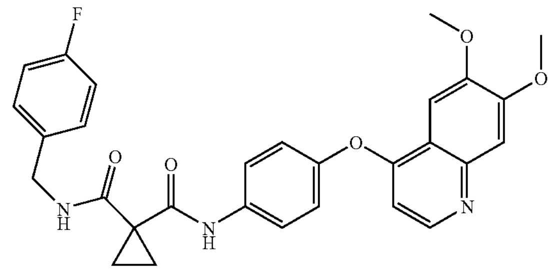 |
| 99 | N-(4-{[6,7-bis(methyloxy)quinolin-4-yl]oxy}phenyl)-N'-(2-morpholin-4-ylethyl)cyclopropane-1,1-dicarboxamide | 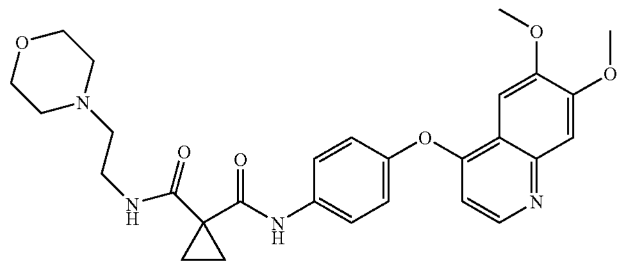 |
| 100 | N-(4-{[6,7-bis(methyloxy)quinolin-4-yl]oxy}phenyl)-N'-[2-(piperidin-1-ylmethyl)phenyl]cyclopropane-1,1-dicarboxamide | 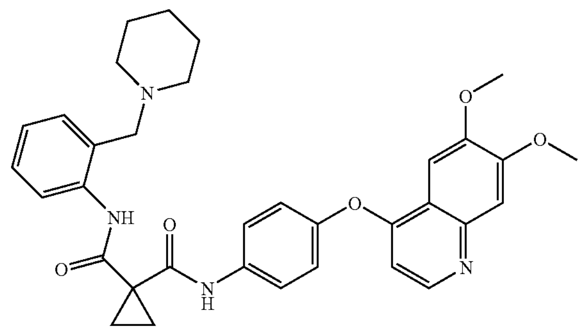 |
| 101 | N-(4-{[6,7-bis(methyloxy)quinolin-4-yl]oxy}phenyl)-N'-[2-pyrrolidin-1-ylmethyl)phenyl]cyclopropane-1,1-dicarboxamide | 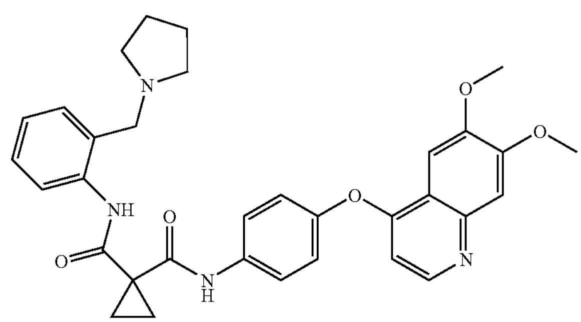 |
| 102 | N-(4-{[6,7-bis(methyloxy)quinolin-4-yl]oxy}phenyl)-N'-[3-(morpholin-4-ylmethyl)phenyl]cyclopropane-1,1-dicarboxamide | 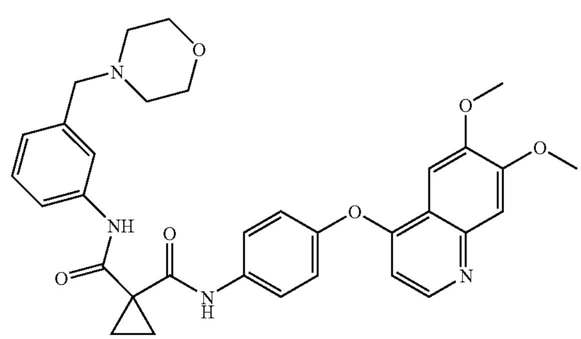 |

TABLE 2-continued

| Entry | Name | Structure |
|---|---|---|
| 103 | N-(4-{[6,7-bis(methyloxy)quinolin-4-yl]oxy}phenyl)-N'-[2-(morpholin-4-ylmethyl)phenyl]cyclopropane-1,1-dicarboxamide | 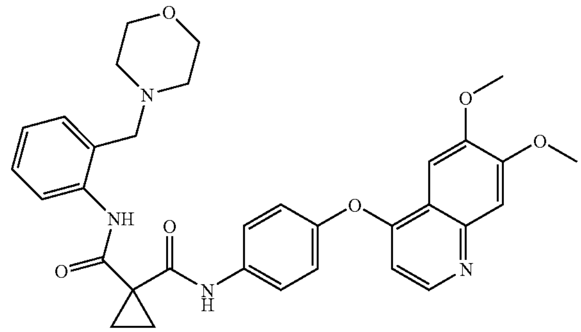 |
| 104 | N-(4-{[6,7-bis(methyloxy)quinolin-4-yl]oxy}phenyl)-N'-phenylcyclopropane-1,1-dicarboxamide | 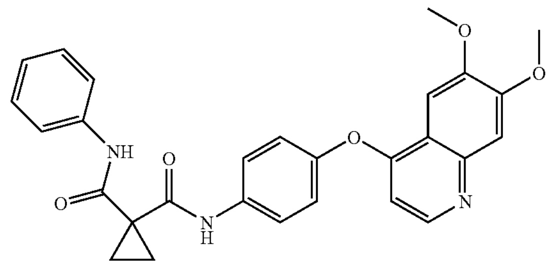 |
| 105 | N-[3-(aminomethyl)phenyl]-N'-(4-{[6,7-bis(methyloxy)quinolin-4-yl]oxy}phenyl)cyclopropane-1,1-dicarboxamide | 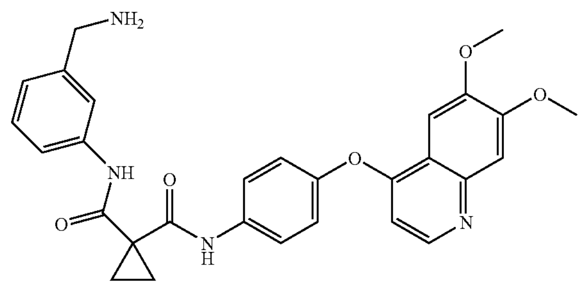 |
| 106 | N-(4-{[6,7-bis(methyloxy)quinolin-4-yl]oxy}phenyl)-N'-[3-(piperidin-1-ylmethyl)phenyl]cyclopropane-1,1-dicarboxamide | 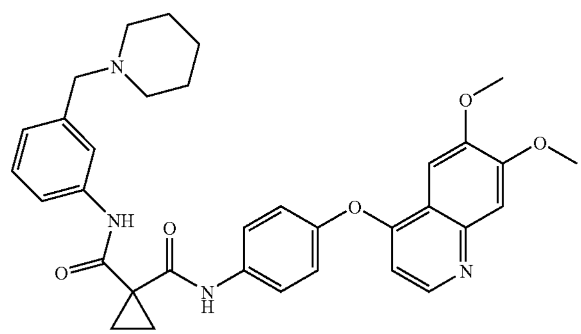 |
| 107 | N-(4-{[6,7-bis(methyloxy)quinolin-4-yl]oxy}phenyl)-N'-[3-(pyrrolidin-1-ylmethyl)phenyl]cyclopropane-1,1-dicarboxamide | 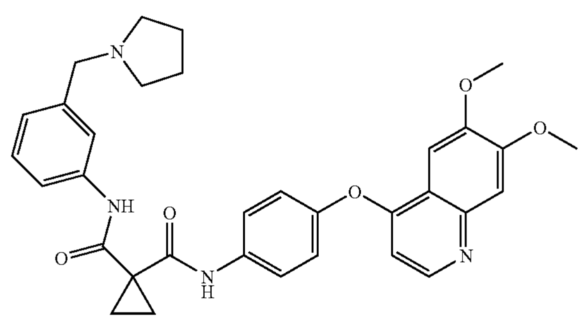 |

Another aspect of the invention is a pharmaceutical composition comprising a compound according to the invention and a pharmaceutically acceptable carrier.

Another aspect of the invention is a metabolite of the compound or the pharmaceutical composition according to the invention.

Another aspect of the invention is a method of modulating the in vivo activity of a kinase, the method comprising administering to a subject an effective amount of the compound or the pharmaceutical composition according to the invention.

Another aspect of the invention is the method according to the preceding paragraph, wherein modulating the in vivo activity of the kinase comprises inhibition of said kinase.

Another aspect of the invention is the method according to the preceding paragraph, wherein the kinase is at least one of c-Met, KDR, c-Kit, flt-3, and flt-4.

Another aspect of the invention is the method according to the preceding paragraph, wherein the kinase is c-Met.

Another aspect of the invention is a method of treating diseases or disorders associated with uncontrolled, abnormal, and/or unwanted cellular activities, the method comprising administering, to a mammal in need thereof, a therapeutically effective amount of the compound or the pharmaceutical composition as described herein.

Another aspect of the invention is a method of screening for a modulator of a kinase, said kinase selected from c-Met, KDR, c-Kit, flt-3, and flt-4, the method comprising combining a compound according to the invention, and at least one candidate agent and determining the effect of the candidate agent on the activity of said kinase.

Another aspect of the invention is a method of inhibiting proliferative activity in a cell, the method comprising administering an effective amount of a composition comprising a compound according to the invention to a cell or a plurality of cells.

As mentioned, although improved quinolines and quinazolines of the invention can be made via conventional serial methods, due to their complex structure, more efficient routes are desirable, particularly convergent syntheses. Thus, the present invention also comprises a process for preparing a compound of Formula XXI,

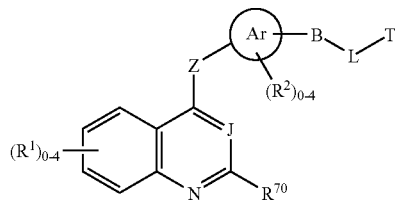

XXI comprising reaction of a compound of Formula XXII, with a compound of Formula XXIII

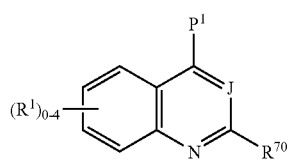

XXII

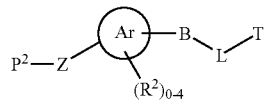

XXIII wherein,
each $R^1$ is independently selected from halogen, $-OR^3$, $-NO_2$, $-NH_2$, $-NR^3R^3$, $-D-R^{50}$ and optionally substituted $C_{1-6}$alkyl;

$R^{70}$ is selected from $-H$, halogen, $-OR^3$, $-S(O)_{0-2}R^3$, $-NO_2$, $-NH_2$, $-NR^3R^3$, and optionally substituted $C_{1-6}$alkyl;

J is selected from $=N-$, $=C(H)-$, $=C(halogen)-$, and $=C(CN)-$;

Z is selected from $-S(O)_{0-2}-$, $-O-$, and $-NR^5-$;

each $R^5$ is independently selected from $-H$, optionally substituted $C_{1-6}$alkyl, optionally substituted aryl, and optionally substituted aryl $C_{1-6}$alkyl;

Ar is either a five- to ten-membered arylene or a five- to ten-membered heteroarylene containing between one and three heteroatoms;

$R^2$ is selected from $-H$, halogen, trihalomethyl, $-CN$, $-NO_2$, $-NH_2$, $-OR^3$, $-NR^3R^3$, $-S(O)_{0-2}R^3$, $-SO_2NR^3R^3$, $-CO_2R^3$, $-C(O)NR^3R^3$, $-N(R^3)SO_2R^3$, $-N(R^3)C(O)R^3$, $-N(R^3)CO_2R^3$, $-C(O)R^3$, and optionally substituted $C_{1-6}$alkyl;

each $R^3$ is independently selected from $-H$, $-Si(R^5)(R^5)R^5$, optionally substituted lower alkyl, optionally substituted aryl, optionally substituted arylalkyl, and optionally substituted heteroarylalkyl;

two $R^3$, together with the nitrogen to which they are attached, form a four- to seven-membered heteroalicyclic, said four- to seven-membered heteroalicyclic optionally containing one additional heteroatom; when one said additional heteroatom is a nitrogen, then said nitrogen is optionally substituted with a group selected from $-H$, trihalomethyl, $-SO_2R^5$, $-SO_2NR^5R^5$, $-CO_2R^5$, $-C(O)NR^5R^5$, $-C(O)R^5$, and optionally substituted lower alkyl;

B is selected from absent, $-N(R^{13})-$, $-N(SO_2R^{13})-$, $-O-$, $-S(O)_{0-2}-$, and $-C(=O)-$;

L is selected from absent, $-C(=S)N(R^{13})-$, $-C(=NR^{14})N(R^{13})-$, $-SO_2N(R^{13})-$, $-SO_2-$, $-C(=O)N(R^{13})-$, $-N(R^{13})-$, $-C(=O)C_{1-2}alkylN(R^{13})-$, $-N(R^{13})C_{1-2}alkylC(=O)-$, $-C(=O)C_{0-1}alkylC(=O)N(R^{13})-$, $-C(=O)-$, $-C_{0-4}alkylene-$, $-C(=O)C_{0-1}alkylC(=O)OR^3-$, $-C(=NR^{14})C_{0-1}alkylC(=O)-$, $-C(=O)C_{0-1}alkylC(=O)-$, and an optionally substituted four- to six-membered heterocyclyl containing between one and three annular heteroatoms and comprising at least one nitrogen;

T is selected from $-H$, $-R^{13}$, $-C_{0-4}alkyl$, $-C_{0-4}alkylQ$, $-OC_{0-4}alkylQ$, $-C_{0-4}alkylOQ$, $-N(R^{13})C_{0-4}alkylQ$, $-SO_2C_{0-4}alkylQ$, $-C(=O)C_{0-4}alkylQ$, $-C_{0-4}alkylN(R^{13})Q$, and $-C(=O)N(R^{13})C_{0-4}alkylQ$, wherein each of the aforementioned $C_{0-4}$alkyl is optionally substituted;

Q is a five- to ten-membered ring system, optionally substituted with between zero and four of $R^{20}$;

each $R^{20}$ is independently selected from $-H$, halogen, trihalomethyl, $-CN$, $-NO_2$, $-NH_2$, $-OR^3$, $-NR^3R^3$, $-S(O)_{0-2}R^3$, $-SO_2NR^3R^3$, $-CO_2R^3$, $-C(O)NR^3R^3$, $-N(R^3)SO_2R^3$, $-N(R^3)C(O)R^3$, $-N(R^3)CO_2R^3$, $-C(O)R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

two of $R^{20}$, together with the atom or atoms to which they are attached, combine to form an optionally substituted three- to seven-membered heteroalicyclic, said optionally substituted three- to seven-membered heteroalicyclic either spiro- to Q or fused to Q;

D is selected from —O—, —S(O)$_{0-2}$—, and —NR$^{15}$—;

$R^{50}$ is either $R^3$, or according to formula XXIV;

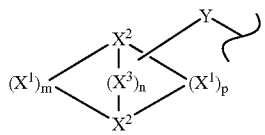

XXIV wherein $X^1$, $X^2$, and optionally $X^3$, represent the atoms of a saturated bridged ring system, said saturated bridged ring system comprising up to four annular heteroatoms represented by any of $X^1$, $X^2$, and $X^3$; wherein, each $X^1$ is independently selected from —C(R$^6$)R$^7$—, —O—, —S(O)$_{0-2}$—, and —NR$^8$—;

each $X^2$ is independently an optionally substituted bridgehead methine or a bridgehead nitrogen;

each $X^3$ is independently selected from —C(R$^6$)R$^7$—, —O—, —S(O)$_{0-2}$—, and —NR$^8$—;

Y is either:
an optionally substituted C$_{1-6}$alkylene linker, between D and either 1) any annular atom of the saturated bridged ring system, except $X^2$ when $X^2$ is a bridgehead nitrogen, or 2) any heteroatom, represented by any of $R^6$ or $R^7$; provided there are at least two carbon atoms between D and any annular heteroatom of the saturated bridged ring system or any heteroatom represented by any of $R^6$ or $R^7$;

or Y is absent, when Y is absent, said saturated bridged ring system, is directly attached to D via an annular carbon of said saturated bridged ring system, unless D is —SO$_2$—, in which case said saturated bridged ring system, is directly attached to D via an any annular atom of said saturated bridged ring system;

m and p are each independently one to four;

n is zero to two, when n is zero, then there is a single bond between the two bridgehead $X^2$'s;

$R^6$ and $R^7$ are each independently selected from —H, halogen, trihalomethyl, —CN, —NH$_2$, —NO$_2$, —OR$^3$, —NR$^3$R$^3$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —NCO$_2$R$^3$, —C(O)R$^3$, optionally substituted C$_{1-6}$alkyl, optionally substituted aryl, optionally substituted aryl C$_{1-6}$alkyl, optionally substituted heterocyclyl, optionally substituted heterocyclyl a C$_{1-6}$alkyl, and a bond to either Y or D; or $R^6$ and $R^7$, when taken together are oxo; or $R^6$ and $R^7$, when taken together with a common carbon to which they are attached, form a optionally substituted three- to seven-membered spirocyclyl, said optionally substituted three- to seven-membered spirocyclyl optionally containing at least one additional annular heteroatom selected from N, O, S, and P;

$R^8$ is selected from —R$^3$, Y, —SO$_2$NR$^3$R$^3$, —CO$_2$R$^3$, —C(O)NR$^3$R$^3$, —SO$_2$R$^3$, and —C(O)R$^3$;

$R^{13}$ is selected from —H, —C(=O)R$^3$, —C(=O)OR$^3$, —C(=O)SR$^3$, —SO$_2$R$^3$, —C(=O)N(R$^3$)R$^3$, and optionally substituted C$_{1-6}$alkyl;

two $R^{13}$, together with the atom or atoms to which they are attached, can combine to form a heteroalicyclic optionally substituted with between one and four of $R^{60}$, said heteroalicyclic comprising up to four annular heteroatoms, and said heteroalicyclic optionally comprising an aryl or heteroaryl fused thereto, in which case said aryl or heteroaryl is optionally substituted with an additional one to four of $R^{60}$;

$R^{14}$ is selected from —H, —NO$_2$, —NH$_2$, —N(R$^3$)R$^3$, —CN, —OR$^3$, optionally substituted C$_{1-6}$alkyl, optionally substituted heteroalicyclyl C$_{1-6}$alkyl, optionally substituted aryl, optionally substituted aryl C$_{1-6}$alkyl and optionally substituted heteroalicyclic;

$R^{15}$ is a group -M$^1$-M$^2$, wherein M$^1$ is selected from absent, —C(=S)N(R$^{13}$)—, —C(=NR$^{14}$)N(R$^{13}$)—, —SO$_2$N(R$^{13}$)—, —SO$_2$—, —C(=O)N(R$^{13}$)—, —C(=O)C(=O)N(R$^{13}$)—, —C$_{0-4}$alkylene-, —C(=O)—, and an optionally substituted four to six-membered heterocyclyl containing between one and three heteroatoms but comprising at least one nitrogen; and M$^2$ is selected from —H, —C$_{0-6}$alkyl, alkoxy, —C(=O)C$_{0-4}$alkylQ, —C$_{0-4}$alkylQ, —OC$_{0-4}$alkylQ-, —N(R$^{13}$)C$_{0-4}$alkylQ-, and —C(=O)N(R$^{13}$)C$_{0-4}$alkylQ;

$R^{60}$ is selected from —H, halogen, trihalomethyl, —CN, —NO$_2$, —NH$_2$, —OR$^3$, —NR$^3$R$^3$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, optionally substituted C$_{1-6}$alkyl, optionally substituted aryl, optionally substituted heteroaryl C$_{1-6}$alkyl, and optionally substituted aryl C$_{1-6}$alkyl;

two of $R^{60}$, when attached to a non-aromatic carbon, can be oxo;

$P^1$ is a suitable leaving group; and $P^2$ is selected from —H, a metal, and a group removed in-situ when combining XXII and XXIII to make XXI.

In one example, the process is according to the preceding paragraph, wherein Ar is para-phenylene as defined by the substitution pattern of -Z- and -B-L-T about said phenylene.

In another example, the process is according to the preceding paragraph, wherein Z is either —O— or —NR$^5$—.

In another example, the process is according to the preceding paragraph, wherein -B-L-T is selected from the following:

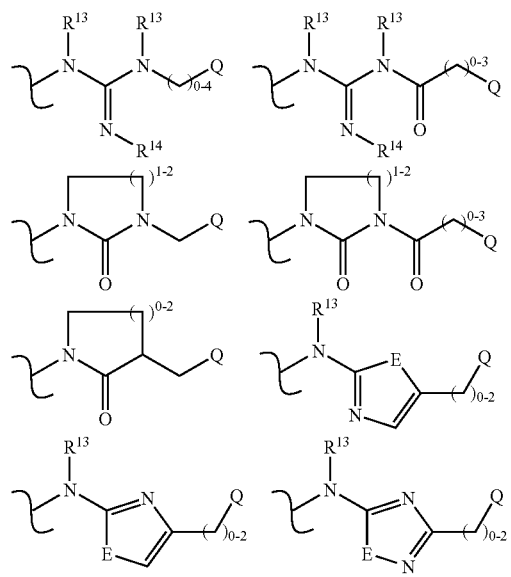

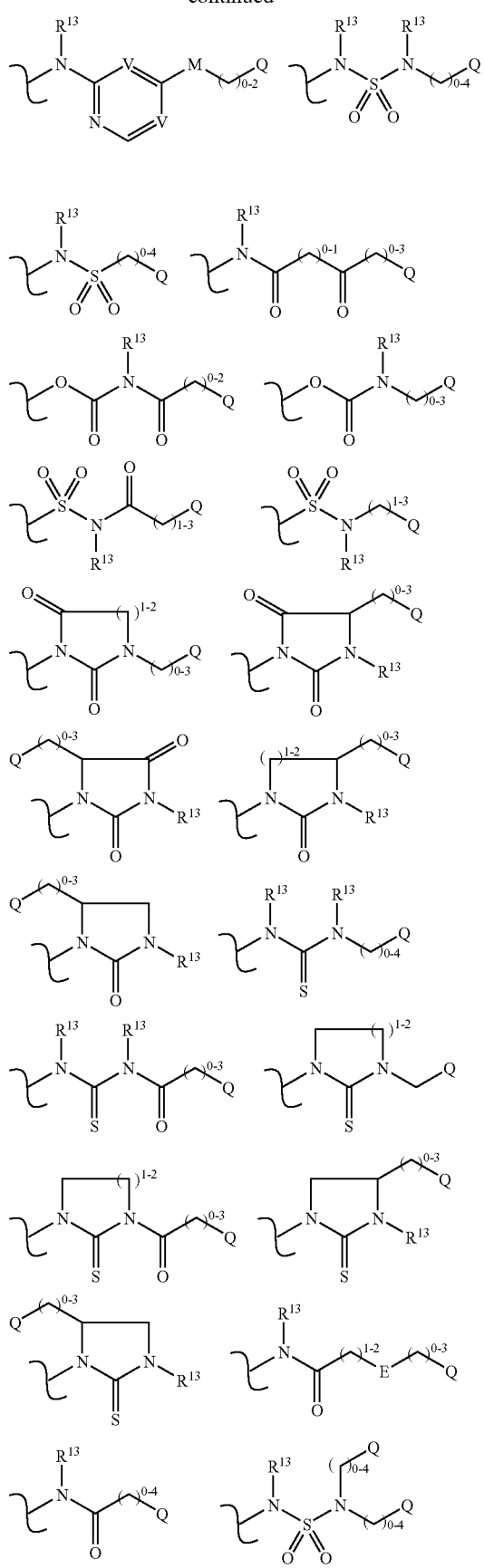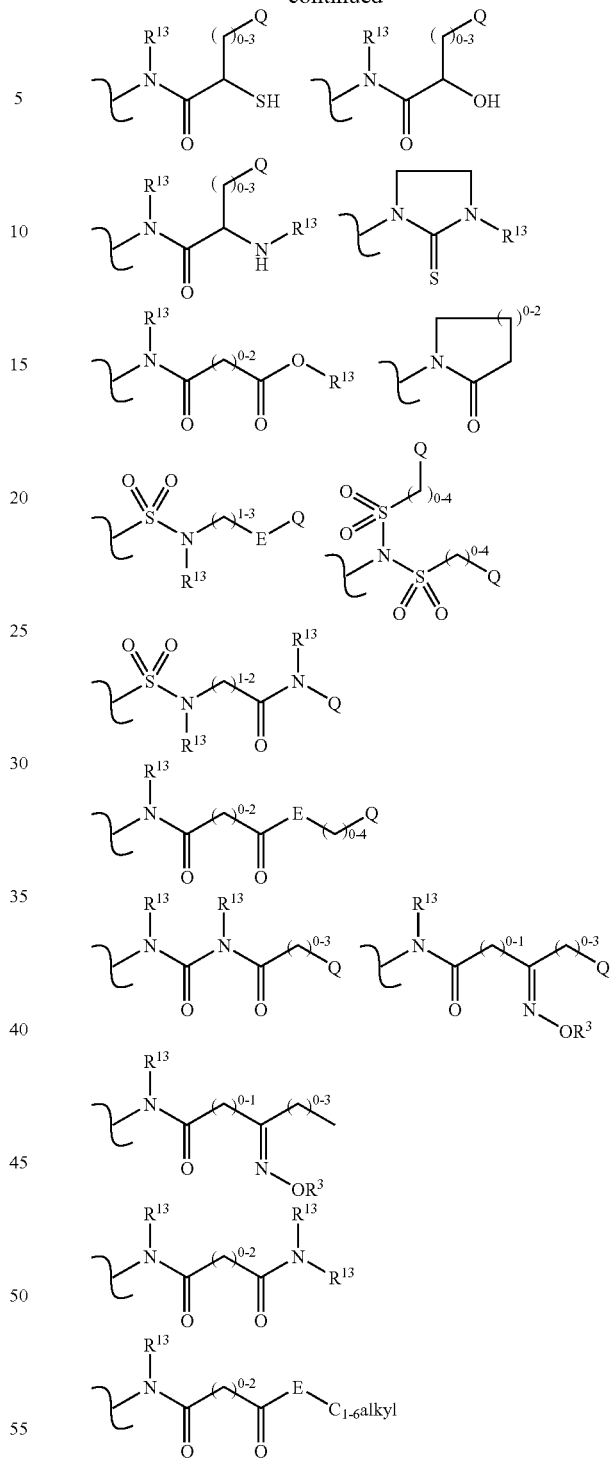

wherein Q, R[20], and R[13] are as defined above; each E is selected from —O—, —N(R[13])—, —CH$_2$, and —S(O)$_{0-2}$—; M is selected from —O—, —N(R[13])—, —CH$_2$—, and —C(=O)N(R[13])—; each V is independently either =N— or =C(H)—; each methylene in any of the above formulae is independently optionally substituted with R[25]; and R[25] is selected from halogen, trihalomethyl, —CN, —NO$_2$, —NH$_2$, —OR[3], —NR[3]R[3], —S(O)$_{0-2}$R[3], —SO$_2$NR[3]R[3], —CO$_2$R[3], —C(O)NR[3]R[3], —N(R[3])SO$_2$R[3], —N(R[3])C(O)R[3], —N(R[3])CO$_2$R[3], —C(O)R[3], optionally substituted aryl, optionally substituted aryl $C_{1-6}$alkyl, heteroaryl $C_{1-6}$alkyl, and optionally substituted $C_{1-6}$alkyl; two of $R^{25}$, together with the carbon or carbons to which they are attached, can combine to form an optionally substituted three- to seven-membered alicyclic or heteroalicyclic; two of $R^{25}$ on a single carbon can be oxo.

In another example, the process is according to the preceding paragraph, wherein there is one of $R^1$ that is -D-$R^{50}$ and another of $R^1$ that is —$OR^{3a}$.

In another example, the process is according to the preceding paragraph, wherein D is —O—.

In another example, the process is according to the preceding paragraph, wherein —O—$R^{50}$ and —$OR^{3a}$ are interchangeably located at the 6-position and 7-position of the quinazoline or quinoline according to Formula XXI.

In another example, the process is according to the preceding paragraph, wherein —$OR^{3a}$ is selected from —OH, —OSi($R^5$)($R^5$)$R^5$, and optionally substituted —$OC_{1-6}$alkyl.

In another example, the process is according to the preceding paragraph, wherein J is =N— or =C(H)—.

In another example, the process is according to the preceding paragraph, wherein -B-L-T is selected from:

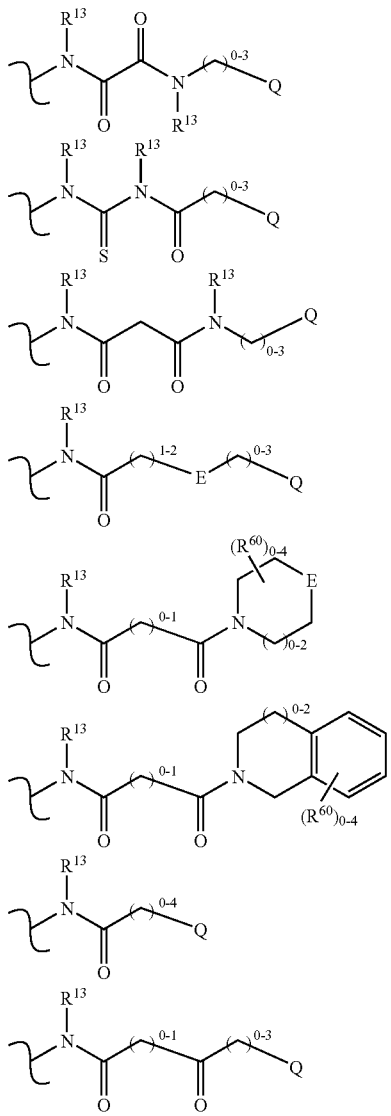

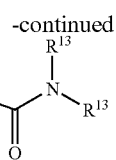

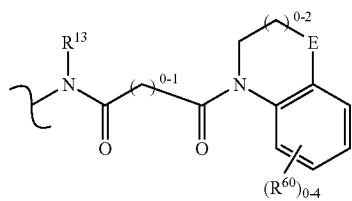

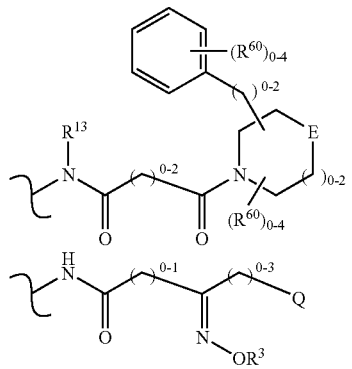

wherein Q, $R^{20}$, $R^{13}$, E, and $R^{60}$ are as defined above; each methylene in any of the above formulae, other than those in a depicted ring, is independently optionally substituted with $R^{25}$; and $R^{25}$ is selected from halogen, trihalomethyl, oxo, —CN, —$NO_2$, —$NH_2$, —$OR^3$, —$NR^3R^3$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, optionally substituted aryl, optionally substituted aryl $C_{1-6}$alkyl, heteroaryl $C_{1-6}$alkyl, and optionally substituted $C_{1-6}$alkyl; two of $R^{25}$, together with the carbon or carbons to which they are attached, can combine to form a three- to seven-membered optionally substituted alicyclic or heteroalicyclic.

In another example, the process is according to the preceding paragraph, wherein Q is selected from the following three formulae:

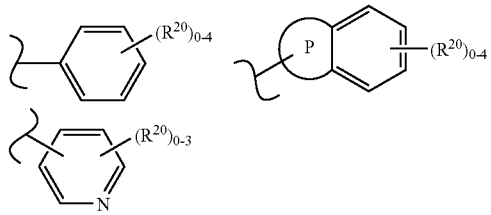

wherein $R^{20}$ is defined as above, and P is a five- to seven-membered ring, including the two shared carbons of the aromatic ring to which P is fused, P optionally containing between one and three heteroatoms.

In another example, the process is according to the preceding paragraph, wherein -B-L-T is either of formula XXV or formula XXVI,

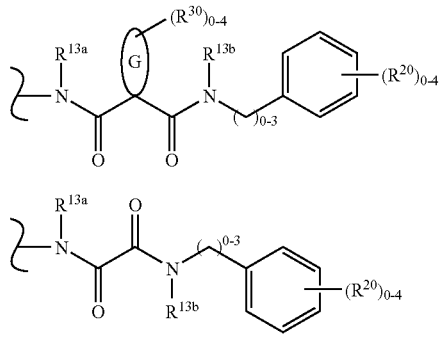

wherein $R^{20}$ is defined as above; G is either an optionally substituted cycloalkyl or an optionally substituted heteroalicyclic; each $R^{30}$ is independently selected from halogen, trihalomethyl, —CN, —NO$_2$, —NH$_2$, —OR$^3$, —NR$^3$R$^3$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, and optionally substituted $C_{1-6}$alkyl; and $R^{3a}$ and $R^{3b}$ are each independently selected from —H and optionally substituted $C_{1-6}$alkyl.

In another example, the process is according to the preceding paragraph, wherein a compound of formula XXIIa is combined with a compound of formula XXIIIa to make a compound of formula XXIa,

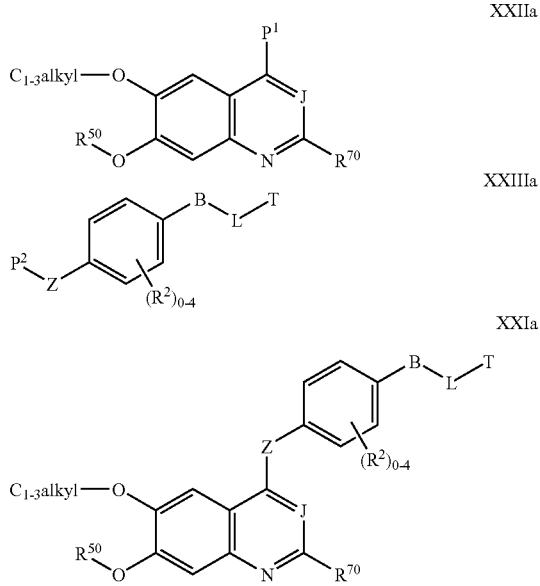

wherein -B-L-T, Z, J, $R^{50}$, and $R^2$ are as defined above; $R^{70}$ is selected from —H, —NO$_2$, —NH$_2$, and —NR$^3$R$^3$; provided when Z is —N(R$^5$)— that $R^5$ is selected from —H, $C_{1-3}$alkyl, and aryl $C_{1-3}$alkyl; $P^1$ is selected from halogen, optionally substituted alkyl-S(O)$_{0-2}$—, optionally substituted arylsulfonate, optionally substituted alkylsulfonate, a group containing boron, an azide, a group containing phosphorus, and a metal; and $P^2$ is selected from —H and a metal.

In another example, the process is according to the preceding paragraph, wherein $P^2$ is selected from —H, lithium, sodium, potassium, cesium, copper, palladium, and titanium.

In another example, the process is according to the preceding paragraph, wherein Z is —O—.

In another example, the process is according to the preceding paragraph, wherein $P^1$ is selected from chlorine, bromine, a toluene sulfonate, and trifluoromethansulfonate.

In another example, the process is according to the preceding paragraph, wherein $R^{70}$ is —H.

In another example, the process is according to the preceding paragraph, wherein J is =C(H)—.

In another example, the process is according to the preceding paragraph, wherein $R^2$ is selected from $C_{1-6}$ alkyl, perfluoro $C_{1-6}$ alkyl, and halogen.

In another example, the process is according to the preceding paragraph, wherein XXIIa and XXIIIa are heated together, optionally with a base, optionally with microwave radiation, to form XXIa.

In another example, the process is according to the preceding paragraph, wherein the base is selected from an organic base, an inorganic base, and a combination of an organic base and an inorganic base.

In another example, the process is according to the preceding paragraph, wherein the base is selected from 2,6-lutidine, 4-N,N-dimethylaminopyridine, and a metal carbonate.

In another example, the process is according to the preceding paragraph, wherein XXIIa and XXIIIa are heated together in a solvent with said base, at between about 40° C. and 200° C. for between about one hour and twenty-four hours to form XXIa.

In another example, the process is according to the preceding paragraph, wherein the solvent is an organic solvent.

In another example, the process is according to the preceding paragraph, wherein one molar equivalent of XXIIa is combined with between about one quarter and four molar equivalents of XXIIIa.

In another example, the process is according to the preceding paragraph, wherein one molar equivalent of XXIIa is combined with more than one but less than two molar equivalents of XXIIIa.

In another example, the process is according to the preceding paragraph, wherein XXIIa is combined with XXIIIa and said base in an aromatic solvent to form a mixture, and said mixture is heated to between about 100° C. and 200° C. for between about one and ten hours to form Ia.

In another example, the process is according to the preceding paragraph, wherein the aromatic solvent is an optionally substituted benzene.

In another example, the process is according to the preceding paragraph, wherein the aromatic solvent is bromobenzene.

In another example, the process is according to the preceding paragraph, wherein the base is 4-N,N-dimethylaminopyridine.

In another example, the process is according to the preceding paragraph, wherein said mixture is heated to reflux for between about three and seven hours.

In another example, the process is according to the preceding paragraph, wherein said mixture is heated to reflux for between about four and six hours.

In another example, the process is as defined seven paragraphs above, wherein one molar equivalent of XXIIa is combined with more than one but less than two molar equivalents of XXIIIa and said base in a non-aromatic solvent to form a mixture, and said mixture is heated to between about 40° C. and 100° C. for between about one and twenty hours to form XXIa.

In another example, the process is according to the preceding paragraph, wherein the non-aromatic solvent comprises a functional group selected from an amide, an ether, a nitrile, a halide, an ester, an amine, and a ketone.

In another example, the process is according to the preceding paragraph, wherein the non-aromatic solvent is N,N-dimethylacetamide.

In another example, the process is according to the preceding paragraph, wherein the base is potassium carbonate.

In another example, the process is according to the preceding paragraph, wherein said mixture is heated to about 50° C. between about ten and twenty hours.

In another example, the process is according to the preceding paragraph, wherein the aromatic solvent is an optionally substituted pyridine.

In another example, the process is according to the preceding paragraph, wherein the aromatic solvent is 2,6-lutidine.

In another example, the process is according to the preceding paragraph, wherein the base is 2,6-lutidine.

In another example, the process is according to the preceding paragraph, wherein said mixture is heated to reflux for between about three and seven hours.

In another example, the process is according to the preceding paragraph, wherein said mixture is heated to reflux for between about four and six hours.

In another example, the process is as eighteen paragraphs defined above, wherein one molar equivalent of XXIIIa is combined with more than one but less than two molar equivalents of XXIIa.

In another example, the process is according to the preceding paragraph, wherein XXIIa is combined with XXIIIa and said base in an aromatic solvent to form a mixture, and said mixture is heated to between about 100° C. and 200° C. for between about ten and twenty hours to form XXIa.

In another example, the process is according to the preceding paragraph, wherein the aromatic solvent is an optionally substituted pyridine.

In another example, the process is according to the preceding paragraph, wherein the aromatic solvent is 2,6-lutidine.

In another example, the process is according to the preceding paragraph, wherein the base is 2,6-lutidine.

In another example, the process is according to the preceding paragraph, wherein said mixture is heated to between about 150° C. and 200° C. for between about fifteen and twenty hours.

In another example, the process is as defined above in any of the twenty-nine preceding paragraphs, wherein a compound of formula XXIIb is substituted for the compound of formula XXIIa, and either a compound of formula XXIIIb or a compound of formula XXIIIc is substituted for the compound of formula XXIIIa, in order to make a compound of formula XXIb or a compound of formula XXIc, respectively,

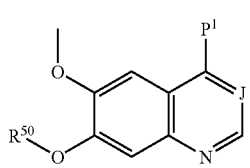

XXIIb

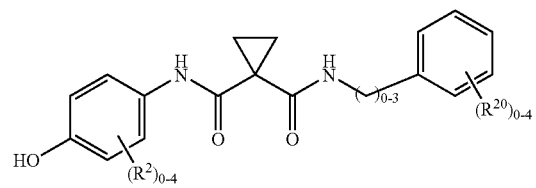

XXIIIb

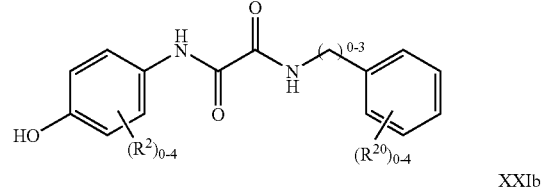

XXIIIc

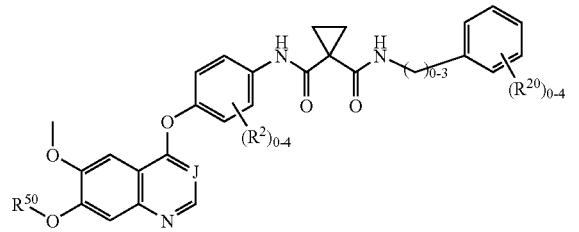

XXIb

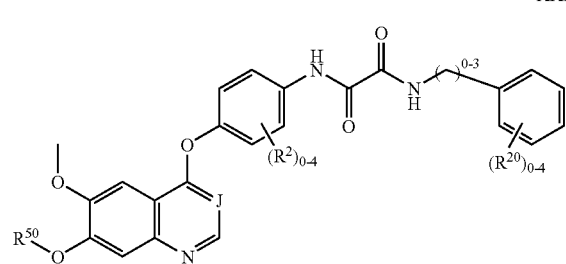

XXIc wherein J, $R^{50}$, $R^{20}$ and $R^2$ are as defined above.

In another example, the process is according to the preceding paragraph, wherein $R^2$, if present, is halogen.

In another example, the process is according to the preceding paragraph, wherein $R^2$, if present, is fluorine.

In another example, the process is according to the preceding paragraph, wherein $R^2$, if present, is up to two fluorines ortho to the oxygen of the phenylene to which $R^2$ is attached.

In another example, the process is used to make a compound listed in either Table 1 or Table 2.

In another example the process is as defined above in any of the fifty-two preceding paragraphs, further comprising converting said compound to a pharmaceutically acceptable salt, hydrate, or prodrug thereof.

DEFINITIONS

As used in the present specification, the following words and phases are generally intended to have the meanings, as set forth below, except to the extent that the context in which they are used indicates otherwise or they are expressly defined to mean something different.

The symbol "—" means a single bond, "═" means a double bond, "≡" means a triple bond. The symbol "⁓" refers to a group on a double-bond as occupying either position on the terminus of a double bond to which the symbol is attached; that is, the geometry, E- or Z-, of the double bond is ambiguous. When a group is depicted removed from its parent formula, the "∽" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

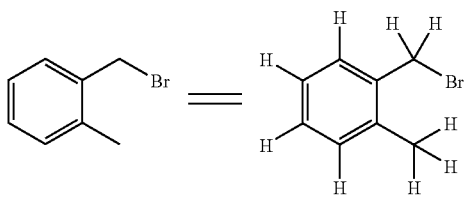

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

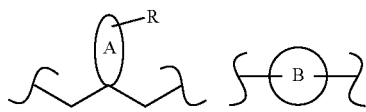

If a group "R" is depicted as "floating" on a ring system, as for example in the formula:

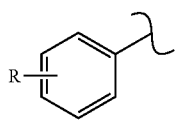

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

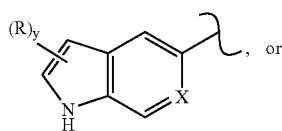

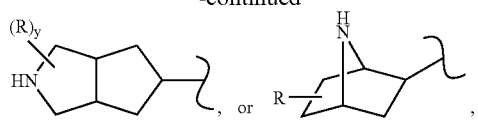

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

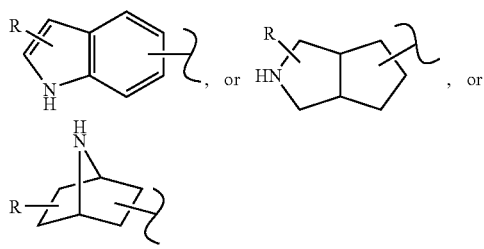

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

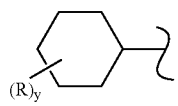

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

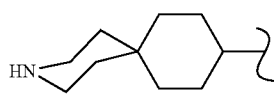

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, alkyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" or "$C_3$ alkyl" each include n-propyl, propenyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene ($—CH_2CH_2—$), propylene ($—CH_2CH_2CH_2—$), dimethylpropylene ($—CH_2C(CH_3)_2CH_2—$), and cyclohexylpropylene ($—CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidene is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as $—OCH_2CH_2OCH_3$, and glycol ethers such as polyethyleneglycol and $—O(CH_2CH_2O)_xCH_3$, where x is an integer of between about two and about twenty, in another example, between about two and about ten, and in a further example between about two and about five. Another exemplary substituted alkoxy group is hydroxyalkoxy or $—OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group $—NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkylidene, or alkylidene radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as $C_{1-6}$ arylalkyl.

"Exo-alkenyl" refers to a double bond that emanates from an annular carbon, and is not within the ring system, for example the double bond depicted in the formula below.

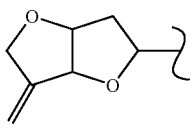

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S-(sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothielyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic. Such terms may be described in more than one way, for example, "lower heterocyclylalkyl" and "heterocyclyl C$_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted arylC$_{1-8}$ alkyl," optional substitution may occur on both the "C$_{1-8}$ alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitution are listed below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system." "Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

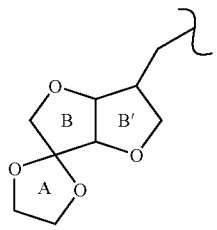

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino and dialkylamino), optionally substituted amidino, optionally substituted aryloxy (for example, phenoxy); optionally substituted arylalkyloxy (for example, benzyloxy), carboxy (—CO$_2$H), carboalkoxy (that is, acyloxy or —OC(=O)R), carboxyalkyl (that is, esters or —CO$_2$R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Suitable leaving group" is defined as the term would be understood by one of ordinary skill in the art; that is, a carbon with such a group attached, upon reaction wherein a new bond is to be formed, loses such a group upon formation of the new bond. The invention pertains particularly with respect convergent synthesis, to reactions where such a leaving group is bonded to a reaction partner that is aromatic, undergoes a bond-forming reaction and remains aromatic. A typical example of such a reaction is a nucleophilic aromatic substitution reaction, as would be understood by one of ordinary skill in the art. However, the invention is not limited to such mechanistic restrictions; for example, reactions where there is, for example, an insertion reaction (for example by a transition metal) into the bond between the aromatic reaction partner and its leaving group followed by reductive coupling can also be used within the scope of the invention. Examples of suitable leaving groups include halogens, optionally substituted aryl or alkyl sulfonates, phosphonates, azides, RS(O)$_{0-2}$— where R is, for example optionally substituted alkyl, optionally substituted aryl, or optionally substituted heteroaryl.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O$_2$)—H, —S(O$_2$)-(optionally substituted alkyl), —S(O$_2$)-optionally substituted aryl), —S(O$_2$)-(optionally substituted heterocyclyl), —S(O$_2$)-(optionally substituted alkoxy), —S(O$_2$)-optionally substituted aryloxy), and —S(O$_2$)-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —OCH$_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH$_2$—" is meant to mean not only "—OCH$_2$—" as drawn, but also "—CH$_2$O—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defomians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgeminoma, malignant teratoma), vulva (squamous cell carcinoma, intraepithelial carcinoma, adenocarcinoma, fibrosarcoma, melanoma), vagina (clear cell carcinoma, squmnous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all puposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular c-Met, c-Kit, KDR, flt-3, or flt-4-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example c-Met, KDR, c-Kit, flt-3, or flt-4, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, c-Met, KDR, c-Kit, flt-3, or flt-4 protein may be done in a number of ways. In one example, the candidate agent (the compound of the invention) is labeled, for example, with a fluorescent or radioactive moiety and binding determined directly. For example, thus may be done by attaching all or a portion of the c-Met, KDR, c-Kit, flt-3, or flt-4 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, c-Met, KDR, c-Kit, flt-3, or flt-4 protein may be labeled at tyrosine positions using $^{125}$I, or with fluorophores. Alternatively, more than one component may be labeled with different labels; using $^{125}$I for the proteins, for example, and a fluorophore for the candidate agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to c-Met, KDR, c-Kit, flt-3, or flt-4.

Candidate agents can encompass numerous chemical classes, though typically they are organic molecules having a molecular weight of more than about 100 daltons and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to c-Met, KDR, c-Kit, flt-3, or flt-4, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to for example c-Met, KDR, c-Kit, flt-3, or flt-4 for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient.

Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to c-Met, KDR, c-Kit, flt-3, or flt-4 and thus is capable of binding to, and potentially modulating, the activity of the c-Met, KDR, c-Kit, flt-3, or flt-4. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to c-Met, KDR, c-Kit, flt-3, or flt-4 with a higher affinity. Thus, if the candidate agent is labeled, the presence of the label on the support, coupled with a lack of competitor binding, may indicate the candidate agent is capable of binding to c-Met, KDR, c-Kit, flt-3, or flt-4.

It may be of value to identify the binding site of c-Met, KDR, c-Kit, flt-3, or flt-4. This can be done in a variety of ways. In one embodiment, once c-Met, KDR, c-Kit, flt-3, or flt-4 has been identified as binding to the candidate agent, the c-Met, KDR, c-Kit, flt-3, or flt-4 is fragmented or modified and the assays repeated to identify the necessary components for binding.

Modulation is tested by screening for candidate agents capable of modulating the activity of c-Met, KDR, c-Kit, flt-3, or flt-4 comprising the steps of combining a candidate agent with c-Met, KDR, c-Kit, flt-3, or flt-4, as above, and determining an alteration in the biological activity of the c-Met, KDR, c-Kit, flt-3, or flt-4. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native c-Met, KDR, c-Kit, flt-3, or flt-4, but cannot bind to modified c-Met, KDR, c-Kit, flt-3, or flt-4.

Positive controls and negative controls may be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Abbreviations and their Definitions

The following abbreviations and terms have the indicated meanings throughout.

| Abbreviation | Meaning |
|---|---|
| Ac | acetyl |
| ATP | adenosine triphosphate |
| BNB | 4-bromomethyl-3-nitrobenzoic acid |
| Boc | t-butyloxy carbonyl |
| br | broad |
| Bu | butyl |
| °C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ere |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylformamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | 0-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| s- | secondary |
| t- | tertiary |
| t or tr | triplet |

| Abbreviation | Meaning |
|---|---|
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| uL | microliter(s) |
| uM | Micromole(s) or micromolar |

Synthesis of Compounds

Schemes 1 and 2 depict general synthetic routes for compounds of the invention and are not intended to be limiting. More specifically, Scheme 1 depicts synthesis of quinazoline compounds, and Scheme 2 depicts synthesis of quinoline compounds. Specific examples are described subsequently to these general synthetic descriptions so as to allow one skilled in the art to make and use either quinazolines or quinolines of the invention.

various stages of the synthesis. The group, $E^1$, may represent either a protecting group, e.g. benzyl, or a group that either has moieties present in compounds of the invention or possesses functionality that serve as a precursors to such groups. Aromatic ring nitration and reduction of the corresponding nitro group are carried out in a regio- and chemoselective manner by methods well known in the art to give anthranilate derivative 3. Formation of quinazolin-4-one 4 is carried out by methods well known in the art, for example by heating 3 in formamide solution in the presence of ammonium formate or for example by heating directly with formamidines hydrochloride. Introduction of 4-position functionality groups is carried out by methods known in the art. For example, quinazolin-4-one 4 is converted to an intermediate quinazoline 5, where "L" represents a leaving group, e.g. chlorine. Quinazoline 5 is then converted to 6 by reaction with a range of nucleophiles, e.g. amines, alcohols, and thiols. After formation of 6, group "Z" is either left "as is" or converted at some subsequent stage to a derivative thereof. For example when Z is —NH—, then the hydrogen on the nitrogen may optionally be replaced with an alkyl group, or when Z is

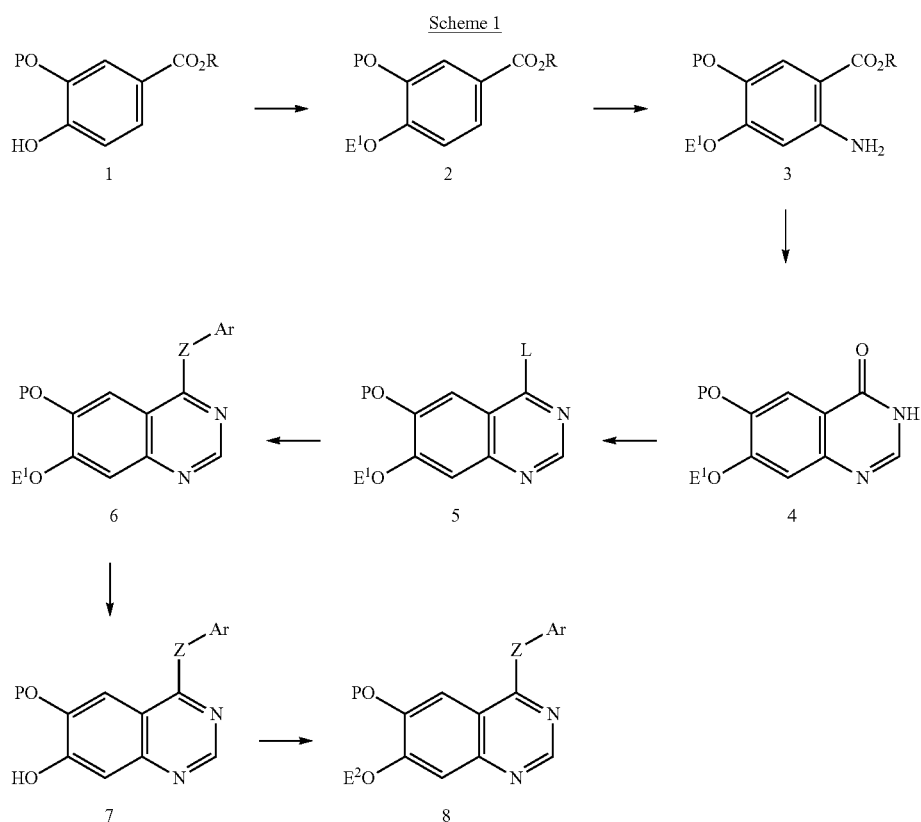

Referring to Scheme 1, a benzoic ester 1, where R is typically but not necessarily a methyl radical and P is typically but not necessarily an alkyl group, is O-alkylated at the oxygen para to the carboxylate group with an electrophile to afford a substituted derivative 2. P is typically a lower alkyl group, but may be a protecting group that is removed later in a synthesis. When P is a lower alkyl group it may possess functionality initially, or be derivatized to contain such functionality at sulfur, then that sulfur atom may be oxidized to, for example, a sulfone. Structure 6 may represent compounds of the invention or, for example when $E^1$ selves as a protecting group, $E^1$ may be removed to provide phenol 7. Introduction of a group $E^2$ is carried out by methods well established in the art; for example alkylation with an appropriately derivatized alkyl halide (or mesylate or the like) to give 8 which also represents compounds of the invention.

Scheme 2

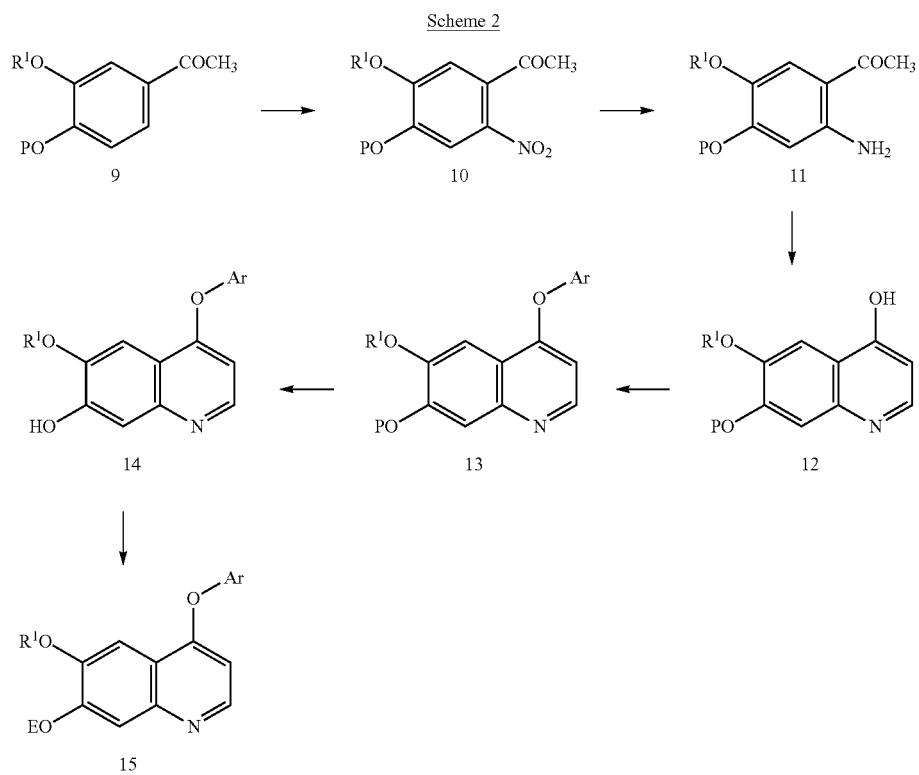

Scheme 2 shows a general route used to make exemplary quinolines of the invention. For example, compound 9 contains an alkyl group, $R^1$, a protecting group, P. The arrangement of the protected and alkylated phenolic oxygens may vary from the pattern depicted in compound 9. Compound 9 is nitrated to provide compound 10. The nitro group of compound 10 is reduced to give aniline 11. Compound II is treated, for example, with ethyl formate under basic conditions followed by acidification and isolation to form 4-hydroxy quinoline 12. Quinoline 12 may be converted to compounds of the invention in a number of ways. For example, the 4-oxygen is used as a nucleophile in a nucleophilic aromatic substitution reaction to form quinoline-aryl-ether 13. In another example, compound 13 is further derivatized, via removal of protecting group P, to afford compound 14. The 7-hydroxy of compound 14 is alkylated, for example with electrophile E, to provide a compound of the invention. As discussed in relation to Scheme 1, variations on any of the above steps are possible, and intermediates in these schemes, for example compounds 12, 13, and 14 may also be compounds of the invention according to formula I. Also, for example, the 4-hydroxy quinoline compound 12 are converted to a corresponding 4-nitrogen or 4-sulfur quinoline using chemistry known in the art to make compounds of the invention, or alternatively the corresponding 4-nitrogen or 4-sulfur quinolines are made via routes analogous to that depicted in Schemes 1 and 2.

Schemes 1 and 2 are illustrative of quinolines and quinazolines having oxygen substitution at their respective 6- and 7-positions; the invention is not so limited, but rather is intended to encompass quinolines and quinazolines not necessarily having substitution, oxygen or otherwise, at their respective 6- or 7-positions.

Schemes 3 and 4 depict generalized synthetic routes to show the process of the invention to make compounds of formula XXI and is not intended to be limiting. More specifically, Schemes 3 and 4 depict convergent syntheses of quinoline and quinazoline compounds as described herein. Specific examples are described subsequently to this general synthetic description so as to allow one of ordinary skill in the art to practice the invention.

Referring to Scheme 3, a benzoic ester 16 for example, where R is typically but not necessarily a methyl radical and $R^1$ is typically but not necessarily one or more alkoxy or hydroxy groups. In a typical synthesis, at least one of $R^1$ within Scheme 3 is a hydroxyl which is converted (or protected) via one or more steps to a group important to the activity of the compounds as described as kinase modulators (in the case that —OH itself is desired in the final compound, then deprotection affords the —OH, vide supra). Preferably, but not necessarily, this group is complete once the synthesis of XXII is complete. By building desired complexity into XXII prior to combination with XXIII, convergent syntheses' advantages over serial syntheses are realized more fully. Regioselective aromatic ring nitration, and reduction of the corresponding nitro group, are carried out in a regio- and chemoselective manner by methods well known in the art to give anthranilate derivative 17. Formation of quinazoline or quinoline 4-one 18 is carried out by methods well known in the art. For example by heating 17 in formamide solution in the presence of ammonium formate, or by heating 17 with formamidine hydrochloride, the quinazoline-4-one analog is made. In another example 17 is treated, for example, with ethyl formate under basic conditions followed by acidification and isolation to form the 4-hydroxy quinoline analog (a tautomer of the 4-one). In this scheme J' represents either carbon or nitrogen atom with the appropriate number of hydrogens to fill their respective normal valence bonding schemes; J' is a precursor to J. Radicals J and $R^{70}$ are in accord with formula XXI. Introduction of 4-position functionality is carried out by methods known in the art. For example, 4-one 18 is converted to XXII, where "$P^1$" represents a suitable leaving group (in accord with formula XXI), e.g. chlorine (via dehydration/chlorination of 18 to give XXII). In another example, a 4-hydroxy analog is converted to a sulfonyl ester, e.g. the trifluoromethane sulfonate.

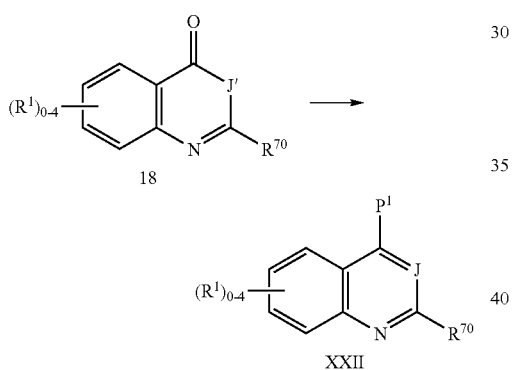

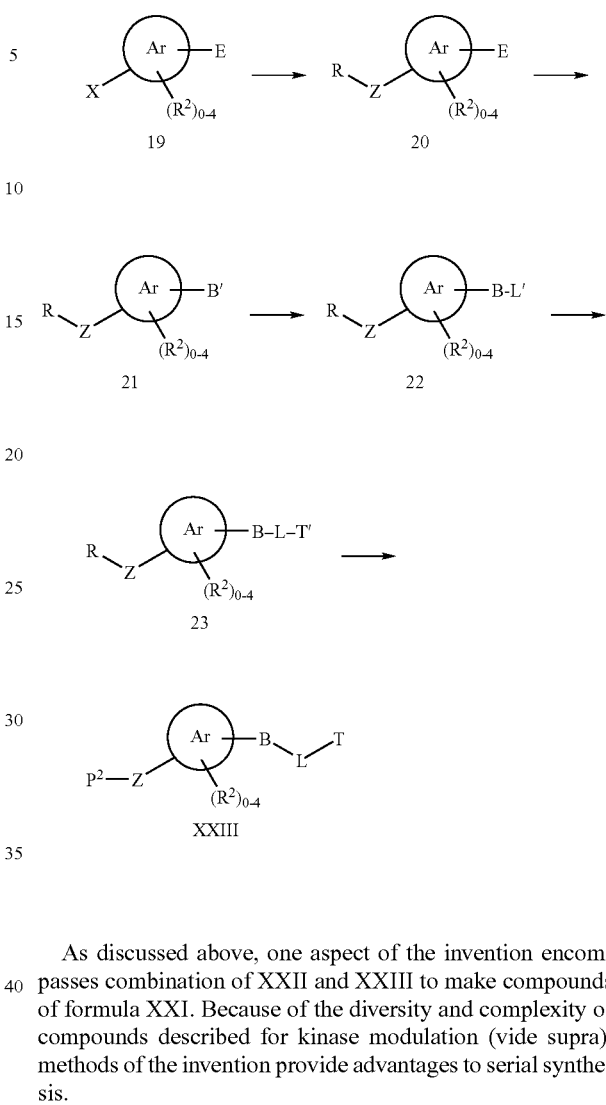

Scheme 4 shows a general route used to make compounds of formula XXIII. For example, aromatic compound 19, where "X" is a leaving group, such as fluorine and "E" is an electron withdrawing group such as nitro, is converted to 20 by reaction with a range of nucleophiles, e.g. amines, alcohols, and thiols (where "Z" is oxygen, nitrogen (substituted or not), or sulfur). In this case, "R" represents a removable group, for example benzyl. In a typical synthesis, after formation of 20, group "E" is either left "as is" or converted at some subsequent stage to a derivative thereof. In the example depicted, E is converted to B', a precursor to B in accord with formula XXI, to make 21. For example if E is a nitro, then B' could might be an amino group, made via reduction of the nitro group. Structure 21 may be further derivatized by synthesis of -B-L-T in accord with formula XXI. In scheme 4, this is depicted as a serial process whereby L', a precursor to L, is introduced to give 22, followed by introduction of T' (a precursor to T) to give 23. In some cases, -L-T is preformed and appended to B. One of ordinary skill in the art would appreciate that variations on any of the above steps are possible. Compound 23 is converted to XXIII via conversion of T' to T and introduction of $P^2$ (for example, when R is benzyl, removal of the benzyl after completion of -B-L-T).

As discussed above, one aspect of the invention encompasses combination of XXII and XXIII to make compounds of formula XXI. Because of the diversity and complexity of compounds described for kinase modulation (vide supra), methods of the invention provide advantages to serial synthesis.

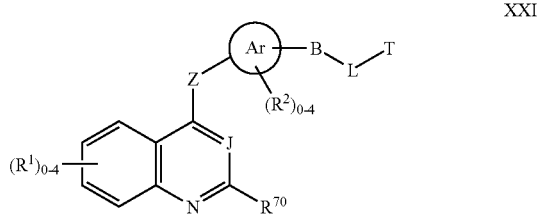

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Generally, but not necessarily, each example set out below describes a multi-step synthesis as outlined above.

Quinoline and Quinazoline Syntheses

Example 1

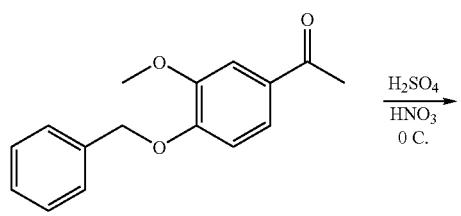

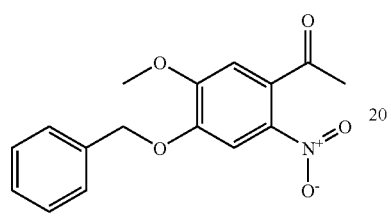

Synthesis of 1-(4-Benzyloxy-5-methoxy-2-nitro-phenyl)-ethanone. 1-(4-Benzyloxy-3-methoxy-phenyl)-ethanone (200 mmol, 51.3 g) dissolved in DCM (750 ml) and the mixture cooled to 0° C. Nitric acid (90%, 300 mmol, 14 ml) was added dropwise to the cooled solution over 20 minutes. Sulfuric acid (96.2%, 300 mmol, 8.75 ml) was then added dropwise over 40 minutes at 0° C.

Additional nitric acid (200 mmol, 9.4 ml) was added dropwise over 20 minutes. The reaction mixture was diluted with water (300 ml) and wash with water (3×200 ml), Sat. NaHCO$_3$ (4×200 ml, or until neutral). The organic layer was dried over Na$_2$SO$_4$ and concentrated.

The crude mixture was recrystallized with DMF to give 22.5 g of the nitro product. The DMF layer was concentrated and recrystallized with ethyl acetate to give additional 8.75 g of the product. The ethyl acetate layer was concentrated and purified on silica column using 20% EtOAc/hexanes to gave another 4.75 g of the product. Total yield is 36 g, (~60%). $^1$H NMR (CDCl$_3$): 7.647 (1H, s), 7.446-7.333 (5H, m), 6.745 (1H, s), 5.210 (2H, s), 3.968 (3H, s), 2.487 (3H, s).

Example 2

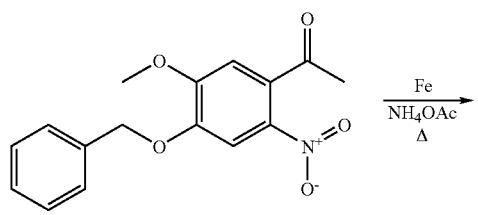

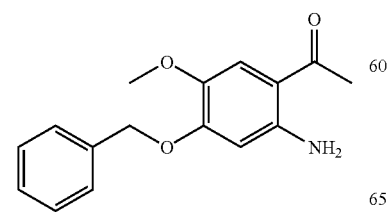

Synthesis of 1-(2-Amino-4-benzyloxy-5-methoxy-phenyl)-ethanone. A Mixture of iron powder (477 mmol, 27 g), ammonium acetate (500 mmol, 31 g), 1-(4-Benzyloxy-5-methoxy-2-nitro-phenyl)-ethanone (120 mmol, 36 g), toluene (500 ml) and water (500 ml) was refluxed overnight until completion. The mixture was filtered through celite and washed with EtOAc. The organic layer was washed with water and Sat. NaCl, dried over Na$_2$SO$_4$, and concentrated to afford the product, 90%. $^1$H NMR (CDCl$_3$): 7.408-7.298 (5H, m), 7.130 (1H, s), 6.155 (2H, br), 6.104 (1H, s), 5.134 (2H, s), 3.834 (3H, s), 2.507 (3H, s). LC/MS (M+1=272).

Example 3

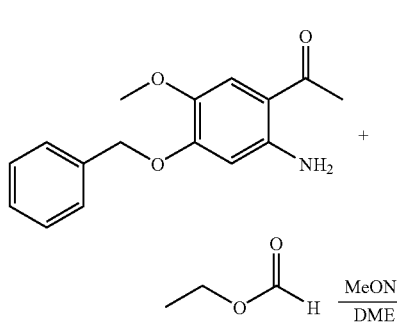

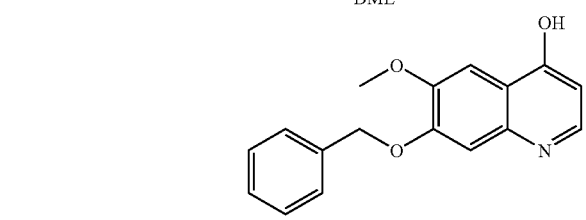

Synthesis of 7-Benzyloxy-6-methoxy-quinolin-4-ol. To a solution of 1-(2-Amino-4-benzyloxy-5-methoxy-phenyl)-ethanone (108 mmol, 29.3 g) in DME (700 ml) was added sodium methoxide (432 mmol, 23.35 g). The mixture was stirred for 30 minutes. Ethyl formate (540 mmol, 44 ml) was added and the mixture was stirred overnight. (Additional sodium methoxide may be needed if reaction is not complete as monitored by LC/MS.) After the reaction was completion, the mixture was diluted with water (40 ml) and acidified to neutral with 1M HCl. The precipitate was filtered and washed with water, dried in vacuo to afford 22 g (72%) of 7-benzyloxy-6-methoxy-quinolin-4-ol. $^1$H NMR (CDCl$_3$): 10.7 (1H, br), 7.703 (1H, s), 7.493-7.461 (1H, t), 7.431-7.413 (2H, br d), 7.372-7.333 (2H, t), 7.296-7.283 (1H, d), 6.839 (1H, s), 6.212-6.193 (1H, d), 5.212 (2H, s), 3.965 (3H, s). LC/MS (M+1=282).

Example 4

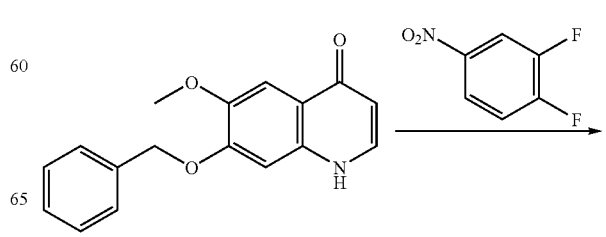

-continued

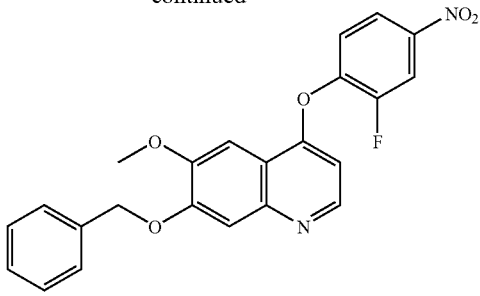

7-Benzyloxy-4-(2-fluoro-4-nitro-phenoxy)-6-methoxy-quinoline. To a round bottom flask equipped with a magnetic stir bar was added 7-Benzyloxy-6-methoxy-1H-quinolin-4-one (12.2 g, 43.3 mmol, 1.0 eq.), acetonitrile (150 ml), DMF (150 ml) and cesium carbonate (28.2 g, 86.5 mmol, 2.0 eq). The mixture was stirred at room temperature for 30 minutes at which time 1,2-difluoro-4-nitro-benzene (7.57 g, 47.6 mmol, 1.1 eq) was added over a 10 minute period. After 2 hours the reaction was complete at which time 75% of the MeCN and DMF was removed and the resulting solution was poured over into ice water. The solid was filtered and dried and further columned with a biotage system. The eluent was 1:3 ethyl acetate/hexane. Removal of the solvent afforded 7-Benzyloxy-4-(2-fluoro-4-nitro-phenoxy)-6-methoxy-quinoline as a pale green solid (7.4 g, 41% yield). $^1$H NMR (400 MHz, CDCl$_3$): 8.53 (d, 1H), 8.42 (dd, 1H), 8.16 (m, 1H), 7.5 (m, 8H), 6.76 (d, 1H), 5.31 (s, 2H), 3.92 (s, 3H); MS (EI) for C$_{23}$H$_{27}$FN$_2$O$_5$: 421 (MH$^+$).

Example 5

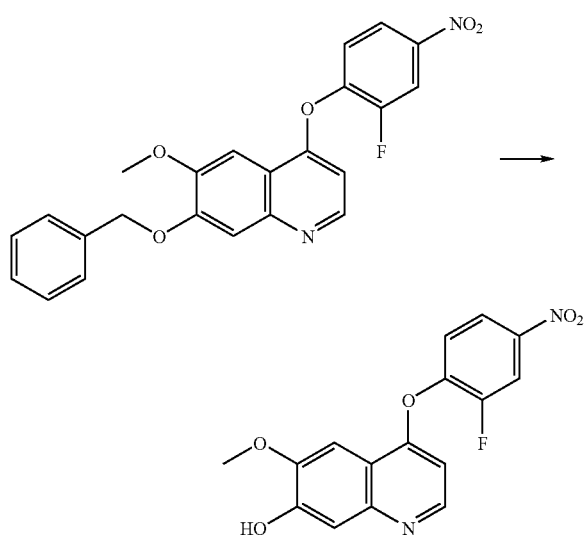

4-(2-Fluoro-4-nitro-phenoxy)-6-methoxy-quinolin-7-ol. To a round bottom flask equipped with a magnetic stir bar was added 7-benzyloxy-4-(2-fluoro-4-nitro-phenoxy)-6-methoxy-quinoline (2.9 g, 6.9 mmol, 1.0 eq) and 33% HBr in acetic acid (30 ml). The mixture was stirred at room temperature for 3 hours and diluted with ether to give a pale white solid. The solid was filtered, washed with ether and dried to yield 4-(2-Fluoro-4-nitro-phenoxy)-6-methoxy-quinolin-7-ol as a pale white solid (2.74 g, 97.5% yield). $^1$H NMR (400 MHz, CDCl$_3$): 11.89 (bs, 1H), 8.87 (d, 1H), 8.57 (d, 1H), 8.30 (d, 1H), 7.89 (m, 1H), 7.73 (s, 1H), 7.55 (s, 1H), 4.03 (s, 3H); MS (EI) for C$_{16}$H$_{11}$FN$_2$O$_5$: 421 (M+H$^+$).

Example 6

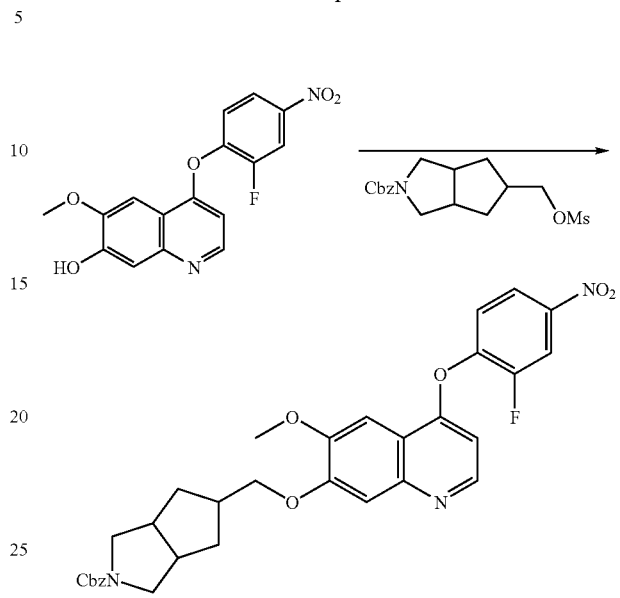

5-[4-(2-Fluoro-4-nitro-phenoxy)-6-methoxy-quinolin-7-yloxymethyl]-hexahydro-cyclopenta[c]pyrrole-2-carboxylic acid benzyl ester. To a round bottom flask equipped with a magnetic stir bar was added 4-(2-Fluoro-4-nitro-phenoxy)-6-methoxy-quinolin-7-ol (2.74 g, 6.7 mmol, 1.0 eq.), DMA (30 ml) and cesium carbonate (6.6 g, 20.2 mmol, 3.0 eq). The mixture was stirred at room temperature for 30 minutes at which time 5-methanesulfonyloxymethyl-hexahydro-cyclopenta[c]pyrrole-2-carboxylic acid benzyl ester (2.6 g, 7.3 mmol, 1.1 eq) was added. The reaction was heated to 75° C. and allowed to stir overnight. After allowing the reaction to cool to room temperature the reaction was poured into water. The solid was filtered and was then dissolved in EtOAc and washed 2× water, 1× brine and dried over NaSO$_4$. The solvent was removed to yield 5-[4-(2-Fluoro-4-nitro-phenoxy)-6-methoxy-quinolin-7-yloxymethyl]-hexahydro-cyclopenta[c]pyrrole-2-carboxylic acid benzyl ester as a cream solid (3.7 g, 94% yield). $^1$H NMR (400 MHz, CDCl$_3$): 8.55 (d, 1H), 8.15 (d, 1H), 8.09 (d, 1H), 7.32 (m, 8H), 6.52 (d, 1H), 5.11 (d, 2H), 4.13 (d, 2H), 3.95 (s, 3H), 3.57 (m, 2H), 3.43 (m, 2H), 2.93 (m, 3H), 2.16 (m, 2H), 1.39 (m, 2H); MS (EI) for C$_{32}$H$_{30}$FN$_3$O$_7$: 588 (M+H$^+$).

Example 7

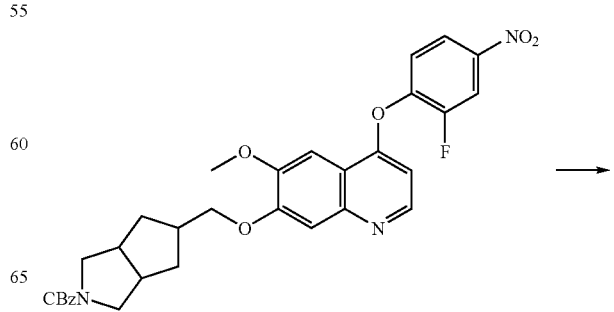

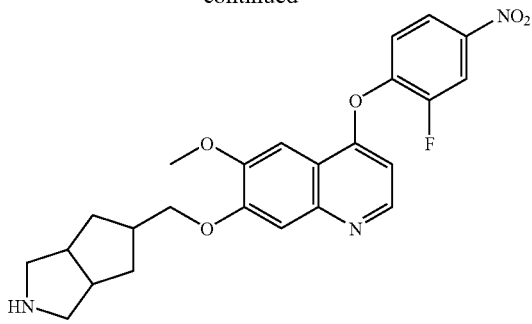

4-(2-Fluoro-4-nitro-phenoxy)-6-methoxy-7-(octahydro-cyclopenta[c]pyrrol-5-ylmethoxy)-quinoline. To a round bottom flask equipped with a magnetic stir bar was added 5-[4-(2-Fluoro-4-nitro-phenoxy)-6-methoxy-quinolin-7-yloxymethyl]-hexahydrocyclopenta-[c]pyrrole-2-carboxylic acid benzyl ester (2.5 g, 4.1 mmol, 1.0 eq), 33% HBr in acetic acid (5 ml) and acetic acid (5 ml). The mixture was stirred at room temperature for 1 hour and diluted with EtOAc to give a pale orange solid. The solid was filtered, washed with EtOAc and dried, giving 4-(2-Fluoro-4-nitro-phenoxy)-6-methoxy-7-(octahydro-cyclopenta[c]pyrrol-5-ylmethoxy)-quinoline (2.1 g, 95% yield). $^1$H NMR (400 MHz, CDCl$_3$): 8.83 (d, 1H), 8.32 (m, 2H), 8.02 (s, 1H), 7.76 (t, 1H), 7.65 (s, 1H), 6.89 (d, 1H), 5.3 (d, 2H), 4.11 (m, 3H), 3.26 (m, 4H), 2.95 (m, 2H), 2.68 (m, 3H), 2.36 (m, 2H), 1.68 (m, 2H); MS (EI) for C$_{24}$H$_{24}$FN$_3$O$_5$: 454 (M+H$^+$).

Example 8

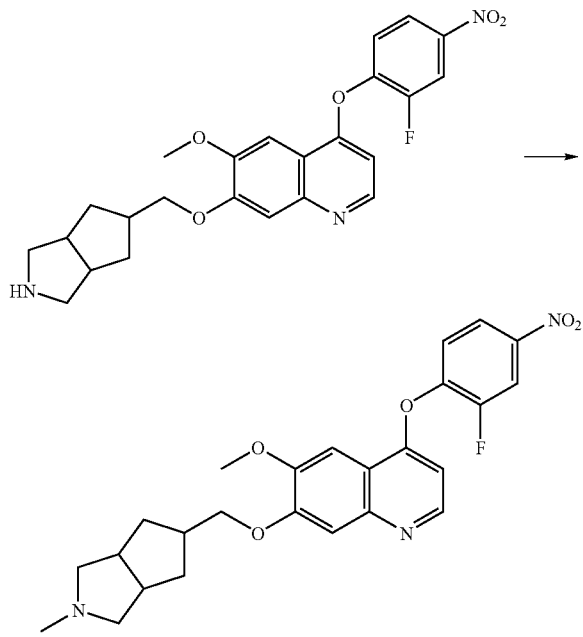

4-(2-Fluoro-4-nitro-phenoxy)-6-methoxy-7-(2-methyl-octahydro-cyclopenta[c]pyrrol-5-ylmethoxy)-quinoline. To a round bottom flask equipped with a magnetic stir bar was added 4-(2-Fluoro-4-nitro-phenoxy)-6-methoxy-7-(octahydro-cyclopenta[c]pyrrol-5-ylmethoxy)-quinoline (2.1 g, 3.9 mmol, 1.0 eq.) and acetonitrile/water 1:1 (5 ml, 5 ml). The reaction mixture was then cooled to 0° C. and 37% solution of formaldehyde in water was added (0.2 g, 7.8 mmol, 2.0 eq). While keeping the temperature at 0° C. Na(OAc)$_3$BH was added (4.4 g, 20.7 mmol, 3.0 eq). After 1 hour the pH was adjusted to 10 and the aqueous was extracted 2×DCM (100 ml). Removal of the DCM resulted in a white solid. The compound was further purified with a biotage system using an eluent EtOAc and 5% MeOH, affording 4-(2-Fluoro-4-nitro-phenoxy)-6-methoxy-7-(2-methyl-octahydrocyclopenta-[c]pyrrol-5-ylmethoxy)-quinoline (0.9 g, 50% yield.). $^1$H NMR (400 MHz, CDCl$_3$): 8.57 (d, 1H), 8.14 (dd, 1H), 8.12 (dd, 1H), 7.41 (s, 2H), 7.34 (t, 1H), 6.54 (d, 1H), 4.19 (d, 2H), 4.01 (s, 3H), 2.61 (m, 4H), 2.43 (m, 1H), 2.33 (s, 3H), 2.11 (m, 4H), 1.32 (m, 2H); MS (EI) for C$_{25}$H$_{26}$FN$_3$O$_5$: 468 (M+H$^+$).

Example 9

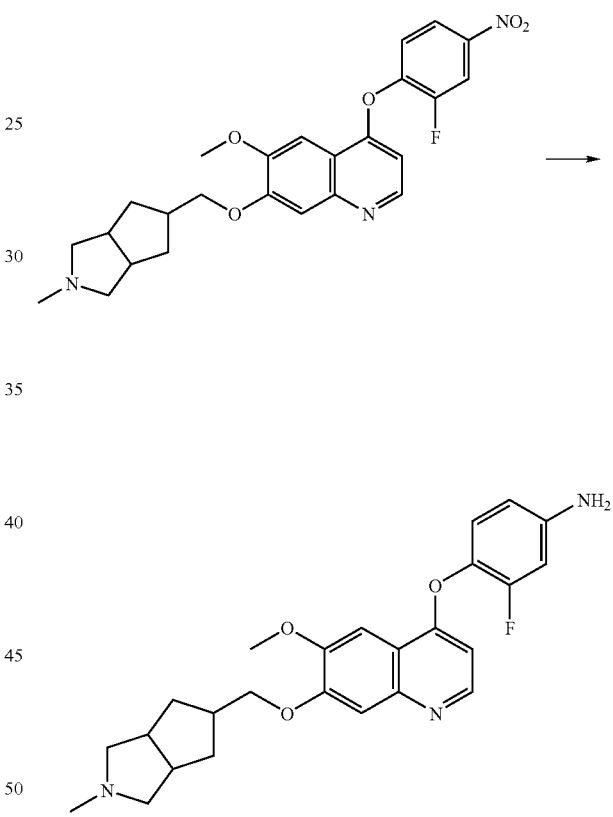

3-Fluoro-4-[6-methoxy-7-(2-methyl-octahydro-cyclopenta[c]pyrrol-5-ylmethoxy-quinolin-4-yloxy]-phenylamine. To a par hydrogenation reaction vessel was added 4-(2-fluoro-4-nitro-phenoxy)-6-methoxy-7-(2-methyl-octahydro-cyclopenta[c]pyrrol-5-ylmethoxy)-quinoline (0.800 g, 1.6 mmol, 1.0 eq.), DMF (50 mil), EtoAc (50 ml), MeOH (50 ml), TEA (5 ml) and 10% Pd/C (200 mg). The vessel was placed on the par hydrogenator at 35 psi overnight. The Pd was filtered and the solvent removed to give 3-fluoro-4-[6-methoxy-7-(2-methyl-octahydro-cyclopenta[c]pyrrol-5-ylmethoxy)-quinolin-4-yloxy]-phenylamine as an off yellow solid (0.78 g, 99% yield). $^1$H NMR (400 MHz, CDCl$_3$): 8.45 (d, 1H), 7.57 (s, 1H), 7.36 (s, 1H), 7.05 (t, 1H), 6.54 (m, 2H), 6.39 (d, 1H), 4.16 (d, 2H), 4.01 (s, 3H), 3.81 (m, 3H), 2.61 (m, 3H), 2.41 (m, 1H), 2.29 (s, 3H), 2.23 (m, 2H); 1.32 (m, 2H); MS (EI) for $C_{25}H_{28}FN_3O_3$: 438 (M+H$^+$).

(m, 1H), 2.27 (m, 2H), 2.01 (s, 3H), 1.36 (m, 2H); MS (EI) for $C_{34}H_{35}FN_4O_4S$: 615 (M+H$^+$).

Example 10

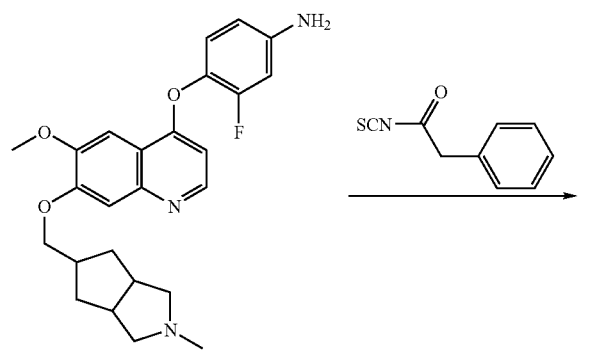

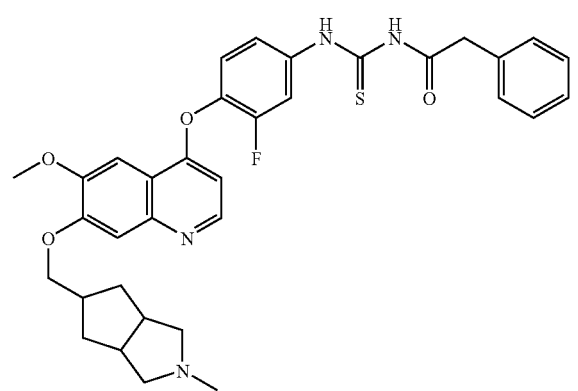

1-{3-Fluoro-4-[6-methoxy-7-(2-methyl-octahydro-cyclopenta[c]pyrrol-5-ylmethoxy)-quinolin-4-yloxy]-phenyl}-3-phenylacetyl-thiourea. To a round bottom flask equipped with a magnetic stir bar was added 3-fluoro-4-[6-methoxy-7-(2-methyl-octahydro-cyclopenta[c]pyrrol-5-ylmethoxy)-quinolin-4-yloxy]-phenylamine (0.78 mg, 1.7 mmol, 1.0 eq.), toluene (10 ml), ethanol (10 ml) and phenyl-acetyl isothiocyanate (1.64 g, 9.2 mmol, 4.5 eq). The reaction mixture was stirred at room temperature overnight. After removal of the solvent the product was purified with a biotage system using an eluent EtOAc and 4% TEA (2 L) then EtOAc, 4% TEA, 1% MeOH (1 L). The solvent was removed to give 1-{3-fluoro-4-[6-methoxy-7-(2-methyl-octahydro-cyclopenta[c]pyrrol-5-ylmethoxy)-quinolin-4-yloxy]-phenyl}-3-phenylacetyl-thiourea (0.5 g, 50% yield). $^1$H NMR (400 MHz, DMSO): 8.48 (d, 1H), 7.92 (dd, 1H), 7.53 (s, 1H), 7.40 (m, 4H), 7.33 (d, 2H), 7.23 (m, 2H), 6.54 (d, 2H), 6.39 (d, 1H), 4.21 (d, 2H), 4.02 (s, 3H), 3.81 (m, 3H), 2.87 (d, 2H), 2.73 (m, 4H), 2.53

Example 11

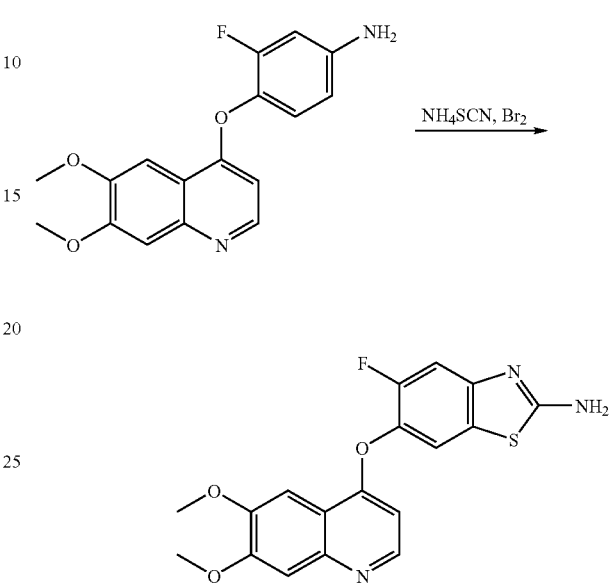

6-(6,7-Dimethoxy-quinolin-4-yloxy)-5-fluoro-benzothiazol-2-ylamine. 4-(6,7-dimethoxy-quinolin-4-yloxy)-3-fluoro-phenylamine (1.00 g, 3.18 mmol) was dissolved in AcOH (8.0 ml), to which was added NH$_4$SCN (486 mg, 6.38 mmol) and the mixture cooled in an ice bath. Br$_2$ (0.33 ml, 6.42 mmol) in AcOH (0.33 µl) was added dropwise with stirring. After addition was complete, the reaction mixture was stirred at room temperature. After one hour, more NH$_4$SCN (1.0 g, 13.11 mmol) was added, followed by more Br$_2$ (0.33 ml, 6.42 mmol) in AcOH (0.33 ml), dropwise with stirring. The reaction mixture was then heated to reflux for several minutes. Upon cooling to room temperature, solids were filtered and washed with AcOH, followed by H$_2$O. The volume of the filtrate was reduced in vacuo and the pH adjusted to pH 9-10 with 1.0N NaOH. The resulting solids were filtered, washed with H$_2$O, and dried under high vacuum to give 6-(6,7-dimethoxy-quinolin-4-yloxy)-5-fluoro-benzothiazol-2-ylamine (568 mg, 48%). $^1$H-NMR (400 MHz, DMSO): 8.45 (d, 1H), 7.82 (d, 1H), 7.73 (br s, 2H), 7.53 (s, 1H), 7.38 (m, 2H), 6.44 (d, 1H), 3.94 (s, 6H). LC/MS Calcd for [M+H]$^+$ 372.1, found 372.2

Example 12

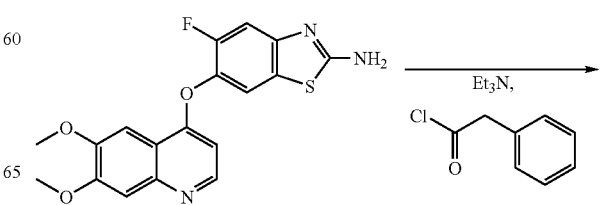

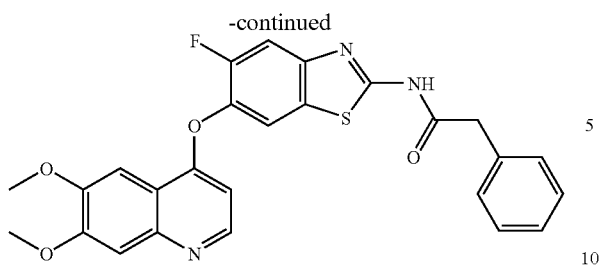

N-[6-(6,7-Dimethoxy-quinolin-4-yloxy)-5-fluoro-benzothiazol-2-yl]-2-phenyl-acetamide. 6-(6,7-dimethoxy-quinolin-4-yloxy)-5-fluoro-benzothiazol-2-ylamine (95 mg, 0.25 mmol), Et₃N (0.10 ml, 0.72 mmol), phenylacetyl chloride (0.044 ml, 0.33 mmol), and THF (1.0 ml) were combined and stirred at room temperature for 1 hr. Additional phenylacetyl chloride (0.044 ml, 0.33 mmol) was added and the mixture heated to reflux for 1-2 hrs. After cooling to room temperature, the reaction mixture was diluted with 1:1 AcCN:H₂O (1.0 ml) and the resulting solids filtered, washed with 1:1 AcCN:H₂O and dried under high vacuum to give N-[6-(6,7-dimethoxy-quinolin-4-yloxy)-5-fluoro-benzothiazol-2-yl]-2-phenyl-acetamide (72 mgs, 59%). ¹H-NMR (400 MHz, DMSO): 12.80 (s, 1H), 8.54 (d, 1H), 8.18 (d, 1H), 7.91 (d, 1H), 7.60 (s, 1H), 7.45 (s, 1H), 7.34 (m, 4H), 7.28 (m, 1H), 6.60 (d, 1H), 3.98 (s, 3H), 3.96 (s, 3H), 3.86 (s, 2H). LC/MS Calcd for [M+H]⁺ 490.1, found 490.0.

Example 13

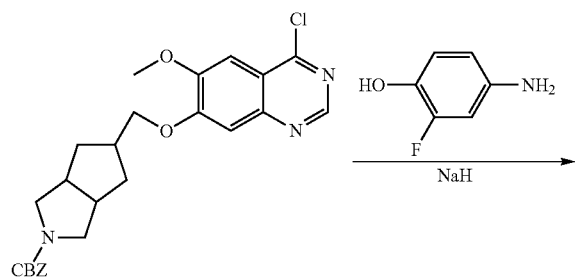

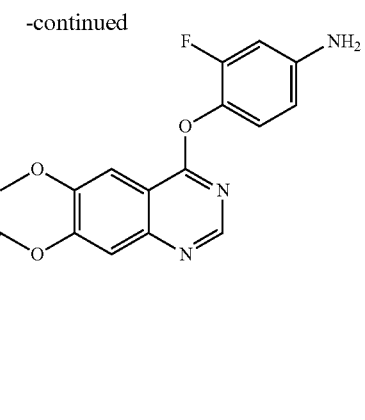

5-[4-(4-Amino-2-fluoro-phenoxy)-6-methoxy-quinazolin-7-yloxymethyl]-hexahydro-cyclopenta[c]pyrrole-2-carboxylic acid benzyl ester. 4-Amino-2-fluoro-phenol (1.53 g, 12.0 mmol) was dissolved in dry DMF (30 ml) to which was added 60% NaH (774 mg, 19.3 mmol). After the mixture was stirred at room temperature for several minutes, a suspension of 5-(4-chloro-6-methoxy-quinazolin-7-yloxymethyl)-hexahydro-cyclopenta[c]pyrrole-2-carboxylic acid benzyl ester (4.70 g, 6.7 mmol) in dry DMF (40 ml) was added. The reaction mixture was stirred at room temperature for 1-2 hrs, then diluted with EtOAc and washed with sat'd NaHCO₃ (3×), H₂O (1×), sat'd NaCl (1×), dried (Na₂SO₄), and concentrated in vacuo to give crude 5-[4-(4-amino-2-fluoro-phenoxy)-6-met oxy-quinazolin-7-yloxymethyl]-hexahydro-cyclopenta[c]pyrrole-2-carboxylic acid benzyl ester (5.6 g, ~100%) which was used in the next reaction without further purification. ¹H-NMR (400 MHz, DMSO): 8.50 (s, 1H), 7.48 (s, 1H), 7.34 (m, 5H), 7.28 (m, 1H), 7.02 (t, 1H), 6.48 (dd, 1H), 6.40 (dd, 1H), 5.40 (br s, 2H), 5.05 (s, 2H), 4.16 (d, 2H), 3.92 (s, 3H), 3.48 (m, 2H), 3.30 (m, 2H), 2.65 (m, 2H), 2.52 (m, 1H), 2.10 (m, 2H), 1.30 (m, 2H). LC/MS Calcd for [M+H]⁺ 559.2, found 559.4.

Example 14

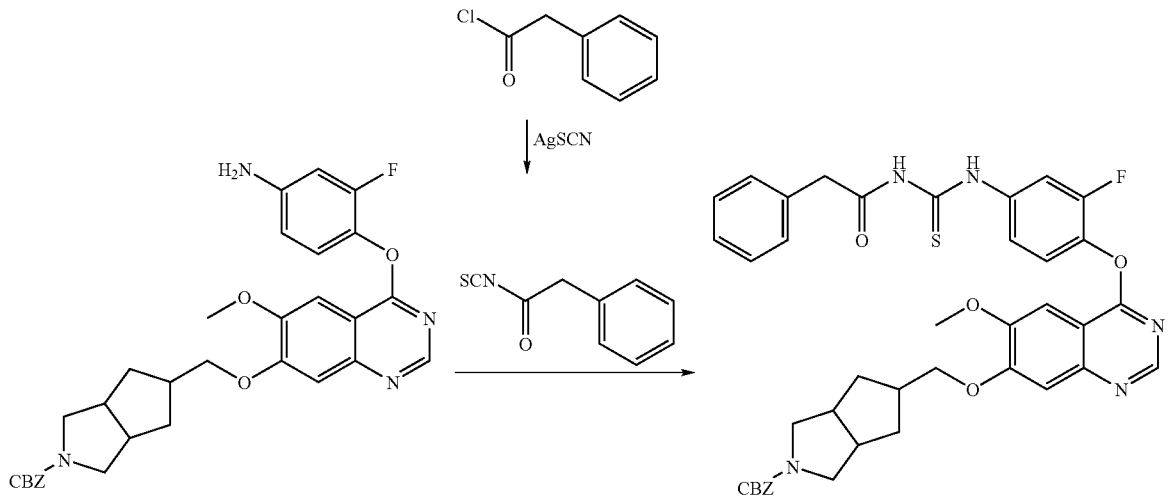

5-{4-[2-Fluoro-4-(3-phenylacetyl-thioureido-phenoxy]-6-methoxy-quinazolin-7-yloxymethyl}-hexahydro-cyclopenta[c]pyrrole-2-carboxylic acid benzyl ester. Phenylacetyl chloride (2.65 ml, 20.00 mmol) and AgSCN (4.92 g, 29.6 mmol) were combined in dry toluene (50 ml) and heated to reflux for 2 hrs. The reaction mixture was allowed to cool to room temperature, the solids were filtered through celite and the filtrate concentrated in vacuo. The resulting oil was combined with 5-[4-(4-amino-2-fluoro-phenoxy)-6-methoxy-quinazolin-7-yloxymethyl]-hexahydro-cyclopenta[c]pyrrole-2-carboxylic acid benzyl ester (5.6 g, 10 mmol) in 1:1 EtOH:toluene (100 ml) and the mixture stirred at room temperature for 1-2 hrs. The reaction mixture was diluted with EtOAc and washed with sat'd $NaHCO_3$ (3×), $H_2O$ (1×), sat'd NaCl (1×), dried ($Na_2SO_4$), and concentrated in vacuo. The resulting oil was purified by flash chromatography (3:1 EtOAc:hexanes) to give 5-{4-[2-fluoro-4-(3-phenylacetyl-thioureido)-phenoxy]-6-methoxy-quinazolin-7-yloxymethyl}-hexahydrocyclopenta[c]pyrrole-2-carboxylic acid benzyl ester (3.61 g, 49%) as a dark brown foam. $^1$H-NMR (400 MHz, DMSO): 12.44 (s, 1H), 11.80 (s, 1H), 8.54 (s, 1H), 7.90 (m, 1H), 7.53 (s, 1H), 7.48 (m, 2H), 7.38 (s, 1H), 7.34 (m, 7H), 7.28 (m, 3H), 5.05 (s, 2H), 4.16 (d, 2H), 3.94 (s, 3H), 3.72 (s, 2H), 3.48 (m, 2H), 3.30 (m, 2H), 2.65 (m, 2H), 2.52 (m, 1H), 2.10 (m, 2H), 1.30 (m, 2H). LC/MS Calcd for [M+H]$^+$ 736.2, found 736.0.

Example 15

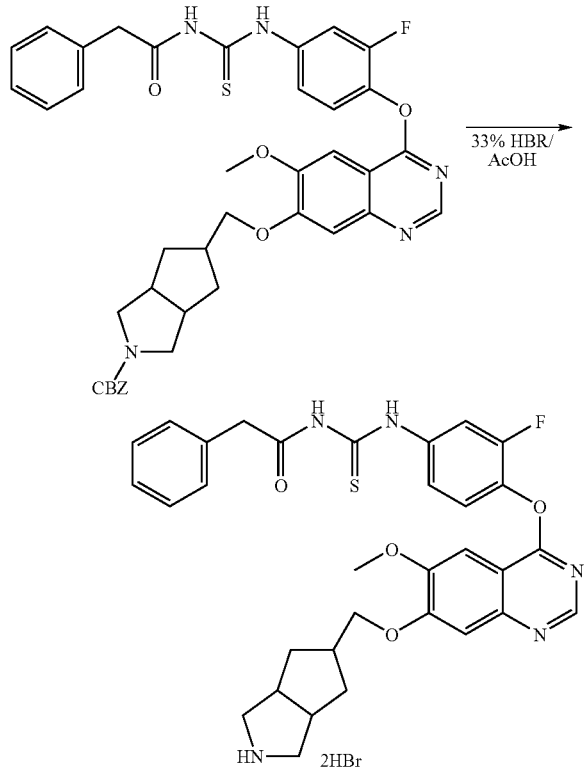

1-{3-Fluoro-4-[6-methoxy-7-(octahydro-cyclopenta[c]pyrrol-5-ylmethoxy)-quinazolin-4-yloxy]-phenyl}-3-phenylacetyl-thiourea, dihydrobromide salt. 5-{4-[2-Fluoro-4-(3-phenylacetyl-thioureido)-phenoxy]-6-methoxy-quinazolin-7-yloxymethyl}-hexahydro-cyclopenta[c]pyrrole-2-carboxylic acid benzyl ester (3.3 g, 4.5 mmol) was dissolved in AcOH (70 ml) to which was added 33% HBr in AcOH (12 ml). The reaction mixture was stirred at room temperature for 1 hr, diluted with $Et_2O$ (1000 ml) and the resulting solids filtered, washed with $Et_2O$, and dried under high vacuum to give the 1-{3-fluoro-4-[6-methoxy-7-(octahydro-cyclopenta[c]pyrrol-5-ylmethoxy)-quinazolin-4-yloxy]-phenyl}-3-phenylacetyl-thiourea, dihydrobromide salt (3.4 g, 100%). $^1$H-NMR (400 MHz, DMSO): 12.42 (s, 1H), 11.80 (s, 1H), 8.84 (br s, 2H), 8.64 (s, 1H), 7.92 (m, 1H), 7.59 (s, 1H), 7.49 (m, 2H), 7.41 (s, 1H), 7.33 (m, 4H), 7.27 (m, 1H), 4.17 (d, 2H), 3.95 (s, 3H), 3.73 (s, 2H), 3.17 (m, 2H), 3.10 (m, 2H), 2.83 (m, 2H), 2.45 (m, 1H), 2.15 (m, 2H), 1.30 (m, 2H). LC/MS Calcd for [M+H]$^+$ 602.2, found 602.1.

Example 16

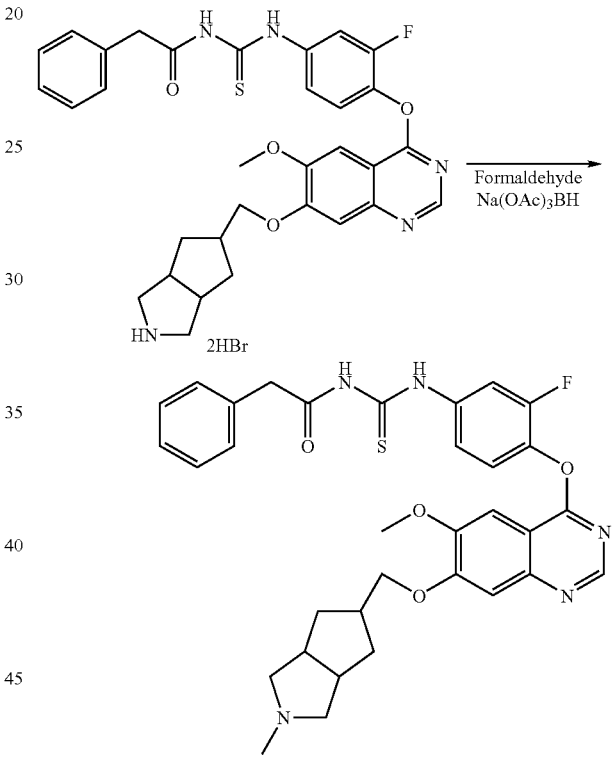

1-{3-Fluoro-4-[6-methoxy-7-(2-methyl-octahydro-cyclopenta[c]pyrrol-5-ylmethoxy)-quinazolin-4-yloxy]-phenyl}-3-phenylacetyl-thiourea. 1-{3-Fluoro-4-[6-methoxy-7-(octahydro-cyclopenta[c]pyrrol-5-ylmethoxy)-quinazolin-4-yloxy]-phenyl}-3-phenylacetyl-thiourea, dihydrobromide salt (3.4 g, 4.5 mmol) was dissolved in a combination of AcCN (100 ml), $H_2O$ (30 ml), and AcOH (2.45 ml). Formaldehyde (37% in $H_2O$, 855 ml, 10.5 mmol) was added and the mixture cooled in an ice bath. Na(OAC)$_3$BH (2.99 g, 14.1 mmol) was added and the reaction mixture was stirred at 0 C for 1 hr, followed by stirring at room temperature for 2 hrs. The reaction mixture was neutralized with the addition of sat'd $NaHCO_3$ and then concentrated in vacuo. The resulting aqueous mixture was extracted with $CH_2Cl_2$ (3×). The combined extractions were washed with sat'd $NaHCO_3$ (1×), sat'd NaCl (1×), dried ($Na_2SO_4$), and concentrated in vacuo. The resulting residue was purified by flash chromatography (100% EtOAc, followed by 4% $Et_3N$ in EtOAc) to give the free base of 1-{3-fluoro-4-[6-methoxy-7-(2-methyl-octahydro-cyclopenta[c]pyrrol-5-ylmethoxy)-quinazolin-4-yloxy]-phenyl}-3-phenylacetyl-thiourea (1.13 g, 40%). The free base was converted to the HCl salt by dissolving the free base in a mixture of 1:1 AcCN:H$_2$O containing 2-3 equivalents of 1 N HCl and lyophilizing to give the HCl salt of 1-{3-fluoro-4-[6-methoxy-7-(2-methyl-octahydro-cyclopenta[c]pyrrol-5-ylmethoxy)-quinazolin-4-yloxy]-phenyl}-3-phenylacetyl-thiourea as a white solid. $^1$H-NMR (400 MHz, DMSO): 12.44 (s, 1H), 11.83 (s, 1H), 10.24 (br s, 1H), 8.59 (s, 1H), 7.93 (m, 1H), 7.59 (s, 1H), 7.50 (m, 2H), 7.42 (s, 1H), 7.36 (m, 4H), 7.30 (m, 1H), 4.20 (m, 2H), 3.95 (s, 3H), 3.73 (s, 2H), 3.39 (m, 2H), 3.06 (m, 2H), 2.95-2.77 (m, 5H), 2.35 (m, 1H), 2.15 (m, 2H), 1.45 (m, 2H). LC/MS Calcd for [M+H]$^+$ 616.2, found 616.2. Alternatively, the free base was converted to the acetate salt by dissolving the free base in a mixture of MeOH and CH$_2$Cl$_2$ to which was added 3 equivalents of acetic acid. The resulting mixture was concentrated in vacuo and the resulting residue lyophilized from 1:1 AcCN:H$_2$O to give the acetate salt of 1-{3-fluoro-4-[6-methoxy-7-(2-methyl-octahydro-cyclopenta[c]pyrrol-5-ylmethoxy)-quinazolin-4-yloxy]-phenyl}-3-phenylacetyl-thiourea as a white solid. $^1$H-NMR (400 MHz, CDCl$_3$): δ 12.45 (s, 1H), 8.65 (s, 1H), 7.98 (dd, 1H), 7.50 (s, 1H), 7.40 (m, 4H), 7.29 (m, 4H), 4.17 (d, 2H), 4.05 (s, 3H), 3.75 (s, 2H), 2.93 (m, 2H), 2.80 (m, 2H), 2.72 (m, 2H), 2.53 (s, 3H), 2.47 (m, 1H), 2.25 (m, 2H), 2.02 (s, 3H), 1.35 (m, 2H). LC/MS Calcd for [M+H]$^+$ 616.2, found 616.2.

Example 17

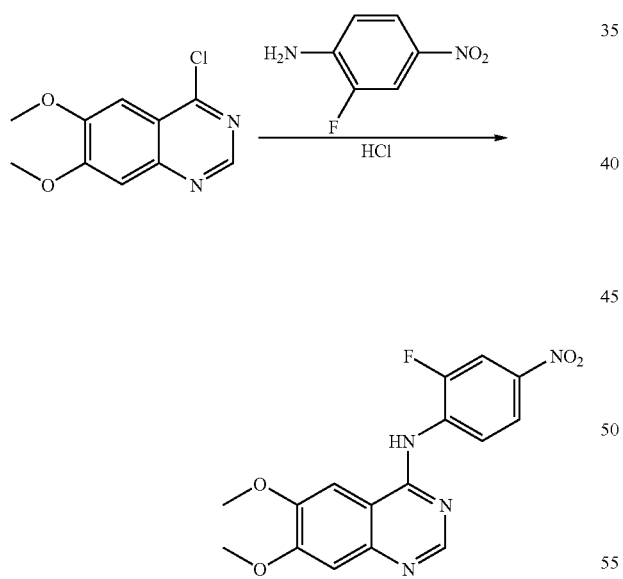

(6,7-Dimethoxy-quinazolin-4-yl)-(2-fluoro-4-nitro-phenyl)-amine. A mixture of 4-chloro-6,7-dimethoxy-quinazoline (548 mg, 2.4 mmol), 2-fluoro-4-nitro-phenylamine (392 mg, 2.5 mmol), AcCN (10 ml), and conc'd HCl (0.050 ml) was heated to reflux for several hrs. After the reaction mixture was allowed to cool to room temperature, the resulting solids were filtered, washed with AcCN and air-dried to give (6,7-dimethoxy-quinazolin-4-yl)-(2-fluoro-4-nitro-phenyl)-amine (673 mgs, 80%). $^1$H-NMR (400 MHz, DMSO): 12.18 (br s, 1H), 8.91 (s, 1H), 8.45 (s, 1H), 8.36 (dd, 1H), 8.24 (dd, 1H), 7.91 (dd, 1H), 7.44 (s, 1H), 4.04 (s, 3H), 4.02 (s, 3H). LC/MS Calcd for [M+H]$^+$ 345.1, found 345.4.

Example 18

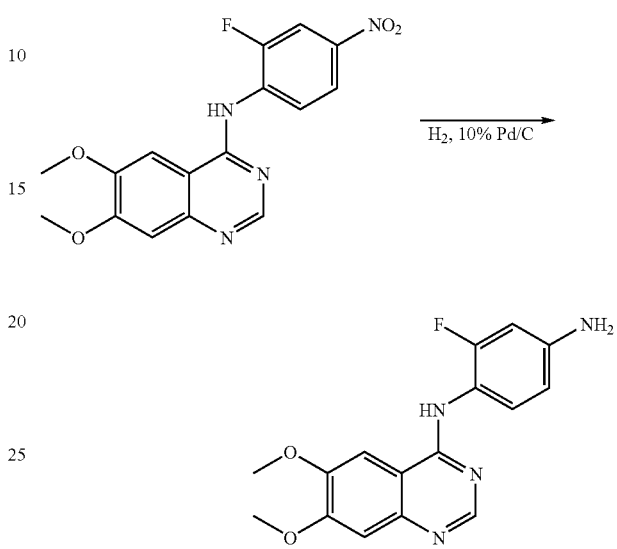

N$^1$-(6,7-Dimethoxy-quinazolin-4-yl)-2-fluoro-benzene-1,4-diamine. (6,7-Dimethoxy-quinazolin-4-yl)-(2-fluoro-4-nitro-phenyl)-amine (673 mg, 1.95 mmol) was dissolved in a combination of DMF (20 ml) and MeOH (20 ml), to which was added 10% Pd/C (227 mg). The mixture was shaken under an atmosphere of H$_2$ on a Parr hydrogenator at 40 psi for 3 hrs. The reaction mixture was filtered through celite and the filtrate concentrated in vacuo. The resulting residue was triturated in EtOAc/Et$_2$O. The resulting solids were filtered, washed with Et$_2$O, and dried under vacuum to give N$^1$-(6,7-dimethoxy-quinazolin-4-yl)-2-fluoro-benzene-1,4-diamine (398 mg, 65%) which was used in the next reaction without further purification. $^1$H-NMR (400 MHz, DMSO): 10.80 (br s, 1H), 10.30 (br s, 1H), 8.63 (s, 1H), 8.15 (s, 1H), 7.33 (s, 1H), 7.15 (m, 1H), 6.45 (m, 1H), 3.96 (s, 6H). LC/MS Calcd for [M+H]$^+$ 315.1, found 315.4.

Example 19

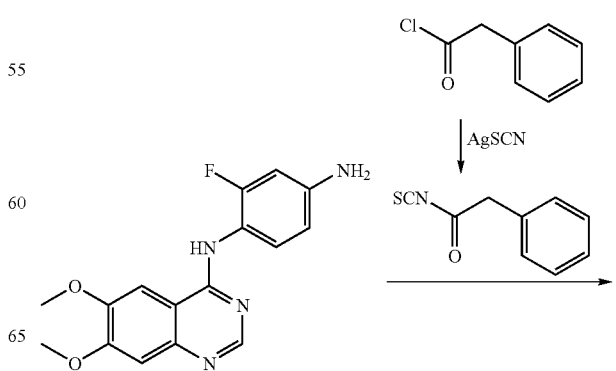

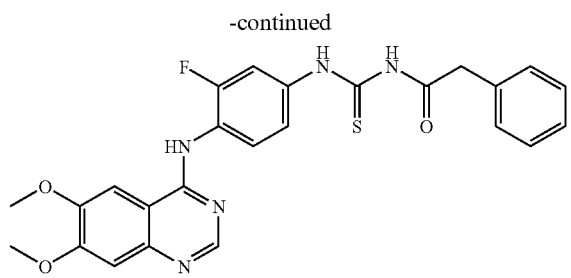

1-[4-(6,7-Dimethoxy-quinazolin-4-ylamino)-3-fluoro-phenyl]-3-phenylacetyl-thiourea. Phenylacetyl chloride (0.18 ml, 1.4 mmol) and AgSCN (338 mg, 2.0 mmol) were combined in dry toluene (5 ml) and heated to reflux for 2 hrs. The reaction mixture was allowed to cool to room temperature, the solids were filtered through celite and the filtrate concentrated in vacuo. The resulting oil was combined with $N^1$-(6,7-Dimethoxy-quinazolin-4-yl)-2-fluoro-benzene-1,4-diamine (398 mg, 1.3 mmol) in 1:1:2 EtOH:toluene:MeOH (30 ml) and the mixture stirred at room temperature overnight. The resulting solids were filtered and washed with toluene, followed by hexanes. The solids were dissolved/suspended in a mixture of EtOAc/MeOH. Insoluble material was filtered and the filtrate concentrated in vacuo. The resulting solids were once again dissolved/suspended in a mixture of EtOAc/MeOH. In soluble material was filtered and the filtrate concentrated in vacuo to give 1-[4-(6,7-dimethoxy-quinazolin-4-ylamino)-3-fluoro-phenyl]-3-phenylacetyl-thiourea (105 mg, 17%). $^1$H-NMR (400 MHz, DMSO): 12.53 (s, 1H), 11.86 (s, 1H), 11.44 (br s, 1H), 8.81 (s, 1H), 8.25 (s, 1H), 7.94 (dd, 1H), 7.54 (m, 2H), 7.16 (m, 5H), 7.10 (m, 1H), 4.02 (s, 6H), 3.84 (s, 2H). LC/MS Calcd for [M+H]$^+$ 492.1, found 492.4.

Example 20

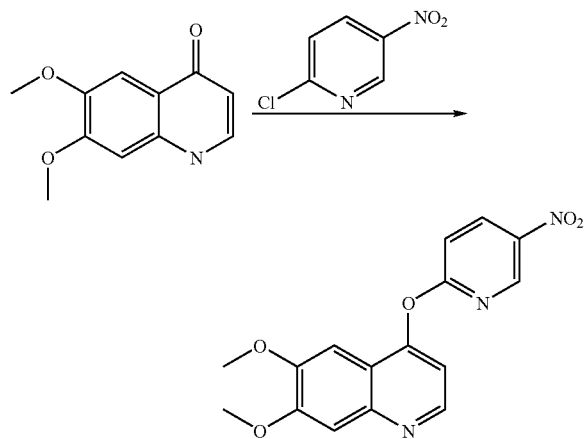

6,7-Dimethoxy-4-(5-nitro-pyridin-2-yloxy)-quinoline. To a round bottom flask equipped with a magnetic stir bar was added 6,7-dimethoxy-1H-quinolin-4-one (1.8 g, 8.77 mmol, 1.0 eq.), anhydrous acetonitrile (90 mL) and $Cs_2CO_3$ (3.13 g, 9.65 mmole, 1.1 eq.). The reaction mixture was stirred at room temperature for 5 minutes. Then, 2-Cl-5-nitropyridine (1.53 g, 9.65 mmol, 1.1 eq.) was added. The reaction mixture was stirred at room temperature for 16 hours. The solids were then filtered off and the filtrate was concentrated via rotary evaporation. The resulting material was taken up in EtOAc, and again the solids were filtered off. The EtOAc filtrate was concentrated. Purification was done on Biotage with solvent system EtOAc 100%. The collected pure fractions were concentrated and dried on high vacuum overnight to give 6,7-dimethoxy-4-(5-nitro-pyridin-2-yloxy)-quinoline as a yellow foam solid (0.902 g, 31.4% yield). $^1$H NMR (400 MHz, CDCl3): 9.08 (d, 1H), 8.74 (d, 1H), 8.60 (dd, 1H), 7.49 (s, 1H), 7.26 (d, 1H), 7.16 (s, 1H), 7.07 (d, 1H), 4.06 (s, 3H), 3.95 (s, 3H); MS (EI) for $C_{16}H_{13}N_3O_5$: 328 (M+H$^+$).

Example 21

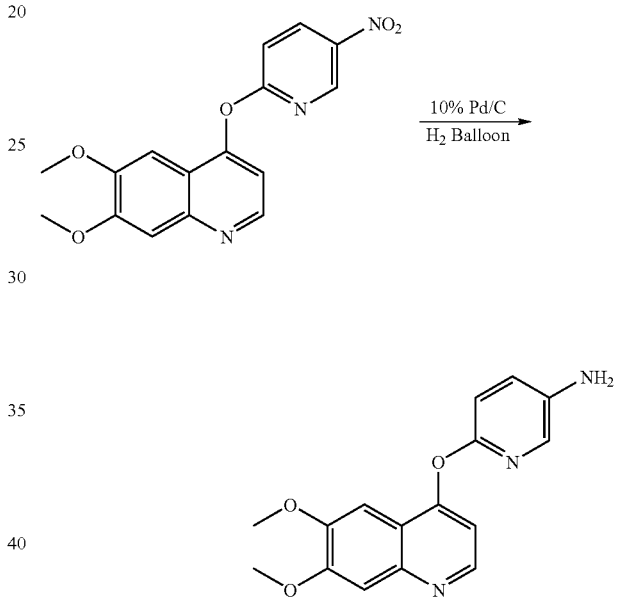

6-(6,7-Dimethoxy-quinolin-4-yloxy)-pyridin-3-ylamine. To a round bottom flask equipped with a magnetic stir bar was added 6,7-dimethoxy-4-(5-nitro-pyridin-2-yloxy)-quinoline (0.46 g, 1.41 mmol, 1.0 eq.), and THF (10 mL), MeOH (4 mL), DMF (2 mL), and TEA (2 mL). The 6,7-Dimethoxy-4-(5-nitro-pyridin-2-yloxy)-quinoline was dissolved completely in the above solution mixture, and was flushed with nitrogen for at least 5 minutes. The Pd/C (10% by weight) (0.090 g, 20% by weight) was then added. A balloon filled with $H_2$ was connected to the flask after the nitrogen was vacuumed out. The reaction mixture was stirred at room temperature for 4 hours. The palladium was filtered out through Celite, and the filtrated was collected and concentrated via rotary evaporation. The resulting oil-like product was taken up into 5 mL of water and 1 mL of acetonitrile and lyophilized to yield 6-(6,7-dimethoxy-quinolin-4-yloxy)-pyridin-3-ylamine as a light brown solid (0.411 g, 98.1%). $^1$H NMR (400 MHz, CDCl3): 8.54 (d, 1H), 7.85 (d, 1H), 7.53 (s, 1H), 7.41 (s, 1H), 7.18 (dd, 1H), 6.96 (d, 1H), 6.61 (d, 1H), 4.05 (s, 3H), 4.03 (s, 3H), 3.73 (s, 2H); MS (EI) for $C_{16}H_{15}N_3O_3$: 298 (M+H$^+$).

Example 22

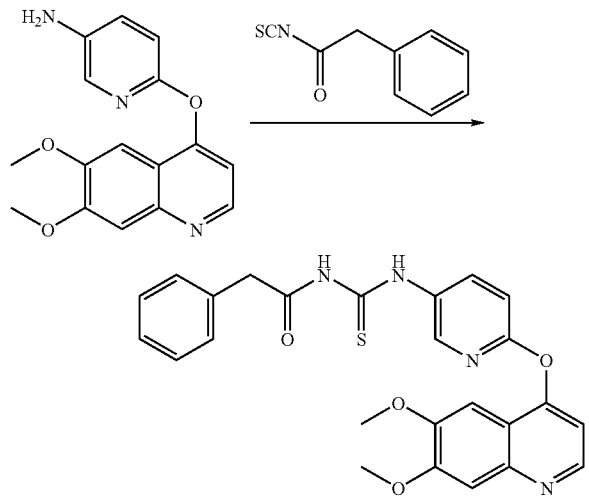

1-[6-(6,7-Dimethoxy-quinolin-4-yloxy)-pyridin-3-yl]-3-phenylacetyl-thiourea. To a round bottom flask equipped with a magnetic stir bar was added 6-(6,7-dimethoxy-quinolin-4-yloxy)-pyridin-3-ylamine (85 mg, 0.0285 mmol, 1.0 eq.), and Phenyl-acetyl isothiocyanate (256 mg, 1.44 mmol, 5.0 eq.) dissolved in EtOAc/MeOH 50:50 (2 mL). The reaction mixture was stirred at room temperature for 12 hours, and the solvent was evaporated via rotary evaporation. Purification was done on Biotage with solvent system 95% EtOAc, 4% TEA and 1% MeOH. The combined pure fractions were concentrated and dried under vacuum overnight to yield 1-[6-(6,7-dimethoxy-quinolin-4-yloxy)-pyridin-3-yl]-3-phenylacetyl-thiourea as a light yellow solid (40.4 mg, 29.7%). $^1$H NMR (400 MHz, CDCl$_3$): 8.65 (d, 1H), 8.33 (d, 1H), 8.27 (dd, 1H), 7.35 (m, 7H), 7.15 (d, 1H), 6.92 (d, 1H), 4.05 (s, 3H), 3.99 (s, 3H), 3.76 (s, 2H); MS (EI) for $C_{25}H_{22}N_4O_4S$: 475 (M+H$^+$).

Example 23

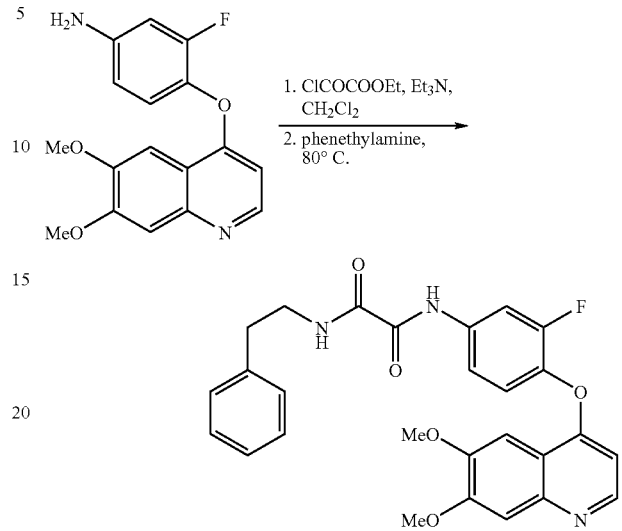

N-[4-(6,7-Dimethoxy-quinolin-4-yloxy)-3-fluoro-phenyl]-N'-phenethyl-oxalamide. To a solution of 4-(6,7-dimethoxy-quinolin-4-yloxy)-3-fluoro-phenylamine (263 mg, 0.83 mmol) and Et$_3$N (0.223 ml, 1.67 mmol) in CH$_2$Cl$_2$ (10 mL) was added dropwise a solution of ethyl oxalyl chloride in CH$_2$Cl$_2$ (1 mL). The stirring was continued for 0.5 h at rt. The reaction mixture was then washed with aqueous saturated NaHCO$_3$ and dried over NaSO$_4$. Removal of the solvent gave the crude oxamate, which was treated with neat phenethylamine (1.0 g, 8.3 mmol) at 80° C. for 3 h. Purification by flash column chromatography (hexanes:EtOAc=1:3) gave N-[4-(6,7-dimethoxy-quinolin-4-yloxy)-3-fluoro-phenyl]-N'-phenethyl-oxalamide (310 mg, 76%). $^1$H NMR (400 MHz, CDCl$_3$) δ 9.35 (br s, 1H), 8.70 (d, J=6.3 Hz, 1H), 7.83 (dd, J=11.9, 2.5 Hz, 1H), 7.60-7.54 (m, 2H), 7.43 (s, 1H), 7.38-7.32 (m, 3H), 7.30-7.20 (m, 4H), 6.41 (d, J=5.3 Hz, 1H), 4.07 (s, 3H), 4.05 (s, 3H), 3.67 (dt, J=7.0, 7.0 Hz, 2H), 2.92 (t, J=7.2 Hz, 2H). LC-MS: 490 [M+H]$^+$

Example 24

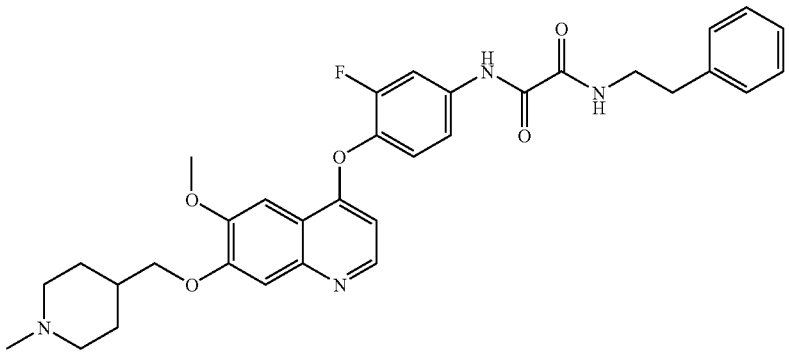

N-{3-Fluoro-4-[6-methoxy-7-(1-methyl-piperidin-4-yl-methoxy)-quinolin-4-yloxy]-phenyl}-N'-phenethyl-oxalamide. To a flask containing 7-benzyloxy-4-(2-fluoro-4-nitrophenoxy)-6-methoxy-quinoline (850 mg, 2.0 mmol) was added 20 mL of 30% HBr in AcOH. The resulted solution was stirred for 4 h at rt; at this time, a large amount of precipitate formed. The crude product was filtered, washed with Et$_2$O and dried in air, giving 4-(2-fluoro-4-nitro-phenoxy)-6-methoxy-7-hydroxyquinoline (609 mg, 92% yield).

To a solution of the 4-(2-fluoro-4-nitro-phenoxy)-6-methoxy-7-hydroxyquinoline (609 mg, 1.8 mmol) in DMF (9 mL) was added K$_2$CO$_3$ (1.24 g, 9.0 mmol) and N-Boc-4-piperidinemethanol mesylate (732 mg, 2.5 mmol). The mixture was then stirred at 80° C. for 2.5 h. After it was cooled to rt, the mixture was loaded directly to a Biotage column, and eluted with solvents (hexanes:EtOAc=1:3). The resulting product, 4-[4-(2-fluoro-4-nitro-phenoxy)-6-methoxy-quinolin-7-yloxymethyl]-piperidine-1-carboxylic acid tert-butyl ester, was obtained as a solid (556 mg, 56%).

To a solution of 4-[4-(2-fluoro-4-nitro-phenoxy)-6-methoxy-quinolin-7-yloxymethyl]-piperidine-1-carboxylic acid tert-butyl ester (305 mg, 0.58 mmol) in CH$_2$Cl$_2$ (1 mL) was added 0.4 mL of TFA. The reaction mixture was stirred for 1.5 h and the solvents were removed under reduced pressure. The crude product was treated with NaBH(OAc)$_3$ (381 mg, 1.80 μmmol) and formaldehyde (0.5 mL, 37% in H$_2$O). The stirring was continued for 12 h. The reaction was quenched with sat. aqueous NaHCO$_3$. 15% NaOH was added until PH=14. The product was extracted with EtOAc. Removal of the solvent in vacuo gave the crude product, 4-(2-fluoro-4-nitro-phenoxy)-6-methoxy-7-(1-methyl-piperidin-4-ylmethoxy)-quinoline, (240 mg, 93%), which was used directly in the next reaction.

To a solution of 4-(2-Fluoro-4-nitro-phenoxy)-6-methoxy-7-(1-methyl-piperidin-4-ylmethoxy)-quinoline (240 mg, 0.54 mmol) in EtOH (20 mL) was added 10% Pd/C (50 mg). The mixture was then hydrogenated on a Parr hydrogenator (40 psi) for 10 h. AcOH was added to dissolve the intermediate (mostly the hydroxylamine) and the hydrogenation was continued for additional 12 h. LC-MS was used to monitor the reaction progress. The solvents were removed under reduced pressure and the resulting crude product of 3-fluoro-4-[6-methoxy-7-(1-methyl-piperidin-4-ylmethoxy)-quinolin-4-yloxy]-phenylamine (about 220 mg) was used directly in the next reaction.

To a 0° C. solution of 3-fluoro-4-[6-methoxy-7-(1-methyl-piperidin-4-ylmethoxy)-quinolin-4-yloxy]-phenylamine (66 mg, 0.13 mmol) and Et$_3$N (0.34 mL) in CH$_2$Cl$_2$ (6 mL) was added slowly ethyl oxalyl chloride (98 mg). The reaction mixture was stirred at rt for 30 min, then diluted with CH$_2$Cl$_2$ and washed with sat. aqueous NaHCO$_3$. After dried over MgSO$_4$ and concentrated, the crude ethyl oxamate was reacted with phenethylamine (80 mg, 0.64 mmol) at 80° C. for 2 h. Purification by HPLC gave product, N-{3-fluoro-4-[6-methoxy-7-(1-methyl-piperidin-4-ylmethoxy)-quinolin-4-yloxy]-phenyl}-N'-phenethyl-oxalamide (52 mg, 68% yield). $^1$H NMR (400 MHz) δ 9.38 (br s, 1H), 8.48 (d, J=5.2 Hz, 1H), 7.83 (dd, J=11.7, 2.6 Hz, 1H), 7.59 (t, J=6.2 Hz, 1H), 7.55 (s, 1H), 7.40-7.20 (8H), 6.39 (d, J=5.3 Hz, 1H), 4.06 (d, J=6.6 Hz, 2H), 4.04 (s, 3H), 3.67 (q, J=6.8 Hz, 2H), 2.98 (br d, J=11.5 Hz, 2H), 2.92 (t, J=7.0 Hz, 2H), 2.34 (s, 3H), 2.10-1.80 (m, 5H), 1.60-1.54 (m, 2H).

Example 25

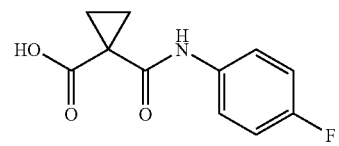

1-(4-Fluoro-phenylcarbamoyl)-cyclopropanecarboxylic acid. The title compound was prepared based on a modified procedure of Shih and Rankin [*Synthetic Communications*, 1996, 26(4), 833-836]: To a mixture of cyclopropane-1,1-dicarboxylic acid (21.2 g, 0.163 mol, 1.0 eq.) in anhydrous THF (200 mL) under nitrogen was added dropwise triethylamine (16.49 g, 0.163 mol, 1.0 eq.) with stirring for 30 minutes at 0° C., followed by the addition of thionyl chloride (19.39 g, 0.163 mol, 1.0 eq.) with stirring for another 30 minutes at 0° C. To the resulting mixture under nitrogen was added dropwise a solution of 4-fluoroaniline (19.92 g, 0.179 mol, 1.1 eq.) in anhydrous THF (100 mL) with stirring for 1.5 hours at 0° C. The reaction mixture was diluted with ethyl acetate and washed with 1N NaOH. The layers were separated, and the ethyl acetate layer was concentrated in vacuo to give a brownish solid. The brownish solid was washed with small amount of cold ethyl acetate, filtered and dried under vacuum to yield 1-(4-fluoro-phenylcarbamoyl)-cyclopropanecarboxylic acid as a white solid (23.71 g, 65.18%). $^1$H NMR (400 MHz, CD$_3$OD): 7.57-7.53 (m, 2H), 7.05-7.00 (m, 2H) 1.46-1.43 (m, 2H), 1.40-1.37 (m, 2H).

Example 26

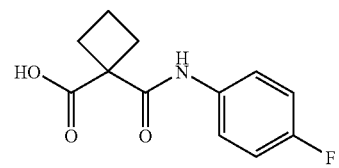

1-(4-Fluoro-phenylcarbamoyl)-cyclobutanecarboxylic acid. To a mixture of cyclobutane-1,1-dicarboxylic acid (10.0 g, 69.4 mmol, 1.0 eq.) in anhydrous THF (100 mL) under nitrogen was added dropwise triethylamine (7.02 g, 69.4 mmol, 1.0 eq.) with stirring for 30 minutes at 0° C., followed by the addition of thionyl chloride (8.25 g, 69.4 mmol, 1.0 eq.) with stirring for another 30 minutes at 0° C. To the resulting mixture under nitrogen was added dropwise a solution of 4-fluoroaniline (8.48 g, 76.3 mmol, 1.1 eq.) in anhydrous THF (50 mL) with stirring for 1.5 hours at 0° C. The reaction mixture was diluted with ethyl acetate and extracted with 2N NaOH. The aqueous phase was titrated with 2N HCl to pH 1-2 and then extracted with ethyl acetate. The organic phase was dried with sodium sulfate and concentrated in vacuo to give 1-(4-fluoro-phenylcarbamoyl)-cyclobutanecarboxylic acid as a light pink solid (5.75 g, 34.9%). $^1$H NMR (400 MHz, CDCl₃ w/5 drop CD₃OD): 7.53-7.48 (m, 2H), 7.06-7.00 (m, 2H), 2.81-2.63 (m, 4H), 2.14-2.02 (m, 2H).

Example 27

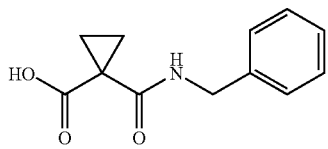

1-Benzylcarbamoyl-cyclopropanecarboxylic acid. The title compound was prepared based on a modified procedure of Shih and Rankin [*Synthetic Communications*, 1996, 26(4), 833-836]: To a mixture of cyclopropane-1,1-dicarboxylic acid (5.0 g, 38.4 mmol, 1.0 eq.) in anhydrous THF (50 mL) under nitrogen was added dropwise triethylamine (3.89 g, 38.4 mmol, 1.0 eq.) with stirring for 30 minutes at 0° C., followed by the addition of thionyl chloride (4.57 g, 38.4 mmol, 1.0 eq.) with stirring for another 30 minutes at 0° C. To the resulting mixture under nitrogen was added dropwise a solution of benzylamine 5 (4.53 g, 42.3 mmol, 1.1 eq.) in anhydrous THF (25 mL) with stirring for 1.5 hours at 0° C. The reaction mixture was diluted with ethyl acetate and extracted with 2N NaOH (to pH 10). The aqueous phase was titrated with 2N HCl to pH 1-2 and then extracted with ethyl acetate. The organic phase was dried with sodium sulfate and concentrated in vacuo to give 1-Benzylcarbamoyl-cyclopropanecarboxylic acid as a white solid (4.39 g, 52.15%). ¹H NMR (400 MHz, CDCl₃): 8.44 (br s, 1H), 7.37-7.33 (m, 2H), 7.32-7.26 (m, 3H), 1.82-1.70 (m, 4H).

Example 28

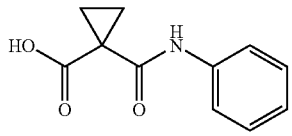

1-Phenylcarbamoyl-cyclopropanecarboxylic acid. To a mixture of cyclopropane-1,1-dicarboxylic acid (5.29 g, 40.7 mmol, 1.0 eq.) in anhydrous THF (50 mL) under nitrogen was added dropwise triethylamine (4.12 g, 40.7 mmol, 1.0 eq.) with stirring for 30 minutes at 0° C., followed by the addition of thionyl chloride (4.84 g, 40.7 mmol, 1.0 eq.) with stirring for another 30 minutes at 0° C. To the resulting mixture under nitrogen was added dropwise a solution of phenylamine 9 (4.17 g, 44.8 mmol, 1.1 eq.) in anhydrous THF (25 mL) with stirring for 1.5 hours at 0° C. The reaction mixture was diluted with ethyl acetate and extracted with 2N NaOH (to pH>10). The aqueous phase was titrated with 2N HCl to pH 1-2 and then extracted with ethyl acetate. The organic phase was dried with sodium sulfate and concentrated in vacuo to give 1-phenylcarbamoyl-cyclopropanecarboxylic acid as a white solid (5.08 g, 60.8%). ¹H NMR (400 MHz, CDCl₃): 10.50 (br s, 1H), 7.56-7.54 (m, 2H), 7.35-7.31 (m, 2H), 7.15-7.10 (m, 1H), 1.94-1.91 (m, 2H), 1.82-1.79 (m, 2H).

Example 29

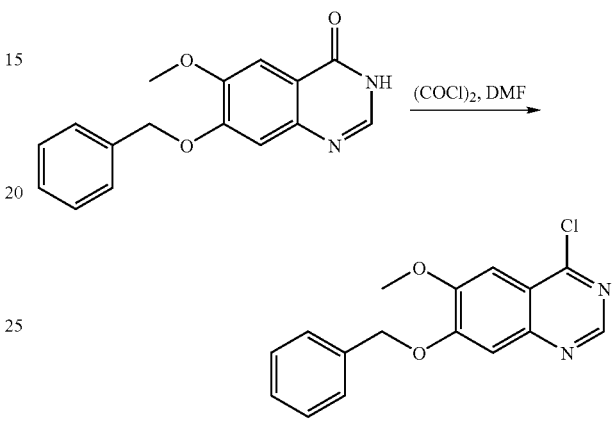

7-Benzyloxy-4-chloro-6-methoxy-quinoline. Dry DMF (8.0 ml, 103 mmol) was dissolved in dry CHCl₃ (40 ml) and cooled in an ice bath. Oxalyl chloride (9.0 ml, 105 mmol) in CH₂Cl₂ (10 ml) was added dropwise with stirring at 0° C. When the bubbling had ceased, this solution was added slowly to an ice-cold solution of 7-benzyloxy-6-methoxy-3H-quinazolin-4-one (10.0 g, 35.4 mmol) in dry CHCl₃ (60 ml) and the mixture was then heated to reflux for 2-3 hrs. After cooling to room temperature, H₂O (100 ml) was added and the phases were separated. The aqueous phase was further extracted with CHCl₃ (2×). The combined CHCl₃ extractions were washed with sat'd NaCl (1×), dried (Na₂SO₄) and concentrated in vacuo. The resulting residue was purified by flash chromatography (1:1 hexanes:EtOAc, followed by 100% EtOAc) to give 7-benzyloxy-4-chloro-6-methoxy-quinoline (5.11 g, 48%). LC/MS Calcd for [M+H]⁺ 301.1, found 301.1.

Example 30

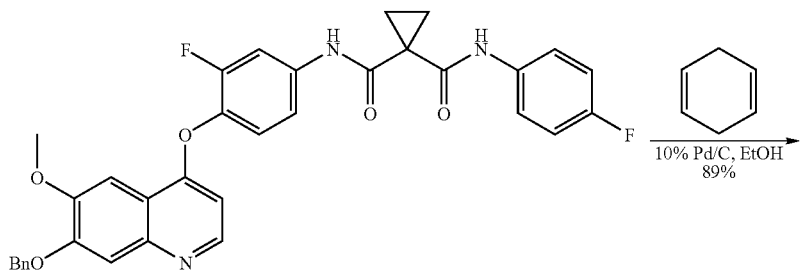

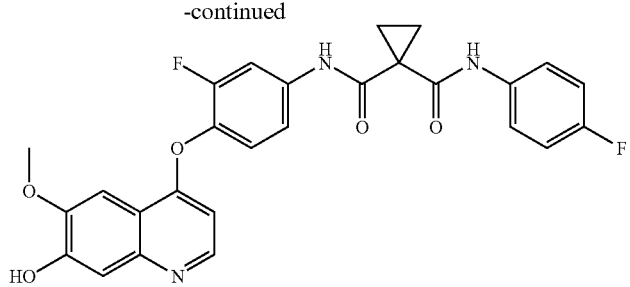

Cyclopropane-1,1-dicarboxylic acid [3-fluoro-4-(7-hydroxy-6-methoxy-quinolin-4-yloxy)-phenyl]-amide(4-fluoro-phenyl)-amide. To a solution of cyclopropane-1,1-dicarboxylic acid [4-(7-benzyloxy-6-methoxy-quinolin-4-yloxy)-3-fluoro-phenyl]-amide (4-fluoro-phenyl)-amide (1.18 g, 2.0 mmol) in EtOH (20 mL) was added 1,4-cyclohexadiene (2.0 mL, 20 mmol) and 10% Pd/C (300 mg). The reaction mixture was then heated to reflux and the stirring was continued for 2 h. It was cooled to room temperature, filtered through celite and washed with MeOH. The MeOH solution was then concentrated under reduced pressure. The residue was taken into EtOAc (200 mL). The EtOAc solution was washed with water, and dried over $Na_2SO_4$. Removal of the solvent under reduced pressure gave 900 mg (89%) of the crude product (90% purity by analytical HPLC), which was used in the next reaction without further purification.

Example 31

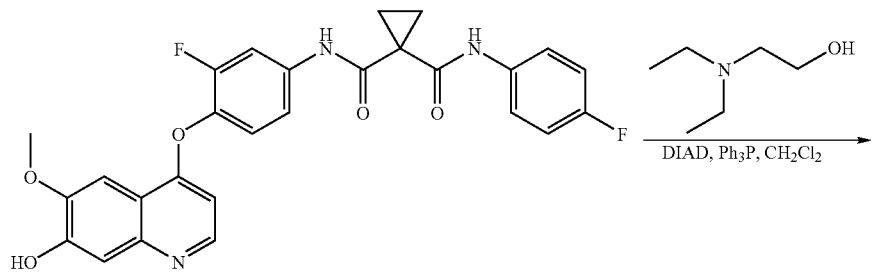

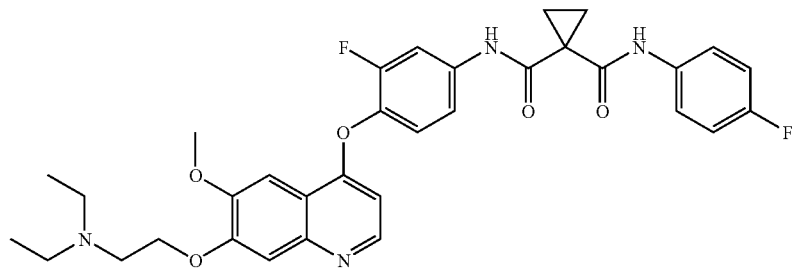

N-(4-{[7-{[2-(Diethylamino)ethyl]oxy}-6-(methyloxy)quinolin-4-yl]oxy}-3-fluorophenyl)-N'-(4-fluorophenyl)cyclopropane-1,1-dicarboxamide. To a mixture of cyclopropane-1,1-dicarboxylic acid [3-fluoro-4-(7-hydroxy-6-methoxy-quinolin-4-yloxy)-phenyl]-amide(4-fluorophenyl)-amide (186 mg, 0.36 mmol) in $CH_2Cl_2$ (10 mL) was added 2-(diethylamino)ethanol (63 mg, 0.54 mmol), and $PPh_3$ (141 mg, 0.54 mmol). DIAD (109 mg, 0.54 mmol) was then added as a $CH_2Cl_2$ (1 mL) solution. The resulted solution was stirred at room temperature for 2 h and the solvent was removed under reduced pressure. To the residue was added 1 N HCl (50 mL), and it was washed with EtOAc (50 mL×2). The aqueous phase was basified by adding 15% NaOH aqueous solution until pH=11-13, and then extracted with ether (50 mL×2). The combined organic layer was dried ($MgSO_4$), and concentrated in vacuo. The residue was purified on preparative HPLC to give N-(4-{[7-{[2-(diethylamino)ethyl]oxy}-6-(methyloxy)quinolin-4-yl]oxy}-3-fluorophenyl)-N'-(4-fluoro-phenyl)cyclopropane-1,1-dicarboxamide (74 mg, 34%) as a pale yellow solid. $^1$H NMR (400 MHz, DMSO-$d_6$) δ 10.40 (br s, 1 H), 10.02 (br s, 1 H), 8.47 (d, J=5.2 Hz, 1 H), 7.91 (br d, J=13.9 Hz, 1 H), 7.54-7.52 (m, 2 H), 7.55-7.50 (m, 1 H), 7.52 (s, 1 H), 7.50-7.40 (m, 1 H), 7.41 (s, 1 H), 7.16 (br t, J=8.7 Hz, 2 H), 6.41 (br d, J=4.7 Hz, 1 H), 4.18 (t, J=6.0 Hz, 2 H), 3.94 (s, 3 H), 2.87 (br t, J=6.3 Hz, 2 H), 2.59 (q, J=7.1 Hz, 4 H), 1.47 (br s, 4 H), 1.00 (t, J=7.0 Hz, 6 H).

Example 32 ture was washed with water (3×200 mL), and saturated sodium bicarbonate (4×200 mL, or until neutral). The organic layer was dried over $Na_2SO_4$ and concentrated. The crude mixture was recrystallized from DMF to give 1-(4-benzyloxy-5-methoxy-2-nitrophenyl)ethanone (36 g, 60%). $^1$H NMR (400 MHz, CDCl$_3$): δ 7.65 (s, 1H), 7.45-7.33 (m, 5H), 6.74 (s, 1H), 5.21 (s, 2H), 3.97 (s, 3H), 2.49 (s, 3H).

1-(2-Amino-4-benzyloxy-5-methoxyphenyl)ethanone. A mixture of iron powder (27 g, 0.48 g atoms), ammonium formate (31 g, 500 mmol), 1-(4-benzyloxy-5-methoxy-2-nitrophenyl)ethanone (36 g, 120 mmol), toluene (500 mL) and water (500 mL) was heated to reflux overnight. The mixture was filtered through celite and washed with ethyl acetate. The combined organic layers were washed with water and brine. The organic layer was dried over $Na_2SO_4$ and concentrated to afford 1-(2-amino-4-benzyloxy-5-methoxyphenyl)ethanone (29.3 g, 90%). $^1$H NMR (CDCl$_3$): δ 7.41-7.30 (m, 5H), 7.13 (s, 1H), 6.16 (br s, 2H), 6.10 (s, 1H), 5.13 (s, 2H), 3.83 (s, 3H), 2.51 (s, 3H). LC/MS (M+H=272).

7-Benzyloxy-6-methoxyquinolin-4-ol. Sodium ethoxide (74.8 g, 1.1 mol) was added to a solution of 1-(2-amino-4-benzyloxy-5-methoxyphenyl)ethanone (29.3 g, 108 mmol) in DME (700 mL) and stirred for 30 min. Ethyl formate (44 mL, 540 mmol) was added and the mixture was stirred overnight (in case of incomplete reaction, additional sodium ethoxide can be added and the reaction monitored by LC/MS). After the reaction was complete, the mixture was diluted with water (40 mL) and acidified to neutral pH with

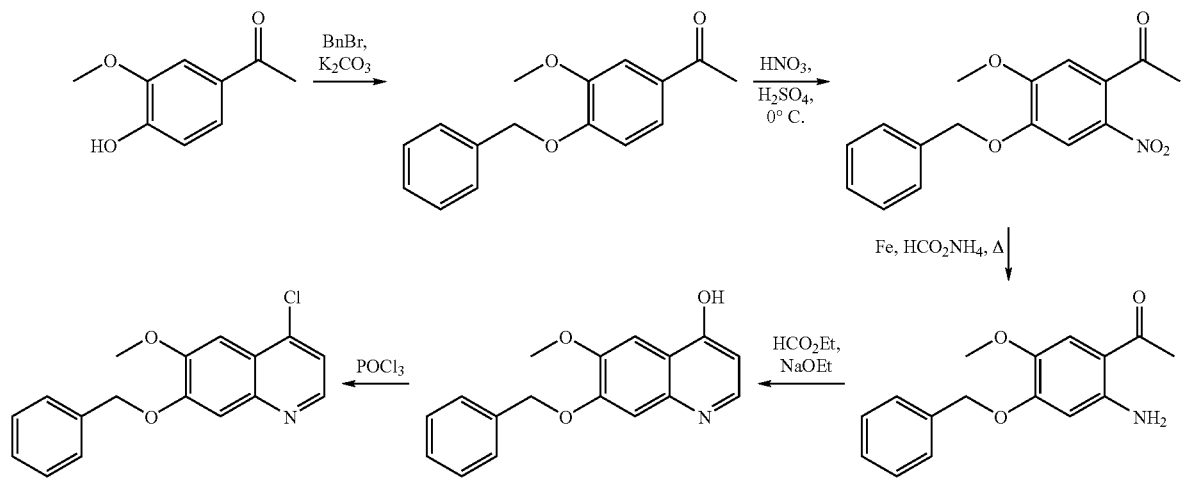

1-(4-Benzyloxy-3-methoxyphenyl)ethanone. A solution of 4-hydroxy-3-methoxyacetophenone (40 g, 240 mmol), benzyl bromide (31.4 mL, 260 mmol) and potassium carbonate (99.6 g, 360 mmol) in DMF (800 mL) was heated to 40° C. overnight. The solution was cooled to room temperature, poured over ice and the resultant solid was filtered. This material was washed with water and dried to give 1-(4-benzyloxy-3-methoxyphenyl)ethanone (61 g, 99%).

1-(4-Benzyloxy-5-methoxy-2-nitrophenyl)ethanone. A stirred solution of 1-(4-benzyloxy-3-methoxyphenyl)ethanone (51.3 g, 200 mmol) in dichloromethane (750 mL) was cooled to 0° C. Nitric acid (90%, 14 mL, 300 mmol) was added dropwise to the cooled solution over 20 min. Sulfuric acid (96.2%, 16.3 mL, 300 mmol) was then added dropwise over 40 min at 0° C. Additional nitric acid (9.4 mL, 200 mmol) was added dropwise over 20 min. The reaction mix- 1M HCl. The solid was filtered, washed with water and dried to afford 7-benzyloxy-6-methoxyquinolin-4-ol (22 g, 72%). $^1$H NMR (400 MHz, CDCl$_3$): δ 10.7 (br s, 1H), 7.70 (s, 1H), 7.49-7.46 (t, 1H), 7.43-7.41 (br d, 2H), 7.37-7.33 (t, 2H), 7.30-7.28 (d, 1H), 6.84 (s, 1H), 6.21-6.19 (d, 1H), 5.21 (s, 2H), 3.96 (s, 3H). LC/MS (M+H=282).

7-Benzyloxy-4-chloro-6-methoxyquinoline. Phosphorus oxychloride (300 mL) was added to 7-benzyloxy-6-methoxyquinolin-4-ol (40 g, 140 mmol) and the mixture heated to reflux for 2 h. The mixture was carefully poured into a mixture of ice and sodium carbonate. The solution was adjusted to pH 8 with the addition of solid sodium bicarbonate and stirred at room temperature overnight. The solid was filtered and washed with water and dried to give 7-benzyloxy-4-chloro-6-methoxyquinoline as a pale brown solid (40.2 g, 95%). $^1$H NMR (400 MHz, d$_6$-DMSO): δ 8.61 (s, 1H), 7.57-7.37 (m, 8H), 5.32 (s, 2H), 3.98 (s, 3H); $^{13}$C NMR (100 MHz, d$_6$-DMSO): δ 152.4, 151.5, 148.5, 146.2, 139.6, 137.0, 129.2, 128.8, 121.7, 120.4, 110.1, 101.9, 70.8, 56.5; IR (cm$^{-1}$): 2359, 2341, 1506, 1456, 1435, 1252, 1227, 1146, 999, 845, 752, 698, 667; LC/MS (M+H=300).

Example 33

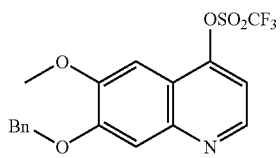

Trifluoromethanesulfonic acid 7-benzyloxy-6-methoxyquinolin-4-yl ester. To a dry 2 L RBF containing 7-benzyloxy-6-methoxyquinolin-4-ol (75.3 g, 267 mmol) was added DCM (1 L), 4-dimethylaminopyridine (3.28 g, 26.8 mmol) and 2,6-lutidine (62 mL, 534 mmol). The mixture was cooled to –20° C. by controlled addition of dry ice to an acetone bath. Trifluoromethanesulfonyl chloride (37 mL, 350 mmol) was added dropwise to the cooled solution with magnetic stirring over 25 minutes. After addition was complete, the mixture was stirred in bath for 20 minutes, then at room temperature for 3 hours. LCMS indicated reaction completion. The reaction mixture was concentrated in vacuo and placed under high vacuum to remove residual 2,6-lutidine. To the resulting brown solids was added methanol (3.5 L). The resulting slurry was stirred with mechanical stirrer for 30 min before adding water (1.5 L). The solids were isolated by filtration, followed by a water wash. The resulting solid was dried under high vacuum overnight yielding trifluoromethanesulfonic acid 7-benzyloxy-6-methoxy-quinolin-4-yl ester as a light brown solid (92.2 g, 83.8%). $^1$H NMR (400 MHz, DMSO, d$_6$): δ 8.82 (d, 1H), 7.67 (s, 1H), 7.59 (d, 1H), 7.54-7.52 (m, 2H), 7.46-7.42 (m, 2H), 7.39-7.36 (m, 1H), 7.23 (s, 1H), 5.35 (s, 2H), 3.97 (s, 3H). LC/MS: M+H=414.

Example 34

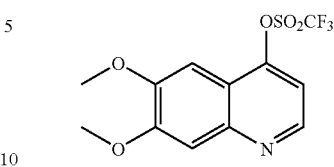

Trifluoromethanesulfonic acid 6,7-dimethoxyquinolin-4-yl ester from 6,7-Dimethoxyquinolin-4-ol. To a dry 1 L RBF containing 6,7-dimethoxy-quinolin-4-ol (20.9 g, 102 mmol), which can be prepared according to the procedure of Riegel, B. (*J. Amer. Chem. Soc.* 1946, 68, 1264), was added DCM (500 mL), 4-dimethylaminopyridine (1.24 g, 10 mmol) and 2,6-lutidine (24 mL, 204 mmol). The mixture was vigorously stirred at RT. Trifluoromethanesulfonyl chloride (14 mL, 132 mmol) was added dropwise to the solution. After addition was complete, the mixture was stirred ice bath for 2 to 3 hrs. On LC/MS indicating the reaction completion, the reaction mixture was concentrated in vacuo and placed under high vacuum to remove residual 2,6-lutidine. To the resulting brown solids was added methanol (250 mL). The resulting slurry was stirred for 30 min before adding water (1 L). The solids were isolated by filtration, followed by a water wash. The resulting solid was dried under high vacuum overnight yielding trifluoromethanesulfonic acid 6,7-dimethoxy-quinolin-4-yl ester as a light brown solid (27 g, 80%). $^1$H NMR (400 MHz, DMSO, d$_6$): δ 8.82 (d, 1H), 7.59 (m, 2H), 7.20 (s, 1H), 3.97 (d, 6H). LC/MS: M+H=338.

Example 35

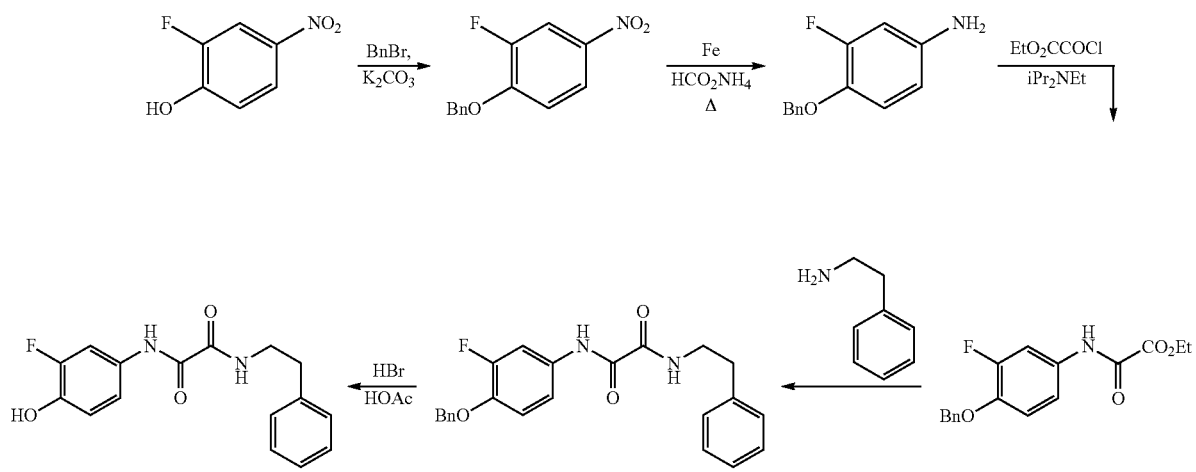

1-Benzyloxy-2-fluoro-4-nitrobenzene. A solution of 2-fluoro-4-nitrophenol (50.0 g, 318 mmol), benzyl bromide (42 mL, 350 mmol) and potassium carbonate (66.0 g, 478 mmol) in DMF (200 mL) was heated to 40° C. overnight. The solution was cooled to room temperature, poured over ice and the resultant solid was filtered. This material was washed with water and dried to give 1-benzyloxy-2-fluoro-4-nitrobenzene (75.0 g, 95%). $^1$H NMR (400 MHz, $d_6$-DMSO): δ 8.19-8.11 (m, 2H), 7.53-7.37 (m, 6H), 5.36 (s, 2H); $^{13}$C NMR (100 MHz, $d_6$-DMSO): δ 152.8, 152.4, 149.9, 140.9, 136.1, 129.3, 129.1, 128.7, 122.0, 115.2, 112.8, 112.6, 71.6; IR (cm$^{-1}$): 1499, 1346, 1279, 1211, 1142, 1072, 986, 885, 812, 789, 754, 742, 700, 648, 577.

4-Benzyloxy-3-fluoroaniline. A mixture of iron powder (45.2 g, 0.809 g atoms), ammonium formate (53.6 g, 0.850 mol), 1-benzyloxy-2-fluoro-4-nitrobenzene (50.0 g, 0.200 mol), toluene (400 mL) and water (400 mL) was heated to reflux overnight. The mixture was filtered through Celite and washed with hot ethyl acetate. The combined organic layers were washed with water and brine, then dried over sodium sulfate and concentrated to afford 4-benzyloxy-3-fluoroaniline (44 g, 100%). $^1$H NMR (400 MHz, $d_6$-DMSO): δ 7.43-7.26 (m, 5H), 6.90 (dd, 1H), 6.49 (dd, 1H), 6.34 (m, 1H), 4.99 (br s, 2H), 4.98 (s, 2H); $^{13}$C NMR (100 MHz, $d_6$-DMSO): δ 171.1, 155.1, 152.7, 144.9, 138.0, 137.2, 129.6, 129.0, 128.5, 118.9, 110.0, 102.9, 72.5; IR (cm$^{-1}$): 1510, 1454, 1277, 1215, 1126, 1007, 957, 843, 800, 789, 739, 694, 604; LC/MS (M+H=218).

Ethyl [(4-benzyloxy-3-fluorophenyl)amino](oxo)acetate. Ethyl oxalyl chloride (44 mL, 3901 mmol) was added to a solution of 4-benzyloxy-3-fluoroaniline (44 g, 180 mmol) in diisopropylethylamine (69 mL, 400 mmol) and stirred at room temperature for 15 min. The mixture was extracted with dichloromethane and washed with water and brine. The organic layer was dried over sodium sulfate and concentrated to afford ethyl [(4-benzyloxy-3-fluorophenyl)amino](oxo) acetate (58.4 g, 100%). $^1$H NMR (400 MHz, $d_6$-DMSO): δ 10.87 (s, 1H), 7.73 (d, 1H), 7.69 (d, 1H), 7.53 (d, 1H), 7.46-7.40 (m, 4H), 5.17 (s, 2H), 4.31 (q, 2H), 1.31 (t, 3H); IR (cm$^{-1}$): 1732, 1705, 1558, 1541, 1508, 1456, 1273, 1186, 1167, 1101, 999, 858, 741, 694; LC/MS (M+H=318).

N-(4-Benzyloxy-3-fluorophenyl)-N'-(2-phenylethyl) ethanediamide. Phenethyl-amine (33 mL, 520 mmol) was added to ethyl [(4-benzyloxy-3-fluorophenyl)amino](oxo) acetate (81 g, 260 mmol) and the mixture was sonicated at room temperature for 30 min. The resulting solid was filtered, washed with water and dried to give N-(4-benzyloxy-3-fluorophenyl)-N'-(2-phenylethyl)ethanediamide (100 g, 99%). $^1$H NMR (400 MHz, $d_6$-DMSO): δ 10.72 (br s, 1H), 9.05 (m, 1H), 8.78 (m, 1H), 7.77 (m, 1H), 7.59 (m, 1H), 7.46-7.19 (m, 8H), 5.16 (m, 2H), 3.45 (m, 2H), 2.83 (m, 2H); IR (cm$^{-1}$): 2980, 2883, 1653, 1522, 1506, 1441, 1385, 1221, 1122, 951, 808, 746, 696, 584; LC/MS (M+H=393).

N-(3-Fluoro-4-hydroxyphenyl)-N'-(2-phenylethyl) ethanediamide. A mixture of N-(4-benzyloxy-3-fluorophenyl)-N'-(2-phenylethyl)ethanediamide (40 g, 100 mmol) and 38% hydrobromic acid in acetic acid (250 mL) was stirred at room temperature overnight. The resulting solid was filtered, washed with water and dried to give N-(3-fluoro-4-hydroxyphenyl)-N'-(2-phenylethyl)ethanediamide as a slightly yellow solid (30.6 g, 99% yield). $^1$H NMR (400 MHz, $d_6$-DMSO): δ 10.60 (s, 1H), 9.02 (t, 1H), 7.70 (d, 1H), 7.47 (d, 1H), 7.32-7.20 (m, 3H), 6.91 (t, 1H), 3.43 (m, 2H), 2.81 (m, 2H); $^{13}$C NMR (100 MHz, $d_6$-DMSO): δ 160.5, 158.8, 152.0, 149.6, 142.2, 139.8, 130.3, 129.3, 129.0, 126.8, 118.1, 117.4, 109.6, 109.3 IR (cm$^{-1}$): 3279, 1653, 1518, 1456, 1279, 1190, 742, 696, 584; LC/MS (M+H=303).

Example 36

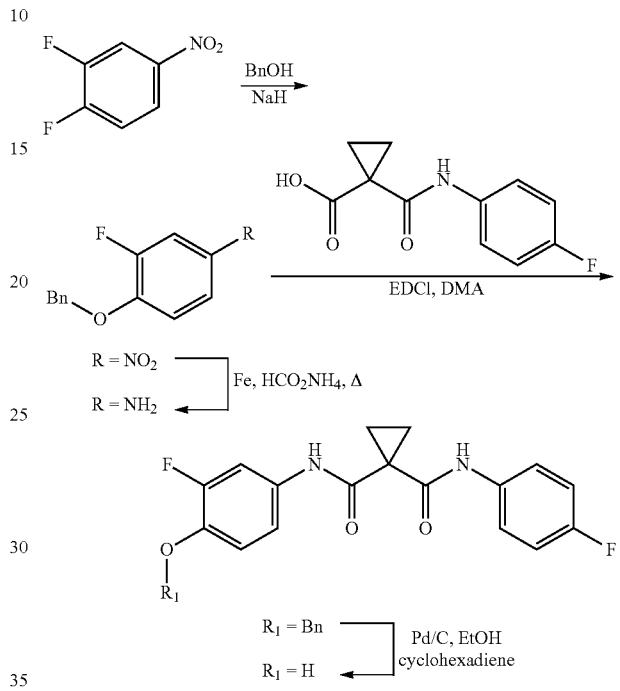

1-Benzyloxy-2-fluoro-4-nitro-benzene. To a slurry of sodium hydride (60% dispersion is oil, 693 mmol, 27.7 g) and dimethylacetamide (600 ml) was added benzyl alcohol (462 mmol, 48 ml) dropwise with stirring under $N_2$. The mixture was stirred for 1 hour at RT and then cooled to 0° C. 3,4-Difluoronitrobenzene (508 mmol, 56.2 ml) was added to the cooled solution and stirred for 1 hour. Reaction mixture poured onto saturated ammonium chloride solution (800 ml) and stirred for 30 minutes, filtered and washed with water. The solid was stirred in ethyl acetate (500 mL), and filtered to give 54 g of product. The ethyl acetate filtrate, after concentrated in vacuo, was triturated with diethyl ether (500 mL), sonicated for 2 hours, and filtered to give another 30 g of product. The ether layer was concentrated and column purified using 5% EtOAc/hexanes as eluent to gave additional 15 g of product. The total yield of 1-benzyloxy-2-fluoro-4-nitrobenzene was 95 g (83%). (Note: the product contains ca. 5% of 3,4-Bis-benzyloxy-nitrobenzene, which is carried into the next step without further purification.) $^1$H NMR (400 MHz, CDCl$_3$): δ 8.04-8.00 (m, 2H), 7.43-7.37 (m, 5H), 7.08 (t, 1H), 5.26 (s, 2H).

4-Benzyloxy-3-fluoro-phenylamine. A mixture of 1-benzyloxy-2-fluoro-4-nitro-benzene (44 g, 178 mmol), toluene (400 ml), ammonium formate (35 g), iron (30 g), and water (400 ml) was heated to reflux with stirring overnight. The reaction mixture was filtered through celite and washed with ethyl acetate (400 ml). The organic layer was separated and washed with brine (300 ml), dried over sodium sulfate and concentrated to give 4-benzyloxy-3-fluoro-phenylamine as an oil (33.7 g, 87%). $^1$H NMR (400 MHz, CDCl$_3$): δ 7.41-

7.29 (m, 5H), 6.79 (t, 1H), 6.45 (dd, 1H), 6.14 (dd, 1H), 5.02 (s, 2H), 3.50 (s, 2H). LC/MS: (M+1) 218.

Cyclopropane-1,1-dicarboxylic acid (4-benzyloxy-3-fluoro-phenyl)-amide (4-fluoro-phenyl)-amide. To a stirred mixture of 4-benzyloxy-3-fluoro-phenylamine (155.3 mmol, 33.7 g), 1-(4-fluoro-phenylcarbamoyl)-cyclopropanecarboxylic acid (170.8 mmol, 38.13 g) and anhydrous dichloromethane (600 ml) was added EDCI (233.9 mmol, 44.7 g) in portions. After stirring at RT for 1 hr, the reaction mixture was diluted with saturated sodium bicarbonate (400 ml) and stirred for 30 minutes. The precipitate was filtered and air dried to give the 1$^{st}$ crop of product. The biphasic filtrate was separated, and the organic phase was washed with brine (300 ml), dried over sodium sulfate, and concentrated. The residue was taken up in DCM (100 ml), stirred for 15 minutes, and filtered to give a 2$^{nd}$ crop of product. The combined yield of cyclopropane-1,1-dicarboxylic acid (4-benzyloxy-3-fluoro-phenyl)-amide (4-fluoro-phenyl)-amide was 64.5 g (98%). $^1$H NMR (400 MHz, CDCl$_3$): δ 8.92 (br s, 1H), 8.88 (br s, 1H), 7.50-7.32 (m, 8H), 7.06-7.02 (m, 3H), 6.97-6.92 (t, 1H), 5.13 (s, 2H), 1.65 (s, 4H). LC/MS: (M+1) 423.

Cyclopropane-1,1-dicarboxylic acid (3-fluoro-4-hydroxy-phenyl)-amide (4-fluoro-phenyl)-amide. A mixture of cyclopropane-1,1-dicarboxylic acid (4-benzyloxy-3-fluoro-phenyl)-amide (4-fluoro-phenyl)-amide (152.8 mmol, 64.5), ethanol (800 ml), cyclohexadiene (764 mmol, 71 ml), and 10% Pd/C (2 g) was refluxed for 2 hours. Reaction mixture cooled and filtered through celite and washed with methanol. The combined filtrate was concentrated and stirred in 0% EtOAc/ether (350 ml). The resulting precipitate was filtered and washed with ether to give a 1$^{st}$ crop of product. The filtrate was concentrated and stirred in DCM (150 ml) to give another precipitate, which was then filtered to give a 2$^{nd}$ crop of product. The combined yield of cyclopropane-1,1-dicarboxylic acid (3-fluoro-4-hydroxy-phenyl)-amide (4-fluoro-phenyl)-amide was 43 g (85%) in 95% purity by HPLC (UV @ 254 nm). $^1$H NMR (400 MHz, DMSO-D6): δ 10.07 (br s, 1H), 9.92 (br s, 1H), 9.64 (br s, 1H), 7.64-7.60 (m, 2H), 7.55-7.51 (m, 1H), 7.17-7.12 (m, 3H), 6.89-6.84 (t, 1H), 1.43 (s, 4H). LC/MS: (M+1) 333.

Example 37

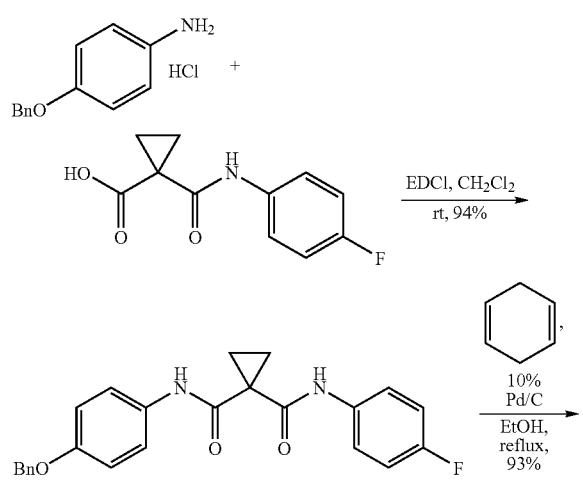

-continued

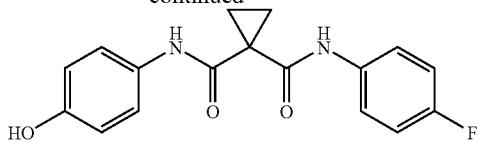

Cyclopropane-1,1-dicarboxylic acid (4-benzyloxy-phenyl)-amide (4-fluoro-phenyl)-amide. To a 0° C. suspension of 4-benzyloxyaniline hydrochloride (47.0 g, 200 mmol) and 1-(4-fluoro-phenylcarbamoyl)-cyclopropanecarboxylic acid (49.1 g, 220 mmol) in CH$_2$Cl$_2$ (400 mL) was added EDCI (38.2 g, 200 mmol). Stirring was continued at rt for 2-4 h until the reaction was complete. CH$_2$Cl$_2$ was removed under reduced pressure. H$_2$O (300 mL) and MeOH (200 mL) were added, and the resulting mixture was stirred at it for 30 min. After filtration and wash with H$_2$O, the solid was transferred to another flask containing 300 mL of sat. aqueous NaHCO$_3$ solution. The mixture was stirred for another 30 min. The solid was filtered, washed with water, and dried over night on a lyophilizer, affording cyclopropane-1,1-dicarboxylic acid (4-benzyloxy-phenyl)-amide (4-fluoro-phenyl)-amide (75.8 g, 95% yield) as an off-white solid.

Cyclopropane-1,1-dicarboxylic acid (4-fluoro-phenyl)-amide (4-hydroxy-phenyl)-amide. To a refluxing mixture of cyclopropane-1,1-dicarboxylic acid (4-benzyloxy-phenyl)-amide (4-fluoro-phenyl)-amide (46 g, 113 mmol), 10% Pd/C (2 g) in EtOH (400 mL) was added dropwise 1,4-cyclohexadiene (62.7 mL, 678 mmol). Stirring was continued for 2-5 h until the reaction was complete. The mixture was cooled to it, filtered through celite, and washed with EtOH. The solution was then concentrated under reduced pressure. To the flask containing the crude product was added CHCl$_3$ (200 mL). The resulting suspension was stirred for 15 min at rt. The solid was filtered, and dried in the air to give cyclopropane-1,1-dicarboxylic acid (4-fluoro-phenyl)-amide (4-hydroxy-phenyl)-amide (34.4 g, 95%, yield).

Example 38

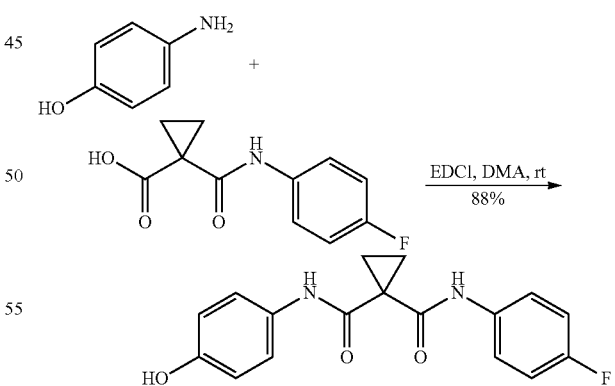

Alternate Synthesis of Cyclopropane-1,1-dicarboxylic acid (4-fluoro-phenyl)-amide (4-hydroxy-phenyl)-amide. To a solution of 4-aminophenol (2.93 g, 26.9 mmol) and 1-(4-fluoro-phenylcarbamoyl)-cyclopropanecarboxylic acid (5.00 g, 22.4 mmol) in DMA (30 mL) was added EDCI (5.15 g, 26.9 mmol). The mixture was stirred vigorously until the reaction was complete (~3 h). With vigorous stirring, the reaction mixture was then poured into a flask containing sat. aqueous NaHCO$_3$ solution (200 mL). The stirring was continued for 1 h. The resulting suspension was then filtered. The solid was washed with water (50 mL), chloroform (50 mL) and dried under vacuum, affording 1-(4-fluoro-phenylcarbamoyl)-cyclopropanecarboxylic acid (6.22 g, 88% yield) as a powder (>95% purity by HPLC and $^1$H NMR).

Example 39

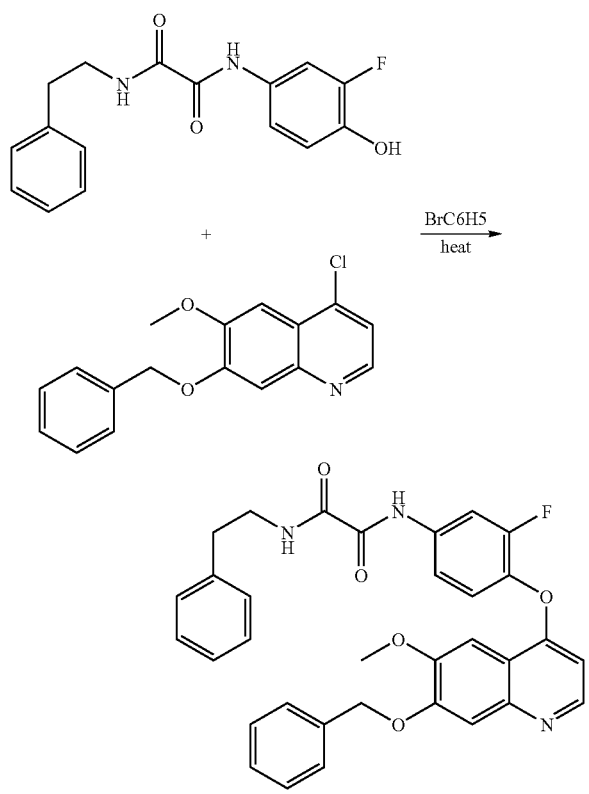

N-{4-[(7-Benzyloxy-6-methoxyquinolin-4-yl)oxy]-3-fluorophenyl}-N'-(2-phenylethyl)ethanediamide. A mixture of 7-benzyloxy-4-chloro-6-methoxyquinoline (30 g, 100 mmol), N-(3-fluoro-4-hydroxyphenyl)-N'-(2-phenylethyl) ethanediamide (32 g, 106 mmol), DMAP (125 g, 1.02 mol) and bromobenzene (500 mL) was heated to reflux for 6 h. The mixture was cooled to room temperature and the bromobenzene was removed under reduced pressure. Methanol (500 mL) was added to the residue and the mixture was stirred at room temperature for 2 h. The resulting solid was filtered, washed with methanol and dried to give N-{4-[(7-benzyloxy-6-methoxyquinolin-4-yl)oxy]-3-fluorophenyl}-N'-(2-phenylethyl)ethanediamide (34 g, 61%). $^1$H NMR (400 MHz, d$_6$-DMSO): δ 11.05 (s, 1H), 9.15 (s, 1H), 8.47 (d, 1H), 8.05 (d, 1H), 7.84 (d, 1H), 7.56-6.36 (m, 13H), 6.46 (d, 1H), 5.32 (s, 2H), 3.97 (s, 3H), 3.47 (q, 2H), 2.86 (t, 2H); $^{13}$C NMR (100 MHz, d$_6$-DMSO): δ 160.5, 160.2, 159.9, 159.5, 155.2, 152.7, 152.2, 150.3, 149.6, 146.9, 139.7, 137.4, 137.3, 137.2, 137.1, 129.3, 129.2, 129.1, 129.0, 128.9, 128.7, 128.6, 126.9, 124.8, 117.9, 115.3, 109.9, 102.8, 99.8, 70.6, 56.5, 41.3, 35.2; IR (cm$^{-1}$): 1657, 1510, 1481, 1433, 1416, 1352, 1310, 1252, 1215, 1609, 986, 891, 868, 850, 742, 696; LC/MS (M+H=566).

Example 40

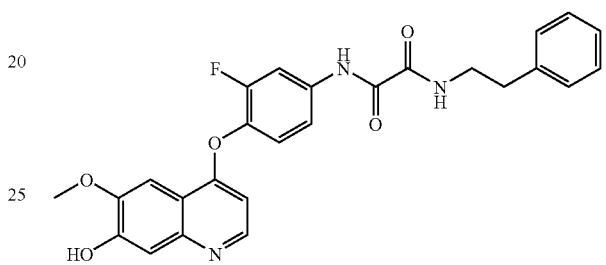

N-{3-Fluoro-4-[(7-hydroxy-6-methoxyquinolin-4-yl) oxy]phenyl}-N'-(2-phenylethyl)ethanediamide. To a solution of N-{4-[(7-benzyloxy-6-methoxyquinolin-4-yl)oxy]-3-fluorophenyl}-N'-(2-phenylethyl)ethanediamide (32 g, 56 mmol) in methanol (200 mL), DMF (100 mL), dichloromethane (100 mL), ethyl acetate (100 mL) and acetic acid (5 mL) was added palladium hydroxide (4.2 g) and the mixture was shaken on a Parr hydrogenator under a hydrogen pressure of 45 psi for 4 h. The resulting suspension was filtered through celite and the solid residue was washed with boiling dichloromethane (2 L) and acetone (2 L). The combined filtrates were evaporated to yield N-{3-fluoro-4-[(7-hydroxy-6-methoxyquinolin-4-yl)oxy]phenyl}-N'-(2-phenylethyl)ethanediamide as an off-white solid (25.6 g, 95%). $^1$H NMR (400 MHz, d$_6$-DMSO): δ 11.06 (s, 1H), 10.25 (br s, 1H), 9.12 (t, 1H), 8.40 (d, 1H), 8.01 (dd, 1H), 7.50-7.44 (m, 2H), 7.31-7.23 (m, 6H), 6.39 (d, 1H), 3.95 (s, 3H), 2.85 (t, 2H), 2.50 (m, 2H); IR (cm–1): 1666, 1624, 1585, 1520, 1481, 1427, 1377, 1256, 1211, 1194, 1022, 880, 850, 839, 802, 750, 700; LC/MS (M+H=476).

Example 41

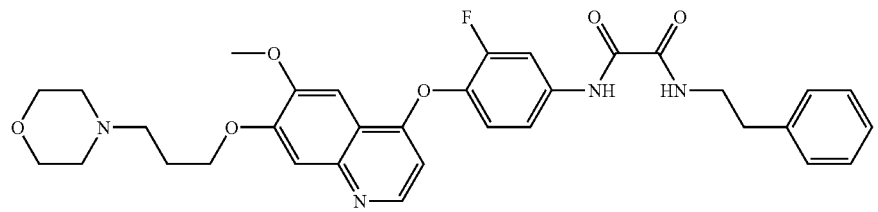

N-(3-Fluoro-4-{[6-methoxy-7-(3-morpholin-4-ylpropoxy)quinolin-4-yl]oxy}phenyl)-N'-(2-phenylethyl)ethanediamide. A solution of N-{3-fluoro-4-[(7-hydroxy-6-methoxyquinolin-4-yl)oxy]phenyl}-N'-(2-phenylethyl)ethanediamide (25.6 g, 54 mmol), N-(3-chloropropyl)molpholine hydrochloride (11.7 g, 592 mmol) and potassium carbonate (16.6 g, 120 mmol) in DMF (300 mL) was heated to 80° C. overnight. Upon cooling, a majority of the DMF (250 mL) was removed on a rotary evaporator, 5% aqueous LiCl (300 mL) was added and the mixture was sonicated at room temperature. The solid was filtered, suspended in 1N HCl and washed with ethyl acetate (2×300 mL). The solution was adjusted to pH 14 using 2N sodium hydroxide and subsequently extracted with dichloromethane (3×200 mL). The organic layer was dried over sodium sulfate, filtered and evaporated to give N-(3-fluoro-4-{[6-methoxy-7-(3-morpholin-4-ylpropoxy)quinolin-4-yl]oxy}phenyl)-N'-(2-phenylethyl)ethanediamide as a yellow solid (24 g, 74%). $^1$H NMR (400 MHz, CDCl$_3$): δ 9.37 (s, 1H), 8.46 (d, 1H), 7.81 (dd, 1H), 7.57 (t, 1H), 7.53 (s, 1H), 7.42 (s, 2H), 7.34-7.20 (m, 6H), 6.39 (d, 1H), 4.27 (t, 2H), 4.03 (s, 3H), 3.71 (m, 4H), 3.65 (q, 2H), 2.91 (t, 2H), 2.56 (br s, 4H), 2.13 (m, 2H); $^{13}$C NMR (100 MHz, d$_6$-DMSO): δ 160.1, 160.0, 159.5, 155.2, 152.7, 152.6, 150.2, 149.5, 147.1, 139.7, 137.3, 137.1, 129.3, 129.1, 126.9, 124.8, 117.9, 115.1, 109.2, 102.7, 99.6, 67.4, 66.9, 56.5, 55.5, 54.1, 41.3, 35.2, 26.4; IR (cm$^{-1}$): 1655, 1506, 1483, 1431, 1350, 1302, 1248, 1221, 1176, 1119, 864, 843, 804, 741, 700; LC/MS (M+H=603).

Example 42

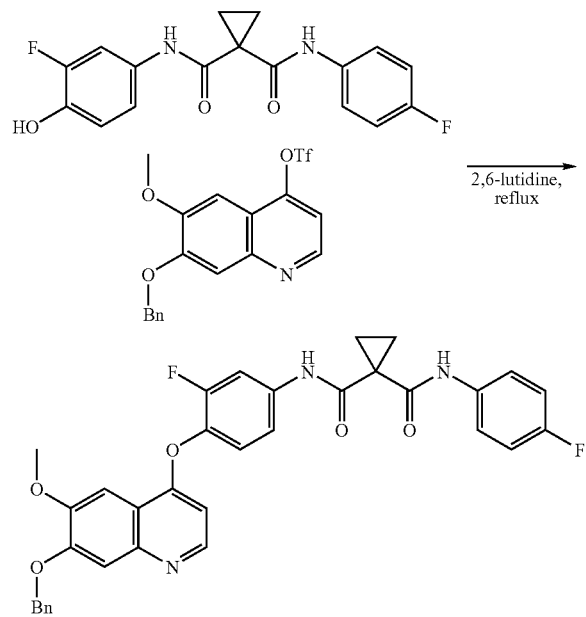

Cyclopropane-1,1-dicarboxylic acid [4-(7-benzyloxy-6-methoxy-quinolin-4-yloxy)-3-fluoro-phenyl]-amide (4-fluoro-phenyl)-amide. To a flask containing cyclopropane-1,1-dicarboxylic acid (3-fluoro-4-hydroxy-phenyl)-amide (4-fluoro-phenyl)-amide (2.25 g, 6.7 mmol) and trifluoromethanesulfonic acid 7-benzyloxy-6-methoxy-quinolin-4-yl ester (1.87 g, 4.5 mmol) was added dry 2,6-lutidine (9 mL). The reaction mixture was heated to reflux (143° C.) with vigorous stirring. The reaction progress was monitored by LC-MS. 2,6-Lutidine was removed under reduced pressure when the reaction was complete (about 6 h). The residue was treated with charcoal (1.5 g) in refluxing EtOAc (50 mL) for 15 min, and filtered through celite. The volume of the filtrate was reduced to about 20 mL and was added 20 mL of 1 N HCl. The crude product precipitated as the HCl salt, which was filtered and washed with EtOAc and H$_2$O (88% purity by analytical HPLC). The HCl salt was free-based with saturated aqueous NaHCO$_3$ solution. Further purification by column chromatography (hexans:EtOAc=1:4) gave cyclopropane-1,1-dicarboxylic acid [4-(7-benzyloxy-6-methoxy-quinolin-4-yloxy)-3-fluoro-phenyl]-amide (4-fluoro-phenyl)-amide as an off-white solid (1.3 g, 48% yield. $^1$H NMR (400 MHz, DMSO, d$_6$): 10.41 (s, 1H), 10.02 (s, 1H), 8.48 (d, 1H), 7.92 (dd, 1H), 7.65 (m, 2H), 7.54 (m, 5H), 7.41 (m, 4H), 7.17 (m, 2H), 6.43 (d, 1H), 5.32 (s, 2H), 3.97 (s, 3H), 1.48 (m, 4H). LC/MS Calcd for [M+H]$^+$ 596.2, found 596.3.

Example 43

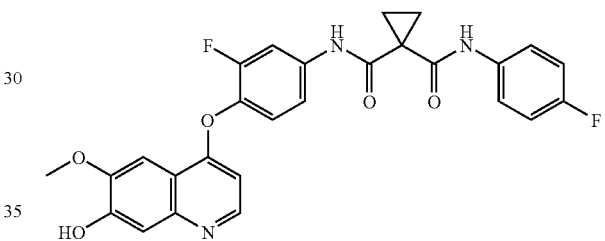

Cyclopropane-1,1-dicarboxylic acid [3-fluoro-4-(7-hydroxy-6-methoxy-quinolin-4-yloxy)-phenyl]-amide (4-fluoro-phenyl)-amide. To a solution of the cyclopropane-1,1-dicarboxylic acid [4-(7-benzyloxy-6-methoxy-quinolin-4-yloxy)-3-fluoro-phenyl]-amide (4-fluoro-phenyl)-amide (22.4 g, 37.6 mmol) in EtOH (340 mL) was added 1,4-cyclohexadiene (35 mL, 376 mmol) and 10% Pd/C (2.08 g). The reaction mixture was then heated at 65° C. with stirring for 3 h (Caution: H$_2$ gas is released from the reaction). It was then allowed to cool to room temperature, and filtered through celite followed by a MeOH wash. The solution was then concentrated under reduced pressure. The yellow residue was taken into EtOAc (1 L). The EtOAc solution was washed with water (1×), brine (2×), dried over MgSO$_4$ and concentrated in vacuo. Cyclopropane-1,1-dicarboxylic acid [3-fluoro-4-(7-hydroxy-6-methoxy-quinolin-4-yloxy)-phenyl]-amide (4-fluoro-phenyl)-amide was obtained as a yellow solid (17.3 g, 91.1% yield), which were carried on to the next reaction without further purification. $^1$H NMR (400 MHz, DMSO, d6): 10.39 (s, 1H), 10.15 (s, 1H), 10.00 (s, 1H), 8.38 (d, 1H), 7.88 (dd, 1H), 7.63 (m, 2H), 7.50 (m, 2H), 7.40 (t, 1H), 7.27 (s, 1H), 7.14 (m, 2H), 6.33 (d, 1H), 3.95 (s, 3H), 1.47 (m, 4H). LC/MS Calcd for [M+H]$^+$ 506.2, found 506.3. Anal. HPLC: 99.4% pure.

Example 44

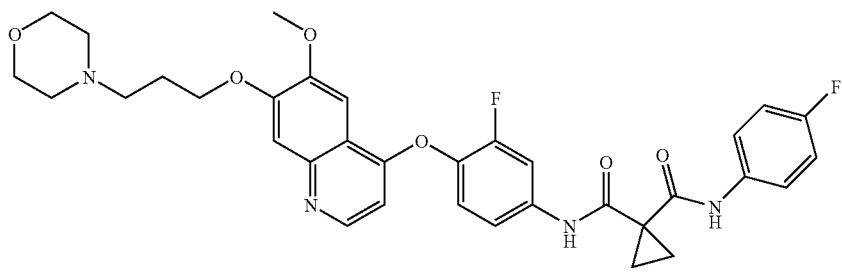

N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide. To a mechanically stirred slurry of cyclopropane-1,1-dicarboxylic acid [3-fluoro-4-(7-hydroxy-6-methoxy-quinolin-4-yloxy)-phenyl]-amide (4-fluoro-phenyl)-amide (16.6 g, 32.8 mmol) and potassium carbonate (13.6 g, 98.6 mmol) in DMF (250 mL) was added 4-(3-chloropropyl)-morpholine hydrochloride (13, 7.92 g, 39.6 mmol). The resulting mixture was heated at 90° C. for 5 hours (until phenol completely consumed). The reaction mixture was allowed to cool to room temperature, then dumped into water (900 mL), followed by extraction with EtOAc (3×). The combined extracts were washed with 5% LiCl (aq.) (3×) and brine (1×) followed by drying over MgSO$_4$ and concentration in vacuo. The crude (18.8 g) obtained as brown solid was further purified by flash chromatography [silica gel, 4-stage gradient system: 1) EtOAc; 2) EtOAc:MeOH:7N NH$_3$/MeOH (95:5:0.5); 3) DCM:MeOH:7N NH$_3$/MeOH (95:5:0.5); 4) DCM:MeOH: 7N NH$_3$/MeOH (93:8:1)], affording N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide was obtained as an off white solid (15.0 g, 72% yield). $^1$H NMR (400 MHz, DMSO-d6): 10.41 (s, 1H), 10.02 (s, 1H), 8.47 (d, 1H), 7.91 (dd, 1H), 7.65 (m, 2H), 7.53 (m, 2H), 7.42 (t, 1H), 7.40 (s, 1H), 7.16 (m, 2H), 6.42 (d, 1H), 4.20 (t, 2H), 3.96 (s, 3H), 3.59 (t, 4H), 2.47 (t, 2H), 2.39 (br, s, 4H), 1.98 (m, 2H), 1.48 (m, 4H). LC/MS Calcd for [M+H]$^+$ 633.3, found 633.0.

Example 45

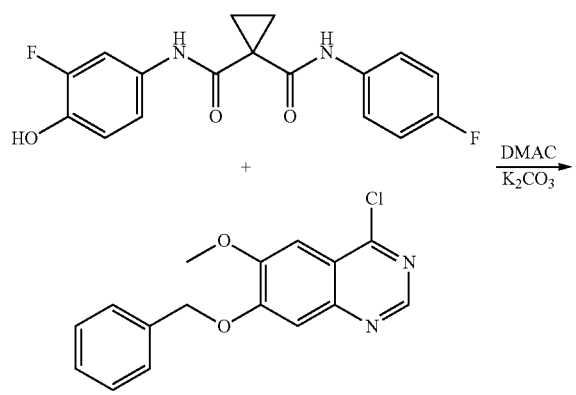

-continued

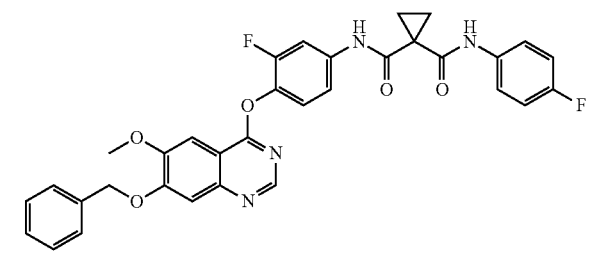

Cyclopropane-1,1-dicarboxylic acid [4-(7-benzyloxy-6-methoxy-quinazolin-4-yloxy)-3-fluoro-phenyl]-amide (4-fluoro-phenyl)-amide: A mixture of 7-benzyloxy-4-chloro-6-methoxy-quinazoline (5 g, 16.67 mmol), cyclopropane-1,1-dicarboxylic acid (3-fluoro-4-hydroxy-phenyl)-amide (4-fluoro-phenyl)-amide (8.3 g, 25 mmol), potassium carbonate (125 mmol, 17.25 g), and dimethylacetamide (125 ml) was heated 50° C. with stirring for 16 h. Reaction mixture was poured onto ice/water (600 ml) and stirred for 30 minutes, and filtered. The solid was dissolved in ethyl acetate and washed with water (1×), brine, and concentrated. The crude was purified on silica get column eluting with 30% acetone in hexanes to yield cyclopropane-1,1-dicarboxylic acid [4-(7-benzyloxy-6-methoxy-quinazolin-4-yloxy)-3-fluoro-phenyl]-amide (4-fluoro-phenyl)-amide (7.5 g, 76%). $^1$H NMR (CDCl$_3$): 8.64 (1H, br. s), 8.55 (1H, s), 8.33 (1H, br. s), 7.74-7.71 (1H, dd), 7.54 (1H, s), 7.48-7.33 (8H, m), 7.31-7.24 (2H, m), 7.06-7.02 (2H, m), 5.32 (2H, s), 4.06 (3H, s), 1.77-1.74 (2H, m), 1.63-1.61 (2H, m).

Example 46

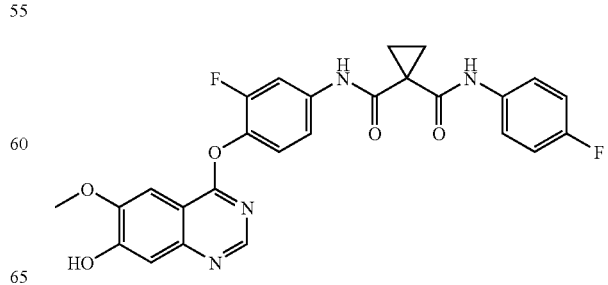

Cyclopropane-1,1-dicarboxylic acid [3-fluoro-4-(7-hydroxy-6-methoxy-quinazolin-4-yloxy)-phenyl]-amide (4-fluoro-phenyl)-amide. To a mixture of cyclopropane-1,1-dicarboxylic acid [4-(7-benzyloxy-6-methoxy-quinazolin-4-yloxy)-3-fluoro-phenyl]-amide (4-fluoro-phenyl)-amide (7.5 g, 12.6 mmol), acetic acid (few drops), dichloromethane (50 ml) and methanol (100 ml) was added 10% Pd/C (700 mg). The mixture was agitated in hydrogen gas (40 psi) until the reaction was complete (ca. 4 hr). The solution was filtered through celite and concentrated to give a crude product as a solid. The crude product was triturated with ether, and filtered. The filter cake was dried in vacuo to yield cyclopropane-1,1-dicarboxylic acid [3-fluoro-4-(7-hydroxy-6-methoxy-quinazolin-4-yloxy)-phenyl]-amide (4-fluoro-phenyl)-amide (6.1 g, 95% yield). $^1$H NMR (dmso-d6): 10.86 (1H, br. s), 10.34 (1H, br. s), 10.04 (1H, br. s), 8.46 (1H, s), 7.84-7.80 (1H, dd), 7.66-7.62 (2H, m), 7.55 (1H, s), 7.47-7.45 (1H, m), 7.41-7.37 (1H, m), 7.24 (1H, s), 7.18-7.13 (2H, t), 3.98 (3H, s), 1.46 (4H, s).

Example 47

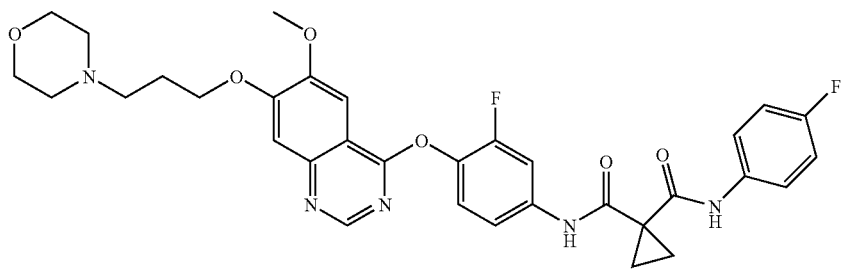

N-[3-Fluoro-4-({6-(methyloxy)-7-[(3-morpholin-4-yl-propyl)oxy]quinazolin-4-yl}oxy)phenyl]-N'-(4-fluorophenyl)cyclopropane-1,1-dicarboxamide. To a mixture of cyclopropane-1,1-dicarboxylic acid [3-fluoro-4-(7-hydroxy-6-methoxy-quinazolin-4-yloxy)-phenyl]-amide (4-fluoro-phenyl)-amide (1.5 g, 2.96 mmol), 4-(3-hydroxypropyl)morpholine (0.623 mL, 4.5 mmol), triphenylphosphine (1.18 g, 4.5 mmol), and dichloromethane (50 mL) was added diisopropyl azodicarboxylate (0.886 mL, 4.5 mmol). The mixture was stirred at room temperature for 16 h, monitored by LCMS. After removal of solvent, the crude mixture was separated by flash column chromatography (silica), eluting with 5% methanol in dichloromethane to give N-[3-fluoro-4-({6-(methyloxy)-7-[(3-morpholin-4-ylpropyl)oxy]quinazolin-4-yl}oxy)phenyl]-N'-(4-fluorophenyl)cyclopropane-1,1-dicarboxamide (890 mg, 47% yield). $^1$H NMR (400 MHz, DMSO-d6): δ 10.36 (br s, 1H), 10.05 (br s, 1H), 8.55 (s, 1H), 7.83 (m, 1H), 7.64 (m, 2H), 7.57 (s, 1H), 7.44 (m, 3H), 7.18 (t, 2H), 4.27 (m, 2H), 3.99 (s, 3H), 3.61 (m, 6H), 2.40 (m, 4H), 2.01 (m, 2H), 1.47 (m, 4H). LC/MS Calcd for [M+H]$^+$ 634.2, found 634.3.

Example 48

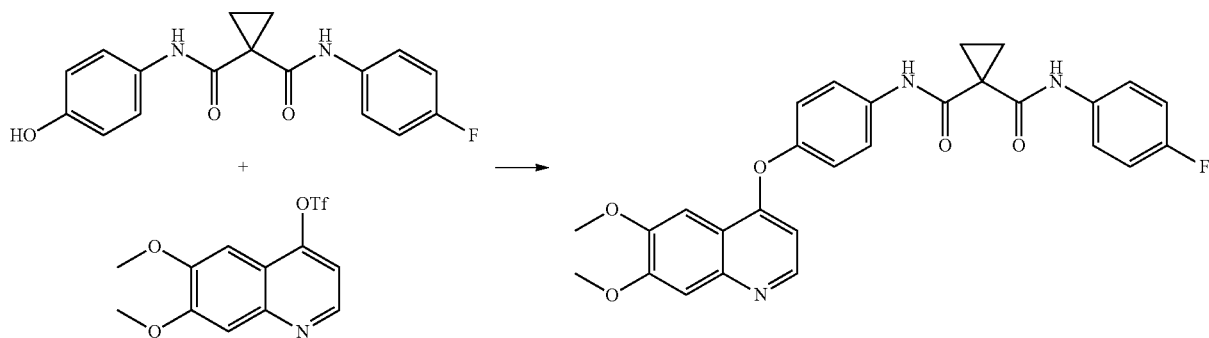

N-(4-{[6,7-bis(methyloxy)quinolin-4-yl]oxy}phenyl)-N'-(4-fluorophenyl)cyclopropane-1,1-dicarboxamide. To a solution of cyclopropane-1,1-dicarboxylic acid (4-fluoro-phenyl)-amide (4-hydroxy-phenyl)-amide (6.98 g, 22.2 mmol) in anhydrous 2,6-lutidine (50 mL) was added trifluoromethanesulfonic acid 6,7-dimethoxy-quinolin-4-yl ester (5 g, 14.8 mmol). The reaction mixture was heated at 165° C. in a sealed pressure tube with stirring for 18 h. The reaction mixture was concentrated on high vacuum to completely remove lutidine. The resulting solid material was dissolved in DCM (250 mL), and washed several times with 1 N sodium hydroxide to remove the excess phenol. The crude mixture was loaded on a silica gel flash column and eluted with 75% EtOAc-hexanes, affording N-(4-{[6,7-bis(methyloxy)quinolin-4-yl]oxy}phenyl)-N'-(4-fluorophenyl)cyclopropane-1,1-dicarboxamide (3.2 g, 44%). $^1$H NMR (400 MHz, $d_6$-DMSO): δ 10.2 (s, 1H), 10.05 (s, 1H), 8.4 (s, 1H), 7.8 (m, 2H), 7.65 (m, 2H), 7.5 (s, 1H), 7.35 (s, 1H), 7.25 (m, 2H), 7.15 (m, 2H), 6.4 (s, 1H), 4.0 (d, 6H), 1.5 (s, 4H). LC/MS: M+H=502.

Example 49

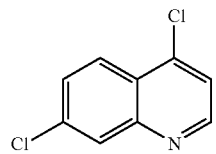

4,7-Dichloroquinoline. Phosphorus oxychloride (4 mL, 429 mmol) was added to 7-chloro-4-hydroxyquinoline 2.86 g, 15.9 mmol) in a round bottom flask equipped with a reflux condenser. The mixture was heated to reflux for 2 h, then allowed to cool to room temperature. The solution was concentrated in vacuo to a thick oil, then dumped over cracked ice. The resulting solution was neutralized with saturated NaHCO$_3$ (aq). The slurry was filtered and washed with water. The solids were dried under vacuum, afforded 4,7-dichloroquinoline as a white solid (2.79 g, 88.5% yield).

Example 50

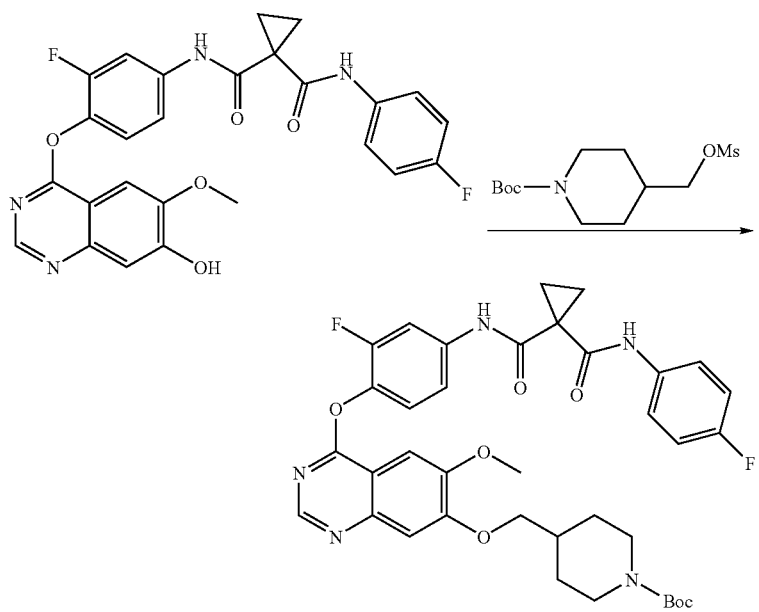

4-[4-(2-Fluoro-4-{[1-(4-fluoro-phenylcarbamoyl)-cyclopropanecarbonyl]-amino}-phenoxy)-6-methoxy-quinazolin-7-yloxymethyl]-piperidine-1-carboxylic acid tert-butyl ester. Cyclopropane-1,1-dicarboxylic acid [3-fluoro-4-(7-hydroxy-6-methoxy-quinazolin-4-yloxy)-phenyl]-amide (4-fluoro-phenyl)-amide (325 mg, 0.64 mmol), 4-methanesulfonyloxymethyl-piperidine-1-carboxylic acid tert-butyl ester (193 mg, 0.66 mmol), K$_2$CO$_3$ (181 mg, 1.31 mmol) were combined in DMF (5 ml) and heated to 80° C. overnight. The reaction was not complete and more 4-methanesulfonyloxymethyl-piperidine-1-carboxylic acid tert-butyl ester (90 mg, 0.31 mmol) and K$_2$CO$_3$ (90 mg, 0.65 mmol) were added and heating at 80° C. continued for another night. The reaction mixture was allowed to cool to room temperature, then diluted with EtOAc and washed with H$_2$O (3×), sat'd NaCl (1×), dried (Na$_2$SO$_4$) and concentrated in vacuo. The resulting crude material was purified by flash chromatography (1:1 hexanes:EtOAc, followed by 1:3 hexanes:EtOAc) to give 4-[4-(2-fluoro-4-{[1-(4-fluoro-phenylcarbamoyl)-cyclopropanecarbonyl]-amino}-phenoxy)-6-methoxy-quinazoline-7-yloxymethyl]-piperidine-1-carboxylic acid tert-butyl ester (273 mg, 60%). LC/MS Calcd for [M+H]$^+$ 704.3, found 704.4.

Example 51

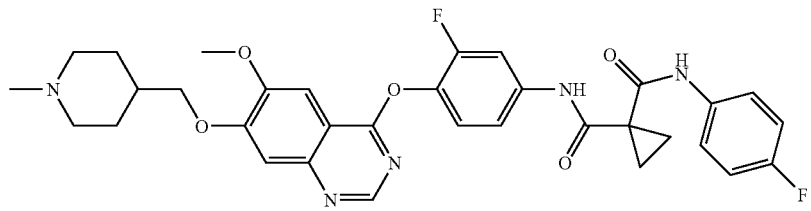

The resulting solids were filtered, washed with Et$_2$O and dried under high vacuum to give cyclopropane-1,1-dicarboxylic acid {3-fluoro-4-[6-methoxy-7-(piperidin-4-ylmethoxy)-quinazolin-4-yloxy]-phenyl}-amide (4-fluorophenyl)-amide, TFA salt (222 mg, 80%). LC/MS Calcd for [M+H]$^+$ 604.2, found 604.3.

Example 52

N-{3-Fluoro-4-[(6-(methyloxy)-7-{[(1-methylpiperidin-4-yl)methyl]oxy}quin-azolin-4-yl)oxy]phenyl}-N'-(4-fluorophenyl)cyclopropane-1,1-dicarboxamide. Cyclopropane-1,1-dicarboxylic acid {3-fluoro-4-[6-methoxy-7-(piperidin-4-ylmethoxy)-quinazolin-4-yloxy]-phenyl}-amide (4-fluoro-phenyl)-amide, TFA salt (222 mg, 0.31 mmol), H$_2$O (3 ml), 37% formaldehyde in H$_2$O (0.18 ml) and acetic acid (27 drops) were combined in acetonitrile (9 ml) to which was slowly added triacetoxyborohydride (561 mg, 2.65 mmol). The mixture was stirred at room temperature for 1-2 hr, then diluted with 1N NaOH and H$_2$O and extracted with CH$_2$Cl$_2$ (3×). The combined CH$_2$Cl$_2$ extractions were washed with sat'd NaCl (1×), dried (Na$_2$SO$_4$) and concentrated in

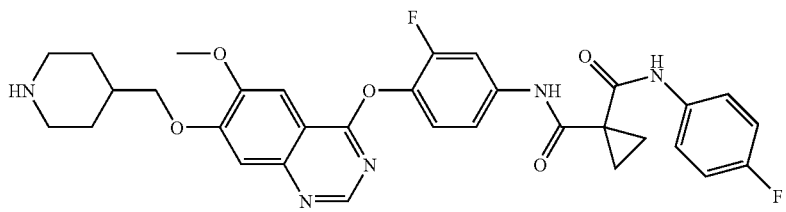

Cyclopropane-1,1-dicarboxylic acid {3-fluoro-4-[6-methoxy-7-(piperidin-4-ylmethoxy)-quinazolin-4-yloxy]-phenyl}-amide (4-fluoro-phenyl)-amide, TFA salt. 4-[4-(2-Fluoro-4-{[1-(4-fluoro-phenylcarbamoyl)-cyclopropanecarbonyl]-amino}-phenoxy)-6-methoxy-quinazolin-7-yloxymethyl]-piperidine-1-carboxylic acid tert-butyl ester (273 mg, 0.39 mmol) was dissolved in CH$_2$Cl$_2$ (8 ml) to which was added TFA (8 ml) and the mixture stirred at room temperature for 1 hr. The reaction mixture was concentrated in vacuo and the resulting oil triturated with Et$_2$O.

vacuo. The resulting residue was dissolved in a minimum of 1:1 dioxane:EtOAc to which was added 4M HCl in dioxane (1-2 ml). The resulting solids were filtered, washed with EtOAc and dried under high vacuum to give N-{3-fluoro-4-[(6-(methyloxy)-7-{[(1-methylpiperidin-4-yl)methyl]oxy}quinazolin-4-yl)oxy]phenyl}-N'-(4-fluorophenyl)cyclopropane-1,1-dicarboxamide, HCl salt (167 mg, 83%). 1HNMR (400 MHz, DMSO-d$_6$): δ 10.40 (s, 1H), 10.17 (br s, 1H) 10.07 (s, 1H), 8.61 (s, 1H), 7.85 (m, 1H), 7.65 (m, 2H), 7.48 (m, 2H), 7.42 (t, 1H), 7.16 (t, 2H), 4.12 (2, 2H), 4.00 (s, 3H), 3.46 (m, 2H), 2.99 (m, 2H), 2.73 (d, 3H), 2.13 (m, 1H), 2.01 (m, 2H), 1.63 (m, 2H), 1.47 (m, 4H). LC/MS Calcd for [M+H]$^+$ 618.2, found 618.3.

Synthesis of Bridged Bicyclics

The following describes synthesis of bridged bicyclics with appended leaving groups for use as, for example, alkylating agents. In the context of this invention, these alkylating agents are used, for example, to alkylate the quinazoline or quinolines on the 6- or 7-oxygens to make compounds of the invention. The invention is not limited to alkylation chemistry to append such bridged bicyclics, but rather the aforementioned description is meant only to be illustrative of an aspect of the invention.

Example 53

1,4:3,6-dianhydro-2-O-methyl-5-O-(methylsulfonyl)-D-glucitol: To a solution of 1,4:3,6-dianhydro-2-O-methyl-D-glucitol (1.19 g, 7.4 mmol) in dichloromethane was added pyridine (1 mL, 12.36 mmol) followed by methanesulfonyl chloride (0.69 mL, 8.92 mmol) and the mixture was allowed to stir at room temperature over 12 hours. The solvent was removed and the amorphous residue was partitioned with ethyl acetate and 0.1M aqueous hydrochloric acid. The aqueous phase was extracted once with additional ethyl acetate and the combined organic layers were washed with saturated aqueous sodium chloride then dried over anhydrous magnesium sulfate. Filtration and concentration followed by drying in vacuo afforded 1,4:3,6-dianhydro-2-O-methyl-5-O-(methylsulfonyl)-D-glucitol (1.67 g, 94% yield) as a colorless oil. GC/MS calculated for $C_8H_{14}SO_6$: 238 ($M^+$).

Example 54

1,4:3,6-dianhydro-5-O-(phenylcarbonyl)-D-fructose ethylene glycol acetal: A solution of 1,4:3,6-dianhydro-5-O-(phenylcarbonyl)-D-fructose (2.00 g, 8.06 mmol), ethylene glycol (5.00 g, 80.6 mmol), and p-toluenesulfonic acid (1.53 g, 8.06 mmol) in benzene (100 mL) was refluxed for 90 min using a Dean-Stark Trap apparatus. The reaction mixture was diluted with ethyl acetate (100 mL), washed with saturated aqueous sodium bicarbonate (2×50 mL) then brine (50 mL), and dried over anhydrous sodium sulfate. Filtration, concentration and column chromatography on silica (1:1 hexane/ethyl acetate) provided 1.44 g (61% yield) of 1,4:3,6-dianhydro-5-O-(phenylcarbonyl)-D-fructose ethylene glycol acetal as a colorless solid. $^1$H NMR (400 MHz; $CDCl_3$): 8.08 (m, 2H), 7.58 (m, 1H), 7.54 (m, 2H), 5.38 (dd, 1H), 4.97 (t, 1H), 4.21-4.02 (m, 7H), 3.86 (d, 1H), 3.75 (d, 1H).

Example 55

1,4:3,6-dianhydro-D-fructose ethylene glycol acetal: To a solution of 1,4:3,6-dianhydro-5-O-(phenylcarbonyl)-D-fructose ethylene glycol acetal (1.44 g, 4.93 mmol) in methanol (40 mL) was added 50% aqueous sodium hydroxide (0.38 g, 4.75 mmol) and the mixture was stirred at room temperature for 30 minutes. Neutralization with 1M HCl, followed by concentration and column chromatography on silica (1:2 hexane/ethyl acetate) provided 0.74 g (80% yield) of 1,4:3,6-dianhydro-D-fructose ethylene glycol acetal as a colorless solid. $^1$H NMR (400 MHz; $CDCl_3$): 4.60 (t, 1H), 4.32 (m, 1H), 4.14 (d, 1H), 4.05-3.98 (m, 5H), 3.82 (s, 2H), 3.62 (dd, 1H), 2.65 (d, 1H).

1,4:3,6-dianhydro-5-O-(methylsulfonyl)-D-fructose ethylene glycol acetal: To a solution of 1,4:3,6-dianhydro-D-fructose ethylene glycol acetal (0.74 g, 3.93 mmol) and triethylamine (1.20 g, 11.86 mmol) in dichloromethane (40 mL) was added methanesulfonyl chloride (0.90 g, 7.88 mmol) at 0° C. under nitrogen. The solution was warmed to room temperature and stirred for 13 h. Dichloromethane (50 mL) was added, and the organic layer was washed with saturated aqueous sodium bicarbonate (30 mL), water (30 mL), and brine (30 mL) then dried over anhydrous sodium sulfate. Filtration and concentration provided 1.02 g (97%) of 1,4:3,6-dianhydro-5-O-(methylsulfonyl)-D-fructose ethylene glycol acetal as a yellow oil. $^1$H NMR (400 MHz; $CDCl_3$): 5.08 (m, 1H), 4.82 (t, 1H), 4.13 (dd, 1H), 4.04 (m, 4H), 3.93 (dd, 1H), 3.87 (d, 1H), 3.81 (d, 1H), 3.13 (s, 3H).

Example 56

1,4:3,6-dianhydro-2-deoxy-2-methylidene-D-arabino-hexitol: To a solution of 1,4:3,6-dianhydro-2-deoxy-2-methylidene-5-O-(phenylcarbonyl)-D-arabino-hexitol (329 mg, 1.34 mmol) in methanol (10 mL) was added 50% aqueous sodium hydroxide (95 mg, 1.19 mmol) and the mixture was stirred at room temperature for 30 minutes. Neutralization with 4M hydrogen chloride in 1,4-dioxane followed by concentration and column chromatography on silica (1:1 hexane/ethyl acetate) provided 141 mg (74%) of 1,4:3,6-dianhydro-2-deoxy-2-methylidene-D-arabino-hexitol as a colorless solid. $^1$H NMR (400 MHz; $CDCl_3$): 5.37 (m, 1H), 5.20 (m, 1H), 4.80 (m, 1H), 4.54 (m, 2H), 4.43 (m, 1H), 4.26 (m, 1H), 3.95 (dd, 1H), 3.54 (dd, 1H), 2.70 (d, 1H).

1,4:3,6-dianhydro-2-deoxy-2-methylidene-5-O-(methylsulfonyl)-D-arabino-hexitol: To a solution of 1,4:3,6-dianhydro-2-deoxy-2-methylidene-D-arabino-hexitol (135 mg, 0.95 mmol) and triethylamine (288 mg, 2.85 mmol) in dichloromethane (10 mL) was added methanesulfonyl chloride (222 mg, 1.94 mmol) at 0° C. under nitrogen. The solution was warmed to room temperature and stirred for 18 h. Dichloromethane (50 mL) was added and the organic layer was washed with saturated aqueous sodium bicarbonate (2×25 mL), water (25 mL) and brine (25 mL) then dried over anhydrous sodium sulfate. Filtration and concentration provided 213 mg (72%) of 1,4:3,6-dianhydro-2-deoxy-2-methylidene-5-O-(methylsulfonyl)-D-arabino-hexitol as a yellow oil. $^1$H NMR (400 MHz; $CDCl_3$): 5.40 (m, 1H), 5.23 (m, 1H), 5.04 (m, 1H), 4.85 (m, 1H), 4.73 (t, 1H), 4.58 (m, 1H), 4.41 (m, 1H), 4.08 (dd, 1H), 3.86 (dd, 1H), 3.14 (s, 3H).

Example 57

1,4:3,6-dianhydro-2-deoxy-5-O-(phenylcarbonyl)-L-arabino-hex-1-enitol: To a mixture of 1,4:3,6-dianhydro-5-O-(phenylcarbonyl)-(D)-glycitol (4.32 g, 17.3 mmol), triethylamine (4.91 mL, 35.3 mmol) and 4-dimethylaminopyridine (0.63 g, 5.2 mmol) in dichloromethane (50 mL) at −10° to −15° was added trifluoromethanesulfonic anhydride (3.48 mL, 20.7 mmol) dropwise over ten minutes and the resulting mixture was stirred at this temperature for 3 hours. The mixture was poured into 100 mL of ice-water and extracted with dichloromethane (3×50 mL). The combined organic layers were washed with brine, dried over anhydrous sodium sulfate, filtered then concentrated. The crude triflate was suspended in toluene (50 mL) followed by addition of 1,8-diazabicyclo[4,5,0]undec-7-ene (5.25 mL, 34.6 mmol) and the mixture was stirred at room temperature for 18 hours. The reaction mixture was poured into ice-water and partitioned then the aqueous portion was extracted with dichloromethane (3×50 mL). The combined organic portion was washed with brine, dried over anhydrous sodium sulfate, filtered and concentrated. The residue was purified by flashed chromatography (silica gel, 5-20% ethyl acetate-hexane) to give 1,4:3,6-dianhydro-2-deoxy-5-O-(phenylcarbonyl)-L-arabino-hex-1- enitol, as a white solid, 3.10 g, 77% yield. $^1$H NMR (400 MHz; CDCl$_3$): 8.08-8.06 (m, 2H), 7.61-7.57 (m, 1H), 7.56-7.43 (m, 2H), 6.62-6.61 (d, 1H), 5.48-5.46 (m, 1H), 5.32-5.26 (m, 1H), 5.13-5.10 (m, 2H), 4.18-4.14 (tr, 1H), 3.61-3.56 (tr, 1H).

Example 58

Methyl 3,6-anhydro-5-O-(phenylcarbonyl)-β-L-glucofuranoside: To a solution of 1,4:3,6-dianhydro-2-deoxy-5-O-(phenylcarbonyl)-L-arabino-hex-1-enitol (1.00 g, 4.3 mmol) in methanol (17 mL) at −4° C. was added 3-chloroperoxybenzoic acid (85%, 1.35 g, 8.6 mmol), and the resulting mixture was slowly warmed to room temperature and stirred for 18 hours. The reaction mixture was concentrated, diluted with dichloromethane (50 mL), washed with saturated aqueous sodium bicarbonate solution, dried over sodium sulfate, filtered and concentrated. The residue was purified by flash chromatography (silica gel, 25-60% ethyl acetate-hexane) to give methyl 3,6-anhydro-5-O-(phenylcarbonyl)-β-L-glucofuranoside as a white solid, 1.03 g, 83% yield. $^1$H NMR (400 MHz; CDCl$_3$): 8.11-8.08 (d, 2H), 7.61-7.56 (tr, 1H), 7.48-7.44 (m, 2H), 5.24-5.17 (m, 2H), 4.96 (s, 1H), 4.57-4.56 (d, 1H), 4.27 (s, 1H), 4.22-4.18 (dd, 1H), 4.08-4.04 (dd, 1H) 3.36 (s, 3H).

Methyl 3,6-anhydro-2-O-methyl-5-O-(phenylcarbonyl)-β-L-glucofuranoside: A mixture of methyl 3,6-anhydro-5-O-(phenylcarbonyl)-β-L-glucofuranoside (1.03 g, 3.7 mmol), silver (I) oxide (0.85 g, 3.7 mmol) and methyl iodide (0.34 mL, 5.5 mmol) in DMF (2 mL) was heated at 60° C. for 1 hour. After cooling to room temperature the reaction mixture was diluted with ethyl acetate (50 mL), filtered over celite, adsorbed on silica gel (10 g) and purified by flash chromatography (silica gel, 5-30% ethyl acetate-hexane) to give methyl 3,6-anhydro-2-O-methyl-5-O-(phenylcarbonyl)-β-L-glucofuranoside as a colorless oil, 0.82 g, 76% yield. $^1$H NMR (400 MHz; CDCl$_3$): 8.11-8.09 (d, 2H), 7.60-7.56 (m, 1H), 7.46-7.44 (m, 2H), 5.24-5.20 (m, 1H), 5.18-5.09 (tr, 1H), 4.99 (s, 1H), 4.61-4.60 (d, 1H), 4.21-4.17 (tr, 1H), 4.08-4.03 (tr, 1H), 3.81 (s, 1H), 3.40 (s, 3H), 3.57 (s, 3H).

Methyl 3,6-anhydro-2-O-methyl-α-D-idofuranoside: A solution of methyl 3,6-anhydro-2-O-methyl-5-O-(phenylcarbonyl)-β-L-glucofuranoside (820 mg, 3.1 mmol) and 50% sodium hydroxide (248 mg, 3.1 mmol) in methanol (10 mL) was stirred at room temperature for 30 minutes. The material was adsorbed on silica gel (5 g) and passed through a short column (15% ethyl acetate in hexanes to 5% methanol in ethyl acetate) to give methyl 3,6-anhydro-2-O-methyl-α-D-idofuranoside as a colorless oil, 420 mg, 85% yield. $^1$H NMR (400 MHz; CDCl$_3$): 5.04 (s, 1H), 5.84-5.81 (tr, 1H), 4.44-4.42 (tr, 1H), 4.25-4.19 (m, 1H), 3.85-3.75 (m, 1H), 3.49 (s, 3H), 3.43 (s, 3H), 2.75-2.72 (d, 1H).

Methyl 3,6-anhydro-2-O-methyl-5-O-(methylsulfonyl)-B-L-glucofuranoside: Methyl 3,6-anhydro-2-O-methyl-α-D-idofuranoside (420 mg, 2.6 mmol) was dissolved in dichloromethane (10 mL) and pyridine (0.36 mL, 3.7 mmol) at 0° C. Methanesulfonyl chloride (0.14 mL, 3.1 mmol) was added and the resulting mixture was stirred at 0° C. for 1 hour then at room temperature for 2 hours. The reaction mixture was washed with water and saturated aqueous sodium bicarbonate solution, dried over anhydrous sodium sulfate, filtered and concentrated to give methyl 3,6-anhydro-2-O-methyl-5-O-(methylsulfonyl)-β-L-glucofuranoside as a colorless oil, 669 mg, 95% yield, which was used without further purification.

Example 59

3,6-anhydro-5-O-(phenylcarbonyl)-α-L-glucofuranose: A mixture of osmium tetroxide (4% in water, 0.25 mL, 0.03 mmol) and N-methylmorpholine (505 mg, 4.3 mmol) in 3 mL of 50% acetone in water was warmed to 60° C. A solution of 1,4:3,6-dianhydro-2-deoxy-5-O-(phenylcarbonyl)-L-arabino-hex-1-enitol (2.00 g, 8.6 mmol) in 6 mL of 50% acetone in water was added over 3 hours. During this time an additional amount of N-methylmorpholine (1.01 g, 8.6 mmol) was added in small portions periodically. Upon completion of the addition process the reaction was stirred for another hour and cooled to room temperature. The crude mixture was applied to a column of silica gel and flashed (0-6% methanol in 1:1 ethyl acetate:hexane) to give 3,6-anhydro-5-O-(phenylcarbonyl)-α-L-glucofuranose as a white solid, 1.5 g, 65% yield. $^1$H NMR (400 MHz; DMSO-d$_6$): 8.01-7.95, (m, 2H), 7.68-7.66 (m, 1H), 7.57-7.53 (m, 2H), 5.18-5.11 (m, 2H), 4.85-4.81 (m, 1H, m), 4.37-4.35 (m, 1H), 4.05-3.96 (m, 2H), 3.85-3.83 (m, 1H).

3,6-anhydro-2-O-methyl-5-O-(phenylcarbonyl)-α-L-glucofuranoside: 3,6-Anhydro-5-O-(phenylcarbonyl)-α-L-glucofuranose (576 mg, 2.2 mmol) was added to a mixture of sodium hydride (60% oil dispersion, 346 mg, 8.7 mmol) and methyl iodide (0.54 mL, 8.7 mmol) in 5 mL of DMF at 0° C. and the resulting mixture was stirred for 1 hour. The reaction mixture was diluted with ethyl acetate and quenched with water (5 mL). The aqueous portion was extracted with ethyl acetate (3×5 mL). The combined organic portion was washed with brine, dried over anhydrous sodium sulfate, filtered, and concentrated. The residue was purified by flashed chromatography (silica gel, 5-20% ethyl acetate in hexane) to give 3,6-anhydro-2-O-methyl-5-O-(phenylcarbonyl)-α-L-glucofuranoside as a white solid, 270 mg, 42% yield. $^1$H NMR (400 MHz; CDCl$_3$): 8.09-8.07 (m, 2H), 7.61-7.57 (m, 1H), 7.48-7.27 (m, 2H), 5.25-5.22 (m, 1H), 5.07-5.06 (d, 1H), 4.94-4.91 (m, 1H), 4.73-4.71 (m, 1H), 4.20-4.16 (m, 1H), 3.96-3.94 (m, 1H), 3.85-3.83 (tr, 1H), 3.50 (s, 3H), 3.42 (s, 3H).

Methyl 3,6-anhydro-2-O-methyl-5-O-(methylsulfonyl)-α-L-glucofuranoside: A solution of methyl 3,6-anhydro-2-O-methyl-5-O-(phenylcarbonyl)-α-L-glucofuranoside (230 mg, 0.92 mmol) and 50% sodium hydroxide (74 mg, 0.92 mmol) in methanol (5 mL) was stirred at room temperature for 30 minutes. The mixture was adsorbed on silica gel (2 g) and passed through a short column (15% ethyl acetate in hexanes to 5% methanol in ethyl acetate) to afford a colorless oil which was employed directly in the next step, 140 mg, 0.72 mmol, 95% yield. The alcohol was dissolved in dichloromethane (5 mL) and pyridine (121 μL, 1.03 mmol) was added at 0° C. Methanesulfonyl chloride (27 μL, 0.88 mmol) was added and the resulting mixture was stirred at 0° C. for 1 hour then at room temperature for 2 hours. The reaction mixture was washed with water and saturated aqueous sodium bicarbonate solution, dried over sodium sulfate, filtered and concentrated to give methyl 3,6-anhydro-2-O-methyl-5-O-(methylsulfonyl)-α-L-glucofuranoside as a colorless oil, 190 mg, 96% yield.

Example 60

3,6-Anhydro-1,2-O-(1-methylethylidene)-5-O-(phenylcarbonyl)-α-L-gluco-furanose: A mixture of 3,6-anhydro-5-O-(phenylcarbonyl)-α-L-gluco-furanose (1.00 g), 2,2-dimethoxy propane (0.63 mL), p-toluenesulfonic acid (20 mg) and benzene (10 mL) was heated at reflux for 3 hours. The reaction mixture was cooled then adsorbed on silica gel (10 g) and purified by flash chromatography (silica gel, 5-35% ethyl acetate in hexanes) to give 3,6-anhydro-1,2-O-(1-methylethylidene)-5-O-(phenylcarbonyl)-α-L-glucofuranose as colorless oil, 0.85 g, 74% yield. $^1$H NMR (400 MHz; CDCl$_3$): 8.08-8.06 (d, 2H), 7.59-7.56 (tr, 1H), 7.46-7.42 (m, 2H), 5.99-5.98 (d, 1H), 5.35-5.31 (tr, 1H), 5.10-5.08 (d, 1H), 4.66-4.65 (d, 1H), 4.61-4.60 (d, 1H), 4.20-4.16 (dd, 1H), 3.91-3.74 (tr, 1H), 1.50 (s, 3H), 1.34 (s, 3H).

3,6-Anhydro-1,2-O-(1-methylethylidene)-5-O-(methylsulfonyl)-α-L-gluco-furanose: A solution of 3,6-anhydro-1,2-O-(1-methylethylidene)-5-O-(phenylcarbonyl)-α-L-glucofuranose (850 mg) and 50% sodium hydroxide (111 mg) in methanol (10 mL) was stirred at room temperature for 30 minutes. The mixture was then adsorbed on silica gel (5 g) and passed through a short column (15% ethyl acetate in hexanes to 5% methanol in ethyl acetate) and the alcohol intermediate, 390 mg, 70% yield, was used immediately in the next step. The alcohol was dissolved in dichloromethane (10 mL) and pyridine (0.32 mL) at 0° C. Methanesulfonyl chloride (0.12 mL) was added and the resulting mixture was stirred at 0° C. for 1 hour then at room temperature for 2 hours. The reaction mixture was washed with water and saturated aqueous sodium bicarbonate solution, dried over anhydrous sodium sulfate, filtered and concentrated to give 3,6-anhydro-1,2-O-(1-methylethylidene)-5-O-(methylsulfonyl)-α-L-glucofuranose as a colorless oil, 485 mg, 90% yield, which was immediately employed in the next step.

Example 61

(3S,8aS)-3-(Chloromethyl)hexahydro-1H-pyrrolo[2,1-c][1,4]oxazine: (S)-(+)-Prolinol (6.00 g, 59.3 mmol) was added to epichlorohydrin (47 mL, 600 mmol) at 0° C. The solution was stirred at 40° C. for 0.5 h and then concentrated in vacuo. The residual oil was cooled in an ice bath and concentrated sulfuric acid (18 mL) was added dropwise with stirring. The mixture was heated at 170-180° C. for 1.5 h, poured into ice (300 mL) and then basified with sodium carbonate to pH~8. The mixture was partitioned with ethyl acetate/hexanes and filtered. The filtrate was separated and the aqueous portion was extracted twice with ethyl acetate. The combined organic portion was dried over sodium sulfate, filtered and concentrated in vacuo to afford oil that was purified by column chromatography (ethyl acetate for less polar product and then 30% methanol in ethyl acetate). (3S,8aS)-3-(Chloromethyl)hexahydro-1H-pyrrolo[2,1-c][1,4]oxazine (less polar product) (1.87 g, 10.7 mmol, 18% yield): $^1$H NMR (400 MHz, CDCl$_3$): 4.06 (dd, 1H), 3.79-3.71 (m, 1H), 3.60-3.48 (m, 2H), 3.36 (dd, 1H), 3.15 (dd, 1H), 3.13-3.06 (m, 1H), 2.21-2.01 (m, 3H), 1.90-1.68 (m, 3H), 1.39-1.24 (m, 1H); MS (EI) for C$_8$H$_{14}$NOCl: 176 (MH$^+$). (3R,8aS)-3-(Chloromethyl)hexahydro-1H-pyrrolo[2,1-c][1,4]oxazine (1.54 g, 3.77 mmol, 15% yield): $^1$H NMR (400 MHz, CDCl$_3$): 3.94-3.77 (m, 4H), 3.55 (dd, 1H), 3.02-2.93 (m, 2H), 2.45 (dd, 1H), 2.29-2.15 (m, 2H), 1.88-1.64 (m, 3H), 1.49-1.38 (m, 1H); MS (EI) for C$_8$H$_{14}$NOCl: 176 (MH$^+$).

Using the same or analogous synthetic techniques and/or substituting with alternative starting materials, the following were prepared:

(3R,8aR)-3-(Chloromethyl)hexahydro-1H-pyrrolo[2,1-c][1,4]oxazine: $^1$H NMR (400 MHz, CDCl$_3$): 4.05 (dd, 1H), 3.79-3.70 (m, 1H), 3.61-3.48 (m, 2H), 3.35 (dd, 1H), 3.15 (dd, 1H), 3.13-3.07 (m, 1H), 2.21-2.01 (m, 3H), 1.89-1.67 (m, 3H), 1.39-1.25 (m, 1H); MS (EI) for C$_8$H$_{14}$NOCl: 176 (MH$^+$).

(3S,8aR)-3-(Chloromethyl)hexahydro-1H-pyrrolo[2,1-c][1,4]oxazine: $^1$H NMR (400 MHz, CDCl$_3$): 3.93-3.77 (m, 4H), 3.55 (dd, 1H), 3.02-2.93 (m, 2H), 2.45 (dd, 1H), 2.30-2.15 (m, 2H), 1.88-1.64 (m, 3H), 1.49-1.37 (m, 1H); MS (EI) for C$_8$H$_{14}$NOCl: 176 (MH$^+$).

Example 62

(3S,8aS)-Hexahydro-1H-pyrrolo[2,1-c][1,4]oxazin-3-ylmethyl acetate: (3S,8aS)-3-(Chloromethyl)hexahydro-1H-pyrrolo[2,1-c][1,4]oxazine (2.30 g, 13.1 mmol) and potassium acetate (12.8 g, 131 mmol) were stirred in dimethylfomamide (25 mL) at 140° C. for 20 h. The mixture was partitioned between ethyl acetate and water. The organic portion was washed twice with water, then with brine, dried over sodium sulfate, filtered and concentrated in vacuo to afford (3S,8aS)-hexahydro-1H-pyrrolo[2,1-c][1,4]oxazin-3-ylmethyl acetate as a brown oil (2.53 g, 12.7 mmol, 97% yield). $^1$H NMR (400 MHz, CDCl$_3$): 4.14-4.02 (m, 3H), 3.81-3.72 (m, 1H), 3.37-3.31 (m, 1H), 3.09 (dt, 1H), 3.00 (dd, 1H), 2.21-2.00 (m, 3H), 2.10 (s, 3H), 1.90-1.67 (m, 3H), 1.39-1.24 (m, 1H); MS (EI) for C$_{10}$H$_{17}$NO$_3$: 200 (MH$^+$).

(3S,8aS)-Hexahydro-1H-pyrrolo[2,1-c][1,4]oxazin-3-ylmethanol: (3S,8aS)-Hexahydro-1H-pyrrolo[2,1-c][1,4]oxazin-3-ylmethyl acetate (2.36 g, 11.9 mmol) was treated with sodium methoxide (25 wt % solution in methanol; 2.7 mL) for 0.5 h. The mixture was cooled in an ice bath and a solution of 4M HCl in 1,4-dioxane (3 mL, 12.0 mmol) was added slowly. The mixture was stirred at room temperature for 5 minutes and then was concentrated in vacuo to afford a suspension which was diluted with dichloromethane, filtered and the filtrate was concentrated in vacuo to afford (3S,8aS)-hexahydro-1H-pyrrolo[2,1-c][1,4]oxazin-3-ylmethanol as a brown oil (1.93 g, >100% yield). $^1$H NMR (400 MHz, CDCl$_3$): 4.05 (dd, 1H), 3.73-3.65 (m, 2H), 3.62-3.56 (m, 1H), 3.39-3.34 (m, 1H), 3.10 (dt, 1H), 3.00-2.95 (m, 1H), 2.24-1.98 (m, 4H), 1.97-1.70 (m, 3H), 1.44-1.28 (m, 1H); MS (EI) for C$_8$H$_{15}$NO$_2$: 158 (MH$^+$).

(3S,8aS)-hexahydro-1H-pyrrolo[2,1-c][1,4]oxazin-3-ylmethyl methanesulfonate: (3S,8aS)-Hexahydro-1H-pyrrolo[2,1-c][1,4]oxazin-3-ylmethanol (1.00 g, 6.37 mmol) was dissolved in dichloromethane (10 mL) and triethylamine (2.4 mL, 17.3 mmol) was added at 0° C. followed by dropwise addition of methanesulfonyl chloride (0.93 mL, 12.0 mmol). The solution was warmed to room temperature and stirred for 1.25 h and then was concentrated in vacuo. The residue was partitioned between ethyl acetate and saturated sodium bicarbonate solution. The organic portion was washed with saturated sodium bicarbonate solution. The combined aqueous portion was extracted with ethyl acetate. The combined organic portion was washed with brine, dried over sodium sulfate, filtered and concentrated in vacuo to afford (3S,8aS)-hexahydro-1H-pyrrolo[2,1-c][1,4]oxazin-3-ylmethyl methanesulfonate as an orange-brown oil (1.20 g, 5.1 mmol, 80% yield). MS (EI) for C$_9$H$_{17}$NO$_4$S: 236 (MH$^+$).

Example 63

Octahydro-2H-quinolizin-3-ylmethanol: Ethyl octahydro-2H-quinolizine-3-carboxylate (2.35 g, 11.1 mmol) was added dropwise to a stirred suspension of lithium aluminum hydride (1 M solution in tetrahydrofuran, 33 mL, 33 mmol) in tetrahydrofuran (50 mL) at 0° C. The reaction was stirred at room temperature for 3 h. The mixture was cooled in an ice bath and ethyl acetate (6 mL) was added slowly, followed by water (1.25 mL), 15% aqueous sodium hydroxide solution (5 mL) and water (1.25 mL). The mixture was filtered through a pad of celite and washed with ether. The filtrate was concentrated in vacuo and dried rigorously to afford octahydro-2H-quinolizin-3-ylmethanol as a yellow oil (1.66 g, 9.82 mmol, 88% yield). MS (EI) for $C_{10}H_{19}NO$: 170 (MH$^+$).

Octahydro-2H-quinolizin-3-ylmethyl methanesulfonate: Octahydro-2H-quinolizin-3-ylmethanol (600 mg, 3.55 mmol) was dissolved in dichloromethane (8 mL) and triethylamine (1.5 mL, 10.8 mmol) was added at 0° C. followed by dropwise addition of methanesulfonyl chloride (0.56 mL, 7.16 mmol). The solution was warmed to room temperature and stirred for 1.25 h and then was concentrated in vacuo. The residue was partitioned between ethyl acetate and saturated sodium bicarbonate solution. The aqueous portion was extracted with ethyl acetate. The combined organic portion was washed with brine, dried over sodium sulfate, filtered and concentrated in vacuo to afford octahydro-2H-quinolizin-3-ylmethyl methanesulfonate as an orange oil (796 mg, 3.22 mmol, 91% yield). MS (EI) for $C_{11}H_{21}NO_3S$: 248 (MH$^+$).

Example 64

(3S,8aS)-3-(Hydroxymethyl)hexahydropyrrolo[1,2-a]pyrazin-1(2H)-one: A solution of methyl 1-[(2S)-3-hydroxy-2-({[(phenylmethyl)oxy]carbonyl}amino)propyl]-L-prolinate (3.50 g, 10.4 mmol) in methanol was added to 5% palladium on carbon (50 wt. % in water) in methanol and treated with hydrogen at 40 psi for 1 h. The mixture was filtered and the filtrate was brought to reflux briefly and then cooled and concentrated in vacuo to afford (3S,8aS)-3-(hydroxymethyl)hexahydropyrrolo[1,2-a]pyrazin-1(2H)-one as a colorless solid (1.50 g, 8.83 mmol, 85% yield). $^1$H NMR (400 MHz, CDCl$_3$): 7.28-7.22 (m, 1H), 3.83-3.75 (m, 1H), 3.69 (dd, 1H), 3.56 (dd, 1H), 3.31 (t, 1H), 3.08 (dd, 1H), 2.92 (dt, 1H), 2.76-2.70 (m, 1H), 2.66 (dd, 1H), 2.28-2.16 (m, 1H), 2.02-1.73 (m, 3H); MS (EI) for $C_8H_{14}N_2O_2$: 171 (MH$^+$).

(3S,8aS)-3-({[(1,1-Dimethylethyl)(dimethyl)silyl]oxy}methyl)hexahydro-pyrrolo[1,2-a]pyrazin-1(2H)-one: To a solution of (3S,8aS)-3-(hydroxymethyl) hexahydropyrrolo[1,2-a]pyrazin-1(2H)-one (1.49 g, 8.82 mmol) in dimethylformamide (20 mL) was added triethylamine (2.45 mL, 17.6 mmol) and 4-dimethylaminopyridine (90 mg, 0.882 mmol). The solution was cooled in an ice bath and tert-butyldimethylsilyl chloride (2.66 g, 17.6 mmol) was added. The mixture was warmed to room temperature and stirred for 14 h. The mixture was concentrated in vacuo and the residue was partitioned between ethyl acetate and water. The aqueous portion was extracted twice with ethyl acetate. The combined organic portion was dried over sodium sulfate, filtered and concentrated in vacuo to afford a pale brown solid which was triturated with ethyl acetate to afford (3S,8aS)-3-({[(1,1-dimethylethyl)(dimethyl)silyl]oxy}methyl) hexahydropyrrolo[1,2-a]pyrazin-1(2H)-one as an off-white solid (1.74 g, 5.84 mmol, 66% yield). $^1$H NMR (400 MHz, CDCl$_3$): 6.09-5.90 (m, 1H), 3.86-3.76 (m, 1H), 3.63 (dd, 1H), 3.44 (dd, 1H), 3.25 (t, 1H), 3.10 (ddd, 1H), 2.98-2.90 (m, 1H), 2.68-2.60 (m, 1H), 2.52 (dd, 1H), 2.28-2.18 (m, 1H), 2.06-1.95 (m, 1H), 1.93-1.74 (m, 2H), 0.90 (s, 9H), 0.07 (s, 6H); MS (EI) for $C_{14}H_{28}N_2O_2Si$: 285 (MH$^+$).

(3S,8aS)-3-({[(1,1-Dimethylethyl)(dimethyl)silyl]oxy}methyl)-2-methylhexahydro pyrrolo[1,2-a]pyrazin-1 (2H-one: (3S,8aS)-3-({[(1,1-Dimethylethyl)(dimethyl)silyl]oxy}methyl)hexahydropyrrolo[1,2-a]pyrazin-1(2H)-one (1.51 g, 5.32 mmol) in dimethylfomamide (8 mL) was added to an ice-cooled suspension of sodium hydride (60 wt. % dispersion in oil; 213 mg, 5.32 mmol) in dimethylformamide (8 mL). The mixture was stirred at 0° C. for 0.25 h and then iodomethane (0.332 mL, 5.32 mmol) was added dropwise. The mixture was stirred at room temperature for 0.5 h and then was stirred at 70° C. for 2 h. The mixture was concentrated in vacuo and the residue was partitioned between ethyl acetate and water. The aqueous portion was extracted with ethyl acetate. The combined organic portion was dried over sodium sulfate, filtered and concentrated in vacuo to afford (3S,8aS)-3-({[(1,1-dimethylethyl)(dimethyl)silyl]oxy}methyl)-2-methylhexahydropyrrolo[1,2-a]pyrazin-1 (2H)-one as a yellow oil (1.552 g, 5.21 mmol) which was dissolved in tetrahydrofuran (20 mL) and treated with tetrabutylammonium fluoride (1.0M solution in tetrahydrofuran; 10.4 mL, 10.4 mmol) for 2 h at room temperature. The mixture was concentrated in vacuo and purified by column chromatography (10% methanol in dichloromethane) to afford (3S,8aS)-3-(hydroxymethyl)-2-methylhexylhydropyrrolo[1,2-a]pyrazin-1(2H)-one as a yellow oil (496 mg, 2.70 mmol, 51% yield from (3S,8aS)-3-({[(1,1-dimethylethyl)(dimethyl)silyl]oxy}methyl)hexylhydropyrrolo[1,2-a]pyrazin-1(2H)-one). $^1$H NMR (400 MHz, CDCl$_3$): 3.98-3.93 (m, 1H), 3.86 (dd, 1H), 3.61-3.55 (m, 1H), 3.29-3.25 (m, 1H), 3.09-3.03 (m, 1H), 3.03-2.97 (m, 1H), 3.02 (s, 3H), 2.93 (dd, 1H), 2.87-2.79 (m, 1H), 2.32-2.21 (m, 1H), 2.00-1.86 (m, 2H), 1.83-1.64 (m, 1H); MS (EI) for $C_9H_{16}N_2O_2$: 185 (MH$^+$).

Example 65

1,2-Dideoxy-1-[(2S)-2-(methoxycarbonyl)-1-pyrrolidinyl]-2-[[(phenylmethoxy) carbonyl]amino]-D-glycero-hexitol: To a solution of 2-deoxy-2-{[(phenylethyloxy) carbonyl]amino}-D-glycero-hexopyranose (5.0 g, 0.016 mol) in methanol (500 mL) was added L-proline methyl ester hydrochloride (2.8 g, 0.022 mol) and sodium cyanoborohydride (3.4 g, 0.054 mol). The solution was heated to 64° C. for 14 h. After cooling to room temperature, the reaction mixture was concentrated in vacuo to afford 1,2-dideoxy-1-[(2S)-2-(methoxycarbonyl)-1-pyrrolidinyl]-2-[[(phenylmethoxy) carbonyl]amino]-D-glycero-hexitol (6.81 g, 100%) as a clear and colorless oil. MS (EI) for $C_{20}H_{31}N_2O_8$: 427 (MH$^+$).

Example 66

Methyl 1-[(2S)-3-hydroxy-2-({[(phenylmethyl)oxy]carbonyl}amino)propyl]-L-prolinate: 1,2-dideoxy-1-[(2S)-2-(methoxycarbonyl)-1-pyrrolidinyl]-2-[[(phenylmethoxy) carbonyl]amino]-D-glycero-hexitol (6.81 g, 0.016 mol) was taken into water (100 mL) and the resulting solution was cooled to 0° C. Sodium periodiate (14.8 g, 0.069 mol) dissolved in water was added dropwise and the resulting mixture was stirred at 0° C. for 2 h. The reaction mixture was partitioned with dichloromethane (3×100 mL), dried over anhydrous magnesium sulfate, filtered and concentrated in vacuo. The residue was taken up in methanol (200 mL) and the resulting solution was cooled to 0° C. Sodium borohydride (1.98 g, 0.052 mol) was added and the reaction mixture was stirred for 1 h at 0° C. The reaction mixture was concentrated in vacuo and partitioned with dichloromethane and saturated aqueous ammonium chloride. The organic layer was dried over anhydrous magnesium sulfate, filtered and concentrated in vacuo. The resulting crude product was purified by column chromatography (5% methanol in dichloromethane) to yield methyl 1-[(2S)-3-hydroxy-2-({[(phenylmethyl)oxy]carbonyl}amino)propyl]-L-prolinate (4.9 g, 92%) as a white solid. MS (EI) for $C_{17}H_{25}N_2O_5$: 337 (MH$^+$).

Methyl 1-[(2S)-3-[(methylsulfonyl)oxy]-2-({[(phenylmethyl)oxy]carbonyl}amino) propyl]-L-prolinate: Methyl 1-[(2S)-3-hydroxy-2-({[(phenylmethyl)oxy] carbonyl}amino) propyl]-L-prolinate (200 mg, 0.594 mmol)

was dissolved in dichloromethane (5 mL) followed by the addition of 4-(dimethylamino)pyridine (3.6 mg, 0.039 mmol) and triethylamine (0.125 mL, 0.891 mmol) and the resulting mixture was cooled to 0° C. Methanesulfonyl chloride (0.060 mL, 0.773 mmol) was added dropwise and the reaction mixture was stirred for 1 h at 0° C. The mixture was partitioned between dichloromethane and saturated aqueous sodium bicarbonate. The organic layer was dried over anhydrous magnesium sulfate, filtered and concentrated in vacuo to afford methyl 1-[(2S)-3-[(methylsulfonyl)oxy]-2-({[(phenylmethyl)oxy]carbonyl}amino)propyl]-L-prolinate (246 mg, 100%) as a clear and colorless oil. MS (EI) for $C_{18}H_{27}N_2O_7S$: 415 (MH$^+$).

Example 67

1,1-Dimethylethyl (3aR,6aS)-5-(hydroxymethyl)hexahydrocyclopenta[c]pyrrole-2(1H)-carboxylate: Under a nitrogen atmosphere, borane tetrahydrofuran complex (1M in THF, 42 mL, 41.9 mmol) was diluted with tetrahydrofuran (42 mL) and cooled with an ice bath. Neat 2,3-dimethylbut-2-ene (5.0 mL, 41.9 mmol) was added in portions over 0.25 h and the solution was stirred at 0° C. for 3 h. A solution of 1,1-dimethylethyl (3aR,6aS)-5-methylidenehexahydrocyclopenta[c]pyrrole-2(1H)-carboxylate (1.98 g, 8.88 mmol) in tetrahydrofuran (10 mL) was added slowly, and the solution was warmed to room temperature and stirred 12 h. After cooling to 0° C., 10% aqueous sodium hydroxide (17 mL, 41.7 mmol) was added slowly, followed by 30% aqueous hydrogen peroxide (13 mL, 128 mmol) and the solution was warmed to room temperature. The solvent was removed in vacuo and the solution was partitioned between water and diethyl ether. The layers were separated and the aqueous layer was further extracted (3×50 mL diethyl ether). The combined organic layers were dried over anhydrous sodium sulfate, filtered and concentrated in vacuo to provide 2.04 (95%) of 1,1-dimethylethyl (3aR,6aS)-5-(hydroxymethyl)hexahydrocyclopenta[c]pyrrole-2(1H)-carboxylate, which was used without purification. $^1$H NMR (400 MHz, CDCl$_3$): 8.50 (broad s, 1H), 3.66-3.46 (m, 3H), 3.20-3.00 (m, 2H), 2.70-2.59 (m, 2H), 2.37-2.18 (m, 1H), 2.04 (m, 1H), 1.84 (broad s, 1H), 1.70-1.55 (m, 1H), 1.46 (s, 9H), 1.17 (m, 1H), 0.93 (m, 1H).

1,1-Dimethylethyl (3aR,6aS)-5-{[(methylsulfonyl)oxy]methyl}hexahydrocyclo-penta [c]pyrrole-2(1H)-carboxylate: Methanesulfonyl chloride (0.2 mL, 2.48 mmol), was added dropwise to a solution of 1,1-dimethylethyl (3aR,6aS)-5-(hydroxymethyl)hexahydro cyclopenta[c]pyrrole-2(1H)-carboxylate (0.40 g, 1.65 mmol) and triethylamine (0.69 mL, 4.95 mmol) in 20 mL dichloromethane at 0° C. and the reaction mixture was stirred for 1 h at room temperature. The solvent was evaporated, the resulting crude mixture was diluted with 100 mL ethyl acetate and washed with water (30 mL), 1M aqueous sodium hydroxide, brine, 1M aqueous hydrochloric acid and brine again. The organic layer was dried over anhydrous sodium sulfate, filtered and concentrated in vacuo. The resulting 1,1-dimethylethyl (3aR,6aS)-5-{[(methylsulfonyl)oxy]methyl}hexahydrocyclo-penta[c]pyrrole-2(1H)-carboxylate was used without further purification. MS (EI) for $C_{14}H_{25}NO_5S$: 320 (MH$^+$), 264 (M-tBu).

Example 68

1,1-Dimethylethyl (3aR,6aS)-5-(hydroxy)-hexahydrocyclopenta[c]-pyrrole-2(1H)-carboxylate: Sodium borohydride (0.15 g, 4.00 mmol), was added to a solution of 1,1-dimethylethyl (3aR,6aS)-5-oxo-hexahydrocyclopenta[c]pyrrole-2(1H)-carboxylate (0.45 g, 2.00 mmol) in 10 mL methanol at 0° C. and the reaction mixture was stirred for 1 h at this temperature. The solvent was evaporated, the crude mixture was diluted with 100 mL ethyl acetate and washed with water (30 mL), 1M aqueous hydrochloric acid and brine. The organic layer was dried over anhydrous sodium sulfate, filtered and concentrated to give 1,1-dimethylethyl (3aR,6aS)-5-(hydroxy)-hexahydrocyclopenta[c]pyrrole-2(1H)-carboxylate (0.44 g, 98%). $^1$H NMR (400 MHz, d$_6$-DMSO): 4.08 (m, 1H), 3.40 (m, 2H), 3.30 (m, 2H), 2.50 (m, 2H), 1.98 (m, 2H), 1.40 (s, 9H), 1.30 (m, 2H). MS (EI) for $C_{12}H_{21}NO_3$: 228 (MH$^+$).

1,1-Dimethylethyl (3aR,6aS)-5-{[(methylsulfonyl)oxy]}hexahydrocyclo-penta[c]pyrrole-2(1H)-carboxylate: Methanesulfonyl chloride (0.18 mL, 2.33 mmol), was added dropwise to a solution of 1,1-dimethylethyl (3aR,6 as)-5-(hydroxy)-hexahydrocyclopenta[c]pyrrole-2(1H)-carboxylate (0.44 g, 1.94 mmol) and triethylamine (0.81 mL, 5.81 mmol) in 10 mL dichloromethane at 0° C. and the reaction mixture was stirred for 1 h at room temperature. The solvent was evaporated, the resulting crude mixture was diluted with 100 mL ethyl acetate and washed with water (30 mL), brine, 1M aqueous hydrochloric acid and brine again. The organic layer was dried over anhydrous sodium sulfate, filtered and concentrated. The resulting crude 1,1-dimethylethyl (3aR,6aS)-5-{[(methylsulfonyl)oxy]}hexahydrocyclopenta[c]pyrrole-2(1H)-carboxylate was used without further purification. MS (EI) for $C_{13}H_{23}NO_5S$: 306 (MH$^+$).

Example 69

3-(Chloromethyl)hexahydro-1H-[1,4]oxazino[3,4-c][1,4] oxazine: A solution of (3R)-morpholin-3-ylmethanol (4.21 g, 36.0 mmol) in 2-(chloromethyl)oxirane (28.2 mL, 0.360 mol) was heated to 40° C. for 3 h and then the solution was concentrated in vacuo. The intermediate was cooled in an ice bath and treated with 30.0 mL of concentrated sulfuric acid. The mixture was heated to 170° C. for 2 h and then allowed to cool to room temperature. The mixture was poured into ice-water and solid sodium bicarbonate was carefully added until the solution was basic. 10% methanol in ethyl acetate was added and the biphasic mixture was filtered. The layers were separated and the aqueous layer was extracted (3×100 mL 10% methanol in ethyl acetate). The combined organic layers were dried over anhydrous sodium sulfate, filtered and concentrated in vacuo. Column chromatography (SiO$_2$, 2:5 hexanes: ethyl acetate) provided 3-(chloromethyl)hexahydro-1H-[1,4] oxazino[3,4-c][1,4]oxazine 2.44 g (35%) as two separated diastereomers. (3R,9aS)-3-(chloromethyl)hexahydro-1H-[1,4]oxazino[3,4-c][1,4]oxazine: (0.886 g, 13% yield): $^1$H NMR (400 MHz, CDCl$_3$): 3.91 (m, 3H), 3.82 (m, 1H), 3.68 (dt, 1H), 3.61 (dd, 1H), 3.47 (dd, 1H), 3.35 (t, 1H), 3.19 (t, 1H), 2.80 (d, 1H), 2.54 (m, 2H), 2.40 (m, 2H); MS (EI) for $C_8H_{14}NO_2Cl$: 192 (MH$^+$). (3S,9aS)-3-(chloromethyl) hexahydro-1H-[1,4]oxazino[3,4-c][1,4]oxazine: (1.55 g, 22% yield): $^1$H NMR (400 MHz, CDCl$_3$): 3.85 (m, 2H), 3.73 (m, 3H), 3.50 (m, 2H), 3.29 (t, 1H), 3.18 (t, 1H), 2.85 (dd, 1H), 2.64 (dd, 1H), 2.40 (m, 2H), 2.17 (t, 1H); MS (EI) for $C_8H_{14}NO_2Cl$: 192 (MH$^+$).

Hexahydro-1H-[1,4]oxazino[3,4-c][1,4]oxazin-3-ylmethyl acetate: A suspension of (3R,9aS)-3-(chloromethyl)hexahydro-1H-[1,4]oxazino[3,4-c][1,4]oxazine (1.97 g, 10.3 mmol) and potassium acetate (10.1 g, 102 mmol) in DMF (20.0 mL) was stirred at 140° C. for 16 h, and then at 150° C. for another 12 h. The reaction mixture was partitioned between water (250 mL) and ethyl acetate (250 mL), the organic layer was washed with 5% lithium chloride (2×100 mL) and brine (100 mL) then dried over anhydrous sodium sulfate and concentrated in vacuo. Column chromatography (SiO$_2$, 1:1 hexane:ethyl acetate, then 100% ethyl acetate) afforded 0.92 g (42%) of hexahydro-1H-[1,4]oxazino[3,4-c][1,4]oxazin-3-ylmethyl acetate as a yellow oil. Distinct diastereomers as described above were converted in this step to give: (3R,9aS)-hexahydro-1H-[1,4]oxazino[3,4-c][1,4]oxazin-3-ylmethyl acetate: $^1$H NMR (400 MHz, CDCl$_3$): 4.18 (dd, 1H), 4.00 (m, 1H), 3.80 (dd, 1H), 3.68 (dt, 1H), 3.60 (dd, 1H), 3.46 (m, 2H), 3.22 (t, 1H), 2.64 (dd, 1H), 2.53 (m, 2H), 2.43-2.35 (m, 2H), 2.10 (s, 3H), and (3S,9aS)-hexahydro-1H-[1,4]oxazino[3,4-c][1,4]oxazin-3-ylmethyl acetate: $^1$H NMR (400 MHz, CDCl$_3$): 4.09 (d, 2H), 3.90-3.82 (m, 2H), 3.75-3.64 (m, 3H), 3.27 (t, 1H), 3.18 (t, 1H), 2.69 (dd, 1H), 2.63 (m, 1H), 2.46-2.33 (m, 2H), 2.16 (t, 1H), 2.10 (s, 3H).

(3R,9aS)-Hexahydro-1H-[1,4]oxazino[3,4-c][1,4]oxazin-3-ylmethyl methane-sulfonate: To a solution of (3R,9aS)-hexahydro-1H-[1,4]oxazino[3,4-c][1,4]oxazin-3-ylmethyl acetate (0.922 g, 4.28 mmol) in methanol (14.0 mL) was added 1.03 mL (4.50 mmol) of sodium methoxide (25% wt. in methanol) dropwise at room temperature. After 5 min., 1.6 mL (6.43 mmol) of 4.0M hydrogen chloride in dioxane was added and a pink precipitate formed. The solution was concentrated in vacuo and the pink solid was taken up in 30.0 mL dichloromethane. This slurry was cooled in an ice bath and triethylamine (3.0 mL, 21.5 mmol) was added, followed by methanesulfonyl chloride (0.37 mL, 4.71 mmol). The resultant yellow solution was stirred for 30 minutes at room temperature. The mixture was then partitioned between dichloromethane and saturated aqueous sodium bicarbonate then the aqueous layer was extracted (3×50 mL dichloromethane). The combined organic layers were dried over anhydrous sodium sulfate, filtered and concentrated in vacuo to provide crude (3R,9aS)-hexahydro-1H-[1,4]oxazino[3,4-c][1,4]oxazin-3-ylmethyl methanesulfonate which was taken on to the following reaction without purification.

Example 70

(8aR)-6-(Chloromethyl)tetrahydro-1H-[1,3]thiazolo[4,3-c][1,4]oxazine: A solution of (4R)-1,3-thiazolidin-4-ylmethanol (0.300 g, 2.52 mmol) in 2-(chloromethyl)oxirane (2.0 mL, 25.5 mmol) was heated under nitrogen to 40° C. for 12 h. The solution was then cooled to room temperature and 2-(chloromethyl)oxirane was removed in vacuo. The crude intermediate was cooled in ice, and was taken up in 2.0 mL of concentrated sulfuric acid. The resulting mixture was heated to 200° C. for 0.5 h then poured carefully onto wet ice, which was allowed to melt. The aqueous solution was carefully made basic using solid sodium bicarbonate and the resulting mixture was filtered using water and 10% methanol in ethyl acetate as eluent. The layers were separated and the aqueous layer was extracted with 10% methanol in ethyl acetate. The combined organic layers were dried over anhydrous sodium sulfate, filtered, and concentrated in vacuo to give 11.6 mg (2.4% yield) of crude (8aR)-6-(chloromethyl)tetrahydro-1H-[1,3]thiazolo[4,3-c][1,4]oxazine as a mixture of diastereomers which was directly taken on to the next step.

Example 71

1,1-Dimethylethyl (3-endo)-3-{2-[(methylsulfonyl)oxy]ethyl}-8-azabicyclo[3.2.1]octane-8-carboxylate: To a solution of 1,1-dimethylethyl (3-endo)-3-(2-hydroxyethyl)-8-azabicyclo[3.2.1]octane-8-carboxylate (30.3 mg, 1.19 mmol) in dichloromethane (4.0 mL), was added triethylamine (0.5 mL, 3.56 mmol) and the solution was cooled to 0° C. under nitrogen. Methanesulfonyl chloride (0.11 mL, 1.42 mmol) was added slowly and mixture was allowed to warm to room temperature and stirred for 1 h. The reaction mixture was partitioned between dichloromethane and water. The aqueous phase was extracted with dichloromethane (2×100 mL). The combined organic layers were dried over anhydrous sodium sulfate, filtered and concentrated in vacuo to provide 35.1 mg (89%) of 1,1-dimethylethyl (3-endo)-3-{2-[(methylsulfonyl)oxy]ethyl}-8-azabicyclo[3.2.1]octane-8-carboxylate, which was carried forward for alkylation without purification.

Example 72

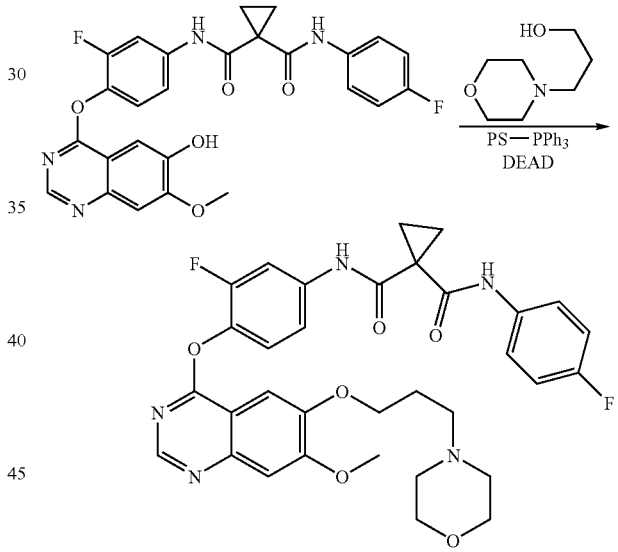

N-[3-Fluoro-4-({7-(methyloxy)-6-[(3-morpholin-4-yl-propyl)oxy]quinazolin-4-yl}oxy)phenyl]-N'-(4-fluorophenyl)cyclopropane-1,1-dicarboxamide. Crude cyclopropane-1,1-dicarboxylic acid [3-fluoro-4-(6-hydroxy-7-methoxy-quinazolin-4-yloxy)-phenyl]-amide (4-fluoro-phenyl)-amide (333 mg, 0.66 mmol), PS—PPh$_3$ resin, (loading=2.33 mmol/g, 797 mg, 1.86 mmol), 3-morpholin-4-yl-propan-1-ol (0.26 ml, 1.88 mmol), and DEAD (0.31 ml, 1.91 mmol) were combined in CH$_2$Cl$_2$ (10 ml) and stirred at room temperature for 1-2 hrs. The reaction mixture was filtered and the resin thoroughly washed with CH$_2$Cl$_2$. The filtrate was concentrated in vacuo and the resulting residue was dissolved in EtOAc and washed with H$_2$O (4×) and sat'd NaCl (1×) and then extracted with 1N HCl (3×). The combined 1N HCl extractions were washed with EtOAc (2×). The acidic aqueous phase was then basified with 1N NaOH and extracted with EtOAc (3×). The combined EtOAc extractions were washed with H$_2$O (1×), sat'd NaCl (1×), dried (Na$_2$SO$_4$), and concentrated in vacuo.

The resulting residue was purified by preparative reverse phase HPLC (25 mM NH$_4$OAc/acetonitrile) and the pure fractions were lyophilized to give cyclopropane-1,1-dicarboxylic acid {3-fluoro-4-[7-methoxy-6-(3-morpholin-4-yl-propoxy)-quinazolin-4-yloxy]-phenyl}-amide (4-fluoro-phenyl)-amide (42.6 mg, 10%). $^1$H NMR (400 MHz, DMSO-d6): δ 10.37 (br s, 1H), 10.05 (br s, 1H), 8.55 (s, 1H), 7.84 (m, 1H), 7.65 (m, 2H), 7.58 (s, 1H), 7.43 (m, 3H), 7.16 (t, 2H), 4.27 (m, 2H), 4.00 (s, 3H), 3.60 (m, 6H), 2.39 (m, 4H), 1.99 (m, 2H), 1.47 (m, 4H). LC/MS Calcd for [M+H]$^+$ 634.2, found 634.1.

Using the same or analogous synthetic techniques and/or substituting with alternative starting materials, the following were prepared:

N-{3-fluoro-4-[(7-(methyloxy)-6-{[(1-methylpiperidin-4-yl)methyl]oxy}quin-azolin-4-yl)oxy]phenyl}-N'-(4-fluorophenyl)cyclopropane-1,1-dicarboxamide: $^1$H NMR (400 MHz, CDCl$_3$): δ 9.67 (s, 1H), 8.59 (s, 1H), 8.43 (s, 1H), 7.75 (d, 1H), 7.52 (s, 1H), 7.46 (m, 2H), 7.31 (s, 1H), 7.20 (m, 2H), 7.06 (t, 2H), 4.04 (d, 2H), 4.03 (s, 3H), 2.98 (d, 2H), 2.34 (s, 3H), 2.12-2.1.95 (m, 5H), 1.76 (m, 2H), 1.64 (m, 2H), 1.57 (m, 2H).

Example 73

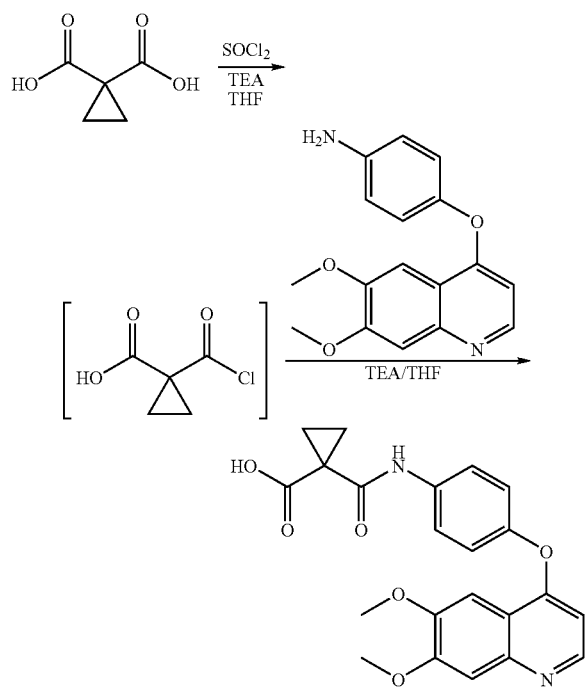

Preparation of 1-[4-(6,7-dimethoxy-quinolin-4-yloxy)-phenylcarbamoyl]-cyclopropanecarboxylic acid. To the cyclopropyl di-carboxylic acid (449 mg, 3.45 mmol) in THF (3.5 mL) was added TEA (485 μL, 3.45 mmol). The resulting solution was stirred at room temperature under a nitrogen atmosphere for 40 minutes before adding thionyl chloride (250 μL, 3.44 mmol). The reaction was monitored by LCMS for the formation of mono acid chloride (quenched the sample with MeOH and looked for corresponding mono methyl ester). After 3 hours stirring at room temperature, 4-(6,7-dimethoxy-quinolin-4-yloxy)-phenylamine (1.02 g, 3.44 mmol) was added as a solid, followed by more THF (1.5 mL).

Continued to stir at room temperature for 16 hours. The resulting thick slurry was diluted with EtOAc (10 mL) and extracted with 1N NaOH. The biphasic slurry was filtered and the aqueous phase was acidified with conc. HCl to pH=6 and filtered. Both solids were combined and washed with EtOAc, then dried under vacuum. The desired product, 1-[4-(6,7-dimethoxy-quinolin-4-yloxy)-phenylcarbamoyl]-cyclopropanecarboxylic acid, was obtained (962 mg, 68.7% yield, 97% pure) as a white solid. $^1$H NMR (D$_2$O/NaOH): 7.97 (d, 1H), 7.18 (d, 2H), 6.76 (m, 4H), 6.08 (d, 1H), 3.73 (s, 3H), 3.56 (s, 3H), 1.15 (d, 4H).

Example 74

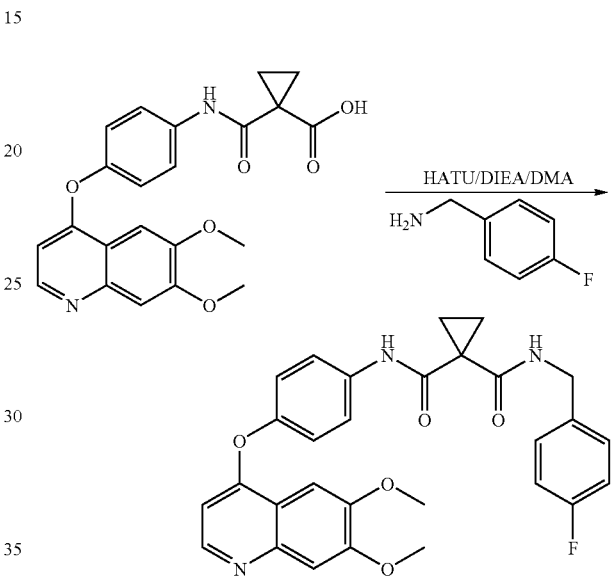

'N-(4-{[6,7-Bis(methyloxy)quinolin-4-yl]oxy}phenyl)-N'-[(4-fluorophenyl)methyl]cyclopropane-1,1-dicarboxamide. To a solution of 1-[4-(6,7-dimethoxy-quinolin-4-yloxy)-phenylcarbamoyl]-cyclopropanecarboxylic acid (74.3 mg, 0.182 mmol), 4-Fluoro benzylamine (25 μL, 0.219 mmol), DIEA (90.0 μL, 0.544 mmol) in DMA (1.0 mL) was added HATU (203 mg, 0.534 mmol). The resulting solution was stirred at room temperature for 1 hour before adding dropwise to water (10 mL) with stirring. The slurry was sonicated, filtered and the solids were washed with 1 N NaOH followed by water. After air drying, the solids were further purified by prep HPLC, affording 'N-(4-{[6,7-bis(methyloxy)quinolin-4-yl]oxy}phenyl)-N'-[(4-fluorophenyl)methyl]cyclopropane-1,1-dicarboxamide (33 mg, 35% yield, 98% pure) as a white solid. $^1$H NMR (DMSO, d$_6$): 10.82 (s, 1H), 8.80 (d, 1H), 8.50 (t, 1H), 7.83 (d, 2H), 7.74 (s, 1H), 7.56 (s, 1H), 7.30-7.38 (m, 4H), 7.15 (t, 2H), 6.80 (d, 1H), 4.32 (d, 2H), 4.04 (s, 3H), 4.03 (s, 3H), 1.42 (s, 4H).

The following compounds were prepared, in a similar manner as above, from the coupling of 1-[4-(6,7-dimethoxy-quinolin-4-yloxy)-phenylcarbamoyl]-cyclopropane carboxylic acid with a corresponding alkylamine or arylamine.

N-(4-{[6,7-Bis(methyloxy)quinolin-4-yl]oxy}phenyl)-N'-[2-(piperidin-1-ylmethyl)phenyl]cyclopropane-1,1-dicarboxamide. $^1$H NMR (DMSO-d6): 10.62 (s, 1H), 8.79 (d, 1H), 8.24 (t, 1H), 7.83 (d, 2H), 7.72 (s, 1H), 7.58 (s, 1H), 7.37 (d, 2H), 6.76 (d, 1H), 4.04 (s, 3H), 4.03 (s, 3H), 3.98 (m, 2H), 3.66 (m, 2H), 3.49 (m, 4H), 3.25 (t, 2H), 3.13 (br., 2H), 1.42 (d, 4H).

N-(4-{[6,7-Bis(methyloxy)quinolin-4-yl]oxy}phenyl)-N'-[2-(piperidin 1-ylmethyl)phenyl]cyclopropane-1,1-dicarboxamide. $^1$H NMR (DMSO-d6): 10.78 (s, 1H), 10.53 (s, 1H), 8.43 (d, 1H), 8.12 (d, 1H), 7.82 (d, 2H), 7.49 (s, 1H), 7.37 (s, 1H), 7.20-7.28 (m, 3H), 7.15 (dd, 1H), 7.01 (td, 1H), 6.35 (d, 1H), 3.93 (s, 3H), 3.92 (s, 3H), 3.47 (s, 2H), 2.17 (br., 4H), 1.49 (m, 4H), 1.41 (m, 4H), 1.32 (br., 2H).

'N-(4-{[6,7-Bis(methyloxy)quinolin-4-yl]oxy}phenyl)-N'-[2-(pyrrolidin-1-ylmethyl)phenyl]cyclopropane-1,1-dicarboxamide. $^1$H NMR (DMSO-d6): 10.98 (s, 1H), 10.56 (s, 1H), 8.42 (d, 1H), 8.10 (dd, 1H), 7.81 (m, 2H), 7.49 (s, 1H), 7.37 (s, 1H), 7.17-7.27 (m, 4H), 7.01 (td, 1H), 6.35 (d, 1H), 3.93 (s, 3H), 3.92 (s, 3H), 3.61 (s, 2H), 2.30 (br., 4H), 1.47 (br., 4H), 1.43 (m, 4H).

'N-(4-{[6,7-Bis(methyloxy)quinolin-4-yl]oxy}phenyl)-N'-[3-(morpholin-4-ylmethyl)phenyl]cyclopropane-1,1-dicarboxamide. $^1$H NMR (DMSO-d$_6$): 10.12 (s, 1H), 10.03 (s, 1H), 8.44 (d, 1H), 7.74 (d, 2H), 7.57 (s, 1H), 7.53 (d, 1H), 7.48 (s, 1H), 7.37 (s, 1H), 7.21 (m, 3H), 6.98 (d, 1H), 6.40 (d, 1H), 3.93 (s, 3H), 3.92 (s, 3H), 3.56 (t, 4H), 3.41 (s, 2H), 2.34 (br., 4H), 1.48 (s, 4H).

'N-(4-{[6,7-Bis(methyloxy)quinolin-4-yl]oxy}phenyl)-N'-[2-(morpholin-4-ylmethyl)phenyl]cyclopropane-1,1-dicarboxamide. $^1$H NMR (DMSO-d6): 10.54 (s, 1H), 10.47 (s, 1H), 8.43 (d, 1H), 8.08 (d, 1H), 7.78 (d, 2H), 7.49 (s, 1H), 7.37 (d, 1H), 7.18-7.30 (m, 4H), 7.03 (t, 1H), 6.37 (d, 1H), 3.94 (s, 3H), 3.93 (s, 3H), 3.50 (s, 2H), 3.44 (br., 4H), 2.20 (br., 4H), 1.48 (d, 4H).

'N-(4-{[6,7-Bis(methyloxy)quinolin-4-yl]oxy}phenyl)-N'-[3-(piperidin-1-ylmethyl)phenyl]cyclopropane-1,1-dicarboxamide. $^1$H NMR (DMSO-d6): 10.0-10.2 (br., 2H), 8.46 (d, 1H), 7.76 (d, 2H), 7.53 (m, 3H), 7.39 (s, 1H), 7.24 (m, 3H), 6.98 (d, 1H), 6.43 (d, 1H), 3.95 (s, 3H), 3.93 (s, 3H), 3.37 (s, 2H), 2.31 (br., 4H), 1.48 (m, 8H), 1.39 (br., 2H).

'N-(4-{[6,7-Bis(methyloxy)quinolin-4-yl]oxy}phenyl)-N'-[3-(pyrrolidin-1-ylmethyl)phenyl]cyclopropane-1,1-dicarboxamide. $^1$H NMR (DMSO-d6): 10.0-10.2 (br., 2H), 8.46 (d, 1H), 7.77 (d, 2H), 7.59 (s, 1H), 7.53 (d, 1H), 7.51 (s, 1H), 7.39 (s, 1H), 7.23 (m, 3H), 6.99 (d, 1H), 6.43 (d, 1H), 3.95 (s, 3H), 3.93 (s, 3H), 3.52 (s, 2H), 2.42 (br., 4H), 1.69 (br, 4H), 1.48 (s, 4H).

Example 75

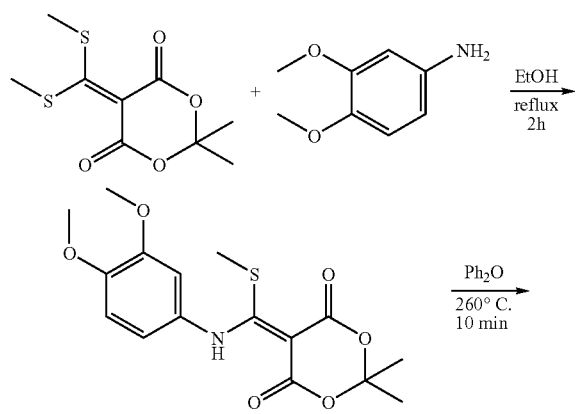

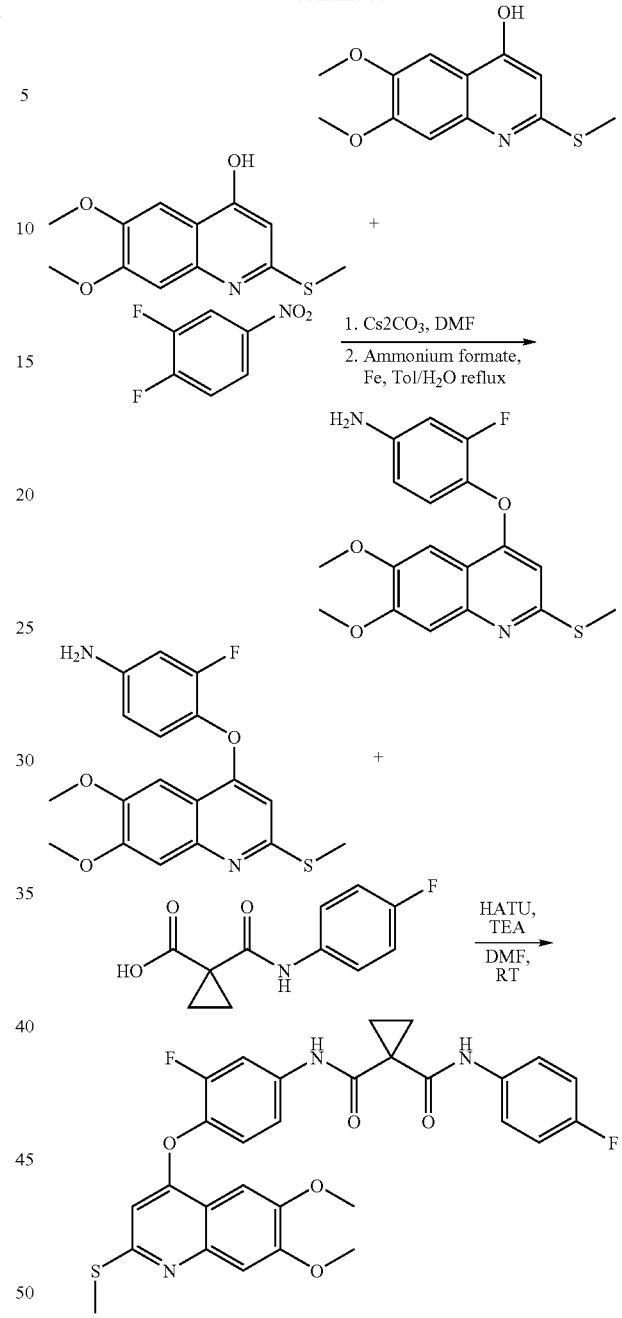

Synthesis of N-(4-{[6,7-bis(methyloxy)-2-(methylthio)quinolin-4-yl]oxy}-3-fluorophenyl)-N'-(4-fluorophenyl)cyclopropane-1,1-dicarboxamide Commercially available 5-(bis-methylsulfanyl-methylene)-2,2-dimethyl-[1,3]dioxane-4,6-dione (3.5 g, 14 mmol) and 3,4-dimethoxyaniline (2.2 g, 14 mmol) were reflux in EtOH (20 mL) for 2 hours. The EtOH was removed under reduced pressure and EtOAc was added to the residue. The product was filtered and washed with cold EtOAc (3×). 5-[(3,4-dimethoxy-phenylamino)-methylsulfanyl-methylene]-2,2-dimethyl-[1,3]dioxane-4,6-dione was obtained as a white solid (1.7 g, 47% yield) and used without further purification. LCMS: m/z 352 (M−H)$^−$.

A mixture of 5-[(3,4-dimethoxy-phenylamino)-methylsulfanyl-methylene]-2,2-dimethyl-[1,3]dioxane-4,6-dione (1.7 g, 6.6 mmol) and diphenylether (3.5 g, 21 mmol) were heated at 260° C. for 10 minutes. The mixture was cooled to room temperature and heptane was added. 6,7-Dimethoxy-2-methylsulfanyl-quinolin-4-ol was filtered and isolated as an orange solid and used without further purification (1.4 g, 83% yield). LCMS: m/z 352 (M+H)$^+$.

A mixture of 6,7-dimethoxy-2-methylsulfanyl-quinolin-4-ol (1.0 g, 4.0 mmol), 3,4-difluoronitrobenzene (0.48 µL, 4.3 mmol), cesium carbonate (2.6 g, 8.0 mmol), and DMF (15 mL) was stirred at room temperature for 12 hours, after which time, the mixture was filtered. The filtrate was extracted with DCM, washed with 10% LiCl$_{(aq.)}$, water, (1×) and brine (1×), followed by drying over Na$_2$SO$_4$ and concentration in vacuo. The crude solids were purified by flash chromatography (silica gel, 5% MeOH in DCM), affording the nitroquinolin (1.3 g, 85.8% yield) as an orange solid. LCMS: m/z 391 (M+H)$^+$. A mixture of nitroquinolin (0.33 g, 0.85 mmol), 5% Pt/S on carbon (0.050 g), ammonium formate (0.40 g, 6.3 mmol) in EtOH (5 mL) was heated at 80° C. for 1 hour The mixture was cooled to room temperature and the solvent removed under reduced pressure. The residue was dissolved in DCM, the mixture filtered, and the precipitate discarded. Removal of the organic solvent afforded 4-(6,7-dimethoxy-2-methylsulfanyl-quinolin-4-yloxy)-3-fluoro-phenylamine as an orange oil (220 mg, 73% yield). LCMS: m/z 361 (M+H)$^+$.

To a mixture of 4-(6,7-dimethoxy-2-methylsulfanyl-quinolin-4-yloxy)-3-fluoro-phenylamine (0.22 g, 0.61 mmol) and 1-(4-Fluoro-phenylcarbamoyl)-cyclopropanecarboxylic acid (0.16 g, 0.73 mmol) in DMF (5 mL) was added TEA (0.25 mL, 1.8 mmol) followed by HATU (0.57 g, 1.5 mmol). The resulting solution was stirred overnight at room temperature. The reaction mixture was dumped into water and extracted with DCM (2×). The combined extracts were washed with 5% LiCl$_{(aq.)}$ (3×), water, (1×) and brine (1×), followed by drying over Na$_2$SO$_4$ and concentration in vacuo. The crude solids were purified by preparatory HPLC with ammonium acetate, affording N-(4-{[6,7-bis(methyloxy)-2-(methylthio)quinolin-4-yl]oxy}-3-fluorophenyl)-N'-(4-fluorophenyl)cyclopropane-1,1-dicarboxamide (0.39 g, 11% yield) as a white solid. $^1$H NMR (DMSO-d$_6$) δ 10.34 (s, 1H), 9.94 (s, 1H), 7.83 (d, 1H), 7.59 (m, 2H), 7.56 (m, 1H), 7.40 (m, 2H), 7.23 (s, 1H), 7.09 (t, 2H), 6.12 (s, 1H), 3.88 (s, 3H), 3.85 (s, 3H), 2.48 (s, 3H), 1.40 (m, 4H).

Example 76

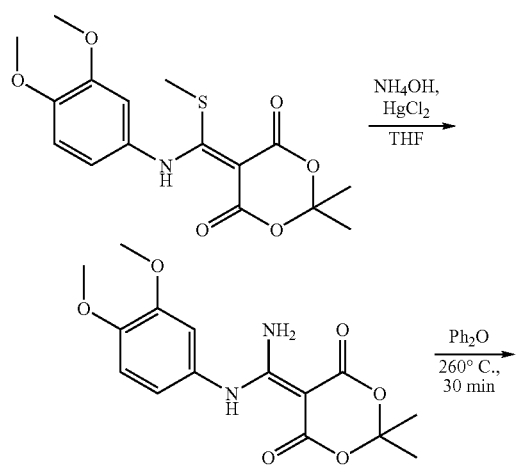

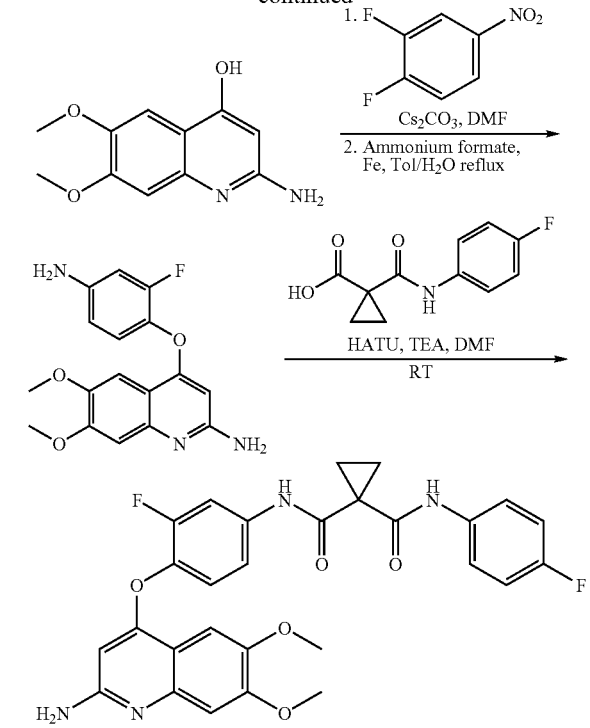

Synthesis of N-(4-{[2-amino-6,7-bis(methyloxy)quinolin-4-yl]oxy}-3-fluorophenyl)-N'-(4-fluorophenyl)cyclopropane-1,1-dicarboxamide. A mixture of 5-[(3,4-dimethoxy-phenylamino)-methylsulfanyl-methylene]-2,2-dimethyl-[1,3]dioxane-4,6-dione (1.0 g, 2.8 mmol), 30% ammonium hydroxide (8.5 mL), HgCl$_2$ (0.76 g, 2.8 mmol) in THF (5 mL) was stirred at room temperature for 30 minutes. The mixture was extracted with DCM and water (3×) and dried with Na$_2$SO$_4$. Concentration in vacuo afforded 5-[amino-(3,4-dimethoxy-phenylamino)-methylene]-2,2-dimethyl-[1,3]dioxane-4,6-dione as a white solid (0.90 g, 97% yield) and this compound was used without further purification. LCMS: m/z 321 (M–H)$^-$.

A mixture of 5-[amino-(3,4-dimethoxy-phenylamino)-methylene]-2,2-dimethyl-[1,3]dioxane-4,6-dione (0.90 g, 2.8 mmol) and diphenylether (3.0 g, 18 mmol) was heated at 260° C. for 30 minutes. The mixture was cooled to room temperature and heptane was added. Product 2-amino-6,7-dimethoxy-quinolin-4-ol was filtered and isolated as an orange solid and used without further purification (0.31 g, 33% yield). LCMS: m/z 221 (M+H)$^+$.

4-(4-Amino-2-fluoro-phenoxy)-6,7-dimethoxy-quinolin-2-ylamine was synthesized from 2-amino-6,7-dimethoxy-quinolin-4-ol in a similar manner as 4-(6,7-dimethoxy-2-methylsulfanyl-quinolin-4-yloxy)-3-fluoro-phenylamine, and obtained as a white solid (4.0% yield). LCMS: m/z 330 (M+H)$^+$.

N-(4-{[2-amino-6,7-bis(methyloxy)quinolin-4-yl]oxy}-3-fluorophenyl)-N'-(4-fluorophenyl)cyclopropane-1,1-dicarboxamide was synthesized from 4-(4-amino-2-fluoro-phenoxy)-6,7-dimethoxy-quinolin-2-ylamine in a similar manner as N-(4-{[6,7-bis(methyloxy)-2-(methylthio)quinolin-4-yl]oxy}-3-fluorophenyl)-N'-(4-fluorophenyl)cyclopropane-1,1-dicarboxamide. It was purified by preparatory HPLC using ammonium acetate and isolated as a white solid (4.0% yield). $^1$H NMR (DMSO-d$_6$) δ 10.34 (s, 1H), 9.95 (s, 1H), 7.82 (d, 1H), 7.58 (m, 2H), 7.44 (d, 1H), 7.33 (t, 1H), 7.25 (s, 1H), 7.09 (t, 2H), 7.07 (s, 1H), 6.17 (br s, 2H), 5.66 (s, 1H), 3.79 (s, 3H), 3.77 (s, 3H), 1.40 (d, 4H). LCMS: m/z 535 (M+H)$^+$.

Example 77

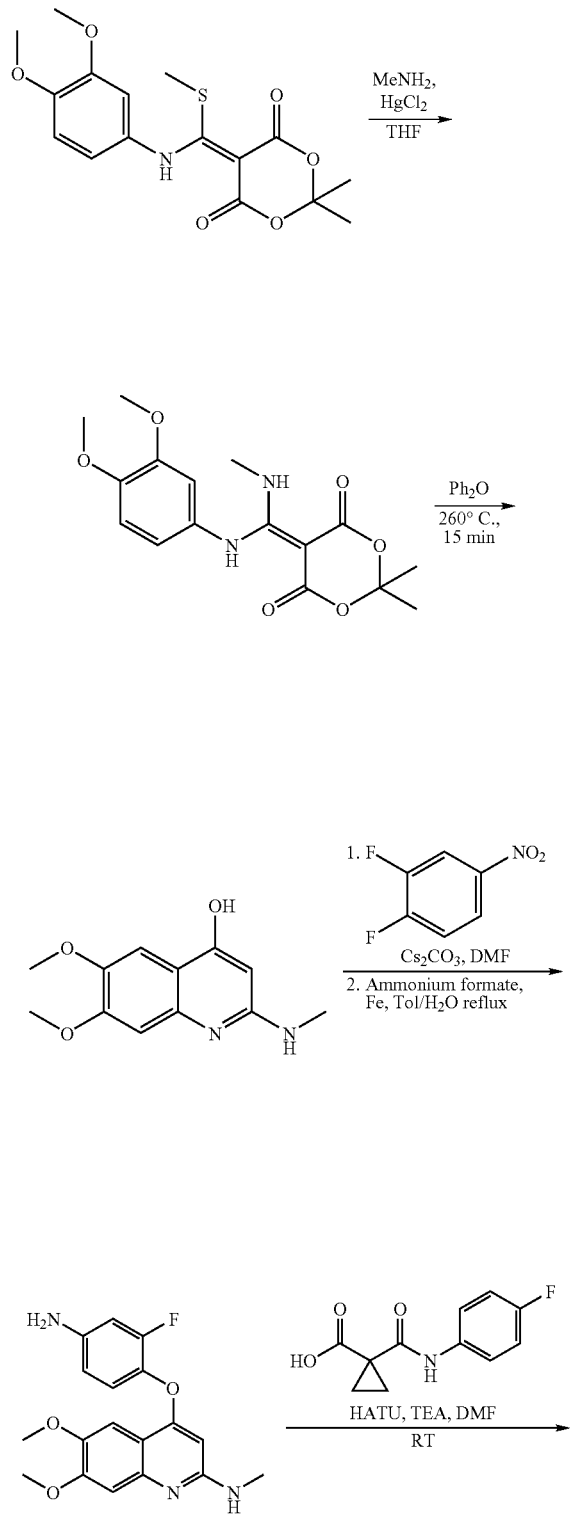

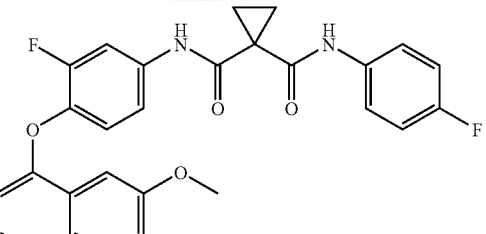

Synthesis of 'N-(3-fluoro-4-{[2-(methylamino)-6,7-bis(methyloxy)quinolin-4-yl]oxy}phenyl)-N'-(4-fluorophenyl)cyclopropane-1,1-dicarboxamide. A mixture of 5-[(3,4-dimethoxy-phenylamino)-methylsulfanyl-methylene]-2,2-dimethyl-[1,3]dioxane-4,6-dione (0.50 g, 1.4 mmol), methylamine (2 M in THF, 0.75 mL. 1.5 mmol), HgCl$_2$ (0.38 g, 1.4 mmol) in THF (5 mL) was stirred at room temperature for 30 minutes. The mixture was extracted with DCM and water (3×) and dried with Na$_2$SO$_4$. Concentration in vacuo afforded 5-[(3,4-dimethoxy-phenylamino)-methylamino-methylene]-2,2-dimethyl-[1,3]dioxane-4,6-dione as a yellow solid (0.48 g, 99% yield) and this compound was used without further purification. LCMS: m/z 335 (M−H)$^−$.

A mixture of 5-[(3,4-dimethoxy-phenylamino)-methylamino-methylene]-2,2-dimethyl-[1,3]dioxane-4,6-dione (0.40 g, 2.8 mmol) and diphenylether (3.0 g, 18 mmol) was heated at 260° C. for 15 minutes. The mixture was cooled to room temperature and heptane was added. Product 6,7-dimethoxy-2-methylamino-quinolin-4-ol was filtered and isolated as a tan solid and used without further purification (0.30 g, quantitative yield). LCMS: m/z 235 (M+H)$^+$.

[4-(4-Amino-2-fluoro-phenoxy)-6,7-dimethoxy-quinolin-2-yl]-methyl-amine was synthesized from 6,7-dimethoxy-2-methylamino-quinolin-4-ol in a similar manner as 4-(4-Amino-2-fluoro-phenoxy)-6,7-dimethoxy-quinolin-2-ylamine, and isolated as a yellow oil (58% yield). LCMS: m/z 330 (M+H)$^+$.

'N-(3-fluoro-4-{[2-(methylamino)-6,7-bis(methyloxy)quinolin-4-yl]oxy}phenyl)-N'-(4-fluorophenyl)cyclopropane-1,1-dicarboxamide was synthesized from [4-(4-amino-2-fluoro-phenoxy)-6,7-dimethoxy-quinolin-2-yl]-methyl-amine in a similar manner as N-(4-{[6,7-bis(methyloxy)-2-(methylthio)quinolin-4-yl]oxy}-3-fluorophenyl)-N'-(4-fluoro-phenyl)cyclopropane-1,1-dicarboxamide. It was purified by preparatory HPLC using ammonium acetate and isolated as a white solid (6.0 mg, 4.0% yield). $^1$H NMR (DMSO-d$_6$) δ 10.42 (s, 1H), 9.91 (s, 1H), 7.88 (dd, 1H), 7.56 (m, 2H), 7.44 (m, 4H), 7.09 (t, 2H), 5.90 (s, 1H), 3.88 (s, 3H), 3.85 (s, 3H), 3.39 (br s, 1H), 2.92 (s, 3H), 1.41 (dt, 4H). LCMS: m/z 535 (M+H)$^+$.

Example 78

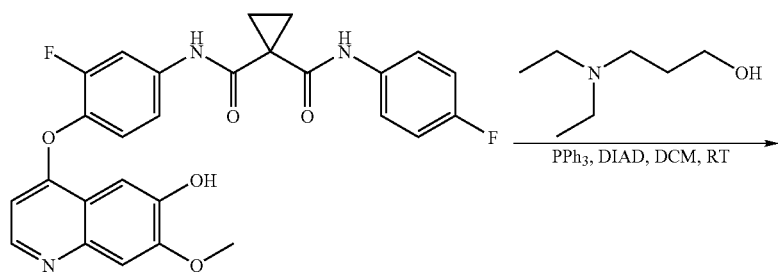

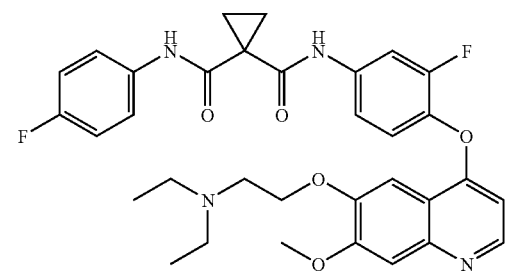

'N-(4-{[6-{[3-(diethylamino)propyl]oxy}-7-(methyloxy) quinolin-4-yl]oxy}-3-fluorophenyl)-N'-(4-fluorophenyl)cyclopropane-1,1-dicarboxamide. To a slurry of cyclopropane-1,1-dicarboxylic acid [3-fluoro-4-(6-hydroxy-7-methoxy-quinolin-4-yloxy)-phenyl]-amide (4-fluoro-phenyl)-amide (0.12 g, 0.23 mmol), hydroxypropyldiethylamine (0.090 mL, 0.61 mmol), triphenylphosphine (0.20 g, 0.76 mmol) in DCM (10 mL) was added DIAD (0.17 mL, 0.86 mmol). The resulting mixture was stirred at room temperature for 12 hours, after which time, the solvent was removed under reduced pressure. The residue was extracted with EtOAc and 1N HCl (6×) and brine (1×) followed by drying with $Na_2SO_4$. Concentration of the organic fraction in vacuo afforded 'N-(4-{[6-{[3-(diethylamino)propyl]oxy}-7-(methyloxy)quinolin-4-yl]oxy}-3-fluorophenyl)-N'-(4-fluorophenyl) cyclopropane-1,1-dicarboxamide as a yellow oil (0.18 g, wet, ca 95% purity by analytical HPLC). Further purification by preparatory HPLC using ammonium acetate afforded the product in 99% purity by analytical HPLC. LCMS: m/z 619 (M+H)+. $^1$H NMR (DMSO-$d_6$) δ 10.37 (br s, 1H), 10.00 (s, 1H), 8.44 (d, 1H), 7.87 (d, 1H), 7.62 (m, 2H), 7.49 (m, 2H), 7.41 (m, 2H), 7.13 (t, 2H), 6.40 (d, 1H), 4.17 (t, 2H), 3.93 (s, 3H), 2.59 (t, 2H), 2.49 (m, 6H), 1.91 (m, 4H), 0.94 (t, 6H).

Example 79

-continued

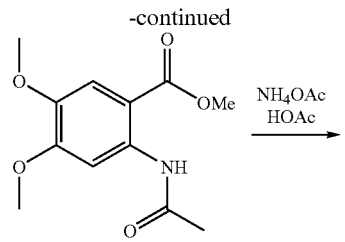

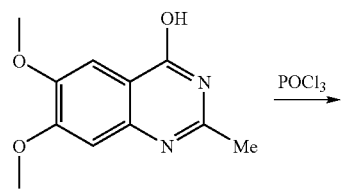

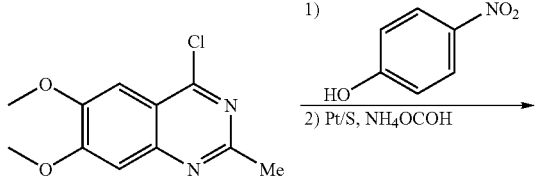

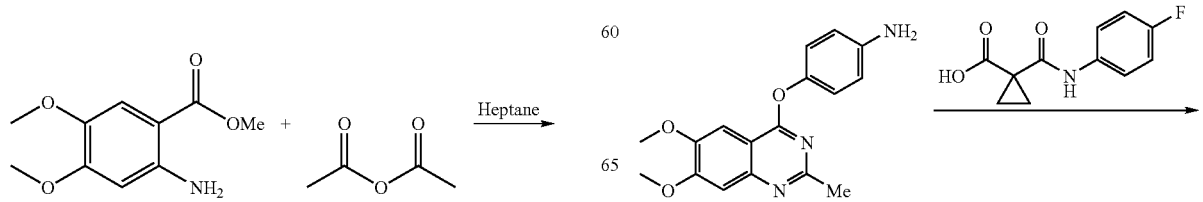

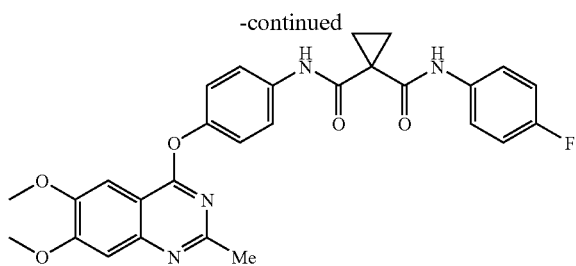

'N-(4-fluorophenyl)-N'-(4-{[2-methyl-6,7-bis(methyloxy)quinazolin-4-yl]oxy}phenyl)cyclopropane-1,1-dicarboxamide. Commercially available 2-amino-4,5-dimethoxy-benzoic acid methyl ester (3 g, 0.014 mol) and acetic anhydride (4.03 mL, 0.0426 mol) were heated in heptane at 100° C. for 3 hours. After removal of heptane in vacuo, the crude product of 2-acetylamino-4,5-dimethoxy-benzoic acid methyl ester was obtained and used without further purification. LC/MS: m/z 254 (M+H).

To the crude 2-acetylamino-4,5-dimethoxy-benzoic acid methyl ester obtained above was added ammonium acetate (7.98 g, 0.104 mol) and acetic acid (10 mL). The mixture was heated at reflux in a pressure tube until the formation of the desired cyclization product, as indicated by LC/MS: m/z 221 (M+H). After cooling to RT, the reaction mixture was diluted with water, and extracted with EtOAc 3 times. The combined organic phase was basified with aq. NaOH solution, and washed 3 times with EtOAc. The aqueous layer was then acidified with aq. HCl and extracted three times with EtOAc. The combined organic extract was dried over $Na_2SO_4$ and concentrated in vacuo, affording 6,7-dimethoxy-2-methyl-quinazolin-4-ol (0.15 g), which was used without further purification. LC/MS: m/z 221 (M+H).

A mixture of 6,7-dimethoxy-2-methyl-quinazolin-4-ol obtained from previous step (0.15 g, 0.68 mmol) and $POCl_3$ (1.59 mL, 17.04 mmol) was heated at reflux for 48 hours. The reaction mixture was poured into ice water, neutralized with $NaHCO_3$, and adjusted to basic with $K_2CO_3$. The mixture was cooled to 0° C. with stirring. The resulting precipitate was filtered, giving 4-chloro-6,7-dimethoxy-2-methyl-quinazoline (0.094 g), which was used without further purification.

A mixture of the chloro quinazoline (0.094 g, 0.397 mmol) obtained above, 4-nitrophenol (0.11 g, 0.795 mmol) and bromobenzene (3 mL) was heated at 160° C. for 48 hours. The solvent was then removed and the reaction was taken up in MeOH. $Et_2O$ was added and the reaction stirred 30 min and the precipitate was filtered, affording 6,7-dimethoxy-2-methyl-4-(4-nitro-phenoxy)-quinazoline (0.081 g) as a very light yellow solid. LC/MS: m/z 342 (M+H).

A mixture of 6,7-dimethoxy-2-methyl-4-(4-nitro-phenoxy)-quinazoline (0.081 g, 0.236 mmole), Pt/S (0.008 g, 15 mol %), ammonium formate (0.098 g, 1.56 mmol) and EtOH (3 mL) was heated with stirring at 70° C. for 3 hours. The reaction mixture was then filtered while hot and washed with hot EtOH. The crude product of 4-(6,7-dimethoxy-2-methyl-quinazolin-4-yloxy)-phenylamine (0.924 g) was obtained as a yellow solid, which was used in the next reaction without further purification. LC/MS: m/z 312 (M+H).

To a mixture of 4-(6,7-dimethoxy-2-methyl-quinazolin-4-yloxy)-phenylamine (0.100 g, 0.321 mmol) and 1-(4-fluoro-phenylcarbamoyl)-cyclopropanecarboxylic acid (0.056 g, 0.386 mmol) in DMF was added DIEA (0.168 mL, 0.963 mmol), followed by HATU (0.183 g, 0.482 mmol). The reaction mixture was stirred at RT for 15 hours. The mixture was diluted with EtOAc, washed with 5% LiCl aq solution three times, dried over $Na_2SO_4$, and concentrated in vacuo. The crude product was purified on preparative HPLC to give 'N-(4-fluorophenyl)-N'-(4-{[2-methyl-6,7-bis(methyloxy)quinazolin-4-yl]oxy}phenyl)cyclopropane-1,1-dicarboxamide (3.2 mg) as a white solid. $^1$H NMR (DMSO-d6) 10.15 (bs, 1H), 10.01 (bs, 1H), 7.69-7.75 (m, 2H), 7.61-7.68 (m, 2H), 7.52 (s, 1H), 7.32 (s, 1H), 7.23-7.29 (m, 2H), 7.12-7.19 (m, 2H), 3.93 (d, 6H), 2.43 (s, 3H), 1.53 (s, 4H).

Example 80

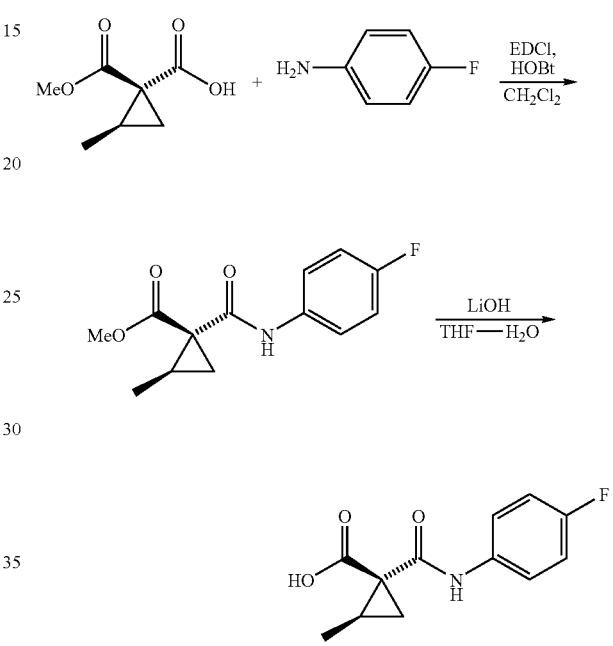

Preparation of 1-(4-Fluoro-phenylcarbamoyl)-2-methyl-cyclopropanecarboxylic acid. 2-Methylcyclopropane-1,1-dicarboxylic acid methyl ester was prepared by following the literature procedure (Baldwin, J. E.; Adlington, R. M.; Rawlings, B. J. Tetrahedron Lett. 1985, 481.) The carboxylic acid (700 mg, 4.4 mmol) was dissolved in $CH_2Cl_2$ (10 mL). To the resulting solution was added 4-fluoroaniline (590 mg, 5.3 mmol), HOBt (890 mg, 6.6 mmol) and EDCI (2.5 g, 13.2 mmol). The stirring was continued for 3 h at rt. $CH_2Cl_2$ (30 mL) was added to the reaction mixture, and the resulting solution was washed with brine, and dried over $Na_2SO_4$. $CH_2Cl_2$ was removed under reduced pressure. Further purification by column chromatography gave 635 mg (57%) of the desired amide.

The methyl ester obtained above was then treated with LiOH.H$_2$O (116 mg, 2.78 mmol, 1.1 eqiv.) in THF (2 mL) and H$_2$O (1 mL) for 3 h at rt. THF was removed under reduced pressure. The aqueous solution was diluted with 20 mL of H$_2$O, washed with ether (10 mL), and acidified with 1 N HCl. The solid was filtered, dissolved in EtOAc, and dried over $Na_2SO_4$. Removal of EtOAc gave the crude product of 1-(4-fluoro-phenylcarbamoyl)-2-methyl-cyclopropane-carboxylic acid, which was used in the next reaction. $^1$H NMR (400 MHz, DMSO-d$_6$) δ 12.99 (br s, 1H), 10.33 (br s, 1H), 7.59 (dd, J=9.0, 5.0 Hz, 2H), 7.11 (dd, J=9.0, 9.0 Hz, 2 H), 1.86-1.78 (m, 1 H), 1.43 (dd, J=9.0, 4.2 Hz, 1 H), 1.30 (dd, J=7.8, 4.3 Hz, 1 H), 1.19 (d, J=6.3 Hz, 3 H).

Example 81

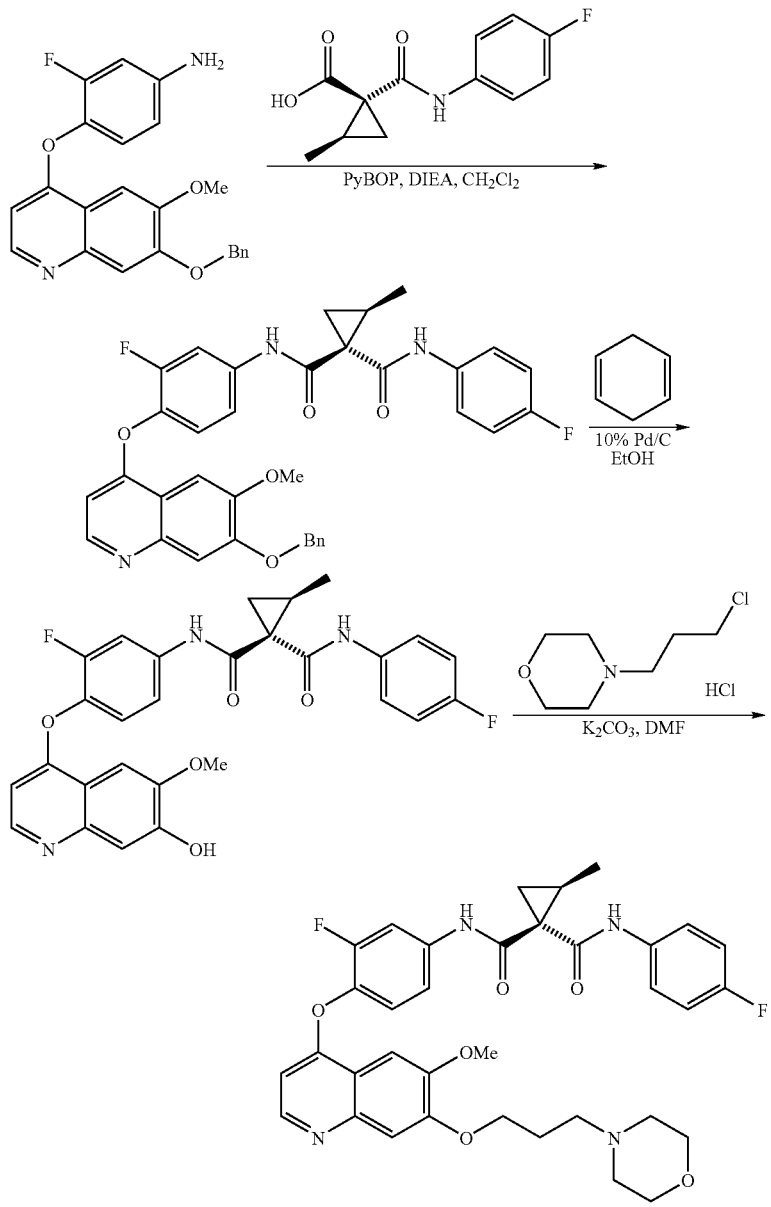

Synthesis of (1S,2R)—N-[3-fluoro-4-({6-(methyloxy)-7-[(3-morpholin-4-ylpropyl) oxy]quinolin-4-yl}oxy)phenyl]-N'-(4-fluorophenyl)-2-methylcyclopropane-1,1-dicarboxamide. To a solution of 4-(7-benzyloxy-6-methoxy-quinolin-4-yloxy)-3-fluoro-phenylamine (150 mg, 0.38 mmol) in CH$_2$Cl$_2$ (3 mL) was added DIEA (341 mg, 2.64 mmol), 1-(4-fluoro-phenylcarbamoyl)-2-methyl-cyclopropanecarboxylic acid (120 mg, 0.49 mmol) and PyBOP (686 mg, 1.32 mmol). The reaction mixture was stirred at rt for 6 h. After standard workup, the crude product was purified by column chromatography.

The coupling product (130 mg, 0.21 mmol) obtained above was dissolved in EtOH (2 mL). 1,4-cyclohexadiene (170 mg, 2.1 mmol) and 10% Pd/C (10 mg) were added. The mixture was stirred for 2 h under reflux. After cooling, the mixture was filtered through Celite, and washed with MeOH. Removal of the solvents gave the crude product (136 mg), which was used in the next reaction.

To a solution of the 7-hydroxyquinoline (136 mg, 0.26 mmol) in DMF (2 mL) was added 4-(3-chloropropyl)morpholine hydrochloride (70 mg, 0.35 mmol) and K$_2$CO$_3$ (69 mg, 0.50 mmol). The reaction mixture was then stirred at 80° C. for 5 h. After cooling, EtOAc (20 mL) was added. The EtOAc solution was washed twice with brine, and dried over Na$_2$SO$_4$. Removal of EtOAc and purification by column chromatography (CH$_2$Cl$_2$: MeOH=10:1) gave '(1S,2R)—N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide. The product was then dissolved in ethyl ether, and treated with 1.5 equiv. of 1 N HCl/ether. Filtration and lyophilization gave the HCl salt of '(1S,2R)—N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide: $^1$H NMR (400 MHz, DMSO-$d_6$) δ 10.49 (br s, 1 H), 10.26 (br s, 1 H), 10.15 (br s, 1 H), 8.74 (br s, 1 H), 7.95 (br d, J=13.2 Hz, 1 H), 7.8-7.5 (m, 6 H), 7.16 (t, J=8.9 Hz, 2 H), 6.82 (br s, 1 H), 4.34 (t, J=5.9 Hz, 2 H), 4.02 (s, 3 H), 3.99 (br s, 2 H), 3.77 (br t, J=12.0 Hz, 2 H), 3.56-3.30 (m, 4 H), 3.17-3.07 (m, 2 H), 2.40-2.30 (m, 2 H), 2.04-1.95 (m, 1 H), 1.45 (dd, J=7.2, 4.7 Hz, 1 H), 1.36 (dd, J=8.5, 4.5 Hz, 1 H), 1.09 (d, J=6.2 Hz, 3 H).

Example 82

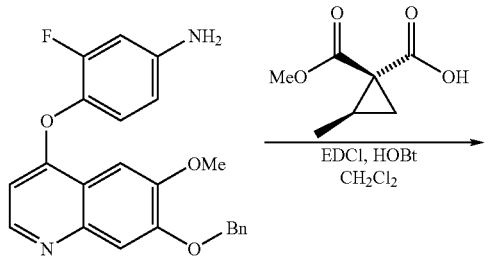

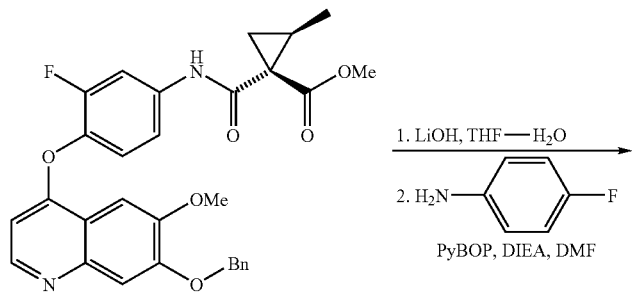

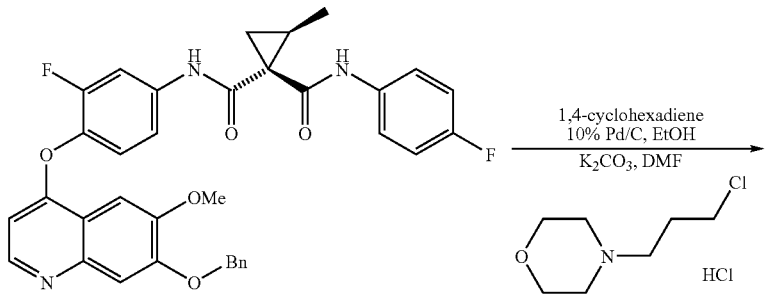

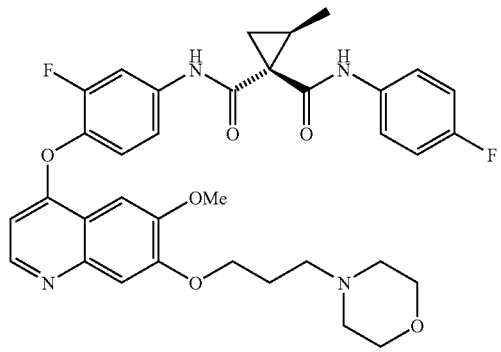

Synthesis of (1R,2R)—N-[3-fluoro-4-({6-(methyloxy)-7-[(3-morpholin-4-ylpropyl)oxy]-quinolin-4-yl}oxy)phenyl]-N'-(4-fluorophenyl)-2-methylcyclopropane-1,1-dicarboxamide. To a solution of 4-(7-benzyloxy-6-methoxy-quinolin-4-yloxy)-3-fluoro-phenylamine (322 mg, 0.82 mmol) and 2-Methyl-cyclopropane-1,1-dicarboxylic acid methyl ester (195 mg, 1.23 mmol) in CH$_2$Cl$_2$ (4 mL) was added HOBt (61 mg, 0.32 mmol) and EDCI (211 mg, 1.64 mmol). The stirring was continued for 12 h at rt. The reaction mixture was then diluted with EtOAc and washed with brine. Removal of organic solvents in vacuo and further purification by column chromatography gave the desired coupling product (153 mg).

The product (153 mg, 0.29 mmol) obtained above was treated with LiOH.H$_2$O (15 mg, 0.35 mmol) in THF (1 mL) and H$_2$O (1 mL) for 2 h. THF was removed. 10 mL of H$_2$O was added to the mixture. The aqueous solution was washed with ether, and acidified with 1 N HCl. The solid was then filtered and dried under vacuum.

The crude carboxylic acid (118 mg, 0.23 μmol) and 4-fluoroaniline (111 mg, 0.27 mmol) were dissolved in DMF (2 mL). To this solution was added DIEA (178 mg, 1.38 mmol) and PyBOP (358 mg, 0.69 mmol). The mixture was stirred overnight at rt. It was then diluted with EtOAc, washed twice with brine. Removal of EtOAc and column chromatography gave the desired product.

The product (66 mg, 0.11 mmol) obtained above was dissolved in EtOH (2 mL). 1,4-cyclohexadiene (80 mg, 1.1 mmol) and 10% Pd/C (10 mg) were added. The mixture was stirred for 2 h under reflux. After cooling, the mixture was filtered through Celite, and washed with MeOH. Removal of the solvents gave the crude product (70 mg), which was used in the next reaction.

To a solution of the 7-hydroxyquinoline (80 mg, 0.15 mmol) in DMF (2 mL) was added 4-(3-chloropropyl)morpholine hydrochloride (62 mg, 0.31 mmol) and K$_2$CO$_3$ (64 mg, 0.46 mmol). The reaction mixture was then stirred at 80° C. for 5 h. After cooling, EtOAc (20 mL) was added. The EtOAc solution was washed twice with brine, and dried over Na$_2$SO$_4$. Removal of EtOAc and purification by column chromatography (CH$_2$Cl$_2$: MeOH=10:1) gave '(1R,2R)—N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide. The product was then dissolved in ethyl ether, and treated with 1.5 equiv. of 1 N HCl/ether. Filtration and lyophilization gave the HCl salt of '(1R,2R)—N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide: $^1$H NMR (400 MHz, DMSO-d$_6$) δ 10.65 (br s, 1 H), 10.54 (br s, 1 H), 9.74 (s, 1 H), 8.75 (br s, 1 H), 8.01 (br d, J=12.9 Hz, 1 H), 7.80-7.50 (m, 6 H), 7.20-7.10 (m, 2 H), 6.84 (br s, 1 H), 4.34 (br t, J=5 Hz, 2 H), 4.04 (s, 3 H), 4.05-3.95 (m, 2 H), 3.77 (br t, J=1 Hz, 2 H), 3.52 (br d, J=12.7 Hz, 4 H), 3.12 (br q, J=9.0 Hz, 2 H), 2.40-2.30 (m, 2 H), 2.10-1.95 (m, 1 H), 1.40-1.30 (m, 2 H), 1.10 (d, J=6.2 Hz, 3 H).

Example 83

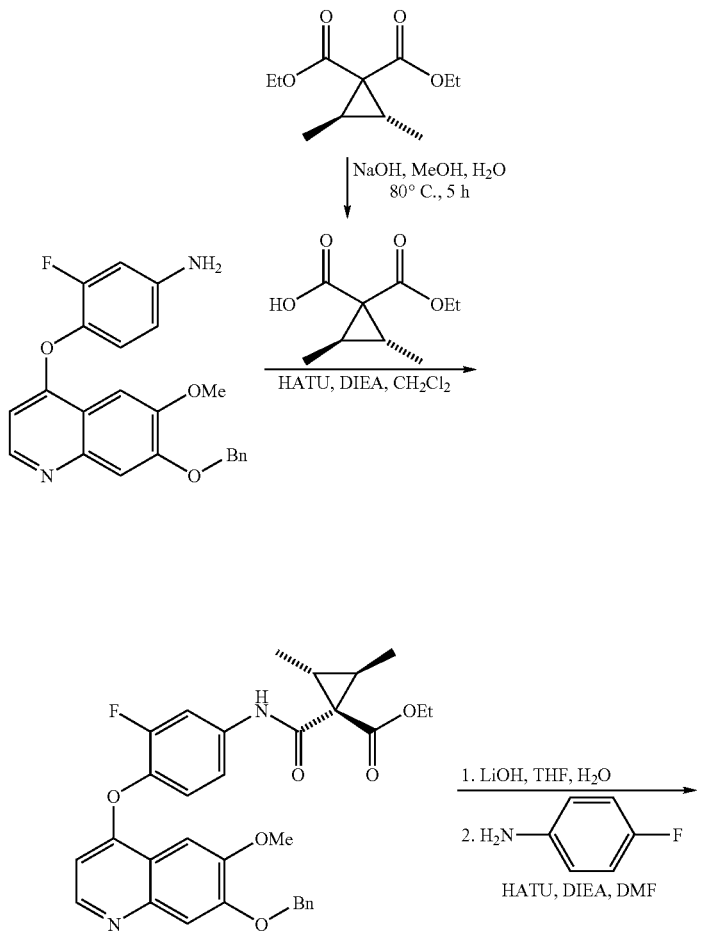

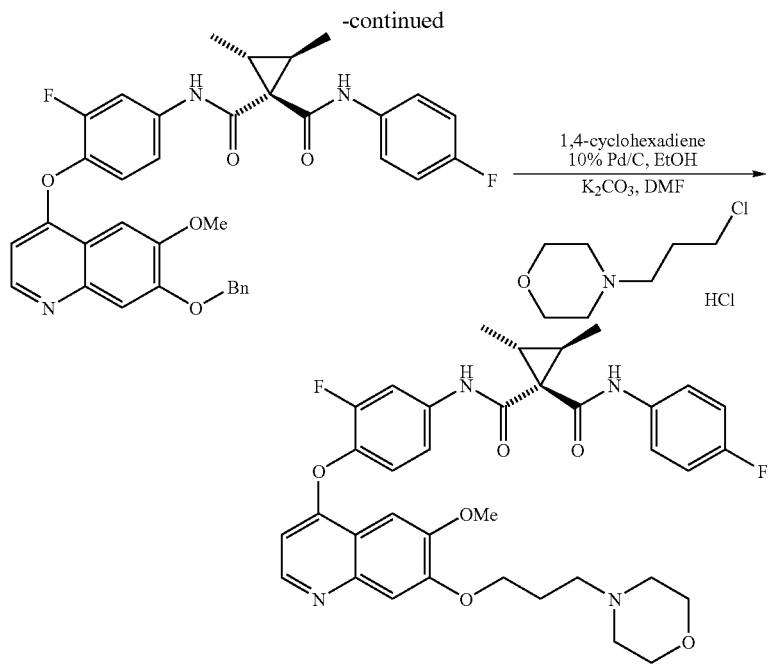

Synthesis of '(2R,3R)—N-[3-fluoro-4-({6-(methyloxy)-7-[(3-morpholin-4-ylpropyl)oxy]-quinolin-4-yl}oxy)phenyl]-N'-(4-fluorophenyl)-2,3-dimethylcyclopropane-1,1-dicarboxamide. 2,3-trans-Dimethyl-cyclopropane-1,1-dicarboxylic acid diethyl ester was prepared by following the literature procedure. (Ohishi, J. Synthesis, 1980, 690.) To a solution of 2,3-trans-dimethyl-cyclopropane-1,1-dicarboxylic acid diethyl ester (6.75 g, 31.5 mmol) in MeOH (30 mL) was added 33 mL of 1 N NaOH aqueous solution. The mixture was stirred at 85° C. for 5 h. MeOH was removed under reduced pressure; the residue was diluted with 40 mL of H$_2$O. The aqueous solution was washed with 20 mL of ether, and acidified with 1 N HCl. Filtration and drying under vacuum gave 4.72 g 80%) of the desired carboxylic acid.

The aniline (1.08 g, 2.78 mmol) and the carboxylic acid (518 mg, 2.78 mmol) prepared above were dissolved in CH$_2$Cl$_2$ (15 mL). HATU (2.11 g, 5.56 mmol) and DIEA (1.8 mL, 11.1 mmol) were added. The reaction mixture was stirred at it overnight. It was then concentrated and diluted with EtOAc. The EtOAc solution was then washed with 5% NaOH and brine. Removal of EtOAc gave the crude coupling product, which was hydrolyzed to the corresponding carboxylic acid by treatment with LiOH.H$_2$O (175 mg, 4.17 mmol) in THF (100 mL) —H$_2$O (50 mL) at 60° C. for 10 h.

The carboxylic acid (850 mg, 1.60 mmol) and 4-fluoroaniline (355 mg, 3.20 mmol) were dissolved in DMF (8 mL). HATU (3.89 g, 3.2 mmol) and DIEA (1.1 ml, 6.4 mmol) were added. The reaction mixture was stirred at rt overnight. H$_2$O (10 mL) was added to the reaction, and a precipitate formed. The solid was filtered, washed with aqueous sat. Na$_2$CO$_3$ and ether. Further purification by column chromatography gave 596 mg (60%) of the desired product. Debenzylation was done by following the standard procedure.

To a solution of the 7-hydroxyquinoline (261 mg, 0.49 mmol) in DMF (5 mL) was added 4-(3-chloropropyl)morpholine hydrochloride (195 mg, 0.98 mmol) and K$_2$CO$_3$ (202 mg, 1.46 mmol). The reaction mixture was then stirred at 80° C. for 4 h. After cooling, EtOAc (20 mL) was added. The EtOAc solution was washed twice with brine, and dried over Na$_2$SO$_4$. Removal of EtOAc and purification by column chromatography (CH$_2$Cl$_2$ MeOH=10:1) gave 122 mg (37%) of '(2R,3R)—N-[3-fluoro-4-({6-(methyloxy)-7-[(3-morpholin-4-ylpropyl)oxy]quinolin-4-yl}oxy)phenyl]-N'-(4-fluorophenyl)-2,3-dimethyl-cyclopropane-1,1-dicarboxamide.

$^1$H NMR (400 MHz, CDCl$_3$) δ 8.44 (d, J=5.1 Hz, 1 H), 8.11 (br s, 1 H), 7.77-7.70 (m, 2 H), 7.53 (s, 1 H), 7.50-7.44 (m, 2 H), 7.40 (s, 1 H), 7.22-7.16 (m, 2 H), 7.06-6.98 (m, 2 H), 6.36 (br d, J=5.1 Hz, 1 H), 4.26 (t, J=7.0 Hz, 2 H), 4.02 (s, 3 H), 3.72 (t, J=4.4 Hz, 4 H), 2.57 (t, J=7.3 Hz, 2 H), 2.50-2.42 (m, 4 H), 2.18-2.10 (m, 2 H), 1.80-1.66 (m, 2 H), 1.30-1.24 (m, 6 H).

Example 84

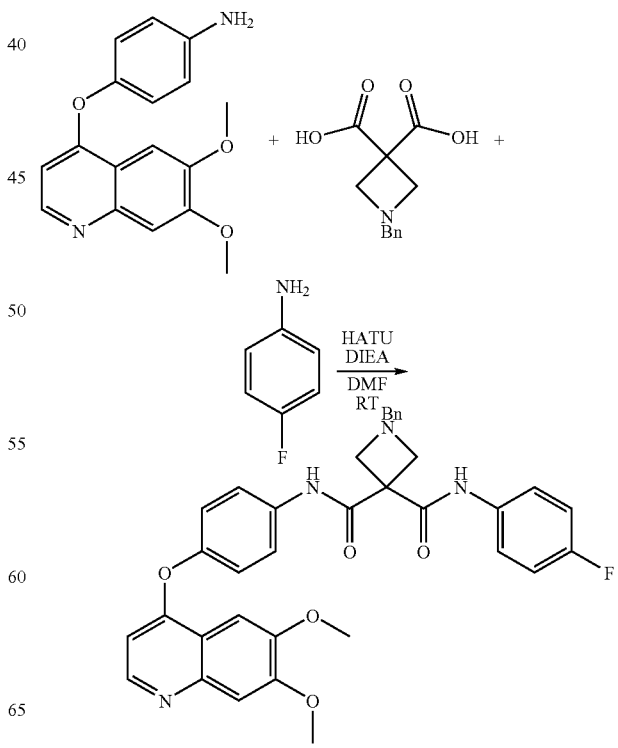

Synthesis of 'N-(4-{[6,7-bis(methyloxy)quinolin-4-yl]oxy}phenyl)-N'-(4-fluorophenyl)-1-(phenylmethyl)azetidine-3,3-dicarboxamide. 1-Benzyl-azetidine-3,3-dicarboxylic acid was prepared by following the literature procedure (Miller, R. A.; et al. Syn. Comm. 2003, 33, 3347). To a solution of 4-(6,7-dimethoxy-quinolin-4-yloxy)-phenylamine (4.2 mmol, 1 equiv.) and 4-fluoroaniline (4.2 mmol, 1 equiv.) in DMF (20 mL) was charged with DIEA (12.6 mmol, 3 equiv.) and a solution of 1-benzyl-azetidine-3,3-dicarboxylic acid (4.2 mmol, 1 equiv.) in DMF (10 mL). The reaction mixture was allowed to stir at RT and monitored by LCMS. The reaction was complete in 6 h. The reaction mixture was diluted with ethyl acetate and washed with 10% LiCl (3×), brine (3×), dried with sodium sulfate, filtered and the solvent was reduced in vacuo. The crude product was purified by silica gel chromatography eluting with 2% of MeOH in EtOAc. The fractions containing the desired product were further purified using preparative HPLC to give 'N-(4-{[6,7-bis(methyloxy)quinolin-4-yl]oxy}phenyl)-N'-(4-fluorophenyl)-1-(phenylmethyl)azetidine-3,3-dicarboxamide (300 mg, 12% yield) as a white solid. $^1$HNMR (DMSO-d6): 10.0 (s, 1H), 9.90 (s, 1H), 8.45 (d, 1H), 7.80 (d, 2H), 7.70 (m, 2H), 7.50 (s, 1H), 7.40 (s, 1H), 7.48-7.15 (m, 9H), 3.95 (s, 6H), 3.70 (s, 4H), 3.60 (s, 2H). LCMS (POS): 607.2 (M+H).

N-(4-{[6,7-bis(methyloxy)quinolin-4-yl]oxy}phenyl)-N'-(4-fluorophenyl)azetidine-3,3-dicarboxamide. To a solution of 'N-(4-{[6,7-bis(methyloxy)quinolin-4-yl]oxy}phenyl)-N'-(4-fluorophenyl)-1-(phenylmethyl)azetidine-3,3-dicarboxamide (300 mg, 0.5 mmol) in MeOH (50 mL) was charged with Pd/C (50% wet, 10% mmol, 265 mg) and acetic acid (2 mL). The reaction mixture was subjected to hydrogenolysis condition under H2 (50 psi) on a Parr Hydrogenator for 16 hr. The reaction mixture was filtered through celite and washed with MeOH. After removal of solvent in vacuo, the crude product was purified using preparative HPLC (solvent system: MeCN/H2O/NH4OAc), affording N-(4-{[6,7-bis(methyloxy)quinolin-4-yl]oxy}phenyl)-N'-(4-fluorophenyl)azetidine-3,3-dicarboxamide (82 mg, 32% yield) as a white solid. $^1$HNMR (DMSO-d6): 8.46 (d, 1H), 7.84 (d, 2H), 7.70 (m, 2H), 7.50 (s, 1H), 7.40 (s, 1H), 7.24 (d, 2H), 7.20 (t, 2H), 6.44 (d, 1H), 4.03 (s, 4H), 3.95 (s, 6H), 1.90 (s, 3H, acetate salt). LCMS (POS): 517.3 (M+H).

Example 85

N-{3-fluoro-4-[(6-(methyloxy)-7-{[(1-methylpiperidin-4-yl)methyl]oxy}quinolin-4-yl)oxy]phenyl}-N'-(4-fluorophenyl)cyclopropane-1,1-dicarboxamide. To a solution of cyclopropane-1,1-dicarboxylic acid {3-fluoro-4-[6-methoxy-7-(piperidin-4-ylmethoxy)-quinolin-4-yloxy]-phenyl}-amide (4-fluoro-phenyl)-amide, TFA salt (~500 mg, 0.71 mmol) in ClCH$_2$H$_2$Cl (8 mL) were added 30% formaldehyde (4 mL) and NaBH(OAc)$_3$ (752 mg, 3.55 mmol). The reaction mixture was stirred overnight. It was then quenched with aqueous sat. NaHCO$_3$, extracted with EtOAc. The organic phase was washed with brine and dried over Na$_2$SO$_4$. Drying salts were filtered, washed with EtOAc and the filtrate concentrated in vacuo to give 210 mgs of crude product. The resulting residue was redissolved in EtOAc and any insoluble material filtered. To the filtrate was added 4M HCl in dioxane (200 µl) and the mixture was stirred at room temperature for 1 hour. Solids were filtered, washed with EtOAc, dried under high vacuum, dissolved in 50% aqueous AcCN and lyophilized to give 'N-{3-fluoro-4-[(6-(methyloxy)-7-{[(1-methylpiperidin-4-yl)methyl]oxy}quinolin-4-yl)oxy]phenyl}-N'-(4-fluorophenyl)cyclopropane-1,1-dicarbox-amide, HCl salt (113 mg, ~25% yield). $^1$HNMR (400 MHz, DMSO-d6): δ 10.51 (s, 1H), 10.30 (br. s, 1H), 10.04 (s, 1H), 8.80 (d, 1H), 7.99 (dd, 1H), 7.55 (m, 2H), 7.67-7.53 (m, 4H), 7.16 (t, 2H), 6.89 (d, 1H), 4.13 (d, 2H), 4.05 (s, 3H), 3.47 (m, 2H), 3.00 (m, 2H), 2.74 (d, 3H), 2.17 (m, 1H), 2.03 (m, 2H), 1.68 (m, 2H), 1.49 (m, 4H). LC/MS Calcd for [M+H]$^+$ 617.3, found 617.4. Anal. HPLC (8 min gradient): 98% pure, 3.11 min.

Example 86

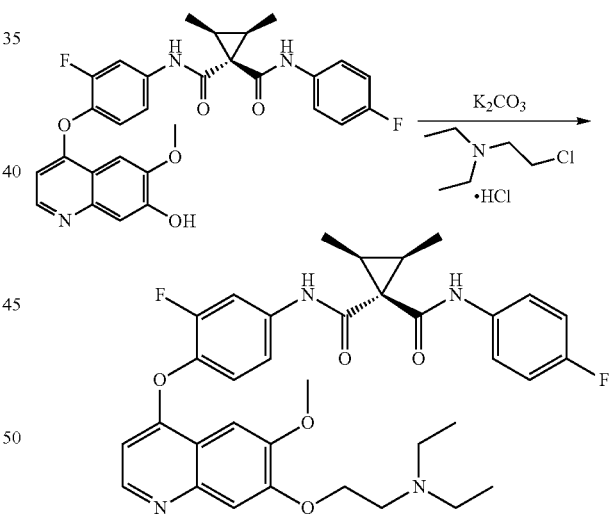

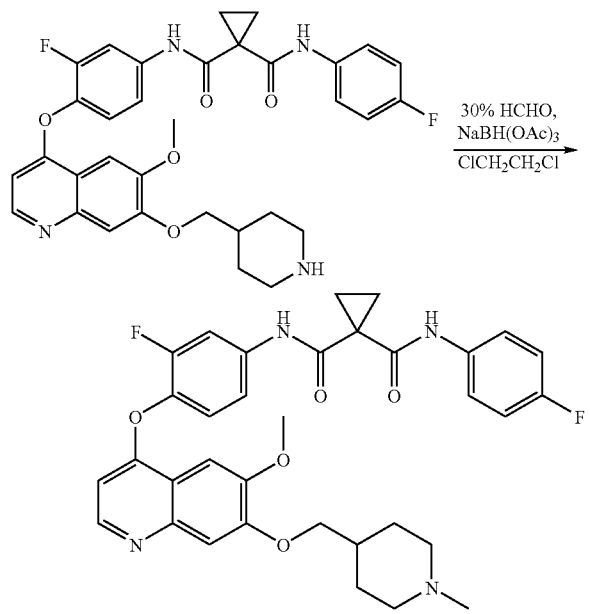

(1R,2R,3S)—N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide. 2,3-Dimethyl-cyclopropane-1,1-dicarboxylic acid [3-fluoro-4-(7-hydroxy-6-methoxy-quinolin-4-yloxy)-phenyl]-amide (4-fluoro-phenyl)-amide (210 mg, 0.39 mmol), DMA (2 mls), (2-chloro-ethyl)-diethyl-amine, HCl salt (73 mg, 0.42 mmol) and K$_2$CO$_3$ (136 mg, 0.98 mmol) were combined and heated at 80 C overnight. The reaction mixture was then diluted with H$_2$O and sonicated. The resulting solids were filtered, washed with H$_2$O and dried under high vacuum. The crude product was then purified by preparative HPLC using an ammonium acetate buffer system and lyophilized to give '(1R,2R,3S)—

N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide (39 mg, 16% yield). $^1$HNMR (400 MHz, DMSO-d6): δ 10.14 (s, 1H), 9.61 (s, 1H), 8.46 (d, 1H), 7.87 (dd, 1H), 7.67 (m, 2H), 7.57 (m, 1H), 7.51 (s, 1H), 7.42 (s, 1H), 7.39 (m, 1H), 7.15 (t, 2H), 6.41 (d, 1H), 4.20 (m, 2H), 3.94 (s, 3H), 2.87 (m, 2H), 2.60 (m, 4H), 1.80 (m, 2H), 1.18 (s, 3H), 1.17 (s, 3H), 1.01 (m, 6H). Note: 0.5 eq of AcOH is present by NMR. LC/MS Calcd for [M+H]$^+$ 633.3, found 633.4. Alal. HPLC (25 min gradient): 96% pure, 18.52 min.

Example 87

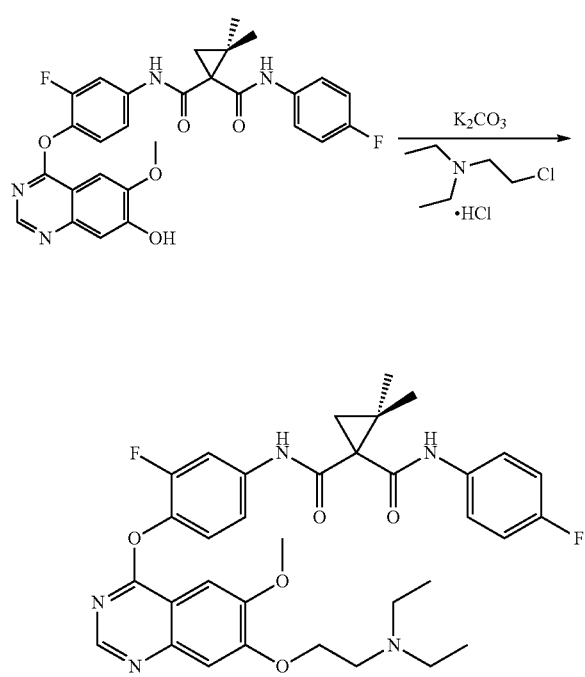

N-(4-{[7-{[2-(diethylamino)ethyl]oxy}-6-(methyloxy)quinazolin-4-yl]oxy}-3-fluorophenyl)-N'-(4-fluorophenyl)-2,2-dimethylcyclopropane-1,1-dicarboxamide. 2,2-Dimethyl-cyclopropane-1,1-dicarboxylic acid [3-fluoro-4-(7-hydroxy-6-methoxy-quinazolin-4-yloxy)-phenyl]-amide (4-fluoro-phenyl)-amide (203 mg, 0.38 mmol), DMA (2 mls), (2-chloro-ethyl)-diethyl-amine, HCl salt (73 mg, 0.42 mmol) and K$_2$CO$_3$ (146 mg, 1.05 mmol) were combined and heated at 80 C overnight. The reaction mixture was then diluted with H$_2$O and extracted with CH$_2$Cl$_2$ (3×). The combined CH$_2$Cl$_2$ extractions were washed with sat'd NaHCO$_3$ (1×), sat'd NaCl (1×), dried (Na$_2$SO$_4$), and concentrated in vacuo. The resulting crude product was purified by flash chromatography (Silica Gel 60, 100% EtOAc, followed by 10% MeOH, 1% triethylamine in EtOAc), then dissolved in 50% aqueous AcCN and lyophilized to give 'N-(4-{[7-{[2-(diethylamino)ethyl]oxy}-6-(methyloxy)quinazolin-4-yl]oxy}-3-fluorophenyl)-N'-(4-fluorophenyl)-2,2-dimethyl-cyclopropane-1,1-dicarboxamide (70 mg, 29% yield). $^1$H NMR (400 MHz, DMSO): δ 10.24 (s, 1H), 10.00 (s, 1H), 8.54 (s, 1H), 7.84 (dd, 1H), 7.66 (m, 2H), 7.56 (s, 1H), 7.51 (m, 1H), 7.43 (m, 2H), 7.18 (t, 2H), 4.26 (m, 2H), 3.98 (s, 3H), 2.88 (m, 2H), 2.59 (m, 4H), 1.58 (m, 2H), 1.18 (s, 6H), 1.00 (t, 6H). LC/MS Calcd for [M+H]$^+$ 634.3, found 634.4. Anal. HPLC (25 min gradient): 94% pure, 24.08 min.

Example 88

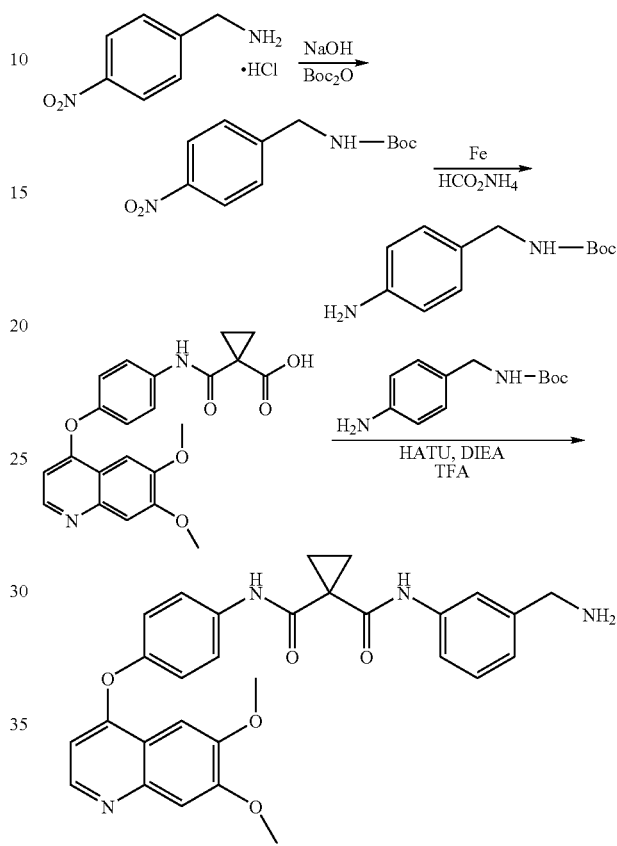

Synthesis of 'N-[3-(aminomethyl)phenyl]-N'-(4-{[6,7-bis(methyloxy)quinolin-4-yl]oxy}phenyl)cyclopropane-1,1-dicarboxamide. (4-Nitro-benzyl)-carbamic acid tert-butyl ester. 4-Nitro-benzylamine, HCl salt (5.19 g, 27.5 mmol) was dissolved in dioxane (100 mls). NaOH (3.4 g, 85.0 mmol) in H$_2$O (20 mls) was added, followed by Boc anhydride (7.6 g, 34.8 mmol). The mixture was stirred at room temperature. After 3 hrs, the reaction mixture was diluted with EtOAc and washed with H$_2$O (3×), sat'd NaCl (1×), dried (Na$_2$SO$_4$), and concentrated in vacuo. The resulting residue was triturated with hexanes, the resulting solids filtered, washed with hexanes and dried under vacuum to give (4-nitro-benzyl)-carbamic acid tert-butyl ester (6.34 g, 91% yield). LC/MS Calcd for [M+H]$^+$ 253.1, found 197.0 (minus t-butyl).

(4-Amino-benzyl)-carbamic acid tert-butyl ester. (4-Nitrobenzyl)-carbamic acid tert-butyl ester (6.34 g, 25.1 mmol), iron powder (6.5 g, 116 mmol), ammonium formate (13.0 g, 206 mmol), H$_2$O (75 mls), and toluene (75 mls) were combined and heated to reflux. After 3 hrs the reaction mixture was allowed to cool and filtered through Celite with thorough washing with EtOAc. The filtrate was transferred to a separatory funnel and the phases separated. The organic phase was further washed with H$_2$O (1×), sat'd NaCl (1×), dried (Na$_2$SO$_4$), and concentrated in vacuo to give (4-amino-benzyl)-carbamic acid tert-butyl ester (5.02 g, 90% yield). LC/MS Calcd for [M+H]$^+$ 223.1, found 167.1 (minus t-butyl).

[3-({1-[4-(6,7-Dimethoxy-quinolin-4-yloxy)-phenylcarbamoyl]-cyclopropane-carbonyl}-amino)-benzyl]-carbamic acid tert-butyl ester. 1-[4-(6,7-Dimethoxy-quinolin-4-yloxy)-phenylcarbamoyl]-cyclopropanecarboxylic acid (254 mg, 0.62 mmol), (4-amino-benzyl)-carbamic acid tert-butyl ester (164 mg, 0.74 mmol), dry DMA (10 mls), HATU (714 mg, 1.88 mmol), and DIEA (325 ml, 1.86 mmol) were combined and stirred at room temperature. After 2 hrs, the reaction mixture is diluted with $H_2O$ and the resulting solids are filtered, washed with $H_2O$, followed by sat'd $NaHCO_3$, and dried under high vacuum to give crude [3-({1-[4-(6,7-dimethoxy-quinolin-4-yloxy)-phenylcarbamoyl]-cyclopropanecarbonyl}-amino)-benzyl]-carbamic acid tert-butyl ester (301 mg, 79% yield) which was used in the next reaction without further purification. LC/MS Calcd for [M+H]$^+$ 613.3, found 613.1.

N-[3-(Aminomethyl)phenyl]-N'-(4-{[6,7-bis(methyloxy)quinolin-4-yl]oxy}phenyl)cyclopropane-1,1-dicarboxamide, TFA salt. [3-({1-[4-(6,7-Dimethoxy-quinolin-4-yloxy)-phenylcarbamoyl]-cyclopropanecarbony}-amino)-benzyl]-carbamic acid tert-butyl ester (50 mg, 0.081 mmol) was dissolved in 50% TFA in $CH_2Cl_2$ (10 mls) and stirred at room temperature. After 2 hrs, the reaction mixture was concentrated in vacuo and the resulting residue was triturated with $Et_2O$. The resulting solids were filtered, washed with $Et_2O$ and dried under high vacuum to give 'N-[3-(aminomethyl)phenyl]-N'-(4-{[6,7-bis(methyloxy)quinolin-4-yl]oxy}phenyl)cyclopropane-1,1-dicarboxamide as the TFA salt (54 mg, 100%). $^1$HNMR (400 MHz, DMSO-d6): δ 10.28 (s, 1H), 10.19 (s, 1H), 8.77 (m, 1H), 8.21 (m, 3H), 7.84 (m, 2H), 7.76 (m, 1H), 7.71 (m, 1H), 7.58 (m, 2H), 7.38 (m, 3H), 7.19 (m, 1H), 6.76 (m, 1H), 4.03 (s, 6H), 3.39 (m, 2H), 1.53 (m, 4H). Note: all peaks are very broad and unresolved. LC/MS Calcd for [M+H]$^+$ 513.2, found 513.4. Anal. HPLC (25 min gradient): 88% pure, 12.39 min.

Table 3 contains $^1$H-NMR data for selected compounds of the invention.

TABLE 3

| Entry | Name | $^1$H-NMR |
|---|---|---|
| 1 | N-[3-fluoro-4-({6-(methyloxy)-7-[(3-piperazin-1-ylpropyl)oxy]quinolin-4-yl}oxy)phenyl]-N'-(4-fluorophenyl)cyclopropane-1,1-dicarboxamide | 1H NMR (DMSO-d6): 10.52 (s, 1H), 10.02 (s, 1H), 9.38 (br., 3H), 8.79 (d, 1H), 7.98 (dd, 1H), 7.74 (s, 1H), 7.65 (m, 3H), 7.54 (m, 2H), 7.15 (t, 2H), 6.86 (d, 1H), 4.33 (t, 2H), 4.04 (s, 3H), 3.17-3.50 (m, 9H), 2.27 (br., 2H), 1.79 (m, 1H), 1.48 (m, 4H). Note: The peak at δ9.38 includes 2 TFA equivalents. |
| 2 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclopropane-1,1-dicarboxamide | 1H NMR (DMSO-d6): 10.41 (s, 1H), 10.03 (s, 1H), 8.47 (d, 1H), 7.90 (dd, 1H), 7.64 (m, 2H), 7.52 (s, 2H), 7.42 (t, 1H), 7.39 (s, 1H), 7.16 (t, 2H), 6.41 (d, 1H), 4.18 (t, 2H), 3.95 (s, 3H), 2.47 (t, 2H), 2.6-2.8 (br., 8H), 2.17 (s, 3H), 1.97 (m, 2H), 1.48 (s, 4H). |
| 3 | N-{3-fluoro-4-[(6-(methyloxy)-7-{[(1-methylpiperidin-4-yl)methyl]oxy}quinolin-4-yl)oxy]phenyl}-N'-(4-fluorophenyl)cyclopropane-1,1-dicarboxamide | 1H NMR (400 MHz, DMSO-d6): d 10.51 (s, 1H), 10.30 (br. s, 1H), 10.04 (s, 1H), 8.80 (d, 1H), 7.99 (dd, 1H), 7.55 (m, 2H), 7.67-7.53 (m, 4H), 7.16 (t, 2H), 6.89 (d, 1H), 4.13 (d, 2H), 4.05 (s, 3H), 3.47 (m, 2H), 3.00 (m, 2H), 2.74 (d, 3H), 2.17 (m, 1H), 2.03 (m, 2H), 1.68 (m, 2H), 1.49 (m, 4H). |
| 4 | N-(4-fluorophenyl)-N'-[4-({6-(methyloxy)-7-[(3-morpholin-4-ylpropyl)oxy]quinolin-4-yl}oxy)phenyl]cyclopropane-1,1-dicarboxamide | $^1$H NMR (400 MHz, DMSO-d6): 8.47 (d, 1H), 8.30 (m, 1H), 8.15 (m, 1H), 7.8 (m, 2H), 7.62 (s, 1H), 7.45 (m, 2H), 7.2 (m, 3H), 7.10 (m, 2H), 6.7 (d, 1H), 4.5 (m, 2H), 4.3 (m, 2H), 4.01 (s, 3H), 3.5 (br, 2H), 3.3 (m, 2H), 3.1 (m, 2H), 2.51 (m, 2H), 1.9 (m, 2H) 1.6 (m, 4H). |
| 5 | N-(4-{[7-{[3-(diethylamino)propyl]oxy}-6-(methyloxy)quinolin-4-yl]oxy}-3-fluorophenyl)-N'-(4-fluorophenyl)cyclopropane-1,1-dicarboxamide | $^1$H NMR (400 MHz, DMSO-d6): 10.58 (s, 1H), 10.31 (bs, 1H), 10.04 (s, 1H), 8.75 (d, 1H), 7.99 (d, 1H), 7.74 (s, 1H), 7.63 (m, 4H), 7.19 (t, 2H), 6.91 (m, 1H), 4.39 (t, 2H), 4.19 (s, 3H), 3.21 (m, 7H), 2.29 (m, 2H), 1.46 (d, 4H), 1.15 (t, 6H). |
| 6 | N-(4-{[6,7-bis(methyloxy)quinolin-4-yl]oxy}-2-chloro-5-fluorophenyl)-N'-(4-fluorophenyl)cyclopropane-1,1-dicarboxamide | 1H NMR (DMSO-d6): 11.56 (s, 1H), 9.77 (s, 1H), 8.50 (d, 1H), 8.32 (d, 1H), 7.82 (d, 1H), 7.59 (m, 2H), 7.51 (s, 1H), 7.42 (s, 1H), 7.20 (t, 2H), 6.55 (d, 1H), 3.95 (s, 3H), 3.94 (s, 3H), 1.73 (m, 2H), 3.65 (m, 2H). |
| 7 | N-(4-{[6,7-bis(methyloxy)-2-(methylthio)quinolin-4-yl]oxy}-3-fluorophenyl)-N'-(4-fluorophenyl)cyclopropane-1,1-dicarboxamide | $^1$H NMR (DMSO-d$_6$) d 10.34 (s, 1H), 9.94 (s, 1H), 7.83 (d, 1H), 7.59 (m, 2H), 7.56 (m, 1H), 7.40 (m, 2H), 7.23 (s, 1H), 7.09 (t, 2H), 6.12 (s, 1H), 3.88 (s, 3H), 3.85 (s, 3H), 2.48 (s, 3H), 1.40 (m, 4H). |
| 8 | N-(4-fluorophenyl)-N'-(4-{[2-methyl-6,7-bis(methyloxy)-quinazolin-4-yl]oxy}phenyl)-cyclopropane-1,1-dicarboxamide | $^1$H NMR (DMSO-d$_6$) 10.15 (bs, 1H), 10.01 (bs, 1H), 7.69-7.75 (m, 2H), 7.61-7.68 (m, 2H), 7.52 (s, 1H), 7.32 (s, 1H), 7.23-7.29 (m, 2H), 7.12-7.19 (m, 2H), 3.93 (d, 6H), 2.43 (s, 3H), 1.53 (s, 4H). |
| 9 | N-(4-{[2-amino-6,7-bis(methyloxy)quinolin-4-yl]oxy}-3-fluorophenyl)-N'-(4-fluorophenyl)cyclopropane-1,1-dicarboxamide | 1H NMR (DMSO-d6) d 10.34 (s, 1H), 9.95 (s, 1H), 7.82 (d, 1H), 7.58 (m, 2H), 7.44 (d, 1H), 7.33 (t, 1H), 7.25 (s, 1H), 7.09 (t, 2H), 7.07 (s, 1H), 6.17 (br s, 2H), 5.66 (s, 1H), 3.79 (s, 3H), 3.77 (s, 3H), 1.40 (d, 4H). |

TABLE 3-continued

| Entry | Name | $^1$H-NMR |
|---|---|---|
| 10 | N-(3-fluoro-4-{[2-(methylamino)-6,7-bis(methyloxy)quinolin-4-yl]oxy}phenyl)-N'-(4-fluorophenyl)cyclopropane-1,1-dicarboxamide | $^1$H NMR (DMSO-d$_6$) d 10.42 (s, 1H), 9.91 (s, 1H), 7.88 (dd, 1H), 7.56 (m, 2H), 7.44 (m, 4H), 7.09 (t, 2H), 5.90 (s, 1H), 3.88 (s, 3H), 3.85 (s, 3H), 3.39 (br s, 1H), 2.92 (s, 3H), 1.41 (dt, 4H). |
| 11 | (1S,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide | $^1$H NMR (400 MHz, DMSO-d$_6$) d 10.49 (br s, 1H), 10.26 (br s, 1H), 10.15 (br s, 1H), 8.74 (br s, 1H), 7.95 (br d, J = 13.2 Hz, 1H), 7.8-7.5 (m, 6H), 7.16 (t, J = 8.9 Hz, 2H), 6.82 (br s, 1H), 4.34 (t, J = 5.9 Hz, 2H), 4.02 (s, 3H), 3.99 (br s, 2H), 3.77 (br t, J = 12.0 Hz, 2H), 3.56-3.30 (m, 4H), 3.17-3.07 (m, 2H), 2.40-2.30 (m, 2H), 2.04-1.95 (m, 1H), 1.45 (dd, J = 7.2, 4.7 Hz, 1H), 1.36 (dd, J = 8.5, 4.5 Hz, 1H), 1.09 (d, J = 6.2 Hz, 3H). |
| 12 | (1R,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide | $^1$H NMR (400 MHz, DMSO-d$_6$) d 10.65 (br s, 1H), 10.54 (br s, 1H), 9.74 (s, 1H), 8.75 (br s, 1H), 8.01 (br d, J = 12.9 Hz, 1H), 7.80-7.50 (m, 6H), 7.20-7.10 (m, 2H), 6.84 (br s, 1H), 4.34 (br t, J = 5 Hz, 2H), 4.04 (s, 3H), 4.05-3.95 (m, 2H), 3.77 (br t, J = 11 Hz, 2H), 3.52 (br d, J = 12.7 Hz, 4H), 3.12 (br q, J = 9.0 Hz, 2H), 2.40-2.30 (m, 2H), 2.10-1.95 (m, 1H), 1.40-1.30 (m, 2H), 1.10 (d, J = 6.2 Hz, 3H). |
| 13 | N-(4-{[6-{[3-(diethylamino)propyl]oxy}-7-(methyloxy)quinolin-4-yl]oxy}-3-fluorophenyl)-N'-(4-fluorophenyl)cyclopropane-1,1-dicarboxamide | $^1$H NMR (DMSO-d$_6$) d 10.37 (br s, 1H), 10.00 (s, 1H), 8.44 (d, 1H), 7.87 (d, 1H), 7.62 (m, 2H), 7.49 (m, 2H), 7.41 (m, 2H), 7.13 (t, 2H), 6.40 (d, 1H), 4.17 (t, 2H), 3.93 (s, 3H), 2.59 (t, 2H), 2.49 (m, 6H), 1.91 (m, 4H), 0.94 (t, 6H). |
| 14 | N-(4-{[6-{[2-(diethylamino)ethyl]oxy}-7-(methyloxy)quinolin-4-yl]oxy}-3-fluorophenyl)-N'-(4-fluorophenyl)cyclopropane-1,1-dicarboxamide | $^1$H NMR (DMSO-d$_6$) d 10.36 (br s, 1H), 9.99 (s, 1H), 8.44 (d, 1H), 7.88 (dd, 1H), 7.62 (m, 2H), 7.57 (m, 2H), 7.41 (m, 2H), 7.13 (t, 2H), 6.40 (d, 1H), 4.17 (t, 2H), 3.93 (s, 3H), 2.85 (t, 2H), 2.56 (q, 4H), 2.49 (m, 4H), 0.98 (t, 6H). |
| 15 | 1,1-dimethylethyl 4-(3-{[4-[(2-fluoro-4-{[(1-{[(4-fluorophenyl)amino]carbonyl}cyclopropyl)-carbonyl]amino}phenyl)oxy]-6-(methyloxy)-quinolin-7-yl]oxy}propyl)-piperazine-1-carboxylate | $^1$H NMR (400 MHz, CDCl$_3$): 10.05 (s, 1H), 8.49-8.27 (t, 1H), 7.79-7.76 (d, 1H), 7.57 (s, 1H), 7.47-7.43 (m, 3H), 7.27-7.20 (m, 1H), 7.09-7.04 (m, 2H), 6.40-6.39 (d, 1H), 4.28-4.25 (t, 2H), 3.50 (s, 3H), 3.47-3.44, (t, 4H), 2.62-2.59 (t, 2H), 2.46-2.44 (t, 4H), 2.18-2.11 (m, 2H), 2.09 (s, 1H), 1.83-1.81 (m, 2H), 1.64-1.61 (t, 2H), 1.47 (s, 9H). |
| 16 | (1R,2R)-N-[3-fluoro-4-({6-(methyloxy)-7-[(3-morpholin-4-ylpropyl)oxy]quinazolin-4-yl}oxy)phenyl]-N'-(4-fluorophenyl)-2-methylcyclopropane-1,1-dicarboxamide | $^1$H NMR (DMSO-d$_6$) d 10.40 (s, 1H), 9.65 (s, 1H), 8.45 (s, 1H), 7.79 (dd, 1H), 7.53 (m, 2H), 7.47 (s, 1H), 7.36 (m, 1H), 7.31 (m, 2H), 7.05 (t, 2H), 4.17 (t, 2H), 3.91 (s, 3H), 3.51 (t, 4H), 2.40 (t, 2H), 2.36 (m, 4H), 1.90 (m, 3H), 1.30 (m, 2H), 1.02 (m, 3H). |
| 17 | (1R,2R)-N-(4-{[7-{[2-(diethylamino)ethyl]oxy}-6-(methyloxy)quinazolin-4-yl]oxy}-3-fluorophenyl)-N'-(4-fluorophenyl)-2-methylcyclopropane-1,1-dicarboxamide | $^1$H NMR (DMSO-d$_6$) d 10.49 (s, 1H), 9.73 (s, 1H), 8.52 (s, 1H), 7.85 (dd, 1H), 7.61 (m, 2H), 7.54 (s, 1H), 7.41 (m, 3H), 7.12 (t, 2H), 7.23 (t, 2H), 3.96 (s, 3H), 2.86 (t, 2H), 2.56 (q, 4H), 1.98 (m, 1H), 1.34 (m, 2H), 1.07 (d, 3H), 0.97 (t, 6H). |
| 18 | N-(4-{[7-{[3-(diethylamino)propyl]oxy}-6-(methyloxy)quinazolin-4-yl]oxy}-3-fluorophenyl)-N'-(4-fluorophenyl)cyclopropane-1,1-dicarboxamide | 1H NMR (DMSO-d6) 8.51 (s, 1H), 7.78-7.84 (m, 1H), 7.58-7.64 (m, 2H), 7.53 (s, 1H), 7.34-7.48 (m, 3H), 7.13 (t, 2H), 4.22 (t, 2H), 3.98 (s, 3H), 2.84 (t, 2H), 2.55 (q, 4H), 1.48 (s, 4H), 1.39 (t, 6H). |
| 19 | N-(4-{[7-{[3-(4-acetylpiperazin-1-yl)propyl]oxy}-6-(methyloxy)quinolin-4-yl]oxy}-3-fluorophenyl)-N'-(4-fluorophenyl)cyclopropane-1,1-dicarboxamide | $^1$H NMR (400 MHz, CDCl$_3$): 10.04 (s, 1H), 8.48-8.47 (d, 1H), 8.21 (s, 1H), 7.79-7.76 (d, 1H), 7.57 (s, 1H), 7.52-7.44 (m, 3H), 7.28-7.20 (m, 2H), 7.09-7.05 (m, 2H), 6.40-6.39 (d, 1H), 4.30-4.26 (t, 2H), 4.04 (s, 3H), 3.64-3.62 (t, 2H), 3.49-3.47 (t, 2H), 2.62-2.58 (t, 2H), 2.50-2.44 (m, 4H), 2.17-2.12 (m, 2H), 2.10 (s, 3H), 1.84-1.81 (m, 2H), 1.64-1.61 (t, 2H). |
| 20 | 1,1-dimethylethyl 4-(3-{[4-[(2-fluoro-4-{[((1R,2R)-1-{[(4-fluorophenyl)amino]carbonyl}-2-methylcyclopropyl)-carbonyl]amino}phenyl)oxy]-6- | $^1$H NMR (400 MHz, DMSO-d$_6$): 10.54 (s, 1H), 9.72 (s, 1H), 8.47-8.46 (d, 1H), 7.96-7.93 (dd, 1H), 7.63-7.61 (m, 2H), 7.52 (br s, 2H), 7.42-7.40 (d, 2H), 7.17-7.12 (m, 2H), 6.44-6.42 (d, 1H), 4.22-4.18 (t, 2H), 3.95 (s, 3H), |

TABLE 3-continued

| Entry | Name | $^1$H-NMR |
|---|---|---|
| | (methyloxy)quinolin-7-yl]oxy}propyl)piperazine-1-carboxylate | 3.42-3.40 (m, 2H), 2.36-2.26 (m, 8H), 2.00-1.98 (m, 3H), 1.58-1.54 (m, 2H), 1.40 (s, 9H), 1.10-1.09 (d, 3H). |
| 21 | N-(4-{[6,7-bis(methyloxy)quinolin-4-yl]oxy}phenyl)-N'-(4-fluorophenyl)-1-(phenylmethyl)azetidine-3,3-dicarboxamide | 1H NMR (DMSO-d6): 10.0 (s, 1H), 9.9 (s, 1H), 8.45 (d, 1H), 7.8 (d, 2H), 7.7 (m, 2H), 7.5 (s, 1H), 7.4 (s, 1H), 7.48-7.15 (m, 9H), 3.95 (s, 6H), 3.7 (s, 4H), 3.6 (s, 2H). |
| 22 | N-(4-{[6,7-bis(methyloxy)quinolin-4-yl]oxy}phenyl)-N'-(4-fluorophenyl)azetidine-3,3-dicarboxamide | 1H NMR (DMSO-d6): 8.46 (d, 1H), 7.84 (d, 2H), 7.70 (m, 2H), 7.50 (s, 1H), 7.40 (s, 1H), 7.24 (d, 2H), 7.20 (t, 2H), 6.44 (d, 1H), 4.03 (s, 4H), 3.95 (s, 6H), 1.90 (s, 3H), acetate salt). |
| 23 | (1R,2S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide | $^1$H NMR (400 MHz, DMSO-d$_6$): 10.26 (s, 1H), 9.75 (s, 1H), 8.47-8.46 (d, 1H), 7.91-7.87 (dd, 1H), 7.70-7.66 (m, 2H), 7.56-7.51 (m, 2H), 7.43-7.38 (m, 2H), 6.42-6.41 (d, 1H), 4.20-4.16 (t, 2H), 3.95 (s, 3H), 2.47-2.43 (m, 2H), 2.40-2.24 (m, 5H), 2.14 (s, 3H), 2.03-1.93 (m, 3H), 1.89 (s, 3H), 1.45-1.42 (m, 1H), 1.38-1.35 (m, 1H), 1.10-1.08 (d, 3H). |
| 24 | (1R,2R)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide | $^1$H NMR (400 MHz, DMSO-d$_6$): 10.56 (s, 1H), 9.75 (s, 1H), 8.47-8.46 (d, 1H), 7.96-7.93 (d, 1H), 7.68-7.61 (m, 2H), 7.53-7.52 (m, 2H), 7.44-7.39 (m, 2H), 7.18-7.12 (m, 2H), 6.44-6.42 (d, 1H), 4.20-4.17 (t, 2H), 3.95 (s, 3H), 3.42-3.30 (m, 3H), 2.46-2.44 (m, 2H), 2.33 (br s, 2H), 2.15 (s, 3H), 2.05-1.94 (m, 2H), 1.89 (s, 5H), 1.40-1.35 (m, 1H), 1.10-1.09 (m, 3H). |
| 25 | (1R,2R)-N-[3-fluoro-4-({6-(methyloxy)-7-[(3-piperazin-1-ylpropyl)oxy]quinolin-4-yl}oxy)phenyl]-N'-(4-fluorophenyl)-2-methylcyclopropane-1,1-dicarboxamide | $^1$H NMR (400 MHz, DMSO-d$_6$): 10.55 (s, 1H), 9.72 (s, 1H), 8.47-8.46 (d, 1H), 7.96-7.93 (d, 1H), 7.68-7.61 (m, 2H), 7.52 (br s, 2H), 7.44-7.40 (m, 2H), 7.17-7.12 (m, 2H), 6.44-6.43 (d, 1H), 4.21-4.18 (t, 2H), 3.95 (s, 3H), 2.79 (br s, 4H), 2.47-2.44 (t, 2H), 2.38 (br s, 3H), 2.04-1.95 (m, 3H), 1.40-1.35 (m, 2H), 1.11-1.09 (m, 5H). |
| 26 | N-(3-fluoro-4-{[7-({3-[4-(1-methylethyl)piperazin-1-yl]propyl}oxy)-6-(methyloxy)quinolin-4-yl]oxy}phenyl)-N'-(4-fluorophenyl)cyclopropane-1,1-dicarboxamide | $^1$H NMR (400 MHz, DMSO-d$_6$): 10.40 (s, 1H), 10.02 (s, 1H), 8.47-8.46 (d, 1H), 7.92-7.89 (d, 1H), 7.66-7.63 (m, 2H), 7.52-7.51 (d, 2H), 7.44-7.39 (m, 2H), 7.19-7.14 (m, 2H), 6.42-6.41 (d, 1H), 4.20-4.17 (t, 2H), 3.95 (s, 3H), 2.70-2.68 (m, 1H), 2.62-2.55 (m, 2H), 2.46-2.33 (m, 8H), 1.99-1.94 (m, 2H), 1.47 (s, 4H), 1.00-0.95 (m, 6H). |
| 27 | N-(4-{[7-{[3-(diethylamino)propyl]oxy}-6-(methyloxy)quinazolin-4-yl]oxy}-3-fluorophenyl)-N'-(4-fluorophenyl)cyclopropane-1,1-dicarboxamide | $^1$H NMR (DMSO-d$_6$)10.34 (s, 1H), 10.01 (s, 1H), 8.50 (s, 1H), 7.81 (dd, 1H), 7.55-7.68 (m, 2H), 7.51-7.55 (m, 2H), 7.33-7.48 (m, 3H), 7.12 (t, 2H), 4.22 (t, 2H), 3.94 (s, 3H), 2.52-2.61 (m, 2H), 2.49-2.51 (m, 4H), 1.83-1.94 (m, 2H), 1.42 (s, 4H), 0.95 (t, 6H). |
| 28 | (1R,2R)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide | $^1$H NMR (DMSO-d$_6$) d 10.52 (s, 1H), 9.70 (s, 1H), 8.44 (d, 1H), 7.92 (dd, 1H), 7.61 (m, 2H), 7.50 (m, 2H), 7.43 (m, 2H), 7.12 (t, 2H), 6.41 (d, 1H), 4.17 (t, 2H), 3.93 (s, 3H), 2.55 (m, 2H), 2.31 (m, 4H), 1.98 (m, 1H), 1.88 (m, 2H), 1.35 (m, 2H), 1.07 (d, 3H), 0.94 (t, 6H). |
| 29 | (1R,2R)-N-(4-{[7-{[2-(diethylamino)ethyl]oxy}-6-(methyloxy)quinolin-4-yl]oxy}-3-fluorophenyl)-N'-(4-fluorophenyl)-2-methylcyclopropane-1,1-dicarboxamide | $^1$H NMR (DMSO-d$_6$) d 10.52 (s, 1H), 9.70 (s, 1H), 8.44 (d, 1H), 7.78 (dd, 1H), 7.61 (m, 2H), 7.51 (m, 2H), 7.41 (m, 2H), 7.12 (t, 2H), 6.41 (d, 1H), 4.17 (t, 2H), 3.93 (s, 3H), 2.85 (t, 2H), 2.57 (q, 4H), 1.98 (m, 1H), 1.34 (m, 2H), 1.07 (d, 3H), 0.98 (t, 6H). |
| 30 | (1R,2S)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide | $^1$H NMR (DMSO-d$_6$) d 10.17 (s, 1H), 9.97 (s, 1H), 8.39 (d, 1H), 7.80 (dd, 1H), 7.62 (m, 2H), 7.45 (m, 2H), 7.31 (m, 2H), 7.09 (t, 2H), 6.34 (d, 1H), 4.12 (t, 2H), 3.88 (s, 3H), 2.46 (m, 2H), 2.40 (m, 4H), 1.92 (m, 1H), 1.84 (m, 2H), 1.37 (m, 1H), 1.29 (m, 1H), 1.01 (d, 3H), 0.89 (t, 6H). |
| 31 | (1R,2S)-N-(4-{[7-{[2-(diethylamino)ethyl]oxy}-6-(methyloxy)quinolin-4-yl]oxy}-3-fluorophenyl)-N'-(4-fluorophenyl)-2- | $^1$H NMR (DMSO-d$_6$) d 10.22 (s, 1H), 10.01 (s, 1H), 8.44 (d, 1H), 7.86 (dd, 1H), 7.66 (m, 2H), 7.49 (m, 2H), 7.39 (m, 2H), 7.14 (m, 2H), 6.39 (d, 1H), 4.18 (m, 2H), 3.92 (s, 3H), 2.85 (t, 2H), 2.57 (q, 4H), 1.97 (m, 1H), 1.42 (m, 1H), |

TABLE 3-continued

| Entry | Name | ¹H-NMR |
|---|---|---|
| | methylcyclopropane-1,1-dicarboxamide | 1.35 (m, 1H), 1.06 (d, 3H), 0.98 (t, 6H). |
| 32 | N-(4-{[7-{[2-(diethylamino)ethyl]oxy}-6-(methyloxy)quinazolin-4-yl]oxy}-3-fluorophenyl)-N'-(4-fluorophenyl)cyclobutane-1,1-dicarboxamide | ¹H NMR (CDCl$_3$) 8.57 (s, 1H), 8.12 (s, 1H), 7.73-7.81 (m, 2H), 7.48-7.53 (m, 2H), 7.32 (s, 1H), 6.98-7.08 (m, 3H), 4.28 (t, 2H), 4.04 (s, 3H), 3.25 (t, 2H), 2.76 (q, 4H), 2.67 (q, 4H), 2.01-2.15 (m, 2H), 1.10 (t, 6H). |
| 33 | (1R,2S)-N-[3-fluoro-4-({6-(methyloxy)-7-[(3-piperazin-1-yl)propyl]oxy}quinolin-4-yl}oxy)phenyl]-N'-(4-fluorophenyl)-2-methylcyclopropane-1,1-dicarboxamide | ¹H NMR (400 MHz, DMSO-d$_6$): 10.28 (s, 1H), 9.80 (s, 1H) 8.47-8.46 (d, 1H), 7.90-7.88 (d, 1H), 7.70-7.62 (m, 2H), 7.56-7.52 (m, 2H), 7.44-7.39 (m, 2H), 7.18-7.12 (m, 2H), 6.44-6.41 (t, 1H), 4.20-4.17 (t, 2H), 3.95 (s, 3H), 2.74-2.72 (t, 3H), 2.46-2.42 (m, 1H), 2.35 (br s, 3H), 2.03-1.93 (m, 3H), 1.87 (s, 4H), 1.43-1.35 (m, 2H), 1.09-1.08 (m, 3H). |
| 34 | (1r,2R,3S)-N-[3-fluoro-4-({6-(methyloxy)-7-[(3-morpholin-4-yl)propyl]oxy}quinolin-4-yl}oxy)phenyl]-N'-(4-fluorophenyl)-2,3-dimethylcyclopropane-1,1-dicarboxamide | ¹H NMR (DMSO-d6): 1H (10.12 ppm, s), 1H (9.6 ppm, s), 1H (8.46 ppm, d), 1H (7.88 ppm, dd), 2H (7.68 ppm, m), 1H (7.56 ppm, d), 1H (7.51 ppm, s), 2H (7.4 ppm, m), 2H (7.13 ppm, t), 1H (6.4 ppm, d), 2H (4.2 ppm, t), 3H (3.94 ppm, s), 4H (3.6 ppm, t), 2H (2.45 ppm, t), 4H (2.37 ppm, m), 2H (1.97 ppm, t), 2H (1.8 ppm, m), 6H (1.28 ppm, d). |
| 35 | (1r,2R,3S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2,3-dimethylcyclopropane-1,1-dicarboxamide | ¹H NMR (DMSO-d6): 1H (10.12 ppm, s), 1H (9.6 ppm, s), 1H (8.46 ppm, d), 1H (7.88 ppm, dd), 2H (7.69 ppm, m), 1H (7.58 ppm, d), 1H (7.51 ppm, s), 2H (7.4 ppm, m), 2H (7.13 ppm, t), 1H (6.4 ppm, d), 2H (4.2 ppm, t), 3H (3.95 ppm, s), 10H (2.35 ppm, m), 3H (2.14 ppm, s), 2H (1.97 ppm, t), 2H (1.8 ppm, m), 6H (1.28 ppm, d). |
| 36 | N-[3-fluoro-4-({6-(methyloxy)-7-[(3-morpholin-4-yl)propyl]oxy}quinazolin-4-yl}oxy)phenyl]-N'-(4-fluorophenyl)cyclobutane-1,1-dicarboxamide | ¹H NMR (400 MHz, DMSO-d6): 8.45 (d, 2H), 8.15 (d, 1H), 7.8 (d, 1H), 7.45 (m, 3H), 7.25 (m, 3H), 7.0 (m, 2H), 4.20 (t, 2H), 4.0 (s, 3H), 3.7 (m, 4H), 2.67 (m, 4H), 2.45 (m, 6H), 2.0 (m, 4H). |
| 37 | (2R,3R)-N-[3-fluoro-4-({6-(methyloxy)-7-[(3-morpholin-4-yl)propyl]oxy}quinolin-4-yl}oxy)phenyl]-N'-(4-fluorophenyl)-2,3-dimethylcyclopropane-1,1-dicarboxamide | ¹H NMR (400 MHz, CDCl$_3$) d 8.44 (d, J = 5.1 Hz, 1H), 8.11 (br s, 1H), 7.77-7.70 (m, 2H), 7.53 (s, 1H), 7.50-7.44 (m, 2H), 7.40 (s, 1H), 7.22-7.16 (m, 2H), 7.06-6.98 (m, 2H), 6.36 (br d, J = 5.1 Hz, 1H), 4.26 (t, J = 7.0 Hz, 2H), 4.02 (s, 3H), 3.72 (t, J = 4.4 Hz, 4H), 2.57 (t, J = 7.3 Hz, 2H), 2.50-2.42 (m, 4H), 2.18-2.10 (m, 2H), 1.80-1.66 (m, 2H), 1.30-1.24 (m, 6H). |
| 38 | (2R,3R)-N-(4-{[7-{[3-(diethylamino)propyl]oxy}-6-(methyloxy)quinolin-4-yl]oxy}-3-fluorophenyl)-N'-(4-fluorophenyl)-2,3-dimethylcyclopropane-1,1-dicarboxamide | ¹H NMR (400 MHz, DMSO-d$_6$) d 10.34 (s, 1H), 10.05 (s, 1H), 8.46 (br s, 1H), 7.93 (br d, J = 4.7 Hz, 1H), 7.54-7.52 (m, 2H), 7.52-7.50 (m, 2H), 7.50-7.30 (m, 2H), 7.20-7.10 (m, 2H), 6.47 (br s, 1H), 4.30-4.20 (m, 2H), 3.95 (s, 3H), 3.40-3.10 (m, 6H), 2.60-2.40 (m, 2H), 1.90-1.80 (m, 2H), 1.30-1.10 (m, 12H). |
| 39 | N-(4-{[7-{[3-(diethylamino)propyl]oxy}-6-(methyloxy)quinolin-4-yl]oxy}-3-fluorophenyl)-N'-(4-fluorophenyl)-2,2-dimethylcyclopropane-1,1-dicarboxamide | 1H NMR (400 MHz, DMSO-d6): d 10.47 (s, 1H), 10.16 (s, 1H), 8.43 (d, 1H), 7.92 (dd, 1H), 7.67 (m, 2H), 7.58 (m, 1H), 7.52 (s, 1H), 7.41 (m, 2H), 7.15 (t, 2H), 6.44 (d, 1H), 4.25 (t, 2H), 3.95 (s, 3H), 3.10 (m, 6H), 2.17 (m, 2H), 1.91 (s, 3H, acetate salt), 1.52 (m, 2H), 1.18 (m, 12H). |
| 40 | N-[3-fluoro-4-({6-(methyloxy)-7-[(3-morpholin-4-yl)propyl]oxy}quinazolin-4-yl}oxy)phenyl]-N'-(4-fluorophenyl)-2,2-dimethylcyclopropane-1,1-dicarboxamide | 1H NMR (400 MHz, DMSO-d6): d 10.21 (s, 1H), 9.97 (s, 1H), 8.51 (s, 1H), 7.81 (dd, 1H), 7.64 (m, 2H), 7.54 (s, 1H), 7.48 (m, 1H), 7.41 (m, 1H), 7.38 (s, 1H), 7.15 (t, 2H), 4.24 (t, 2H), 3.97 (s, 3H), 3.58 (m, 4H), 2.45 (t, 2H), 2.38 (m, 4H), 1.97 (m, 2H), 1.58 (m, 2H), 1.18 (s, 3H), 1.17 (s, 3H). |
| 41 | (1R,2R,3S)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide | 1H NMR (400 MHz, DMSO-d6): d 10.14 (s, 1H), 9.61 (s, 1H), 8.46 (d, 1H), 7.87 (dd, 1H), 7.67 (m, 2H), 7.57 (m, 1H), 7.51 (s, 1H), 7.42 (s, 1H), 7.39 (m, 1H), 7.15 (t, 2H), 6.41 (d, 1H), 4.20 (m, 2H), 3.94 (s, 3H), 2.87 (m, 2H), 2.60 (m, 4H), 1.80 (m, 2H), 1.18 (s, 3H), 1.17 (s, 3H), 1.01 (m, 6H). Note: 0.5eq of AcOH is present by NMR. |
| 42 | N-(4-{[7-{[2-(diethylamino)ethyl]oxy}-6-(methyloxy)quinazolin-4- | 1H NMR (400 MHz, DMSO): d 10.24 (s, 1H), 10.00 (s, 1H), 8.54 (s, 1H), 7.84 (dd, 1H), 7.66 (m, 2H), 7.56 (s, 1H), 7.51 (m, 1H), 7.43 (m, |

TABLE 3-continued

| Entry | Name | ¹H-NMR |
|---|---|---|
| | yl]oxy}-3-fluorophenyl)-N'-(4-fluorophenyl)-2,2-dimethylcyclopropane-1,1-dicarboxamide | 2H), 7.18 (t, 2H), 4.26 (m, 2H), 3.98 (s, 3H), 2.88 (m, 2H), 2.59 (m, 4H), 1.58 (m, 2H), 1.18 (s, 6H), 1.00 (t, 6H). |
| 43 | N-(4-{[7-{[3-(diethylamino)propyl]oxy}-6-(methyloxy)quinazolin-4-yl]oxy}-3-fluorophenyl)-N'-(4-fluorophenyl)-2,2-dimethylcyclopropane-1,1-dicarboxamide | 1H NMR (400 MHz, DMSO-d6): d 10.21 (s, 1H), 9.97 (s, 1H), 8.51 (s, 1H), 7.82 (dd, 1H), 7.64 (m, 2H), 7.54 (s, 1H), 7.48 (m, 1H), 7.41 (m, 1H), 7.37 (s, 1H), 7.15 (t, 2H), 4.23 (t, 2H), 3.97 (s, 3H), 2.56 (m, 2H), 2.46 (m, 4H), 1.91 (m, 2H), 1.58 (m, 2H), 1.18 (s, 6H), 0.96 (t, 6H). |
| 44 | N-(4-{[7-{[3-(diethylamino)propyl]oxy}-6-(methyloxy)quinazolin-4-yl]oxy}-3-fluorophenyl)-N'-(4-fluorophenyl)cyclobutane-1,1-dicarboxamide | 1H NMR (CDCl3): 8.57 (s, 1H), 8.50 (s, 1H), 8.11 (s, 1H), 7.81 (dd, 1H), 7.53 (m, 3H), 7.28 (m, 4H), 7.04 (t, 2H), 4.24 (t, 2H), 4.04 (s, 3H), 2.95 (t, 2H), 2.84 (q, 4H), 2.75 (m, 4H), 2.21 (m, 2H), 2.02 (m, 2H), 1.18 (t, 6H). |
| 45 | N-{3-fluoro-4-[(6-(methyloxy)-7-{[3-(4-methylpiperazin-1-yl)propyl]oxy}quinazolin-4-yl)oxy]phenyl}-N'-(4-fluorophenyl)cyclobutane-1,1-dicarboxamide | 1H NMR (CDCL3): 8.57 (s, 1H), 8.49 (s, 1H), 8.10 (s, 1H), 7.80 (d, 1H), 7.70 (br., 1H), 7.52 (m, 3H), 7.31 (m, 3H), 7.04 (t, 2H), 4.26 (t, 2H), 4.04 (s, 3H), 2.62-2.77 (m, 14H), 2.40 (s, 3H), 2.13 (m, 2H), 2.01 (m, 2H). |
| 46 | (2R,3R)-N-[3-fluoro-4-({6-(methyloxy)-7-[(3-morpholin-4-ylpropyl)oxy]quinazolin-4-yl}oxy)phenyl]-N'-(4-fluorophenyl)-2,3-dimethylcyclopropane-1,1-dicarboxamide | ¹H NMR (400 MHz, CDCl₃) d 8.59 (s, 1H), 8.11 (br s, 1H), 7.80-7.76 (m, 2H), 7.53 (s, 1H), 7.50-7.46 (m, 2H), 7.34 (s, 1H), 7.26-7.24 (m, 2H), 7.06-7.00 (m, 2H), 4.28 (t, J = 6.6 Hz, 2H), 4.05 (s, 3H), 3.73 (br t, J = 4.4 Hz, 4H), 2.57 (t, J = 7.0 Hz, 2H), 2.52-2.45 (m, 4H), 2.18-2.10 (m, 2H), 1.80-1.68 (m, 2H), 1.28-1.20 (m, 6H). |
| 47 | N-(4-{[7-{[3-(diethylamino)propyl]oxy}-6-(methyloxy)quinolin-4-yl]oxy}-3-fluorophenyl)-N'-(4-fluorophenyl)cyclobutane-1,1-dicarboxamide | ¹H NMR (400 MHz, DMSO-d₆): 9.98 (s, 1H), 9.72 (s, 1H), 8.45-8.43 (d, 1H), 7.97-7.94 (dd, 1H), 7.73-7.69 (m, 2H), 7.65-7.52 (m, 3H), 7.44-7.39 (m, 1H), 7.18-7.14 (m, 2H), 6.43-6.42 (d, 1H), 4.20-4.19 (t, 2H), 3.95 (s, 3H), 2.70-2.66 (m, 6H), 2.45 (br s, 2H), 1.91-1.84 (m, 6H), 0.98 (br s, 6H). |
| 48 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclobutane-1,1-dicarboxamide | ¹H NMR (400 MHz, DMSO-d₆): 9.99 (s, 1H), 9.73 (s, 1H), 8.45-8.43 (d, 1H), 7.97-7.93 (dd, 1H), 7.73-7.69 (m, 2H), 7.65-7.52 (m, 3H), 7.44-7.38 (m, 2H), 7.18-7.14 (m, 2H), 6.43-6.42 (d, 1H), 4.19-4.16 (t, 3H), 3.95 (s, 3H), 2.70-2.66 (m, 4H), 2.47-2.33 (m, 8H), 2.15 (s, 3H), 1.98-1.94 (m, 2H), 1.90-1.84 (m, 4H). |
| 49 | (2R,3R)-N-(4-{[7-{[2-(diethylamino)ethyl]oxy}-6-(methyloxy)quinazolin-4-yl]oxy}-3-fluorophenyl)-N'-(4-fluorophenyl)-2,3-dimethylcyclopropane-1,1-dicarboxamide | ¹H NMR (400 MHz, CDCl₃) d 8.59 (br s, 1H), 8.29 (br s, 1H), 7.93 (s, 1H), 7.77 (d, J = 10.8 Hz, 1H), 7.53 (s, 1H), 7.50-7.45 (m, 2H), 7.32 (s, 1H), 7.26-7.22 (m, 2H), 7.05-6.99 (m, 2H), 4.27 (t, J = 6.6 Hz, 2H), 4.04 (s, 3H), 3.03 (t, J = 6.5 Hz, 2H), 2.67 (q, J = 7.0 Hz, 4H), 1.80-1.70 (m, 2H), 1.22 (br t, J = 5.3 Hz, 6H), 1.09 (br t, J = 7.2 Hz, 6H). |
| 50 | (2R,3R)-N-(4-{[7-{[3-(diethylamino)propyl]oxy}-6-(methyloxy)quinazolin-4-yl]oxy}-3-fluorophenyl)-N'-(4-fluorophenyl)-2,3-dimethylcyclopropane-1,1-dicarboxamide | ¹H NMR (400 MHz, CDCl₃) d 8.58 (s, 1H), 8.40-8.36 (m, 1H), 8.02-7.96 (m, 1H), 7.80-7.75 (m, 1H), 7.53 (s, 1H), 7.52-7.50 (m, 2H), 7.31 (s, 1H), 7.28-7.20 (m, 2H), 7.02 (t, J = 8.5 Hz, 2H), 4.25 (t, J = 6.3 Hz, 2H), 4.04 (s, 3H), 3.00-2.90 (m, 2H), 2.88-2.80 (m, 4H), 2.30-2.20 (m, 2H), 1.76-1.68 (m, 2H), 1.25-1.15 (m, 12H). |
| 51 | (2R,3R)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide | ¹H NMR (400 MHz, CDCl₃) d 8.47 (d, J = 5.2 Hz, 1H), 8.17 (br s, 1H), 7.80-7.74 (m, 2H), 7.55 (s, 1H), 7.52-7.46 (m, 2H), 7.42 (s, 1H), 7.24-7.20 (m, 2H), 7.05 (t, J = 8.6 Hz, 2H), 6.38 (br d, J = 5.4 Hz, 1H), 4.27 (t, J = 6.4 Hz, 2H), 4.03 (s, 3H), 3.04 (br t, J = 7.2 Hz, 2H), 2.68 (q, J = 6.8 Hz, 4H), 1.80-1.68 (m, 2H), 1.26 (d, J = 6.4 Hz, 6H), 1.09 (br t, J = 7.2 Hz, 6H). |
| 52 | N-(4-{[6,7-bis(methyloxy)quinolin-4-yl]oxy}phenyl)-N'-[(4-fluorophenyl)methyl]cyclopropane-1,1-dicarboxamide | 1H NMR (DMSO-d6): 10.82 (s, 1H), 8.80 (d, 1H), 8.50 (t, 1H), 7.83 (d, 2H), 7.74 (s, 1H), 7.56 (s, 1H), 7.30-7.38 (m, 4H), 7.15 (t, 2H), 6.80 (d, 1H), 4.32 (d, 2H), 4.04 (s, 3H), 4.03 (s, 3H), 1.42 (s, 4H). |

TABLE 3-continued

| Entry | Name | $^1$H-NMR |
|---|---|---|
| 53 | N-(4-{[6,7-bis(methyloxy)quinolin-4-yl]oxy}phenyl)-N'-(2-morpholin-4-ylethyl)cyclopropane-1,1-dicarboxamide | 1H NMR (DMSO-d6): 10.62 (s, 1H), 8.79 (d, 1H), 8.24 (t, 1H), 7.83 (d, 2H), 7.72 (s, 1H), 7.58 (s, 1H), 7.37 (d, 2H), 6.76 (d, 1H), 4.04 (s, 3H), 4.03 (s, 3H), 3.98 (m, 2H), 3.66 (m, 2H), 3.49 (m, 4H), 3.25 (t, 2H), 3.13 (br., 2H), 1.42 (d, 4H). |
| 54 | N-(4-{[6,7-bis(methyloxy)quinolin-4-yl]oxy}phenyl)-N'-[2-(piperidin-1-ylmethyl)phenyl]cyclopropane-1,1-dicarboxamide | 1H NMR (DMSO-d6): 10.78 (s, 1H), 10.53 (s, 1H), 8.43 (d, 1H), 8.12 (d, 1H), 7.82 (d, 2H), 7.49 (s, 1H), 7.37 (s, 1H), 7.20-7.28 (m, 3H), 7.15 (dd, 1H), 7.01 (td, 1H), 6.35 (d, 1H), 3.93 (s, 3H), 3.92 (s, 3H), 3.47 (s, 2H), 2.17 (br., 4H), 1.49 (m, 4H), 1.41 (m, 4H), 1.32 (br., 2H). |
| 55 | N-(4-{[6,7-bis(methyloxy)quinolin-4-yl]oxy}phenyl)-N'-[2-(pyrrolidin-1-ylmethyl)phenyl]cyclopropane-1,1-dicarboxamide | 1H NMR (DMSO-d6): 10.98 (s, 1H), 10.56 (s, 1H), 8.42 (d, 1H), 8.10 (dd, 1H), 7.81 (m, 2H), 7.49 (s, 1H), 7.37 (s, 1H), 7.17-7.27 (m, 4H), 7.01 (td, 1H), 6.35 (d, 1H), 3.93 (s, 3H), 3.92 (s, 3H), 3.61 (s, 2H), 2.30 (br., 4H), 1.47 (br., 4H), 1.43 (m, 4H). |
| 56 | N-(4-{[6,7-bis(methyloxy)quinolin-4-yl]oxy}phenyl)-N'-[3-(morpholin-4-ylmethyl)phenyl]cyclopropane-1,1-dicarboxamide | 1H NMR (DMSO-d6): 10.12 (s, 1H), 10.03 (s, 1H), 8.44 (d, 1H), 7.74 (d, 2H), 7.57 (s, 1H), 7.53 (d, 1H), 7.48 (s, 1H), 7.37 (s, 1H), 7.21 (m, 3H), 6.98 (d, 1H), 6.40 (d, 1H), 3.93 (s, 3H), 3.92 (s, 3H), 3.56 (t, 4H), 3.41 (s, 2H), 2.34 (br., 4H), 1.48 (s, 4H). |
| 57 | N-(4-{[6,7-bis(methyloxy)quinolin-4-yl]oxy}phenyl)-N'-[2-(morpholin-4-ylmethyl)phenyl]cyclopropane-1,1-dicarboxamide | 1H NMR (DMSO-d6): 10.54 (s, 1H), 10.47 (s, 1H), 8.43 (d, 1H), 8.08 (d, 1H), 7.78 (d, 2H), 7.49 (s, 1H), 7.37 (d, 1H), 7.18-7.30 (m, 4H), 7.03 (t, 1H), 6.37 (d, 1H), 3.94 (s, 3H), 3.93 (s, 3H), 3.50 (s, 2H), 3.44 (br., 4H), 2.20 (br., 4H), 1.48 (d, 4H). |
| 58 | N-(4-{[6,7-bis(methyloxy)quinolin-4-yl]oxy}phenyl)-N'-phenylcyclopropane-1,1-dicarboxamide | 1H NMR (DMSO-d6): 10.14 (s, 1H), 10.03 (s, 1H), 8.44 (d, 1H), 7.74 (d, 2H), 7.62 (d, 2H), 7.48 (s, 1H), 7.37 (s, 1H), 7.27-7.31 (m, 2H), 7.19-7.23 (m, 2H), 7.05 (t, 1H), 6.41 (d, 1H), 3.93 (s, 6H), 3.92 (s, 3H), 1.48 (s, 4H). |
| 59 | N-[3-(aminomethyl)phenyl]-N'-(4-{[6,7-bis(methyloxy)-quinolin-4-yl]oxy}phenyl)-cyclopropane-1,1-dicarboxamide | 1H NMR (400 MHz, DMSO-d6): d 10.28 (s, 1H), 10.19 (s, 1H), 8.77 (m, 1H), 8.21 (m, 3H), 7.84 (m, 2H), 7.76 (m, 1H), 7.71 (m, 1H), 7.58 (m, 2H), 7.38 (m, 3H), 7.19 (m, 1H), 6.76 (m, 1H), 4.03 (s, 6H), 3.39 (m, 2H), 1.53 (m, 4H). Note: all peaks are very broad and unresolved. |
| 60 | N-(4-{[6,7-bis(methyloxy)quinolin-4-yl]oxy}phenyl)-N'-[3-(piperidin-1-ylmethyl)-phenyl]cyclopropane-1,1-dicarboxamide | 1H NMR (DMSO-d6): 10.0-10.2 (br., 2H), 8.46 (d, 1H), 7.76 (d, 2H), 7.53 (m, 3H), 7.39 (s, 1H), 7.24 (m, 3H), 6.98 (d, 1H), 6.43 (d, 1H), 3.95 (s, 3H), 3.93 (s, 3H), 3.37 (s, 2H), 2.31 (br., 4H), 1.48 (m, 8H), 1.39 (br., 2H). |
| 61 | N-(4-{[6,7-bis(methyloxy)quinolin-4-yl]oxy}phenyl)-N'-[3-(pyrrolidin-1-ylmethyl)-phenyl]cyclopropane-1,1-dicarboxamide | 1H NMR (DMSO-d6): 10.0-10.2 (br., 2H), 8.46 (d, 1H), 7.77 (d, 2H), 7.59 (s, 1H), 7.53 (d, 1H), 7.51 (s, 1H), 7.39 (s, 1H), 7.23 (m, 3H), 6.99 (d, 1H), 6.43 (d, 1H), 3.95 (s, 3H), 3.93 (s, 3H), 3.52 (s, 2H), 2.42 (br., 4H), 1.69 (br, 4H), 1.48 (s, 4H). |

Assays

Kinase assays were performed by measurement of incorporation of $\gamma$-$^{33}$P ATP into immobilized myelin basic protein (MBP). High binding white 384 well plates (Greiner) were coated with MBP (Sigma #M-1891) by incubation of 60 ul/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and $\gamma$-$^{33}$P ATP was added to start the reaction (2×10$^6$ cpm of $\gamma$-$^{33}$P ATP per well (3000 Ci/mmole) and either 10 μM or 30 μM unlabeled ATP, typically. The reactions were carried out for 1 hour at room temperature with shaking. Plates were washed 7× with TBS, followed by the addition of 50 μl/well scintillation fluid (Wallac). Plates were read using a Wallac Trilux counter. This is only one format of such assays, various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the conditions of the assay. Exemplary compositions have IC$_{50}$'s of, for example, less than about 100 μM, less than about 10 μM, less than about 1 μM, and further for example having IC$_{50}$'s of less than about 100 nM, and still further, for example, less than about 10 nM. The K$_i$ for a compound may be determined from the IC$_{50}$ based on three assumptions. First, only one compound molecule binds to the enzyme and there is no cooperatively. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + K_d) - \sqrt{(E_0 + I_0 + K_d)^2 - 4E_0 I_0}}{2E_0}\right]$$

where V is the observed rate, $V_{max}$, is the rate of the free enzyme, $I_0$ is the inhibitor concentration, $E_0$ is the enzyme concentration, and $K_d$ is the dissociation constant of the enzyme-inhibitor complex.

Kinase Specificity Assays:

Kinase activity and compound inhibition are investigated using one or more of the three assay formats described below. The ATP concentrations for each assay are selected to be close to the Michaelis-Menten constant ($K_M$) for each individual kinase. Dose-response experiments are performed at 10 different inhibitor concentrations in a 384-well plate format. The data are fitted to the following four-parameter equation:

$$Y = Min + (Max - Min)/(1 + (X/IC_{50})^H)$$

where Y is the observed signal, X is the inhibitor concentration, Min is the background signal in the absence of enzyme (0% enzyme activity), Max is the signal in the absence of inhibitor (100% enzyme activity), $IC_{50}$ is the inhibitor concentration at 50% enzyme inhibition and H represents the empirical Hill's slope to measure the cooperatively. Typically H is close to unity.

c-Met Assay c-Met biochemical activity was assessed using a Luciferase-Coupled Chemiluminescent Kinase assay (LCCA) format as described above. Again, kinase activity was measured as the percent ATP remaining following the kinase reaction. Remaining ATP was detected by luciferase-luciferin-coupled chemiluminescence. Specifically, the reaction was initiated by mixing test compounds, 1 µM ATP, 1 µM poly-EY and 10 nM c-Met (baculovirus expressed human c-Met kinase domain P948-S1343) in a 20 uL assay buffer (20 mM Tris-HCL pH7.5, 10 nM MgCl$_2$, 0.02% Triton X-100, 100 mM DTT, 2 mM MnCl$_2$). The mixture is incubated at ambient temperature for 2 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase.

KDR Assay

KDR biochemical activity was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 3 µM ATP, 1.6 µM poly-EY and 5 nM KDR (baculovirus expressed human KDR kinase domain D807-V1356) in a 20 uL assay buffer (20 mM Tris-HCL pH7.5, 10 mM MgCl$_2$, 0.01% Triton X-100, 1 mM DTT, 3 mM MnCl$_2$). The mixture is incubated at ambient temperature for 4 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase.

flt-4 Assay

Biochemical activity for flt-4 was assessed using an Alphascreen Tyrosine Kinase protocol. AlphaScreen™ (Perkin Elmer) technology is a proximity assay employing microparticles. Singlet oxygen derived from a donor bead following laser excitation results in chemiluminescence when in proximity (100 Å) to an acceptor bead due to biomolecular interactions. For the Flt-4 assay, donor beads coated with streptavidin and acceptor beads coated with PY100 anti-phosphotyrosine antibody were used (Perkin Elmer). Biotinylated poly(Glu,Tyr) 4:1 (Perkin Elmer) was used as the substrate. Substrate phosphorylation was measured by addition of donor/acceptor beads by chemiluminescence following donor-acceptor bead complex formation. Test compounds, 5 µM ATP, 3 mM biotinylated poly(Glu, Tyr) and 1 nM Flt-4 (baculovirus expressed human Flt-4 kinase domain D725-R1298) were combined in a volume of 20 µL in a 384-well white, medium binding microtiter plate (Greiner). Reaction mixtures were incubated for 1 hr at ambient temperature. Reactions were quenched by addition of 10 uL of 15-30 mg/mL AlphaScreen bead suspension containing 75 mM Hepes, pH 7.4, 300 mM NaCl, 120 mM EDTA, 0.3% BSA and 0.03% Tween-20. After 2-16 hr incubation at ambient temperature plates were read using an AlphaQuest reader (Perkin Elmer). $IC_{50}$ values correlate well with those determined by radiometric assays.

flt-3 Assay

Biochemical activity for flt-3 was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 5 µM ATP, 3 µM poly-EY and 5 nM Flt-3 (baculovirus expressed human Flt-3 kinase domain R571-S993) in a 20 uL assay buffer (20 mM Tris-HCL pH7.5 mM MgCl$_2$, 0.01% Triton X-100, 1 mM DTT, 2 mM MnCl$_2$). The mixture is incubated at ambient temperature for 3 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 µunits of light/mL luciferase.

c-Kit Assay c-Kit biochemical activity was assessed using AlphaScreen™ (Perkin Elmer) technology, described above. Test compounds, ATP, biotinylated poly(Glu, Tyr) and c-Kit kinase were combined in a volume of 20 µL in a 384-well white, medium binding microtiter plate (Greiner). Reaction mixtures were incubated for 1 hr at ambient temperature. Reactions were quenched by addition of 10 uL of 15-30 mg/mL AlphaScreen bead suspension containing 75 mM Hepes, pH 7.4, 300 mM NaCl, 120 mM EDTA, 0.3% BSA and 0.03% Tween-20. After 16 µl incubation at ambient temperature plates were read using an AlphaQuest reader (Perkin Elmer).

Structure Activity Relationships

Table 4 shows structure activity relationship data for selected compounds of the invention. Inhibition is indicated as $IC_{50}$ with the following key: A=$IC_{50}$ less than 50 nM, B=$IC_{50}$ greater than 50 nM, but less than 500 nM, C=$IC_{50}$ greater than 500 μM, but less than 5000 nM, and D=$IC_{50}$ greater than 5,000 nM. Depending upon the functionality about the quinazoline or quinoline, exemplary compounds of the invention exhibit selectivity for any of c-Met, KDR, c-Kit, flt-3, and flt-4. Abbreviations for enzymes listed in Tables 2-3 are defined as follows: c-Met refers to hepatocyte growth factor receptor kinase; KDR refers to kinase insert domain receptor tyrosine kinase; flt-4, fms-like tyrosine kinase-4, representative of the FLK family of receptor tyrosine kinases; c-Kit, also called stem cell factor receptor or steel factor receptor; and flt-3, fms-like tyrosine kinase-3. Empty cells in the tables indicate lack of data only.

TABLE 4

| Entry | Name | c-Met | KDR | c-Kit | flt3 | flt4 |
|---|---|---|---|---|---|---|
| 1 | N-[({3-fluoro-4-[(6-(methyloxy)-7-{[(3aR,6aS)-octahydrocyclopenta[c]pyrrol-5-ylmethyl]oxy}quinazolin-4-yl)oxy]phenyl}amino)carbonothioyl]-2-phenylacetamide | | A | | | A |
| 2 | N-{[(3-fluoro-4-{[7-({[(3aR,6aS)-2-methyloctahydrocyclopenta[c]pyrrol-5-yl]methyl}oxy)-6-(methyloxy)quinazolin-4-yl]oxy}phenyl)amino]carbonothioyl}-2-phenylacetamide | A | A | A | | A |
| 3 | N-{[(4-{[6,7-bis(methyloxy)quinolin-4-yl]oxy}-3-fluorophenyl)(methyl)amino]carbonothioyl}-2-phenylacetamide | C | | | | |
| 4 | 1-(4-{[6,7-bis(methyloxy)quinolin-4-yl]oxy}-3-fluorophenyl)imidazolidin-2-one | C | | C | C | |
| 5 | 1-(4-{[6,7-bis(methyloxy)quinolin-4-yl]oxy}-3-fluorophenyl)-3-(phenylmethyl)imidazolidin-2-one | C | | B | C | |
| 6 | 1-(4-{[6,7-bis(methyloxy)quinolin-4-yl]oxy}-3-fluorophenyl)-3-(phenylacetyl)imidazolidin-2-one | B | | | | |
| 7 | ethyl [(4-{[6,7-bis(methyloxy)quinolin-4-yl]oxy}-3-fluorophenyl)amino](oxo)acetate | B | B | C | | B |
| 8 | N-{[(4-{[6,7-bis(methyloxy)quinazolin-4-yl]amino}-3-fluorophenyl)amino]carbonothioyl}-2-phenylacetamide | A | B | C | | B |
| 9 | N'-(4-{[6,7-bis(methyloxy)quinolin-4-yl]oxy}-3-fluorophenyl)-N-methyl-N-(2-phenylethyl)sulfamide | C | | | | |
| 10 | N-(4-{[6,7-bis(methyloxy)quinolin-4-yl]oxy}-3-fluorophenyl)-3-(phenylmethyl)-1,2,4-oxadiazol-5-amine | C | | B | C | |
| 11 | 1-(4-{[6,7-bis(methyloxy)quinolin-4-yl]oxy}-3-fluorophenyl)piperidin-2-one | C | | C | C | |
| 12 | N-(4-{[6,7-bis(methyloxy)quinolin-4-yl]oxy}-3-fluorophenyl)-N'-(phenylmethyl)ethanediamide | B | B | B | C | B |
| 13 | N-(4-{[6,7-bis(methyloxy)quinolin-4-yl]oxy}-3-fluorophenyl)-4-phenyl-1,3-thiazol-2-amine | C | | C | B | |
| 14 | N-(4-{[6,7-bis(methyloxy)quinolin-4-yl]oxy}-3-fluorophenyl)-N'-(2-phenylethyl)ethanediamide | A | A | A | C | A |
| 15 | N-(4-{[6,7-bis(methyloxy)quinolin-4-yl]oxy}-3-fluorophenyl)-1-phenylmethanesulfonamide | C | | C | B | |
| 16 | N-(4-{[6,7-bis(methyloxy)quinolin-4-yl]oxy}-3-fluorophenyl)-2-phenylethanesulfonamide | C | | C | C | |
| 17 | 4-{[6,7-bis(methyloxy)quinolin-4-yl]oxy}-3-fluoro-N-(phenylmethyl)benzenesulfonamide | C | | C | C | |
| 18 | 4-{[6,7-bis(methyloxy)quinolin-4-yl]oxy}-3-fluoro-N-methyl-N-(phenylmethyl)benzenesulfonamide | C | | C | C | |
| 19 | 4-{[6,7-bis(methyloxy)quinolin-4-yl]oxy}-3-fluoro-N-(2-phenylethyl)benzenesulfonamide | C | | C | C | |
| 20 | 4-{[6,7-bis(methyloxy)quinolin-4-yl]oxy}-3-fluoro-N-methyl-N-(2-phenylethyl)benzenesulfonamide | C | | C | C | |
| 21 | 4-{[6,7-bis(methyloxy)quinolin-4-yl]oxy}-3-fluoro-N-(3-phenylpropyl)benzenesulfonamide | C | | | | |
| 22 | 1-(4-{[6,7-bis(methyloxy)quinolin-4-yl]oxy}-3-fluorophenyl)pyrrolidin-2-one | C | | C | B | |
| 23 | 4-{[6,7-bis(methyloxy)quinolin-4-yl]oxy}phenyl (phenylmethyl)carbamate | C | | | | |
| 24 | 4-{[6,7-bis(methyloxy)quinolin-4-yl]oxy}phenyl (2-phenylethyl)carbamate | C | | | | |
| 25 | 4-{[6,7-bis(methyloxy)quinolin-4-yl]oxy}-3-fluoro-N-methyl-N-(3-phenylpropyl)benzenesulfonamide | C | | | | |
| 26 | N-(4-{[6,7-bis(methyloxy)quinolin-4-yl]oxy}-3-fluorophenyl)-N'-phenylethanediamide | B | D | C | | C |
| 27 | 4-{[6,7-bis(methyloxy)quinolin-4-yl]amino}-N-(3-phenylpropyl)benzamide | C | | | | |
| 28 | N-{[(3-fluoro-4-{[7-{[(2-methyloctahydrocyclopenta[c]pyrrol-5-yl)methyl]oxy}-6-(methyloxy)quinolin-4- | A | A | A | A | A |

TABLE 4-continued

| Entry | Name | c-Met | KDR | c-Kit | flt3 | flt4 |
|---|---|---|---|---|---|---|
|  | yl]oxy}phenyl)amino]carbonothioyl}-2-phenylacetamide |  |  |  |  |  |
| 29 | N-[(Z)-[(4-{[6,7-bis(methyloxy)quinolin-4-yl]oxy}-3-fluorophenyl)amino](imino)methyl]-2-phenylacetamide | C |  |  |  |  |
| 30 | 4-{[6,7-bis(methyloxy)quinolin-4-yl]oxy}-3-fluoro-N-[2-(phenyloxy)ethyl]benzenesulfonamide | C |  |  |  |  |
| 31 | This type of multiplicative nomenclature is not supported in current version! | C |  |  |  |  |
| 32 | N-(4-{[6,7-bis(methyloxy)quinolin-4-yl]oxy}-3-fluorophenyl)-3-phenylpropane-1-sulfonamide | C |  |  |  |  |
| 33 | N~2~-[(4-{[6,7-bis(methyloxy)quinolin-4-yl]oxy}-3-fluorophenyl)sulfonyl]-N-phenylglycinamide | C |  |  |  |  |
| 34 | N-(6-{[6,7-bis(methyloxy)quinolin-4-yl]oxy}pyridin-3-yl)-2-phenylacetamide | C |  |  |  |  |
| 35 | N-{[(6-{[6,7-bis(methyloxy)quinolin-4-yl]oxy}pyridin-3-yl)amino]carbonothioyl}-2-phenylacetamide | A | C | D |  | C |
| 36 | 6-{[6,7-bis(methyloxy)quinolin-4-yl]oxy}-1,3-benzothiazol-2-amine | C |  | C | C |  |
| 37 | 6-{[6,7-bis(methyloxy)quinolin-4-yl]oxy}-5-fluoro-1,3-benzothiazol-2-amine | C |  | C | C |  |
| 38 | N-(6-{[6,7-bis(methyloxy)quinolin-4-yl]oxy}-5-fluoro-1,3-benzothiazol-2-yl)-2-phenylacetamide | B | C | D |  | B |
| 39 | N-(4-{[6,7-bis(methyloxy)quinolin-4-yl]oxy}-3-fluorophenyl)-N'-(2-morpholin-4-ylethyl)ethanediamide | C |  | B | B |  |
| 40 | 1,1-dimethylethyl {2-[(4-{[6,7-bis(methyloxy)quinolin-4-yl]oxy}-3-fluorophenyl)amino]-2-oxoethyl}(phenylmethyl)carbamate | C |  |  |  |  |
| 41 | N-(4-{[6,7-bis(methyloxy)quinolin-4-yl]oxy}-3-fluorophenyl)-N~2~-(phenylmethyl)glycinamide | B |  |  |  |  |
| 42 | N~2~-acetyl-N-(4-{[6,7-bis(methyloxy)quinolin-4-yl]oxy}-3-fluorophenyl)-N~2~-(phenylmethyl)glycinamide | C |  |  |  |  |
| 43 | N-(6-{[6,7-bis(methyloxy)quinolin-4-yl]oxy}-1,3-benzothiazol-2-yl)-2-phenylacetamide | B |  |  |  |  |
| 44 | 1,1-dimethylethyl {2-[(6-{[6,7-bis(methyloxy)quinolin-4-yl]oxy}pyridin-3-yl)-amino]-2-oxoethyl}(phenylmethyl)carbamate | C |  |  |  |  |
| 45 | N-(6-{[6,7-bis(methyloxy)quinolin-4-yl]oxy}pyridin-3-yl)-N~2~-(phenylmethyl)glycinamide | C |  |  |  |  |
| 46 | N~2~-acetyl-N-(6-{[6,7-bis(methyloxy)quinolin-4-yl]oxy}pyridin-3-yl)-N~2~-(phenylmethyl)glycinamide | C |  |  |  |  |
| 47 | N-(6-{[6,7-bis(methyloxy)quinolin-4-yl]oxy}pyridin-3-yl)-3-phenylpropanamide | C |  |  |  |  |
| 48 | N-(6-{[6,7-bis(methyloxy)quinolin-4-yl]oxy}pyridin-3-yl)-4-phenylbutanamide | C |  |  |  |  |
| 49 | N-(6-{[6,7-bis(methyloxy)quinolin-4-yl]oxy}pyridin-3-yl)-N~2~-methyl-N~2~-(phenylmethyl)glycinamide | C |  |  |  |  |
| 50 | N-(4-{[6,7-bis(methyloxy)quinolin-4-yl]oxy}-3-fluorophenyl)-N'-{2-[4-(methyloxy)phenyl]ethyl}ethanediamide | C |  | C | C |  |
| 51 | N-(4-{[6,7-bis(methyloxy)quinolin-4-yl]oxy}-3-fluorophenyl)-N~2~-methyl-N~2~-(phenylmethyl)glycinamide | B | A | B | B | A |
| 52 | N-{[(4-{[6,7-bis(methyloxy)quinolin-4-yl]amino}phenyl)amino]carbonothioyl}-2-phenylacetamide | A | B | B | C | A |
| 53 | N-(6-{[6,7-bis(methyloxy)quinolin-4-yl]oxy}-5-fluoro-1,3-benzothiazol-2-yl)-3-phenylpropanamide | C |  |  |  |  |
| 54 | N-{[(6-{[6,7-bis(methyloxy)quinolin-4-yl]oxy}-5-chloropyridin-3-yl)amino]carbonothioyl}-2-phenylacetamide | A | B | C |  | B |
| 55 | N-(4-{[6,7-bis(methyloxy)quinolin-4-yl]oxy}-3-fluorophenyl)-N'-(2,3-dihydro-1H-inden-1-yl)ethanediamide | A | B | B |  | B |
| 56 | N-(4-{[6,7-bis(methyloxy)quinolin-4-yl]oxy}-3-fluorophenyl)-N'-(2,3-dihydro-1H-inden-2-yl)ethanediamide | C |  |  |  |  |
| 57 | N-(4-{[6,7-bis(methyloxy)quinolin-4-yl]oxy}-3-fluorophenyl)-N'-(1,2,3,4-tetrahydronaphthalen-1-yl)ethanediamide | B | B | C |  | C |
| 58 | N'-(4-{[6,7-bis(methyloxy)quinolin-4-yl]oxy}-3-fluorophenyl)-N-(2-phenylethyl)-N-(phenylmethyl)sulfamide | 1470.06 |  |  |  |  |

TABLE 4-continued

| Entry | Name | c-Met | KDR | c-Kit | flt3 | flt4 |
|---|---|---|---|---|---|---|
| 59 | N-(4-{[6,7-bis(methyloxy)quinolin-4-yl]oxy}-3-fluorophenyl)-N~2~-(trifluoroacetyl)glycinamide | B | C | B | | B |
| 60 | N-{2-[(4-{[6,7-bis(methyloxy)quinolin-4-yl]oxy}-3-fluorophenyl)amino]-2-oxoethyl}benzamide | B | A | A | A | A |
| 61 | N-(6-{[6,7-bis(methyloxy)quinolin-4-yl]oxy}pyridin-3-yl)-N'-(4-fluorophenyl)propanediamide | A | B | B | | B |
| 62 | N-(4-{[6,7-bis(methyloxy)quinolin-4-yl]oxy}-3-fluorophenyl)-N'-[(2S)-1,2,3,4-tetrahydronaphthalen-2-yl]ethanediamide | C | | | | |
| 63 | N-(4-{[6,7-bis(methyloxy)quinolin-4-yl]oxy}-3-fluorophenyl)-N'-[2-(4-methylphenyl)ethyl]ethanediamide | C | | C | C | |
| 64 | N-(4-{[6,7-bis(methyloxy)quinolin-4-yl]oxy}-3-fluorophenyl)-N'-(2-phenylpropyl)ethanediamide | B | A | B | B | B |
| 65 | N-(4-{[6,7-bis(methyloxy)quinolin-4-yl]oxy}-3-fluorophenyl)-N'-[2-(4-chlorophenyl)ethyl]ethanediamide | A | C | B | C | C |
| 66 | N-(4-{[6,7-bis(methyloxy)quinolin-4-yl]oxy}-3-fluorophenyl)-N,N'-bis(phenylmethyl)sulfamide | C | | | | |
| 67 | N-(4-{[6,7-bis(methyloxy)quinolin-4-yl]oxy}-3-fluorophenyl)-N,N'-bis(2-phenylethyl)sulfamide | C | | | | |
| 68 | ethyl [(6-{[6,7-bis(methyloxy)quinolin-4-yl]oxy}-5-chloropyridin-3-yl)amino](oxo)acetate | C | | | | |
| 69 | N-(6-{[6,7-bis(methyloxy)quinolin-4-yl]oxy}-5-chloropyridin-3-yl)-N'-(2-phenylethyl)ethanediamide | C | | | | |
| 70 | N-(6-{[6,7-bis(methyloxy)quinolin-4-yl]oxy}-5-chloropyridin-3-yl)-N'-(4-fluorophenyl)propanediamide | A | B | B | | C |
| 71 | N-(4-{[6,7-bis(methyloxy)quinolin-4-yl]oxy}-3-fluorophenyl)-N'-[(2R)-1,2,3,4-tetrahydronaphthalen-2-yl]ethanediamide | B | D | B | | C |
| 72 | N-(4-{[6,7-bis(methyloxy)quinolin-4-yl]oxy}-3-fluorophenyl)-N'-[2-(1-methylpyrrolidin-2-yl)ethyl]ethanediamide | C | | C | C | |
| 73 | N-(4-{[6,7-bis(methyloxy)quinolin-4-yl]oxy}-3-fluorophenyl)-N'-[2-(phenyloxy)ethyl]ethanediamide | B | B | B | | C |
| 74 | N-(4-{[6,7-bis(methyloxy)quinolin-4-yl]oxy}-3-fluorophenyl)-N'-[2-hydroxy-1-(phenylmethyl)ethyl]urea | B | | | | |
| 75 | 1-(4-{[6,7-bis(methyloxy)quinolin-4-yl]oxy}-3-fluorophenyl)-3-[(4-methylphenyl)sulfonyl]-4-(phenylmethyl)imidazolidin-2-one | B | B | B | B | B |
| 76 | N'-(4-{[6,7-bis(methyloxy)quinolin-4-yl]oxy}-3-fluorophenyl)-N-methyl-N-(2-phenylethyl)ethanediamide | A | B | B | B | B |
| 77 | N-(4-{[6,7-bis(methyloxy)quinolin-4-yl]oxy}-3-fluorophenyl)-N'-{[3-(trifluoromethyl)phenyl]methyl}ethanediamide | B | | B | B | |
| 78 | N-(4-{[6,7-bis(methyloxy)quinolin-4-yl]oxy}-3-fluorophenyl)-N'-{2-[3-(trifluoromethyl)phenyl]ethyl}ethanediamide | C | | A | B | |
| 79 | N-(6-{[6,7-bis(methyloxy)quinolin-4-yl]oxy}-5-chloropyridin-3-yl)-3-oxo-4-phenylbutanamide | C | | | | |
| 80 | N-(6-{[6,7-bis(methyloxy)quinolin-4-yl]oxy}-5-chloropyridin-3-yl)-2-[3-(trifluoromethyl)phenyl]acetamide | C | | | | |
| 81 | 6-{[6,7-bis(methyloxy)quinolin-4-yl]oxy}-5-fluoro-N-[2-(phenyloxy)ethyl]-1,3-benzothiazol-2-amine | B | | | | |
| 82 | 6-{[6,7-bis(methyloxy)quinolin-4-yl]oxy}-5-fluoro-N-(2-piperidin-1-ylethyl)-1,3-benzothiazol-2-amine | C | | | | |
| 83 | 6-{[6,7-bis(methyloxy)quinolin-4-yl]oxy}-5-fluoro-N-methyl-N-(2-phenylethyl)-1,3-benzothiazol-2-amine | C | | | | |
| 84 | 6-{[6,7-bis(methyloxy)quinolin-4-yl]oxy}-5-fluoro-N-(2-pyrrolidin-1-ylethyl)-1,3-benzothiazol-2-amine | C | | | | |
| 85 | 6-{[6,7-bis(methyloxy)quinolin-4-yl]oxy}-5-fluoro-N-{[3-(trifluoromethyl)phenyl]methyl}-1,3-benzothiazol-2-amine | C | | | | |
| 86 | 6-{[6,7-bis(methyloxy)quinolin-4-yl]oxy}-5-fluoro-N-{2-[3-(trifluoromethyl)phenyl]ethyl}-1,3-benzothiazol-2-amine | C | | | | |
| 87 | N-(6-{[6,7-bis(methyloxy)quinolin-4-yl]oxy}-5-chloropyridin-3-yl)-N'-[3-(trifluoromethyl)phenyl]propanediamide | C | | | | |
| 88 | N-(6-{[6,7-bis(methyloxy)quinolin-4-yl]oxy}-5-fluoro-1,3-benzothiazol-2-yl)-2-[3-(trifluoromethyl)phenyl]acetamide | C | A | B | B | B |

TABLE 4-continued

| Entry | Name | c-Met | KDR | c-Kit | flt3 | flt4 |
|---|---|---|---|---|---|---|
| 89 | N-(4-{[6,7-bis(methyloxy)quinolin-4-yl]oxy}-3-fluorophenyl)-N~2~-{[3-(trifluoromethyl)phenyl]methyl}glycinamide | B | A | B | B | A |
| 90 | N-(4-{[6,7-bis(methyloxy)quinolin-4-yl]oxy}-3-fluorophenyl)-N~2~-(2-phenylethyl)glycinamide | B | | | | |
| 91 | N-(4-{[6,7-bis(methyloxy)quinolin-4-yl]oxy}-3-fluorophenyl)-N~2~-{2-[3-(trifluoromethyl)phenyl]ethyl}glycinamide | B | B | B | B | A |
| 92 | 1,1-dimethylethyl {2-[(6-{[6,7-bis(methyloxy)quinolin-4-yl]oxy}-5-chloropyridin-3-yl)amino]-2-oxoethyl}(phenylmethyl)carbamate | C | | | | |
| 93 | N-(6-{[6,7-bis(methyloxy)quinolin-4-yl]oxy}-5-chloropyridin-3-yl)-N~2~-(phenylmethyl)glycinamide | C | | | | |
| 94 | N-(6-{[6,7-bis(methyloxy)quinolin-4-yl]oxy}-5-fluoro-1,3-benzothiazol-2-yl)-2-[3,5-bis(trifluoromethyl)phenyl]acetamide | C | B | B | D | C |
| 95 | N-(6-{[6,7-bis(methyloxy)quinolin-4-yl]oxy}-5-fluoro-1,3-benzothiazol-2-yl)-2-[2-chloro-5-(trifluoromethyl)phenyl]acetamide | A | A | B | B | B |
| 96 | N-{3-fluoro-4-[(6-(methyloxy)-7-{[(1-methylpiperidin-4-yl)methyl]oxy}quinolin-4-yl)oxy]phenyl}-N'-(2-phenylethyl)ethanediamide | A | A | A | A | A |
| 97 | N-(4-{[6,7-bis(methyloxy)quinolin-4-yl]oxy}-3-fluorophenyl)-N'-(1,2,3,4-tetrahydroisoquinolin-1-ylmethyl)ethanediamide | C | | | | |
| 98 | N-(4-{[6,7-bis(methyloxy)quinolin-4-yl]oxy}-3-fluorophenyl)-N'-[(2-methyl-1,2,3,4-tetrahydroisoquinolin-1-yl)methyl]ethanediamide | B | B | B | A | B |
| 99 | N-(4-{[6,7-bis(methyloxy)quinolin-4-yl]oxy}-3-fluorophenyl)-N~2~-methyl-N~2~-{[3-(trifluoromethyl)phenyl]methyl}glycinamide | C | | | | |
| 100 | N-(4-{[6,7-bis(methyloxy)quinolin-4-yl]oxy}-3-fluorophenyl)-N~2~-methyl-N~2~-{2-[3-(trifluoromethyl)phenyl]ethyl}glycinamide | C | | | | |
| 101 | N-(4-{[6,7-bis(methyloxy)quinolin-4-yl]oxy}-3-fluorophenyl)-N~2~-methyl-N~2~-(2-phenylethyl)glycinamide | C | | | | |
| 102 | 1-(4-{[6,7-bis(methyloxy)quinolin-4-yl]oxy}-3-fluorophenyl)-4-(phenylmethyl)imidazolidin-2-one | B | B | B | B | C |
| 103 | N-(6-{[6,7-bis(methyloxy)quinolin-4-yl]oxy}pyridazin-3-yl)-N'-(4-fluorophenyl)propanediamide | A | C | B | A | C |
| 104 | N-(6-{[6,7-bis(methyloxy)quinolin-4-yl]oxy}-5-chloropyridin-3-yl)-N'-(2-chlorophenyl)propanediamide | B | | | | |
| 105 | N-(6-{[6,7-bis(methyloxy)quinolin-4-yl]oxy}-5-chloropyridin-3-yl)-N'-(3-chlorophenyl)propanediamide | C | | | | |
| 106 | N-(6-{[6,7-bis(methyloxy)quinolin-4-yl]oxy}-5-chloropyridin-3-yl)-N~2~-methyl-N~2~-(phenylmethyl)glycinamide | C | | | | |
| 107 | N-(6-{[6,7-bis(methyloxy)quinolin-4-yl]oxy}-5-chloropyridin-3-yl)-N'-(4-chlorophenyl)propanediamide | B | | | | |
| 108 | (2E)-N-(4-{[6,7-bis(methyloxy)quinolin-4-yl]oxy}phenyl)-2-[(methyloxy)imino]propanamide | B | B | | | |
| 109 | (2E)-N-(4-{[6,7-bis(methyloxy)quinolin-4-yl]oxy}phenyl)-2-[(ethyloxy)imino]propanamide | B | A | | | |
| 110 | (2E)-N-(4-{[6,7-bis(methyloxy)quinolin-4-yl]oxy}phenyl)-2-{[(phenylmethyl)oxy]imino}propanamide | B | B | | | |
| 111 | N-(4-{[6,7-bis(methyloxy)quinolin-4-yl]oxy}phenyl)-1-(phenylmethyl)prolinamide | C | C | | | |
| 112 | 1-(4-{[6,7-bis(methyloxy)quinolin-4-yl]oxy}phenyl)-3-[(4-methylphenyl)sulfonyl]-4-(phenylmethyl)imidazolidin-2-one | B | C | B | C | C |
| 113 | 1-(4-{[6,7-bis(methyloxy)quinolin-4-yl]oxy}phenyl)-4-(phenylmethyl)imidazolidin-2-one | C | C | | | |
| 114 | N-(4-{[6,7-bis(methyloxy)quinolin-4-yl]oxy}phenyl)-4-(phenylmethyl)-4,5-dihydro-1,3-oxazol-2-amine | C | B | | | |
| 115 | 6,7-bis(methyloxy)-4-({4-[4-(phenylmethyl)piperazin-1-yl]phenyl}oxy)quinoline | C | C | | | |
| 116 | 1-(4-{[6,7-bis(methyloxy)quinolin-4-yl]oxy}phenyl)-4-(phenylmethyl)piperazin-2-one | C | C | | | |
| 117 | N-(4-{[6,7-bis(methyloxy)quinolin-4-yl]oxy}phenyl)-N~2~-(phenylmethyl)alaninamide | C | C | | | |
| 118 | N-(4-{[6,7-bis(methyloxy)quinolin-4-yl]oxy}phenyl)-N~2~-methyl-N~2~-(phenylmethyl)alaninamide | C | C | | | |

TABLE 4-continued

| Entry | Name | c-Met | KDR | c-Kit | flt3 | flt4 |
|---|---|---|---|---|---|---|
| 119 | N-(4-{[6,7-bis(methyloxy)quinolin-4-yl]oxy}phenyl)-N~2~-(phenylmethyl)leucinamide | C | C | | | |
| 120 | N-(4-{[6,7-bis(methyloxy)quinolin-4-yl]oxy}phenyl)-N~2~-methyl-N~2~-(phenylmethyl)leucinamide | C | C | | | |
| 121 | N-(4-{[6,7-bis(methyloxy)quinolin-4-yl]oxy}phenyl)-N~2~-(phenylmethyl)valinamide | C | C | | | |
| 122 | N-[5-chloro-6-({6-(methyloxy)-4-[(piperidin-4-ylmethyl)oxy]quinolin-7-yl}oxy)pyridin-3-yl]-N'-(4-fluorophenyl)propanediamide | C | C | | | |
| 123 | 1-(4-{[6,7-bis(methyloxy)quinolin-4-yl]oxy}phenyl)-4-(phenylmethyl)tetrahydropyrimidin-2(1H)-one | C | C | | | |
| 124 | N-[3-fluoro-4-({6-(methyloxy)-7-[(piperidin-4-ylmethyl)oxy]quinolin-4-yl}oxy)phenyl]-N'-(2-phenylethyl)ethanediamide | A | A | A | A | A |
| 125 | N-(6-{[6,7-bis(methyloxy)quinolin-4-yl]oxy}-5-chloropyridin-3-yl)-N'-(4-fluorophenyl)cyclopropane-1,1-dicarboxamide | A | A | B | A | B |
| 126 | N-(6-{[6,7-bis(methyloxy)quinolin-4-yl]oxy}-5-chloropyridin-3-yl)-N'-(4-fluorophenyl)cyclobutane-1,1-dicarboxamide | C | C | | | |
| 127 | N-(4-{[6,7-bis(methyloxy)quinolin-4-yl]oxy}phenyl)-N~2~-methyl-N~2~-(phenylmethyl)valinamide | C | C | | | |
| 128 | (2E)-N-(4-{[6,7-bis(methyloxy)quinolin-4-yl]oxy}phenyl)-2-[(phenyloxy)imino]propanamide | C | A | | | |
| 129 | (2E)-N-(4-{[6,7-bis(methyloxy)quinolin-4-yl]oxy}phenyl)-2-phenyl-2-{[(phenylmethyl)oxy]imino}ethanamide | B | C | | | |
| 130 | 6,7-bis(methyloxy)-4-({4-[4-(phenylmethyl)piperidin-1-yl]phenyl}oxy)quinoline | C | C | | | |
| 131 | N-(4-{[6,7-bis(methyloxy)quinolin-4-yl]oxy}-3-fluorophenyl)-N'-{[2-(1-methylethyl)-1,2,3,4-tetrahydroisoquinolin-1-yl]methyl}ethanediamide | B | B | | | |
| 132 | N-(4-{[6,7-bis(methyloxy)quinolin-4-yl]oxy}-3-fluorophenyl)-N'-[(2-ethyl-1,2,3,4-tetrahydroisoquinolin-1-yl)methyl]ethanediamide | B | C | | | |
| 133 | 1,1-dimethylethyl 4-({[4-{[3-chloro-5-({3-[(4-fluorophenyl)amino]-3-oxopropanoyl}amino)pyridin-2-yl]oxy}-6-(methyloxy)quinolin-7-yl]oxy}methyl)piperidine-1-carboxylate | B | C | | | |
| 134 | N-[5-chloro-6-({6-(methyloxy)-7-[(piperidin-4-ylmethyl)oxy]quinolin-4-yl}oxy)pyridin-3-yl]-N'-(4-fluorophenyl)propanediamide | A | B | B | A | |
| 135 | N-{5-chloro-6-[(6-(methyloxy)-7-{[(1-methylpiperidin-4-yl)methyl]oxy}quinolin-4-yl)oxy]pyridin-3-yl}-N'-(4-fluorophenyl)propanediamide | A | B | B | A | |
| 136 | N-(4-{[7-{[3-(diethylamino)propyl]oxy}-6-(methyloxy)quinolin-4-yl]oxy}-3-fluorophenyl)-N'-(2-phenylethyl)ethanediamide | A | A | A | B | A |
| 137 | N-[3-fluoro-4-({6-(methyloxy)-7-[(3-morpholin-4-ylpropyl)oxy]quinolin-4-yl}oxy)phenyl]-N'-(2-phenylethyl)ethanediamide | A | A | A | B | A |
| 138 | N-[3-fluoro-4-({6-(methyloxy)-7-[(3-piperidin-1-ylpropyl)oxy]quinolin-4-yl}oxy)phenyl]-N'-(2-phenylethyl)ethanediamide | A | A | A | A | |
| 139 | N-(4-{[7-{[2-(diethylamino)ethyl]oxy}-6-(methyloxy)quinolin-4-yl]oxy}-3-fluorophenyl)-N'-(2-phenylethyl)ethanediamide | A | A | A | A | A |
| 140 | N'-{3-fluoro-4-[(6-(methyloxy)-7-{[(1-methylpiperidin-4-yl)methyl]oxy}quinolin-4-yl)oxy]phenyl}-N-methyl-N-(2-phenylethyl)ethanediamide | A | A | | | B |
| 141 | N-(3-fluoro-4-{[7-({[(3aR,5r,6aS)-2-methyloctahydrocyclopenta[c]pyrrol-5-yl]methyl}oxy)-6-(methyloxy)quinolin-4-yl]oxy}phenyl)-N'-2-phenylethyl)ethanediamide | A | A | A | A | A |
| 142 | N-(3-fluoro-4-{[7-({[(3aR,6aS)-2-methyloctahydrocyclopenta[c]pyrrol-5-yl]methyl}oxy)-6-(methyloxy)quinazolin-4-yl]oxy}phenyl)-N'-(2-phenylethyl)ethanediamide | A | A | A | A | A |
| 143 | 2-(3,4-dihydroisoquinolin-2(1H)-yl)-N-{3-fluoro-4-[(6-(methyloxy)-7-{[(1-methylpiperidin-4-yl)methyl]oxy}quinolin-4-yl)oxy]phenyl}-2-oxoacetamide | A | A | | | |
| 144 | N-[3-fluoro-4-({6-(methyloxy)-7-[(piperidin-4-ylmethyl)oxy]quinolin-4-yl}oxy)phenyl]-2-oxo-2-(3-phenylpyrrolidin-1-yl)acetamide | A | A | A | A | A |

TABLE 4-continued

| Entry | Name | c-Met | KDR | c-Kit | flt3 | flt4 |
|---|---|---|---|---|---|---|
| 145 | N-[3-fluoro-4-({6-(methyloxy)-7-[(piperidin-4-ylmethyl)oxy]quinolin-4-yl}oxy)phenyl]-2-oxo-2-(2-phenylmorpholin-4-yl)acetamide | A | B | B | B | |
| 146 | N-[2-(dimethylamino)-2-phenylethyl]-N'-[3-fluoro-4-({6-(methyloxy)-7-[(piperidin-4-ylmethyl)oxy]quinolin-4-yl}oxy)phenyl]ethanediamide | A | A | B | A | |
| 147 | N-[3-fluoro-4-({6-(methyloxy)-7-[(piperidin-4-ylmethyl)oxy]quinolin-4-yl}oxy)phenyl]-N'-(2-oxo-2-phenylethyl)ethanediamide | A | B | B | B | B |
| 148 | N-(6-{[6,7-bis(methyloxy)quinolin-4-yl]oxy}-5-chloropyridin-3-yl)-2,2-difluoro-N'-(4-fluorophenyl)propanediamide | C | C | | | |
| 149 | N-{3-fluoro-4-[(6-(methyloxy)-7-{[(1-methylpiperidin-4-yl)methyl]oxy}quinolin-4-yl)oxy]phenyl}-N'-(phenylmethyl)ethanediamide | A | A | A | B | A |
| 150 | N-[3-fluoro-4-({6-(methyloxy)-7-[(piperidin-4-ylmethyl)oxy]quinolin-4-yl}oxy)phenyl]-N'-[2-(2-fluorophenyl)ethyl]ethanediamide | A | A | A | A | A |
| 151 | N-[2-(3-chlorophenyl)ethyl]-N'-[3-fluoro-4-({6-(methyloxy)-7-[(piperidin-4-ylmethyl)oxy]quinolin-4-yl}oxy)phenyl]ethanediamide | A | A | A | A | A |
| 152 | N-[3-fluoro-4-({6-(methyloxy)-7-[(piperidin-4-ylmethyl)oxy]quinolin-4-yl}oxy)phenyl]-N'-{2-[2-(methyloxy)phenyl]ethyl}ethanediamide | A | A | A | A | A |
| 153 | N-[3-fluoro-4-({6-(methyloxy)-7-[(piperidin-4-ylmethyl)oxy]quinolin-4-yl}oxy)phenyl]-N'-(2-pyridin-3-ylethyl)ethanediamide | A | B | B | B | |
| 154 | N-[3-fluoro-4-({6-(methyloxy)-7-[(piperidin-4-ylmethyl)oxy]quinolin-4-yl}oxy)phenyl]-N'-(phenylmethyl)ethanediamide | A | A | A | B | A |
| 155 | N-{2-[2,5-bis(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | A | A | A | A |
| 156 | N-[3-fluoro-4-({6-(methyloxy)-7-[(piperidin-4-ylmethyl)oxy]quinolin-4-yl}oxy)phenyl]-N'-{2-[2-(trifluoromethyl)phenyl]ethyl}ethanediamide | A | A | A | A | C |
| 157 | N-{2-[2-(ethyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | A | A | A | A |
| 158 | N-[2-(2,4-dimethylphenyl)ethyl]-N'-[3-fluoro-4-({6-(methyloxy)-7-[(piperidin-4-ylmethyl)oxy]quinolin-4-yl}oxy)phenyl]ethanediamide | A | B | B | A | B |
| 159 | N-[3-fluoro-4-({6-(methyloxy)-7-[(piperidin-4-ylmethyl)oxy]quinolin-4-yl}oxy)phenyl]-N'-[(1S)-2-(4-methylphenyl)-1-phenylethyl]ethanediamide | B | C | | | |
| 160 | N-[2-(4-chlorophenyl)ethyl]-N'-[3-fluoro-4-({6-(methyloxy)-7-[(piperidin-4-ylmethyl)oxy]quinolin-4-yl}oxy)phenyl]ethanediamide | A | A | A | A | B |
| 161 | ({3-fluoro-4-[(6-(methyloxy)-7-{[(1-methylpiperidin-4-yl)methyl]oxy}quinolin-4-yl)oxy]phenyl}amino)(oxo)acetic acid | B | C | | | |
| 162 | N-[3-fluoro-4-({6-(methyloxy)-7-[(piperidin-4-ylmethyl)oxy]quinolin-4-yl}oxy)phenyl]-N'-[2-(3-fluorophenyl)ethyl]ethanediamide | A | A | | | A |
| 163 | N-[2-(2-chlorophenyl)ethyl]-N'-[3-fluoro-4-({6-(methyloxy)-7-[(piperidin-4-ylmethyl)oxy]quinolin-4-yl}oxy)phenyl]ethanediamide | A | A | A | B | A |
| 164 | N-[3-fluoro-4-({6-(methyloxy)-7-[(piperidin-4-ylmethyl)oxy]quinolin-4-yl}oxy)phenyl]-N'-{2-[3-(methyloxy)phenyl]ethyl}ethanediamide | A | A | A | A | A |
| 165 | N-(1,2-diphenylethyl)-N'-[3-fluoro-4-({6-(methyloxy)-7-[(piperidin-4-ylmethyl)oxy]quinolin-4-yl}oxy)phenyl]ethanediamide | A | A | B | B | C |
| 166 | N-[2-(2,4-dichlorophenyl)ethyl]-N'-[3-fluoro-4-({6-(methyloxy)-7-[(piperidin-4-ylmethyl)oxy]quinolin-4-yl}oxy)phenyl]ethanediamide | A | B | B | A | B |
| 167 | N-{2-[3,4-bis(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | B | B | B | |
| 168 | N-[2-(4-ethylphenyl)ethyl]-N'-[3-fluoro-4-({6-(methyloxy)-7-[(piperidin-4-ylmethyl)oxy]quinolin-4-yl}oxy)phenyl]ethanediamide | A | B | B | B | C |
| 169 | N-{2-[4-(ethyloxy)phenyl]ethyl}-N'-[3-fluoro-4-({6-(methyloxy)-7-[(piperidin-4-ylmethyl)oxy]quinolin-4-yl}oxy)phenyl]ethanediamide | B | C | B | B | |
| 170 | N-{2-[4-(ethyloxy)-3-(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | B | C | B | |

TABLE 4-continued

| Entry | Name | c-Met | KDR | c-Kit | flt3 | flt4 |
|---|---|---|---|---|---|---|
| 171 | N-[3-fluoro-4-({6-(methyloxy)-7-[(piperidin-4-ylmethyl)oxy]quinolin-4-yl}oxy)phenyl]-N'-{2-[4-(phenyloxy)phenyl]ethyl}ethanediamide | B | C | C | C | |
| 172 | N-{2-[3-(ethyloxy)-4-(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | C | B | B | |
| 173 | N-[3-fluoro-4-({6-(methyloxy)-7-[(piperidin-4-ylmethyl)oxy]quinolin-4-yl}oxy)phenyl]-N'-(2-pyridin-2-ylethyl)ethanediamide | A | A | A | B | B |
| 174 | N-[3-fluoro-4-({6-(methyloxy)-7-[(piperidin-4-ylmethyl)oxy]quinolin-4-yl}oxy)phenyl]-N'-(2-pyridin-4-ylethyl)ethanediamide | A | B | B | B | C |
| 175 | N-[3-fluoro-4-({6-(methyloxy)-7-[(piperidin-4-ylmethyl)oxy]quinolin-4-yl}oxy)phenyl]-N'-[2-(4-fluorophenyl)ethyl]ethanediamide | A | A | A | A | A |
| 176 | N-[2-(2-bromophenyl)ethyl]-N'-[3-fluoro-4-({6-(methyloxy)-7-[(piperidin-4-ylmethyl)oxy]quinolin-4-yl}oxy)phenyl]ethanediamide | A | A | A | A | A |
| 177 | N-[2-(2-chloro-6-fluorophenyl)ethyl]-N'-[3-fluoro-4-({6-(methyloxy)-7-[(piperidin-4-ylmethyl)oxy]quinolin-4-yl}oxy)phenyl]ethanediamide | A | A | A | B | A |
| 178 | N-[3-fluoro-4-({6-(methyloxy)-7-[(piperidin-4-ylmethyl)oxy]quinolin-4-yl}oxy)phenyl]-N'-[(2R)-2-phenylpropyl]ethanediamide | A | A | A | B | A |
| 179 | N-(2,3-dihydro-1H-inden-1-yl)-N'-[3-fluoro-4-({6-(methyloxy)-7-[(piperidin-4-ylmethyl)oxy]quinolin-4-yl}oxy)phenyl]ethanediamide | A | A | A | A | A |
| 180 | N-{3-fluoro-4-[(6-(methyloxy)-7-{[(1-methylpiperidin-4-yl)methyl]oxy}quinolin-4-yl)oxy]phenyl}-N'-(2-methylpropyl)ethanediamide | A | B | B | B | |
| 181 | N-{3-fluoro-4-[(6-(methyloxy)-7-{[(1-methylpiperidin-4-yl)methyl]oxy}quinolin-4-yl)oxy]phenyl}-N'-(3-methylbutyl)ethanediamide | A | B | B | B | B |
| 182 | N-{3-fluoro-4-[(6-(methyloxy)-7-{[(1-methylpiperidin-4-yl)methyl]oxy}quinolin-4-yl)oxy]phenyl}-N'-[(2R)-2-phenylpropyl]ethanediamide | A | A | A | A | A |
| 183 | N-{3-fluoro-4-[(6-(methyloxy)-7-{[(1-methylpiperidin-4-yl)methyl]oxy}quinolin-4-yl)oxy]phenyl}-N'-(2-phenylpropyl)ethanediamide | A | A | A | A | A |
| 184 | N-(2,3-dihydro-1H-inden-2-yl)-N'-{3-fluoro-4-[(6-(methyloxy)-7-{[(1-methylpiperidin-4-yl)methyl]oxy}quinolin-4-yl)oxy]phenyl}ethanediamide | A | A | A | B | A |
| 185 | N-[3-fluoro-4-({6-(methyloxy)-7-[(piperidin-4-ylmethyl)oxy]quinolin-4-yl}oxy)phenyl]-N'-[(1R)-1-phenylethyl]ethanediamide | A | B | B | B | |
| 186 | N-[3-fluoro-4-({6-(methyloxy)-7-[(piperidin-4-ylmethyl)oxy]quinolin-4-yl}oxy)phenyl]-N'-[(1S)-1-phenylethyl]ethanediamide | A | B | A | B | C |
| 187 | N-[2-(3-bromophenyl)ethyl]-N'-[3-fluoro-4-({6-(methyloxy)-7-[(piperidin-4-ylmethyl)oxy]quinolin-4-yl}oxy)phenyl]ethanediamide | A | A | A | A | A |
| 188 | N-[2-(2,6-dichlorophenyl)ethyl]-N'-[3-fluoro-4-({6-(methyloxy)-7-[(piperidin-4-ylmethyl)oxy]quinolin-4-yl}oxy)phenyl]ethanediamide | A | A | A | A | A |
| 189 | N-[2-(1,3-benzodioxol-5-yl)ethyl]-N'-[3-fluoro-4-({6-(methyloxy)-7-[(piperidin-4-ylmethyl)oxy]quinolin-4-yl}oxy)phenyl]ethanediamide | A | A | B | A | B |
| 190 | N-{5-chloro-6-[(6-(methyloxy)-7-{[(1-methylpiperidin-4-yl)methyl]oxy}quinolin-4-yl)oxy]pyridin-3-yl}-N'-(4-fluorophenyl)cyclopropane-1,1-dicarboxamide | A | A | B | A | A |
| 191 | N-{2-[3-bromo-4-(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | A | B | B | B |
| 192 | N-{2-[3,5-bis(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | A | A | B | B |
| 193 | N-[3-fluoro-4-({6-(methyloxy)-7-[(piperidin-4-ylmethyl)oxy]quinolin-4-yl}oxy)phenyl]-N'-[2-(2-methylphenyl)ethyl]ethanediamide | A | A | A | B | A |
| 194 | N-[3-fluoro-4-({6-(methyloxy)-7-[(piperidin-4-ylmethyl)oxy]quinolin-4-yl}oxy)phenyl]-N'-[2-(3-methylphenyl)ethyl]ethanediamide | A | A | A | A | A |
| 195 | N-{2-[3-(ethyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | A | B | B | B |

TABLE 4-continued

| Entry | Name | c-Met | KDR | c-Kit | flt3 | flt4 |
|---|---|---|---|---|---|---|
| 196 | N-[2-(3,4-dimethylphenyl)ethyl]-N'-[3-fluoro-4-({6-(methyloxy)-7-[(piperidin-4-ylmethyl)oxy]quinolin-4-yl}oxy)phenyl]ethanediamide | A | A | B | B | B |
| 197 | N-[2-(2,5-dimethylphenyl)ethyl]-N'-[3-fluoro-4-({6-(methyloxy)-7-[(piperidin-4-ylmethyl)oxy]quinolin-4-yl}oxy)phenyl]ethanediamide | A | A | A | A | A |
| 198 | N-{2-[3-chloro-4-(propyloxy)phenyl]ethyl}-N'-[3-fluoro-4-({6-(methyloxy)-7-[(piperidin-4-ylmethyl)oxy]quinolin-4-yl}oxy)phenyl]ethanediamide | B | C | | | |
| 199 | N-{2-[4-(butyloxy)-3-chlorophenyl]ethyl}-N'-[3-fluoro-4-({6-(methyloxy)-7-[(piperidin-4-ylmethyl)oxy]quinolin-4-yl}oxy)phenyl]ethanediamide | B | C | | | |
| 200 | N-{2-[4-(1,1-dimethylethyl)phenyl]ethyl}-N'-[3-fluoro-4-({6-(methyloxy)-7-[(piperidin-4-ylmethyl)oxy]quinolin-4-yl}oxy)phenyl]ethanediamide | B | C | | | |
| 201 | N-{2-[4-(aminosulfonyl)phenyl]ethyl}-N'-[3-fluoro-4-({6-(methyloxy)-7-[(piperidin-4-ylmethyl)oxy]quinolin-4-yl}oxy)phenyl]ethanediamide | A | B | B | B | B |
| 202 | N-[3-fluoro-4-({6-(methyloxy)-7-[(piperidin-4-ylmethyl)oxy]quinolin-4-yl}oxy)phenyl]-N'-{2-[4-hydroxy-3-(methyloxy)phenyl]ethyl}ethanediamide | A | B | B | A | B |
| 203 | N-[3-fluoro-4-({6-(methyloxy)-7-[(piperidin-4-ylmethyl)oxy]quinolin-4-yl}oxy)phenyl]-N'-{2-[3-hydroxy-4-(methyloxy)phenyl]ethyl}ethanediamide | A | B | B | B | B |
| 204 | N-[(2,4-dichlorophenyl)methyl]-N'-[3-fluoro-4-({6-(methyloxy)-7-[(piperidin-4-ylmethyl)oxy]quinolin-4-yl}oxy)phenyl]ethanediamide | A | A | A | A | B |
| 205 | N-[3-fluoro-4-({6-(methyloxy)-7-[(piperidin-4-ylmethyl)oxy]quinolin-4-yl}oxy)phenyl]-N'-{[4-fluoro-2-(trifluoromethyl)phenyl]methyl}ethanediamide | A | A | B | A | A |
| 206 | N-[3-fluoro-4-({6-(methyloxy)-7-[(piperidin-4-ylmethyl)oxy]quinolin-4-yl}oxy)phenyl]-N'-[(1R)-1-(4-methylphenyl)ethyl]ethanediamide | A | B | B | B | B |
| 207 | N-[3-fluoro-4-({6-(methyloxy)-7-[(piperidin-4-ylmethyl)oxy]quinolin-4-yl}oxy)phenyl]-N'-{[3-fluoro-4-(trifluoromethyl)phenyl]methyl}ethanediamide | A | B | B | B | B |
| 208 | N-[(3-chloro-4-fluorophenyl)methyl]-N'-[3-fluoro-4-({6-(methyloxy)-7-[(piperidin-4-ylmethyl)oxy]quinolin-4-yl}oxy)phenyl]ethanediamide | A | A | A | A | B |
| 209 | N-[3-fluoro-4-({6-(methyloxy)-7-[(piperidin-4-ylmethyl)oxy]quinolin-4-yl}oxy)phenyl]-N'-{(1S)-1-[3-(methyloxy)phenyl]ethyl}ethanediamide | A | B | B | B | B |
| 210 | N-[3-fluoro-4-({6-(methyloxy)-7-[(piperidin-4-ylmethyl)oxy]quinolin-4-yl}oxy)phenyl]-N'-[(1R)-1-naphthalen-2-ylethyl]ethanediamide | A | B | B | B | |
| 211 | N-{[4-chloro-3-(trifluoromethyl)phenyl]methyl}-N'-[3-fluoro-4-({6-(methyloxy)-7-[(piperidin-4-ylmethyl)oxy]quinolin-4-yl}oxy)phenyl]ethanediamide | A | A | A | A | A |
| 212 | N-[3-fluoro-4-({6-(methyloxy)-7-[(piperidin-4-ylmethyl)oxy]quinolin-4-yl}oxy)phenyl]-N'-[(1S)-1-(4-methylphenyl)ethyl]ethanediamide | A | B | C | B | |
| 213 | N-[3-fluoro-4-({6-(methyloxy)-7-[(piperidin-4-ylmethyl)oxy]quinolin-4-yl}oxy)phenyl]-N'-{[6-(trifluoromethyl)pyridin-3-yl]methyl}ethanediamide | A | B | C | B | B |
| 214 | N-[3-fluoro-4-({6-(methyloxy)-7-[(piperidin-4-ylmethyl)oxy]quinolin-4-yl}oxy)phenyl]-N'-[(2-methylphenyl)methyl]ethanediamide | A | A | A | A | B |
| 215 | N-[3-fluoro-4-({6-(methyloxy)-7-[(piperidin-4-ylmethyl)oxy]quinolin-4-yl}oxy)phenyl]-N'-[(3-methylphenyl)methyl]ethanediamide | A | A | A | B | A |
| 216 | N-[3-fluoro-4-({6-(methyloxy)-7-[(piperidin-4-ylmethyl)oxy]quinolin-4-yl}oxy)phenyl]-N'-{[4-fluoro-3-(trifluoromethyl)phenyl]methyl}ethanediamide | A | A | B | A | A |
| 217 | N-[(3,5-dichlorophenyl)methyl]-N'-[3-fluoro-4-({6-(methyloxy)-7-[(piperidin-4-ylmethyl)oxy]quinolin-4-yl}oxy)phenyl]ethanediamide | A | A | A | A | A |
| 218 | N-[3-fluoro-4-({6-(methyloxy)-7-[(piperidin-4-ylmethyl)oxy]quinolin-4-yl}oxy)phenyl]-N'-[(1R)-1,2,3,4-tetrahydronaphthalen-1-yl]ethanediamide | A | B | B | B | A |
| 219 | N-[3-fluoro-4-({6-(methyloxy)-7-[(piperidin-4-ylmethyl)oxy]quinolin-4-yl}oxy)phenyl]-N'-[(1S)-1,2,3,4-tetrahydronaphthalen-1-yl]ethanediamide | A | A | A | A | A |
| 220 | N-cyclopentyl-N'-[3-fluoro-4-({6-(methyloxy)-7-[(piperidin-4-ylmethyl)oxy]quinolin-4-yl}oxy)phenyl]ethanediamide | A | B | B | B | B |

TABLE 4-continued

| Entry | Name | c-Met | KDR | c-Kit | flt3 | flt4 |
|---|---|---|---|---|---|---|
| 221 | N-[1-(4-bromophenyl)ethyl]-N'-[3-fluoro-4-({6-(methyloxy)-7-[(piperidin-4-ylmethyl)oxy]quinolin-4-yl}oxy)phenyl]ethanediamide | A | B | B | B | B |
| 222 | N-[3-fluoro-4-({6-(methyloxy)-7-[(piperidin-4-ylmethyl)oxy]quinolin-4-yl}oxy)phenyl]-N'-[(2-fluorophenyl)methyl]ethanediamide | A | A | B | B | A |
| 223 | N-[2-(3,4-dichlorophenyl)ethyl]-N'-[3-fluoro-4-({6-(methyloxy)-7-[(piperidin-4-ylmethyl)oxy]quinolin-4-yl}oxy)phenyl]ethanediamide | A | A | A | A | |
| 224 | N-[3-fluoro-4-({6-(methyloxy)-7-[(piperidin-4-ylmethyl)oxy]quinolin-4-yl}oxy)phenyl]-N'-[(4-fluorophenyl)methyl]ethanediamide | A | A | A | A | A |
| 225 | N-[(2,3-difluorophenyl)methyl]-N'-[3-fluoro-4-({6-(methyloxy)-7-[(piperidin-4-ylmethyl)oxy]quinolin-4-yl}oxy)phenyl]ethanediamide | A | A | B | B | A |
| 226 | N-[3-fluoro-4-({6-(methyloxy)-7-[(piperidin-4-ylmethyl)oxy]quinolin-4-yl}oxy)phenyl]-N'-[2-(phenyloxy)ethyl]ethanediamide | A | A | A | A | A |
| 227 | N-(2,2-diphenylethyl)-N'-[3-fluoro-4-({6-(methyloxy)-7-[(piperidin-4-ylmethyl)oxy]quinolin-4-yl}oxy)phenyl]ethanediamide | A | B | B | A | B |
| 228 | N-[3-fluoro-4-({6-(methyloxy)-7-[(piperidin-4-ylmethyl)oxy]quinolin-4-yl}oxy)phenyl]-N'-{2-[4-(methyloxy)phenyl]ethyl}ethanediamide | A | B | B | B | B |
| 229 | N-[3-fluoro-4-({6-(methyloxy)-7-[(piperidin-4-ylmethyl)oxy]quinolin-4-yl}oxy)phenyl]-N'-(2-phenylpropyl)ethanediamide | A | A | A | A | A |
| 230 | N-[2-(4-bromophenyl)ethyl]-N'-[3-fluoro-4-({6-(methyloxy)-7-[(piperidin-4-ylmethyl)oxy]quinolin-4-yl}oxy)phenyl]ethanediamide | A | A | B | B | B |
| 231 | N-(4-{[7-{[(1-ethylpiperidin-4-yl)methyl]oxy}-6-(methyloxy)quinolin-4-yl]oxy}-3-fluorophenyl)-2-oxo-2-(2-phenylmorpholin-4-yl)acetamide | A | B | B | B | B |
| 232 | N-[3-fluoro-4-({6-(methyloxy)-7-[(piperidin-4-ylmethyl)oxy]quinolin-4-yl}oxy)phenyl]-N'-{[3-fluoro-5-(trifluoromethyl)phenyl]methyl}ethanediamide | A | A | B | A | B |
| 233 | N-[(3,5-difluorophenyl)methyl]-N'-[3-fluoro-4-({6-(methyloxy)-7-[(piperidin-4-ylmethyl)oxy]quinolin-4-yl}oxy)phenyl]ethanediamide | A | A | A | B | A |
| 234 | N-{[2-chloro-5-(trifluoromethyl)phenyl]methyl}-N'-[3-fluoro-4-({6-(methyloxy)-7-[(piperidin-4-ylmethyl)oxy]quinolin-4-yl}oxy)phenyl]ethanediamide | A | A | B | A | B |
| 235 | N-(4-{[6,7-bis(methyloxy)quinolin-4-yl]oxy}-3-fluorophenyl)-N'-[2-(dimethylamino)-2-phenylethyl]ethanediamide | B | B | B | A | |
| 236 | N-[3-fluoro-4-({6-(methyloxy)-7-[(piperidin-4-ylmethyl)oxy]quinolin-4-yl}oxy)phenyl]-N'-{[4-(methyloxy)phenyl]methyl}ethanediamide | A | A | A | B | B |
| 237 | N-[3-fluoro-4-({6-(methyloxy)-7-[(piperidin-4-ylmethyl)oxy]quinolin-4-yl}oxy)phenyl]-N'-{[4-(trifluoromethyl)phenyl]methyl}ethanediamide | A | B | B | B | A |
| 238 | N-[3-fluoro-4-({6-(methyloxy)-7-[(piperidin-4-ylmethyl)oxy]quinolin-4-yl}oxy)phenyl]-N'-{[3-(methyloxy)phenyl]methyl}ethanediamide | A | A | A | A | B |
| 239 | N-[3-fluoro-4-({6-(methyloxy)-7-[(piperidin-4-ylmethyl)oxy]quinolin-4-yl}oxy)phenyl]-N'-{[3-(trifluoromethyl)phenyl]methyl}ethanediamide | A | A | A | A | B |
| 240 | N-[3-fluoro-4-({6-(methyloxy)-7-[(piperidin-4-ylmethyl)oxy]quinolin-4-yl}oxy)phenyl]-N'-({3-[(trifluoromethyl)oxy]phenyl}methyl)ethanediamide | A | A | A | A | A |
| 241 | N-[3-fluoro-4-({6-(methyloxy)-7-[(piperidin-4-ylmethyl)oxy]quinolin-4-yl}oxy)phenyl]-N'-{[2-(methyloxy)phenyl]methyl}ethanediamide | A | A | A | A | A |
| 242 | N-[3-fluoro-4-({6-(methyloxy)-7-[(piperidin-4-ylmethyl)oxy]quinolin-4-yl}oxy)phenyl]-N'-{[2-(trifluoromethyl)phenyl]methyl}ethanediamide | A | A | A | A | A |
| 243 | N-[(3-chlorophenyl)methyl]-N'-[3-fluoro-4-({6-(methyloxy)-7-[(piperidin-4-ylmethyl)oxy]quinolin-4-yl}oxy)phenyl]ethanediamide | A | A | A | B | B |
| 244 | N-[3-fluoro-4-({6-(methyloxy)-7-[(piperidin-4-ylmethyl)oxy]quinolin-4-yl}oxy)phenyl]-N'-({2-[(trifluoromethyl)oxy]phenyl}methyl)ethanediamide | A | A | A | A | A |
| 245 | N-[(2-chlorophenyl)methyl]-N'-[3-fluoro-4-({6-(methyloxy)-7-[(piperidin-4-ylmethyl)oxy]quinolin-4-yl}oxy)phenyl]ethanediamide | A | A | A | A | A |

TABLE 4-continued

| Entry | Name | c-Met | KDR | c-Kit | flt3 | flt4 |
|---|---|---|---|---|---|---|
| 246 | N-[3-fluoro-4-({6-(methyloxy)-7-[(piperidin-4-ylmethyl)oxy]quinolin-4-yl}oxy)phenyl]-N'-({4-[(trifluoromethyl)oxy]phenyl}methyl)ethanediamide | A | B | B | B | B |
| 247 | N-{3-fluoro-4-[(6-(methyloxy)-7-{[(1-methylpiperidin-4-yl)methyl]oxy}quinolin-4-yl)oxy]phenyl}-N'-{[4-(methyloxy)phenyl]methyl}ethanediamide | A | B | A | B | |
| 248 | N-{3-fluoro-4-[(6-(methyloxy)-7-{[(1-methylpiperidin-4-yl)methyl]oxy}quinolin-4-yl)oxy]phenyl}-N'-{[4-(trifluoromethyl)phenyl]methyl}ethanediamide | A | B | B | B | B |
| 249 | N-(4-{[7-[(azetidin-3-ylmethyl)oxy]-6-(methyloxy)quinolin-4-yl]oxy}-3-fluorophenyl)-N'-(2-phenylethyl)ethanediamide | A | A | | | |
| 250 | N-(3-fluoro-4-{[7-{[(1-methylazetidin-3-yl)methyl]oxy}-6-(methyloxy)quinolin-4-yl]oxy}phenyl)-N'-(2-phenylethyl)ethanediamide | A | A | A | A | A |
| 251 | N-[3-fluoro-4-({6-(methyloxy)-7-[(piperidin-4-ylmethyl)oxy]quinolin-4-yl}oxy)phenyl]-N'-(2-hydroxy-2-phenylethyl)ethanediamide | B | B | B | B | |
| 252 | N-(6-{[6,7-bis(methyloxy)quinolin-4-yl]oxy}-5-chloropyridin-3-yl)-N'-(2,4-difluorophenyl)propanediamide | A | C | | | |
| 253 | N'-(6-{[6,7-bis(methyloxy)quinolin-4-yl]oxy}-5-chloropyridin-3-yl)-N-(4-fluorophenyl)-N-methylpropanediamide | B | C | | | |
| 254 | N-[3-fluoro-4-({6-(methyloxy)-7-[(piperidin-4-ylmethyl)oxy]quinolin-4-yl}oxy)phenyl]-N'-[(1R)-1-phenylpropyl]ethanediamide | A | B | B | B | B |
| 255 | N-[3-fluoro-4-({6-(methyloxy)-7-[(piperidin-4-ylmethyl)oxy]quinolin-4-yl}oxy)phenyl]-N'-[(1S)-1-phenylpropyl]ethanediamide | A | B | C | B | |
| 256 | N-[(3,4-difluorophenyl)methyl]-N'-[3-fluoro-4-({6-(methyloxy)-7-[(piperidin-4-ylmethyl)oxy]quinolin-4-yl}oxy)phenyl]ethanediamide | A | A | A | B | A |
| 257 | N-[(2,6-difluorophenyl)methyl]-N'-[3-fluoro-4-({6-(methyloxy)-7-[(piperidin-4-ylmethyl)oxy]quinolin-4-yl}oxy)phenyl]ethanediamide | A | A | A | B | A |
| 258 | N-{3-fluoro-4-[(6-(methyloxy)-7-{[(1-methylpiperidin-4-yl)methyl]oxy}quinolin-4-yl)oxy]phenyl}-N'-[2-(4-fluorophenyl)ethyl]ethanediamide | A | A | A | A | A |
| 259 | N-{3-fluoro-4-[(6-(methyloxy)-7-{[(1-methylpiperidin-4-yl)methyl]oxy}quinolin-4-yl)oxy]phenyl}-N'-phenylethanediamide | A | B | C | C | B |
| 260 | N-[3-fluoro-4-({6-(methyloxy)-7-[(piperidin-4-ylmethyl)oxy]quinolin-4-yl}oxy)phenyl]-N'-(3-fluorophenyl)ethanediamide | A | C | B | C | C |
| 261 | N-(3-chloro-4-fluorophenyl)-N'-[3-fluoro-4-({6-(methyloxy)-7-[(piperidin-4-ylmethyl)oxy]quinolin-4-yl}oxy)phenyl]ethanediamide | A | C | C | B | B |
| 262 | N-[3,4-bis(methyloxy)phenyl]-N'-[3-fluoro-4-({6-(methyloxy)-7-[(piperidin-4-ylmethyl)oxy]quinolin-4-yl}oxy)phenyl]ethanediamide | A | C | C | B | B |
| 263 | N-[3-fluoro-4-({6-(methyloxy)-7-[(piperidin-4-ylmethyl)oxy]quinolin-4-yl}oxy)phenyl]-N'-(3-methylbutyl)ethanediamide | A | B | A | B | B |
| 264 | N-(3,3-dimethylbutyl)-N'-[3-fluoro-4-({6-(methyloxy)-7-[(piperidin-4-ylmethyl)oxy]quinolin-4-yl}oxy)phenyl]ethanediamide | A | A | A | A | B |
| 265 | N-[5-chloro-6-({6-(methyloxy)-7-[(3-piperidin-1-ylpropyl)oxy]quinolin-4-yl}oxy)pyridin-3-yl]-N'-(4-fluorophenyl)propanediamide | A | B | B | A | B |
| 266 | N-[5-chloro-6-({6-(methyloxy)-7-[(3-morpholin-4-ylpropyl)oxy]quinolin-4-yl}oxy)pyridin-3-yl]-N'-(4-fluorophenyl)propanediamide | A | B | B | A | B |
| 267 | N-(5-chloro-6-{[7-{[3-(diethylamino)propyl]oxy}-6-(methyloxy)quinolin-4-yl]oxy}pyridin-3-yl)-N'-(4-fluorophenyl)propanediamide | A | B | B | A | B |
| 268 | N-[(4-chlorophenyl)methyl]-N'-[3-fluoro-4-({6-(methyloxy)-7-[(piperidin-4-ylmethyl)oxy]quinolin-4-yl}oxy)phenyl]ethanediamide | A | A | | | |
| 269 | N-{[3,5-bis(methyloxy)phenyl]methyl}-N'-[3-fluoro-4-({6-(methyloxy)-7-[(piperidin-4-ylmethyl)oxy]quinolin-4-yl}oxy)phenyl]ethanediamide | A | A | | A | |
| 270 | N-[(4-butylphenyl)methyl]-N'-[3-fluoro-4-({6-(methyloxy)-7-[(piperidin-4-ylmethyl)oxy]quinolin-4-yl}oxy)phenyl]ethanediamide | A | B | B | B | B |

TABLE 4-continued

| Entry | Name | c-Met | KDR | c-Kit | flt3 | flt4 |
|---|---|---|---|---|---|---|
| 271 | N-[3-fluoro-4-({6-(methyloxy)-7-[(piperidin-4-ylmethyl)oxy]quinolin-4-yl}oxy)phenyl]-N'-[2-(4-methylphenyl)ethyl]ethanediamide | A | B | B | A | B |
| 272 | N-{[3,5-bis(trifluoromethyl)phenyl]methyl}-N'-[3-fluoro-4-({6-(methyloxy)-7-[(piperidin-4-ylmethyl)oxy]quinolin-4-yl}oxy)phenyl]ethanediamide | A | A | C | B | |
| 273 | N-[3-fluoro-4-({6-(methyloxy)-7-[(piperidin-4-ylmethyl)oxy]quinolin-4-yl}oxy)phenyl]-N'-(pyrazin-2-ylmethyl)ethanediamide | B | C | C | B | |
| 274 | N-[3-fluoro-4-({6-(methyloxy)-7-[(piperidin-4-ylmethyl)oxy]quinolin-4-yl}oxy)phenyl]-N'-(pyridin-2-ylmethyl)ethanediamide | A | B | B | B | B |
| 275 | N-[3-fluoro-4-({6-(methyloxy)-7-[(piperidin-4-ylmethyl)oxy]quinazolin-4-yl}oxy)phenyl]-N'-(2-phenylethyl)ethanediamide | A | A | A | A | A |
| 276 | N-{3-fluoro-4-[(6-(methyloxy)-7-{[(1-methylpiperidin-4-yl)methyl]oxy}quinazolin-4-yl)oxy]phenyl}-N'-(2-phenylethyl)ethanediamide | A | A | A | A | A |
| 277 | N-[3-fluoro-4-({6-(methyloxy)-7-[(piperidin-4-ylmethyl)oxy]quinolin-4-yl}oxy)phenyl]-N'-{[2-fluoro-3-(trifluoromethyl)phenyl]methyl}ethanediamide | A | A | A | A | A |
| 278 | N-{2-[2-bromo-6-(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | A | A | A | A |
| 279 | N-{2-[3,4-bis(methyloxy)phenyl]ethyl}-N'-[3-fluoro-4-({6-(methyloxy)-7-[(piperidin-4-ylmethyl)oxy]quinolin-4-yl}oxy)phenyl]-N-methylethanediamide | B | B | B | A | B |
| 280 | N-{2-[5-bromo-2-(methyloxy)phenyl]ethyl}-N'-[3-fluoro-4-({6-(methyloxy)-7-[(piperidin-4-ylmethyl)oxy]quinolin-4-yl}oxy)phenyl]ethanediamide | A | A | A | A | A |
| 281 | N-[3-fluoro-4-({6-(methyloxy)-7-[(piperidin-4-ylmethyl)oxy]quinolin-4-yl}oxy)phenyl]-N'-{[2-fluoro-5-(trifluoromethyl)phenyl]methyl}ethanediamide | A | A | B | A | B |
| 282 | N-[5-chloro-6-({6-(methyloxy)-7-[(piperidin-4-ylmethyl)oxy]quinolin-4-yl}oxy)pyridin-3-yl]-N'-(4-fluorophenyl)cyclopropane-1,1-dicarboxamide | A | A | A | A | A |
| 283 | N-[3-fluoro-4-({6-(methyloxy)-7-[(piperidin-4-ylmethyl)oxy]quinolin-4-yl}oxy)phenyl]-N'-[1-(4-fluorophenyl)ethyl]ethanediamide | A | A | B | A | B |
| 284 | N-[3-fluoro-4-({6-(methyloxy)-7-[(piperidin-4-ylmethyl)oxy]quinolin-4-yl}oxy)phenyl]-N'-[(1S)-2-oxo-1-(phenylmethyl)-2-pyrrolidin-1-ylethyl]ethanediamide | A | C | B | B | C |
| 285 | N-{3-fluoro-4-[(6-(methyloxy)-7-{[(3aR,6aS)-octahydrocyclopenta[c]pyrrol-5-ylmethyl]oxy}quinazolin-4-yl)oxy]phenyl}-N'-(2-phenylethyl)ethanediamide | A | A | A | A | A |
| 286 | N-[2-(4-aminophenyl)ethyl]-N'-[3-fluoro-4-({6-(methyloxy)-7-[(piperidin-4-ylmethyl)oxy]quinolin-4-yl}oxy)phenyl]ethanediamide | A | B | B | B | B |
| 287 | N-[3-fluoro-4-({6-(methyloxy)-7-[(piperidin-4-ylmethyl)oxy]quinolin-4-yl}oxy)phenyl]-2-oxo-2-[4-(phenylmethyl)piperidin-1-yl]acetamide | A | A | B | A | B |
| 288 | N-(4-{[6,7-bis(methyloxy)quinolin-4-yl]oxy}phenyl)-N'-(4-fluorophenyl)propanediamide | A | A | A | A | A |
| 289 | N-(4-{[6,7-bis(methyloxy)quinolin-4-yl]oxy}phenyl)-N'-(4-fluorophenyl)cyclopropane-1,1-dicarboxamide | A | A | A | A | 5.581 |
| 290 | N-(6-{[6,7-bis(methyloxy)quinolin-4-yl]oxy}-5-chloropyridin-3-yl)-N'-(3-fluorophenyl)propanediamide | B | C | | | |
| 291 | N-(6-{[6,7-bis(methyloxy)quinolin-4-yl]oxy}-5-chloropyridin-3-yl)-N'-phenylpropanediamide | A | C | B | A | C |
| 292 | N-(6-{[6,7-bis(methyloxy)quinolin-4-yl]oxy}-5-chloropyridin-3-yl)-N'-(4-fluorophenyl)-2,2-dimethylpropanediamide | B | B | B | A | B |
| 293 | N-ethyl-N'-[3-fluoro-4-({6-(methyloxy)-7-[(piperidin-4-ylmethyl)oxy]quinolin-4-yl}oxy)phenyl]ethanediamide | A | B | B | B | B |
| 294 | N-[3-fluoro-4-({6-(methyloxy)-7-[(piperidin-4-ylmethyl)oxy]quinolin-4-yl}oxy)phenyl]-N'-(1-methylethyl)ethanediamide | A | B | B | B | C |
| 295 | N-butyl-N'-[3-fluoro-4-({6-(methyloxy)-7-[(piperidin-4-ylmethyl)oxy]quinolin-4-yl}oxy)phenyl]ethanediamide | A | B | B | B | B |

TABLE 4-continued

| Entry | Name | c-Met | KDR | c-Kit | flt3 | flt4 |
|-------|------|-------|-----|-------|------|------|
| 296 | N-[3-fluoro-4-({6-(methyloxy)-7-[(piperidin-4-ylmethyl)oxy]quinolin-4-yl}oxy)phenyl]-N'-[2-(methyloxy)ethyl]ethanediamide | B | B | B | B | C |
| 297 | N-(cyclopropylmethyl)-N'-[3-fluoro-4-({6-(methyloxy)-7-[(piperidin-4-ylmethyl)oxy]quinolin-4-yl}oxy)phenyl]ethanediamide | A | B | B | B | B |
| 298 | N-[3-fluoro-4-({6-(methyloxy)-7-[(piperidin-4-ylmethyl)oxy]quinolin-4-yl}oxy)phenyl]-N'-(2-morpholin-4-ylethyl)ethanediamide | B | A | B | A | B |
| 299 | N-[3-fluoro-4-({6-(methyloxy)-7-[(piperidin-4-ylmethyl)oxy]quinolin-4-yl}oxy)phenyl]-2-oxo-2-pyrrolidin-1-ylacetamide | A | B | B | B | B |
| 300 | N-ethyl-N'-[3-fluoro-4-({6-(methyloxy)-7-[(piperidin-4-ylmethyl)oxy]quinolin-4-yl}oxy)phenyl]-N-methylethanediamide | A | B | C | B | B |
| 301 | N-(6-{[6,7-bis(methyloxy)quinolin-4-yl]oxy}-5-chloropyridin-3-yl)-N'-(phenylmethyl)cyclopropane-1,1-dicarboxamide | A | C | B | B | B |
| 302 | N-(6-{[6,7-bis(methyloxy)quinolin-4-yl]oxy}-5-chloropyridin-3-yl)-N'-(2-phenylethyl)cyclopropane-1,1-dicarboxamide | C | C | | | |
| 303 | N-{4-[(7-chloroquinolin-4-yl)oxy]-3-fluorophenyl}-N'-(4-fluorophenyl)cyclopropane-1,1-dicarboxamide | A | A | C | C | B |
| 304 | N-(4-{[7-{[2-(diethylamino)ethyl]oxy}-6-(methyloxy)quinolin-4-yl]oxy}-3-fluorophenyl)-N'-(4-fluorophenyl)cyclopropane-1,1-dicarboxamide | A | A | A | A | A |
| 305 | N-(6-{[6,7-bis(methyloxy)quinolin-4-yl]oxy}-5-chloropyridin-3-yl)-N'-phenylcyclopropane-1,1-dicarboxamide | A | B | B | A | |
| 306 | N-(6-{[6,7-bis(methyloxy)quinolin-4-yl]oxy}-2-methylpyridin-3-yl)-N'-(4-fluorophenyl)cyclopropane-1,1-dicarboxamide | A | B | B | C | B |
| 307 | N-(4-{[7-{[2-(diethylamino)ethyl]oxy}-6-(methyloxy)quinolin-4-yl]oxy}-3-fluorophenyl)-N'-(4-fluorophenyl)cyclobutane-1,1-dicarboxamide | A | A | A | B | A |
| 308 | N-{4-[(7-chloroquinolin-4-yl)oxy]phenyl}-N'-(4-fluorophenyl)cyclopropane-1,1-dicarboxamide | A | A | B | C | B |
| 309 | N-[5-chloro-6-({6-(methyloxy)-7-[(phenylmethyl)oxy]quinolin-4-yl}oxy)pyridin-3-yl]-N'-(4-fluorophenyl)cyclopropane-1,1-dicarboxamide | A | C | C | B | C |
| 310 | N-(4-{[6,7-bis(methyloxy)quinazolin-4-yl]oxy}phenyl)-N'-(4-fluorophenyl)cyclopropane-1,1-dicarboxamide | A | A | A | A | A |
| 311 | N-(4-{[6,7-bis(methyloxy)quinazolin-4-yl]oxy}-3-fluorophenyl)-N'-(4-fluorophenyl)cyclopropane-1,1-dicarboxamide | A | A | B | A | A |
| 312 | N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide | A | A | A | A | A |
| 313 | N-[3-fluoro-4-({6-(methyloxy)-7-[(3-piperidin-1-ylpropyl)oxy]quinolin-4-yl}oxy)phenyl]-N'-(4-fluorophenyl)cyclopropane-1,1-dicarboxamide | A | A | A | A | A |
| 314 | N-[3-fluoro-4-({6-(methyloxy)-7-[(3-piperidin-1-ylpropyl)oxy]quinolin-4-yl}oxy)phenyl]-N'-(4-fluorophenyl)cyclobutane-1,1-dicarboxamide | A | A | A | B | A |
| 315 | N-[3-fluoro-4-({6-(methyloxy)-7-[(3-morpholin-4-ylpropyl)oxy]quinazolin-4-yl}oxy)phenyl]-N'-(4-fluorophenyl)cyclopropane-1,1-dicarboxamide | A | A | A | A | A |
| 316 | N-{3-fluoro-4-[(6-(methyloxy)-7-{[(1-methylpiperidin-4-yl)methyl]oxy}quinazolin-4-yl)oxy]phenyl}-N'-(4-fluorophenyl)cyclopropane-1,1-dicarboxamide | A | A | A | A | A |
| 317 | N-(4-{[6,7-bis(methyloxy)quinolin-4-yl]oxy}-2-methylphenyl)-N'-(4-fluorophenyl)cyclopropane-1,1-dicarboxamide | A | A | A | C | A |
| 318 | N-(4-fluorophenyl)-N'-[2-methyl-6-({6-(methyloxy)-7-[(3-morpholin-4-ylpropyl)oxy]quinolin-4-yl}oxy)pyridin-3-yl]cyclopropane-1,1-dicarboxamide | A | A | B | B | B |
| 319 | N-(4-{[6,7-bis(methyloxy)quinolin-4-yl]oxy}-3-fluorophenyl)-N'-(4-fluorophenyl)cyclopropane-1,1-dicarboxamide | A | A | A | A | A |
| 320 | N-(6-{[6,7-bis(methyloxy)quinolin-4-yl]oxy}-5-chloro-2-methylpyridin-3-yl)-N'-(4-fluorophenyl)cyclopropane-1,1-dicarboxamide | A | C | C | B | C |
| 321 | N-[3-fluoro-4-({7-(methyloxy)-6-[(3-morpholin-4-ylpropyl)oxy]quinazolin-4-yl}oxy)phenyl]-N'-(4-fluorophenyl)cyclopropane-1,1-dicarboxamide | A | A | B | A | A |

TABLE 4-continued

| Entry | Name | c-Met | KDR | c-Kit | flt3 | flt4 |
|---|---|---|---|---|---|---|
| 322 | N-[3-fluoro-4-({7-(methyloxy)-6-[(3-morpholin-4-ylpropyl)oxy]quinolin-4-yl}oxy)phenyl]-N'-(4-fluorophenyl)cyclopropane-1,1-dicarboxamide | A | A | A | A | A |
| 323 | N-(4-{[6,7-bis(methyloxy)quinolin-4-yl]oxy}-3,5-difluorophenyl)-N'-(4-fluorophenyl)cyclopropane-1,1-dicarboxamide | A | A | B | A | A |
| 324 | N-(4-{[6,7-bis(methyloxy)quinolin-4-yl]oxy}-2,5-difluorophenyl)-N'-(4-fluorophenyl)cyclopropane-1,1-dicarboxamide | A | A | A | A | A |
| 325 | N-{3-fluoro-4-[(7-(methyloxy)-6-{[(1-methylpiperidin-4-yl)methyl]oxy}quinazolin-4-yl)oxy]phenyl}-N'-(4-fluorophenyl)cyclopropane-1,1-dicarboxamide | A | A | B | A | A |
| 326 | N-[5-fluoro-2-methyl-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide | A | A | B | B | B |
| 327 | N-(4-{[6,7-bis(methyloxy)quinolin-4-yl]oxy}-2,3,5-trifluorophenyl)-N'-(4-fluorophenyl)cyclopropane-1,1-dicarboxamide | A | A | B | B | B |
| 328 | N-(4-{[6,7-bis(methyloxy)quinolin-4-yl]oxy}-5-fluoro-2-methylphenyl)-N'-(4-fluorophenyl)cyclopropane-1,1-dicarboxamide | A | B | B | C | C |
| 329 | N-(4-{[6,7-bis(methyloxy)quinolin-4-yl]oxy}-2-chloro-5-methylphenyl)-N'-(4-fluorophenyl)cyclopropane-1,1-dicarboxamide | A | B | B | C | B |
| 330 | N-(3-fluoro-4-{[6-hydroxy-7-(methyloxy)quinolin-4-yl]oxy}phenyl)-N'-(4-fluorophenyl)cyclopropane-1,1-dicarboxamide | A | A | A | A | A |
| 331 | N-(4-fluorophenyl)-N'-[2-methyl-4-({6-(methyloxy)-7-[(3-morpholin-4-ylpropyl)oxy]quinolin-4-yl}oxy)phenyl]cyclopropane-1,1-dicarboxamide | A | A | A | B | A |
| 332 | N-[3-fluoro-4-({6-(methyloxy)-7-[(3-piperazin-1-ylpropyl)oxy]quinolin-4-yl}oxy)phenyl]-N'-(4-fluorophenyl)cyclopropane-1,1-dicarboxamide | A | A | A | A | A |
| 333 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclopropane-1,1-dicarboxamide | A | A | A | A | A |
| 334 | N-{3-fluoro-4-[(6-(methyloxy)-7-{[(1-methylpiperidin-4-yl)methyl]oxy}quinolin-4-yl)oxy]phenyl}-N'-(4-fluorophenyl)cyclopropane-1,1-dicarboxamide | A | A | A | A | A |
| 335 | N-(4-fluorophenyl)-N'-[4-({6-(methyloxy)-7-[(3-morpholin-4-ylpropyl)oxy]quinolin-4-yl}oxy)phenyl]cyclopropane-1,1-dicarboxamide | A | A | A | A | A |
| 336 | N-(4-{[7-{[3-(diethylamino)propyl]oxy}-6-(methyloxy)quinolin-4-yl]oxy}-3-fluorophenyl)-N'-(4-fluorophenyl)cyclopropane-1,1-dicarboxamide | A | A | A | A | A |
| 337 | N-(4-{[6,7-bis(methyloxy)quinolin-4-yl]oxy}-2-chloro-5-fluorophenyl)-N'-(4-fluorophenyl)cyclopropane-1,1-dicarboxamide | A | B | B | C | C |
| 338 | N-(4-{[6,7-bis(methyloxy)-2-(methylthio)quinolin-4-yl]oxy}-3-fluorophenyl)-N'-(4-fluorophenyl)cyclopropane-1,1-dicarboxamide | C | C | | | |
| 339 | N-(4-fluorophenyl)-N'-(4-{[2-methyl-6,7-bis(methyloxy)quinazolin-4-yl]oxy}phenyl)cyclopropane-1,1-dicarboxamide | C | C | | | |
| 340 | N-(4-{[2-amino-6,7-bis(methyloxy)quinolin-4-yl]oxy}-3-fluorophenyl)-N'-(4-fluorophenyl)cyclopropane-1,1-dicarboxamide | C | C | | | |
| 341 | N-(3-fluoro-4-{[2-(methylamino)-6,7-bis(methyloxy)quinolin-4-yl]oxy}phenyl)-N'-(4-fluorophenyl)cyclopropane-1,1-dicarboxamide | C | C | | | |
| 342 | (1S,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide | A | A | B | A | A |
| 343 | (1R,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide | A | A | A | A | A |
| 344 | N-(4-{[6-{[3-(diethylamino)propyl]oxy}-7-(methyloxy)quinolin-4-yl]oxy}-3-fluorophenyl)-N'-(4-fluorophenyl)cyclopropane-1,1-dicarboxamide | A | A | | A | |
| 345 | N-(4-{[6-{[2-(diethylamino)ethyl]oxy}-7-(methyloxy)quinolin-4-yl]oxy}-3-fluorophenyl)-N'-(4-fluorophenyl)cyclopropane-1,1-dicarboxamide | A | A | | A | |

TABLE 4-continued

| Entry | Name | c-Met | KDR | c-Kit | flt3 | flt4 |
|---|---|---|---|---|---|---|
| 346 | 1,1-dimethylethyl 4-(3-{[4-[(2-fluoro-4-{[(1-{[(4-fluorophenyl)amino]carbonyl}cyclopropyl)carbonyl]amino}phenyl)oxy]-6-(methyloxy)quinolin-7-yl]oxy}propyl)piperazine-1-carboxylate | A | A | | B | |
| 347 | (1R,2R)-N-[3-fluoro-4-({6-(methyloxy)-7-[(3-morpholin-4-ylpropyl)oxy]quinazolin-4-yl}oxy)phenyl]-N'-(4-fluorophenyl)-2-methylcyclopropane-1,1-dicarboxamide | A | A | | | |
| 348 | (1R,2R)-N-(4-{[7-{[2-(diethylamino)ethyl]oxy}-6-(methyloxy)quinazolin-4-yl]oxy}-3-fluorophenyl)-N'-(4-fluorophenyl)-2-methylcyclopropane-1,1-dicarboxamide | A | A | | B | |
| 349 | N-(4-{[7-{[3-(diethylamino)propyl]oxy}-6-(methyloxy)quinazolin-4-yl]oxy}-3-fluorophenyl)-N'-(4-fluorophenyl)cyclopropane-1,1-dicarboxamide | A | A | | A | |
| 350 | N-(4-{[7-{[3-(4-acetylpiperazin-1-yl)propyl]oxy}-6-(methyloxy)quinolin-4-yl]oxy}-3-fluorophenyl)-N'-(4-fluorophenyl)cyclopropane-1,1-dicarboxamide | A | A | | A | |
| 351 | 1,1-dimethylethyl 4-(3-{[4-[(2-fluoro-4-{[(((1R,2R)-1-{[(4-fluorophenyl)amino]carbonyl}-2-methylcyclopropyl)carbonyl]amino}phenyl)oxy]-6-(methyloxy)quinolin-7-yl]oxy}propyl)piperazine-1-carboxylate | A | A | | B | |
| 352 | N-(4-{[6,7-bis(methyloxy)quinolin-4-yl]oxy}phenyl)-N'-(4-fluorophenyl)-1-(phenylmethyl)azetidine-3,3-dicarboxamide | A | C | | C | |
| 353 | N-(4-{[6,7-bis(methyloxy)quinolin-4-yl]oxy}phenyl)-N'-(4-fluorophenyl)azetidine-3,3-dicarboxamide | B | C | | C | |
| 354 | (1R,2S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide | A | A | | A | |
| 355 | (1R,2R)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide | A | A | | A | |
| 356 | (1R,2R)-N-[3-fluoro-4-({6-(methyloxy)-7-[(3-piperazin-1-ylpropyl)oxy]quinolin-4-yl}oxy)phenyl]-N'-(4-fluorophenyl)-2-methylcyclopropane-1,1-dicarboxamide | A | A | | A | |
| 357 | N-(3-fluoro-4-{[7-({3-[4-(1-methylethyl)piperazin-1-yl]propyl}oxy)-6-(methyloxy)quinolin-4-yl]oxy}phenyl)-N'-(4-fluorophenyl)cyclopropane-1,1-dicarboxamide | A | A | | A | |
| 358 | N-(4-{[7-{[3-(diethylamino)propyl]oxy}-6-(methyloxy)quinolin-4-yl]oxy}-3-fluorophenyl)-N'-(4-fluorophenyl)cyclopropane-1,1-dicarboxamide | A | A | | A | |
| 359 | (1R,2R)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide | A | A | | A | |
| 360 | (1R,2R)-N-(4-{[7-{[2-(diethylamino)ethyl]oxy}-6-(methyloxy)quinolin-4-yl]oxy}-3-fluorophenyl)-N'-(4-fluorophenyl)-2-methylcyclopropane-1,1-dicarboxamide | A | A | | A | |
| 361 | (1R,2S)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide | A | A | | A | |
| 362 | (1R,2S)-N-(4-{[7-{[2-(diethylamino)ethyl]oxy}-6-(methyloxy)quinolin-4-yl]oxy}-3-fluorophenyl)-N'-(4-fluorophenyl)-2-methylcyclopropane-1,1-dicarboxamide | A | A | | A | |
| 363 | N-(4-{[7-{[2-(diethylamino)ethyl]oxy}-6-(methyloxy)quinazolin-4-yl]oxy}-3-fluorophenyl)-N'-(4-fluorophenyl)cyclobutane-1,1-dicarboxamide | A | A | | | |
| 364 | (1R,2S)-N-[3-fluoro-4-({6-(methyloxy)-7-[(3-piperazin-1-ylpropyl)oxy]quinolin-4-yl}oxy)phenyl]-N'-(4-fluorophenyl)-2-methylcyclopropane-1,1-dicarboxamide | A | A | | A | |
| 365 | (1r,2R,3S)-N-[3-fluoro-4-({6-(methyloxy)-7-[(3-morpholin-4-ylpropyl)oxy]quinolin-4-yl}oxy)phenyl]-N'-(4-fluorophenyl)-2,3-dimethylcyclopropane-1,1-dicarboxamide | A | B | | B | |
| 366 | (1r,2R,3S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2,3-dimethylcyclopropane-1,1-dicarboxamide | A | B | | B | |

TABLE 4-continued

| Entry | Name | c-Met | KDR | c-Kit | flt3 | flt4 |
|---|---|---|---|---|---|---|
| 367 | (1r,2R,3S)-N-[3-fluoro-4-({6-(methyloxy)-7-[(3-morpholin-4-ylpropyl)oxy]quinazolin-4-yl}oxy)phenyl]-N'-(4-fluorophenyl)-2,3-dimethylcyclopropane-1,1-dicarboxamide | B | A | | B | |
| 368 | (1r,2R,3S)-N-{3-fluoro-4-[(6-(methyloxy)-7-{3-(4-methylpiperazin-1-yl)propyl]oxy}quinazolin-4-yl)oxy]phenyl}-N'-(4-fluorophenyl)-2,3-dimethylcyclopropane-1,1-dicarboxamide | A | A | | B | |
| 369 | N-[3-fluoro-4-({6-(methyloxy)-7-[(3-morpholin-4-ylpropyl)oxy]quinazolin-4-yl}oxy)phenyl]-N'-(4-fluorophenyl)cyclobutane-1,1-dicarboxamide | B | A | | B | |
| 370 | (2R,3R)-N-[3-fluoro-4-({6-(methyloxy)-7-[(3-morpholin-4-ylpropyl)oxy]quinolin-4-yl}oxy)phenyl]-N'-(4-fluorophenyl)-2,3-dimethylcyclopropane-1,1-dicarboxamide | A | A | | B | |
| 371 | (2R,3R)-N-(4-{[7-{[3-(diethylamino)propyl]oxy}-6-(methyloxy)quinolin-4-yl]oxy}-3-fluorophenyl)-N'-(4-fluorophenyl)-2,3-dimethylcyclopropane-1,1-dicarboxamide | A | A | | B | |
| 372 | N-(4-{[7-{[3-(diethylamino)propyl]oxy}-6-(methyloxy)quinolin-4-yl]oxy}-3-fluorophenyl)-N'-(4-fluorophenyl)-2,2-dimethylcyclopropane-1,1-dicarboxamide | A | A | | B | |
| 373 | N-[3-fluoro-4-({6-(methyloxy)-7-[(3-morpholin-4-ylpropyl)oxy]quinazolin-4-yl}oxy)phenyl]-N'-(4-fluorophenyl)-2,2-dimethylcyclopropane-1,1-dicarboxamide | A | A | | C | |
| 374 | (1r,2R,3S)-N-(4-{[7-{[3-(diethylamino)propyl]oxy}-6-(methyloxy)quinolin-4-yl]oxy}-3-fluorophenyl)-N'-(4-fluorophenyl)-2,3-dimethylcyclopropane-1,1-dicarboxamide | A | B | | B | |
| 375 | N-(4-{[7-{[2-(diethylamino)ethyl]oxy}-6-(methyloxy)quinolin-4-yl]oxy}-3-fluorophenyl)-N'-(4-fluorophenyl)-2,2-dimethylcyclopropane-1,1-dicarboxamide | A | A | | C | |
| 376 | (1r,2R,3S)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide | A | B | | B | |
| 377 | N-[3-fluoro-4-({6-(methyloxy)-7-[(3-morpholin-4-ylpropyl)oxy]quinolin-4-yl}oxy)phenyl]-N'-(4-fluorophenyl)-2,2-dimethylcyclopropane-1,1-dicarboxamide | A | A | | B | |
| 378 | N-(4-{[7-{[2-(diethylamino)ethyl]oxy}-6-(methyloxy)quinazolin-4-yl]oxy}-3-fluorophenyl)-N'-(4-fluorophenyl)-2,2-dimethylcyclopropane-1,1-dicarboxamide | A | B | | C | |
| 379 | N-(4-{[7-{[3-(diethylamino)propyl]oxy}-6-(methyloxy)quinazolin-4-yl]oxy}-3-fluorophenyl)-N'-(4-fluorophenyl)-2,2-dimethylcyclopropane-1,1-dicarboxamide | A | A | | C | |
| 380 | N-(4-{[7-{[3-(diethylamino)propyl]oxy}-6-(methyloxy)quinazolin-4-yl]oxy}-3-fluorophenyl)-N'-(4-fluorophenyl)cyclobutane-1,1-dicarboxamide | A | A | | B | |
| 381 | N-{3-fluoro-4-[(6-(methyloxy)-7-{[3-(4-methylpiperazin-1-yl)propyl]oxy}quinazolin-4-yl)oxy]phenyl}-N'-(4-fluorophenyl)cyclobutane-1,1-dicarboxamide | A | A | | B | |
| 382 | N-[3-fluoro-4-({6-(methyloxy)-7-[(3-piperazin-1-ylpropyl)oxy]quinazolin-4-yl}oxy)phenyl]-N'-(4-fluorophenyl)cyclobutane-1,1-dicarboxamide | A | A | | B | |
| 383 | (2R,3R)-N-[3-fluoro-4-({6-(methyloxy)-7-[(3-morpholin-4-ylpropyl)oxy]quinazolin-4-yl}oxy)phenyl]-N'-(4-fluorophenyl)-2,3-dimethylcyclopropane-1,1-dicarboxamide | A | A | | C | |
| 384 | N-(4-{[7-{[3-(diethylamino)propyl]oxy}-6-(methyloxy)quinolin-4-yl]oxy}-3-fluorophenyl)-N'-(4-fluorophenyl)cyclobutane-1,1-dicarboxamide | A | A | | C | |
| 385 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclobutane-1,1-dicarboxamide | A | A | | C | |
| 386 | (1R,2R)-N-(4-{[7-{[3-(diethylamino)propyl]oxy}-6-(methyloxy)quinazolin-4-yl]oxy}-3-fluorophenyl)-N'-(4-fluorophenyl)-2-methylcyclopropane-1,1-dicarboxamide | A | A | | A | |
| 387 | (1R,2R)-N-{3-fluoro-4-[(6-(methyloxy)-7-{[3-(4-methylpiperazin-1-yl)propyl]oxy}quinazolin-4- | A | A | | A | |

TABLE 4-continued

| Entry | Name | c-Met | KDR | c-Kit | flt3 | flt4 |
|---|---|---|---|---|---|---|
| | yl)oxy]phenyl}-N'-(4-fluorophenyl)-2-methylcyclopropane-1,1-dicarboxamide | | | | | |
| 388 | (2R,3R)-N-(4-{[7-{[2-(diethylamino)ethyl]oxy}-6-(methyloxy)quinazolin-4-yl]oxy}-3-fluorophenyl)-N'-(4-fluorophenyl)-2,3-dimethylcyclopropane-1,1-dicarboxamide | B | A | | C | |
| 389 | (2R,3R)-N-(4-{[7-{[3-(diethylamino)propyl]oxy}-6-(methyloxy)quinazolin-4-yl]oxy}-3-fluorophenyl)-N'-(4-fluorophenyl)-2,3-dimethylcyclopropane-1,1-dicarboxamide | A | A | | B | |
| 390 | (1R,2R)-N-[3-fluoro-4-({6-(methyloxy)-7-[(3-piperazin-1-ylpropyl)oxy]quinazolin-4-yl}oxy)phenyl]-N'-(4-fluorophenyl)-2-methylcyclopropane-1,1-dicarboxamide | A | A | | A | |
| 391 | (2R,3R)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide | A | A | | B | |
| 392 | N-(4-{[6,7-bis(methyloxy)quinolin-4-yl]oxy}phenyl)-N'-[(4-fluorophenyl)methyl]cyclopropane-1,1-dicarboxamide | B | B | | A | |
| 393 | N-(4-{[6,7-bis(methyloxy)quinolin-4-yl]oxy}phenyl)-N'-(2-morpholin-4-ylethyl)cyclopropane-1,1-dicarboxamide | C | D | | B | |
| 394 | N-(4-{[6,7-bis(methyloxy)quinolin-4-yl]oxy}phenyl)-N'-[2-(piperidin-1-ylmethyl)phenyl]cyclopropane-1,1-dicarboxamide | B | D | | B | |
| 395 | N-(4-{[6,7-bis(methyloxy)quinolin-4-yl]oxy}phenyl)-N'-[2-(pyrrolidin-1-ylmethyl)phenyl]cyclopropane-1,1-dicarboxamide | B | C | | B | |
| 396 | N-(4-{[6,7-bis(methyloxy)quinolin-4-yl]oxy}phenyl)-N'-[3-(morpholin-4-ylmethyl)phenyl]cyclopropane-1,1-dicarboxamide | B | A | | A | |
| 397 | N-(4-{[6,7-bis(methyloxy)quinolin-4-yl]oxy}phenyl)-N'-[2-(morpholin-4-ylmethyl)phenyl]cyclopropane-1,1-dicarboxamide | B | C | | B | |
| 398 | N-(4-{[6,7-bis(methyloxy)quinolin-4-yl]oxy}phenyl)-N'-phenylcyclopropane-1,1-dicarboxamide | A | A | | A | |
| 399 | N-[3-(aminomethyl)phenyl]-N'-(4-{[6,7-bis(methyloxy)quinolin-4-yl]oxy}phenyl)cyclopropane-1,1-dicarboxamide | B | A | | B | |
| 400 | N-(4-{[6,7-bis(methyloxy)quinolin-4-yl]oxy}phenyl)-N'-[3-(piperidin-1-ylmethyl)phenyl]cyclopropane-1,1-dicarboxamide | B | A | | | |
| 401 | N-(4-{[6,7-bis(methyloxy)quinolin-4-yl]oxy}phenyl)-N'-[3-(pyrrolidin-1-ylmethyl)phenyl]cyclopropane-1,1-dicarboxamide | A | A | | | |

What is claimed is:

1. A method of treating a disease or disorder, comprising administering to a mammal in need of the treatment a therapeutically effective amount of a compound having the following structure:

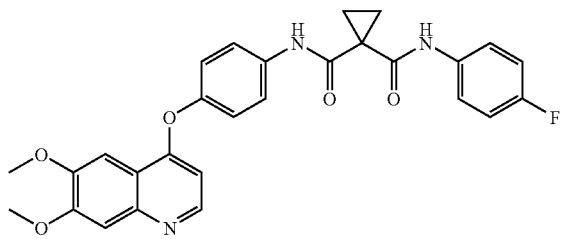

or a pharmaceutically acceptable salt thereof, or a composition containing a) a therapeutically effective amount of the compound or a pharmaceutically acceptable salt thereof; and optionally b) an excipient, wherein the disease or disorder is, ovarian cancer, prostate cancer, or lung cancer or a pharmaceutically acceptable salt thereof.

2. The method according to claim 1, wherein the disease or disorder is lung cancer.

3. The method according to claim 1, wherein the disease or disorder is ovarian cancer.

4. The method according to claim 1, wherein the disease or disorder is prostate cancer.

* * * * *